(12) United States Patent
CaJacob et al.

(10) Patent No.: US 7,625,738 B1
(45) Date of Patent: Dec. 1, 2009

(54) NUCLEIC ACID MOLECULES ENCODING A FERROCHELATASE ENZYME OR FRAGMENT THEREOF

(75) Inventors: Claire A. CaJacob, St. Louis, MO (US); Jingdong Liu, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 269 days.

(21) Appl. No.: 11/329,175

(22) Filed: Jan. 11, 2006

Related U.S. Application Data

(63) Continuation of application No. 09/233,218, filed on Jan. 20, 1999, now abandoned, which is a continuation-in-part of application No. 09/229,413, filed on Jan. 12, 1999, now abandoned, and a continuation-in-part of application No. 09/227,586, filed on Jan. 8, 1999, now abandoned, and a continuation-in-part of application No. 09/198,779, filed on Nov. 24, 1998, now abandoned.

(60) Provisional application No. 60/067,000, filed on Nov. 24, 1997, provisional application No. 60/066,873, filed on Nov. 25, 1997, provisional application No. 60/069,472, filed on Dec. 9, 1997, provisional application No. 60/074,201, filed on Feb. 10, 1998, provisional application No. 60/074,280, filed on Feb. 10, 1998, provisional application No. 60/074,281, filed on Feb. 10, 1998, provisional application No. 60/074,282, filed on Feb. 10, 1998, provisional application No. 60/074,565, filed on Feb. 12, 1998, provisional application No. 60/074,566, filed on Feb. 12, 1998, provisional application No. 60/074,567, filed on Feb. 12, 1998, provisional application No. 60/074,789, filed on Feb. 19, 1998, provisional application No. 60/075,459, filed on Feb. 19, 1998, provisional application No. 60/075,460, filed on Feb. 19, 1998, provisional application No. 60/075,461, filed on Feb. 19, 1998, provisional application No. 60/075,462, filed on Feb. 19, 1998, provisional application No. 60/075,463, filed on Feb. 19, 1998, provisional application No. 60/075,464, filed on Feb. 19, 1998, provisional application No. 60/077,229, filed on Mar. 9, 1998, provisional application No. 60/077,230, filed on Mar. 9, 1998, provisional application No. 60/077,231, filed on Mar. 9, 1998, provisional application No. 60/078,031, filed on Mar. 16, 1998, provisional application No. 60/078,368, filed on Mar. 18, 1998, provisional application No. 60/080,844, filed on Apr. 7, 1998, provisional application No. 60/083,067, filed on Apr. 27, 1998, provisional application No. 60/083,386, filed on Apr. 29, 1998, provisional application No. 60/083,387, filed on Apr. 29, 1998, provisional application No. 60/083,388, filed on Apr. 29, 1998, provisional application No. 60/083,389, filed on Apr. 29, 1998, provisional application No. 60/084,684, filed on May 8, 1998, provisional application No. 60/085,222, filed on May 13, 1998, provisional application No. 60/085,223, filed on May 13, 1998, provisional application No. 60/085,224, filed on May 13, 1998, provisional application No. 60/085,245, filed on May 13, 1998, provisional application No. 60/085,183, filed on May 21, 1998, provisional application No. 60/086,184, filed on May 21, 1998, (Continued)

(51) Int. Cl.
| | |
|---|---|
| *C12N 9/00* | (2006.01) |
| *C12N 9/88* | (2006.01) |
| *C12N 1/20* | (2006.01) |
| *C12N 15/00* | (2006.01) |
| *C07H 21/04* | (2006.01) |
| *A01H 9/00* | (2006.01) |

(52) U.S. Cl. .................... 435/232; 435/183; 435/252.3; 435/320.1; 536/23.2; 800/295

(58) Field of Classification Search ................. 435/183, 435/232, 252.3, 302.1; 536/23.2
See application file for complete search history.

(56) References Cited

U.S. PATENT DOCUMENTS

| | | | |
|---|---|---|---|
| 4,784,949 | A | 11/1988 | Gelfand et al. |
| 4,956,282 | A | 9/1990 | Goodman et al. |
| 5,011,912 | A | 4/1991 | Hopp et al. |
| 6,093,545 | A | 7/2000 | Goodearl et al. |

FOREIGN PATENT DOCUMENTS

| | | |
|---|---|---|
| WO | WO 00/18922 | 4/2000 |

OTHER PUBLICATIONS

Hansson et al. Accession AF020791. Oct. 3, 1997.*
Chica et al. Curr Opin Biotechnol. Aug. 2005; 16(4):378-84.*
Seffernick et al. J. Bacteriol. Apr. 2001; 183 (8): 2405-10.*
Witkowski et al. Biochemistry. Sep. 7, 1999; 38(36): 11643-50.*
U.S. Appl. No. 09/815,254, filed Mar. 23, 2001, Boukharov et al.
U.S. Appl. No. 10/425,114, filed Mar. 28, 2003, Liu et al.

(Continued)

*Primary Examiner*—Christian L Fronda
(74) *Attorney, Agent, or Firm*—Matthew L. Madsen; Ying-Horng Liu; Arnold & Porter LLP

(57) ABSTRACT

The present invention is in the field of plant biochemistry. More specifically the invention relates to nucleic acid sequences from plant cells, in particular, nucleic acid sequences from maize and soybean associated with the tetrapyrrole pathway. The invention encompasses nucleic acid molecules that encode proteins and fragments of proteins. In addition, the invention also encompasses proteins and fragments of proteins so encoded and antibodies capable of binding these proteins or fragments. The invention also relates to methods of using the nucleic acid molecules, proteins and fragments of proteins and antibodies, for example for genome mapping, gene identification and analysis, plant breeding, preparation of constructs for use in plant gene expression and transgenic plants.

15 Claims, No Drawings

Related U.S. Application Data

(60) provisional application No. 60/086,185, filed on May 21, 1998, provisional application No. 60/086,186, filed on May 21, 1998, provisional application No. 60/086,187, filed on May 21, 1998, provisional application No. 60/086,188, filed on May 21, 1998, provisional application No. 60/086,339, filed on May 21, 1998, provisional application No. 60/089,524, filed on Jun. 16, 1998, provisional application No. 60/089,810, filed on Jun. 18, 1998, provisional application No. 60/089,814, filed on Jun. 18, 1998, provisional application No. 60/091,247, filed on Jun. 30, 1998, provisional application No. 60/092,036, filed on Jul. 8, 1998, provisional application No. 60/099,667, filed on Sep. 9, 1998, provisional application No. 60/099,668, filed on Sep. 9, 1998, provisional application No. 60/099,670, filed on Sep. 9, 1998, provisional application No. 60/099,697, filed on Sep. 9, 1998, provisional application No. 60/100,672, filed on Sep. 16, 1998, provisional application No. 60/100,673, filed on Sep. 16, 1998, provisional application No. 60/100,674, filed on Sep. 16, 1998, provisional application No. 60/101,130, filed on Sep. 21, 1998, provisional application No. 60/101,132, filed on Sep. 21, 1998, provisional application No. 60/108,996, filed on Nov. 18, 1998, provisional application No. 60/109,018, filed on Nov. 18, 1998, provisional application No. 60/071,064, filed on Jan. 9, 1998, provisional application No. 60/090,170, filed on Jun. 22, 1998, provisional application No. 60/092,036, filed on Jul. 8, 1998, provisional application No. 60/071,479, filed on Jan. 13, 1998, provisional application No. 60/085,533, filed on May 15, 1998, provisional application No. 60/089,806, filed on Jun. 18, 1998, provisional application No. 60/089,807, filed on Jun. 18, 1998, provisional application No. 60/089,808, filed on Jun. 18, 1998, provisional application No. 60/089,811, filed on Jun. 18, 1998, provisional application No. 60/089,812, filed on Jun. 18, 1998, provisional application No. 60/089,813, filed on Jun. 18, 1998, provisional application No. 60/091,247, filed on Jun. 30, 1998, provisional application No. 60/091,405, filed on Jun. 30, 1998, provisional application No. 60/099,697, filed on Sep. 9, 1998, provisional application No. 60/100,963, filed on Sep. 17, 1998, provisional application No. 60/101,343, filed on Sep. 22, 1998, provisional application No. 60/101,344, filed on Sep. 22, 1998, provisional application No. 60/101,347, filed on Sep. 22, 1998, provisional application No. 60/101,508, filed on Sep. 22, 1998, provisional application No. 60/101,707, filed on Sep. 25, 1998, provisional application No. 60/104,124, filed on Oct. 13, 1998, provisional application No. 60/104,126, filed on Oct. 13, 1998, provisional application No. 60/104,127, filed on Oct. 13, 1998, provisional application No. 60/104,128, filed on Oct. 13, 1998, provisional application No. 60/111,981, filed on Dec. 11, 1998, provisional application No. 60/072,027, filed on Jan. 21, 1998, provisional application No. 60/072,888, filed on Jan. 27, 1998, provisional application No. 60/076,709, filed on Mar. 4, 1998, provisional application No. 60/076,912, filed on Mar. 6, 1998, provisional application No. 60/078,031, filed on Mar. 16, 1998, provisional application No. 60/083,390, filed on Apr. 29, 1998, provisional application No. 60/084,684, filed on May 8, 1998, provisional application No. 60/085,057, filed on May 8, 1998, provisional application No. 60/085,429, filed on May 8, 1998, provisional application No. 60/085,245, filed on May 13, 1998, provisional application No. 60/085,533, filed on May 15, 1998, provisional application No. 60/085,940, filed on May 19, 1998, provisional application No. 60/086,339, filed on May 21, 1998, provisional application No. 60/086,594, filed on May 22, 1998, provisional application No. 60/086,608, filed on May 22, 1998, provisional application No. 60/087,422, filed on Jun. 1, 1998, provisional application No. 60/087,631, filed on Jun. 2, 1998, provisional application No. 60/087,762, filed on Jun. 2, 1998, provisional application No. 60/087,972, filed on Jun. 4, 1998, provisional application No. 60/087,973, filed on Jun. 4, 1998, provisional application No. 60/088,441, filed on Jun. 8, 1998, provisional application No. 60/089,627, filed on Jun. 16, 1998, provisional application No. 60/089,789, filed on Jun. 18, 1998, provisional application No. 60/090,170, filed on Jun. 22, 1998, provisional application No. 60/090,856, filed on Jun. 26, 1998, provisional application No. 60/090,928, filed on Jun. 26, 1998, provisional application No. 60/091,035, filed on Jun. 29, 1998, provisional application No. 60/091,247, filed on Jun. 30, 1998, provisional application No. 60/091,405, filed on Jun. 30, 1998, provisional application No. 60/092,036, filed on Jul. 8, 1998, provisional application No. 60/100,963, filed on Sep. 17, 1998, provisional application No. 60/110,108, filed on Nov. 25, 1998, provisional application No. 60/110,109, filed on Nov. 25, 1998, provisional application No. 60/111,033, filed on Dec. 4, 1998, provisional application No. 60/111,742, filed on Dec. 10, 1998.

OTHER PUBLICATIONS

U.S. Appl. No. 11/329,160, filed Jan. 11, 2006, Bhat et al.
U.S. Appl. No. 11/329,388, filed Jan. 11, 2006, Andersen et al.
U.S. Appl. No. 11/330,082, filed Jan. 12, 2006, Buehler et al.
U.S. Appl. No. 11/330,083, filed Jan. 12, 2006, Byrum et al.
U.S. Appl. No. 11/330,364, filed Jan. 12, 2006, Abad et al.
U.S. Appl. No. 11/331,019, filed Jan. 13, 2006, Fincher et al.
U.S. Appl. No. 11/331,032, filed Jan. 13, 2006, Fincher et al.
U.S. Appl. No. 11/352,295, filed Feb. 13, 2006, Andersen et al.
U.S. Appl. No. 11/353,150, filed Feb. 14, 2006, Andersen et al.
U.S. Appl. No. 11/486,299, filed Jul. 14, 2006, Byrum.
U.S. Appl. No. 11/490,207, filed Jul. 21, 2006, Brown et al.
U.S. Appl. No. 11/491,125, filed Jul. 24, 2006, Boukharov et al.
U.S. Appl. No. 11/491,178, filed Jul. 24, 2006, Hinkle et al.
U.S. Appl. No. 11/491,371, filed Jul. 24, 2006, Byrum.
U.S. Appl. No. 11/497,489, filed Aug. 2, 2006, Byrum et al.
U.S. Appl. No. 11/503,243, filed Aug. 14, 2006, Kovalic et al.
U.S. Appl. No. 11/520,715, filed Sep. 14, 2006, Liu et al.
U.S. Appl. No. 11/521,349, filed Sep. 15, 2006, Byrum et al.
U.S. Appl. No. 11/595,983, filed Nov. 13, 2006, Boukharov et al.
AA501409, EST Database (Aug. 19, 1997).
Aach et al., "*ent*-Kaurene Biosynthesis in a Cell-Free System From Wheat (*Triticum aestivum* L.) Seedlings and the Localisation of *ent*-Kaurene Synthetase in Plastids of Three Species", *Planta* 197(2), 333-342 (1995).
Adams et al., "Complementary DNA Sequencing: Expressed Sequence Tags and Human Genome Project", *Science* 252(5013), 1651-1656 (1991).
Ait-Ali et al., "The *LS* Locus of Pea Encodes the Gibberellin Biosynthesis Enzyme *ent*-Kaurene Synthase A", *Plant J.* 11(3), 443-454 (1997).

Anaviev et al., "Oat-Maize Chromosome Addition Lines: A New System for Mapping the Maize Genome", *Proc. Natl. Acad. Sci. USA* 94, 3524-3529 (1997).

Anton et al., "Sequencing and Overexpression of the *Escherichia coli aroE* Gene Encoding Shikimate Dehydrogenase", *Biochem. J.* 249, 319-326 (1988).

Attwood, "The Babel of Bioinoformatics", *Science* 290(5491), 471-473 (2000).

Bensen et al., "Cloning and Characterization of the Maize An1 Gene", *Plant Cell* 7, 75-84.

Bentley, "The Shikimate Pathway—A Metabolic Tree with Many Branches," *Critical Rev. Biochem. Mol. Biol.* 25(5), 307-384 (1990).

Birkenbihl et al., "Cosmid-Derived Map of *E.coli* Strain BHE2600 in Comparison to the Map of Strain W3110", *Nucleic Acids Res.* 17(13), 5057-5069 (1989).

Bishop et al., "The Tomato *Dwarf* Gene Isolated by Heterologous Transposon Tagging Encodes the First Member of a New Cytochrome P450 Family", *Plant Cell* 8, 959-969 (1996).

Bonner et al., "Cloning of cDNA Encoding the Bifunctional Dehydroquinase-Shikimate Dehydrogenease of Aromatic-Amino-Acid Biosynthesis in *Nicotiana tabacum*", *Biochem J.* 362, 11-14 (1994).

Bork, "Powers and Pitfalls in Sequence Analysis: The 70% Hurdle", *Genome Res.*, 10, 398-400 (2000).

Bougri et al., "Members of a Low-Copy No. Gene Family Encoding Glutamyl-tRNA Reductase are Differentially Expressed in Barley," *Plant J.* 9(6), 867-878 (1996).

Broun et al., "Catalytic Plasticity of Fatty Acid Modification Enzymes Underlying Chemical Diversity of Plant Lipids", *Science* 282, 1315-1317 (1998).

Bukanov et al., "Ordered Cosmid Library and High-Resolution Physical-Genetic Aap of *Helicobacter pylori* Strain NCTC11638", *Mol. Microbiol.* 11(3), 509-523 (1994).

Charles et al., "Isolation, Characterization and Nucleotide Sequences of the *aroC* Genes encoding Chorismate Synthase from *Salmonella typhi* and *Escherichia coli*", *J. Gen. Microbiol.* 136, 353-358 (1990).

Chen et al., "Microcolinearity in *sh2*-Homologous Regions of the Maize, Rice, and Sorghum Genomes", *Proc. Natl. Acad. Sci. USA* 94, 3431-3435 (1997).

Coulson et al., "Toward a Physical Map of the Genome of the Nematode *Caenorhabditis elegans*", *Proc. Natl. Acad. Sci. USA* 83, 7821-7825 (1986).

Day et al., "Cloning of the cDNA for Glutamyl-tRNA Synthetase from *Arabidopsis thaliana*", *Biochim. Biophys. Acta* 1399(2-3):219-224 (1998).

Duncan et al., "The Overexpression and Complete Amino Acid Sequence of *Escherichia coli* 3-Dehydroquinase", *Biochem. J.* 238, 475-483 (1986).

Eberhard et al., "Cloning and Expression in Yeast of a Higher Plant Chorismate Mutase", *FEBS Lett.* 334(2), 233-236 (1993).

Ebert et al., "Identification of an Essential Upstream Element in the Nopaline Synthase Promoter by Stable and Transient Assays", *Proc. Natl. Acad. Sci. USA* 84(16), 5745-5749 (1987).

Efstratiadis et al., "Enzymatic in vitro Synthesis of Globin Genes", *Cell* 7, 279-288 (1976).

Eiglmeier et al., "Use of an Ordered Cosmid Library to Deduce the Genomic Organization of *Mycobacterium leprae*", *Mol. Microbio.* 7(2), 197-206 (1993).

Evans et al., "Immunodetection of Recombinant Proteins Based on Antibodies Directed Against a Metal Binding Peptide Engineered for Purification by Immobilized Metal Affinity Chromatography," *J. Immunol. Meth.*156(2), 231-238 (1992) (Abstract Only).

Entrez Accession No. M21071 J03227 (Sep. 15, 1989).
Entrez Accession No. 170374 (Sep. 15, 1989).
Entrez Accession No. M27715 (Jun. 15, 1990).
Entrez Accession No. 153878 (Jun. 15, 1990).
Entrez Accession No. X59509 S55160 (Jun. 30, 1993).
Entrez Accession No. 48906 (Jun. 30, 1993).
Entrez Accession No. Y00710 (Sep. 12, 1993).
Entrez Accession No. 40978 (Sep. 12, 1993).
Entrez Accession No. Z26519 (Dec. 2, 1993).
Entrez Accession No. 429153 (Dec. 2, 1993).
Entrez Accession No. 551666 (Jan. 25, 1995).
Entrez Accession No. X81413 (Jan. 25, 1995).
Entrez Accession No. M87280 M99707 (Apr. 12, 1995).
Entrez Accession No. 551855 (Apr. 12, 1995).
Entrez Accession No. 313150 (Jun. 13, 1995).
Entrez Accession No. X73535 (Jun. 13, 1995).
Entrez Accession No. X04306 (Jul. 12, 1995).
Entrez Accession No. 40973 (Jul. 12, 1995).
Entrez Accession No. D63474 D16312 (Jul. 27, 1995).
Entrez Accession No. 474964 (Jul. 27, 1995).
Entrez Accession No. 987267 (Jul. 31, 1995).
Entrez Accession No. U32579 (Sep. 16, 1995).
Entrez Accession No. X82831 (Mar. 1, 1996).
Entrez Accession No. 1213067 (Mar. 1, 1996).
Entrez Accession No. 1220402 (Mar. 5, 1996).
Entrez Accession No. M63245 (Mar. 11, 1996).
Entrez Accession No. W49458 (May 28, 1996).
Entrez Accession No. 1421741 (Oct. 17, 1996).
Entrez Accession No. U54770 (Oct. 18, 1996).
Entrez Accession No. X86101 (Nov. 8, 1996).
Entrez Accession No. 520943 (Feb. 26, 1997).
Entrez Accession No. 2160544 (Jun. 5, 1997).
Entrez Accession No. U63652 (Jun. 6, 1997).
Entrez Accession No. 2257714 (Jul. 15, 1997).
Entrez Accession No. U93215 (Jul. 15, 1997).
Entrez Accession No. 2224890 (Jul. 31, 1997).
Entrez Accession No. 2224892 (Jul. 31, 1997).
Entrez Accession No. U61385 (Aug. 1, 1997).
Entrez Accession No. U61386 (Aug. 1, 1997).
Entrez Accession No. 2316104 (Aug. 8, 1997).
Entrez Accession No. AF010169 (Aug. 9, 1997).
Entrez Accession No. 1524045 (Aug. 20, 1997).
Entrez Accession No. X96943 (Aug. 20, 1997).
Entrez Accession No. Y12809 (Dec. 2, 1997).
Entrez Accession No. D88382 (Mar. 17, 1998).
Entrez Accession No. 3068709 (Apr. 2, 1998).
Entrez Accession No. AF058763 (Aug. 16, 1998).
Entrez Accession No. 3420233 (Apr. 20, 1998).
Entrez Accession No. AF049236 (Apr. 22, 1998).
Entrez Accession No. AF038152 (May 7, 1998).
Entrez Accession No. 2708690 (May 7, 1998).
Entrez Accession No. AC003058 (May 16, 1998).
Entrez Accession No. 3135277 (May 16, 1998).
Entrez Accession No. 3288821 (Jul. 20, 1998).
Entrez Accession No. AF063901 (Jul. 21, 1998).
Entrez Accession No. 3435196 (Sep. 21, 1998).
Entrez Accession No. AF067773 (Sep. 22, 1998).
Entrez Accession No. 3694811 (Sep. 24, 1998).
Entrez Accession No. AJ225107 (Oct. 1, 1998).
Entrez Accession No. 3093410 (Oct. 1, 1998).
Entrez Accession No. AF060481 (Oct. 4, 1998).
Entrez Accession No. 3925407 (Nov. 24, 1998).
Entrez Accession No. AF083948 (Nov. 25, 1998).
Entrez Accession No. AB015492 (Dec. 11, 1998).
Entrez Accession No. 4001680 (Dec. 11, 1998).
Entrez Accession No. AF017431 (Jan. 2, 1999).
Entrez Accession No. 3080490 (Jan. 12, 1999).
Entrez Accession No. AL022602 (Jan. 12, 1999).
Entrez Accession No. AB011416 (Feb. 5, 1999).
Entrez Accession No. AAC17095 GI:315616 (Apr. 5, 1999).
Entrez Accession No. AP000836; GI:6539551 (Aug. 12, 2000).
Entrez Accession No. AY013245 (May 7, 2002).

Fiedler et al., "The Formation of Homogentisate in the Biosynthesis of Tocopherol and Plastoquinone in Spinach Chloroplasts", *Planta* 155, 511-515 (1982).

Garbe et al., "The *Mycobacterium tuberculosis* Shikimate Pathway Genes: Evolutionary Relationship Between Biosynthetic and Catabolic 3-Dehydroquinases", *Mol. Gen. Genet.* 228, 385-392 (1991).

Gasser et al., "Structure, Expression, and Evolution of the 5-Enolpyruvylshikimate-3-Phosphate Synthase Genes of Petunia and Tomato", *J. Biol. Chem.* 263,4280-4289 (1988).

Gaubier et al., "A Chlorophyll Synthetase Gene from *Arabidopsis thaliana*", *Mol. Gen. Genet.* 249, 58-64 (1995).

GenBank Accession No. U03774 (Jun. 22, 1994).

GenBank Accession No. L37750 (Aug. 3, 1995).
GenBank Accession No. H30177 (Aug. 16, 1995).
GenBank Accession No. W21756 (May 6, 1996).
GenBank Accession No. X80265 (Feb. 26, 1997).
GenBank Accession No. E03435 (Sep. 29, 1997).
GenBank Accession No. AF015462 (Jul. 16, 1998).
Genbank Accession No. AC005922 (Nov. 14, 1998).
GenBank Accession No. X74737 (Jan. 21, 1999).
GenBank Accession No. AU033328 (Apr. 28, 1999).
GenBank Accession No. AQ402486 (Mar. 13, 1999).
GenBank Accession No. AI861202 (Jul. 19, 1999).
GenBank Accession No. AC018632 (Dec. 15, 1999).
GenBank Accession No. AI834598 (Feb. 2, 2000).
GenBank Accession No. AZ134591 (Jun. 2, 2000).
GenBank Accession No. BE428765 (Jul. 26, 2000).
GenBank Accession No. BF542512 (Dec. 11, 2000).
GenBank Accession No. AW871780 (Dec. 11, 2001).
GenBank Accession No. BQ603510 (Jun. 24, 2002).
GenBank Accession No. DR37H4T (Nov. 22, 2002).
GenBank Accession No. BX513761 (May 27, 2003).
GenEMBL Accession No. AF096555 (Jul. 22, 1999).
GenEMBL Accession No. AL096768 (Dec. 12, 1999).
GenSeq Accession No. AAZ35275 (Mar. 27, 2000).
Gerhold et al., "It's the genes! EST access to human genome content", *BioEssays* 18(2), 973-981 (1996).
Gibson et al., "The Bacteriochlorophyll Biosynthesis Gene, *bchM*, of *Rhodobacter sphaeroides* Encodes S-Adenosyl-l-Methionine: Mg Protoporphyrin IX Methyltransferase", *FEBS Lett.* 352, 127-130 (1994).
Goers et al., "The Differential Allosteric Regulation of Two Chorismate-Mutase Isoenzymes of *Nicotiana silvestris*", *Planta* 162, 117-124 (1984).
Goff, "Rice as a Model for Cereal Genomics", *Curr. Opin. Plant Biol.* 2, 86-89 (1999).
Hedden et al., "Gibberellin Biosynthesis: Enzymes, Genes and Their Regulation", *Annu. Rev. Plant Physiol. Plant Mol. Biol.* 48,431-460 (1997).
Herrmann, "The Shikimate Pathway as an Entry to Aromatic Secondary Metabolism," *Plant Physiol.* 107, 7-12 (1995).
Hong, "A Rapid and Accurate Strategy for Rice Contig Map Construction by Combination of Fingerprinting and Hybridization", *Plant Mol. Biol.* 35,129-133 (1997).
Hundle et al., "Functional Assignment of *Erwinia herbicola* Eho10 Carotenoid Genes Expressed in*Escherichia coli*", *Mol. Gen. Genet.* 245, 406-416 (1994).
Ibba, "Biochemistry and Bioinformatics: When Worlds Collide," *Trends in Biochem. Sci.* 27(2), 64 (2000).
Iyer et al.,"Quod erat demonstrandum? The Mystery of Experimental Validation of Apparently Erroneous Computational Analysis of Protein Aequences", *Genome Biol.* 2(12), 1-11 (2001).
Johnston et al., "Cloning and Characterization of Potato cDNAs Involved in Tetrapyrrole Biosynthesis: Ferrochelatase (Accession No. AJ005802), Chloroplatic Protoporphyrinogen IX Oxidase (Accession No. AJ225107), and Mitochondrial Protoporphyrinogen IX Oxidase (Accession No. AJ225108)", *Plant Physiol.* 118, 329-331 (1998).
Keon et al., "Isolation and Heterologous Expression of a Gene Encoding 4-Hydroxyphenylpyruvate Dioxygenase from the Wheat Leaf-Spot Pathogen, *Mycosphaerella graminicola*", *FEMS Microbiol. Lett.* 161, 337-343 (1998).
Kidwell et al., "Transposable Elements as Sources of Variation in Animals and Plants", *Proc. Natl. Acad. Sci. USA* 94, 7704-7711 (1997).
Kim et al., "Construction and Characterization of a Human Bacterial Artificial Chromosome Library", *Genomics* 34, 213-218 (1996).
Knott et al., "Randomly Picked Cosmid Clones Overlap the *pyr*B and *ori*C gap in the Physical Map of the *E.coli* Chromosome", *Nucleic Acids Res.* 16, 2601-2612 (1988).
Ko et al, "An 'Equalized cDNAs' Library by the Reassociation of Short Double-Stranded cDNAs", *Nucleic Acids Res.* 18(19), 5705-5711 (1990).
Kyrpides et al., "Whole-Genome Sequence Annotation: 'Going Wrong With Confidence'", *Mol. Microbiol.* 32, 886-887 (1999).

Kurata et al., "A 300 Kilobase Interval Genetic Map of Rice Including 883 Expressed Sequences," *Nature Gen.* 8(4), 362-372 (1994).
Lange et al., "Cloning and Expression of a Gibberellin 2β,3β-Hydroxylase cDNA from Pumpkin Endosperm," *Plant Cell* 9(8), 1459-1467 (1997).
Lange "Cloning Gibberellin Dioxygenase Genes from Pumpkin Endosperm by Heterologous Expression of Enzyme Activities in *Escherichia coli*", *Proc. Natl. Acad. Sci. USA* 94(12), 6553-6558 (1997).
Lange et al., "Expression Cloning of a Gibberellin 20-Oxidase, a Multifunctional Enzyme Involved in Gibberellin Biosynthesis", *Proc. Natl. Acad. Sci. USA* 91(18), 8552-8556 (1994).
Liepman et al., "Sequence Analysis of a cDNA Encoding Alanine:Glyoxylate Amino Transferase from *Arabidopsis*(Accession No. AF063901)", *Plant Physiol*.117, 1125-1127 (1998).
Lim et al., "Porphobilinogen Deaminase is Encoded by a Single Gene in *Arabidopsis thaliana* and Is Targeted to the Chloroplasts," *Plant Mol. Biol.* 26, 863-872 (1994).
Mahairas et al., "Sequence-Tagged Connectors: A Sequence Approach to Mapping and Scanning the Human Genome", *Proc. Natl. Acad. Sci. USA* 96, 9739-9744 (1999).
Martin et al., "MYB Transcription Factors in Plants", *Trends Genet.* 13(2), 67-73 (1997).
Martin et al., "Mendel's Dwarfing Gene: cDNAs from the *Le* Alleles and Function of the Expressed Proteins", *Proc. Natl. Acad. Sci. USA*, 94(16):8907-8911 (1997).
McCombie et al.,"*Caenorhabditis elegans* Expressed Sequence Tags Identify Gene Families and Disease Gene Homologues," *Nature Gen.* 1, 124-131(1992).
Meinkoth et al., "Hybridization of Nucleic Acids Immobilized on Solid Supports", *Anal. Biochem.* 138, 267-284 (1984).
Mende et al., "The Geranylgeranyl Diphosphate Synthase Gene of *Gibberella fujikuroi*: Isolation and Expression", *Mol. Gen. Genet.* 255(1), 96-105 (1997).
Mohan et al., "Genome Mapping, Molecular Markers and Marker-Assisted Selection Crop Plants", *Mol. Breed.* 3, 87-103 (1997).
Nakane et al., "Nucleotide Sequence of the Shikimate Kinase Gene (*arol*) of *Bacillus subtilis*", *J. Ferment. Bioeng.* 77, 312-314 (1994).
Nakayashiki et al., "Nucleotide Sequence of a cDNA Clone Encoding Glutamyl-tRNA Reductase from Rice (Accession No. AB011416)", *Plant Physiol.* 117, 332 (1998).
NCBI Accession No. S42508 (May 8, 1993).
NCBI Accession No. D23883 (Nov. 29, 1993).
NCBI Accession No. AAA34069, corresponding to gi:535771 (Sep. 11, 1994).
Norris et al., "Complementation of the *Arabidopsis pds 1* Mutation with the Gene Encoding *p*-Hydroxyphenylpuruvate Dioxygenase", *Plant Physiol.* 117, 1317-1323 (1998).
Oka et al., "Replication Origin of the *Escherichia coli* K-12 Chromosome: The Size and Structure of the Minimum DNA Segment Carrying the Information for Autonomous Replication", *Mol. Gen. Genet*.178(1), 9-20 (1980).
Okubo et al., "Large Scale cDNA Sequencing for Analysis of Quantitative and Qualitative Aspects of Gene Expression", *Nature Gen.* 2, 173-179 (1992).
Phillips et al., "Isolation and Expression of Three Gibberellin 20-Oxidase cDNA Clones from *Arabidopsis*", *Plant Physiol.* 108(3), 1049-1057 (1995).
Porra, "Recent Progress in Porphyrin and Chlorophyll Biosynthesis", *Photochem. Photobiol.* 65(3), 492-516 (1997).
Russell et al., "Structural Features can be Unconserved in Proteins with Similar Folds. An Analysis of Side-Chain to Side-Chain Contacts Secondary Structure and Accessibility", *J. Mol. Biol.* 244, 332-350 (1994).
Sakamoto et al., "An Overview of Gibberellin Metabolism Enzyme Genes and Their Related Mutants in Rice", *Plant Physiol.* 134, 1642-1653 (2004).
Schmitz et al., "The Tomato Blind Gene Encodes a MYB Transcription Factor that Controls the Formation of Lateral Meristems", *Proc. Nat. Acad. Sci.* 99(2), 1064-1069 (2002).
Schünmann et al., "Identification of Three cDNA Clones Expressed in the Leaf Extension Zone and with Altered Patterns of Expression in the *Slender* Mutant of Barley: A Tonoplast Intrinsic Protein, a Putative Structural Protein and Protochlorophylide Oxidoreductase," *Plant Mol. Biol.* 31, 529-537 (1996).

Seffernick et al., "Melamine Deaminase and Atrazine Chlorohydrolase: 98 Percent Identical but Functionally Different", *J. Bacteriol.* 183(8), 2405-2410 (2001).

Sigma Chemical Catalogue (Sigma Chemical Co.; P.O. Box 14508, St. Louis MO 63178) 1993, product Nos. 01256, 03628, 04375, pp. 736-737.

Smith et al., "Partial Purification and Characterization of the Gibberellin $A_{20}3\beta$-Hydroxylase from Seeds of *Phaseolus vulgaris*", *Plant Physiol.* 94:1390-1401 (1990).

Smith et al., "The First Step of Gibberellin Biosynthesis in Pumpkin is Catalyzed by at Least Two Copalyl Diphosphate Synthases Encoded by Differentially Regulated Genes", *Plant Physiol.* 118, 1411-1419 (1998).

Stammers et al., "Rapid Purification and Characterization of HIV-1 Reverse Transcriptase and RNaseH Engineered to Incorporate a C-terminal Tripeptide α-Tubulin Epitope", *FEBS Lett.* 283(2), 298-302 (1991).

Tanaka et al., "The Third Member of the *hemA* gene Family Encoding Glutamyl-tRNA Reductase is Primarily Expressed in *Roots in Hordeum vulgare*", *Photosynthesis Res.* 53, 161-171 (1997).

Tanksley et al., "Chromosome landing: a paradigm for map-based gene cloning in plants with large genomes", *Trends in Genet.* 11(2), 63-68 (1995).

Tikhonov et al., "Colinearity and its Exceptions in Orthologous *adh* Regions of Maize and Sorghum", *Proc. Natl. Acad. Sci. USA* 96, 7409-7414 (1999).

van de Loo et al., "An Oleate 12-Hydroxylase from *Ricirus communis* L. is a Fatty Acyl Desaturase Homolog", *Proc. Nat. Acad. Sci*. 92, 6743-6747 (1995).

Venter et al., "A New Strategy for Genome Sequencing", *Nature* 381, 364-366 (1996).

Venter et al., "The Sequence of the Human Genome" *Science* 291, 1304-1351 (2001).

Wang et al., "Construction of a Rice Bacterial Artificial Chromosome Library and Identification of Clones Linked to the Xa-21 Disease Resistance Locus", *Plant J.* 7(3), 525-533 (1995).

Wells et al., "The Chemokine Information Source: Identification and Characterization of Novel Chemokines Using the WorldWideWeb and Expressed Sequence Tag Databases", *J. Leukocyte Biol.* 61(5), 545-550 (1997).

Wendel et al., "New Isozyme Systems for Maize (*Zea mays* L.): Aconitate Hydratase, Adenylate Kinase, NADH Dehydrogenase, and Shikimate Dehydrogenase", *Biochem. Genet.* 26(5-6), 421-446 (1988) (Abstract Only).

Wenzel et al., "Physical mapping of the *Mycoplasma pneumoniae* genome", *Nucleic Acids Res.* 16(17), 8323-8336 (1988).

Winkler et al., "The Maize *Dwarf3* Gene Encodes a Cytochrome P450-Mediated Early Step in Gibberellin Biosynthesis", *Plant Cell* 7(8), 1307-1317 (1995).

Woese et al., "Conservation of Primary Structure in 16S Ribosomal RNA", *Nature* 254, 83-85 (1975).

Written Description Training Material, Example 7, pp. 30-32.

Yomo et al., "Histochemical Studies on Protease Formation in the Cotyledons of Germinating Bean Seeds," *Planta* 112(1), 35-43 (1973).

Zhang et al., "Physical Mapping of the Rice Genome with BACs", *Plant Mol. Biol.* 35, 115-127 (1997).

Zhang et al., "Construction and Characterization of Two Rice Bacterial Artificial Chromosome Libraries from the Parents of a Permanent Recombinant Inbred Mapping Population", *Mol. Breeding 2*, 11-24 (1996).

Zwick et al., "Physical Mapping of the *liguleless* Linkage Group in *Sorghum bicolor* Using Rice RFLP-Selected Sorghum BACs", *Genetics* 248, 1983-1992 (1998).

\* cited by examiner

```
                          SEQUENCE LISTING

<160> NUMBER OF SEQ ID NOS: 677

<210> SEQ ID NO 1
<211> LENGTH: 257
<212> TYPE: DNA
<213> ORGANISM: Glycine max

<400> SEQUENCE: 1
tgctgcttct ggaaattttc attggaattt tgaagatgtt gctaaatcaa ttgtgtgcat      60
gatgatgtct ggcccattct tgacaggata tacccagact atgaatgatt ggtacgaccg     120
agaaattgat gcaataaatg aaccttatag accaattcct tctggggcaa tatctgagaa     180
tgaggtaatc actcaaatat gggtgttgct gcttggtggt ctttctctgg ctggtatatt     240
ggacatatgg gcagggc                                                    257

<210> SEQ ID NO 2
<211> LENGTH: 272
<212> TYPE: DNA
<213> ORGANISM: Glycine max
<220> FEATURE:
<223> OTHER INFORMATION: unsure at all n locations

<400> SEQUENCE: 2
cacatgtaag catctcaagc tctgctgaat cttcaatggc ttctctactc aacatggttt      60
ctgttccatc aagaatatca ccaagctcac acacgagaac cacttcaang caatctcgaa     120
ctgttttgcc accatttct gtctcatttt ccaggaggag attatcaatt agagcaacag     180
aaactgatac taatgaagtt caatctcagg cgccgggtac agcaccatca aaagatggtt     240
caagcttcaa ccagctcctt ggtattaaag ga                                  272
```

<210> SEQ ID NO 3
<211> LENGTH: 156
<212> TYPE: DNA
<213> ORGANISM: Glycine max

<400> SEQUENCE: 3

```
aagaaacaaa taagtggaag attcgtcttc aacttacaaa gccagtcact tggcctccat      60
taatttgggg tgtagtttgt ggagctgctg cttctggaaa ttttcattgg aattttgaga     120
tgttgctaaa tcaattgtgt gcatgatgat gtctgg                                156
```

<210> SEQ ID NO 4
<211> LENGTH: 348
<212> TYPE: DNA
<213> ORGANISM: Glycine max

<400> SEQUENCE: 4

```
agtacggctg cgagaagacg acagaagggg aaggcatctt caagctctga atctgcaatg      60
gcttctctac tcaacatggt ttcggttcca ccaagaatat caccaacctc acacaccaga     120
atcgcttcgc ttcaagctcg acccgttttg ccaccctttt ctgtctcatt ttccaggagg     180
agactatcaa ttagagcaac agaaactgat accaatgaag ttcaatctca ggcaccgggt     240
gcagcgccat ctaaagatgg ttcaagcttc aatcagcttc tggtatcaa aggagctgcc     300
caagaaacaa ataaatggaa aattcgtctt caactcacaa agcctgtc                  348
```

<210> SEQ ID NO 5
<211> LENGTH: 245
<212> TYPE: DNA
<213> ORGANISM: Glycine max
<220> FEATURE:
<223> OTHER INFORMATION: unsure at all n locations

<400> SEQUENCE: 5

```
ctctgaatct gcaatggctt ctctactcaa catggtttcg gttncaccaa gactatcact      60
cnnctcacac accagaatcg cttcgcttca agctcgaccc gtttgccacc cttttctgtc     120
tcattttcca ggaggagact atcaattaga gcaacagaaa ctgataccaa tgaagttcaa     180
tctcaggcac cgggtgcagc gccatctaaa gatggttcaa gcttcaatca gcttcttggt     240
atcaa                                                                   245
```

<210> SEQ ID NO 6
<211> LENGTH: 268
<212> TYPE: DNA
<213> ORGANISM: Glycine max

<400> SEQUENCE: 6

```
tggcatcttc aagctctgaa tctgcaatgg cttctctact caacatggtt tcggttccac      60
caagaatatc accaacctca cacaccagaa tcgcttcgct tcaagctcga cccgttttgc     120
caccctttc tgtctcattt tccaggagga gactatcaat tagagcaaca gaaactgata     180
ccaatgaagt tcaatctcag gcaccgggtg cagcgccatc taaagatggt tcaagcttca     240
atcagcttct tggtatcaaa ggagctgc                                         268
```

<210> SEQ ID NO 7
<211> LENGTH: 278
<212> TYPE: DNA
<213> ORGANISM: Glycine max

```
<400> SEQUENCE: 7
cggctgcgag aagacgacag aagggctcag agtactgtta ttgaaaggca aaggacaata      60
gagtatacct gaagccctag agccctatcc ccttcaacac ttttgaagtc attgacaata     120
gcaattccca actgcaatgt gatttaacaa caacattaat aaccattttt atttgacata     180
ttatcatatt catatccaac aaaatgtcat gaagaatata ttacatactc cagctatgct     240
gtataggagt gtgagaacaa ttatatctgg tgtaagag                             278

<210> SEQ ID NO 8
<211> LENGTH: 248
<212> TYPE: DNA
<213> ORGANISM: Glycine max

<400> SEQUENCE: 8
cggctgcgag aagacgacag aagggctcag agtactgtta ttgaaaggca aaggacaata      60
gagtatacct gaagccctag agccctatcc ccttcaacac ttttgaagtc attgacaata     120
gcaattccca actgcaatgt gatttaacaa caacattaat aaccattttt atttgacata     180
ttatcatatt catatccaac aaaatgtcat gaagaatata ttacatactc cagctatgct     240
gtatagga                                                              248

<210> SEQ ID NO 9
<211> LENGTH: 258
<212> TYPE: DNA
<213> ORGANISM: Glycine max
<220> FEATURE:
<223> OTHER INFORMATION: unsure at all n locations

<400> SEQUENCE: 9
gncanctgct anggancccta cntncactgg cngagggctt tgaacttagc ctnnnggaca      60
aatcatctng ggcatttcct cctctcgcgc cngttgctng aggacttgga naaatncgag     120
tacccttcaa aggcttgatn atcgtaggnt cacacgacag ggnacacaaa cacattggct     180
ggtaatgtac ctcccaaggc gaaccttggn ggacttgagg ggacttcagg gtggtttgaa     240
tgggctaaag agctcagc                                                   258

<210> SEQ ID NO 10
<211> LENGTH: 270
<212> TYPE: DNA
<213> ORGANISM: Glycine max

<400> SEQUENCE: 10
gtcaatttgt tgataacttt aggcaatcag gccggccact ggatgtgctt gtttgcaatg      60
ctgcggttta cttgccaact gccagggaac ctacatatac tgctgatggc tttgaactca     120
gtgttggaac caaccatctc gggcatttcc tcctttcgcg ccttttgctt gacgacttga     180
acaaatctga ctacccttcg aagcggttga tcatgtaggc tcaatcacag gaaacaccaa     240
cacattggct ggaatgtgcc acccaggcta                                      270

<210> SEQ ID NO 11
<211> LENGTH: 258
<212> TYPE: DNA
<213> ORGANISM: Glycine max
<220> FEATURE:
<223> OTHER INFORMATION: unsure at all n locations

<400> SEQUENCE: 11
caggaaacac caacacattg gctggaaatg tgccacccaa ggctaacctt ggtgacatga      60
```

```
gggggactagc tggaggcttg aatgggctaa acacttcagc catgatagat ggaggatcct      120
ttgacggcgc taaggcatac aaggacagca aagtctgcaa catgcttaca atgccagaat      180
tccaacagga ggtcccngtt ganaccnngg natnacatnt gcncccntan cccngggttn      240
ttcncccaaa ngggnttt                                                    258

<210> SEQ ID NO 12
<211> LENGTH: 270
<212> TYPE: DNA
<213> ORGANISM: Glycine max

<400> SEQUENCE: 12
gacggcgcta aggcatacaa ggacagcaaa gtctgcaaca tgcttacaat gcaagaattc       60
cacagaagat accatgatga aactgggatc acatttgctt ccctttaccc aggttgcatc      120
gccacaacag gcttgttcag agagcacatt cccttgttca gacttctctt ccctccattc      180
caaaagtaca taaccaaggg ctttgtctca gaagatgaat caggaaagag acttgcacag      240
gttgtgagtg atccaagcct aacaaaatca                                       270

<210> SEQ ID NO 13
<211> LENGTH: 262
<212> TYPE: DNA
<213> ORGANISM: Glycine max

<400> SEQUENCE: 13
caggctgctt ctttcccat tgctaaagag ggaaagtctg gtgtttctct caggtacacc        60
acaatgttcg gtgtttcatt gtcggatact ctcaaatctg acgctcagct tttcctcatt      120
gacatgcaaa gaaacaccaa caccttggct ggacatgtgc cacccaaggc taaccttggt      180
gacttgaggg gactagctgg aggcttgaat gggctaaaca cttcagccat gatagatgga      240
ggatcctttg atggcaccaa gg                                               262

<210> SEQ ID NO 14
<211> LENGTH: 279
<212> TYPE: DNA
<213> ORGANISM: Glycine max
<220> FEATURE:
<223> OTHER INFORMATION: unsure at all n locations

<400> SEQUENCE: 14
ccatttgctt ccctttaccc cggttgcatt gccacaacag gcctgttcag agagcacatt       60
cccttgttca naactctgtt ccctccattc cagaagtaca taaccaaagg ctatgtctca      120
gaagatgaag caggaaagag acttgctcag gttgtaagtg atccaagcct aacaaaatct      180
ggtgtttact ggagctggaa caaagcatca gcttcgtttg aaaaccagtt gtctcaggag      240
gccagtgata cagagaaggc tcgtaagatc tgggagnta                             279

<210> SEQ ID NO 15
<211> LENGTH: 346
<212> TYPE: DNA
<213> ORGANISM: Glycine max

<400> SEQUENCE: 15
aaacaaagga cccagtttta cattttttt tgttcctgag ttccaatggc tcttcaggct        60
gcttccttgg tttctgcttc tttttctatt gctaaagagg gaaagtctgg tgtatctctc      120
agggacacca caatgtttgg tgtttcattg tcggatactc tcaaatctga cttcagctct      180
```

| | |
|---|---|
| ccctcatcga cttgcaaaag ggaattccaa caaaaatttg gccctttgag ggttcagtca | 240 |
| gtggcaacaa caactccagg agtcaccaag gcttcaccag aaggcaagaa aactttgagg | 300 |
| aaaggcagtg ttattatcac tggggcttcc tctggattag gctggc | 346 |

<210> SEQ ID NO 16
<211> LENGTH: 256
<212> TYPE: DNA
<213> ORGANISM: Glycine max

<400> SEQUENCE: 16

| | |
|---|---|
| ctaaaacaaa ggacccagtt ttacattttt ttcctgagtt ccaatggctc ttcaggctgc | 60 |
| ttccttggtt tctgcttctt tttctattgc taaagaggga aagtctggtg tatctctcag | 120 |
| ggacaccaca atgtttggtg tttcattgtc ggatactctc aaatctgact tcagctctcc | 180 |
| ctcatcgact tgcaaaaggg aattccaaca aaaatttggc cctttgaggg ttcagtcagt | 240 |
| ggcaacaaca actcca | 256 |

<210> SEQ ID NO 17
<211> LENGTH: 269
<212> TYPE: DNA
<213> ORGANISM: Glycine max

<400> SEQUENCE: 17

| | |
|---|---|
| cagttttaca tttttttttg ttcctgagtt ccaatggctc ttcaggctgc ttccttggtt | 60 |
| tctgcttctt tttctattgc taaagaggga aagtctggtg tatctctcag ggacaccaca | 120 |
| atgtttggtg tttcattgtc ggatactctc aaatctgact tcagctctcc ctcatcgact | 180 |
| tgcaaaaggg aattccaaca aaaatttggc cctttgaggg ttcagtcagt ggcaacaaca | 240 |
| actccaggag tcaccaaggc ttcaccaga | 269 |

<210> SEQ ID NO 18
<211> LENGTH: 358
<212> TYPE: DNA
<213> ORGANISM: Glycine max
<220> FEATURE:
<223> OTHER INFORMATION: unsure at all n locations

<400> SEQUENCE: 18

| | |
|---|---|
| gaaacattct aaaacaaagg acccagtttt acattttttnt ttgttcctga gttccaatgg | 60 |
| ctcttcaggc tgcttccttg gtttctgctt ctttttctat gctaaagag ggaaagtctg | 120 |
| gtgtatctct caggacacc acaatgtttg gtgtttcatt gtcggatact ctcaaatctg | 180 |
| acttcagctc tccctcatcg acttgcaaaa gggaattcca acaaaaattt ggccctttga | 240 |
| gggttcagtc agtggcaaca acaactccag gagtcaccaa ggttcaccag aaggcaagaa | 300 |
| ctttgaggaa ggcagtgnta taccatgggg cttcctctgg attagcctgg cactgcta | 358 |

<210> SEQ ID NO 19
<211> LENGTH: 264
<212> TYPE: DNA
<213> ORGANISM: Glycine max

<400> SEQUENCE: 19

| | |
|---|---|
| aaacattcta aaacaaagga cccagtttta catttttttt tgttcctgag ttccaatggc | 60 |
| tcttcaggct gcttccttgg tttctgcttc ttttttctatt gctaaagagg gaaagtctgg | 120 |
| tgtatctctc agggacacca caatgtttgg tgtttcattg tcggatactc tcaaatctga | 180 |
| cttcagctct ccctcatcga cttgcaaaag ggaattccaa caaaaatttg gccctttgag | 240 |

```
ggttcagtca gtggcaacaa caac                                              264

<210> SEQ ID NO 20
<211> LENGTH: 253
<212> TYPE: DNA
<213> ORGANISM: Glycine max

<400> SEQUENCE: 20
acattctaaa acaaaggacc cagttttaca tttgttttg ttcctgagtt ccaatggctc         60
ttcaggctgc ttccttggtt tctgcttctt tttctattgc taaagaggga aagtctggtg      120
tatctctcag ggacaccaca atgtttggtg tttcattgtc ggatactctc aaatctgact      180
tcagctctcc ctcatcgact tgcaaaaggg aattccaaca aaaatttggc cctttgaggg      240
ttcagtcagt ggc                                                         253

<210> SEQ ID NO 21
<211> LENGTH: 256
<212> TYPE: DNA
<213> ORGANISM: Glycine max

<400> SEQUENCE: 21
acattctaaa acaaaggacc cagttttaca tttttgtttg ttcctgagtt ccaatggctc       60
ttcaggctgc ttccttggtt tctgcttctt tttctattgc taaagaggga aagtctggtg      120
tatctctcag ggacaccaca atgtttggtg tttcattgtc ggatactctc aaatctgact      180
tcagctctcc ctcatcgact tgcaaaaggg aattccaaca aaaatttggc cctttgaggg      240
ttcagtcagt ggcaac                                                      256

<210> SEQ ID NO 22
<211> LENGTH: 277
<212> TYPE: DNA
<213> ORGANISM: Glycine max

<400> SEQUENCE: 22
atttttattt gttcctgagt tccaatggct cttcaggctg cttccttggt ttctgcttct       60 cttttctattg ctaaagaggg aaagtctggt gtatctctca gggactccac aatgtttggt     120
gtttcattgt cggatactct caaatctgac ttcagctctc tctcatcgac ttgcaaaagg      180
gaattccaac aaaaatttgg cccgttaagg gttcagtcag tggcaacaac aactccagga      240
gtcaccaagg cttcaccaga aggcgatgaa atttgag                               277

<210> SEQ ID NO 23
<211> LENGTH: 256
<212> TYPE: DNA
<213> ORGANISM: Glycine max

<400> SEQUENCE: 23
gaaacattct aaaacaaagg acccagtttt acattttttt tgttcctgag ttccaatggc       60
tcttcaggct gcttccttgg tttctgcttc ttttctatt gctaaagagg gaaagtctgg      120
tgtatctctc agggacacca caatgtttgg tgtttcattg tcggatactc tcaaatctga      180
cttcagctct ccctcatcga cttgcaaaag ggaattccaa caaaaatttg gccctttgag      240
ggttcagtca gtggca                                                      256

<210> SEQ ID NO 24
<211> LENGTH: 269
<212> TYPE: DNA
```

<213> ORGANISM: Glycine max

<400> SEQUENCE: 24

| | | | | | |
|---|---|---|---|---|---|
| gttttacatt | ttttttttgt | tcctgagttc | caatggctct | tcaggctgct | tccttggttt | 60 |
| ctgcttcttt | ttctattgct | aaagagggaa | agtctggtgt | atctctcagg | gacaccacaa | 120 |
| tgtttggtgt | ttcattgtcg | gatactctca | aatctgactt | cagctctccc | tcatcgactt | 180 |
| gcaaaaggga | attccaacaa | aaatttggcc | ctttgagggt | tcagtcagtg | gcaacaacaa | 240 |
| ctccaggagt | caccaaggct | tcaccagaa | | | | 269 |

<210> SEQ ID NO 25
<211> LENGTH: 251
<212> TYPE: DNA
<213> ORGANISM: Glycine max

<400> SEQUENCE: 25

| | | | | | |
|---|---|---|---|---|---|
| gcttctttcc | ccattgctaa | agagggaaag | tctggtgttt | ctctcaggta | caccacaatg | 60 |
| ttcggtgttt | cattgtcgga | tactctcaaa | tcagacttca | gcttttcctc | attgacatgc | 120 |
| aaaagggaat | tccaacaaaa | aattggccct | tgagggttc | agtcagtggc | aacaaccact | 180 |
| ccaggagtca | ccaaggcttc | accagaaggc | aagaaaactt | tgaggaaagg | cagtgttatt | 240 |
| gtcactgggc | t | | | | | 251 |

<210> SEQ ID NO 26
<211> LENGTH: 246
<212> TYPE: DNA
<213> ORGANISM: Glycine max

<400> SEQUENCE: 26

| | | | | | |
|---|---|---|---|---|---|
| ggctcgagaa | cattctaaaa | caaaggaccc | aattttacat | ttttttcact | tcctgagttc | 60 |
| caatggctct | tcaggctgct | tccttggttt | ctgcttcttt | ttctattgct | aaagagggaa | 120 |
| agtctggtgt | atctctcagg | gacaccacaa | tgtttggtgt | ttcattgtcg | gatactctca | 180 |
| aatctgactt | cagctctccc | tcatcgactt | gcaaaaggga | attccaacaa | aaatttggcc | 240 |
| ctttga | | | | | | 246 |

<210> SEQ ID NO 27
<211> LENGTH: 254
<212> TYPE: DNA
<213> ORGANISM: Glycine max

<400> SEQUENCE: 27

| | | | | | |
|---|---|---|---|---|---|
| gaaacattct | aaaacaaagg | acccagtttt | acatttttt | ttgttcctga | gttccaatgg | 60 |
| ctcttcaggc | tgcttccttg | gtttctgctt | cttttttctat | tgctaaagag | ggaaagtctg | 120 |
| gtgtatctct | caggacacc | acaatgtttg | gtgtttcatt | gtcggatact | ctcaaatctg | 180 |
| acttcatctc | tccctcatcg | acttgcaaaa | gggaattcca | acaaaaattt | ggcccttga | 240 |
| gggttcagtc | agtg | | | | | 254 |

<210> SEQ ID NO 28
<211> LENGTH: 259
<212> TYPE: DNA
<213> ORGANISM: Glycine max
<220> FEATURE:
<223> OTHER INFORMATION: unsure at all n locations

<400> SEQUENCE: 28

| | | | | | |
|---|---|---|---|---|---|
| aaacaaagga | cccagtttta | cattttttt | tgttcctgag | ttccaatggc | tcttcaggct | 60 |

```
gcttccttgg tttctgcttc tttttctatt gctaaagagg gaaagtctgg tgtatctctc      120
agggacacca caatgtttgg tgtttcattg tcggatactc tcaaatctna cttcagctct      180
ccctcatcga cttgcaaaag ggaattccaa canaaatttg gccccgggtt cagtcagtgg      240
naacaacaac ncgnggagt                                                   259
```

<210> SEQ ID NO 29
<211> LENGTH: 249
<212> TYPE: DNA
<213> ORGANISM: Glycine max
<220> FEATURE:
<223> OTHER INFORMATION: unsure at all n locations

<400> SEQUENCE: 29

```
aaacattcta aaacaaagga cccagttttta catttttntt tgttcctgag ttccaatggc      60
tnctccaggc tgcttccttg gtttctgctt cttttncta t tgttaaagag ggaaagttct     120
ggtgtatctc tcagggacac cacnatgttt ggtgtttcat tgtcggatac tctcaaatct     180
gacttcagct ctccctcatc gacttgcaaa aggggaattcc aacanaaatt tggcccttttg    240 agggttcag                                                              249
```

<210> SEQ ID NO 30
<211> LENGTH: 230
<212> TYPE: DNA
<213> ORGANISM: Glycine max

<400> SEQUENCE: 30

```
gaaacattct aaaacaaagg acccagtttt acattttttt ttgttcctga gttccaatgg      60
ctcttcaggc tgcttcctgt ggtttctgct tcttttttcta ttgctaaaga gggaaagtct     120
ggtgtatctc tcagggacac cacaatgttt ggtgtttcat tgtcggatac tctcaaatct     180
gacttcagct ctccctcatc gacttgcaaa agggaattcc aacaaaaatt                 230
```

<210> SEQ ID NO 31
<211> LENGTH: 445
<212> TYPE: DNA
<213> ORGANISM: Glycine max
<220> FEATURE:
<223> OTHER INFORMATION: unsure at all n locations

<400> SEQUENCE: 31

```
gcgagaagac gacagaaggg gtctcagaag atgaagcagg aaagagactt gctcaggttg      60
taagtgatcc aagcctaaca aaatctggtg tttactggag ctgaaacaaa gcatcagctt     120
cgtttgaaaa ccagttgtct caggaggcca gtgatacaga aaggctcgt aagatctggg      180 agattagtga gaaacttgtt ggttttgcct aagtgggagg agcctccaac atcccatgtt     240
gttctagaga ccttgcactt gcatggagga agaaaatgat gtctcaaaag agtggataga     300
taacatccta tcattttgaa tgcattgatg ttgttttgtt agctaggagc ttctttgctt     360
tgatgtaagg tgtcaatggc tttttgtgaa tcaagactca ataaaatcat tcagccatgt     420
gggtgtggtg aagttgctca taana                                            445
```

<210> SEQ ID NO 32
<211> LENGTH: 256
<212> TYPE: DNA
<213> ORGANISM: Glycine max

<400> SEQUENCE: 32

```
attgctcagg ttgtaagtga tccaagccta acaaaatctg gtgtttactg gagctggaac    60
aaagcatcag cttcgtttga aaaccagttg tctcaggagg ccagtgatac agagaaggct   120
cgtaagatct gggagattag tgagaaactt gttggttttg cctaagtggg aggagcctcc   180
aacatcccat gttgttctag agaccttgca cttgcatgga ggaagaaaat gacgtctcaa   240
aagagtggat agataa                                                   256
```

<210> SEQ ID NO 33
<211> LENGTH: 259
<212> TYPE: DNA
<213> ORGANISM: Glycine max
<220> FEATURE:
<223> OTHER INFORMATION: unsure at all n locations

<400> SEQUENCE: 33

```
ggctaaacag ctcagccatg attgatggtg gagacttcga tggtgccaag gcgtacaagg    60
acagcaaagt ctgcaatatg ctcacaatgc aagaattcca cagacgattc catgaggaaa   120
ctggaatcac atttgcttcc ctttaccccg gttgcattgc cacaacaggc ctgttcagag   180
agcacttccc ttgttcagaa actctgttnc cctcccattc agaagtacat aaaccaaag   240 gctatgtctc cggaagatg                                                259
```

<210> SEQ ID NO 34
<211> LENGTH: 176
<212> TYPE: DNA
<213> ORGANISM: Glycine max

<400> SEQUENCE: 34

```
agcataatgc cacaaatgca gaatttcaca gacgattcca tgaggatact ggaatcacat    60
ttgcttccct ttaccccggt tgcattgcca acaggcct gttcagagag cacattccct    120
tgttcagaac tctgtccctc cattccagaa gtacataacc aaagggctat gtctca       176
```

<210> SEQ ID NO 35
<211> LENGTH: 256
<212> TYPE: DNA
<213> ORGANISM: Glycine max
<220> FEATURE:
<223> OTHER INFORMATION: unsure at all n locations

<400> SEQUENCE: 35

```
caggaaagag acttgcacag gttgtgagtg atccacnccc taacaaaatc aggtgtttac    60
tggagctgga acgcggcctc tgcttcgttt gaaaaccaat tgtcccaaga agccagcgat   120
gcagataagg tcgcaaggtt tgggagatta gtgagaaact tactggtttg cttaagtgg   180 tactttggca gcttccaata tccatcttga tttagggaca tttgtcatgg agttcaataa   240
catctcagaa gagttt                                                   256
```

<210> SEQ ID NO 36
<211> LENGTH: 248
<212> TYPE: DNA
<213> ORGANISM: Glycine max
<220> FEATURE:
<223> OTHER INFORMATION: unsure at all n locations

<400> SEQUENCE: 36

```
caggaaagag acttgcacag gttgtgagtg atccaagcct aacaaaatca ggtgtttact    60
ggagctggaa cgcggncctg ctgcttcgtt tgaaaaccaa ttgtgcccaa gaagccagcg   120
atgcagataa ggctncgcaa ggtttgggag attagtgaga aacttactgg tttgggctaa   180
```

```
gtggtacttt ggcagcttcc caatatccat ctgatttagg gacattgtca ggagttcaat    240
aacatctc                                                              248

<210> SEQ ID NO 37
<211> LENGTH: 335
<212> TYPE: DNA
<213> ORGANISM: Glycine max

<400> SEQUENCE: 37
ggtgtgtctc tcaaggactc caccttgttc ggtctttcat tttcagaacc tatcaaagct    60
aacttcagct cttctgcatt gaggtgtcag agggaattcg aacaaaagct ctgtgctgtg    120
agggccgaaa cagtggctac agcctctcca gcagttacca agtctacacc agaagggaag    180
aaaacattga ggaagggcag tgttgtgata actggggctt catctggact aggcctggcc    240
actgctaagg ctttggctga gacgggaaaa tggcatgtaa taatggcctg cagggattac    300
ctcaaagctg caagagctgc aaaatccgct ggcat                                335

<210> SEQ ID NO 38
<211> LENGTH: 258
<212> TYPE: DNA
<213> ORGANISM: Glycine max

<400> SEQUENCE: 38
cggaaaatgg catgtaataa tggcctgcag ggattacctc aaagctgcaa gagctgcaaa    60
atccgctggc atggctaagg aaaactacac catcatgcac taggaccttg cctcgctcga    120
cagtgtccgc caatttgttg ataacttcag aagatcggaa atgccgttag atgtgctggt    180
ttgcaatgct gctgtttact tgccaactgc taaggaacct accttcactg ctgagggctt    240
tgaacttagt gttgggac                                                   258

<210> SEQ ID NO 39
<211> LENGTH: 246
<212> TYPE: DNA
<213> ORGANISM: Glycine max

<400> SEQUENCE: 39
aaacattgag gaagggcagt gttgtgataa ctggggcttc atctggacta ggcctggcca    60
ctgctaaggc tttggctgag acgggaaaat ggcatgtaat aatggcctgc agggattacc    120
tcaaagctgc aagagctgca aaatccgctg gcatggctaa ggaaaactac accatcatgc    180
acttggacct tgcctcgctc gacagtgtcc gccaatttgt tgataacttc agaagatcgg    240
aaatgc                                                                246

<210> SEQ ID NO 40
<211> LENGTH: 260
<212> TYPE: DNA
<213> ORGANISM: Glycine max
<220> FEATURE:
<223> OTHER INFORMATION: unsure at all n locations

<400> SEQUENCE: 40
ctgcaaganc tgcaaaatcc gctggcatgg ctaaggaaaa ctacaccatg aatgcacttg    60
gaccttgcct cgctcgacag tgtccgccaa tttgttgata acttcagaag atcagaaatg    120
ccgttagatg tgctggtttg ccatgctgct gtttacttgc caactgctaa ggaacctacc    180
ttcactgctg agggctttga acttagtgtt gggacaaatc atctggggca tttcctcctc    240
```

```
tcgcgcctgt tgcttgagga                                              260

<210> SEQ ID NO 41
<211> LENGTH: 278
<212> TYPE: DNA
<213> ORGANISM: Glycine max
<220> FEATURE:
<223> OTHER INFORMATION: unsure at all n locations

<400> SEQUENCE: 41
attttcagaa cctatcaaag ctaacttcag ctcttctgca ttgaggttna agagggaatt    60
cgaacaaaaa gctctgtgct gtgagggccg aaacagtggc tacagcctct ccagcagtta  120
ccaagtctac accagaaggg aagaanacat tgaggaaggg cagtgttgtg ataactgggg  180
cttcatctgg actaggcctg gccactgcta aggctttggc tgagacggga aaatggcatg  240
taataatggc ctgcagggat tacctcaaag ctgcaaga                          278

<210> SEQ ID NO 42
<211> LENGTH: 248
<212> TYPE: DNA
<213> ORGANISM: Glycine max

<400> SEQUENCE: 42
ctgtgctgtg agggccgaaa cagtggctac agcctctcca gcagttacca agtctacacc   60
agaagggaac gaaaacattg aggaagggca gtgttgtgat aactggggct tcatctggac  120
taggcctggc cactgctaag gctttggctg agacgggaaa atggcatgta ataatggcct  180
gcagggatta cctcaaagct gcaagagctg caaaatccgc tggcatggct aaggaaaact  240
acactgtc                                                           248

<210> SEQ ID NO 43
<211> LENGTH: 280
<212> TYPE: DNA
<213> ORGANISM: Glycine max

<400> SEQUENCE: 43
gtgtctctca aggactccac cttgttcggt ctttcatttt cagaacctat caaagctaac   60
ttcagctctt ctgcattgag gtgcaagagg gaattcgaac aaaagctctg tgctgtgagg  120
gccgaaacag tggctacagc cttccagcag ttaccaagtc tacaccagaa gggaagaaaa  180
cattgaggaa gggcagtgtt gtgataactg ggcttcatc tggactaggc ctggccactg   240
ctaaggcttt ggctgagacg ggaaaatggc atgtaataat                        280

<210> SEQ ID NO 44
<211> LENGTH: 269
<212> TYPE: DNA
<213> ORGANISM: Glycine max

<400> SEQUENCE: 44
aaagagtggt gtgtctctca aggactccac cttgttcggt ctttcatttt cagaacctat   60
caaagctaac ttcagctctt ctgcattgag gtgtaagagg gaattcgaac aaaagctctg  120
tgctgtgagg gccgaaacag tggctacagc ctctccagca gttaccaagt ctacaccaga  180
agggaagaaa acattgagga agggcagtgt tgtgataact ggggcttcat ctggactagg  240
cctggccact gctaaggctt tggctgaga                                    269

<210> SEQ ID NO 45
<211> LENGTH: 236
```

```
<212> TYPE: DNA
<213> ORGANISM: Glycine max

<400> SEQUENCE: 45
cgaaacagtg gctacagcct ctccagcagt taccaagtct acaccagaag ggaagcaaac    60
attgaggaag ggcagtgttg tgataactgg ggcttcatct ggactaggcc tggccactgc   120
taaggctttg gctgagacgg gaaaatggca tgtaataatg gcctgcaggg attacctcaa   180
agctgcaaga gctgcaaaat ccgctggcat ggctaaggaa aactacacca tcatgc       236

<210> SEQ ID NO 46
<211> LENGTH: 211
<212> TYPE: DNA
<213> ORGANISM: Glycine max

<400> SEQUENCE: 46
ctcgagcgtg cgagaagaga cagaagggggg aaaatggcat gtaataatgg cctgcaggga    60
ttacctcaaa gctgcaagag ctgcaaaatc cgctggcatg gctaaggaaa actacaccat   120
catgcacttg gaccttgcct cgctcgacag tgtccgccaa tttgttgata acttcagaag   180
atcggaaatg ccgttagatg tgctggtttg c                                   211

<210> SEQ ID NO 47
<211> LENGTH: 276
<212> TYPE: DNA
<213> ORGANISM: Glycine max
<220> FEATURE:
<223> OTHER INFORMATION: unsure at all n locations

<400> SEQUENCE: 47 cttttttttct tcttcttgaa atggctctcc aggctgcttc tcctgttcct gcttctttct    60
cggttcttaa agagggaaag agtggtgtgt ctctcaagga ctccaccttg ttcggtcttt   120
cattttcaga acctatcaaa gctaacttca gctcttctgc attgaggtgc aagagggaat   180
tcgancaaaa gctctgtgct gtgagggccg aaacagtggc tacagcctct ccagcagtta   240
ccaagtctac accagaaggg aagnaaacat tgagga                              276

<210> SEQ ID NO 48
<211> LENGTH: 269
<212> TYPE: DNA
<213> ORGANISM: Glycine max

<400> SEQUENCE: 48
cttctcttgt tcctgcttct ttctcggttc ttaaagaggg aaagagtggt gtgtctctca    60
aggactccac cttgttcggt cttccatttt cagaacctat caaagctaac ttcagctctt   120
ctgcattgag gtgcaagagg gaattcgaac aaaagctctg tgctgtgagg gccgaaacag   180
tggctacagc ctctccagca gttaccaagt ctacaccaga agggaagaaa acattgagga   240
agggcagtgt tgtgataact ggggcttca                                      269

<210> SEQ ID NO 49
<211> LENGTH: 279
<212> TYPE: DNA
<213> ORGANISM: Glycine max

<400> SEQUENCE: 49
tagtcaaaat ctagtttcat acttttgttc ttcttcttga aatggctctc caggctgctt    60
ctcttgttcc tgcttctttc tcggttctta agagggaaa gagtggtgtg tctctcaagg   120
```

```
attccacctt gttcggtctt tcattttcag aacctatcaa agctaacttc agctcttctg      180
cattgaggtg caagagggaa ttcgaacaaa agctctgtgc tgtgagggcc gaaacagtgg      240
ctacagcctc tccagcagtt accaagtcta caccagaag                            279
```

<210> SEQ ID NO 50
<211> LENGTH: 257
<212> TYPE: DNA
<213> ORGANISM: Glycine max

<400> SEQUENCE: 50

```
ttctcttgtt cctgcttctt tctcggttct taaagaggga agagtggtg tgtctctcaa      60 ggactccacc ttgttcggtc tttcattttc agaacctatc aaagctaact tcagctcttc     120
tgcattgagg ttcaagaggg aattcgaaca aaagctctgt gctgtgaggg ccgaaacagt     180
ggctacagcc tctccagcag ttaccaagtc tacaccagaa gggaagataa cattgaggaa     240
gggcagtgtt gtgataa                                                    257
```

<210> SEQ ID NO 51
<211> LENGTH: 243
<212> TYPE: DNA
<213> ORGANISM: Glycine max

<400> SEQUENCE: 51

```
ggctgcttct cttgttcctg cttctttctc ggttcttaaa gagggaaaga gtggtgtgtc     60
tctcaaggac tccaccttgt tcggtctttc attttcagaa cctatcaaag ctaacttcag     120
ctcttctgca ttgaggtgca gagggaatt cgaacaaaag ctctgtgctg tgagggccga     180
aacagtggct acagcctctc cagcagttac caagtctaca ccagaaggga gaaaacatt     240 gag                                                                   243
```

<210> SEQ ID NO 52
<211> LENGTH: 277
<212> TYPE: DNA
<213> ORGANISM: Glycine max
<220> FEATURE:
<223> OTHER INFORMATION: unsure at all n locations

<400> SEQUENCE: 52

```
caatattgta aaactcaaaa tctagtttca tactttttt cttcttcttg aaatggctct      60
ccaggctgct tctcttgttc ctgcttcttt ctcggttctt aaagagggaa agagtggtgt     120
gtctctcaag gactccacct tgttcggtct ttcattttca gaacctatca aagctaactt     180
cagctcttct gcattgaggt ncaagaggga attcgaacaa aagctctntg ctgtgagggc     240
cgaaacagtg gctacagcct ctccagcagt taccaag                              277
```

<210> SEQ ID NO 53
<211> LENGTH: 271
<212> TYPE: DNA
<213> ORGANISM: Glycine max
<220> FEATURE:
<223> OTHER INFORMATION: unsure at all n locations

<400> SEQUENCE: 53

```
cttttttct tcttcttgaa tggctctcca ggctgcttct cttgancctg cttccttctc      60
ggttcttaaa gagggaaaga gtggtgtgtc tctcaaggac tccaccttgt tcggtctttc    120
attttcagaa cctatcaaag ctaacttcag ctcttctgca ttgaggttaa gagggaattc    180
gaacaaaagc tcngtgctgt gagggccgaa acagtggcta cagcctctcc agcagttacc    240
```

```
aagtctacac cagaaggcaa nnaacattga g                              271
```

<210> SEQ ID NO 54
<211> LENGTH: 269
<212> TYPE: DNA
<213> ORGANISM: Glycine max
<220> FEATURE:
<223> OTHER INFORMATION: unsure at all n locations

<400> SEQUENCE: 54

```
cnatattgta aaactcaaaa tctagtttca tactttttt cttcttcttg aaatggctct    60
ccaggctgct tctcttgttc ctgcttcttt ctcggttctt aaagagggaa agagtggtgt   120
gtctctcaag gactccacct tgttcggtct ttcattttca gaacctatca aagctaactt   180
cagctcttct gcattgaggt ccaagaggga attcgaacaa aagctctgtg ctgtgagggc   240
cgaaacagtg gctanagcct ctccagcag                                    269
```

<210> SEQ ID NO 55
<211> LENGTH: 282
<212> TYPE: DNA
<213> ORGANISM: Glycine max

<400> SEQUENCE: 55

```
tcaaaatcta gtttcatact tttcatcttc ttcttgaaat ggctctccag gctgcttctc    60
ttgttcctga ttctttctcg gttcttaaag acggtgagat gtggtgtgtc tctcaaggac   120
tccacctagt tcggtctggc attttcagaa cctatcaaag ctaacttaag ctcttctgca   180
ttgaggtgca agagggattc cgcacaaaag ctctgtgctg tgagtgccga cagtggct     240
acagcgtctg cagcagttac caagtctaca cgagaaggga ag                      282
```

<210> SEQ ID NO 56
<211> LENGTH: 263
<212> TYPE: DNA
<213> ORGANISM: Glycine max

<400> SEQUENCE: 56

```
acttctcttg ttcctgcttc tttctcggtt cttaaagagg gacagagtgg tgtgtctctc    60
aaggactccg cttgttcggt cttttcatttt cagaacctat caaagctaac ttcagctctt   120
ctgcattgag gtgcaagagg gaattcgaac aatcgctctg tgctgtgagg ccgaaacag    180
tggttacagc ctctccagca gttaccaagt ctacaccaga tgggaagaaa acattgagtg   240
aaggagtgtg gtgaaactgg ggc                                          263
```

<210> SEQ ID NO 57
<211> LENGTH: 313
<212> TYPE: DNA
<213> ORGANISM: Glycine max

<400> SEQUENCE: 57

```
gaaatggctc tccaggctgc ttctcttgtt cctgcttctt tctcggttct taaagaggga    60
aagagtggtg tgtctctcaa ggactccacc ttgttcggtc tttcattttc agaacctatc   120
aaagctaact tcagctcttc tgcattgagg tgcaagaggg aattcgaaca aaagctctgt   180
gctgtgaggg ccgaaacagt ggctacagcc tctccagcag ttaccaagtc tacaccagaa   240
ggcaagaaaa cattgaggaa gggcagtgtt gtgataactg gggcttcatc tggacgaggc   300
ctggccactg cta                                                     313
```

<210> SEQ ID NO 58
<211> LENGTH: 266
<212> TYPE: DNA
<213> ORGANISM: Glycine max

<400> SEQUENCE: 58

```
ccgtgataac acactaacac caccacttca tcaactttac ttgacaacaa tattgtaaaa      60
ctcaaaatct agtttcatac ttttgttctt cttcttgaaa tggctctcca ggctgcttct     120
cttgttcctg cttctttctc ggttcttaaa gagggaaaga gtggtgtgtc tctcaaggac     180
tccaccttgt tcggtctttc attttcagaa cctatcaaag ctaacttcag ctcttctgca     240
ttgaggtgca gagggaatt cgaaca                                           266
```

<210> SEQ ID NO 59
<211> LENGTH: 277
<212> TYPE: DNA
<213> ORGANISM: Glycine max

<400> SEQUENCE: 59

```
caccatcact tcatcaactt tacttgacaa caatattgta aaactcaaaa tctagtttca      60
tactttttt cttcttcttg aaatggctct ccaggctgct tctcttgttc ctgcttcttt     120
ctcggttctt aaagagggaa agagtggtgt gtctctcaag gactccacct tgttcggtct     180
ttcattttca gaacctatca agctaacttc agctcttct gcattgaggt gcaagaggga     240
attcgaacaa aagctctgtg ctgtgagggc cgaaaca                              277
```

<210> SEQ ID NO 60
<211> LENGTH: 151
<212> TYPE: DNA
<213> ORGANISM: Glycine max

<400> SEQUENCE: 60

```
gcatctttct cggttcttaa agagggaaag actggtgtgt cactcacgga ttccaccttg      60
tacggtcttt cattttcaga acctatcaaa gctaacttca gctcttctgc attgaggtgc     120
aagagggaat cgaacaaaa actctgtgct g                                     151
```

<210> SEQ ID NO 61
<211> LENGTH: 266
<212> TYPE: DNA
<213> ORGANISM: Glycine max

<400> SEQUENCE: 61

```
caccacttca tcaactttac ttgacaacaa tattgtaaaa ctcaaaatct agtttcatac      60
ttttttact cttcttgaaa tggctctcca ggctgcttct cttgttcctg cttctttctc     120
ggttcttaaa gagggaaaga gtggtgtgtc tctcaaggac tccaccttgt tcggtctttc     180
attttcagaa cctatcaaag ctaacttcag ctcttctgca ttgaggtgca gagggaatt     240
cgaacaaaag ctctgtgctg tgaggg                                          266
```

<210> SEQ ID NO 62
<211> LENGTH: 229
<212> TYPE: DNA
<213> ORGANISM: Glycine max

<400> SEQUENCE: 62

```
ttcatcaact ttacttgaca acaatattgt aaaactcaaa atctagtttc atactttttt      60
tcttcttctt gaatggctc tccaggctgc ttctcttgtt cctgcttctt tctcggttct     120
```

```
taaagaggga aagagtggtg tgtctctcaa ggactccacc ttgttcggtc tttcattttc    180
agaacctatc aaagctaact tcagctcttc tgcattgagg tgcaagagg               229

<210> SEQ ID NO 63
<211> LENGTH: 268
<212> TYPE: DNA
<213> ORGANISM: Glycine max

<400> SEQUENCE: 63
cccgtgataa cacactaaca ccatcacttc atcaacttta cttgacaaca atattgtaaa    60
actcaaaatc tagtttcata cttttattcg tcttctttaa atggctctcc aggctgcttc    120
tcttgttcct gcttctttct cggttcttaa atagggaaag agtggtgtgt ctctcaagga    180
ctccaccttg ttcggtcttt cattttcaga acctatcaaa gctaacttca gctcttctgc    240
attgaggttc aagagggaat tcgaacaa                                       268

<210> SEQ ID NO 64
<211> LENGTH: 278
<212> TYPE: DNA
<213> ORGANISM: Glycine max
<220> FEATURE:
<223> OTHER INFORMATION: unsure at all n locations

<400> SEQUENCE: 64
tatnatacca cttcatcaac ctnacnctga caacaatatt gtaaaactcn naatctagtt    60
tcatactttt tttcttcttc ttgaaatggc tctccaggct gcttctcttg ttcctgcttc    120
tttctcggtt cttaaagagg gaaagagtgg tgtgtctctc aaggactcca ccttgttcgg    180
tctttcattt tcagaaccta tcaaagctaa cttcagctct tctgcattga ggtntcaaga    240
gggaattcga acaaaagctc tgtgctgtga gggccgaa                            278

<210> SEQ ID NO 65
<211> LENGTH: 275
<212> TYPE: DNA
<213> ORGANISM: Glycine max

<400> SEQUENCE: 65
ttcatcaact ttacttgaca acaatattgt aaaattcaaa atctagtttc atacttttat    60
tcttcttctt gaaatggctc tccaggctgc ttctcttgtt cctgcttctt tctcggttct    120
taaagaggga aagagtggtg tgtctctcaa ggactccacc ttgttcggtc tttcattttc    180
agaacctatc aaagctaact tcagctcttc tgcattgagg tttaagaggg aattcgaaca    240
aaagctctgt gctgtgaggg ccgaaacagt ggcta                               275

<210> SEQ ID NO 66
<211> LENGTH: 344
<212> TYPE: DNA
<213> ORGANISM: Glycine max
<220> FEATURE:
<223> OTHER INFORMATION: unsure at all n locations

<400> SEQUENCE: 66
caatattgta naactcaaaa tctagtttca ctttttctt ctacttcttg aaatggctct     60
ccaggctgct tctcttgttc ctgcttcttt ctcggttctt aaagagggaa agagtggtgt    120
gtttctcaag gactccacct tgttcggtct ttcattttca gaaccttta tagctaactt    180 cagctcttct gcattgaggt gtaagaggga attcgaacaa aagctctgtg ctgtgagggc    240
```

```
cgaaacagtg gctacagcct ctccagcagt taccaagtct acaccagaag ggacgtcaac    300
attgaggaag ggcagtgttg tgataactgg ggcttcatct ggac                     344

<210> SEQ ID NO 67
<211> LENGTH: 255
<212> TYPE: DNA
<213> ORGANISM: Glycine max

<400> SEQUENCE: 67
cgccgtgata acacactaac accaccactt catcaacttt acttgacaac aatattgtaa    60
aactcaaaat ctagtttcat acttttttc ttcttcttga atggctctc caggctgctt    120 ctcttgttcc tgattcttac tcggttctta aagagggaaa gagtggtgtg tctctcaagg    180
actccacctt gttcggtctt tcattttcag aacctatcaa agctaacttc agctcttctg    240
cattgaggtg caaga                                                     255

<210> SEQ ID NO 68
<211> LENGTH: 249
<212> TYPE: DNA
<213> ORGANISM: Glycine max

<400> SEQUENCE: 68
ttttcattac cgccgtgata acacactaac accaccactt catcaacttt acttgacaac    60
aatattgtaa aactcaaaat ctagtttcat acttttttc ttcttcttga atggctctc    120 caggctgctt ctcttgttcc tgcttctttc tcggttctta aagagggaaa gagtggtgtg    180
tctctcaagg actccacctt gttcggtctt tcattttcag aacctatcaa agctaacttc    240
agctcttct                                                            249

<210> SEQ ID NO 69
<211> LENGTH: 249
<212> TYPE: DNA
<213> ORGANISM: Glycine max

<400> SEQUENCE: 69
cacactaaca ccaccacttc atcaacttta cttgacaaca atattgtaaa actcaaaatc    60
tagtttcata cttttttct tcttcttgaa atggctctcc aggctgcttc tcttgttcct    120
gcttctttct cggttcttaa agagggaaag agtggtgtgt ctctcaagga ctccaccttg    180
ttcggtcttt cattttcaga acctatcaaa gctaacttca gctcttctgc attgaggttc    240
aagagggaa                                                            249

<210> SEQ ID NO 70
<211> LENGTH: 294
<212> TYPE: DNA
<213> ORGANISM: Glycine max

<400> SEQUENCE: 70
caatattgta aaactcaaaa tctagtttca tacttttttt cttcttcttg aaatggctct    60
ccaggctgct tctcttgttc ctgcttcttt ctcggttctt aaagagggaa agagtggtgt    120
gtctctcaag gactccacct tgttcggtct ttcattttca gaacctatca aagctaactt    180
cagctcttct gcattgaggt gcaagaggga attcgaacaa aagctctgtg ctgtgagggc    240
cgaaacagtg gctacagcct ctccagcagt taccaagtct acaccagaag gaa           294

<210> SEQ ID NO 71
<211> LENGTH: 270
```

```
<212> TYPE: DNA
<213> ORGANISM: Glycine max

<400> SEQUENCE: 71
ctccaggctg cttctcttgt tcctgcttct ttctcggttc ttaaagaggg aaagagtggt    60
gtgtctctca aggactccac cttgttcggt ctttcatttt cagaacctat caaagctaac   120
ttcagctctt ctgcattgag gtgcaagagg gaattcgaac aaaagctctg tgctgtgagg   180
gccgaaacag tggctacagc ctctccagca gttaccaagt ctacaccaga aggcaagata   240
acattgagaa gggcagtgtt gtgataactg                                    270

<210> SEQ ID NO 72
<211> LENGTH: 254
<212> TYPE: DNA
<213> ORGANISM: Glycine max

<400> SEQUENCE: 72
attaccgccg tgataacaca ctaacaccac cacttcatca actttacttg acaacaatat    60
tgtaaaactc aaaatctagt ttcatacttt ttttcttctt cttgaaaggc tctccaggct   120
gcttctcttg ttcctgcttc tttctcggtt cttaaagagg gaaagagtgg tgtgtctctc   180
aaggactcca ccttgttcgg tctttcattt tcagaaccta agctaacttc agctcttctg   240
cattgaggtg caag                                                    254

<210> SEQ ID NO 73
<211> LENGTH: 100
<212> TYPE: DNA
<213> ORGANISM: Glycine max
<220> FEATURE:
<223> OTHER INFORMATION: unsure at all n locations

<400> SEQUENCE: 73
ccctgcaggc cattattaca aagctgcaag agctgcaaaa tccgctggca tggctaagga    60
aaactacacc atcatgcanc ttggaccttg cctcgctcga                        100

<210> SEQ ID NO 74
<211> LENGTH: 262
<212> TYPE: DNA
<213> ORGANISM: Glycine max

<400> SEQUENCE: 74
cgccgtgata acacactaac accaccactt catcaacttt acttgacaac aatattgtaa    60
aactcaaaat ctagtttcat actttttttc ttcttcttga atggctctc caggctgctt   120 ctcttgttcc gcttctttct cggttcttaa agagggaaag agtggtgtgt ctctcaagga   180
ctccaccttg ttcggtcttt cattttcaga acctatcaaa gctaacttca tcttctgcat   240
tgaggtgcaa gagggaattc ga                                          262

<210> SEQ ID NO 75
<211> LENGTH: 184
<212> TYPE: DNA
<213> ORGANISM: Glycine max

<400> SEQUENCE: 75
gtgataacac actaacacca ccacttcatc aactttactt gacaacaata ttgtaaaact    60
caaaatctag tttcatactt tttttcttct cttgaaatg ctctccagg ctgcttctct   120 tgttcctgct tctttctcgg ttcttaaaga gggaaagagt ggtgtgtctc tcaaggactc   180
```

-continued

```
<210> SEQ ID NO 76
<211> LENGTH: 229
<212> TYPE: DNA
<213> ORGANISM: Glycine max

<400> SEQUENCE: 76
ggaaccacac attttttcatt accgccgtga taacacacta acaccaccac ttcatcaact    60
ttacttgaca acaatattgt aaaactcaaa atctggtttc atacttttt tcttcttctt    120 gaaatggctc tccaggctgc ttctcttgtt cctgcttctt tctcggttct taaagaggga    180
aagagtggtg tgtctctcaa ggactccacc ttgttcggtc tttcatttt                229

<210> SEQ ID NO 77
<211> LENGTH: 270
<212> TYPE: DNA
<213> ORGANISM: Glycine max
<220> FEATURE:
<223> OTHER INFORMATION: unsure at all n locations

<400> SEQUENCE: 77
attaccgtcg tgataacaca ctaacaccac cacttcatca actttacttg acaacaatat    60
tgtaaaactc aaaatctagt nnnnnnnnnn nnnnnnnnnn nnngaaatgg ctctccaggc    120
tgcttctctt gttcctgctt cttctcggt tcttaaagag ggaaagagtg gtgtgtctct    180
caaggactcc accttgttcg gtctttcatt ttcagaacct atcanagcta acttcagctc    240
ttctgcatga gngntagang gantcgaaca                                     270

<210> SEQ ID NO 78
<211> LENGTH: 267
<212> TYPE: DNA
<213> ORGANISM: Glycine max

<400> SEQUENCE: 78
ggctgcgaga agacgacaga aggggaacca cacattttc attaccgccg tgataacaca    60
ctaacaccac cacttcatca actttacttg acaacaatat tgtaaaactc aaaatctagt    120 ttcatactt tttcttctt cttgaaatgg ctctccaggc tgcttctctt gttcctgctt    180 cttctcggt tcttaaagag ggaaagagtg gtgtgtctct caaggactcc accttgttcg    240
gtctttcatt ttcagaacct atcaaag                                        267

<210> SEQ ID NO 79
<211> LENGTH: 158
<212> TYPE: DNA
<213> ORGANISM: Glycine max

<400> SEQUENCE: 79 tcaaatcta gtttcatact tttttcttc ttcttgaaat ggctctccag gctgcttctc    60
ttgttcctgc ttctttctcg gttcttaaag agggaaagag tggtgtgtct ctcaaggact    120
ccaccttgtt cggtctttca ttttcagaac ctatcaaa                           158

<210> SEQ ID NO 80
<211> LENGTH: 278
<212> TYPE: DNA
<213> ORGANISM: Glycine max

<400> SEQUENCE: 80
cacactaaca ccaccacttc atcaacttta cttgacaaca atattgtaaa actcaaaatc    60
```

-continued

```
tagtttcata cttttttct tcttcttgaa atggctctcc aggctgcttc tcttgttcct      120
gcttctttct cggttcttaa gagggaaaga gtggtgtgtc tctcaaggac tccaccttgt      180
tcggtctttc attttcagaa cctatcaaag ctaacttcag ctcttctgca ttgaggtgca      240
agagggaatt cgaacaaaag ctctgtgctg tgagggcc                             278
```

<210> SEQ ID NO 81
<211> LENGTH: 285
<212> TYPE: DNA
<213> ORGANISM: Glycine max

<400> SEQUENCE: 81

```
cacggctgcg aaagacgaca gaagggggacc acacattttt cattaccgcc gtgataacac      60
actaacacca ccagctcatc aactttactt gacaacaata ttgtaaaact caaaatctag     120
tttcatactt ttttcttct tcttgaaatg gctctccagg ctgcttctct tgttcctgct      180
tctttctcgg ttcttaaaga gggaaagagt ggtgtgtctc tcaaggactc caccttgttc     240
ggtctttcat tttcagaact atcaaagcta attcagctct tctgc                     285
```

<210> SEQ ID NO 82
<211> LENGTH: 269
<212> TYPE: DNA
<213> ORGANISM: Glycine max

<400> SEQUENCE: 82

```
ggttaccatt atttctttat aactatacta ctcatcagct gcatggtatt tttgctttca      60
ttgttggtgt tgttgttgat ccacttcatc aactttactt gacaacaaga ttgtaaaact     120
caaaatctag tttcatactt ttttcttct tcttgaaatg gctctccagg ctgcttctct      180
tgttcctgct tctttctcgg ttcttaaagc gggcaagagt ggtgtgtctc tcaaggactc     240
caccttgttc ggtctttcat tttcagaac                                      269
```

<210> SEQ ID NO 83
<211> LENGTH: 260
<212> TYPE: DNA
<213> ORGANISM: Glycine max

<400> SEQUENCE: 83

```
acggcgagaa gacgacagaa ggggaaccac acatttttca ttaccgccgt gataacacac      60
taacaccacc acttcatcaa ctttacttga caacaatatt gtaaaactca aaatctagtt     120
tcatactttt tttcttcttc ttgaaatggc tctccaggct gcttctcttg ttcctgcttc     180
tttctcggtt cttaaagagg gaaagagtgg tgtgtctctc aaggactcca ccttgttcgg     240
tctttcattt tcagaaccta                                                260
```

<210> SEQ ID NO 84
<211> LENGTH: 108
<212> TYPE: DNA
<213> ORGANISM: Glycine max

<400> SEQUENCE: 84

```
ttcagctctg ctgcattgag gtgccagagg gaattcgaac aaaagctctg tgctgtgagg      60
gccgaaacag tggctacagc ctctccagca gttaccaagt ctacacca                 108
```

<210> SEQ ID NO 85
<211> LENGTH: 258
<212> TYPE: DNA

<213> ORGANISM: Glycine max

<400> SEQUENCE: 85

```
caatattgta aaactcaaaa tctagtttca tactttttt cttcttcttg aaatggctct      60
ccaggctgcc tctcttgttc ctgcttcttt ctcggttctt aaagagggaa agagtggtgt    120
gtctctcaag gactcacctt gttcggtctt tcattttcag aacctatcaa agctaacttc    180
agctcttctg cattgaggtg taagagggaa ttcgaacaaa agctctgtgc tgtgagggcc    240
gaaacagtgg ctacagcc                                                  258
```

<210> SEQ ID NO 86
<211> LENGTH: 250
<212> TYPE: DNA
<213> ORGANISM: Glycine max

<400> SEQUENCE: 86

```
caatattgta aaactcaaaa tctagtttca tactttttt cttcttcttg aaatggctct      60
ccaggctgct tctcttgttc ctgcttcttt ctcggttctt aaagagggaa agagtggtgt    120
gtctctcaag gctccacctt gttcggtctt tcattttcag aacctatcaa agctaacttc    180
agctcttctg cattgaggtg caagagggaa ttcgaacaaa agctctgtgc tgtgaggcga    240
aacagtggct                                                          250
```

<210> SEQ ID NO 87
<211> LENGTH: 260
<212> TYPE: DNA
<213> ORGANISM: Glycine max
<220> FEATURE:
<223> OTHER INFORMATION: unsure at all n locations

<400> SEQUENCE: 87

```
caaaaatttg gccctttgag ggttcagtca gtggcaacaa caactccagg agtcaccaag      60
gcttcaccag aaggcaagaa nactttgagg aaaggcagtg ttattatcac tggggcttcc    120
tctggattag gcctggccac tgctaaggct ttggctgaga caggaaagtg gcatgtgata    180
atggcctgcc gggatttcct caaagccgaa anngctgcga atctgccgg cattgctaag     240
gaaaactaca ctattatgca                                                260
```

<210> SEQ ID NO 88
<211> LENGTH: 281
<212> TYPE: DNA
<213> ORGANISM: Glycine max

<400> SEQUENCE: 88

```
caacaaaaaa ttggcccttt gagggttcag tcagtggcaa caaccactcc aggagtcacc      60
aaggcttcac cagaaggcaa gaaaactttg aggaaaggca gtgttattgt cactgggctt    120
cctctggatt aggcctggcc acggccaagg ctttggctga cacaggaaag tggcatgtga    180
ttatgcactg cagggatttc ctcaaagctg agagggctgc aaaatctgct ggcattgcta    240
aggaaattgt gtctcttgat agtgtgaggc aatttgtgga t                        281
```

<210> SEQ ID NO 89
<211> LENGTH: 385
<212> TYPE: DNA
<213> ORGANISM: Glycine max

<400> SEQUENCE: 89

```
ctttgaactt agtgttgggc caaataattt gggcgttttc gtctctctcg cctgttgctt      60
```

```
gaggacttgg aaaaatccga ttacccttca aagcgcttga tcatcgttgg ttcaatatca    120
cggaacacac acacattggc tggtaatgta cctcccaagg ctaaccttgg tgacttgagg    180
ggacttcaag gtggtttgaa tgggcttaac agctcagcca tgattgatgg tggagacttc    240
gatggtgcca aggcgtacaa ggacagcaaa gtctgcaata tgctcacaat gcaagaattc    300
cacagacgat ttcatgagga aaactgaatc acatttgctt cctttaacc ccggtgcatt     360 gccacaacag gcctgttcag agagc                                          385
```

```
<210> SEQ ID NO 90
<211> LENGTH: 241
<212> TYPE: DNA
<213> ORGANISM: Glycine max
<220> FEATURE:
<223> OTHER INFORMATION: unsure at all n locations

<400> SEQUENCE: 90
gataacttca gaagatcgga aatgccgtta gatgtgctgg tttgcaatgc tgctgtttac    60
ttgccaactg ctaaggaacc taccttcact gctgagggct ttgaacttag tgttgggaca   120
aatcatctgg ggcatttcct cctctcgcgc ctgttgcttg aggacttgga aaaatccgat   180
tacccttcaa agcgcttgat catcgttggt tcaataacag ggnacacaaa cacattggct   240
g                                                                  241
```

```
<210> SEQ ID NO 91
<211> LENGTH: 267
<212> TYPE: DNA
<213> ORGANISM: Glycine max

<400> SEQUENCE: 91
ctcctctcgc gcctgttgct tgaggacttg gaaaaatccg attacccttc aaagcgcttg    60
atcatcgttg gttcaataac agggaacaca aacacattgg ctggtaatgt acctcccaag   120
gctaaccttg gtgacttgag gggacttcag gtggtttga atgggctaaa cagctcagcc    180
atgattgatg gtggagagat cgatggtgcc aaggcgtaca aggacagcaa agtctgcaat   240
atgctcacaa tgcaagaatt ccacaga                                       267
```

```
<210> SEQ ID NO 92
<211> LENGTH: 256
<212> TYPE: DNA
<213> ORGANISM: Glycine max

<400> SEQUENCE: 92
ttagatgtgc tggtttgcaa tgctgctgtt tacttgccaa ctgctaagga acctaccttc    60
actgctgagg gctttgaact agtgttggg acaaatcatc tggggcattt cctcctctcg    120
cgcctgttgc ttgaggactt ggaaaaatcc gattaccctt caaagcgctt gatcatcgtt   180
ggttcaataa cagggaacac aaacacattg gctggtaatg tacctcccaa ggctaacctt   240
ggtgacttga ggggat                                                   256
```

```
<210> SEQ ID NO 93
<211> LENGTH: 260
<212> TYPE: DNA
<213> ORGANISM: Glycine max

<400> SEQUENCE: 93
cttcactgct gagggctttg aacttagtgt tgggacaaat catctggggc atttcctcct    60
```

```
ctcgcgcctg ttgcttgagg acttggaaaa atccgattac ccttcaaagc gcttgatcat    120
cgttggttca ataacaggga acacaaacac attggctggt aatgtacctc ccaaggctaa    180
ccttggtgac ttgaggggac ttcagggtgg tttgaatggg ctaaacagct cagccatgat    240
tgatggtgga gattcgatgg                                                 260

<210> SEQ ID NO 94
<211> LENGTH: 274
<212> TYPE: DNA
<213> ORGANISM: Glycine max
<220> FEATURE:
<223> OTHER INFORMATION: unsure at all n locations

<400> SEQUENCE: 94
cntaccttca ctgctgaggg ctttganctt antgttngng acaaattcat ctggggcatt     60
tcctcctctc gcgcctgttg cttgaggact tggaaaaatc cgattaccct tcaaagcgct    120
tgatcatcgt tggttcaata cagggaacaa caaacacatt ggctggtaat gtactcccaa    180
ggctaacctt ggtgacttga ggggacttca gggtggtttg aatgggctaa acagctcagc    240
catgattgat ggtggagatt cgatggtgcc aagc                                 274

<210> SEQ ID NO 95
<211> LENGTH: 284
<212> TYPE: DNA
<213> ORGANISM: Glycine max

<400> SEQUENCE: 95
cagtattgtg aaatgttgaa agcagacgag tggcctgttt gtgcatttat ttctcaagat     60
tgtcgtccag caaatccatc ggaagaagcg cacaatgttc aaacatcgta tgaagtgtgg    120
gagaagacat tagagatgat tggccttccc tcagatgctg tggaaaggct tttagatggg    180
gaagaagtta aatgccgtta tggacaagaa cagtaatcta atatacaata tctcccttaa    240
tctgtaaggg cacttccatt atttatagct agtaatgagc attt                      284

<210> SEQ ID NO 96
<211> LENGTH: 265
<212> TYPE: DNA
<213> ORGANISM: Glycine max
<220> FEATURE:
<223> OTHER INFORMATION: unsure at all n locations

<400> SEQUENCE: 96
aagagagaga tggcaacgac gacgtcgtct tcaagcgagg nagcaccgaa cactaagaag     60
aacaagaagg agcgtttagg ttggntagaa tggttaagag gttggttcta tttggtctac    120
gaaatgctct ttcagcgcat catggcgagc cacttgcaca accctatgcc tctccctcct    180
gtaaacgacc tcacttgcat tgtcaccggc tccaccagcg gcattggcct cgaaattgct    240
aggcaattgg ctcagtcagg ggccc                                           265

<210> SEQ ID NO 97
<211> LENGTH: 135
<212> TYPE: DNA
<213> ORGANISM: Glycine max
<220> FEATURE:
<223> OTHER INFORMATION: unsure at all n locations

<400> SEQUENCE: 97
ggaaagaaca atggttggca gtaggtatac tacaagtaac tcctcaatcc catgtaagan     60
aacaaaaggc agcttcttta atgccagtat tgcacaacac ctcagactag tacaanaaaa    120
```

```
aacaaagaaa agggg                                                  135

<210> SEQ ID NO 98
<211> LENGTH: 129
<212> TYPE: DNA
<213> ORGANISM: Glycine max

<400> SEQUENCE: 98
ccatttgcca ttggatggcg ctgctagaat ttgtactggt gccaccagtt tcctctccct  60
ttatgtccca gatgagtacc caagtggcaa aaattagatt agactaatat atatatattg 120
ttttatcag                                                        129

<210> SEQ ID NO 99
<211> LENGTH: 270
<212> TYPE: DNA
<213> ORGANISM: Glycine max

<400> SEQUENCE: 99
gtccaggccc ggtggcggcg gtggcattag cagggtcctt caagacggtg ccgtttggga  60
aaaaggctgg ggttaatgcc cctgttgttt acggtgtcat gccacctgac gcatatcgtg 120
ctgccaaggg tgttcctacc gatcaaaaac ctggtcctgt gcctttcttc gctgctggaa 180
tcagctccgt tttacaccca agaacccgt ttgcccctac cctacatttc aactatcgct 240
attttgaaac cgatgctcct aaagatgctc                                 270

<210> SEQ ID NO 100
<211> LENGTH: 264
<212> TYPE: DNA
<213> ORGANISM: Glycine max
<220> FEATURE:
<223> OTHER INFORMATION: unsure at all n locations

<400> SEQUENCE: 100
aattgcgaag gggacgatat gttgaattca atttggtata tgatagnggt acaacatttg  60
gnctgaaaac tggagggaga atagagagta tacttgtttc tctcccactg actgctcggt 120
gggaatacga tcataaaccg gaagaaggaa gcgaagaatg gaaactcttg gacgcatgca 180
tcaaccccaa ggaatggatc taattcatca gttgacccccc caatttgtca gcttttttaat 240 ttaataataa gggagcttgt ttct                                       264

<210> SEQ ID NO 101
<211> LENGTH: 249
<212> TYPE: DNA
<213> ORGANISM: Glycine max

<400> SEQUENCE: 101
ctcccttatt attaaattaa aaagctgaca aattggggg tcaactgatg aattagatcc  60
attccttggg gttgatgcat gcgtccaaga gtttccattc ttcgcttcct tcttccggtt 120
tatgatcgta ttcccaccga gcagtcagtg ggagagaaac aagtatactc tctattctcc 180
ctccagtttt cagtccaaat gttgtacccc tatcatatac caaattgaat tcaacatatc 240
gtccccttc                                                        249

<210> SEQ ID NO 102
<211> LENGTH: 262
<212> TYPE: DNA
<213> ORGANISM: Glycine max
```

```
<400> SEQUENCE: 102
ggagatgctc ctttcctttg ctactgaatg tgcaaattct gttattcctg cttatttacc      60
tatcatagag aaaaggaagg atttgccctt caatgatcat cagaaagcat ggcaacaatt     120
gcgaagggga cgatatgttg aattcaattt ggtatatgat aggggtacaa catttggact     180
gaaaactgga gggagaatag agagtatact tgtttctctc ccactgactg ctcggtggga     240
atacgatcaa aaccggaaga ag                                              262

<210> SEQ ID NO 103
<211> LENGTH: 240
<212> TYPE: DNA
<213> ORGANISM: Glycine max

<400> SEQUENCE: 103
agatgctcct ttcctttgct actgaatgtg caaattctgt tattcctgct tatttaccta      60
tcatagagaa aaggaaggat ttgcccttca atgatcatca gaaagcatgg caacaattgc     120 gaagggacg atatgttgaa ttcaatttgg tatatgatag ggtacaaca tttggactga       180 aaactggagg gagaatagag agtatacttg tttctctccc actgactgct cggtgggaat     240

<210> SEQ ID NO 104
<211> LENGTH: 249
<212> TYPE: DNA
<213> ORGANISM: Glycine max

<400> SEQUENCE: 104
acggctgcga gaagacgaca gaagggatg atcttaatga ctatgatcag gagatgctcc       60
tttcctttgc tactgaatgt gcaaattctg ttattcctgc ttatttacct atcatagaga     120 aaggaagga tttgcccttc aatgatcatc agaaagcatg gcaacatttg cgaacgggga      180
cgatatgttg aattcaattt ggtatatgat aggggtacaa catttggact gaaaactgga     240
gggagaata                                                             249

<210> SEQ ID NO 105
<211> LENGTH: 250
<212> TYPE: DNA
<213> ORGANISM: Glycine max
<220> FEATURE:
<223> OTHER INFORMATION: unsure at all n locations

<400> SEQUENCE: 105
aattgcgnag gggangatat gntgaatnca attnggtana tgntanngga acaacanttg      60
gactgaatnc tggaggggag aatagagagt atacttgttt ctctcncact gactgctcgg     120
tgggaatacg atcatnaacc ggnagangga agcgaagact ggnaactctt ggncgcatgc     180
atnaacccca aggaatggat ctaattcatc agttgacccc ccaatttgtc agcttttaa      240 tttaataata                                                            250

<210> SEQ ID NO 106
<211> LENGTH: 268
<212> TYPE: DNA
<213> ORGANISM: Glycine max

<400> SEQUENCE: 106
ggatttgccc ttcaatgatc atcagaaagc atggcaacaa ttgcgaaggg gacgatatgt      60
tgaattcaat ttggtatatg ataggggtac aacatttgga ctgaaaactg agggagaat     120 agagagtata cttgtttctc tcccactgac tgctcggtgg aatacgatc ataaaccgga     180
```

```
agaaggaagc gaagaatgga aactcttgga cgcatgcatc aaccccaagg aatggatcta    240
attcatcagt tgaccccca atttgtca                                        268
```

<210> SEQ ID NO 107
<211> LENGTH: 268
<212> TYPE: DNA
<213> ORGANISM: Glycine max

<400> SEQUENCE: 107

```
acggctgcga aagacgaca gaagggggaga aaaggaagga tttgcccttc aatgatcatc    60
agaaagcatg gcaacaattg cgaaggggac gatatgttga attcaatttg gtatatgata   120
ggggtacaac atttggactg aaaactggag ggagaataga gagtatactt gtttctctcc   180
cactgactgc tcggtgggaa tacgatcata aaccggaaga aggaagcgaa gaatggaaac   240
tcttggacgc atgcatcaac cccaagga                                      268
```

<210> SEQ ID NO 108
<211> LENGTH: 321
<212> TYPE: DNA
<213> ORGANISM: Glycine max

<400> SEQUENCE: 108

```
ggaagacctt atcatctccg aatttcattt tcagaagcct ctttgggaat caaatccgaa    60
gcatgatgca ttgtgcgagc attgtctcgg ctccgtccta cgcgttccct tttctctctg   120
gctccgcttc cactactcca actgcgatct cgctcactaa gcgcagttgg aagccacctc   180
cgagcatggc aaaaggccca gtcagagcca ccgtttctat agagaaagag accccggagg   240
ccaatcgtcc cgaaacgttt ctcagaggag tggacgaggc ccagtcttcc acttcggttc   300
gggcccgctt cgagaagatg a                                             321
```

<210> SEQ ID NO 109
<211> LENGTH: 282
<212> TYPE: DNA
<213> ORGANISM: Glycine max

<400> SEQUENCE: 109

```
cacatccgaa gcatgatgca ttgtgcgagc attgtctcgg ctccgtccta cgcgttccct    60
tttctctctg gctccgcttc cactactcca actgcgatct cgctcactaa gcgcagttgg   120
aagccacctc cgagcatggc aaaaggccca gtcagagcca ccgtttctat agagaaagag   180
accccggagg ccaatcgtcc cgaaacgttt ctcagaggag tggacgaggc ccagtcttcc   240
acttcggttc gggcccgctc tcgagaagat gataagggac gc                      282
```

<210> SEQ ID NO 110
<211> LENGTH: 260
<212> TYPE: DNA
<213> ORGANISM: Glycine max

<400> SEQUENCE: 110

```
ccttatcatc tccgaatttc attttcagaa gcctctttgg gaatcaaatc cgaagcatga    60
tgcattgtgc gagcattgtc tcggctccgt cctacgcgtt ccttttctc tctggctccg   120 cttccactac tccaactgcg atctcgctca ctaagcgcag ttggaagcca cctccgagca   180
tggcaaaagg cccagtcaga gccaccgttt ctatagagaa agaccccg gaggccaatc   240 gtcccgaaac gtttctcaga                                               260
```

<210> SEQ ID NO 111
<211> LENGTH: 269
<212> TYPE: DNA
<213> ORGANISM: Glycine max

<400> SEQUENCE: 111

```
ctctttggga atcaaatccg aagcatgatg cattgtgcga gcattgtctc ggctccgtcc      60
tacgcgttcc cttttctctc tggctccgct ccactactcc aactgcgat  ctcgctcact     120
aagcgcagtt ggaagccacc tccgagcatg gcaaaaggcc cagtcagagc cacgtttcta    180
tagagaaaga taccccggag ccaatcgtcc cgaaacgtt  tctcagagga gtggacgagg    240
cccagtcttc cacttcggtt cgggcccgc                                       269
```

<210> SEQ ID NO 112
<211> LENGTH: 260
<212> TYPE: DNA
<213> ORGANISM: Glycine max

<400> SEQUENCE: 112

```
tgtgcgagca ttgtctcggc tccgtcctac gcgttccctt ttctctctgg ctccgcttcc      60
actactccaa ctgcgctctc gctcactaag cgcagttgga agccacctcc gagcatggca    120
aaaggcccag tcagagccac cgtttctata gagaaagaga ccccggaggc caatcgtccc    180
gaaacgtttc tcagaggagt ggacgaggcc cagtcttcca cttcggttcg ggcccgcttc    240
gagaagatga taagggaggc                                                 260
```

<210> SEQ ID NO 113
<211> LENGTH: 279
<212> TYPE: DNA
<213> ORGANISM: Glycine max
<220> FEATURE:
<223> OTHER INFORMATION: unsure at all n locations

<400> SEQUENCE: 113

```
gaagacttta tcatttccga atttcntttt cagangcctc tttgggaatc anntccnnng      60
catgatgcat tgtngcgagc nttgtctacg gctccgtcct acgcgttccc ttttcgctct    120
ggctccgctt ccactactcc aactgcgntc tcgctcacta agcgcagttg gaagccacct    180
ccgagnatgg caaaaggccc agtcagagcc accgtttcta tagagaaaga accccggag     240
gccaatcgtc ccgaaacgtt tctcagagga gtggacgag                            279
```

<210> SEQ ID NO 114
<211> LENGTH: 247
<212> TYPE: DNA
<213> ORGANISM: Glycine max

<400> SEQUENCE: 114

```
ctccgaattt cattttcaga agcctctttg gaatcaaat  tggagtgtct gcaatccact      60
ccgaagcatg atgcattgtg cgagcattgt ctcggctccg tcctacgcgt tccttttcg     120
ctctggctcc gctctccact actccaactg cgatctcgct ctcaagcgc  agttggaagc    180
cacctccgag catggcaaaa gcccagtcag agccaccgtt tctatagaga aagagacccc    240
ggaggcc                                                               247
```

<210> SEQ ID NO 115
<211> LENGTH: 253
<212> TYPE: DNA
<213> ORGANISM: Glycine max

<400> SEQUENCE: 115

```
cagaagcctc tttgggaatc aaatccgaag catgatgcat tgtgcgagca ttgtctcggc    60
tccgtcctac gcgttccctt ttctctctgg ctccgcttcc actactccaa ctgccctctc   120
gctcactacg cgcagttgga agccacctcc gagcatggca aaaggcccag tcagagccac   180
cgtttctata gagatagaga ccccggaggc caatcgtccc gaaacgtttc tcagaggagt   240
ggacgaggcc cag                                                      253
```

<210> SEQ ID NO 116
<211> LENGTH: 268
<212> TYPE: DNA
<213> ORGANISM: Glycine max

<400> SEQUENCE: 116

```
tcgagcgcgt tcccttttct ctctggctcc gcttccacta ctccacatgc gctctcgctc    60
actaagcgca gttggaagcc acctccgagc atggcaaaag gcccagtcag agccaccgtt   120
tctatagaga aagagacccc ggaggccaat cgtcccgaaa cgtttctcag aggagtcgtc   180
gaggcccagt cttccacttc ggttcgggcc cgcttcgaga agatgataag ggaggcccag   240
gacaccgtgt gcagtgccct cgaggccg                                      268
```

<210> SEQ ID NO 117
<211> LENGTH: 238
<212> TYPE: DNA
<213> ORGANISM: Glycine max

<400> SEQUENCE: 117

```
atccgaagca tgatgcattg tgcgagcatt gtctcggctc cgtcctacgc gttccctttt    60
ctctctggct ccgcttccac tactccaact gcgatctcgc tcactaagcg cagttggaag   120
ccacctccga gcatggcaaa aggcccagtc agagccaccg tttctataga gaaagacacc   180
ccggaggcca atggtcccga acgtttctc agaggagtgg acgaggccca ttcttcca     238
```

<210> SEQ ID NO 118
<211> LENGTH: 250
<212> TYPE: DNA
<213> ORGANISM: Glycine max

<400> SEQUENCE: 118

```
tccgaagcat gatgcattgt gcgagcattg tctcggctcc gtcctacgcg ttccttttc    60 tctctggctc cgcttccact actccaactg ccctctcgct cactaagcgc agttggaagc   120
cacctccgag catggcaaaa ggaccagtca gagccaccgt ttctacagag acagagaccc   180
cggaggccaa tcgtcccgaa acgtttctca gaggagtgga cgaggccaag tcttccactt   240
cggttcgggc                                                          250
```

<210> SEQ ID NO 119
<211> LENGTH: 267
<212> TYPE: DNA
<213> ORGANISM: Glycine max

<400> SEQUENCE: 119

```
actcgagccg attcggctcg agctctttgg gaatcaaatc cgaaacatga tgcattgtgc    60
gaccattgtc tcggctccgt cactacgcgt tccttttct ctctggctcc gcttccacta   120
ctccaactac tactctcgct cactaagcgc agttggaagc cacctccgag catggcaaaa   180
```

```
ggcccagtca gagccaccgt ttctatagag acagacaccc cggaagccaa ttctcccgaa    240
acgtttctca gacgactgga cgaggcc                                        267

<210> SEQ ID NO 120
<211> LENGTH: 119
<212> TYPE: DNA
<213> ORGANISM: Glycine max

<400> SEQUENCE: 120 tcatttttcag aagcctcttt gggaatcaaa tccgaagcat gatgcattac gcgagcattg    60
tctcggctcc gtcctacgcg ttcccttttc tctctggctc cgcttccaca caacatacg    119

<210> SEQ ID NO 121
<211> LENGTH: 117
<212> TYPE: DNA
<213> ORGANISM: Glycine max
<220> FEATURE:
<223> OTHER INFORMATION: unsure at all n locations

<400> SEQUENCE: 121
cgaatttcat tttcagaagc ctctttggga atcaaatccg aagcatgatg cattgngcga    60
gcattgtctc ggctccgtcc tacgcgttcc cttttctctc tggctccgct tccacaa     117

<210> SEQ ID NO 122
<211> LENGTH: 94
<212> TYPE: DNA
<213> ORGANISM: Glycine max

<400> SEQUENCE: 122
caaatccgaa gcatgatgca ttgtgcgagc attgtctcgg ctccgtccta cgcgttccct    60
tttctctctg gctccgcttc cacacaacat acga                                94

<210> SEQ ID NO 123
<211> LENGTH: 81
<212> TYPE: DNA
<213> ORGANISM: Glycine max

<400> SEQUENCE: 123
cattttcaga agcctctttg gaatcaaat ccgaagcatg atgcattgtg cgagcattgt    60
ctcggctccg tcctacgcgt t                                              81

<210> SEQ ID NO 124
<211> LENGTH: 246
<212> TYPE: DNA
<213> ORGANISM: Glycine max
<220> FEATURE:
<223> OTHER INFORMATION: unsure at all n locations

<400> SEQUENCE: 124
cgagacccgg aggccaatcg tcncgaaacg tttctcagag gagtggacga gtgccagtct    60
tccacttcgg ttcgggcntc gttcgagaag atgataaagg gaggcccagg acaccgtgtg   120
cagtgccctc gaggccgctg atggtggggc ccagttcaag gaggacgttt ggtccaggcc   180
cggtggcggc ggtggcatta gcagggtcct tcaagacggt gccgtttggg agaaggctgg   240
ggttaa                                                              246

<210> SEQ ID NO 125
<211> LENGTH: 261
<212> TYPE: DNA
<213> ORGANISM: Glycine max
```

<400> SEQUENCE: 125

```
gaaagagacc ccggaggcca atcgtcccga aacgtttctc agaggagtgg acgaggccca    60
gtcttccact tcggttcggg cctgcttcga aagatgata agggaggccc aggacaccgt    120
gtgcagtgcc ctcgaggccg ctgatggtgg ggcccagttc atggaggacg tttggtccag   180
gcccggtggc ggcggtggca ttagcagggt ccttcaagac ggtgccgttt gggagaaggc   240
tggggttaat gtctctgttg t                                             261
```

<210> SEQ ID NO 126
<211> LENGTH: 239
<212> TYPE: DNA
<213> ORGANISM: Glycine max
<220> FEATURE:
<223> OTHER INFORMATION: unsure at all n locations

<400> SEQUENCE: 126

```
accaatcgtc ccgaaacgtt tctcagagga gtggacgagg cccagtcttc cacttcggtt    60
cgggcccgct tcgagaagat gataagggag gcccaggaca ccgtgtgcag tgccctcgag   120
gccgctgatg gtggggccca gttcaaggag gacgtttggt ccaggcccgg tggcggcggt   180
ggcnncagca ggtccttcaa gacggtgccg tttgggagaa ggctgggggtt aatgtctct   239
```

<210> SEQ ID NO 127
<211> LENGTH: 162
<212> TYPE: DNA
<213> ORGANISM: Glycine max

<400> SEQUENCE: 127

```
atcaagtgct tgttatgatg agtcagaatg ttagcttgtt gtactaggtg gattgtaaat    60
cacgtatttt gctagagtca tccgcgtaaa gcgtgaaaat gcagaaaatt acaaatgtct   120
aggctgcgtc tgtagtatac ctactgccaa ccattgttct tt                     162
```

<210> SEQ ID NO 128
<211> LENGTH: 114
<212> TYPE: DNA
<213> ORGANISM: Glycine max
<220> FEATURE:
<223> OTHER INFORMATION: unsure at all n locations

<400> SEQUENCE: 128

```
atcaagtgct tgttcatgat ggtcagaatg ttagcttgtt gtactaggtg gattgtaaat    60
cacgtatctt gctagagtnc tccgcgcgga gcgtgaanat gcagagaatt acaa        114
```

<210> SEQ ID NO 129
<211> LENGTH: 253
<212> TYPE: DNA
<213> ORGANISM: Glycine max

<400> SEQUENCE: 129

```
ggcgtctgcc aaaaccaaaa ggtcagactg ttggatcttt ccggaaggga cttaccatgt    60
tgcctgatgc aatttctgcc agactaggca acaaagtaaa gttatcttgg aagctttcaa   120
gtattagtaa actggatagt ggagagtaca gtttgacata tgaaacacca gaaggagtgg   180
tttcttttgca gtgcaaaact gttgtcctga ccattccttc ctatgttgct agtacatgcc   240
tgcgtcctct gtc                                                      253
```

<210> SEQ ID NO 130

<211> LENGTH: 298
<212> TYPE: DNA
<213> ORGANISM: Glycine max
<220> FEATURE:
<223> OTHER INFORMATION: unsure at all n locations

<400> SEQUENCE: 130

```
gctgcagatg cactttcaaa gttttattac cctccagttg ctgcagtttc catatcctat      60
ccanaagaag ctattagatc agaatgcttg atagatggtg agttgaaggg ggttggtcaa     120
ttgcatccac gtagacaagg agtggaaaca ttaggaacta tatacagctc atcactattc     180
cccaaccgag caccacgacg gaaggttcta ctcttgaatt acattggagg agcaactaat     240
actggaattt tatcgaagac ggacagtgaa cttgtggaaa cagttgatcg agatttga      298
```

<210> SEQ ID NO 131
<211> LENGTH: 283
<212> TYPE: DNA
<213> ORGANISM: Glycine max

<400> SEQUENCE: 131

```
caattatata taatctcctg ctgactcgtc tttttctttg gaataatgat atactgtcaa      60
aaaccatata taatctcctg ctgacacatc tttttctttt cttttcttta tatcattttc     120
cttattagtt tctttgttta ctgcagtgac gagcttagga aaattgttac ttctgacctg     180
agaaagttgt tgggagcaga gggggaacca acatttgtta accatttcta ttggagtaaa     240
ggctttcctt tgtatggacg taactatggg tcagttctta agc                       283
```

<210> SEQ ID NO 132
<211> LENGTH: 250
<212> TYPE: DNA
<213> ORGANISM: Glycine max

<400> SEQUENCE: 132

```
tgacaatttt gatgatagag gtggataata aagctgcagt ccttggttat atcggggcac      60
cgctcactct ggcatcacat gtgattgaag gtggttcatc accaaacttc tcgcaaataa     120
agagattggc tttctcagca tccaagatcc tgcactcgtt actgcagaag tttacgacat     180
ctctggcgag atacattctc taccaagctg acaatggagc tcaagctgtt cagatctttg     240
attcatgggc                                                            250
```

<210> SEQ ID NO 133
<211> LENGTH: 235
<212> TYPE: DNA
<213> ORGANISM: Glycine max

<400> SEQUENCE: 133

```
tgacaatttt gaggaaagag gtggataata aagctgcagt ccttggtttt gtcggggcac      60
cgttcactct ggcatcatat gtggttgaag gtggttcatc aaaaaacttc tcaaaaataa     120
agagattggc tttctcagaa tccaagatcc tgcactcgtt actgcagaag tttacaacat     180
caatggcaag atacattcaa taccaagctg acaatggagc tcaagctgtt cagat          235
```

<210> SEQ ID NO 134
<211> LENGTH: 282
<212> TYPE: DNA
<213> ORGANISM: Glycine max
<220> FEATURE:
<223> OTHER INFORMATION: unsure at all n locations

<400> SEQUENCE: 134

-continued

```
gtggacaact accacctgaa atgtgggaac gctggtcaaa gccttatatc aaagagattg      60
taaatttggt cangaaaaaa tgccctgggg taccaattgt tctttatata aacggaaatg     120
gtggtcttct tgagcgtatg anagacaccg gagttgatgt tatagggcta gactggacag     180
tggatatggc agatggaaga agaagattgg gtagtgggat aggtgttcag ggaaatgtgg     240
accctgccta cttattctcc cctcttgatg ccctgactga ag                       282
```

<210> SEQ ID NO 135
<211> LENGTH: 256
<212> TYPE: DNA
<213> ORGANISM: Glycine max

<400> SEQUENCE: 135

```
gggggatcct gttagtcgtc ctccggcatg gatgatgcgc aggccggaa ggtacatggc      60 tgtttacaaa aagcttgctg agaaatatcc atccttccga gagaggtcag agacaactga    120
tctcattgtg gaaatttctt tgcagccttg gaatgctttc aggcctgatg gagtaattat    180
cttctcggac atccttacac cacttcctgc gtttggagtt gattttgaca tagaagaagt    240 aagggacct gttata                                                     256
```

<210> SEQ ID NO 136
<211> LENGTH: 386
<212> TYPE: DNA
<213> ORGANISM: Glycine max
<220> FEATURE:
<223> OTHER INFORMATION: unsure at all n locations

<400> SEQUENCE: 136

```
ttcaggctca gccgcatagt taaggaaccg aaactccaca taggaatcac ttggtttctt      60
tgctctcccc caacccaatg gctacttcca ttaacagcag tgctctgggg tggaaacatt    120
catccttctt cgtacaatcc aataatggct tcaacgttgc ttcgcctcct ttcaaaccaa    180
agccgncacg ctcctccaac ttttctctct attgctctgc cgcctcctct tcttctgatc    240
cactgttggt taaggctgct aggggagatc ctgttagtcg tcctccagca tggatgatgc    300
gccaggcagg aaggtacatg gctgtttaca aaaatcttgc tgagaaatat ccatccttcc    360
gagagaggtc agagacaact gaactc                                         386
```

<210> SEQ ID NO 137
<211> LENGTH: 291
<212> TYPE: DNA
<213> ORGANISM: Glycine max

<400> SEQUENCE: 137

```
aggttttaca tccaattgac ctggacaggc ttaaatttgt tggagattca ctaaagatac      60
tgcgccaaga ggttggtggt catgcagctg ttttgggttt tgtgggagca ccttggacaa    120
tagcaacata tatagtggaa gggggtacaa cacgcacata taaccatt aagagcatgt    180 gccacactgc cccacatgta ttgaggactt tgctttctca tttgacgcag gcaatagctg    240
attacgttat tttccaagtg gagtctgggg ctcattgcat acaaatattt g              291
```

<210> SEQ ID NO 138
<211> LENGTH: 288
<212> TYPE: DNA
<213> ORGANISM: Glycine max
<220> FEATURE:
<223> OTHER INFORMATION: unsure at all n locations

```
<400> SEQUENCE: 138
gcgccaagag gttggtggtc atgcagctgt tttgggtttt gtgggagcac cttgggacaa      60
tagcaacata tatagtggaa gggggtacaa cacgcacata tacaaccatt aagagcatgt     120
gccacactgc cccacatgta ttgaggactt tgctttctca tttgacgcag gcaatagctg     180
attacgttat tttccaagtg gagtctgggg ctcattgcat acaaatattt gattcatgnc     240 ngtgacaat accacctgaa atgtgggaac gctggtcaaa gccttata                    288

<210> SEQ ID NO 139
<211> LENGTH: 261
<212> TYPE: DNA
<213> ORGANISM: Glycine max

<400> SEQUENCE: 139
aaagatactg cgccaagagg ttggtggtca tgcagctgtc ttgggttttg tgggagcacc      60
ttggacaata gcaacatata tagtggaagg gggtacaaca cgcacatata caaccattaa     120
gagcatgtgc cacactgccc cacatgtatt gaggactttg ctttctcatt tgacgcaggc     180
aatagctgat tacgttattt tccaagtgga gtctggggct cattgcatac aaatattaga     240
tcatggggtg acaactacc a                                                 261

<210> SEQ ID NO 140
<211> LENGTH: 213
<212> TYPE: DNA
<213> ORGANISM: Glycine max

<400> SEQUENCE: 140
gacaatagca acatatatag tggaaggggg tacaacacgc acatatacaa ccattaagag      60
catgtgccac actgccccac atgtattgag gactttgctt tctcatttga cgcaggcaat     120
agctgattac gttatttttcc aagtggagtc tggggctcat tgcatacaaa tatttgattc    180
atggggtgga caactaccac tgaaatgtgg gga                                   213

<210> SEQ ID NO 141
<211> LENGTH: 236
<212> TYPE: DNA
<213> ORGANISM: Glycine max

<400> SEQUENCE: 141
tgttgaaaga cccccggttt ggctcatgag gcaagcaggg aggtacatga agagttacca      60
aaccatctgt gagaaatatc cttcattccg tgaaagatct gaaaatgttg atctcgtggt     120
ggaaatttct ctgcaaccat ggcatgtttt taagcccgat ggagtgattt tattctcaga     180
cattcttacc ccactttctg gaatgaatat accctttgat attgtgaagg gtaagg          236

<210> SEQ ID NO 142
<211> LENGTH: 263
<212> TYPE: DNA
<213> ORGANISM: Glycine max

<400> SEQUENCE: 142
tttggctcat gaggcaagca gggaggtaca tgaagagtta ccaaaccatc tgtgagaaat      60
atccttcatt ccgtgaaaga tctgaaaatg ttgatctcgt ggtggaaatt tctctgcaac     120
cgtggcatgt tttcaagcct gatggagtga ttttattctc agacattctt accccacttt     180
ctggaatgaa atacccttt gatattgtga agggtaaggg tcctgttata tttgatccta     240
ttcacacatc tgcccaggtt gat                                              263
```

<210> SEQ ID NO 143
<211> LENGTH: 258
<212> TYPE: DNA
<213> ORGANISM: Glycine max

<400> SEQUENCE: 143

```
gcttttgcta aatgcagttc gcgggataga tgttgaaaga cccccggttt ggctcatgag      60
gcaagcaggg aggtacatga agagttacca aaccatctgt gagaaatatc cttcattccg     120
tgaaagatct gaaaatgtga tctcgtggtg gaaatttctc tgcaaccgtg gcatgttttc     180
aagcctgatg gagtgatttt attctcagac attcttaccc cactttctgg aatgaatata     240
ccctttgata ttgtgaag                                                   258
```

<210> SEQ ID NO 144
<211> LENGTH: 262
<212> TYPE: DNA
<213> ORGANISM: Glycine max

<400> SEQUENCE: 144

```
caaacatgct ttgcgtcaac actgccttca cctctttctt gcccagaaaa tcaatttgct      60
tcttttcctc caaatcaacc accccaattt cctgcaccct ccaaggaaca gttgcagaac     120
caaaatctac agctgctggt gaacctcttt tgctaaatgc agttcgtggg atagatgttg     180
aaagaccccc ggtttggctc atgaggcaag cagggaggta catgaagagt taccaaacca     240
tctgtgagag atatccttca tt                                              262
```

<210> SEQ ID NO 145
<211> LENGTH: 283
<212> TYPE: DNA
<213> ORGANISM: Glycine max

<400> SEQUENCE: 145

```
acttgttatc tatacagatg ttgcattaga tccttattca tcagatgggc atgatggcat      60
agttagagaa gatggagtta ttatgaatga tgagacagtt catcagctat gtaaacaagc     120
tgtagcccag gcccaagctg agcagatgt tgtccagtct agtgatatga tggatggtcg     180
ggtaggagca ctgcgtgcag ctctggatgc tgaaggcgtt cagcatgtat ctataatgtc     240
ctatacagca aagtatgcaa gttcttttta tggtccattt aga                       283
```

<210> SEQ ID NO 146
<211> LENGTH: 316
<212> TYPE: DNA
<213> ORGANISM: Glycine max

<400> SEQUENCE: 146

```
ctgagatgcg ggaggatgaa tctgaaggag ctgacattct cttggtgaag cctggtcttc      60
cttacttgga tatcataagg ctgctcaggg ataattctcc tttgccaatt gcagcatacc     120
aggtttctgg tgaatatgca atgataaagg ctgccggtgc tctcaaaatg atagacgaag     180
aaaaggttat gatggagtca ctgatgtgcc tccgaagggc cggtgctgat atcatcctca     240
catattctgc tctgcaagct gccagatgtt tgtgtggaga aagagtgaa gttctctgat      300
tatgtagggc gttgtt                                                     316
```

<210> SEQ ID NO 147
<211> LENGTH: 271
<212> TYPE: DNA

<213> ORGANISM: Glycine max

<400> SEQUENCE: 147

```
tcgccggtaa ggttccgccg gcgcctcccg tgccgcccag accggcggct cccggttgga      60
acaccggtgg ttccttcact tccacaccac cggcgtcctc gtcggaaccg gaagtcgccg     120
gcgcttcggt cggcttttca ggaaacgagc atttcgccgg cgaatttcgt gtatccgctt     180
ttcattcacg aaggtgaaga ggatactcca attgggcta tgcctggatg ctacaggctt      240
gggtggaggc atggacttgt agaagaggtt g                                    271
```

<210> SEQ ID NO 148
<211> LENGTH: 275
<212> TYPE: DNA
<213> ORGANISM: Glycine max
<220> FEATURE:
<223> OTHER INFORMATION: unsure at all n locations

<400> SEQUENCE: 148

```
aagcctggtc ttccttactt ggatatcata agtctgctca gggataattc tcctttgcca     60
attgcagcat accaggttct tttctttgcc cattctagca ctaggcaaaa cgtttctgat    120
aaaaagttga tcagatattc aatacatttt aaccagtgga attctgcntt aagcttgctg    180
caagtgacag angtctatac gtagtagaca aatatcacac ctctagttta atatcaggct    240
gaggtacaag tttatggttg ctttaacagt tattg                               275
```

<210> SEQ ID NO 149
<211> LENGTH: 191
<212> TYPE: DNA
<213> ORGANISM: Glycine max
<220> FEATURE:
<223> OTHER INFORMATION: unsure at all n locations

<400> SEQUENCE: 149

```
ccggtgctga tatcatcctc acatattctg ctctgcaagc tgccagatgt ttgtgtggag      60
agaagaggtg aagttctctg attatgcagg gcgttgttca tgtagaaggt tgaagagttt    120
anaaanccca gtnccggngn tncgggnnnt cnnaaaattt taaaagggnc cccgcggttt    180
ntcnaaaang a                                                          191
```

<210> SEQ ID NO 150
<211> LENGTH: 250
<212> TYPE: DNA
<213> ORGANISM: Glycine max

<400> SEQUENCE: 150

```
aggagatgaa gcatacagtg aaaatggttt agtgcctcgg acaatacgtt tgctcaagga      60
taagttacca gaccttggta accaatccag aggtggaata aatcctaat ccgtcagatg     120
ggcatgatgg catagtaaga gaagatgaag taataatgat tatgagacag gtcatcagcc    180
atggtaacaa gctgtagacc aaggccaagc tggagcagat gttgtcagtc ctagtgatat    240
gatggatggt                                                            250
```

<210> SEQ ID NO 151
<211> LENGTH: 357
<212> TYPE: DNA
<213> ORGANISM: Glycine max

<400> SEQUENCE: 151

```
acggctgcga caagacgaga taatgtggct gattggtaac gtagtgaatc ctgtgcatac     60
```

```
atccgctcgt agcctcttcc tgcgactctc ttctcagtgg gtctccgtat tctccctcaa    120
tcctattaac cttttcttct ttcatttccc accccattct ataatcaatc agtgtcaatg    180
gcttcttcaa tcgctaatgc gccttctgcg ttcaattctc agtactactt tggtctcaga    240
acgccactga ggtccttcaa cttttcttct cctcaagctg ccaaacttcc acgctcgcat    300
tgccttttcg tcgtcagagc ctccgattcg gtcttcgaaa ccgccgttgt cgccggt      357

<210> SEQ ID NO 152
<211> LENGTH: 418
<212> TYPE: DNA
<213> ORGANISM: Glycine max

<400> SEQUENCE: 152
agcccaggcg tcagtacggc tgcgagaaga cgacagaagg ggatggttga ctggttgttt    60
tttaaattgc atgaaacatt tatttgttct tatagaaaaa gttacaagta agtcttcact    120
gcaagtagaa gatattggat ccagttccag ggttgaactc catacgatta tttttttaata  180 gaaaaattga ctgtgacgta gctgtggagg acacgattgg taaagtattg aatccttcct   240
gcgactcttt tctcattggt tcactgtgtt ctccaaacac atctcagaat ctcttgtatt   300
attattcaat caatcaatgg cttcttcaat ccctaatgga cctccctctg cgttgaattc   360
ccagttctac gatgatctca gaccgccaca gaggaccttc aacttttcct ttcttcaa     418

<210> SEQ ID NO 153
<211> LENGTH: 243
<212> TYPE: DNA
<213> ORGANISM: Glycine max

<400> SEQUENCE: 153
agcccaagcg tcagtacagc tgcgagagga ggacagaagg ggattctaca atcaatcaat   60
ggcaatggct tcatcaatcc ctaatgcgcc ttctgcgttc aattctcaaa gctacgttgg   120
tctcaggtcg ccactgagga ccttcaactt ttcttctcct caaggtggca aaaatcctcg   180
ctcccaacgc cttttcgacg tcagagcctc cgaatccgag ttccaagccg ccgttgtccc   240
cgg                                                                243

<210> SEQ ID NO 154
<211> LENGTH: 277
<212> TYPE: DNA
<213> ORGANISM: Glycine max
<220> FEATURE:
<223> OTHER INFORMATION: unsure at all n locations

<400> SEQUENCE: 154
cgcagtcnga ggancctcca cagatatnca nctcttaatg tgcaggaana tttccgnggc   60
aatgtcnana caaggttaan aaagctcaat gagggggttg tccaagctac actattagca   120
ttnnctggac tcaaacgctt aatatgacag anaatgtgac ttcaatccta tcantagatg   180
atatgcttcc agctgttgnc caaggtgcca ttggaattgc ctgtagaagt gatgnnnata   240
anatggcaga atacattgat tcacttaatc atganga                            277

<210> SEQ ID NO 155
<211> LENGTH: 285
<212> TYPE: DNA
<213> ORGANISM: Glycine max

<400> SEQUENCE: 155
```

```
tatgagatga agcatacagt gaaaatggtt tagtgcctcg gacaatacgt ttgctcaagg      60
ataagtaccc agaccttgtt atctatacag atgttgcatt agatccttat tcgtcagatg     120
ggcatgatgg catagttaga gaagatggag ttattatgaa tgatgagaca gttcatcagc     180
tatgtaaaca agctgtagcc caggcccaag ctggagcaga tgttgtcagt cctagtgata     240
tgatggatgg tcgggtagga gcactgcgtg cagctcttga tgctg                    285

<210> SEQ ID NO 156
<211> LENGTH: 275
<212> TYPE: DNA
<213> ORGANISM: Glycine max

<400> SEQUENCE: 156
acggctgcga gaagacgaca gaaggggatg ctttgaagtc tcccacagga gatgaagcat      60
acaatgaaaa tggtttagtg cctcgaacaa tacgtttgct caaggataag tacccagacc     120
ttgttatcta tacagatgtt gcattagatc cttattcatc agatgggcat gatggcatag     180
ttagagaaga tggagttatt atgaatgatg agacagttca tcagctatgt aaacaagctg     240
tagcccaggc ccaagctgga gcagatgttg tcagt                                275

<210> SEQ ID NO 157
<211> LENGTH: 262
<212> TYPE: DNA
<213> ORGANISM: Glycine max

<400> SEQUENCE: 157
ttttagtctc ccacaggaga tgaagcatac aatgaaaatg gtttagtgcc tcgaacaata      60
cgtttactca aggataagta cccagacctt gttatctata cagatgttgc attagatcct     120
tattcatcag atgggcatga tggcatagtt agagaagatg gagttattat gaatgatgag     180
acagttcatc agctatgtaa acaagctgta gcccaggtca tatgactgtc ttctataaac     240
attttcaact gtaggcagtt ac                                              262

<210> SEQ ID NO 158
<211> LENGTH: 289
<212> TYPE: DNA
<213> ORGANISM: Glycine max

<400> SEQUENCE: 158
gaaaaggtta tgatggagtc actgatgtgc ctccgaaggc cggtgctgat atcatcctca      60
catattctgc tctgcaagct gccagatgtt tgtgtggaga gaagaggtga agttctctga     120
ttatgtaggg cgttgttcat gtagaaggtt gaagagtttta taatccagt atctgctgga    180 ttttggttat tgtaaattgt ttaagaggga catggaggtt tgtgtataga gagacattca     240
taataaaata ttatggcctc gtttgattta atatatgtaa ggacataat                 289

<210> SEQ ID NO 159
<211> LENGTH: 255
<212> TYPE: DNA
<213> ORGANISM: Glycine max
<220> FEATURE:
<223> OTHER INFORMATION: unsure at all n locations

<400> SEQUENCE: 159
ggttatgatg gagtcactga tgtgcctccg aagggccggt gctgatatca tcctcacata      60
ttctgctctg caagctgcca gatgtttgtg tggagagaag aggtgaagtt ctctgattat     120
gtagggcgtt gttcatgtag aaggttgaag agtttataat accagtatct gctggatttt     180
```

```
ggttattgta aattgtttaa gagggacatg gnggtttgtg tatagagaga cattcctaat    240
taaatattag ggccc                                                    255

<210> SEQ ID NO 160
<211> LENGTH: 262
<212> TYPE: DNA
<213> ORGANISM: Glycine max
<220> FEATURE:
<223> OTHER INFORMATION: unsure at all n locations

<400> SEQUENCE: 160
tcgggtaggn gcactgcgtg cagctctgga tgctgaaggc tttcagcatg tttctataat    60
gtcctataca gcaaagtatg caagttcttt tnatggtcca tttagagagg cactagactc   120 aaaccccgg tttggagaca agaaaactta tcagatgaac ccagctaatt acagagaggc    180
tctgactgag atgcgggagg atgaatctga aggagctgac attctcttgg tgaagcctgg   240
tcttccttac ttggatatca ta                                            262

<210> SEQ ID NO 161
<211> LENGTH: 253
<212> TYPE: DNA
<213> ORGANISM: Glycine max

<400> SEQUENCE: 161
gacagttcat cagctatgta aacaagctgt agcccaggcc caagctggag cagatgttgt    60
cagtcctagt gatatgatgg atggtcgggt aggagcactg cgtgcagctc tggatgctga   120
aggctttcag catgtttcta atgtcctta tacagcaaag tatgcaagtt cttttatgg    180 tccatttaga gaggcactag actcaaaccc ccggtttgga gacaagaaaa cttatcagat   240
gaacccagct aat                                                      253

<210> SEQ ID NO 162
<211> LENGTH: 249
<212> TYPE: DNA
<213> ORGANISM: Glycine max

<400> SEQUENCE: 162
gttgtcagtc ctagtgatat gatggatggt cgggtaggag cactgcgtgc agctctggat    60
gctgaaggct ttcagcatgt ttctataatg tcctatacag caaagtatgc aagttctttt   120
tatggtccat ttagagaggc actagactca aaccccggt tggagacaa gaaaacttat    180 cagatgaacc cagctaatta cagagaggct ctgactgaga tgcgggagga tgaatctgaa   240
ggagctgac                                                           249

<210> SEQ ID NO 163
<211> LENGTH: 248
<212> TYPE: DNA
<213> ORGANISM: Glycine max

<400> SEQUENCE: 163
gacagttcat cagctatgta aacaagctgt agcccaggcc caagctggag cagatgttgt    60
cagtcctagt gatatgatgg atggtcgggt aggagcactg cgtgcagctc tggatgctga   120
aggctttcag catgtttcta atgtcctta tacagcaaag tatgcaagtt cttttatgg    180 tccatttaga gaggcactag actcaaaccc ccggtttgga gacaagaaaa cttatcagat   240
gaacccag                                                            248
```

<210> SEQ ID NO 164
<211> LENGTH: 414
<212> TYPE: DNA
<213> ORGANISM: Glycine max

<400> SEQUENCE: 164

| | | | | | | |
|---|---|---|---|---|---|---|
| acccacgcgt | ccgtacggct | ggagaagacg | acagaagggg | attctataat | caatcaatgg | 60 |
| caatggcttc | ttcaatccct | aatgcgcctt | ctgcgttcaa | ttctcagagc | tacgttggtc | 120 |
| tcagagcgcc | actgaggacc | ttcaactttt | cttctcctca | agctgccaaa | attcctcgct | 180 |
| cccaacgcct | tttcgtcgtc | agagcctccg | attcggagtt | cgaagccgcc | gttgtcgccg | 240 |
| gtaaggttcc | gccggcgcct | cccgtgccgc | ccagaccggc | ggctccggtt | ggaacaccgg | 300 |
| tggttccttc | acttccactt | caccggcgtc | tcgtcggaa | ccggaagtcg | ccggcgcttc | 360 |
| ggtcggcttt | tcaggaaacg | agcatttcgc | cggcgaattt | cgtgtatccg | cttt | 414 |

<210> SEQ ID NO 165
<211> LENGTH: 394
<212> TYPE: DNA
<213> ORGANISM: Glycine max

<400> SEQUENCE: 165

| | | | | | | |
|---|---|---|---|---|---|---|
| tacggctgcg | agaagacgac | agaaggggat | aatcaatcaa | tggcaatggc | ttcttcaatc | 60 |
| cctaatgcgc | cttctgcgtt | caattctcag | agctacgttg | gtctcagagc | gccactgagg | 120 |
| accttcaact | tttcttctcc | tcaagctgcc | aaaattcctc | gctcccaacg | ccttttcgtc | 180 |
| gtcagagcct | ccgattcgga | gttcgaagcc | gccgttgtcg | ccggtaaggt | tccgccggcg | 240 |
| cctcccgtgc | cgcccagacc | ggcggctccg | gttggaacac | cggtggttcc | ttcacttcca | 300 |
| cttcaccggc | gtcctcgtcg | gaaccggaag | tcgccggcgc | ttcggtcggc | ttttcaggaa | 360 |
| acgagcattt | cgccggcgaa | tttcgtgtat | ccgc | | | 394 |

<210> SEQ ID NO 166
<211> LENGTH: 283
<212> TYPE: DNA
<213> ORGANISM: Glycine max
<220> FEATURE:
<223> OTHER INFORMATION: unsure at all n locations

<400> SEQUENCE: 166

| | | | | | | |
|---|---|---|---|---|---|---|
| gcttcttcaa | tccctaatgc | gccttctgcg | ttcaattctc | agagctacgt | tggtctcaga | 60 |
| gcgccactga | ggaccttcaa | cttttcttct | cctcaagctg | ccaaaattcc | tcgctcccaa | 120 |
| cgccttttcg | tcgtcagagc | ctccgattcg | gagttcgnag | ccgccgttgt | cgccggtaag | 180 |
| gttcnccgg | cgcctcccgt | gccgcccaga | ccggcggctc | cggttggaac | accggtggtt | 240 |
| ccttcacttc | cacttcaccg | gcgtcctcgt | cggaaccgga | agt | | 283 |

<210> SEQ ID NO 167
<211> LENGTH: 286
<212> TYPE: DNA
<213> ORGANISM: Glycine max
<220> FEATURE:
<223> OTHER INFORMATION: unsure at all n locations

<400> SEQUENCE: 167

| | | | | | | |
|---|---|---|---|---|---|---|
| aatccctaat | gcgccttctg | cgttcaattc | tcagagctac | gttggtctca | gagcgccact | 60 |
| gaggaccttc | aactttctt | ctcctcaagc | tgccaaaatt | cctcgctccc | aacgcctttt | 120 |
| cgtcgtcaga | gcctccgatt | cggagttcga | agccgncgtt | gtcgccggta | aggttccgcc | 180 |

```
ggngcctccc gtnccgccca gaccggcggc tccggttgga acaccggtgg ttccttcact    240
tccacttcac cggcgtcctc gtcggaaccg gaagtcgcgg cgcttt                   286
```

<210> SEQ ID NO 168
<211> LENGTH: 278
<212> TYPE: DNA
<213> ORGANISM: Glycine max

<400> SEQUENCE: 168

```
cttcaatccc taatgcgcct tctgcgttca attctcagag ctacgttggt ctcagagcgc    60
cactgaggac cttcaacttt tcttctcctc aagctgccaa aattcctcgc tcccaacgcc    120
ttttcgtcgt cagagcatcc gattcggagt tcgaagccgc cgttgtcgcc ggtaaggttc    180
cgccggcgcc tcccgtgccg cccagaccgg cggctccggt tggaacaccg gtggttcctt    240
cacttccact tcaccggcgt cctcgtcgga accggaag                            278
```

<210> SEQ ID NO 169
<211> LENGTH: 268
<212> TYPE: DNA
<213> ORGANISM: Glycine max

<400> SEQUENCE: 169

```
ggcttcttca atccctaatg cgccttctgc gttcaattct cagagctacg ttggtctcag    60
agcgccactg aggaccttca acttttcttc cctcaagctg ccaaaattc ctcgctccca     120 acgccttttc gtcgtcagag cctccgattc ggagttcgaa gccgccgttg tcgccggtaa    180
ggttccgccg gcgcctcccg tgccgcccag accggcggct ccggttggaa caccggtggt    240
tccttcactt ccacttcacc ggcgtcct                                       268
```

<210> SEQ ID NO 170
<211> LENGTH: 356
<212> TYPE: DNA
<213> ORGANISM: Glycine max

<400> SEQUENCE: 170

```
attgaatcct gtgcatacat cctcacttat cctcttcctg cgactctctt ctcattggtt    60
ctccgtattc tccctcaatc ctattaacct tttcttcttt catttcccac ccattctat    120 aatcaatcaa tggcaatggc ttcttcaatc cctaatgcgc cttctgcgtt caattctcag    180
agctacgttg gtctcagagc gccactgagg accttcaact tttcttctcc tcaagctgcc    240
aaaattcctc gctcccaacg ccttttcgtc gtcagagcct ccgattcgga gttcgaagcc    300
gccgttgtcg ccggtaaggt tccgccggcg cctcccgtgc cgcccagacc ggcggc       356
```

<210> SEQ ID NO 171
<211> LENGTH: 287
<212> TYPE: DNA
<213> ORGANISM: Glycine max

<400> SEQUENCE: 171

```
gcttcttcaa tccctaatgc gccttctgct gttcaatgtc tcgagagctc acgttcgggt    60
ctccagcagc gaccacttgc aggacgcttg cagacgtttt gcttagctcc tacgaagctt    120
ggcgcaaata ttgcctgcgc tacccatacg ccttttacgt cgtcagagcc tccgattcgg    180
agttcgaagc cgccgttgtc gccggtaagg ttccgccggc gcctcccgtg ccgcccagac    240
cggcggctcc ggttggaaca ccggtggttc cttcacttcc acttcac                 287
```

<210> SEQ ID NO 172
<211> LENGTH: 259
<212> TYPE: DNA
<213> ORGANISM: Glycine max

<400> SEQUENCE: 172

| | | | | | |
|---|---|---|---|---|---|
| atggcaatgg | cttcttcaat | ccctaatgcg | ccttctgcgt | tcaattctca | gagctacgtt | 60 |
| ggtctcagag | cgccactgag | gaccttcaac | ttttcttctc | ctcaagctgc | caaaattcct | 120 |
| cgctcccaac | gccttttcgt | cgtcagagcc | tccgattcgg | agttcgaagc | cgccgttgtc | 180 |
| gccggtaagg | ttccgccggc | gcctcccgtg | ccgcccagac | cggcggctcc | ggttggaaca | 240 |
| ccggtggttc | cttcacttc | | | | | 259 |

<210> SEQ ID NO 173
<211> LENGTH: 258
<212> TYPE: DNA
<213> ORGANISM: Glycine max
<220> FEATURE:
<223> OTHER INFORMATION: unsure at all n locations

<400> SEQUENCE: 173

| | | | | | |
|---|---|---|---|---|---|
| ggcttcttca | atccctaatg | cgccttctgc | gttcaattct | cagagctacg | ttggtctcag | 60 |
| agcgccactg | aggaccttca | acttttcttc | tcctcaagct | gccaaaattc | ctcgctccca | 120 |
| acgccttttc | gtcgtcagag | cctccgattc | ggagttcgaa | gccgccgttg | tcgccggtaa | 180 |
| ggttccgccg | gcgcctcccg | tgncgcccag | accggcggct | ccggttggaa | caccggtggt | 240 |
| tccttcattc | cattcacc | | | | | 258 |

<210> SEQ ID NO 174
<211> LENGTH: 234
<212> TYPE: DNA
<213> ORGANISM: Glycine max

<400> SEQUENCE: 174

| | | | | | |
|---|---|---|---|---|---|
| ggcttcttca | atccctaatg | cgccttctgc | gttcaattct | cagagctacg | ttggtctcag | 60 |
| agcgccactg | aggaccttca | acttttcttc | tcctcaagct | gccaaaattc | ctcgctccca | 120 |
| acgccttttc | gtcgtcagag | cctccgattc | ggagttcgaa | gccgccgttg | tcgccggtaa | 180 |
| ggttccgccg | gcgcctcccg | tgccgcccag | accggcggct | ccggttggaa | cacc | 234 |

<210> SEQ ID NO 175
<211> LENGTH: 251
<212> TYPE: DNA
<213> ORGANISM: Glycine max
<220> FEATURE:
<223> OTHER INFORMATION: unsure at all n locations

<400> SEQUENCE: 175

| | | | | | |
|---|---|---|---|---|---|
| gcttcttcaa | tccctaatgc | gccttctgcg | ttcaattctc | agagctacgt | tggtctcaga | 60 |
| gcgccactga | ggaccttcaa | cttttcttct | cctcaagctg | ccaaaattcc | tcgctcccaa | 120 |
| cgccttttcg | tcgtcagagc | ctccgattcg | gagttcgang | ccgccgttgt | cgccggtnag | 180 |
| gttccgccgg | cgcntcccgt | nccgcccaga | ccggcggctc | cggttggaac | aaccggtggt | 240 |
| tccttcactt | c | | | | | 251 |

<210> SEQ ID NO 176
<211> LENGTH: 279
<212> TYPE: DNA
<213> ORGANISM: Glycine max

<400> SEQUENCE: 176

```
atccctaatg cgccttctgc gttcaattct cagagctacg ttggtctcag agcgccactg      60
aggaccttca acttttcttc tcctcaagct gccaaaattc ctcgctccca acgccttttc     120
gtcgtcagag cctccgattc ggagttcgaa gccgccgttg tcgccggtaa ggttccgccg     180
gcgcctcccg tgccgcccag accggcggct ccggttggaa caccggtggt tccttcactt     240
ccacttcacc ggcgtcctcg tcggaaccgg aagtcgccg                             279
```

<210> SEQ ID NO 177
<211> LENGTH: 266
<212> TYPE: DNA
<213> ORGANISM: Glycine max

<400> SEQUENCE: 177

```
ggcttcttca atccctaatg cgccttctgc gttcaattct cagagctacg ttggtctcag      60
agcgccactg aggaccttca acttttcttc tcctcaagct gccaaaattc ctcgctccca     120
acgccttttc gtcgtcagag cctccgattc ggagttcgaa gccgccgttg tcgccggtaa     180
ggttccgccg gcgcctcccg tgccgcccag accggcggct ccggttggaa caccggtggt     240
tccttcactt ccacttcacc ggcgtc                                          266
```

<210> SEQ ID NO 178
<211> LENGTH: 287
<212> TYPE: DNA
<213> ORGANISM: Glycine max

<400> SEQUENCE: 178

```
atcctattaa ccttttcttc tttcatttcc cacccattc tatagtcaat caatggcaat       60
ggcttcttca atccctaatg cgccttctgc gctcaattct cagagctacg ttggtctcag     120
agcgccactg aggaccttca acttttcttc tcctcaagct gccaaaattc ctcgctccca     180
acgccttttc gtcgtcagag cctccgattc ggagttcgaa gccgccgttg tcgccggtaa     240
ggttccgccg gcgcctcccg tgccgcccag accggcggct ccggttg                   287
```

<210> SEQ ID NO 179
<211> LENGTH: 236
<212> TYPE: DNA
<213> ORGANISM: Glycine max

<400> SEQUENCE: 179

```
caatggcaat ggcttcttca atccctaatg cgccttctgc gttcaattct cagagctacg      60
ttggtctcag agcgccactg aggaccttca acttttcttc tcctcaagct gccaaaattc     120
ctcgctccca acgccttttc gtcgtcagag cctccgattc ggagttcgaa gccgccgttg     180
tcgccggtac agttccgccg gcgctcccgt gccgcccaga ccggcggctc cggttg         236
```

<210> SEQ ID NO 180
<211> LENGTH: 395
<212> TYPE: DNA
<213> ORGANISM: Glycine max
<220> FEATURE:
<223> OTHER INFORMATION: unsure at all n locations

<400> SEQUENCE: 180

```
tacggatgcg agaagacgac agaaggggga ttggtaaagt attgaatcct gtgcatacat      60
cctcacttat cctcttcctg cgactctctt ctcattggtt ctccgtattc tccctcaatc     120
```

```
ctattaacct tttcttcttt catttcccac cccattctat aatcaatcaa tggcaatggc    180
ttcttcaatc cctaatgcgc cttctgcgtt caattctcag agctacgttg gtctcagagc    240
gccactgagg accttcaact tttcttctcc tcaagctgcc aaaattcctc gctcncaacg    300 cctttttcgtc gtcagagcct ccgattcgga gttcgaagcc gccgttgtcg ccggtaaggt    360
tccgccggcg cctcccgtgc cgcccagacc ggcgg                                 395

<210> SEQ ID NO 181
<211> LENGTH: 227
<212> TYPE: DNA
<213> ORGANISM: Glycine max

<400> SEQUENCE: 181
tggcttcttc aatccctaat gcgccttctg cgttcaattc tcagagctac gttggtctca    60
gagcgccact gaggaccttc aacttttctt ctcctcaagc tgccaaaatt cctcgctccc    120
aacgcctttt cgtctcagag cctccgattc ggagttcgaa gccgccgttg tcgccggtaa    180
ggttccgccg gcgcctcccg tgccgcccag accggcggct ccggttg                   227

<210> SEQ ID NO 182
<211> LENGTH: 271
<212> TYPE: DNA
<213> ORGANISM: Glycine max
<220> FEATURE:
<223> OTHER INFORMATION: unsure at all n locations

<400> SEQUENCE: 182
ggcttcttca atccctaatg cgccttctgc gttcaattct cagagctacg ttggtctcag    60
agcgccactg aggaccttca acttttcttc tcctcaagct gccaaaattc ctcgctccca    120
acgccttttc gtcgtcagag cctccgattc ggagttcgaa gcagccgttg tcgccggtaa    180
ggttccgccg gngcttccnt gccgnacaga ccggcgggtc cngttggnac aacggtggtt    240
ccttaattcc actnancggc gtcctntcng a                                    271

<210> SEQ ID NO 183
<211> LENGTH: 256
<212> TYPE: DNA
<213> ORGANISM: Glycine max

<400> SEQUENCE: 183
cggctcgaga aaattgactg tcacgtagct gaagctgatt gagctacgtt ggtctcagag    60
cgccactgag gaccttcaac ttttcttctc tcaagctgc caaaattcct cgctcccaac    120
gccttttcga cgtcagagcc tccgattcgg agttcgaagc cgccgttgtc gccggtaagg    180
ttccgccggc gcctcccgtg ccgcccagac cggcggctcc ggttggaaca ccggtggttc    240
cttcacttcc acttca                                                     256

<210> SEQ ID NO 184
<211> LENGTH: 246
<212> TYPE: DNA
<213> ORGANISM: Glycine max

<400> SEQUENCE: 184
accttgtctt ctttcatttc caccccatt ctataatcaa tcaatggcaa ttgcttcttc    60
aatccctaat gcgccttctg cgttcaattc tcagagctac gttggtctca gagcgccact    120
gaggaccttc aactttgctt ctcctcaagc tgccaaaatt cctcgctccc aacgcctttt    180
cgtcgtcaga gcctccgatt cggagttcga agccgccgtt gtcgccggta agttccgccg    240
```

```
gcgctt                                                                  246

<210> SEQ ID NO 185
<211> LENGTH: 253
<212> TYPE: DNA
<213> ORGANISM: Glycine max

<400> SEQUENCE: 185
cgactctctt ctcattggtt ctccgtattc tccctcaatc ctattaacct tttcttcttt      60
catttcccac cccattctat aatcaatcaa tggcaatggc ttcttcaatc cctaatgcgc     120
cttctgcgtt caattctcag agctacgttg gtctcagagc gccactgagg accttcaact     180
tttcttctcc tcaagctgcc aaaattcctc gctcccaacg cctttttcgtc gtcagagcct    240 ccgattcgga gtt                                                        253

<210> SEQ ID NO 186
<211> LENGTH: 148
<212> TYPE: DNA
<213> ORGANISM: Glycine max

<400> SEQUENCE: 186
ctgcgttcaa ttctcagagc tacgttggtc tcagagcgcc actgaggacc ttcaactttt      60
cttctcctca agctgccaaa attcctcgct cccaacgcct ttcgtcgtc agagcctccg      120 attcggagtt cgaagccgcc gttgtcgc                                        148

<210> SEQ ID NO 187
<211> LENGTH: 271
<212> TYPE: DNA
<213> ORGANISM: Glycine max

<400> SEQUENCE: 187
cggctcgagg ctgaagctga ttggtaaagt attgaatcct gtgcatacat cctcacttat      60
cctcttcctg cgactctctt ctcattggtt ctccgtattc tccctcaatc ctattaacct     120
tttcttcttt catttcccac ccattctata atcaatcaat ggcaatggct tcttcaatcc     180
ctaatgcgcc ttctgcgttc aattctcaga gctacgttgg tctcagagcg ccactgagga     240
ccttcaactt ttcttctcct caagctgcca a                                    271

<210> SEQ ID NO 188
<211> LENGTH: 104
<212> TYPE: DNA
<213> ORGANISM: Glycine max

<400> SEQUENCE: 188
atggcttctt caatccctaa tgcgccttct gcgttcaatt ctcagagcta cgttggtctc      60
agagcgccac tgaggacctt caacttttct tctcctcaag ctgc                      104

<210> SEQ ID NO 189
<211> LENGTH: 64
<212> TYPE: DNA
<213> ORGANISM: Glycine max

<400> SEQUENCE: 189
agcttcttca atccctaatg cgccttctgc gttcaattct cagagctacg ttggtctcag      60
agcg                                                                   64

<210> SEQ ID NO 190
```

<211> LENGTH: 266
<212> TYPE: DNA
<213> ORGANISM: Glycine max

<400> SEQUENCE: 190

| | | |
|---|---|---|
| tcggctcact cgagcgaatc ggctcaggaa aattgactgt gacgtagcac atcctgattg | 60 | |
| gtaaactatt gaatcctgtg catacatcct cacttatcct cttcctgcga ctctcttctc | 120 | |
| cttggttctc cgtattctcc ctcaatccta ttaaccttt cttctttcat ttcccacccc | 180 | |
| attctataat caatcaatgg caatggcttc ttcaatccct aatgcgcctt ctgcgttcaa | 240 | |
| ttctcagagc tacgttggtc tcagag | 266 | |

<210> SEQ ID NO 191
<211> LENGTH: 264
<212> TYPE: DNA
<213> ORGANISM: Glycine max

<400> SEQUENCE: 191

| | | |
|---|---|---|
| ctcatataga aaattgactg tgacgttgct gaagctgatt ggtaaagtat tgaatcctgt | 60 | |
| gcatacatcc tcacttatcc tcttcctgcg actctcttct cattggttct ccgtattctc | 120 | |
| cctcaatcct attgaccttt tcttctttca tttcccaccc cattctataa tcaatcaatg | 180 | |
| gcaatggctt cttcaatccc taatgcgcct tctgcgttca attctcagag ctacgttggt | 240 | |
| ctcagagcgc cactgaggac cttc | 264 | |

<210> SEQ ID NO 192
<211> LENGTH: 335
<212> TYPE: DNA
<213> ORGANISM: Glycine max
<220> FEATURE:
<223> OTHER INFORMATION: unsure at all n locations

<400> SEQUENCE: 192

| | | |
|---|---|---|
| atatgctnnc cagctgttgc ccaaggtgcn attggaatag cctgtagaag taacgatgat | 60 | |
| aaaatgnnca gaatacctcn ncttcattga atcatgaaga acaagacta gcagtttgct | 120 | |
| gtgaaagagc cttccttgan aagtagaagg atntgccgna nnctattgca ggctatgcta | 180 | |
| gcagaaacga ggatggcaat tgcttgttta gaggatagtt gcttcccctg atggaacccg | 240 | |
| cgtgctcgaa actccagaat ggttcanatg cttttcgaaga tatgataaag atgggtaaga | 300 | |
| tgctggagag gagctctttc tcgagctgac ntgct | 335 | |

<210> SEQ ID NO 193
<211> LENGTH: 257
<212> TYPE: DNA
<213> ORGANISM: Glycine max

<400> SEQUENCE: 193

| | | |
|---|---|---|
| gaacagcgaa atcgacatcg ctgtccattc gatgaaggat gttcctactt acttgcctga | 60 | |
| taaaacaatt ctgccatgta accttccgcg agaggatgtc agagatgcat ttatatcctt | 120 | |
| gactgcagct tccttagctg atcttccccc tgcaagtgtt attggtactg cttcgttaag | 180 | |
| gcgaaagtca cagatcctcc acagatatcc atctcttaat gtgcaggaaa atttccgtgg | 240 | |
| caatgtccaa acaaggt | 257 | |

<210> SEQ ID NO 194
<211> LENGTH: 269
<212> TYPE: DNA
<213> ORGANISM: Glycine max

```
<220> FEATURE:
<223> OTHER INFORMATION: unsure at all n locations

<400> SEQUENCE: 194
cgtttaaata tgacggaaaa tgtgacttcg atcctatcaa ttgatgacat gcttccagct      60
gttgcccaag gtgcaattgg aatagcctgt agaagtaatg atgataaaat ggcggaatac    120
cttgcttcac tgaatcatga agaaacaaga ctagcagttt cctgcgaaag angcttcctt    180
gaaaagttgg aagggtctgc cgcactccta ttgcaggcta tgctagcaga aatgaggatg    240
gcaattgctt gtttagagga ttagttgca                                      269

<210> SEQ ID NO 195
<211> LENGTH: 259
<212> TYPE: DNA
<213> ORGANISM: Glycine max

<400> SEQUENCE: 195
tgatgataaa atggcggaat accttgcttc actgaatcat gaagaaacaa gactagcagt      60
ttcctgtgaa agatccttcc ttgaaaagtt ggaagggtct gccgcactc ctattgcagg     120 ctatgctagc agaaatgagg atggcaattg cttgtttaga ggattagttg catcccctga    180
tggaatccgt gtgcttgaaa cttccagaat tggcccatat gcgttcgcag atatgataaa    240
gatgggtaag gatgctgga                                                 259

<210> SEQ ID NO 196
<211> LENGTH: 205
<212> TYPE: DNA
<213> ORGANISM: Glycine max

<400> SEQUENCE: 196
cttaagtatg acagaaaatg tgacttcaat cctatcaatt gatgatatgc ttccagctgt      60
tgcccaaggt gctattggaa tagcatgtag aagtgatgac gataaaatgg cggaatacat    120
tgctacactt aatcatgaag aaacaagact agcagttgtc tgtgagaggg cctttcttca    180
gactttggat gggtctgccg cactc                                          205

<210> SEQ ID NO 197
<211> LENGTH: 271
<212> TYPE: DNA
<213> ORGANISM: Glycine max

<400> SEQUENCE: 197
ctgcttcgtt aaggcgaaag tcacagatcc tccacagata tccatctctt aatgtgcagg      60
aaaatttccg tggcaatgtc caaacaaggt taagaaaact caatgagggg ttgtccaag     120 ctacactatt agcattagct ggactcaaac gcttaagtat gacagaaaat gtgacttcaa    180
tcctatcaat agatgatatg cttccagctg ttgcccaagg tgccattgga attgcctgta    240
gaagtgatga cgataaaatg gcagaataca t                                   271

<210> SEQ ID NO 198
<211> LENGTH: 287
<212> TYPE: DNA
<213> ORGANISM: Glycine max

<400> SEQUENCE: 198
attggaattg cctgtagaag tgatgacgat aaaatggcag aatacattga ttcacttaat      60
catgaagaaa caaggctagc agttgtctgt gaaagggcct tcttcagac tttggatggg    120
```

```
tcttgccgca ctcctattgc agggtatgct tgtagaaacg aggatggcaa ttgtttgttt      180
agaggattag ttgcttcccc tgatggaacc agagtgctag agacatccag ggttggtcca      240
tatgctgttg aagatatgat tgagatgggt aaggatgctg gcaagga                   287
```

<210> SEQ ID NO 199
<211> LENGTH: 276
<212> TYPE: DNA
<213> ORGANISM: Glycine max
<400> SEQUENCE: 199

```
attgggaatt gcctgtagaa gtgatgacga taaaatggca gaatacattg attcacttaa      60
tcatgaagaa acaaggctag cagttgtctg tgaaagggcc tttcttcaga ctttggatgg     120
gtcttgccgc actcctattg cagggtatgc ttgtagaaac gaggatggca attgtttgtt     180
tagaggatta gttgcttccc ctgatggaac cagagtgcta gagacatcca gggttggtcc     240
atatgctgtt gaagatatga ttgagatggg taagga                              276
```

<210> SEQ ID NO 200
<211> LENGTH: 285
<212> TYPE: DNA
<213> ORGANISM: Glycine max
<400> SEQUENCE: 200

```
attggaattg cctgtagaag tgatgacgat aaaatggcag aatacattga ttcacttaat      60
ccatgaagaa acaaggctag cagttgtctg tgaaagggcc tttcttcaga ctttggatgg     120
gtcttgccgc actcctattg cagggtatgc ttgtagaaac gaggatggca attgtttgtt     180
tagaggatta gttgcttccc ctgatggaac cagagtgcta gagacatcca gggttggtcc     240
atatgctgtt gaagatatga ttgagatggg taaggatgct ggcaa                    285
```

<210> SEQ ID NO 201
<211> LENGTH: 259
<212> TYPE: DNA
<213> ORGANISM: Glycine max
<400> SEQUENCE: 201

```
gtgaaagggc ctttcttcag actttggatg ggtcttgccg cactcctatt gcagggtatg      60
cttgtagaaa cgaagatggc aattgtttgt ttagaggatt agttgcttcc ctgatggaa     120 ccagagtgct agagacatcc agggttggtc catatgctgt tgaagatatg attgagatgg     180
gtaaggatgc tggcaaggag cttctgtctc gggctggacc taacttcttc agtagttagc     240
agcagatgat taaagtgtg                                                 259
```

<210> SEQ ID NO 202
<211> LENGTH: 285
<212> TYPE: DNA
<213> ORGANISM: Glycine max
<220> FEATURE:
<223> OTHER INFORMATION: unsure at all n locations
<400> SEQUENCE: 202

```
gcagacagaa gcgaacgnaa cggggttgcc tcaacaattc gctgttgttg ttctcttctc      60
ttctctttga catgaatact ctttcttcca cgctccatgg cggcaggctt ccccgctcag     120
cttcgaaaac caaaaccgca tctctctcca aatgccatcg catttgggtc accaaagctt     180
ctgttgccgt tgagcaacaa actaaggtcg ctctcatcag aattggtacc agaggaagtc     240
cactagctct agcacaagca tatgagacca gagacaaact catgg                    285
```

<210> SEQ ID NO 203
<211> LENGTH: 282
<212> TYPE: DNA
<213> ORGANISM: Glycine max

<400> SEQUENCE: 203

| | |
|---|---:|
| agcagacaga agcgagcgaa acggggttgc ctcaacaatt cgctgttgtt gttctcttct | 60 |
| cttctctttg acatgaatac tctttcttcc acgctccatg gcgggaggct tccccgctca | 120 |
| gcttcgaaaa ccaaaaccgc atctctctcc aaatgccatc gcatttgggt caccaaagct | 180 |
| tctgttgccg ttgagcaaca aactaaggtc gctctcatca gaattggtac cagaggaagt | 240 |
| ccactagctc tagcacaagc atatgagacc agagacaaac tc | 282 |

<210> SEQ ID NO 204
<211> LENGTH: 251
<212> TYPE: DNA
<213> ORGANISM: Glycine max

<400> SEQUENCE: 204

| | |
|---|---:|
| ccgaacgaaa cggggttgcc tcaacaattc gctgttgttg ttctcttctc ttctctttga | 60 |
| catgaatact ctttcttcca cgctccatgg cgggtggctt ccccgctcag cttcgaaaac | 120 |
| cacaaccgca tctctctcca aatgccatcg catttgggtc accaaagctt ctgttgccgt | 180 |
| tgagcaacaa actaaggtcg ctctcatcag aattggtacc agaggaagtc cactagctct | 240 |
| agcacaagca t | 251 |

<210> SEQ ID NO 205
<211> LENGTH: 327
<212> TYPE: DNA
<213> ORGANISM: Glycine max

<400> SEQUENCE: 205

| | |
|---|---:|
| atcggcaagg taaggcaatt gaagttgtga atggagact gtctgctctg cattggtgtt | 60 |
| cccatctttc agaatcacaa cttcagcttt ctccaaatgt ggcatcaggg cttccattgc | 120 |
| cgttgagcaa caaacttcgc agactaaggt tgctctcctc aaaattggta ccagaggaag | 180 |
| tccactagct ctggctcagg catatgagac cagagacaag ctcatggcat cacatccaga | 240 |
| gctagcggaa gaggggcta ttcagattgt gataatgaaa caactggtg acaaaatact | 300 |
| atcacagcca cttgcagaca tcggcgg | 327 |

<210> SEQ ID NO 206
<211> LENGTH: 390
<212> TYPE: DNA
<213> ORGANISM: Glycine max

<400> SEQUENCE: 206

| | |
|---|---:|
| gaaatggaga ctctctgctc tgcattggtg ttcccatctt tcagaatcac aacttcagct | 60 |
| ttctccaaat gtggcatcag ggctttcatt gccgttgagc aacatacttc gcagactaag | 120 |
| gttgctctcc tcaaaattgg taccagagga agtccactag ctctggctca tgcatatgag | 180 |
| accagagaca atctcatggc atcacatcca gagctagcgg atgaagggc tattcagatc | 240 |
| gtgataataa aaacaactgg tgacattata ctatcacagc cacttgcaga catcggcggt | 300 |
| aagggcctgt ccacaatcga tatagacgag gcactcatta acggtgacat tgacatcgcc | 360 |
| gttcactcta tgaaagatgt acccacttac | 390 |

```
<210> SEQ ID NO 207
<211> LENGTH: 256
<212> TYPE: DNA
<213> ORGANISM: Glycine max

<400> SEQUENCE: 207
cgttgctctc ctcagaattg gtaccagagg aagtccacta gctctggctc acgcatatga    60
gaccagagac aagctcatgg catcacatgc agagctagca caagaagggg ctattcagat   120
tgtaataatc aaaacaactg gtgacaaaat actatcacag ccacttgcag acattggtgg   180
gaagggccta ttcacaaaag aaatagatga ggcactcata acggtgacca ttgacatcgc   240
tgtccactca atgaaa                                                   256

<210> SEQ ID NO 208
<211> LENGTH: 289
<212> TYPE: DNA
<213> ORGANISM: Glycine max
<220> FEATURE:
<223> OTHER INFORMATION: unsure at all n locations

<400> SEQUENCE: 208
ggagaccctc tgnctctgca ttggtgttcc catctttcag aatcagnact tcagctttct    60
ccaaatgtgg catcagggcn tccattgccg ttgagcaaca aanttcccag actaaggttg   120
ctctcctcag aattggtacc agaggaagtc cactagctct ggctcaggca tatgagacca   180
gagacaagct catggcatca catgcagagc tagcagaaga aggggctatt cagnttgtaa   240
taataanaac nactggtgac aanatactat cacagccact tgcagacat              289

<210> SEQ ID NO 209
<211> LENGTH: 259
<212> TYPE: DNA
<213> ORGANISM: Glycine max
<220> FEATURE:
<223> OTHER INFORMATION: unsure at all n locations

<400> SEQUENCE: 209
agggcttcca ttgccgttga gcaacaaact tcccagacta aggttgctct cctcagaatt    60
ggtaccagag gaagtccact agctctggct cncgcatatg agaccagaga caagctcatg   120
gcatnccatg cagagctagc agaagaaggg gctattcaga ttgtaataat aaaaacaact   180
ggtgacaaaa tactatcaca gccacttgca gacattggtg ggaagggcct attcacaaaa   240
gaatagatga ggcatcata                                                259

<210> SEQ ID NO 210
<211> LENGTH: 268
<212> TYPE: DNA
<213> ORGANISM: Glycine max

<400> SEQUENCE: 210
ctctctgctc tgcattggtg ttcccatatt tcagaatcac aacttcagct ttctccaaat    60
gtggcatcag ggcttccatt gccgttgagc aacaaacttc gcagactaag gttgctctcc   120
tcaaaattgg taccagagga agtccactag ctctggctca ggcatatgag accagagaca   180
agctcatggc atcacatcca gagctagcgg aagaagggc tattcagatt gtgataataa   240
aaacaactgg tgacaaaata ctatcaca                                      268

<210> SEQ ID NO 211
<211> LENGTH: 270
```

```
<212> TYPE: DNA
<213> ORGANISM: Glycine max

<400> SEQUENCE: 211
ggagactctc tgctctgcat tggtgttccc atctttcaga atcacaactt cagctttctc      60
caaatgtggc atcagggctt ccattgccgt tgagcaacaa acttcgcaga ctaaggttgc     120
tctcctcaaa attggtacca gaggaagtcc actagctctg gctcaggcat atgagaccag     180
agacaagctc atggcatcac atccagagct agcggaagaa ggggctattc agattgtgat     240
aataaaaaca actggtgaca aaatactatc                                      270

<210> SEQ ID NO 212
<211> LENGTH: 295
<212> TYPE: DNA
<213> ORGANISM: Glycine max
<220> FEATURE:
<223> OTHER INFORMATION: unsure at all n locations

<400> SEQUENCE: 212
tggagaccct ctgctctgca ttggtgttcc catctttcag aatcagaact tcagctttct      60
ccaaatgtgg catcagggct tccattgccg ttgagcaaca aacttcccag actaaggttg     120
ctctcctcag aattggtacc agaggaagtc cactagctct ggctcaggca tatgagacca     180
gagacaagct catggcatca catgcagagc tagcagaaga aggggctatt cagattgtat     240
aataanaaca actggtgaca aaatatatca cagccattgc agacattggt gggag          295

<210> SEQ ID NO 213
<211> LENGTH: 267
<212> TYPE: DNA
<213> ORGANISM: Glycine max

<400> SEQUENCE: 213
ctctctgctc tgcattggtg ttcccatctt tcagaatcac aacttcagct ttctccaaat      60
gtggcatcag ggcttccatt gccgttgagc aacaaacttc gcagactaag gttgctctcc     120
tcaaaattgg taccagagga agtccatagc tctggctcag gcatatgaga ccagagacaa     180
gctcatggca tcacatccag agctagcgga agaagggget attcagattg tgataataaa     240
aacaactggt gacaaatact atcacag                                         267

<210> SEQ ID NO 214
<211> LENGTH: 251
<212> TYPE: DNA
<213> ORGANISM: Glycine max

<400> SEQUENCE: 214
tggagactct ctgctctgca ttggtgttcc catctttcag aatcacaact tcagctttct      60
ccaaatgtgg catcagggct tccattgccg ttgagcaaca acttcgcag actaaggttg      120 ctctcctcaa aattggtacc agaggaagtc cactagctct ggctcaggca tatgagacca     180
gagacaagct catggcatca catccagagc tagcggaaga agggget att cagattgtga    240 taataaaaac a                                                          251

<210> SEQ ID NO 215
<211> LENGTH: 159
<212> TYPE: DNA
<213> ORGANISM: Glycine max
<220> FEATURE:
<223> OTHER INFORMATION: unsure at all n locations
```

```
<400> SEQUENCE: 215
ccacttcagc tttctccaaa tgtggcatca gggcttccat tgccgttgag caacaaactt      60
cccagactaa ggttgctctc ctcagaattg gtaccagagg aagtccacta gctctggctc     120
aggcatatgn gaccagagac aagntcatgg catcacang                            159

<210> SEQ ID NO 216
<211> LENGTH: 270
<212> TYPE: DNA
<213> ORGANISM: Glycine max

<400> SEQUENCE: 216
gttcccatct ttcagaatca gaacttcagc tttctccaaa tgtggcatca gggcttccat      60
tgccgttgag caacaaactt cccagactaa ggttgctctc ctcagaattg gtaccagagg     120
aaggtaccct acccttaaaa ataacacctt tagcttctta tgagcatttc ttttaaagaa     180
caagtctgtg aaaatattga gtcctgaatc tcttcaaaac tttgccctca ttttcaaatt     240
tagttttcaa tgctagtttt atgacagaaa                                      270

<210> SEQ ID NO 217
<211> LENGTH: 147
<212> TYPE: DNA
<213> ORGANISM: Glycine max

<400> SEQUENCE: 217
gtgaaatgga gaccctctgc tctgcattgg tgttcccatc tttcagaatc agaacttcag      60
ctttctccaa atgtggcatc agggcttcca ttgccgttga gcaacaaact cccagacta     120 aggttgctct cctcagaatt ggtacca                                         147

<210> SEQ ID NO 218
<211> LENGTH: 253
<212> TYPE: DNA
<213> ORGANISM: Glycine max
<220> FEATURE:
<223> OTHER INFORMATION: unsure at all n locations

<400> SEQUENCE: 218
ccaagaccga caacaaactc actcttacca agtccgagga agctttcgct gctgccaagg      60
agcngatgcc tggaggtgtc aactccccag ttngtgcctt caaatccgtg ggtggtcaac     120
caattgtgat tgattcagtc aaagggtctc gtatgtggga catcgacggc aatgagtaca     180
ttgactacgt cggttcttgg ggtcccgcaa tcattggtca cgctgatgat caagtgcttt     240
cagctctggt tgt                                                        253

<210> SEQ ID NO 219
<211> LENGTH: 264
<212> TYPE: DNA
<213> ORGANISM: Glycine max

<400> SEQUENCE: 219
tgcgtgcgtg agcgtcttac ctttccatta tcaaaatgac tgtttcagct atcacaggct      60
cgcagtctca cctcttgcca tggttagcga tacctctttc ctctcccacg cgctctcgaa     120
tcgtcgcaat ggccgtatcc gtcgtcccca agaccgacaa caactcact cttaccaagt     180 ccgaagcagc tttcgctgct gccaaggagc tgctgcctgg cggtgtcaac tccccagttc     240
gtaccttcaa atccgtaggt ggtc                                            264
```

```
<210> SEQ ID NO 220
<211> LENGTH: 157
<212> TYPE: DNA
<213> ORGANISM: Glycine max

<400> SEQUENCE: 220
ctcgtctgag ggctgttacc atggccatgc tgatcctttt cgtgttaagg caggtagtgg      60
agttgccacc ttgggacttc ctgattctcc cggtgtcccc aaagctgaca ctgtggaaac     120
ccttacagcg ccctacaatg atactgccgc cgtcgag                              157

<210> SEQ ID NO 221
<211> LENGTH: 266
<212> TYPE: DNA
<213> ORGANISM: Glycine max

<400> SEQUENCE: 221
aaacccgatt ttcataattt cttgcgcaag atcaccaagg agaacaatac ccttcttgtg      60
tttgatgaag ttatgactgg gtttcgtttg tcatacggag gtgctcaaga gtattttggc     120
ataactcctg atatacaact ctaggaaaga tcattggtgg aggtctgccg gtgggggctt     180
atggagggag gagggatatt atggagaagg tggcaccagc tggcccaatg tatcaggctg     240
ggaccttgag tgggaacctt tggcca                                          266

<210> SEQ ID NO 222
<211> LENGTH: 250
<212> TYPE: DNA
<213> ORGANISM: Glycine max

<400> SEQUENCE: 222
aaaggagaaa ttgccgcagt tttcctcgaa cctgttgttg gaaacgctgg tttcattgtt      60
cctaagcctg attttcatag tttcttgcgc aagatcacca aggagaacaa taccctttct     120
gtgtttgatg aagtcatgac tggatttcgt ttgtcatatg gaggtgctca agagtattat     180
ggcataactc cagatataac aactctagga aagatcattg gtggaggtct gccggtaggg     240
cttatggagg                                                            250

<210> SEQ ID NO 223
<211> LENGTH: 256
<212> TYPE: DNA
<213> ORGANISM: Glycine max

<400> SEQUENCE: 223
gctcaagagt attttggcat aactcctgat ataacaactc taggaaagat cattggtgga      60
ggtctgccgg tgggggctta tgagggagg agggatatta tggagaaggt ggcaccagct     120
ggcccaatgt atcaggctgg gaccttgagt gggaaccctt tggccatgac tgcaggaata     180
cagaccctgc agcgtattaa ggagccagga acttatgagt acttggacaa atcaccggt     240 gagcttgttc agggca                                                     256

<210> SEQ ID NO 224
<211> LENGTH: 288
<212> TYPE: DNA
<213> ORGANISM: Glycine max
<220> FEATURE:
<223> OTHER INFORMATION: unsure at all n locations

<400> SEQUENCE: 224
tttaggnagc tgatgcctgg anggcgtgaa ctccccagtt cgtgncttca aatccgtggg     60
```

-continued

```
tggtcaacca attgtgattg attcagtcaa agggtctcgt atgtgggata tcgatggcaa      120
tgagtacatt gactacgttg gttcctgggg tcctgcaatc attggtcacg ctgatgatca      180
ggtgcttgca gctctgggtg aaaccatgaa ganaggaacc agctttgggt gcaccctgtc      240
tgctggaaaa cacttttggc agagctgggt tatcgatgcc gtnccca                   288
```

<210> SEQ ID NO 225
<211> LENGTH: 283
<212> TYPE: DNA
<213> ORGANISM: Glycine max
<220> FEATURE:
<223> OTHER INFORMATION: unsure at all n locations

<400> SEQUENCE: 225

```
attttgcaga tgccaaaaag agtgatacgg ccaagtttgc taggccctt tggggaatgc       60 tggcggaagg tgtctatttg gcaccttccc agnttgangc nggcttcacc agcttggcac     120
atacttctgn tgacataaaa aagacgatan ccgctgntga aaggttttc anggagntct     180 gatggttaaa ttttgntttg ttgcaaattt aattntcgga gggtgaattt ttaggtcaat     240
ttngattatt gttatggcag ttgctttcgn tatgatctgt atc                        283
```

<210> SEQ ID NO 226
<211> LENGTH: 249
<212> TYPE: DNA
<213> ORGANISM: Glycine max

<400> SEQUENCE: 226

```
gggtcctgca atcattggtc acgctgatga tcaggtgctt gcagctctgg gtgaaaccat       60
gaagaaagga accagctttg gtgcaccctg tctgctggaa acactttggg cagagctggt     120
tatcgatgcc gtccccagca ttgaaatggt tcggtttgtc aattcaggca ctgaagcttg     180
catgggtgcg ctccgtctgg cccgtgctta taccggaaga gagaagatca tcaagtttga     240
gggctgtta                                                              249
```

<210> SEQ ID NO 227
<211> LENGTH: 442
<212> TYPE: DNA
<213> ORGANISM: Glycine max

<400> SEQUENCE: 227

```
ataaggcttt gcatttcatt tgagagagag agcgtcttac ctttccatta tcaaaatggg       60
tgggtcggct atcacaggag cgaggctaac cctagggata gggttggcga tacctctttc     120
ctctcccacg cgctctcgaa ccgtcgcaat ggccgtatcc gtcgacccca agaccgacaa     180
caaactcact cttaccaagt ccgaggaagc tttcgctgct gccaaggtac gcatgaccct     240
cctcttcctt ccttccttcc tcctttcaat tttgattttt gattttgat ttcaggagct     300 gatgcctgga ggtgtcaact ccccagttcg tgccttcaaa tccgtgggtg gtcaaccaat     360
tgtgattgat tcagtcaaag ggtctcgtat gtgggacatc gacggcaatg agtacattga     420
ctacgtcggt tcttggggtc cc                                               442
```

<210> SEQ ID NO 228
<211> LENGTH: 275
<212> TYPE: DNA
<213> ORGANISM: Glycine max
<220> FEATURE:
<223> OTHER INFORMATION: unsure at all n locations

<400> SEQUENCE: 228

```
tcaaaatggc tgtttcggct atcacaggag cgaggctaac cctagggata gggttggcga    60
tacctctttc ctctcccacg cgctctcgaa ccntcgcaat ggccgtatcc gtcgacccca   120
agaccgacaa caaactcact cttaccaagt ccgaggaagc tttcgctgct gccaaggagc   180
tgatgcctgg aggtgtcaac tccccagttc gtgccttcaa atccgtgggt ggtcaaccaa   240
ttgtgattga ttcagtcaaa gggtctcgta tgtgg                              275
```

<210> SEQ ID NO 229
<211> LENGTH: 261
<212> TYPE: DNA
<213> ORGANISM: Glycine max

<400> SEQUENCE: 229

```
acccacgcgt ccgacggctg caagaggacg acagaagggg aaggctttgc atttcatttg    60
agagagagag cgtcttacct ttccattatc aaaatggctg tttccgctat cacaggagcc   120
aagctaaccc taaggataag gttggcgata cctccttcct ctcccaagcg ctctcgaacc   180
gtcgcaatgg ccgtatccgt cgaccccaag accgacaaca aactcaatcc taccaagtcc   240
gaagaagctt tcgctgctgc c                                             261
```

<210> SEQ ID NO 230
<211> LENGTH: 289
<212> TYPE: DNA
<213> ORGANISM: Glycine max
<220> FEATURE:
<223> OTHER INFORMATION: unsure at all n locations

<400> SEQUENCE: 230

```
ggagaggata aggctttgca tttcatttga gaganagagc gtcttacctt tccattatca    60
aaatggctgt tcggctatc acaggagcga ggctaaccct agggataggg ttggcgatac   120
ctctttcctc tcccacgcgc tctcgaaccg tcgcaatggc cgtatccgtc gaccccaaga   180
ccgacaacaa actcactctt accaagtccg aggaagcttt cgctgctgcc aaggagctga   240
tgcctggagg tgtcaactcc ccagttcgtg ccttcaaatc cgtgggtgg               289
```

<210> SEQ ID NO 231
<211> LENGTH: 252
<212> TYPE: DNA
<213> ORGANISM: Glycine max

<400> SEQUENCE: 231

```
agcgtcttac ctttccatta tcaaaatggc tgtttcggct atcacaggag cgaggctaac    60
cctagggata gggttggcga tacctctttc ctctcccacg cgctctcgaa ccgtcgcaat   120
ggccgtatcc gtcgacccca agaccgacaa caaactcact cttaccaagt ccgaggaagc   180
tttcgctgct gccaaggagc tgatgcctgg aggtgtcaac tccccagttc gtgccttcaa   240
atccgtgggt gg                                                       252
```

<210> SEQ ID NO 232
<211> LENGTH: 281
<212> TYPE: DNA
<213> ORGANISM: Glycine max

<400> SEQUENCE: 232

```
ggctttgcat ttcatttgag agagagagcg tcttaccttt ccattatcaa aatggctgtt    60
tcggctatca caggagcgag gctaacccta gggatagggt tggcgatacc tctttcctct   120
```

```
cccacgcgct ctcgaaccgt cgcaatggcc gtatccgtcg accccaagac cgacaacaaa      180
ctcactctta ccaagtccga ggaagctttc gctgctgcca aggagctgat gcctggaggt      240
gtcaactccc cagttcgtgc cttcaaatcc gtgggtggtc a                          281
```

<210> SEQ ID NO 233
<211> LENGTH: 276
<212> TYPE: DNA
<213> ORGANISM: Glycine max

<400> SEQUENCE: 233

```
taaggctttg catttcattt gagagagaga gcgtcttacc tttccattat caaaatggct       60
gtttcggcta tcacaggagc gaggctaacc ctagggatag ggttggcgat acctcttttcc     120 tctcccacgc gctctcgaac cgtcgcaatg gccgtatccg tcgacccaa gaccgacaac      180 aaactcactc ttaccaagtc cgaggaagct ttcgctgctg ccaaggagct gatgcctgga      240
ggtgtcaact ccccagttcg tgccttcaaa tccgtg                                276
```

<210> SEQ ID NO 234
<211> LENGTH: 276
<212> TYPE: DNA
<213> ORGANISM: Glycine max

<400> SEQUENCE: 234

```
ttgcatttca tttgagagag agagcgtctt acctttccat tatcaaaatg gctgtttcgg       60
ctatcacagg agcgaggcta accctaggga tagggttggc gatacctctt tcctctccca      120
cgcgctctcg aaccgtcgca atggccgtat ccgtcgaccc aagaccgac aacaaactca      180 ctcttaccaa gtccgaggaa gctttcgctg ctgccaagga gctgatgcct ggaggccgtc      240
aatccccagt tcgtgccttc aaatccgtgg gtggtc                                276
```

<210> SEQ ID NO 235
<211> LENGTH: 251
<212> TYPE: DNA
<213> ORGANISM: Glycine max

<400> SEQUENCE: 235

```
tttgcatttc atttgagaga gagagcgtct tacctttcca ttatcaaaat ggctgtttcg       60
gctatcacag gagcgaggct aaccctaggg atagggttgg cgatacctct ttcctctccc      120
acgcgctctc gaaccgtcgc aatggccgta ccgtcgacc caagaccga caacaaactc      180 actcttacca gtccgagga agctttcgct gctgcaagga gctgatgcct ggaggtgtca      240
actccccagt t                                                            251
```

<210> SEQ ID NO 236
<211> LENGTH: 271
<212> TYPE: DNA
<213> ORGANISM: Glycine max

<400> SEQUENCE: 236

```
cggctcgaca aggctttgca tttcatttga gagagagagc gtcttacctt tccattatca       60
aaatggctgt tcggctatc acaggagcga ggctaaccct agggataggg ttggcgatac      120
ctctttcctc tcccacgcgc tctcgaaccg tcgcaatggc cgtatccgtc gaccccaaga      180
ccgacaacaa actcactctt accaagtccg aggaagcttt cgctgctgcc aaggagctga      240
tgcctggagg tgtcaactcc ccagttcgtg c                                     271
```

<210> SEQ ID NO 237
<211> LENGTH: 257
<212> TYPE: DNA
<213> ORGANISM: Glycine max

<400> SEQUENCE: 237

```
ggagaggata aggctttgca tttcatttga gagagagagc gtcttaactt tacattatca    60
aaatggctgt tcggctatc acaggagcga ggctaaatct agggataggg ttggcgatac    120
ctctttcctc tcccacgcgc tctcgaaccg tcgcaatggc cgtatccgtc gaccccaaga   180
ccgacaacaa actcactctt accaagtccg aggaagcttt cgctgctgcc aaggagctga   240
tgcctggagg tgtcaac                                                  257
```

<210> SEQ ID NO 238
<211> LENGTH: 153
<212> TYPE: DNA
<213> ORGANISM: Glycine max
<220> FEATURE:
<223> OTHER INFORMATION: unsure at all n locations

<400> SEQUENCE: 238

```
acaggagcga ggctaacccct agggataggg ttggcgatan ctctttcctc tcncactccg    60
ctctcgaacc ntcgcaatgg ccgtatccgt cgaccccaag acngacaaca aactcactct   120
taccaagtcc gaggaagctt tcgctgctgc caa                                153
```

<210> SEQ ID NO 239
<211> LENGTH: 104
<212> TYPE: DNA
<213> ORGANISM: Glycine max
<220> FEATURE:
<223> OTHER INFORMATION: unsure at all n locations

<400> SEQUENCE: 239

```
acggctgcga aagacgaca aaggggggag cgtcttacct ttccattatc aaaatggcta    60
tttcggctat cacaggagcg aggctaaacc tagggatagg gttg                    104
```

<210> SEQ ID NO 240
<211> LENGTH: 268
<212> TYPE: DNA
<213> ORGANISM: Glycine max

<400> SEQUENCE: 240

```
ggctgggacc ttgagtggga acccttggc catgactgca ggaatacaga ccctgcagcg    60
tattaaggag ccaggaactt atgagtactt ggacaaaatc accggtgagc ttgttcaggg   120
cattattgaa gctggaaaga gggcaggcca tgcaatatgt ggtggtcata taaggggggat   180
gtttgggttt tcttcacag aaggaccagt gtataatttt gcagatgcca aaaagagtga   240
tacggacaag tttctaggtt cttttggg                                      268
```

<210> SEQ ID NO 241
<211> LENGTH: 256
<212> TYPE: DNA
<213> ORGANISM: Glycine max

<400> SEQUENCE: 241

```
gaaggtggca ccagctggcc caatgtatca ggctgggacc ttgagtggga acccttggc    60
catgactgca ggaatacaga ccctgcagcg tattaaggag ccaggaactt atgagtactt   120
ggacaaaatc accggtgagc ttgttcaggg cattattgaa gctggaaaga gggcaggcca   180
```

```
tgcaatatgt ggtggtcata taaggggggat gtttgggttt ttcttcacag aaggaccagt      240
gtataatttt gcagat                                                       256
```

```
<210> SEQ ID NO 242
<211> LENGTH: 253
<212> TYPE: DNA
<213> ORGANISM: Glycine max

<400> SEQUENCE: 242
ggcaccagct ggcccaatgt atcaggctgg gaccttgagt gggaacccctt tggccatgac     60 tgcaggaata cagaccctgc agcgtattaa ggagccagga acttatgagt acttggacaa    120
aatcaccggt gagcttgttc agggcattat tgaagctggg aagagggcag gccatgcaat    180
atgtggtggt catataaggg ggatgtttgg gttttctttc acagaaggac cagtgtataa    240
ttttgcagat gcc                                                         253
```

```
<210> SEQ ID NO 243
<211> LENGTH: 269
<212> TYPE: DNA
<213> ORGANISM: Glycine max

<400> SEQUENCE: 243
ctcgagccgc tcgagccggt ctgctggaaa acactttggc agagctggtt atcaatgcgg      60
tccccagcat tgcaatggtt cgctttgtca attcaggcac cgaagcttgc atgggtgcac    120
tacgtctcgc ccgagcttat accggaagag agaagatcat caagtttgag ggctgttacc    180
atggccatgc tgatcctttt cttgttaagg caggtagtgg agttgccacc ttgggacttc    240
ctgattctcc cggtgtcccc aaagctgcc                                        269
```

```
<210> SEQ ID NO 244
<211> LENGTH: 266
<212> TYPE: DNA
<213> ORGANISM: Glycine max

<400> SEQUENCE: 244
ctcgagccgc tcgagccggt ctgctggaaa acactttggc agagctggtt atcaatgcgg      60
tacccagcat taccaatggt tcgctttgtc aattcaggca ccgaagcttg catgggtgca    120
ctacgtctcg cccgagctta taccggaaga gagaagatca tcaagtttga gggctgttac    180
catggccatg ctgatccttt tcttgttaag gcaggtagtg gagttgccac cttgggactt    240
cctgattctc ccggtgtccc caaagc                                           266
```

```
<210> SEQ ID NO 245
<211> LENGTH: 266
<212> TYPE: DNA
<213> ORGANISM: Glycine max

<400> SEQUENCE: 245
tcaagtttga gggctgttac cgtggccatg ctgatccttt tcttgttaag gcaggtagtg      60
gagttgccac cttaggactt cctgattctc ccggtgtccc caaagctgcc actttttgaaa   120 cccttacagc cccctacaat gacaccgagg ccattgagaa actcttcgag gccaacaaag    180
gagaaattgc cgcagttttc ctcgaacctg ttgttggaaa cgctggtttc attgttccta    240
agcctgattt tcatagtttt cttgcgc                                          266
```

```
<210> SEQ ID NO 246
<211> LENGTH: 238
```

```
<212> TYPE: DNA
<213> ORGANISM: Glycine max

<400> SEQUENCE: 246
gttaccatgg ccatgctgat ccttttcttg ttaaggcagg tagtggagtt gccaccttgg      60
gacttcctga ttctcccggt gtccccaaag ctgccacttt tgaaacccct acagccccct    120
acaatgacac tgccgccgtt gagaagctct tgaggctaa caaggagaa atcgctgctg      180 ttttcctcga acctgttgtt ggaaacgctg gtttcattgt tcctaaaccg attttcat      238

<210> SEQ ID NO 247
<211> LENGTH: 232
<212> TYPE: DNA
<213> ORGANISM: Glycine max

<400> SEQUENCE: 247
gggagatctg attgttaaat tttgttttgt tgcgaattta gttttcagtt ggtgaattt      60 gtaggtcaat ttagattatt atggcagttg ctttcgttat gatctgtatc attttcccat    120
cctgtatcta cccagtgtat tatgttgagc tgtaagttac ttgaatgtga agcatgtaag    180
cattcgaatt cattgtttaa ctcctaattc tagttccaca tgttatgttt tt            232

<210> SEQ ID NO 248
<211> LENGTH: 82
<212> TYPE: DNA
<213> ORGANISM: Glycine max

<400> SEQUENCE: 248
ccatcctgta tctacccagt gtattatgtt gagctgtaag ttacttgaat gtgaagcatg      60
taagcattcg aattcattgt tt                                               82

<210> SEQ ID NO 249
<211> LENGTH: 406
<212> TYPE: DNA
<213> ORGANISM: Glycine max
<220> FEATURE:
<223> OTHER INFORMATION: unsure at all n locations

<400> SEQUENCE: 249
acgcccacgc gtccgtacgg ctgcgagaag acgacagaag ggggtgttgg atgaggcgaa      60
actcgagagt gtaaggtttt gcatttcatt tgacgaagag tgagagagtc ttatctgtcg    120
tctctgatct ctgatcgcat cttcattccg aaaatggctg tttcggctat cactggagcg    180
aggctaactc tagggatgtc tctttcctct tccacgcgat cacgaaccgt cgcaatggcc    240
gtatctatcg accccaagac cgataacana ctcactctta ccaagtccga ggaagcttcc    300
gctgcggcca aagagctgat gcctggaggc gtgaactccc cagttcgtgc cttcanatcc    360
gtgggtggtc anacaattgt gattgattca gtcaaagggg ctcgta                   406

<210> SEQ ID NO 250
<211> LENGTH: 305
<212> TYPE: DNA
<213> ORGANISM: Glycine max

<400> SEQUENCE: 250
cccacgcgtc cgtacggctg cgagaagacg acagaagggg gagagtgtaa ggttttgcat      60
ttcatttgac gaagagtgag agagtcttat ctgtcgtctc tgatctctga tcgcatcttc    120
attccgaaaa tggctgtttc ggctatcact ggagcgaggc taactctagg gatgtctctt    180
```

```
tcctcttcca cgcgatcacg aaccgtcgca atggccgtat ctatcgaccc caagaccgat    240
aacaaactca ctcttaccaa gtccgaggaa gctttcgctg cggccaagga gctgatgcct    300
ggagg                                                                305
```

<210> SEQ ID NO 251
<211> LENGTH: 296
<212> TYPE: DNA
<213> ORGANISM: Glycine max

<400> SEQUENCE: 251

```
gaaactcgag agtgtaaggt tttgcatttc atttgacgaa gagtgagaga gtcttatctg     60
tcgtctctga tctctgatcg catcttcatt ccgaaaatgg ctgtttcggc tatcactgga    120
gcgaggctaa ctctagggat gtctctttcc tcttccacgc gatcaacaac acaagcaatg    180
gccgtatcta tcgaccccaa gaccgataac aaactcactc ttaccaagtc gaggaagct    240 ttcgctgcgg ccaaggagct gatgcctgga ggcgtgaact ccccagttcg tgcctt        296
```

<210> SEQ ID NO 252
<211> LENGTH: 266
<212> TYPE: DNA
<213> ORGANISM: Glycine max

<400> SEQUENCE: 252

```
ctgcgagaag acgacagaag ggggagagtg taaggttttg catttcattt gacgaagagt     60
gagagagtct tatctgtcgt ctctgatctc tgatcgcatc ttcattccga aaatggctgt    120
ttcggctatc actggagcga ggctaactct agggatgtct ctttcctctt ccacgcgatc    180
acgaaccgtc gcaatggccg tatctatcga ccccaagacc gataacaaac tcactcttac    240
caagtccgag gaagctttcg ctgcgg                                          266
```

<210> SEQ ID NO 253
<211> LENGTH: 293
<212> TYPE: DNA
<213> ORGANISM: Glycine max
<220> FEATURE:
<223> OTHER INFORMATION: unsure at all n locations

<400> SEQUENCE: 253

```
ggttttgcat tcatttgac gaagagtgag agagtcttat ctgtcgtctc tgatctctga     60
tcgcatcttc attccgaaaa tggtgtttcg gctatcactg gagcgaggta actctaggga    120
tgtctctttc ctcttccacg cgatcacgaa ctgaagcaat ggccgtatct atcgacccca    180
agaccgataa caaacncatc ttaccaagtt cgaggaagtt tcgctgcggc caaggagtga    240
tgctggaggc gtgaactccc cagttcgtgc cttcaaatcc gtgggtggtc aac           293
```

<210> SEQ ID NO 254
<211> LENGTH: 273
<212> TYPE: DNA
<213> ORGANISM: Glycine max

<400> SEQUENCE: 254

```
gttggagagg cgaaactcga gagtgtaagg ttttgcattt catttgacga agagtgagag     60
agtcttatct gtcgtctctg atctctgatc gcatcttcat tccgaaaatg gctgtttcgg    120
ctatcactgg agcgaggcta actctaggga tgtctctttc ctcttccacg cgatcacgaa    180
tccccgcaat ggccgtatct atcgacccca agaccgataa caaactcact cttaccaagt    240
ccgaggaagc tttcgctgcg gccaaggagc tga                                  273
```

<210> SEQ ID NO 255
<211> LENGTH: 267
<212> TYPE: DNA
<213> ORGANISM: Glycine max
<220> FEATURE:
<223> OTHER INFORMATION: unsure at all n locations

<400> SEQUENCE: 255
gggcgaaact cgagagtgta aggttttgca tttcatttga cgaagagtga gagagtctta      60
tctgtcncct ctgatctctg atcgnatctn cattccgaan atggctgttt cggctatcac     120
tggnncgagg ctaactctan ggatgtcnct ntnctcttcc angngatcac gcnntnnncg     180
naanggacgn anctatcgac cccaagacng ataacaaatn actctnacca ngtccgngga     240
agctttcgct gcggccaagg agntnat                                         267

<210> SEQ ID NO 256
<211> LENGTH: 254
<212> TYPE: DNA
<213> ORGANISM: Glycine max

<400> SEQUENCE: 256
ggcgaaactc gagagtgtaa ggttttgcat ttcatttgac gaagagtgag agagtcttat      60
ctgtcgtctc tgatctctga tcgcatcttc attccgaaaa tggctgtttc ggctatcact     120
ggagcgaggc taactctagg gatgtctctt tcctcttcca cgcgatcacg aacccatgca     180
atggccgtat ctatcgaccc caagaccgat aacaaactca ctcttaccaa gtccgaggaa     240
gctttcgctg cggc                                                       254

<210> SEQ ID NO 257
<211> LENGTH: 254
<212> TYPE: DNA
<213> ORGANISM: Glycine max
<220> FEATURE:
<223> OTHER INFORMATION: unsure at all n locations

<400> SEQUENCE: 257
gttggatgag gcgaaactcg agagtgtaag gttttgcatt tcatttgacg aagagtgaga      60
gagtcttatc tgtcgtctct gatctctgat cgcatcttca ttccgaaaat ggctgattcg     120
gctatcactg gagcgccgtt aactctaggg atgtcttctt cctcgtgcag gcgacctcga     180
acgctggnaa tggccgtatc tatcgacccc aagaccgata acaaactcac tcttaccaag     240
tccgaggaag cttt                                                       254

<210> SEQ ID NO 258
<211> LENGTH: 270
<212> TYPE: DNA
<213> ORGANISM: Glycine max
<220> FEATURE:
<223> OTHER INFORMATION: unsure at all n locations

<400> SEQUENCE: 258
aggttttgca tttcatttga cgaagagtga gagagtctta tctgtcgnnt ctgatntntg      60
atcgcatctt cattccgaaa atggcngttt cggctatcac tggagcgagg ctaagtntag     120
ggatgtctct ttacctnttc cacgcgatca cgaaccacac gcaatggccg tatctatcga     180
cccnaagacc gctaacaaan tcantctnac caagttccga ggaagntttg gnngcgggcc     240
aagggagtga tgcctggagg cgtgaactcc                                      270

```
<210> SEQ ID NO 259
<211> LENGTH: 165
<212> TYPE: DNA
<213> ORGANISM: Glycine max

<400> SEQUENCE: 259
ggcgaaactc gagagtgtaa ggttttgcat ttcatttgac gaagagtgag agagtcttat      60
ctgtcgtctc tgatctctga tcgcatcttc attccgaaaa tggctgtttc ggctatcact     120
ggagcgaggc taactctagg gatgtctctt cctcttcca cacaa                      165

<210> SEQ ID NO 260
<211> LENGTH: 161
<212> TYPE: DNA
<213> ORGANISM: Glycine max
<220> FEATURE:
<223> OTHER INFORMATION: unsure at all n locations

<400> SEQUENCE: 260
cgaaactcga gagtgtaagg ttttgcattt catttgacga agagtgagan agtcttatct      60
gtcgtctctg atctctgatc gcatcttcat tcccgaaaat ggctgtttcg gctatcactg     120
gagcgaggct aactctaggg atgtctcttt cctcttccac a                         161

<210> SEQ ID NO 261
<211> LENGTH: 153
<212> TYPE: DNA
<213> ORGANISM: Glycine max

<400> SEQUENCE: 261
aaggttttgc atttcatttg acgaagagtg agagagtctt atctgtcgtc tctgatctct      60
gatcgcatct tcattccgaa aatggctgtt tcggctatca ctggagcgag gctaactcta     120
gggatgtctc tttcctcttc cacacaacat acg                                  153

<210> SEQ ID NO 262
<211> LENGTH: 241
<212> TYPE: DNA
<213> ORGANISM: Glycine max

<400> SEQUENCE: 262
cttcatttga cgaagagtga gagagtctta tctgtcgtct ctgatctctg atcgcatctt      60
cattccgaaa atggctgttt cggctatcag tggagcgagg ctaactctag ggatgtctct     120
ttcctgttcc acgcgatgta aagatgatg atggccgca tctatcgacc tctagacagc      180
taagatactc agtcttagga ggtccgagga agctttcgct gtggccaagg attgatgtcc     240
a                                                                     241

<210> SEQ ID NO 263
<211> LENGTH: 130
<212> TYPE: DNA
<213> ORGANISM: Glycine max
<220> FEATURE:
<223> OTHER INFORMATION: unsure at all n locations

<400> SEQUENCE: 263
gcgaaactcg agagtgtaag gttttgcatn tcatttgacg aagagtgaga gagtcttatc      60
tgtcgnntct gatctctgat cgcatcttca ttccgaaaat ggctgtttcg gctatcactg     120
gagcgaggct                                                            130
```

<210> SEQ ID NO 264
<211> LENGTH: 169
<212> TYPE: DNA
<213> ORGANISM: Glycine max

<400> SEQUENCE: 264
cgctcgagcg aatcggctca cggctcgagg ttttgcattt actttgacga agagtgacga      60
gagtcttatc tgtcgtctct gatctctgat cgcatcttca ttccgaaaat ggctgtttcg     120
gctatcactg gagcgaggct aactctaggg atgtctcttt cctcttcca                169

<210> SEQ ID NO 265
<211> LENGTH: 181
<212> TYPE: DNA
<213> ORGANISM: Glycine max
<220> FEATURE:
<223> OTHER INFORMATION: unsure at all n locations

<400> SEQUENCE: 265
gcgaaactcg anagtgtaag gnttngcatt ncanttgacg aagagtgaga gagtctnatc      60
tgtcgngctc tgatntnnga tcgcatcntc attccganaa tggctgtttc ggctatcact     120
ggagcgaggc taactctagg gangtctctn ncctcttcca cacaacatac gagnntcntc     180
g                                                                    181

<210> SEQ ID NO 266
<211> LENGTH: 342
<212> TYPE: DNA
<213> ORGANISM: Glycine max
<220> FEATURE:
<223> OTHER INFORMATION: unsure at all n locations

<400> SEQUENCE: 266
anacactgnt aaagtgaaga nggtgaatgg agatgtgtct gagaacaaca aaggaggnag      60
caaaccttca gcagaaatag atcttccaga tgctgaagtt ggaaaagttc gcttgcgatt     120
tgcacctgaa ccaagtggtt atcttcatat tggacactca aaagcagctt tgttgaacaa     180
tattttgctg agcgatacca gggtcaggtt attgtncgnt ctgatgatan caatcctgct     240
aaagagagca atgaatttgt ggacaacctg attaaagata ttgatacatt gggcatcana     300
tatgaacaaa ttacatatac atcagattac ttccctgagt tg                       342

<210> SEQ ID NO 267
<211> LENGTH: 290
<212> TYPE: DNA
<213> ORGANISM: Glycine max

<400> SEQUENCE: 267
agctgccgga gataaagcta caacatatac taaaaggata tggcttgacc ttgctgatgc      60
agtgtcttta tcagcaggtg aggaagtaac attgatggat tggggaaatg ccatagtgaa     120
ggaaatagag aaggaccaag atggaaatat catagggttg agtggtgttt tgcatctaga     180
aggatctgtg aagaccacaa aattgaaact cacttggcta cctgagatag atgaactagt     240
tagcctgaca ttagtggagt ttgattatct aattacaaag aaaaagcttg                290

<210> SEQ ID NO 268
<211> LENGTH: 248
<212> TYPE: DNA
<213> ORGANISM: Glycine max

<400> SEQUENCE: 268

```
tcggaattca gcgcgaggga tagcaatcct gctaaagtaa gcaatgaatt tgtggacaac    60
cttattaaag atggtgatac attgggtatc aaatatgaac aaatgacata tacgtcagag   120
tacttccctg agttgatgga gatggctgaa aaattaattc gccagggtaa agcatatgtt   180
gatgacacac cacgtgaaca aatgcaaaaa gagagattgg atggcataga ttctaaatgc   240
agaaataa                                                            248
```

<210> SEQ ID NO 269
<211> LENGTH: 258
<212> TYPE: DNA
<213> ORGANISM: Glycine max

<400> SEQUENCE: 269

```
ggcattgttg tgtggcggca cgccatggtc gaaggttact atttcaccat tttccaccac    60
tcccacaccc ctcgcacctt cttcttccaa cgacgccgtt tctcagtctc tgctgctttc   120
tccgaacaac aaccaccgcc acccgttcgc gttcgtttcg ctccttctcc caccggaaac   180
ctccacgtcg gcggtgcccg aacggccctc ttcaactact tgttcgcaag gtccaaaggt   240
gggaaatttg tgctgaga                                                 258
```

<210> SEQ ID NO 270
<211> LENGTH: 267
<212> TYPE: DNA
<213> ORGANISM: Glycine max

<400> SEQUENCE: 270

```
actgagtaga tggagatgga tgaaaaatta gttcgccagg gaaaagcata tgttgatgac    60
atagcacgtg aacaaatgca aaagagaga atggatggca tagattctaa atgcagaaat   120
aatagtgtag aggagaatct aaaattgtgg aaggaaatgt tggcaggaac agagaggggg   180
ttgcagtgtt gtgtccgtgg caagttggat atgcaggacc caaacaaatc acttagagat   240 cctgttttatt atcgttgcaa tccaatg                                      267
```

<210> SEQ ID NO 271
<211> LENGTH: 245
<212> TYPE: DNA
<213> ORGANISM: Glycine max

<400> SEQUENCE: 271

```
tgatgcacga tttcctacag tgcaaggaat tgtgcgtaga ggtttgaaaa ttgaagccct    60
gatacagttt attgttgagc aggggcgtc caaaaatctc aatctcatgg aatgggacaa   120
gctctggacc attaataaga agattattga ccctgtctgt cctagacaca ctgctgtcat   180
tgcagacaga cgtgttttgt tgactctcac tgatggtcct gagtatcctt ttgtccgcat   240
catac                                                              245
```

<210> SEQ ID NO 272
<211> LENGTH: 280
<212> TYPE: DNA
<213> ORGANISM: Glycine max

<400> SEQUENCE: 272

```
attgcaggaa cagagagggg cttgcagtgt tgtgtccgtg gcaagttgga tatgcaggac    60
ccaaacaaat cacttagaga tcctgtttat atcgttgca atccaatgcc ccatcataga   120
attggatcca agtataaagt gtatccaact tatgattttg cttgtccata tgttgattct   180
atagaaggaa tcacgcatgc ccttcgatct agtgaatacc atgatcgcaa tgcccagtat   240
```

```
tactggattc aagaggacat gggtcttaga aaagttctta                             280

<210> SEQ ID NO 273
<211> LENGTH: 276
<212> TYPE: DNA
<213> ORGANISM: Glycine max

<400> SEQUENCE: 273
aggttgagtg gtgttttgca tcttgaagga tctgtgaaga ccacaaaatt gaaactcact       60
tggctacctg agatagatga actagttagc ctgacattag tggagtttga ttatctaatt      120
acaaagaaaa agcttgaaga agggaggatt tcattgatgt ggttaaccca tgtaccaaaa      180
aggagacttt agcttatgga gactccaaca tgcgaaatct tcagcgtgga gatttattgc      240
aactggagag aaagggatat ttcaggtgtg atttac                                276

<210> SEQ ID NO 274
<211> LENGTH: 283
<212> TYPE: DNA
<213> ORGANISM: Glycine max

<400> SEQUENCE: 274
agcaggtatt cgtgctgagt cagattctag agataattat tctcctggat ggaagtattc       60
caactgggaa atgaaagggg ttcctctaag aattgaaatt gggccaaagg atttagcaaa      120
taagcaggtc atcaactttg ccagtgtttt atcaattctc atatttgtca ttttgcttcc      180
acactgttag ttttttcagtg aacaccaaat aaatctcttt gaattttgca taggttcgca      240
ctgttcgacg tgataatggt gcaaagatag acattgctag tgc                        283

<210> SEQ ID NO 275
<211> LENGTH: 403
<212> TYPE: DNA
<213> ORGANISM: Glycine max

<400> SEQUENCE: 275
caaaaccatt tgcgttgtcg cagtcgcagt caaaggccaa ggcaaaaccc taaattgtct       60
cacactttcg tcggaatccg ctttttggctt tttccgtgac aagatgccgg cgaaggacga      120
cggctccgac aaggagaagt gccttgatct ctttctgaaa atcggcttag acgagcgcac      180
cgctaaaaac accgtcgcaa acaacaaagt caccgccaat cttactgcag tcatctacga      240
ggccggtgtt attgatggat gcagccgagc ggttggaaat cttctttaca cggttgcaac      300
gaagtaccct gcaaatgcct tgccacatcg cccaacattg ctacagtaca ttgtctcgtt      360
aaggtgaaaa caactgcaca gttagatgca gcattatcat ttc                        403

<210> SEQ ID NO 276
<211> LENGTH: 445
<212> TYPE: DNA
<213> ORGANISM: Glycine max
<220> FEATURE:
<223> OTHER INFORMATION: unsure at all n locations

<400> SEQUENCE: 276
gagaaaatgg cgctgctgtg angcggttgc catggnacga aggtnaatag tgnctctaca       60
tgttnnaatc aatcntaaca ccccnaggna cntnnttatt cnaangacgc aagtttctna      120
atctctgatg tctttagaac aacgnaacat ccgtcgnag tcgttttgct ncttctacaa       180
cggaaacctt acatatcggc atgttccacg aacgggccct cttnaactac ttgttcgnaa      240
```

```
ggtccaaang tggaaaattt gtgctgaata attgaggaca ctgacttgga naggtccagt    300
agggagttat gaggaggcca atgctcaaag atctttcttg gcttggactt gattgggatn    360
aaggncctgg tgttgaacgg gattatggcc ttatangcag tctgagagga attcttatcc    420
aaccaatntc nggaaaacct acanc                                          445
```

```
<210> SEQ ID NO 277
<211> LENGTH: 277
<212> TYPE: DNA
<213> ORGANISM: Glycine max
<220> FEATURE:
<223> OTHER INFORMATION: unsure at all n locations

<400> SEQUENCE: 277
gtttattatc gttgcaatcc aatgcnccat catagaattg gatccaagta taaagtgtat     60
ccaacttatg attttgcttg tccatatgtt gattctatag aaggaatcac gcatgccctt    120
cgatctagtg aacccatga ttgcaatgcc cagtattact ggattcaaga ggacatgggt    180
cttagaaaag ttcttatcta cgaatttagc cggtncgaat atggtctaca ctcttctgag    240
caaacgaaag cttttgtggt ttgtacaaaa tgggaaa                             277
```

```
<210> SEQ ID NO 278
<211> LENGTH: 255
<212> TYPE: DNA
<213> ORGANISM: Glycine max

<400> SEQUENCE: 278
agattctaga gataattatt ctcctggatg gaagtattct aattgggaaa tgaaaggtgt     60
tcctctaaga attgaaattg ggccaaagga tttagcaaat aagcaggttc gtgctgttcg    120
acgtgataat ggagcaaaga tagcattgct agtgctgatt tggttgtgga aataaaaaag    180
ttgcttgata ctattcaaca gaacctgttt gatgttgcaa acaaaaacg agatgaatgc    240 attcagatca tacac                                                     255
```

```
<210> SEQ ID NO 279
<211> LENGTH: 258
<212> TYPE: DNA
<213> ORGANISM: Glycine max

<400> SEQUENCE: 279
agattctaga gataattatt ctcctggatg gaagtattct aattgggaaa tgaaaggtgt     60
tcctctaaga attgaaattg ggccaaagga tttagcaaat aagcaggttc gtgctgttcg    120
acgtgataat ggagcaaaga tagacatgct agtgctgatt tggttgtgga aataaaaaag    180
ttgcttgata ctattcaaca gaacctgttt gatgttgcaa acaaaaacg agatgaatgc    240 attcagatca tacacact                                                  258
```

```
<210> SEQ ID NO 280
<211> LENGTH: 265
<212> TYPE: DNA
<213> ORGANISM: Glycine max

<400> SEQUENCE: 280
agattctaga gataattatt ctcctggatg gaagtattct aattgggaaa tgaaaggtgt     60
tcctctaaga attgaaattg ggccaaagga tttagcaaat aagcaggttc gtgctgttcg    120
acgtgataat ggagcaaaga tagacattgc agtgctgatt tggttgtgga aataaaaaag    180
ttgcttgata ctattcaaca gaacctgttt gatgttgcaa acaaaaacg agatgaatgc    240
```

```
attcagatca tacacacttg ggatg                                           265

<210> SEQ ID NO 281
<211> LENGTH: 264
<212> TYPE: DNA
<213> ORGANISM: Glycine max
<220> FEATURE:
<223> OTHER INFORMATION: unsure at all n locations

<400> SEQUENCE: 281
tcctgctaaa gaaagcaatg aatttgtgga caaccttatt aaagatattg atacattggg     60
tatcaaatat gaacaaatta catatacgtc agattacttc cctgagttga tggagatggc    120
tgaaaaatta attcgccagg gtaaagcata tgttgatgac acaccacgtg aacaaatgcn    180
aaaagagaga atggatggca tagattctaa atgcagaaat aatagtgtag aggagaatct    240
aaaattgtgg aaggnaatga ttgc                                          264

<210> SEQ ID NO 282
<211> LENGTH: 263
<212> TYPE: DNA
<213> ORGANISM: Glycine max

<400> SEQUENCE: 282
cctgattaaa gatattgata cattgggcat caaatatgaa caaattacat atacatcaga     60
ttacttccct gagttgatgg aaatggctga aaaattaatt cgcgagggta aacatatgt    120 tgatgacact ccacgtgaac aaatgcaaaa agagagaatg gatggcatag aatctaaatg    180
cagaaataat atagtagagg agaatctaaa actgtggaag gaaatgattg caggaacaga    240
gaggggattg cagtgttgtg tcc                                           263

<210> SEQ ID NO 283
<211> LENGTH: 267
<212> TYPE: DNA
<213> ORGANISM: Glycine max

<400> SEQUENCE: 283
ttgggcatca aatatgaaca aattacatat acatcagatt acttccctga gttgatggaa     60
atggctgaaa aattaattcg cgagggtaaa acatatgttg atgacactcc acgtgaacaa    120
atgcaacaag agagaatgga tggcatagaa tctaaatgca gaataatat agtagaggag    180 aatctaaaac tgtggaagga aatgattgca ggaacagaga ggggattgca gtgttgtgtc    240
cgtggcaagt tggatatgca ggaccca                                       267

<210> SEQ ID NO 284
<211> LENGTH: 269
<212> TYPE: DNA
<213> ORGANISM: Glycine max

<400> SEQUENCE: 284
atgggagttc agcaaaccca ctccattcat caggagtcgc gagtttcttt ggcaagaagg     60
gcacactgct tttgcaacaa aggatgaagc agatgcagag gttcttgaga ttctggaatt    120
atataggcgt atatacgaag agatttggca gttcctgtca taagggtaa gaaaagtgag    180 cttgagaagt ttgctggtgg actctacact accagtgttg aggcatttat tccaaacact    240
ggtcgtggta tccaaggtgc aacttctca                                     269

<210> SEQ ID NO 285
```

```
<211> LENGTH: 422
<212> TYPE: DNA
<213> ORGANISM: Glycine max

<400> SEQUENCE: 285
gtccaaacgg cagcgagaag acgacagaag gggtcagatg ggagttcagc aaccccactc      60
cattcatcag gagtcgtgag tttctttggc aagaagggca cactgctttt gcttcaaagg     120
aggaagcaga tgcagaggtt cttgagattc tggaattata taggcgtata tacgaagagt     180
atttggcagt tcctgtcata aagggtaaga aaagtgagct tgagaagttt gctggtggac     240
tctacactac tagtgttgag gcatttattc caaacactgg tcgtggtata caaggtgcaa     300
cttctcattg tttgggccaa aattttgcta aatgtttgga gataaacttt gaaaatgaaa     360
agggagagag agcaatggtc tggcagaatt catgggccta gtactcgaa actatcggtg     420 tc                                                                    422

<210> SEQ ID NO 286
<211> LENGTH: 240
<212> TYPE: DNA
<213> ORGANISM: Glycine max

<400> SEQUENCE: 286
aaattatata ggcgtatata cgaagagtat ttggcagttc ctgtcataaa gggtaagaaa      60
agtgagcttg agaagtttgc tggtggactc tacactacca gtgttgaggc atttattcca     120
aacactggtg tggtatccaa ggtgcaactt ctcattgttt gggccaaaat tttgctaaaa     180
tgtttgagat aaactttgaa atgaaaaggg agagaaagc aatggtctgg cagaattcat     240

<210> SEQ ID NO 287
<211> LENGTH: 378
<212> TYPE: DNA
<213> ORGANISM: Glycine max

<400> SEQUENCE: 287
ggaggctaca attttttgagc tacgttatcg aacaaatgtg ggtgagttgc ttgggcgtgt      60
gcgcaaagag ctgccatggg gtgatgcaaa agttgccaag caacttgttg atgcgcaact     120
atatgaacta cttggtgatc ggacagcagc agatgatgaa aagccttcta gaaagaagaa     180
ggagaaacct gctaaagtag aggataaggc agctcctgtt tctacccctg aaaagtcacc     240
tgaagaagac gttaatccat ttttaatatt ccctaatcca gaggaaaatt tcaaggtgca     300
tactgaagtg cctttttagtg atggtagtat tttgagatgt tgcaatacaa gagatctgct     360
tgacaaacac ttaaaagc                                                   378

<210> SEQ ID NO 288
<211> LENGTH: 269
<212> TYPE: DNA
<213> ORGANISM: Glycine max

<400> SEQUENCE: 288
aacaaatgca aaagagaga atggatggca tagaatctaa atgcagaaat aatatagtag      60
aggagaatct aaaactgtgg aaggaaatga ttgcaggaac agagagggga ttgcagtgtt     120
gtgtccgtgg caagttggat atgcaggacc caaacaaatc acttagagat cctgtatatt     180
atcgttgcaa tccaatgccc catcatagaa ttggatccaa gtataaagtg tatccaactt     240
atgatttcgc ttgtccatat gttgatgct                                       269
```

<210> SEQ ID NO 289
<211> LENGTH: 258
<212> TYPE: DNA
<213> ORGANISM: Glycine max

<400> SEQUENCE: 289

```
aacaaatgca aaagagaga atggatggca tagaatctaa atgcagaaat aatatagtag        60
aggagaatct aaaactgtgg aaggaaatga ttgcaggaac agagagggga ttgcagtgtt       120
gtgtccgtgg caagttggat atgcaggacc caaacaaatc acttagagat cctgtatatt      180
atcgttgcaa tccaatgccc catcatagaa ttggatccaa gtataaagtg tatccaactt      240
atgatttcgc ttgtccat                                                    258
```

<210> SEQ ID NO 290
<211> LENGTH: 251
<212> TYPE: DNA
<213> ORGANISM: Glycine max
<220> FEATURE:
<223> OTHER INFORMATION: unsure at all n locations

<400> SEQUENCE: 290

```
aggcgatctc ggttgggaag cggggaagat ggggaagctt gtaattaagc atttggctgc        60
caacncggtg cagaagaatg gttgttgtta acaggactga agagaaagtt aatgccattc       120
ggaaagagtt gaaggatgtt gagattgtat ttagaccatt ttcagatatg ctggcgtgtg      180
ctgctgaagc tgatgtgatc ttccaccagca cagcgtctga atcaccatgt tctctaaaca      240
gaatgtgcag a                                                           251
```

<210> SEQ ID NO 291
<211> LENGTH: 240
<212> TYPE: DNA
<213> ORGANISM: Glycine max

<400> SEQUENCE: 291

```
atttgcatag ggctgaacat tcacactgct cccgttgaga tgcgtgagaa gcttgcaatt        60
ccagaatccc attgggctca ggctattaag gacctttgcg ctttgaacca tatcgaagaa      120
gccgcggttc tcagcacgtg taaccgcatg gagatctatg ttgtggctct ttcccagcac      180
cgtggtgtta aggaagttac tgattggatg tctaaggtga gcgggatttc aatacctgag      240
```

<210> SEQ ID NO 292
<211> LENGTH: 275
<212> TYPE: DNA
<213> ORGANISM: Glycine max
<220> FEATURE:
<223> OTHER INFORMATION: unsure at all n locations

<400> SEQUENCE: 292

```
aggaagcagc tgttctgagc acctgcaaca gaatggaaat atatgttgtt gctctgtcca        60
agcaccgtgg tgttaaagaa gtcactgaat ggatgtccaa acangtggg attccagttg       120 cagatctttg ccagcatcag tttctgctat acaacaaaga tgccacacaa caccttttg      180 aagtatctgc aggtcttgat tctctagtgt tgggagaagg tcaatccttg cccaggtgan      240
gcaggttgtc aatttggaca aggnttaang ncttc                                 275
```

<210> SEQ ID NO 293
<211> LENGTH: 276
<212> TYPE: DNA
<213> ORGANISM: Glycine max
<220> FEATURE:

<223> OTHER INFORMATION: unsure at all n locations

<400> SEQUENCE: 293

```
ggtaagaact tgagacaaaa cattgctgct ggtgcagtan ncnnnnagtt catcaactgt      60
antncnggga cntnattnag gctaccngaa gnctcacatg ncatgcaagg ntgttggtca     120
ttggagctgg gnagatcgga agcttgtgat caagcattn gtggcaaaag ggtgcacaaa     180
gatggtggtt gtcatagagt gangagagag ttgccgcgat ccgtgaagaa atcaagatgt    240
tgagataatc tacaagccac tctcggagat gctcac                              276
```

<210> SEQ ID NO 294
<211> LENGTH: 271
<212> TYPE: DNA
<213> ORGANISM: Glycine max

<400> SEQUENCE: 294

```
ctcgagcgga ataagctact tcatggtccc atgcagcacc taaggtgtga tgggaacaat     60
gatagtagtc tgagtgaagt acttgagaat atgcgcgccc ttaacagaat gtatgatctt    120
gagacagaaa cttccttgat cgaagaaaag atcagagtca agatggaacg ggttcagaag    180
tagattcttc ttcaattggt ttagttttac ttgattactg tgggggctgc aatcctcgcc    240
attttgtaca ctacagtagt tgattgaggc c                                    271
```

<210> SEQ ID NO 295
<211> LENGTH: 130
<212> TYPE: DNA
<213> ORGANISM: Glycine max

<400> SEQUENCE: 295

```
ggcaatcatt gctgaagaat ctaagcaatt tgaagcttgg agggactcgc tggaaactgt     60
tcctactatt aagaaattga gggcttatgc tgaaagaatc aggcttgctg agcttgagaa    120
gtgcttaggt                                                            130
```

<210> SEQ ID NO 296
<211> LENGTH: 426
<212> TYPE: DNA
<213> ORGANISM: Glycine max

<400> SEQUENCE: 296

```
cccacgcgtc cgaacatttg gtggcaaaag gttgcaaaaa gatggtggtt gtcaatagaa     60
ctgatgagag agttgctgca atacgtgaag aactgaagga tattgagatt atctacaaac    120
ccctttcaga aatgctcacc tgtgctggcg aagcagattt agttttcacc agtactgcat    180
cagaaaaccc attattcttg aaagaacatg tcaaggacct tcctcctgca agtcaagaag    240
ttggaggccg tcgctttttc attgatatct ctgttccccg gaatgtgggt tcatgtgtct    300
cagaccttga gtctgtgcga gtttacaatg ttgacgacct taaagaggtt gtggctgcca    360
ataaagagga tcgcctaaga aaagcaatgg acgcacaggc aatcattgct gaaaaatcta    420
agcaat                                                                426
```

<210> SEQ ID NO 297
<211> LENGTH: 271
<212> TYPE: DNA
<213> ORGANISM: Glycine max

<400> SEQUENCE: 297

```
aggataggct aagaagagcc atggaggctc aagcaatcat tggtgaagaa tcaaaacaat     60
```

```
ttgaggcttg gagagactca ttggaaactg ttcctaccat taaaaagttg agggcatatg    120
ctgaaagaat aaggcttgct gagcttgaga agtgcctagg taagatgggt gatgatatca    180
acaagaagac acaaagagct gtggatgatc ttagcagggg tatagtgaat aagttgcttc    240
atgggccaat gcaacacttg aggtgtgatg g                                   271

<210> SEQ ID NO 298
<211> LENGTH: 266
<212> TYPE: DNA
<213> ORGANISM: Glycine max

<400> SEQUENCE: 298
agaaaagcca tggaggctca agcaatcatt ggtgaagaat caaaacaatt tgaggcttgg     60
agagactcat tggaaactgt tcctaccatt aaaaagttga gggcatatgc tgaaagaata    120
aggcttgctg agcttgagaa gtgcctaggt aagatgggtg atgatatcaa caagaagaca    180
caaagagctg tggatgatct tagcaggggt atagtgaata agttggcttc atgggccaat    240
gcaacacttg agtgtgatgg cagtga                                         266

<210> SEQ ID NO 299
<211> LENGTH: 289
<212> TYPE: DNA
<213> ORGANISM: Glycine max

<400> SEQUENCE: 299
cacaattctc ccttcaaagt ttcaatggct gtttcaacca gcttctcggg tgtaaagttg     60
gaggctttgt tgctgaaatg tggttcctcc aatgctgcca ccaccaccac tcatatatca    120
tgttttggca aaacagaaaa gacacttgtt cagagtcaga gaggggctat tcgttgtgag    180
gcttcttctg cttctgatgt tgtggctgat gccaccaaga aagctgctag tgtctctgct    240
cttgagcagc ttaagacctc tgcagctgat aggtatacaa aggaaagga                289

<210> SEQ ID NO 300
<211> LENGTH: 289
<212> TYPE: DNA
<213> ORGANISM: Glycine max
<220> FEATURE:
<223> OTHER INFORMATION: unsure at all n locations

<400> SEQUENCE: 300
cacaattctc ccttcanagt ttcaatggct gtttcaacca gcttctcggg tgtaaagttg     60
gaggctttgt tgctganatg tggttcctcc aatgctgcca ccaccaccac tcatatatca    120
tgttttggca aaacagaaaa gacacttgtt cagagtcaga gaggggctat tcgttgtgag    180
gcttctnctg cttctgatgt tgtggctgat gccaccaaga aagctgctan tgtctctgct    240
cttgagcagc ttaagacctc tgcagctgat aggtatacna aggaaagga                289

<210> SEQ ID NO 301
<211> LENGTH: 266
<212> TYPE: DNA
<213> ORGANISM: Glycine max

<400> SEQUENCE: 301
cagggcttga ctcacttgtt cttggggaag gtcaaattct tgctcaggtg aagcaggttg     60
tgaaagctgg acagggagtg cctggttttg ataagaaaat cagtggtttg ttcaagcagg    120
cgatatcggt tgggaagcgg gttagaaccg agactaacat ttcatctgga tcagtttctg    180
```

```
taagctcggc tgctgtggag cttgcactga tgaagctacc ggaaattacc tttgctgatt      240
ctggagtgtt ggtggttggt gctggg                                            266

<210> SEQ ID NO 302
<211> LENGTH: 275
<212> TYPE: DNA
<213> ORGANISM: Glycine max

<400> SEQUENCE: 302
cgcgcacatc tatttgaagt ggcgtcaggg cttgactcac ttgttcttgg ggaaggtcaa       60
attcttgctc aggtgaagca ggttgtgaaa gctggacagg gagtgcctgg ttttgataag     120
aaaatcagtg gtttgttcaa gcaggcgata tcggttggga agcgggttag aaccgagact     180
aacatttcat ctggatcagt ttctgtaagc tcggctgctg tggagctgca ctgatgaagc     240
taccggattc ctcctttgct gattctggag tgttg                                 275

<210> SEQ ID NO 303
<211> LENGTH: 288
<212> TYPE: DNA
<213> ORGANISM: Glycine max

<400> SEQUENCE: 303
cttgagcagc ttaagacctc tgcagctgat aggtatacaa aggaaaggag cagcatcatg      60
gttattggac tgagtgtgca tagtacacct gtggaaatgc gtgaaaaact tgccatacca     120
gaagcagaat ggccaagagc cattgcggag tttgtagtct gaatcatatt gaggaagcag     180
ctgttctgag cacctgcaac agaatggaga tatatgttgt tgctctgtcc aagcaccgcg     240
gtgtcaaaga agtcactgaa tggatgtcca aaacaagtgg gatcccgg                  288

<210> SEQ ID NO 304
<211> LENGTH: 299
<212> TYPE: DNA
<213> ORGANISM: Glycine max

<400> SEQUENCE: 304
agtgtgcata gtacacctgt ggaaatgcgt gaaaaacttg ccataccaga agcagaatgg      60
ccaagagcca ttgcggagtt tgtagtctga atcatattga ggaagcagct gttctgagca     120
cctgcaacag aatggagata tatgttgttg ctcttccaag caccgcgttg tcaaagaagt     180
cactgaatgg atgtccaaaa caagtgggat cccggttgca gacctttgcc agcatcagtt     240
tctgctatac aacaaagatg cgacacagca ccttttttgaa gtatctgctg gtcttgatt     299

<210> SEQ ID NO 305
<211> LENGTH: 260
<212> TYPE: DNA
<213> ORGANISM: Glycine max
<220> FEATURE:
<223> OTHER INFORMATION: unsure at all n locations

<400> SEQUENCE: 305
gagcagcatc atggttattg gactgagtgt gcatagtaca cctgtggaaa tgcgtgaaaa      60
acttgccata ccagaagcag aatggccaag agccattgcg gagtttgtag tctgaatcat     120
attgaggaag cagcngttct gagcacctgc aacagaatgg agatatatgt ngttgctctg     180
tccangcacc gcggtgtcaa agnagtcact gaatggntgt ccaaaacaag tnggntcccg     240
gttgcagact ttgccagcat                                                  260
```

```
<210> SEQ ID NO 306
<211> LENGTH: 440
<212> TYPE: DNA
<213> ORGANISM: Glycine max

<400> SEQUENCE: 306
gggttctcct gaatccgcaa tggccgtttc aaccactttc tccggtgcca aattggaggg      60
gctattgctc aaatgttctt cctcctcttc ctcaccaccg ccttcaaggt catcattcac     120
cactttcccc ggccaaaaca gaagaaccct cattcagaga ggggttattc gctgcgacgc     180
tcagccctct gatgcatcat ctgttgctcc aaataatgcc accgctctct ccgctcttga     240
gcagctcaag acttctgcag ctgatagata caaaggaa agaagcagca ttatcgccat       300
tgggctcagt gtgcacactg cacctgtgga atgcgtgaa aaacttgcca ttccagaagc      360
agaatggcct agagctattg cagagctgtg tagtctgaat catatttgag aagcagctgt     420
tctgagtacc ctgcatcgaa                                                 440

<210> SEQ ID NO 307
<211> LENGTH: 272
<212> TYPE: DNA
<213> ORGANISM: Glycine max

<400> SEQUENCE: 307
ctgaaatcaa ggttgttgct ggtgaccctt ataactcaga cccacaagat ccagaattca      60
tgggtgttga agtcagagag cgtgtacttc caaggagagg aactttctgt tgtcttgacc     120
aaaattaaca tggttgattt gcattgggag ctacagaaga tagagtgtgt ggaacaattg     180
acattgagaa agccctgact gagggtgtca aggcatttga gcctggacta tggctaaagc     240
taatagggga atctatatgt tgatgaagtt aa                                   272

<210> SEQ ID NO 308
<211> LENGTH: 254
<212> TYPE: DNA
<213> ORGANISM: Glycine max

<400> SEQUENCE: 308
gtcttacaac ggctttagag ttggactaaa tgcggagaaa agtggtgacg ttggacgtat      60
aatgattgtt gcaatcactg atggcagagc caatatatca ttgaaaaggt caactgaccc     120
tgaagctgcc gcagctactg atgccccaaa accttcagca caagaattga aggatgaaat     180
tcttgaggtg gccggaaaga tatataaagc aggaatgtct ctccttgtca tcgacactga     240
aaataagttt gtct                                                       254

<210> SEQ ID NO 309
<211> LENGTH: 253
<212> TYPE: DNA
<213> ORGANISM: Glycine max

<400> SEQUENCE: 309
actttctgtt gtcttgacca aaattaacat ggttgatttg ccattgggag ctacagaaga      60
tagagtgtgt ggaacgattg acattgagaa agccctgact gagggtgtca aggcatttga     120
gcctggacta ctggctaaag ctaatagggg aatcttatat gttgatgaag ttaatctttt     180
ggatgatcac ttggtggatg tgttgttgga ttctgctgcg gatggaacac agtagagaga     240
gagggaattt cta                                                        253

<210> SEQ ID NO 310
```

```
<211> LENGTH: 253
<212> TYPE: DNA
<213> ORGANISM: Glycine max

<400> SEQUENCE: 310
tgttactctt aacagagaac aattaaaata cctggttatt gaagctttac ggggcggttg      60
ccagggacat agagctgatc tatttgctgc ccgtgttgca aagtgcttag ctgctttgga     120
gggacgtgaa aaggtttatg tggatgacct aaaaaaagct gtagaattgg tcattctacc     180
ccggtcaatc gttactgaga acccaccaga tcaacaaaac cagcctcctc ccctccgcc      240 tcctccacaa aat                                                        253

<210> SEQ ID NO 311
<211> LENGTH: 162
<212> TYPE: DNA
<213> ORGANISM: Glycine max

<400> SEQUENCE: 311
gcatgatgat ctccacatgt ctgtctgtca actaaaacac tattgcgttt catgatatat      60
caaattgtga acatgctatg tgttaatgtt tctttaaagc ataatccata gccccttatg     120
tttaatcaaa ccaaaattat gccctagttt tttttttttt gg                        162

<210> SEQ ID NO 312
<211> LENGTH: 232
<212> TYPE: DNA
<213> ORGANISM: Glycine max

<400> SEQUENCE: 312
aaaaaagaac agagagagaa gaatgaaatc tatctatctt cttatccgaa gtctgggagg      60
ccaataggaa gcacgccagc tgctacgaat ggtgaataaa agacaaaaga aacaaactgc     120
tacatagcat acagtctgtc ttctcttctc ttctccggtt atggcgtccg ccttgggcac     180
ttcttcaatt gcggttctgc cttcgcgcta cttctcttct tcttcttcca ag             232

<210> SEQ ID NO 313
<211> LENGTH: 262
<212> TYPE: DNA
<213> ORGANISM: Glycine max
<220> FEATURE:
<223> OTHER INFORMATION: unsure at all n locations

<400> SEQUENCE: 313
cacttaatcc aggctcagaa gattgctttt aacgagagcc agangccggt gtacccattt      60
tctgctatag tgggacacga tgagatgaag ctttgccttc tcctaaatgt aattnatccc     120
aagattggag gtgtaatgat catggggac agaggaacgg ggaaatctac aactgttaga     180
tcattggtag atttgcttcc tgaaatcaag gttgttgctg gtgaccatat attcagaccc     240
agaggatcca gattcatggg tg                                              262

<210> SEQ ID NO 314
<211> LENGTH: 280
<212> TYPE: DNA
<213> ORGANISM: Glycine max
<220> FEATURE:
<223> OTHER INFORMATION: unsure at all n locations

<400> SEQUENCE: 314
actctctcta acttcagggc agagctatgg gcggaaattt tatggaggaa ttggaattca      60
tggcatcaag ggaaggtctc agctctcagt tgccaatgtt gccactgaag ttaactctgt     120
```

```
agaacaggcc caaagtattg cttctaaaga aagccagagg ccagtatacc catttctgc     180 catagtngga caagatgaga tgaagctttg tcttctcctt aatgtgattg atcctaagat    240
tggaggtgta atgatcaggg ggatagggc acagggaaat                            280
```

<210> SEQ ID NO 315
<211> LENGTH: 238
<212> TYPE: DNA
<213> ORGANISM: Glycine max

<400> SEQUENCE: 315

```
ttttgctcgg aatttcctgt gtagaaggaa ctcatgaatc ttattgatgt ttaacgacaa     60
tgaaaatctc cacagaaaag gtaaaatgta aataatgaag tagcattata ctcatggaat    120
accacagaat acaaaccgtg ttacatctat gatcctcagc tgaataccct ataaaatttc    180
tcagtgacaa gtaaacctga gtctatagac tccaagggat cctttctaag acggtgtc     238
```

<210> SEQ ID NO 316
<211> LENGTH: 273
<212> TYPE: DNA
<213> ORGANISM: Glycine max

<400> SEQUENCE: 316

```
ttagggaagg gctcagctct cggttaccaa tgttgccact gaagttaact ctgtagaaca     60
ggctcagagt attgcttcta agaaagcca gaggccagta tacccatttt ctgccatagt    120
tggacaagat gagatgaagc tttgtcttct ccttaatgtg attgatccta agattggagg    180
tgtaatgatc atgggggata ggggcacagg gaaatctaca acggtcaggt cattggttga    240
tttacttccc gaaatcaagg ttgttgctgg tga                                 273
```

<210> SEQ ID NO 317
<211> LENGTH: 283
<212> TYPE: DNA
<213> ORGANISM: Glycine max

<400> SEQUENCE: 317

```
agactcattg gatcggttga tgttgaggag tctgtgaaaa caggcacaac tgttttccag     60
ccaggcttgc ttgcagaagc tcatagaggt gttttatatg ttgatgaaat taatcttttg    120
gatgagggta tcagtaattt gctccttact gtattgagtg aaggagtaaa tactgttgaa    180
agagagggga tcagtttcaa gcacccttgc aggccccttc tcattgccac ctataaccca    240
gaagagggtg ctgttcgtga acatctgctg daccgcattg cga                      283
```

<210> SEQ ID NO 318
<211> LENGTH: 173
<212> TYPE: DNA
<213> ORGANISM: Glycine max
<220> FEATURE:
<223> OTHER INFORMATION: unsure at all n locations

<400> SEQUENCE: 318

```
gctcgaggcg ccgntcanac gacgagccgc gagtgcgtgg cggcgtggga cgaggtggag     60
gagctgagcg cggcggcgag ccacgccaaa tacaagctaa aggaaaagga ctccgacccg    120
ctcgagacct actgcaagga caatccggag accattgagt gcaaaacttt cga           173
```

<210> SEQ ID NO 319
<211> LENGTH: 263
<212> TYPE: DNA

<213> ORGANISM: Glycine max

<400> SEQUENCE: 319

```
aggaattccg agattcttac aaagccgagc aagagaagct ccaacaacaa attacatcag    60
caaggagtgt tctttcttct gttcagattg atcaagatct caaggtgaaa atctccaagg   120
tgtgtgctga gttgaatgtg gatggattaa gaggagacat agtaacaaat agagctgcaa   180
aagctcttgc tgctctgaag gaaagagaca agtaagtgc agaggatatt gctactgtca    240
tccctaactg cttgagacac cgt                                           263
```

<210> SEQ ID NO 320
<211> LENGTH: 322
<212> TYPE: DNA
<213> ORGANISM: Glycine max

<400> SEQUENCE: 320

```
atagctttgg gagcaaaaac tgcacaaagc tcctcagtgc ccccaagtt ttcctttcaa     60
agcaattttg tgctttgctt tgaatgtctt ccttttcgat ccctacactt caatttgtag   120
caagaggaat tgttgtttc ctacttagca tgattattta tcaatggcgt ctttggtatc    180
ttcagcattt actcttccaa gctctaaacc tgaccagctt caatcacttg ccccgaaaca   240
tcttttcat cagtcattcc ttcccaagaa agccaattac aatggtagct caaaatcctc    300
tctgaaaatt aaatgtgctg tc                                            322
```

<210> SEQ ID NO 321
<211> LENGTH: 410
<212> TYPE: DNA
<213> ORGANISM: Glycine max
<220> FEATURE:
<223> OTHER INFORMATION: unsure at all n locations

<400> SEQUENCE: 321

```
cagtcattac tttgactcan accccgacta atctggntca gaatctaagg aaagatggga    60
agaagcctag tgcatacatt gctgatacaa ccacagccaa tgctcaggta cgtacactnt   120
ctgagacggt tagacttgac gcaagaacca agctgttgaa tccaaagtgg tatgaaggca   180
tgttgtctac tggatatgag ggtgtacgcg agatcgagaa gagactcacc aatacagtgg   240
ggtggagtgc aacttcaggc caagttgata actgggtgta tgaagaagcc aacacaactt   300
tcattcaaga tgagcaaatg ctgaacaagc tcatgagcac taatccaaac tccttcagga   360
aactggtgca gacattcttg gaagccaatg gacgtggtta ttgggaaact              410
```

<210> SEQ ID NO 322
<211> LENGTH: 324
<212> TYPE: DNA
<213> ORGANISM: Glycine max

<400> SEQUENCE: 322

```
gaaaaataac acacatttga aactcaaact gaaatgggtg catagctttg gggcaaaaac    60
tacacaaaac tcctcattgc ccccaagttt tttctttcaa agcaattttg cactttttg    120
ctttcattgt cttcaatttg tagtaagagg aaattgttgt ttcctactta gcttgattat   180
tattatcaat ggcttcttta gtatcttcac aatttacact accaagttct aaacctgacc   240
agcttcattc tcttgctcag aagcatcttt ttctccactc tttccttccc aagaaggcca   300
attacaatgg tagcagctca aaat                                          324
```

<210> SEQ ID NO 323
<211> LENGTH: 340
<212> TYPE: DNA
<213> ORGANISM: Glycine max
<220> FEATURE:
<223> OTHER INFORMATION: unsure at all n locations

<400> SEQUENCE: 323

```
gaagaagtaa tacatgacaa agaagctcaa tttagcagcc caaatctgaa cgttgcttac      60
aaaatgaatg tccgagaata ccaaagtcta actccctatg ccacagcatt agaagaaaac     120
tggggaaaac ctcctgggaa tctgaattca gatggagaga atctattggt atatgggaaa     180
caatatggta atgtattcat aggtgttcaa cccacatttg gctatgaagg cgatcctatg     240
cggttgcttt tctccaaatc tgcaagtcct catcatggat ttgcagcatn atactctttt     300
gtttgagaaa ttttcaaagc tgaagcggtt cttcattttg                           340
```

<210> SEQ ID NO 324
<211> LENGTH: 264
<212> TYPE: DNA
<213> ORGANISM: Glycine max

<400> SEQUENCE: 324

```
ggcgaagaac agaatgaaga ggaagaacaa gaggatgaca aggatgaaga gaatgaacaa      60
cagcaagaac aattacctga agagtttatc tttgatgctg aaggtggctt ggtagatgaa     120
aaactcctct tctttgccca acaagcacag agacgccgtg ggagggctgg aagggcaaaa     180
aatgttatat tttccgagga tagaggccga tacatcaagc ccatgcttcc aaagggccct     240
gtaaagagat tagctgtaga tgca                                            264
```

<210> SEQ ID NO 325
<211> LENGTH: 246
<212> TYPE: DNA
<213> ORGANISM: Glycine max

<400> SEQUENCE: 325

```
caaaatcaag aatcaggcga agaacagaat gaagaggaag aacaagagga tgacaaggat      60
gaagagaatg aacaacagca agaacaatta cctgaagagt ttatctttga tgctgaaggt     120
ggcttggtag atgaaaaact cctcttcttt gcccaacaag cacagagacg ccgtgggagg     180
gctggaaggg caaaaaatgt tatattttcc gaggatagag gccgatacat caagcccatg     240
cttcca                                                                246
```

<210> SEQ ID NO 326
<211> LENGTH: 264
<212> TYPE: DNA
<213> ORGANISM: Glycine max
<220> FEATURE:
<223> OTHER INFORMATION: unsure at all n locations

<400> SEQUENCE: 326

```
cnagagcaga gaagantcag agaatggcaa ctatgactgg cgtgagcctt tcatgcccca      60
gggttttctt caacgcatca ggctcaccgc aaaacgcgca tgcttattgt attttgtcca     120
gcagattcta tgacttgaca ggactgcaga atggaattct gaagcgaggg agagagattt     180
tcctcactgg ttgctacctc cgaactccca ctggaggttc tggacattca cgtcttttgc     240
caacagagta tcttgtgatt ctat                                            264
```

<210> SEQ ID NO 327

<211> LENGTH: 284
<212> TYPE: DNA
<213> ORGANISM: Glycine max
<220> FEATURE:
<223> OTHER INFORMATION: unsure at all n locations

<400> SEQUENCE: 327

```
cagagaagaa tcagagaatg gcaactatga ctgnngtgag cntttcatgc cccagggttt      60
tcttcaacgc atcaggctca ccgcaaaacg cgcatgctta ttgtattttg tccagcagat     120
tctatgactt gacaggactg cagaatggaa ttctgaagcg agggagagag attttcctca     180
cnngttgcta cctccgaact cccactggag gttctgtgaca ttcacgtctt ttgccaacag     240
agtatcttgt gattctattg gatgaagact tccagaagga aatt                       284
```

<210> SEQ ID NO 328
<211> LENGTH: 392
<212> TYPE: DNA
<213> ORGANISM: Glycine max

<400> SEQUENCE: 328

```
ggccgataca tcaagcccat gcttccaaag ggccctgtaa agagattagc tgtagatgca      60
acccttagag ctgctgcacc ttatcaaaaa ttgcgaaggg caaagattc tggaaacaat     120
agaaaggtat ttgtggagaa aacggacatg agggcaaaga gaatggcacg taaggcagga     180
gcattggtga tatttgttgt tgatgcaagt ggaagcatgg cattgaacag gatgcagaat     240
gcaaaaggtg cagcacttaa gcttctggct gaaagttata caagcaggga tcaggtatct     300
ataattccat tccgtggaga tgcagctgaa gttctcctgc caccttctag atcaatttca     360
atggcaagga aacgtcttga aaggcttcca tg                                   392
```

<210> SEQ ID NO 329
<211> LENGTH: 274
<212> TYPE: DNA
<213> ORGANISM: Glycine max

<400> SEQUENCE: 329

```
gtggagaaaa cggacatgag ggcaaagaga atggcacgta aggcaggagc attggtgata      60
tttgttgttg atgcaagtgg aagcatggca ttgaacagga tgcagaatgc aaaaggtgca     120
gcacttaagc ttctggctga agttataca agcagggatc aggtatctat aattccattc     180
cgtggagatg cagctgaagt tctcctgcca ccttctagat caatttcaat ggcaaggaaa     240
cgtcttgaaa ggcttccatg tggtggaggt cccc                                 274
```

<210> SEQ ID NO 330
<211> LENGTH: 247
<212> TYPE: DNA
<213> ORGANISM: Glycine max

<400> SEQUENCE: 330

```
attagctgta gatgcaaccc ttagagctgc tgcaccttat caaaaattgc gaaggcaaa       60
agattctgga aacaatagaa aggtatttgt ggagaaaacg gacatgaggg caaagagaat     120
ggcacgtaag gcaggagcat tggtgatatt tgttgttgat gcaagtggaa gcatggcatt     180
gaacaggatg cagaatgcaa aaggtgcagc acttaagctt ctggctgaaa gttatacaag     240
cagggat                                                               247
```

<210> SEQ ID NO 331
<211> LENGTH: 292

<212> TYPE: DNA
<213> ORGANISM: Glycine max
<220> FEATURE:
<223> OTHER INFORMATION: unsure at all n locations

<400> SEQUENCE: 331

```
tngagggcaa agagaatggc acgtaaggna ggancatcgg tgatatttgt ggttgatgca      60
agtggaagca tggcattgaa caggatgcag aatgcaaaag gtgcagcact taagcttctg     120
gctgaaagtt atacaagcag ggatcaggtc tctaaattcc attccgtgga gacgcagctg     180
aagttcttct gccaccttct agatcaattg caancgnaag gaaacgtctt gagaggctcc     240
atgtggtgga gggtccccac ttgctcaggt ctacaacggc tgttagagtt gg             292
```

<210> SEQ ID NO 332
<211> LENGTH: 378
<212> TYPE: DNA
<213> ORGANISM: Glycine max

<400> SEQUENCE: 332

```
agacgggtgc gagaagacga cagaagggga taagtgccat aacacataaa cagaatggct      60
tccacgtttg gcgcatcttc aattaccttc ctctcttcac gatactactc gtctcaggcc     120
cttgccaccg attcaccctc tctaaccaca gtgcagatat ttgggcgcaa gttttgcgga     180
ggaagaaatg gatttcacag cgtcaaggga aggtctctgt tcgcggttgc gagtgttctt     240
gccactcaac ttaactctgc ataataggct cagaagattg cttttaccga gagccgagag     300
tcagtgtacc cattttcggc tatagttgga caggatgaaa tgaagctttg ccttctccta     360
aatgtgattg atcccaaa                                                   378
```

<210> SEQ ID NO 333
<211> LENGTH: 277
<212> TYPE: DNA
<213> ORGANISM: Glycine max

<400> SEQUENCE: 333

```
aaaaagaatg gcttccacgt ttggcgcatc ttcaattacc ttcctctctt cacgatacta      60
ctcttcccaa tcccttgcca ccgattctcc ctctctaacc acagtgcaga tatttgggcg     120
caagttttgc ggcggaggaa atggatttca gcgtcaag gaaggtctc tgttcccggt        180
tgcgagtgtt cttgccactc aacttaactc tgcacaacag gctcagaaga ttgcttttac     240
cgagagccag aggccagtgt acccatttcg gctatag                              277
```

<210> SEQ ID NO 334
<211> LENGTH: 256
<212> TYPE: DNA
<213> ORGANISM: Glycine max

<400> SEQUENCE: 334

```
taaaaagaat ggcttccacg tttggcgcat cttcaattac cttcctctct tcacgatact      60
tctcttccca tcccttgcc accgattctc cctctctaac cacagtgcag atatttgggc     120
gcaagttttg cggcggagga atggatttc acagcgtcaa gggaaggtct ctgttcccgg     180
ttgcgagtgt tcttgccact caacttaact ctgcacaaca ggctcagaag attgcttta     240
ccgagagcca gaggcc                                                     256
```

<210> SEQ ID NO 335
<211> LENGTH: 396
<212> TYPE: DNA

<213> ORGANISM: Glycine max

<400> SEQUENCE: 335

```
ggcaactatg actggtgtga gcctttcatg ccccagggtt ttcttcaacg catcagcctc     60
accgcaaaac gcgcatgctg taaagttctc acttccaccc agccaagcag tgcgaccggg    120
tagtatcaag ttgggtcgcg tgatgaggat ccgacccgtt cgcgctgcgc ctgagcgcat    180
atcggagaag gtggaggaga gcataaagaa cgcgcaggag gcgtgcgccg gcgatccgac    240
gagcggcgag tgcgtggcgg cgtgggacga ggtggaggag ctgagcgcgg cggcgagcca    300
cgccagggac aagcaaaagg aaaaggactc gacccgctc gagaattact gcaaggacaa    360
cccggagacc attgagtgca aaactttcga agactg                             396
```

<210> SEQ ID NO 336
<211> LENGTH: 356
<212> TYPE: DNA
<213> ORGANISM: Glycine max

<400> SEQUENCE: 336

```
gagaatggca actatgactg gtgtgagcct ttcatgcccc agggtggtct tcaacgcatg     60
agcctcaccg cataacgcgc atgctgtaaa gttctcactt ccacccagcc aagcagtgcg    120
accgggtagt atcaagttgg gtcgcgtgat gaggatccga cccgttcgcg ctgcgcctga    180
gcgcatatcg gagaaggtgg aggagagcat aaagaacgcg caggaggcgt gcgccgacga    240
tccgacgagc ggcgagtgcg tgacggcgtg ggacgaggtg gaggagctga gcgcggcggc    300
tagccacgcc agggacacgc aaatggtaat ggacttcgac ccgctcgaga attact       356
```

<210> SEQ ID NO 337
<211> LENGTH: 273
<212> TYPE: DNA
<213> ORGANISM: Glycine max

<400> SEQUENCE: 337

```
agaatggcaa ctatgactgg tgtgagcctt tcatgcccca gggttttctt caacgcatca     60
gcctcaccgc aaaacgcgca tgctgtaaag ttctcacttc cacccagcca agcagtgcga    120
ccgggtagta tcaagttggg tcgcgtgatg aggatccgac ccgttcgcgc tgcgcctgag    180
cgcatatcgg agaaggtgga ggagagcata agaacgcgc aggaggcgtg cgccggcgat    240
ccgacgagcg gcgagtgcgt ggcggcgtgg gac                                273
```

<210> SEQ ID NO 338
<211> LENGTH: 272
<212> TYPE: DNA
<213> ORGANISM: Glycine max
<220> FEATURE:
<223> OTHER INFORMATION: unsure at all n locations

<400> SEQUENCE: 338

```
aagaatcaga gaatggcaac tatgactggt gtgagccttt catgcccag gttttcttc      60
aacgcatcag cctcaccgca aaacgcgcat gctgtaaagt tctcacttcc acccagccaa    120
gcagtncgac cgggtagtat caagttgggt cgcgtgatga ggatccgacc cgttcgcgct    180
gcgcctgagc gcatatcgga gaaggtgag gagagcataa agaacgcgca ggaggcgtgc    240
gccggcgatc cgacgagcgg cgagtgcgtg gc                                  272
```

<210> SEQ ID NO 339
<211> LENGTH: 273

<212> TYPE: DNA
<213> ORGANISM: Glycine max
<220> FEATURE:
<223> OTHER INFORMATION: unsure at all n locations

<400> SEQUENCE: 339

| | | |
|---|---|---|
| gaatcagaga atggcaacta tgactggtgt gagcctttca tgccccaggg ttttcttcaa | 60 |
| cgcatcagcc tcaccgcaaa acgcgcatgc tgtaaagttc tcacttccac ccagccaagc | 120 |
| agtccgaccg ggtagtatca agttgggtcg cgtgatgagg atccgacccg ttcgngtgcg | 180 |
| cctgagcgca tatcggagaa ggtggaggag agcataaaga acgcgcagga ggcgtgcgcc | 240 |
| ggcgatccga cgagcggcga gtgcgtggcg gcg | 273 |

<210> SEQ ID NO 340
<211> LENGTH: 253
<212> TYPE: DNA
<213> ORGANISM: Glycine max

<400> SEQUENCE: 340

| | | |
|---|---|---|
| cagagaatgg caactatgac tggtgtgagc ctttcatgcc ccagggtttt cttcaacgca | 60 |
| tcagcctcac cgcaaaacgc gcatgctgta aagttctcac ttccacccag ccaagcagtg | 120 |
| cgaccgggta gtatcaagtt gggtcgcgtg atgaggatcc gacccgttcg cgctgcgcct | 180 |
| gagcgcatat cggagaaggt ggaggagagc ataagaacg cgcaggaggc gtgcgccggc | 240 |
| gatccgacga gcg | 253 |

<210> SEQ ID NO 341
<211> LENGTH: 283
<212> TYPE: DNA
<213> ORGANISM: Glycine max
<220> FEATURE:
<223> OTHER INFORMATION: unsure at all n locations

<400> SEQUENCE: 341

| | | |
|---|---|---|
| gtaactatga ctggtgtgag cctttcatgc cccagggttt tcttcaacgc atcagcctca | 60 |
| ctgnaaaacg cgcatgatgt aaagttctca cttccacaca gcatagaagg tggatcgggt | 120 |
| agtatcaagt tgggtcgcgt gatgaggatc cgagccgttc gcgctgcgcc tgagcgcata | 180 |
| tcggagaagg tggaggagag catacagaac gcgcaggagg cgtgcgccgg cgatcagttg | 240 |
| agcggcgagt gcgtggcggc gtgggacgat gtggaggagc tga | 283 |

<210> SEQ ID NO 342
<211> LENGTH: 251
<212> TYPE: DNA
<213> ORGANISM: Glycine max

<400> SEQUENCE: 342

| | | |
|---|---|---|
| gagaatggca actatgactg gtgtgagcct ttcatgcccc agggttttct tcaacgcatc | 60 |
| agcctcaccg caaaacgcgc atgctgtaaa gttctcactt ccacccagcc aagcagtgag | 120 |
| accgggtagt atcaagttgg gtcgcgtgat gaggatccga cccgttcgcg ctgcgcctga | 180 |
| gcgcatatcg gagaaggtgg agagcataa agaacgcgcg gaggctgcgc ggcgatccga | 240 |
| cgagcggcga t | 251 |

<210> SEQ ID NO 343
<211> LENGTH: 271
<212> TYPE: DNA
<213> ORGANISM: Glycine max

```
<400> SEQUENCE: 343 aaacccctc cagagaacaa gaatcaaaga atggcaacta tgactggtgt gagcctttca      60
agccccaggg ttttcttcaa cgcatcaccc tcaccgcaaa acacgtacgc cgtaaagttc     120
gcagttccac tcagccaagg gatgcgactt ggtagtgtca ggttgggtcg ggtgatgagg     180
atccgacccg ttcgcgcagt ccagagcgca tttcggagaa ggtggaggag agcataaaga    240
acgcgcagga ggcgtgcgcc ggcgacccga c                                    271

<210> SEQ ID NO 344
<211> LENGTH: 257
<212> TYPE: DNA
<213> ORGANISM: Glycine max

<400> SEQUENCE: 344
gcctttcaag ccccagggtt ttcttcaacg catcaccctc accgcaaaac acgtacgccg      60
taaagttcgc agttccactc agccaaggga tacgacttgg tagtgtcagg ttgggtcggg    120
tgatgaggat ccgacccgtt cgcgcactcc agagcgcatt tcggagaagg tggaggagag    180
cataaagaac gcgcaggagg cgtgcgccgg cgacccgacg agcggcgagt gcgtggcggc    240
gtgggacgag gtggagg                                                   257

<210> SEQ ID NO 345
<211> LENGTH: 281
<212> TYPE: DNA
<213> ORGANISM: Glycine max
<220> FEATURE:
<223> OTHER INFORMATION: unsure at all n locations

<400> SEQUENCE: 345
gagaatggca actatgactg gtgtgagcct ttcatgcccc agggttttct tcaacgcatc      60
agtctcaccg naaaacgcgc atgctgtaaa gttctcactt tcanacagcc aagaagacac    120
aaagggtagt atcaagttgg gtcgcgtgat gaggatccga cccgttcgag ctgcgtctga    180
gcgcatatcg gagaaggtgg aggagagctg aaggaacgcg caggaggcgt gcgccggcga    240
tccgacgagc ggcgagtgcg tagcggcgtg ggacgaggtg g                        281

<210> SEQ ID NO 346
<211> LENGTH: 249
<212> TYPE: DNA
<213> ORGANISM: Glycine max

<400> SEQUENCE: 346
gagaatggca actatgactg gtgtgagcct ttcatgcccc agggttttct tcaacgcatc      60
agcctcaccg caaaacgcgc atgctgtaaa gttctcactt ccagccagcc tatgagtctt    120
accgggtagt agcaagttgg gtcgcgtgat gatgatccga cccgttcgcg ctgcgcctga    180
gcgcatatcg gagaaggtgg aggagagcaa acagaacgcg ctaggaggcg tacgccggcg    240
atccgacga                                                            249

<210> SEQ ID NO 347
<211> LENGTH: 240
<212> TYPE: DNA
<213> ORGANISM: Glycine max

<400> SEQUENCE: 347
cgtccgatag gatgcgagaa gacgacagaa ggggagagaa caagaatcaa agaatggcaa      60
ctatgactgg tgtgagcctt tcaagcccca gggttttctt caacgcatca ccctcgccgc    120
```

```
aaaacacgta cgccgtaaag ttcgcagttc cactcagcca agggactcga cttggtagtg    180
tcaggttggg tcgggtgatg aggatgcgag ccgttcgcgc agctccagag cgcagttcgg    240
```

<210> SEQ ID NO 348
<211> LENGTH: 91
<212> TYPE: DNA
<213> ORGANISM: Glycine max

<400> SEQUENCE: 348

```
gagaatggga actatgactg gtgtgagcgt tcatgcgcc agggttttct gcaacgcatc    60
agcgtcaggg caaaacgcgc atagtgtaaa g                                   91
```

<210> SEQ ID NO 349
<211> LENGTH: 119
<212> TYPE: DNA
<213> ORGANISM: Glycine max

<400> SEQUENCE: 349

```
ctcgagccga gagaatggca actatgactg gtgtgagcct tcatgcccc agggttttct    60 tcaacgcatc agcctcacgg caaaacgcgc atgctgtaaa gttctcactt ccacccagc    119
```

<210> SEQ ID NO 350
<211> LENGTH: 175
<212> TYPE: DNA
<213> ORGANISM: Glycine max

<400> SEQUENCE: 350

```
gaagaatcag agaatggcaa ctatgactgg tgtgagcctt tcatgcccca ggttttctt    60 caacgcatca gcctcaccgc aaaacgcgca tgctgtaaag ttctcacttc cacccagcca    120
agcagtgcga ccgggtagta tcaagttggg tcgcgtgatg aggatccgac ccgtt         175
```

<210> SEQ ID NO 351
<211> LENGTH: 285
<212> TYPE: DNA
<213> ORGANISM: Glycine max

<400> SEQUENCE: 351

```
gaagaatcag agaatggcaa ctatgactgg tgtgagcctt tcatgcccca gggttttctt    60
caacgcatca ggctcaccgc aaaacgcgca tgctgtaaag ttctctttta ttgtatttg    120 tccagcagat tctatgactt gacaggactg cagaatggaa ttctgaagcg agggagagag    180
attttcctca ctggttgcta cctccgaact cccactggag gttctggaca ttcacgtctt    240
ttgccaacag agtatcttgt gattctattg gatgaagact tccaa                    285
```

<210> SEQ ID NO 352
<211> LENGTH: 111
<212> TYPE: DNA
<213> ORGANISM: Glycine max
<220> FEATURE:
<223> OTHER INFORMATION: unsure at all n locations

<400> SEQUENCE: 352

```
gaatggcaac tatgactggt gtgagccttt natgccccag ggttttcttc aacgcatnag    60
cntcacnngn aaaacgcgca tgctgtaaag ttctcanttc cacacaacat a             111
```

<210> SEQ ID NO 353
<211> LENGTH: 156
<212> TYPE: DNA

```
<213> ORGANISM: Glycine max

<400> SEQUENCE: 353
cttagacctc atcatcataa accccctcca gagaacaaga acatccgaa tggcaactat      60 gactggtgtg agcctttcaa gccccagggt tttcttcaac gcatcaccct caccgcaaaa    120
cacgtacgcc gtaaagttcg cagttccact cagcca                              156

<210> SEQ ID NO 354
<211> LENGTH: 136
<212> TYPE: DNA
<213> ORGANISM: Glycine max

<400> SEQUENCE: 354
tcatcataaa ccccctccag agaacaagaa tcacagaatg caactatga ctggtgtgag      60 cctttcaagc cccagggttt tcttcaacgc atcaccctca ccgcaaaaca cgtacgccgt    120
aaagttcgca gttcca                                                    136

<210> SEQ ID NO 355
<211> LENGTH: 85
<212> TYPE: DNA
<213> ORGANISM: Glycine max
<220> FEATURE:
<223> OTHER INFORMATION: unsure at all n locations

<400> SEQUENCE: 355
ctatgactgg tgtgagcctt tcaagcccca gggttntctt caacgcatca ccctcacngc     60
aaaacacgta cgccgtaaag ttcgc                                           85

<210> SEQ ID NO 356
<211> LENGTH: 356
<212> TYPE: DNA
<213> ORGANISM: Glycine max

<400> SEQUENCE: 356
ctctctgaaa tgggtttcgc tttggcatac acagcatctg ttgttgctc aaacctacaa      60 tttcagtctc tgttattcgc tgctgcttca ttgagatcaa aaccgtgtct ctctctctgc    120
aactctactt atcgacccaa acgcattctc cagcgttctc caattgttgg cgctcagtct    180
gaaaatggag ctctggttac ttcggagaag cccgacacta attacggaag acaatacttc    240 ccctcgctg ctgttgtagg ccaagattct ataaaaactg ctcttttact tggtgcaatt    300
gaccccgggg ttggaggaat tgccatatca ggaaagcgag gaactgccaa aactgt        356

<210> SEQ ID NO 357
<211> LENGTH: 339
<212> TYPE: DNA
<213> ORGANISM: Glycine max
<220> FEATURE:
<223> OTHER INFORMATION: unsure at all n locations

<400> SEQUENCE: 357
anatgggttt cgctttggca ttcacagctt cttctacttg ctgntcaaat ctacaatctc     60
agtctctgtt attcgctgct gctgcattga gatcaaaacc gtgtctctct ctctgcaaca    120
cttatcgacc caaacgcatt cggaagcgtt ctcnaattgt tggcgctcaa tctgaaaacg    180
gagctctcgt tacttccgag aagcctgaca ctaattacgg nagacaatac ttccccctcg    240
ctgctgttgt aggccaagat gctataaaaa ctgctctttt acttggggcc attgaccctg    300
ggattggagg aattgccata tcatgaaagc gaggnactg                           339
```

<210> SEQ ID NO 358
<211> LENGTH: 284
<212> TYPE: DNA
<213> ORGANISM: Glycine max
<220> FEATURE:
<223> OTHER INFORMATION: unsure at all n locations

<400> SEQUENCE: 358

```
tccggttatg gcgtccgcct tgggcacttc ttcaattgcn gttctgcctt cgcgctactt      60
ctcttcttct tcctcccagc cttccattca cactctctct nnaacttcag ggcagaacta     120
tgggcggaag ttttatggag gaattggaat ccatggcata aagggaaggg ctcagctctc     180
ggttaccaat gttgccactg aagttaactc tgnagaacag gctcagagta ttgcttctaa     240
aganagccag aggccagtat acccattttc tgccatantt ggnc                     284
```

<210> SEQ ID NO 359
<211> LENGTH: 263
<212> TYPE: DNA
<213> ORGANISM: Glycine max

<400> SEQUENCE: 359

```
tggcgtccgc cttgggcact tcttcaattg cggttctgcc ttcgcgctac ttctcttctt      60
cttcttccaa gccttccatt cacactctct ctctaacttc agggcagaac tatgggcgga     120
agttttatgg aggaattgga atccatggca taaagggaag gctcagctc tcggttacca     180
atgttgccac tgaagttaac tctgtagaac aggctcagag tattgcttct aaagaaagcc     240
agaggccagt atacccattt tct                                             263
```

<210> SEQ ID NO 360
<211> LENGTH: 280
<212> TYPE: DNA
<213> ORGANISM: Glycine max
<220> FEATURE:
<223> OTHER INFORMATION: unsure at all n locations

<400> SEQUENCE: 360

```
gtctgtcttc tcttctcttc tccggttatn gcgtccgcct tgggcacttc ttcaattgcg      60
gttctgcctt cgggtactc tcttcttctt cttccaagcc ttccattcac actctctctc     120
taacttcagg gcagaactat gggcggaagt tttatggagg aattggaatc catggcataa     180
agggaagggc tcagctctcg gttaccaatg ttgccactga agttaactct gtagaacagg     240
ctcagagtat tgcttctaaa gaaagccaga ggccagtata                           280
```

<210> SEQ ID NO 361
<211> LENGTH: 278
<212> TYPE: DNA
<213> ORGANISM: Glycine max
<220> FEATURE:
<223> OTHER INFORMATION: unsure at all n locations

<400> SEQUENCE: 361

```
tctgctccgg ttatggcntc cgncttgggc acttcttcaa ttgcngntct gccttncncg      60
ctacttctct ncntcttctt ccaagccttc cattcanact cnctctctaa cttcanggca     120
gaactatggg cggaagtttt atggaggaat tggaatccat ggnataaang gaagggctca     180
gctctcggtt accaatgttg ncantgnagt taactctgna naacaggctc aganttattgc     240
ttctaaagaa agccagaggc cagtataccc attttctg                             278
```

```
<210> SEQ ID NO 362
<211> LENGTH: 283
<212> TYPE: DNA
<213> ORGANISM: Glycine max

<400> SEQUENCE: 362
attgctacat agcacacact ccctcttctc ttctacggtt atggcgtcca cgttgggcac    60
ttcttcaatt gcggttcttc cttcgcgctg catctcttct tttcttcca agccttccat   120 tcacacactc tctctaactt cagggcagag ctatgggcgg aaattttatg gaggaattgg   180
aattcatggc atcaagggaa ggtctcagct ctcagttgcc aatgttgcca ctgaagttaa   240
ctctgtagaa caggcccaaa gtattgcttc taaagaaagc cag                    283

<210> SEQ ID NO 363
<211> LENGTH: 273
<212> TYPE: DNA
<213> ORGANISM: Glycine max
<220> FEATURE:
<223> OTHER INFORMATION: unsure at all n locations

<400> SEQUENCE: 363
gnaacaaatt gctacatagc acacactccc tcttctcttc tacggttatg cgtccacgt    60 tgggcacttc ttcaattgcg gttcttcctt cgcgctgcat ctcttctttt cttccaagc   120 cttccattca cacactctct ctaacttcag ggcagagcta tgggcggaaa ttttatgnag   180
gaattggaat tcatggcatc aagggaaggt ctcagctctc agttgccaat gttgccactg   240
aagttaactc tgtagaacag gcccaaagta ttg                                273

<210> SEQ ID NO 364
<211> LENGTH: 259
<212> TYPE: DNA
<213> ORGANISM: Glycine max

<400> SEQUENCE: 364
caaattgcta catagcacac actccctctt ctcttctacg gttatggcgt ccacgttggg    60
cacttcttca attgcggttc ttccttcgcg ctgcatctct tctttttctt ccaagccttc   120
cattcacaca ctctctctaa cttcagggca gagctatggg cggaaatttt atggaggaat   180
tggaattcat ggcatcaagg gaaggtctca gctctcagtt gccaatgttg ccactgaagt   240
taactctgta gaacaggcc                                                259

<210> SEQ ID NO 365
<211> LENGTH: 253
<212> TYPE: DNA
<213> ORGANISM: Glycine max

<400> SEQUENCE: 365
acggctgcga agacgacag aagggacgg ttatggcgtc cacgttgggc acttcttcaa    60
ttgcggttct tccttcgcgc tgcatctctt ctttttcttc caagccttcc attcacacac   120
tctctctaac ttcagggcag agctatgggc ggaaattttta tggaggaatt ggaattcatg   180
gcatcaaggg aaggtctcag ctctcagttg ccaatgttgc cactgaagtt aactctgtag   240
aacaggccca aag                                                      253

<210> SEQ ID NO 366
<211> LENGTH: 243
<212> TYPE: DNA
<213> ORGANISM: Glycine max
```

```
<220> FEATURE:
<223> OTHER INFORMATION: unsure at all n locations

<400> SEQUENCE: 366
aataaaagac aaaagaaaca aaangctaca tagcatacag tctgtcttct cttctcttct      60
ccggttatgg cgtccgcctt gggcacttct tcaattgcgg ttctgccttc gcgctacttc    120
tcttcttctt cttccaagcc ttccattcac actctctctc taacttcagg cagaactat     180
gggcggaagt tttatggagg aattggaatc catggcataa agggaagggc tcagctctcg    240
gtt                                                                  243

<210> SEQ ID NO 367
<211> LENGTH: 259
<212> TYPE: DNA
<213> ORGANISM: Glycine max
<220> FEATURE:
<223> OTHER INFORMATION: unsure at all n locations

<400> SEQUENCE: 367
gcacacactc cctcttctct tctacggtta tggcgtccac gttgggcact tcttcaattg     60
cggttcttcc ttcgcgctgc atctcttctt tttcttccaa gccttccatt cacacactct    120
ctctaacttc agggcagagc tatgggcgga aattttatgg aggaattgga attcatgggc    180
atcaagggaa ngtctcagct ctcagttgcc aatgttgcca ctgaagttaa ctctgtagaa    240
caggcccaaa gtattgctt                                                 259

<210> SEQ ID NO 368
<211> LENGTH: 163
<212> TYPE: DNA
<213> ORGANISM: Glycine max

<400> SEQUENCE: 368
caaattgcta catagcacac actccctctt ctcttctacg gttatggcgt ccacgttggg     60
cacttcttca attgcggttc ttccttcgcg ctgcatctct tctttttctt ccaagccttc    120
cattcacaca ctctctctaa cttcagggca gagctatggg cgg                      163

<210> SEQ ID NO 369
<211> LENGTH: 151
<212> TYPE: DNA
<213> ORGANISM: Glycine max

<400> SEQUENCE: 369
gaaattgcta catagcacac actccctctt ctcttctacg gttatggcgt ccacgttggg     60
cacttcttca attgcggttc ttccttcgcg ctgcatctct tctttttctt ccaagccttc    120
cattcacaca ctctctctaa cttcagggca g                                   151

<210> SEQ ID NO 370
<211> LENGTH: 232
<212> TYPE: DNA
<213> ORGANISM: Glycine max

<400> SEQUENCE: 370
gaagaatgaa atctatctat cttcttatcc gaagcccgtg aggccaataa gaagcacgtc     60
agctgctatg aatggtgaat aaaacacaaa agaaacaaat tgctacatag cacacactcc    120
ctcttctctt ctacggttat ggcgtccacg ttgggcactt cttcaattgc ggttcttcct    180
tcgcgctgca tctcttcttt ttcttccaag ccttccattc acacactctc tc            232
```

```
<210> SEQ ID NO 371
<211> LENGTH: 107
<212> TYPE: DNA
<213> ORGANISM: Glycine max

<400> SEQUENCE: 371
tacggctgga agacgacaga aggggaata aaacacaaaa gacacaaatt gctacatagc        60
acacactccc tcttctcttc tacggttatg gcgtccacgt tgggcac                    107

<210> SEQ ID NO 372
<211> LENGTH: 235
<212> TYPE: DNA
<213> ORGANISM: Glycine max

<400> SEQUENCE: 372
ctcgagccga atcggctcga ggcagattaa aagggatgga attaccaagc ttgttattct       60
tccactttat ccacaatttt caatatcaac cagtggctca agcctacgtc tactggagag     120
tatattccga gaggatgagt atctagtcaa catgcagcac acagtaatac catcatggta     180
tcaacgtgaa ggatacataa aggccatggc aaatttgatt gagaaagagt tgaga          235

<210> SEQ ID NO 373
<211> LENGTH: 250
<212> TYPE: DNA
<213> ORGANISM: Glycine max

<400> SEQUENCE: 373
gaccaggcac ttgcaattaa aatggctttg gaagcaaagg gcatctcttc aaatgtctac       60
gttgggatgc gatactggta cccatttacc gaagaagcaa ttcagcaaat taagagggac     120
agaataacaa ggcttgtggt actacccctt tatccccagt tttctatatc cacaactgga     180
tcaagcatcc gtgttcttga gcatatattc agggaagatg cctacttgtc taagctccct     240
gtttccatta                                                             250

<210> SEQ ID NO 374
<211> LENGTH: 254
<212> TYPE: DNA
<213> ORGANISM: Glycine max

<400> SEQUENCE: 374
ggaatgtgtt gatttgatca tggaagagct tgaaaagaga aagataacta atgcatacac       60
ccttgcttat cagagtagag ttggacctgt ggaatggtta aaaccctata cagatgagac     120
aataattgaa cttgggaaaa agggagtaaa aagcctgctg gctgtaccaa ttagctttgt     180
cagcgagcat attgaaactc tcgaagaaat tgatgttgag tacaaagaat tggctctaaa     240
ctctggtata gaaa                                                        254

<210> SEQ ID NO 375
<211> LENGTH: 248
<212> TYPE: DNA
<213> ORGANISM: Glycine max

<400> SEQUENCE: 375 gaaaagttg gtgtgctgct tctcaatcta ggaggaccag agacattgaa tgacgttcaa        60
ccttttctgt ttaatctttt tgcagatcct gatatcattc gtcttccaag gttgtttcgg     120
tttctccagc gaccattggc aaaattgatt tctgtacttc ggtctcctaa atccaaggaa     180
gggtatgctg ctattggtgg tggctctcct ttacgcaaaa ttacagatga ccaggcactc     240
```

```
gcaattaa                                                                    248

<210> SEQ ID NO 376
<211> LENGTH: 275
<212> TYPE: DNA
<213> ORGANISM: Glycine max

<400> SEQUENCE: 376
aattgacatg gagtacaagg aattggctct tgaatctggc atcaagaatt gggcacgtgt           60
acctgccctt ggtgttaccc cttccttcat tacagattta gcagatgcag taatagaagc          120
tctcccatca gcaacagcaa tatatgcacc gaccagaacc tctgaagatg ttgatcatga          180
cccagttaga tattttatca agatgttctt tggttcaatc ttggcattca tcttgttctt          240
gtcacccaaa atgatcacgg cattcaggaa tcatg                                     275

<210> SEQ ID NO 377
<211> LENGTH: 288
<212> TYPE: DNA
<213> ORGANISM: Glycine max

<400> SEQUENCE: 377
ccttccttca tacagattta gcagatgcag taatagaagc tctcccatca gcaacagcaa           60
tatatgcacc gaccagaacc tctgaagatg ttgatcatga cccagttaga tattttatca          120
agatgttctt tggttcaatc ttggcattca tcttgttctt gtcacccaaa atgatcacgg          180
cattcaggaa tcatgtcatt tagaagaatt aaatcctgct tgctgaattc aatctgcaag          240
catatagatg aagcctattg atagcaacaa agtatacttt gattttttt                      288

<210> SEQ ID NO 378
<211> LENGTH: 282
<212> TYPE: DNA
<213> ORGANISM: Glycine max

<400> SEQUENCE: 378
atggaaaaaa gggagtgaaa agtctgctcg ctgttccaat tagcttcgtc agtgagcata           60
ttgaaactct agaagaaatt gatgttgaat acaaagagtt ggctctagaa tctggtatag          120
aaaagtgggg ccgtgttcct gctctaggat gcgaacctac cttcatttct gatttggcag          180
atgccgttat tgagagtctc ccatatgttg gtgccatgac agcttcagac cttgaagctc          240
aacaatcctc gttccatggg cagtgtagaa gagttattgg ca                             282

<210> SEQ ID NO 379
<211> LENGTH: 237
<212> TYPE: DNA
<213> ORGANISM: Glycine max

<400> SEQUENCE: 379
catccgtgtt cttgagcata tattcaggga agatgcctac ttgtctaagc tccctgtttc           60
cattataaac tcttggtatc aacgagaagg ttatattaag tcaatggcta acttaattca          120
gaaagagctc cagagttttt ctgaaccaaa agaggtaatg atattttca gtgcccatgg           180 tgtacctgtc agttacgttg aggaagctgg ggatccatac cgagaccaaa tggagga            237

<210> SEQ ID NO 380
<211> LENGTH: 253
<212> TYPE: DNA
<213> ORGANISM: Glycine max
```

```
<400> SEQUENCE: 380
actggatcaa gcatccgtgt tcttgagcat atattcaggg aagatgccta cttgtctaac      60
ctccctgttt ccattataaa ctcttggtat caacgagaag gttatattaa gtcaatggct     120
aacttaattc agaaagagcg ccagagtttt tcttaaccaa aagaggtaat gatattttc      180 agtgcccatg gtgtacctgt caagtacgtt gagggagctg gggatccata ccgagaccaa     240
atggaggagt gca                                                        253

<210> SEQ ID NO 381
<211> LENGTH: 269
<212> TYPE: DNA
<213> ORGANISM: Glycine max

<400> SEQUENCE: 381
ttcttgagca tatattcagg gaagatgcct acttgtctaa ctccctgttt ccattataa      60 actcttggta tcaacgagaa ggttatatta gtcaatggc taacttaatt cagaaagagc     120
tccagagttt ttctgaacca aaagaggtaa tgatatttt cagtgcccat ggtgtacctg     180
tcagttacgt tgaggaagct ggggatccat accgagacca atggaggag tgcatcttct     240 tgatcatgca agagttgaaa gctagagga                                       269

<210> SEQ ID NO 382
<211> LENGTH: 251
<212> TYPE: DNA
<213> ORGANISM: Glycine max

<400> SEQUENCE: 382
aagagctcca gagttttcct gaaccaaaag aggtaatgat attttcagt gcccatggtg      60 tacctgtcag ttacgttgag gaagctgggg atccataccg agaccaaatg gaggagtgca    120
tcttcttgat catgcaagag ttgaaagcta gaggaattag taatgagcac actcttgctt    180
atcagagtcg agtgggtcct gtacagtggc tgaaaccata tactgatgaa gttctcgttg    240
agcttggcca a                                                          251

<210> SEQ ID NO 383
<211> LENGTH: 275
<212> TYPE: DNA
<213> ORGANISM: Glycine max

<400> SEQUENCE: 383
ttaattcaga aagagctcca gagttttcct gaaccaaaag aggtaatgat attttcagt      60 gcccatggtg tacctgtcag ttacgttgag gaagctgggg atccataccg agaccaaatg    120
gaggagtgca tcttcttgat catgcaagag ttgaaagcta gaggaattag taatgagcac    180
actcttgctt atcagagtcg agtgggtcct gtacagtggc tgaaaccata tactgatgaa    240
gttctcgttg agcttggcca aaaaggtgtg aagag                                275

<210> SEQ ID NO 384
<211> LENGTH: 168
<212> TYPE: DNA
<213> ORGANISM: Zea mays

<400> SEQUENCE: 384 cttctcttaca tatattcagc accacctctc aagctcgagc agaatggatg gattgggaac    60
ttcgctctgg gtgcgagtta catcagcttg ccctggtggg ctggccaggc gttatttgga    120
actcttacac cagatatcag tgtcttgact actttgtaca gcatagct                  168
```

<210> SEQ ID NO 385
<211> LENGTH: 256
<212> TYPE: DNA
<213> ORGANISM: Zea mays

<400> SEQUENCE: 385

```
attgaagggg ataggactct ggggcttcag tcacttcctg ttgcttttgg gatggaaact      60
gcaaaatgga tttgtgttgg agcaattgat atcactcaat tatctgttgc aggttaccta     120
ttgagcaccg gtaagctgta ttatgccctg gtgttgcttg gctaacaat tcctcaggtg      180
ttctttcagt tccagtactt cctgaaggac cctgtgaagt atgatgtcaa atatcaggca     240
agcgcacaac cattct                                                     256
```

<210> SEQ ID NO 386
<211> LENGTH: 411
<212> TYPE: DNA
<213> ORGANISM: Zea mays

<400> SEQUENCE: 386

```
cccacgcgtc cgcccacgcg tccgcccacg cgtccgccca cgcgtccgag cacacacggg      60
cgcatcaggg cctagctcga gtccactact tgaaaaacag gaaaaaggtt gcgtttgagg     120
agatgacgaa gctcgtggag atagccagcc actgcgcgtc ggcatatgaa aagcggtcgg     180
aatacggtga gcgcgaagct gcgaggagcg acctgaacat ggcgacgctt cttgatccta     240
ccaggactta tccttacaga tacagagcag ctgtactgat ggacgaaggc aaggaggagg     300
aggcgatcgc ggagctgtca ggagccatag cttttcaagcc ggaccttcag ctgctgcacc    360
ttcgcgcggc gttcttcgac tccatgggcg agcgcgagag cgccctgtgg g              411
```

<210> SEQ ID NO 387
<211> LENGTH: 484
<212> TYPE: DNA
<213> ORGANISM: Zea mays
<220> FEATURE:
<223> OTHER INFORMATION: unsure at all n locations

<400> SEQUENCE: 387

```
ntggggttnn ctagagggga gggggggcaat tgatggaagt cttcaattcc gtttcgnacc     60
nncccgcccc acgcgtccgc cgacgccaaa acgcgaagg cgaacgccat ggccccgaat      120
aagagcaccc gcggcggatg actccagttt caaccagctg ctcggtatca aaagtgctta     180
gccagggaac ggccttttgg aaaatccgcc ttaacttaac taagccggtg acatggcctc     240
cgcttgtttg gggagttctc tgtggagcag ctgcctctgg aaatttccac tggacagttg     300
aagatgtcgc aaaatctatt gtatgcatga taatgtctgg tccatgcctt acaggataca     360
cacagacact taatgactgg tatgatcgag acattgatgc aattaatgag ccttatcggc     420
ctattccatc aggtgctata tcaganaacg aggtaataac ccagatctgg gtgctattgc     480
tagg                                                                  484
```

<210> SEQ ID NO 388
<211> LENGTH: 301
<212> TYPE: DNA
<213> ORGANISM: Zea mays

<400> SEQUENCE: 388

```
ccaaggcccc gaataacgca cccgcggcgg atggctccag tttcaaccag ctgctcggta      60
```

```
tcaagggtgc taagcaagac agcgacatgt ggcagatgcg tcttcaactt actaagccgg    120
tgacatggcc tccgcttgtt tggggagttc tctgtggagc agctgcctct ggaaatttcc    180
agtggacagt tgaagatgtc gcaaaatcta ttgtatgcat gataatgtct ggtccatgcc    240
ttacaggata cgcacagaca cttaatgact ggtatgatcg agacattgat gcaattagtg    300
a                                                                    301
```

<210> SEQ ID NO 389
<211> LENGTH: 284
<212> TYPE: DNA
<213> ORGANISM: Zea mays

<400> SEQUENCE: 389

```
tgaagatgtc gcaaaatcta ttgtatgcat gataatgtct ggtccatgcc ttacaggata     60
cacacagaca cttaatgact ggtatgatcg agacattgat gcaattaatg agccttatcg    120
gcctattcca tcaggtgcta tatcagaaaa cgaggtaata cccagatct gggtgctatt    180 gctaggaggg cttggattgg gtgctttgtt agatgtgtgg gcaggacatg attttcctat    240
tgtgttttat cttgctgtgg gtggctcctt actttcttac atat                     284
```

<210> SEQ ID NO 390
<211> LENGTH: 256
<212> TYPE: DNA
<213> ORGANISM: Zea mays

<400> SEQUENCE: 390

```
caattaatga gccttatcgg cctattccat caggtgctat atcagaaaac gaggtaataa     60
cccagatctg gtgctattg ctaggagggc ttggattggg tgctttgtta gatgtgtggg    120
caggacatga ttttcctatt tgttttatc ttgctgtggg tggctcccta ctttcctaca    180
tatattcagc accactctc aagctccagc agaatggatg gaatgggaac ttcgctctgg    240
gtgcgagtta catcag                                                   256
```

<210> SEQ ID NO 391
<211> LENGTH: 318
<212> TYPE: DNA
<213> ORGANISM: Zea mays

<400> SEQUENCE: 391

```
gcatgataat gtctggtcca tgccttacag gatacacaca gacacttaat gactggtatg     60
atcgagacat tgatgcaatt aatgagcctt atcggcctat tccatcaggt gctatatcag    120
aaaacgaggt aataacccag atctgggtgc tattgctagg agggcttgga ttgggtgctt    180
tgttagatgt gtgggcagga catgattttc ctattgtgtt ttatcttgct gtgggtggct    240
ccttactttc ttacatatat tcagcaccac ctctcaagct caagcagaat ggatggattg    300
ggaacttcgc tctgggtg                                                  318
```

<210> SEQ ID NO 392
<211> LENGTH: 272
<212> TYPE: DNA
<213> ORGANISM: Zea mays

<400> SEQUENCE: 392

```
ctggtgtaag agttccaaat aacgcctggc cagcccacca gggcaagatg atgtaactct     60 aacccgagc gaagttccca atccatccat tctgcttgag cttgagaggt ggtgctgaat    120
atatgtaaga aagtaaggag ccacccacag caagataaaa cacaataggab aaatcatgtc    180
```

```
ctgcccacac atctaacaaa gcacccaatc caagccctcc tagcaatagc acccagatct    240
gggttattac ctcgttttct gatatagcac ct                                  272
```

<210> SEQ ID NO 393
<211> LENGTH: 288
<212> TYPE: DNA
<213> ORGANISM: Zea mays

<400> SEQUENCE: 393

```
cacacagaca cttaatgact ggtatgatcg agacattgat gcaattaatg agccttatcg    60
gcctattcca tcaggtgcta tatcagaaaa cgaggtaata acccagatct gggtgctatt    120
gctaggaggg cttggattgg gtgctttgtt agatgtgtgg gcaggacatg attttcctat    180
tgtgttttat cttgctgtgg gtggctcctt actttcttac atatattcag caccacctct    240
caagctcaag cagaatggat ggattgggaa cttcgctctg ggtgcgag                288
```

<210> SEQ ID NO 394
<211> LENGTH: 256
<212> TYPE: DNA
<213> ORGANISM: Zea mays

<400> SEQUENCE: 394

```
caattcctca ggtgttcttt cagttccagt acttcctgaa ggaccctgtg aagtatgatg    60
tcaaatatca ggcaagcgca caaccattct tcgtactggg cctactggtg acagcactgg    120
caaccagcca ttaatgaagg caaacttaaa cagaacgagc aaccgttctg ataccgaaga    180
ggcacgtctg gtgaccatta ataagctagc tgcttgtgtg cagggtagga agagaacgtc    240
tttttacttg tagaac                                                    256
```

<210> SEQ ID NO 395
<211> LENGTH: 280
<212> TYPE: DNA
<213> ORGANISM: Zea mays

<400> SEQUENCE: 395

```
caattcctca ggtgttcttt cagttccagt acttcctgaa ggaccctgtg aagtatgatg    60
tcaaatatca ggcaagcgca caaccattct tcgtactggg cctactggtg acagcactgg    120
caaccagcca ttaatgaagg caaacttaaa cagaacgagc aaccgttctg ataccgaaga    180
ggcacgtctg gtgaccatta ataagctagc tgcttgtgtg cagggtagga agagaacgtc    240
tttttacttg tagaacacag atcgattttg taagggttat                          280
```

<210> SEQ ID NO 396
<211> LENGTH: 287
<212> TYPE: DNA
<213> ORGANISM: Zea mays

<400> SEQUENCE: 396

```
cccacgcgtc cgtattcagc accacctctc aagctcaagc agaatggatg gattgggaac    60
ttcgctctgg gtgcgagtta catcagcttg ccctggtggg ctggccaggc gttatttgga    120
actcttacac cagatatcat tgtcttgact actttgtaca gctagctgg gctagggatt    180 gctattgtaa atgatttcaa gagtattgaa ggggatagga ctctggggct tcagtcactt    240
cctgttgctt ttgggatgga aactgcaaaa tggatttgtg ttggagc                  287
```

<210> SEQ ID NO 397

<211> LENGTH: 152
<212> TYPE: DNA
<213> ORGANISM: Zea mays

<400> SEQUENCE: 397

```
cagcaccacc tctcaagctc aagcagaatg gatggattgg gaacttcgct ctgagtgcga      60
gttacatcag cttgccctgg tgggctggcc aggcgttatt tggaactctt acaccagata     120
tcattgtcta gactacttcg tacagcatag ct                                   152
```

<210> SEQ ID NO 398
<211> LENGTH: 298
<212> TYPE: DNA
<213> ORGANISM: Zea mays

<400> SEQUENCE: 398

```
agggcttcgt gtcggaggcg gagtccggca agaggctggc gcaggtggtc agcgacccca      60
gcctcaccaa gtcgggggtg tactggagct ggaacaagga ctcggcgtcg ttcgagaacc     120
agctgtcgca ggaggccagc gatccggaga aggccaagaa gctctgggag atcagcgaga     180
agctcgtggg gcttccttga gctccccgca caggaaaaag cgacatgatg aatctgtcga     240
gcagaggagc tttcgcttcg ttgtattatg tgtaacatta gcatccattt gtttgttt       298
```

<210> SEQ ID NO 399
<211> LENGTH: 218
<212> TYPE: DNA
<213> ORGANISM: Zea mays

<400> SEQUENCE: 399

```
ggggagttcg acggcgccaa ggcatacaag gacagcaagg tgtgcaacat gctgacgatg      60
caggagttcc accgccggta ccacgaggag acgggcgtga ccttcgcgtc gctctacccg     120
ggctgcatcg ccaccagggg cctgttccgc gaacaaattc cgctgttccg gctgtgctcc     180
gcccgccgtt ccagaagtac atcaccaggg tacgtctc                             218
```

<210> SEQ ID NO 400
<211> LENGTH: 317
<212> TYPE: DNA
<213> ORGANISM: Zea mays

<400> SEQUENCE: 400

```
gtcacttctc cacgaacaaa agcgcatcga tctcgctgtc gtcactcctc gtcacccagc      60
cacgaacaga ggcaccaccc agcatggccc tgcaggcggc gctactccca tacaccctct     120
catccgtccc caagaagtgc agcctcgccg tcgcggcgaa tgacacggca ttccttagcg     180
tatcctacaa gaaggtgcac gcggcgtcac tgtccgtgaa aacgcggtgg cgactaccgc     240
gcctgtggcc acgccggggt ccagcacggc ggtcaacgat gggaagaaga ccgtgcggca     300
tgccgtggtg gtgatca                                                   317
```

<210> SEQ ID NO 401
<211> LENGTH: 172
<212> TYPE: DNA
<213> ORGANISM: Zea mays

<400> SEQUENCE: 401

```
gcagaagtcc gactacccgt cccggcggct tatcatcctc gggtccatca ccggcaacag      60
caacacgctg gccgggaaca tcccgcccaa ggcgggctg gcgaccttc gcgggctcgc      120
ggcggggctg cgcggccaga acggctctgc catgatcgac ggcttcgaga gc            172
```

```
<210> SEQ ID NO 402
<211> LENGTH: 313
<212> TYPE: DNA
<213> ORGANISM: Zea mays

<400> SEQUENCE: 402
aaatcctcag tcctcaggct gctcacagtt cgtgctatcc gctcgcgctc ccggtagtct      60
gcctgctcgg caattcggca tggcgctcca ggccgcgacg tccttcctcc cctcggccct     120
ctcggcgcgc aaggaggggt cgtcggtgaa ggactcggcg ttcttgggtg tccatctcgc     180
ggacgatggc ctcaagctgg agaccgctgc tctgggccta cgcaccaaga gggtgatcac     240
gtcggtggcc atccgcgcgc aggcggcagc ggtgtcctca ccatcagtat accccgcgtc     300
gccgtccggc aag                                                        313

<210> SEQ ID NO 403
<211> LENGTH: 252
<212> TYPE: DNA
<213> ORGANISM: Zea mays

<400> SEQUENCE: 403
cccagccaaa tcctcagtcc tcaggctgct cacagttcgt gctatccgct cgcgctcccg      60
gtagtctgcc tgctcggcaa ttcggcatgg cgctccaggc cgcgacgtcc ttcctcccct     120
caggccctct gcggcgcgca aggtaggggt cgtcggtgaa ggactcggcg ttcttgggtg     180
tccatctcgc ggacgatggc ctcaagctgg agaccgctgc tatgggccta cgcaccaaga     240
gggtgatcac gt                                                         252

<210> SEQ ID NO 404
<211> LENGTH: 399
<212> TYPE: DNA
<213> ORGANISM: Zea mays

<400> SEQUENCE: 404
accacgcgtc cgcatacaag gacagcaagg tgtgcaacat gctgacgatg caggagttcc      60
accgccggta ccacgaggag acgggcgtga ccttcgcgtc gctctacccg ggctgcatcg     120
ccaccacggg cctgttccgc gagcacatcc cgctgttccg cctgctcttc ccgccgttcc     180
agaagtacat caccaagggg tacgtctccg aggaggaggc cgggaagcgg ctggcgcagg     240
tggtgagcga cccccagcctg accaagtccg gcgtgtactg gagctggaac aagaactccg     300
cgtccttcga gaaccagctc tctgaggagg ccagcgacgc cgacaaggcc aagaagctct     360
gggagatcag cgagaagctc gtcggcttgg cgtgatgcc                            399

<210> SEQ ID NO 405
<211> LENGTH: 442
<212> TYPE: DNA
<213> ORGANISM: Zea mays
<220> FEATURE:
<223> OTHER INFORMATION: unsure at all n locations

<400> SEQUENCE: 405
acaccggcac accaacacgc tggccgggaa catcccgccc aaggccgggc tgggcgacct      60
ccgcggcgtg gcggcggngc tgcgcggcca gaacggctct gccatgatcg acggctccga     120
gagcttcgac ggcgccaagg cgtacaagga cagcaagatc tgcaacatgc taacaatgca     180
ggagctgcac cggcggtacc acgaggagac gggcatcacg ttcgcgtcgc tctacccggg     240
```

| | |
|---|---|
| gtgcatcgcc accacggggc tgttccgcga gcacatcccg ctgttccggc tgctcttccc | 300 |
| gccgttccag aagttcgtca ccaaaggctt cgtgtcggaa gcggagtccg gcaagaagct | 360 |
| ggcgcatgtg gtcagcgacc ccagcctcac caagtcggng gtgtactgga gctggaacaa | 420 |
| ggactccgcg tcgttcgaga ac | 442 |

<210> SEQ ID NO 406
<211> LENGTH: 442
<212> TYPE: DNA
<213> ORGANISM: Zea mays

<400> SEQUENCE: 406

| | |
|---|---|
| gcgatcacgg gcgacgccaa cacgctggcc ggtgacatct cgcccaaggc cgggctgggc | 60 |
| gacctccgcg gcctcgcggc ggggctgcgc ggccagaacg gctctgccat gatcgacggc | 120 |
| tccgagagct tcgacggcgc caaggcgtac aaggacagca agatctgcaa catgctcacc | 180 |
| atgcaggagc tgcaccggcg gtaccacgag gagacgggca tcacgttcgc gtcgctctac | 240 |
| ccggggtgca tcgccaccac ggggctgttc cgcgagcaca tcccgctgtt ccgcctgctc | 300 |
| ttcccgcctt tccagaagtt cgtcaccaag ggcttcgtgt cggaggcgga gtccggcaag | 360 |
| aggctggcgc atgtggtcag cgaccccagc cttaccaaag tcggggtgta ctggagctgg | 420 |
| aacaggggac tcgcgtcgtt cg | 442 |

<210> SEQ ID NO 407
<211> LENGTH: 352
<212> TYPE: DNA
<213> ORGANISM: Zea mays

<400> SEQUENCE: 407

| | |
|---|---|
| ctcctggcgc gcctgctcct ggacgacatg cagaagtccg actaccgtc ccggcgagtc | 60 |
| atcatcctcg gctccatcac cggcaacacc aacacgctgg ccgggaacat cccgcccaag | 120 |
| gccgggctgg gcgacctgcg cggcctcgcg gcggggctgc gcgccagaa cggctctgcc | 180 |
| atgatcgacg gctccgagag cttcgacggc gccaaggcgt acaaggacag caagatctgc | 240 |
| aacatgctca ccatgcagga gctgcaccgg cggtaccacg aggagacggg catcacgttc | 300 |
| gcgtcgctct acccggggtg catcgccacc acggcgctgt tccgcgagca ca | 352 |

<210> SEQ ID NO 408
<211> LENGTH: 277
<212> TYPE: DNA
<213> ORGANISM: Zea mays

<400> SEQUENCE: 408

| | |
|---|---|
| ctggccggga acatcccgcc caaggccggg ctgggcgacc tccgcggcct cgcggcgggg | 60 |
| ctgcgcggcc agaacggctc tgccatgatc gacggctccg agagcttcga cggcgccaag | 120 |
| gcgtacaagg acagcaagat ctgcaacatg ctaacaatgc aggagctgca ccggcggtac | 180 |
| cacgaggaga cgggcatcac gttcgcgtcg ctctacccgg ggtgcatcgc caccacgggg | 240 |
| ctgttccgcg agcacatccc gctgttccgg ctgctct | 277 |

<210> SEQ ID NO 409
<211> LENGTH: 272
<212> TYPE: DNA
<213> ORGANISM: Zea mays

<400> SEQUENCE: 409

| | |
|---|---|
| gacggcgcca aggcatacaa ggacagcaag gtgtgcaaca tgctgacgat gcaggagttc | 60 |

```
caccgccggt accacgagga cgggcgtg accttcgcgt cgctctaccc gggctgcatc    120
gccaccacgg gcctgttccg cgagcacatc ccgctgttcc gcctgctctt cccgccgttc    180
cagaagtaca tcaccaaggg gtacgtctcc gaggaggagg ccgggaagcg gctggcgcag    240
gtggtgagcg accccagcct gaccaagtcc gg                                  272

<210> SEQ ID NO 410
<211> LENGTH: 309
<212> TYPE: DNA
<213> ORGANISM: Zea mays

<400> SEQUENCE: 410
cactggccgg gaacatcccg cccaaggccg ggctgggcga cctccgcagc ctcgcggcgg    60
ggctgcgcgg ccagaacggc tctgccatga tcgacggctc cgagagcttc gacggcgcca    120
aggcgtacaa ggacagcaag atctgcaaca tgctcaccat gcaggagctg caccggcggt    180
accacgagga cgggcatc acgttcgcgt cgctctaccc ggggtgcatc gccaccacgg    240
ggctgttccg cgagcacatc ccgctgttcc gcctgctctt cccgccgttc cagaagttcg    300
tcaccaagg                                                            309

<210> SEQ ID NO 411
<211> LENGTH: 264
<212> TYPE: DNA
<213> ORGANISM: Zea mays

<400> SEQUENCE: 411
cagaacggct ctgccatgat cgacggctcc gagagcttcg acggcgccaa ggcgtacaag    60
gacagcaaga tctgcaacat gctcaccatg caggagctgc accggcggta ccacgaggag    120
acgggcatca cgttcgcgtc gctctacccg gggtgcatcg ccaccacggg gctgttccgc    180
gagcacatcc cgctgttccg cctgctcttc ccgccttttcc agaagttcgt caccaagggc    240
ttcgtgtcgg aggcggagtc cggc                                           264

<210> SEQ ID NO 412
<211> LENGTH: 267
<212> TYPE: DNA
<213> ORGANISM: Zea mays

<400> SEQUENCE: 412
gctcggtgat gatcgacggc ggggagttcg acggcgccaa ggcatacaag gacagcaagg    60
tgtgcaacat gctgacgatg caggagttcc accgccggta ccacgaggag acggccgtga    120
ccttcgggtc gctctacccg ggctgaatgg caacaacggg cctgttccgg gaacacatcc    180
cgctgttccg gctgctcttc ccgccgttcc agaagtacat caccaagggg gtacgtctcc    240
gaggaggagg ccgggaagcg ctggcgc                                        267

<210> SEQ ID NO 413
<211> LENGTH: 302
<212> TYPE: DNA
<213> ORGANISM: Zea mays

<400> SEQUENCE: 413
ggcgtacaag gacagcaaga tctgcaacat gctcaccatg caggagctgc accggcggta    60
ccacgaggag acgggcatca cgttcgcgtc gctctacccg gggtgcatcg ccaccacggg    120
gctgttccgc gagcacatcc cgctgttccg cctgctcttc ccgccgttcc agaagttcgt    180
```

```
caccaagggc ttcgttccga agcggaaccg gcaagaagct tgcgcaggtg gtcagcgacc      240
ccagcctcac caagtcgggg gtgtactgga gctggaacaa ggactcggcg tcgttcgaga      300
ac                                                                    302
```

<210> SEQ ID NO 414
<211> LENGTH: 291
<212> TYPE: DNA
<213> ORGANISM: Zea mays

<400> SEQUENCE: 414

```
ggcgcgcctg ctcctggacg acatgcagaa gtccgactac ccgtcccgcc gcctcatcat       60
cctcggctcc atcaccggca acaccaacac gctggccggg aacatcccgc ccaaggccgg      120
gctgggcgac ctccgcagcc tcgggcgggg ctgcgcggcc agaacggctc tgccatgatc      180
gacggctccg agagcttcga cggcgccaag gcgtacaagg acagcaagat ctgcaacatg      240
ctaacaatgc aggagctgca ccggcggtac cacgaggaga cgggcatcac g               291
```

<210> SEQ ID NO 415
<211> LENGTH: 268
<212> TYPE: DNA
<213> ORGANISM: Zea mays

<400> SEQUENCE: 415

```
cgagcacatc ccgctgttcc gcctgctctt cccgccgttc cagaagtaca tcaccaaggg       60
gtacgtctcc gaggaggagg ccgggaagcg gctggcgcag gtggtgagcg accccagcct      120
gaccaagtcc ggcgtgtact ggagctggaa caagaactcc gcgtccttcg agaaccagct      180
ctctgaggag ccagctgac gcgacaaggc caagaagctc tgggagatcc gcgagaagct      240
cgtcggcttg gcgtgatgcc caccgtgc                                        268
```

<210> SEQ ID NO 416
<211> LENGTH: 296
<212> TYPE: DNA
<213> ORGANISM: Zea mays

<400> SEQUENCE: 416

```
cccacgcgtc cgaacacgct ggccgggaac atcccgccca aggccgggct gggcgacctc       60
cgcggcctcg gcggggctg cgcggccaga acggctctgc caggatcgac ggctccgaga      120
gcttcgacgg cgccaaggcg tacaaggaca gcaagatctg caacatgctc accatgcagg      180
agctgcaccg gcggtaccac gaggagacgg gcatcacgtt cgcgtcgctc tacccggggt      240
gcatcgccac cacggggctg ttccgcgagc acatcccgct gttccgcctg ctcttc         296
```

<210> SEQ ID NO 417
<211> LENGTH: 255
<212> TYPE: DNA
<213> ORGANISM: Zea mays

<400> SEQUENCE: 417

```
gcctgctctt cccgccattc cagaagtaca tcaccaaggg gtacgtctcc gaggaggagg       60
ccgggaagcg gctgtcgcag gtcgtgagcg accccagcct gaccaagtcc ggcgtgtact      120
ggagctggaa caagaactcg gcgtccttcg agaaccagct ctctgaggag ccagcgacg      180 ccgacaaggc caagaagctc tgggagatca gcgagaagct cgtcagcttg gcgtgacgac      240
ctgatgtcca cagtg                                                      255
```

<210> SEQ ID NO 418
<211> LENGTH: 326
<212> TYPE: DNA
<213> ORGANISM: Zea mays

<400> SEQUENCE: 418

| | |
|---|---|
| cggacgcgtg ggcggacgcg tgggaagta catcaccaag gggtacgtct ccgaggagga | 60 |
| ggccgggaag cggctggcgc agtggtgag cgacccagc ctgaccaagt ccggcgtgta | 120 |
| ctggagctgg aacaagaact ccgcgtcctt cgagaaccag ctctctgagg aggccagcga | 180 |
| cgccgacaag gccaagaagc tctgggagat cagcgagaag ctcgtcggct tggcgtgatg | 240 |
| cccaccgtgg ccggcgccgg cagccggcga cagttttttcc tacctaggac atgctcatta | 300 |
| gttggtctca gtcgagtagt cgacgt | 326 |

<210> SEQ ID NO 419
<211> LENGTH: 290
<212> TYPE: DNA
<213> ORGANISM: Zea mays

<400> SEQUENCE: 419

| | |
|---|---|
| ctccgaggag gaggccggga agcggctgtc gcaggtcgtg agcgacccca gcaccgacca | 60 |
| agtccggcgt gtactggagc tggaacaaga actcggcgtc cttcgagaac cagctctctg | 120 |
| aggaggccag cgacgccgac aaggccaaga agctctggga gatcagcgag aagctcgtcg | 180 |
| gcttggcgtg acgacctgat gcccaccgtg gccggcgccg gcagccggtg acagttttttt | 240 |
| cctaggacat gttcgttact tgatctcagt cgacgcgtgg tgcactcgtg | 290 |

<210> SEQ ID NO 420
<211> LENGTH: 217
<212> TYPE: DNA
<213> ORGANISM: Zea mays

<400> SEQUENCE: 420

| | |
|---|---|
| cccacgcgtc cgctgggcca cttcctcctg gcgcgcctgc tcctggacga catgcagaag | 60 |
| tccgactacc cgtcccgccg cctcgtcatc ctcggctcca tcaccggcaa caccaacacg | 120 |
| ctggccggga acatcccgcc caaggccggg ctgggcgacc tccgcggcct cgcggcgggg | 180 |
| ctgcgcggcc agaacggctc tgccatgatc gacggct | 217 |

<210> SEQ ID NO 421
<211> LENGTH: 242
<212> TYPE: DNA
<213> ORGANISM: Zea mays

<400> SEQUENCE: 421

| | |
|---|---|
| ctccgaggag gagggaagc ggctggcgca ggtggtgagc gaccccagcc tgaccaagtc | 60 |
| cggcgtgtac tggagctgga acaagaactc cgcgtcctac gagaaccagc tctctgagga | 120 |
| ggccagcgac gccgacaagg ccaagaagct ctgggagatc agcgagaagc tcgtcggctt | 180 |
| ggcgtgatgc ccaccgtggc cggcgccggc agccggcgac agttttttcct acctaggaca | 240 |
| tg | 242 |

<210> SEQ ID NO 422
<211> LENGTH: 116
<212> TYPE: DNA
<213> ORGANISM: Zea mays

<400> SEQUENCE: 422

```
tgccggtacc acgaggagac gggcgtgacc ttcgcgtcgc tctacccggg ctgcatcgcc      60
accacgggcc tgttccgcga gcacatcccg ctgttccgcc tgctcttccc gccgtt         116

<210> SEQ ID NO 423
<211> LENGTH: 133
<212> TYPE: DNA
<213> ORGANISM: Zea mays

<400> SEQUENCE: 423
tctcgagccg aatctggctc gaggaggaac atcccgccca aggccgacct gggcgacctc      60
cgacgcctcg cggcggggct gcacggccat aacggctctg ccatgatcga cggctccgag     120
agcttcgacg gcg                                                        133

<210> SEQ ID NO 424
<211> LENGTH: 364
<212> TYPE: DNA
<213> ORGANISM: Zea mays

<400> SEQUENCE: 424
cgcaagggca cggcggtcat caccggcgcg tcgtccggcc tcggcctcgc cacggcgaag      60
gccctggcgg agacaggcaa gtggcacgtc atcatggcct gccgcgactt cctcaaggcg     120
tcgcgcgcgg ccaaggcggc cggcatggac aaggacagct tcaccgtcgt gcacctggac     180
ctcgcctccc tggacagcgt ccgccagttc gtcaagaacg tgcgccagct ggagatgccc     240
atcgacgtgg tggtctgcaa cgccgtcgtg taccagccca ccgccaagga gccgtcctac     300
accgccgacg gcttcgagat gagcgtcggc gtcaaccaac ctggccactt tctcctcgcg     360
cgcg                                                                  364

<210> SEQ ID NO 425
<211> LENGTH: 289
<212> TYPE: DNA
<213> ORGANISM: Zea mays

<400> SEQUENCE: 425
cctggacctc gcctccctgg acagcgtccg ccagttcgtc aggaacgtgc gccactgaga      60
gatgcccatc gacgtggtgg tctgcaacgc cgccgtgtac cagcccaccg ccaaggagcc     120
gtcctacacc gccgacggct cgagatgag cgtcggcgtc aaccacctcg ccacttcct      180 cctcgcgcgc gagctcctca gcgacctcca gtcctccgac taccctcta agcgcctcat     240 catcgtcggc tccatcaccg ggaacacgta cacgctggcg gggaacgtg                289

<210> SEQ ID NO 426
<211> LENGTH: 331
<212> TYPE: DNA
<213> ORGANISM: Zea mays

<400> SEQUENCE: 426
atccgcacac gcgtccgcgt catcatgggc tgccgcgatt ccacaaggc gtcgcgcgca      60 gccaaagcag ccggcatgga caaggacagc ttcaccgtcg tgcacctgga cctcgcctcc     120
ctcgacagcg tccgccagtt cgtcaagaac gtgcgccagc tggagatgcc cgtcgacgtg     180
gtggtctgca acgccgccgt gtaccagccc accgccaagg agccgtccta caccgccgac     240
ggcttcgaga tgagcgtcgg cgtcaaacac ctcggccact tcctcctcgc ccgcgagctc     300
ctcagcgacc tccagtcctc cgactatccc t                                    331
```

<210> SEQ ID NO 427
<211> LENGTH: 280
<212> TYPE: DNA
<213> ORGANISM: Zea mays

<400> SEQUENCE: 427

```
gtggtggtct gcaacgccgc cgtgtaccag cccaccgcca aggagccgtc ctacaccgcc      60
gacggcttcg agatgagcgt cggcgtcaac cacctcggcc atttcctcct cgcccgcgag     120
ctcctcagcg acctccagtc ctccgactac ccctctaagc gcctcatcat cgtcggctcc     180
atcaccggga acacgaacac gctggcgggg aacgtgcccc cgaactcgaa cctgggcgac     240
ctgcgcggcc tcgccggcgg cctcaacggc gttggcagct                           280
```

<210> SEQ ID NO 428
<211> LENGTH: 285
<212> TYPE: DNA
<213> ORGANISM: Zea mays

<400> SEQUENCE: 428

```
gagcgtcggc gtcaaccacc tcggccattt cctcctcgcc cgcgagctcc tcagcgacct      60
ccagtcctcc gactacccct ctaagcgcct catcatcgtc ggctccatca ccgggaacac     120
gaacacgctg gcggggaacg tgcccccgaa ggcgaacctg gcgacctgc gcggcctcgc     180
cggcggcctc aacggcgttg gcagctcggt gatgatcgac ggcggggagt tcgacggcgc     240
caaggcatac aaggacagca aggtgtgcaa catgctgacg atgca                     285
```

<210> SEQ ID NO 429
<211> LENGTH: 282
<212> TYPE: DNA
<213> ORGANISM: Zea mays

<400> SEQUENCE: 429

```
cccacgcgtc cgcaccggcg cgtcgtccgg cctcggcctc gccacggcga aggccctcgc      60
ggagacaggc aagtggcacg tcatcatggc ctgccgcgac ttcctcaagg cgtcgcgcgc     120
ggccaaggcg gccggcatgg acaaggacag cttcaccgtc gtgcacctgg acctcgcctc     180
cctggacagc gtccgccagt tcgtcaggaa cgtgcgccag ctggagatgc ccatcgacgt     240
ggtggtctgc aacgccgccg tgtaccagcc caccgccaag ga                        282
```

<210> SEQ ID NO 430
<211> LENGTH: 276
<212> TYPE: DNA
<213> ORGANISM: Zea mays

<400> SEQUENCE: 430

```
cccacgcgtc cggtcaggaa cgtgcgccac tggagatgcc catcgacgtg gtggtctgca      60
acgccgccgt gtaccagccc accgccaagg agccgtccta caccgccgac ggcttcgaga     120
tgagcgtcgg cgtcaaccac ctcggccatt tcctcctcgc ccgcgagctc ctcagcgacc     180
tccagtcctc cgactacccc tctaagcgcc tcatcatcgt cggctccatc accgggaaca     240
cgaacacgct ggcggggaac gtgccccgac agcgaa                               276
```

<210> SEQ ID NO 431
<211> LENGTH: 229
<212> TYPE: DNA
<213> ORGANISM: Zea mays

<400> SEQUENCE: 431

```
ccaaaacctg cagagggtga gcaggtcggc ggacatccgc gcgcagacgg cagcggtgtc    60
ctccccgtca gtgaccccg cgtcgccgtc tggcaagaag accctccgca agggcacggc    120
ggtcatcacc ggcgcgtcgt ccggcctcgg cctcgccacg gcgaaggccc tcgcggagac   180
aggcaagtgg cacgtcatca tggcctgccg cgacttctca aggcgtcgc                229
```

<210> SEQ ID NO 432
<211> LENGTH: 394
<212> TYPE: DNA
<213> ORGANISM: Zea mays

<400> SEQUENCE: 432

```
aggaagaacc cagccaaatc ctcagtcctc aggctgctcg cagctcgtgc cgtccactct    60
cccccgaggc attctcttgc gttcgctgct cgacatggcg ctccaggcgg cgacgtcctt   120
cctcccctct gccctctccg cgcgcaagga ggggtcggtg aaggactcgg cgtcgttctt   180
gggtgttcgt ctcgcggcgg atgggctcaa gctggacacc accgctctgg gcctacgcac   240
cgtgagggtg agcaggtcgg cggacatccg cgcgcagacg cagcggtgt cctccccgtc    300 agtgaccct gcgtcgccgt ctggcaagaa gaccctccgc attggcacgg cggtcatcat    360
cggcgcgtcg tccggcctcg gcctcgccac ggcg                              394
```

<210> SEQ ID NO 433
<211> LENGTH: 275
<212> TYPE: DNA
<213> ORGANISM: Zea mays

<400> SEQUENCE: 433

```
gttcgtctcg cggcggatgg cctcaagctg gacaccaccg ctctgggcct acgcaccgtg    60
agggtgagca ggtcggcgga catccgcgcg cagacggcag cggtgtcctc cccgtcagtg   120
acccccgcgt cgccgtctgg caagaagacc ctccgcaagg gcacggcggt catcaccggc   180
gcgtcgtccg gcctcggcct cgccacggcg aaggccctcg cggagacagg caagtggcac   240
gtcatcatgg cctgccgcga cttcctcaag gcgtc                              275
```

<210> SEQ ID NO 434
<211> LENGTH: 418
<212> TYPE: DNA
<213> ORGANISM: Zea mays
<220> FEATURE:
<223> OTHER INFORMATION: unsure at all n locations

<400> SEQUENCE: 434

```
agaggaagaa gaagaaccca gccaaatcct cagtcttcag gctgctcaca gctcgtgccg    60
tccactctcc cccgaggcag tctcttgcgt tcgctgctcg acatggcgct ccaggcggcg   120
acgtcctttc tccccctcgg ccctctccgcg cgcaaggagg ggtcggtgaa ggactcggcg   180
tcgttcttgg gtgttcgtct cgcggcggat ggcctcaagc tggacaccac cgctctgggc   240
ctacgcaccg tgagggtgag caggtcggcg gacatccgcg cgcagacggc agcggtgtcc   300
tcnccgtcag tgacnccccgc gtccccgtct ggcaanaaga cctccgnaag ggnaanggcg   360
gtcatnaacg gggggctngn tagggcncng gggnnncnna gggngaaggg ngccncnt    418
```

<210> SEQ ID NO 435
<211> LENGTH: 321
<212> TYPE: DNA
<213> ORGANISM: Zea mays

<400> SEQUENCE: 435

```
agccaaatcc tcagtcttca ggctgctcac agctcgtgcc gtccactctc ccccgaggca    60
gtctcttgcg ttcgctgctc gacatggcgc tccaggcggc gacgtccttt ctcccctcgg   120
ccctctccgc gcgcaaggag gggtcggtga aggactcggc gtcgttcttg ggtgttcgtc   180
tcgcggcgga tggcctcaag ctggacacca ccgctctggg cctacgcacc gtgagggtga   240
gcaggtcggc ggacatccgc gcgcagacgg cagcggtgtc ctccccgtca gtgacccgc    300 gatcgcgtct ggcaagaaga c                                             321
```

<210> SEQ ID NO 436
<211> LENGTH: 112
<212> TYPE: DNA
<213> ORGANISM: Zea mays

<400> SEQUENCE: 436

```
ctcgcccgcg agctcctcag cgacctccag tcctccgact actcctctaa gcgcctcatc    60
atcgtcagct ccatcaccgg gaacacgaac acgctggcgg ggaacgtgcc cc           112
```

<210> SEQ ID NO 437
<211> LENGTH: 296
<212> TYPE: DNA
<213> ORGANISM: Zea mays

<400> SEQUENCE: 437

```
gactagttct agatcccccc gcggagcaga gaggaagaag aagaacccag ccaaatcctc    60
agtcttcagg ctgctcacag ctcgtgccgt ccactctccc ccgaggcagt ctcttgcgtt   120
cgctgctcga catggcgctc caggcggcga cgtcctttct cccctcggcc ctctccgcgc   180
gcaaggaggg gtcggtgaag gactcggcgt cgttcttggg tgttcgtctc gcggcggatg   240
gcctcaagct ggacaccacc gctctgggcc tacgcaccgt gagggtgagc aggtcg       296
```

<210> SEQ ID NO 438
<211> LENGTH: 175
<212> TYPE: DNA
<213> ORGANISM: Zea mays

<400> SEQUENCE: 438

```
cgacatggcg ctccaggcgg cgacgtcctt tctcccctcg gccctctccg cgcgcaagga    60
ggggtcggtg aaggactcgg cgtcgttctt gggtgttcgt ctcgcggcgg atggcctcaa   120
gctggacacc accgctctgg gcctacgcac cgtggaggtg agcaggtcag cggac        175
```

<210> SEQ ID NO 439
<211> LENGTH: 301
<212> TYPE: DNA
<213> ORGANISM: Zea mays

<400> SEQUENCE: 439

```
agaagaaccc agccaaatcc tcagtccttca ggctgctcac agctcgtgcc gtccactctc    60
ccccgagcca gtctcttgcg ttcgctgctc gacatggcgc tccaggcggc gacgtccttc   120
ctcccctctg ccctctccgc gcgcaaggag gggtcggtga aggactcggc gtcgttcttg   180
ggtgttcgtc tcgcggcgga tggcctcaag ctggacacca ccgctctggg cctacgcacc   240
gtgagggtga gcaggtcggc ggacatccgc gcgcagacgg cagcggtgtc ctccccgtca   300
g                                                                   301
```

<210> SEQ ID NO 440

<211> LENGTH: 261
<212> TYPE: DNA
<213> ORGANISM: Zea mays

<400> SEQUENCE: 440

```
gtgaaggact cggcgtcgtt cttgggtgtt cgtctcgcgg cggatggcct caagctggac      60
accaccgctc tgggcctacg caccgtgagg gtgagcaggt cggcggacat ccgcgcgcag     120
acggcagcgg tgtcctcccc gtcagtgacc cccgcgtcgc cgtctggcaa gaagaccctc     180
cgcataggca cggcggtcat caccggcgcg tcgtccggcc tcggcctcgg cacggcgaag     240
gccctcgcgg agacaggcaa g                                               261
```

<210> SEQ ID NO 441
<211> LENGTH: 84
<212> TYPE: DNA
<213> ORGANISM: Zea mays

<400> SEQUENCE: 441

```
gtccggcctc ggcctcgcca cggcgaaggc cctcgcggag acaggcaagt ggcacgtcat      60
catggcctgc cgcgacttcc tcaa                                             84
```

<210> SEQ ID NO 442
<211> LENGTH: 352
<212> TYPE: DNA
<213> ORGANISM: Zea mays

<400> SEQUENCE: 442

```
cggacgcgtg ggctgtcggt gagatcgctt gtggcgacga cggcgcctgt ggccacgccg      60
gggtccagca cggcggccaa ggatgggaag aagaccgtgc ggcagggcgt ggtggtgatc     120
acgggcgcgt cgtcggggtt gggcctggcg gcggccaagg cgctggcgga gaccggcaag     180
tggcacgtgg tgatggcctg ccgcgacttc tcaaggcgg ccaaggcggc caagggcgcc     240
ggcatggcgg acggcagcta caccatcatg cacctggacc tggccttcct cgacagcgtg     300
cggcagttcg tggacagctt ccggcgcgcc ggcatgccgc tcgactcgct cg             352
```

<210> SEQ ID NO 443
<211> LENGTH: 279
<212> TYPE: DNA
<213> ORGANISM: Zea mays

<400> SEQUENCE: 443

```
acgggcgcgt cgtcggggtt gggcctggcg gcggccaagg cgctggcgga gaccggcaag      60
tggcacgtgg tgatggcctg ccgcgacttc ctcaaggcgg ccaaggcggc caagggcgcc     120
ggcatggcgg acggcagcta caccatcatg cacctggacc tggcctccct cgacagcgtg     180
cggcagttcg tggacagctt ccggcgcgcc ggcatgccgc tcgactcgct cgtctgcaac     240
gccgccatct accggcccac ggcatagacg ccgacgttc                             279
```

<210> SEQ ID NO 444
<211> LENGTH: 221
<212> TYPE: DNA
<213> ORGANISM: Zea mays

<400> SEQUENCE: 444

```
aaagcgcatc gatctcgctg tcgtcactcc tcgtcaccca gccaaggcgc tggcggagac      60
cggcaagtgg cacgtggtga tggcctgccg cgacttcctc aaggcggcca aggcggccaa     120
gggcgccggc atggcggacg gcagctacac catcatgcac ctggacctgg cctccctcga     180
```

-continued cagcgtgcgg cagttcgtgg acagcttccg gcgcgccggc a                221

<210> SEQ ID NO 445
<211> LENGTH: 310
<212> TYPE: DNA
<213> ORGANISM: Zea mays

<400> SEQUENCE: 445
agtgcagcct cgccgtcgcg gcgaaggaca cggcattcct tagcgtatcc cagaagaagg    60
tgcaggcggc gtcgctgtcg gtgagaacgc gggtggcgac gacggcgcct gtggccacgc   120
cggggtccag cacggcggcc aaggatggga agaagaccgt gcggcagggc gtggtggtga   180
tcacgggcgc gtcgtcgggg ttgggcctgg cggcggccaa ggcgctggcg agaccggca    240
agtggcacgt ggtgatggcc tgccgcgact cctcaaggc ggccaatgcg gccaagggcg    300
ccggcatggc                                                          310

<210> SEQ ID NO 446
<211> LENGTH: 295
<212> TYPE: DNA
<213> ORGANISM: Zea mays

<400> SEQUENCE: 446
cccacgcgtc cgcggcgaag gacacggcat tccttagcgt atcccagaag aaggtgcagg    60
cggcgtcgct gtcggtgaga acgcgggtgg cgacgacggc gcctgtcgcc acgccggggt   120
ccagcacggc ggccaaggat gggaagaaga ccgtgcggca gggcgtggtg gtgatcacgg   180
gcgcgtcgtc ggggttgggc ctggcggcgg ccaaggcgct ggcggagacc ggcaagtggc   240
acgtggtgat ggcctgccgc gacttcctca aggcggccaa ggcggccaag ggcgc        295

<210> SEQ ID NO 447
<211> LENGTH: 444
<212> TYPE: DNA
<213> ORGANISM: Zea mays

<400> SEQUENCE: 447
cggacgcgtg ggcgaacaaa agcgcatcga tctcgctgtc gtcactcctc gtcacccagg    60
cacgaacaga ggcaccaccc agcatggccc tgcaggcggc gctcctctca tccaccctct   120
catccgtccc caagaagtgc agcctcgccg tcgcggcgaa ggacacggca ttccttagcg   180
tatcccagaa ggtcagtgat cagctgcatc tgcatgctgc actcgcagtc acaatgcgct   240
tgaattgaac gtgtcactca ctctgtcgtg agcatgccat gcgtgcagaa ggtgcaggcg   300
gcgtcgctgt cggtgagagt cacttcgcca tctaccggcc cacggcaagg acgccgacgt   360
tcacggcgga cggatacgag atgagcgtcg gcgtcaacca cctgggccac ttcctcctgg   420
cgcgcctgct cctggacgac atgc                                          444

<210> SEQ ID NO 448
<211> LENGTH: 423
<212> TYPE: DNA
<213> ORGANISM: Zea mays

<400> SEQUENCE: 448
cccacgcgtc cgcccacgcg tccgcggact cgtgggcttc gccacgaaca aaagcgcatc    60
gatctcgctg tcgtcactcc tcgtcaccca gccacgaaca gaggcaccac ccagcatggc   120
cctgcaggcg gcgctcctcc catccaccct ctcatccgtc cccaagaagt gcagcctcgc   180

```
cgtcgcggcg aaggacacgg cattccttag cgtatcccag aagaaggtgc aggcggcgtc      240
gctgtcggtg agaacgcggg tggcgacgac ggcgcctgtg ccacgccgg ggtccagcac      300 ggcggccaag gatgggaaga agaccgtgcg gcagggcgtg gtggtgatca cgggcgcgtc      360
gtcggggttg ggcctggcgg cggccaaggc gctggcggag accggcaagt ggcacgtggt      420
gat                                                                  423
```

<210> SEQ ID NO 449
<211> LENGTH: 279
<212> TYPE: DNA
<213> ORGANISM: Zea mays

<400> SEQUENCE: 449

```
cgctgtcgtc actcctcgtc acccagccac gaacagaggc accacccagc atggccctgc       60
aggcggcgct cctcccatcc accctctcat ccgtccccaa gaagtgcagc ctcgccgtcg      120
cggcgaagga cacggcattc cttagcgtat cccacggcgc ggacgccgac gttcacggcg      180
gacgggtacg agatgagcgt cggcgtcaac cacctgggcc acttcctcct ggcgcgcctg      240
ctcctggacg acatgcagaa gtccgactac acgtcccgc                            279
```

<210> SEQ ID NO 450
<211> LENGTH: 396
<212> TYPE: DNA
<213> ORGANISM: Zea mays

<400> SEQUENCE: 450

```
gacttcgcca cgaacaaaag cgcatcgatc tcgctgtcgt cactcctcgt cacccagcca       60
cgaacagagg caccacccag catggccctg caggcggcgc tcctcccatc caccctctca      120
tccgtcccca agaagtgcag cctcgccgtc gcggcgaagg acacggcatt ccttagcgta      180
tcccagaaga aggtgcaggc ggcgtcgctg tcggtgagaa cgcgggtggc gacgacggcg      240
cctgtggcca cgccggggtc cagcacggcg gccaaggatg gaagaagac cgtgcggcag      300 ggcgtggtgg tgatcacggg cgcgtcgtcg gggttgggcc tggcggcggc caaggcgctg      360
gcggagaccg gcaagtggca cgtggtgatg gcctgc                               396
```

<210> SEQ ID NO 451
<211> LENGTH: 375
<212> TYPE: DNA
<213> ORGANISM: Zea mays

<400> SEQUENCE: 451

```
cagagtcact tcgccacgaa caaatgcgca tcgatctcgc tgtcgtcact cctcgtcacc       60
cagccacgaa cagaggcacc acccagcatg gccctgcagg cggcgctcct cccatccacc      120
ctctcatccg tccccaagaa gtgcagcctc gccgtcgcgg cgaaggacac ggcattcctt      180
agcgtatccc agaagaaggt gcaggcggcg tcgctgtcgg tgagaacgcg ggtggcgacg      240
acggcgcctg tggccacgcc ggggtccagc acggcggcca aggatgggaa gaagaccgtg      300
cggcagggcg tggtggtgat cacgggcgcg tcgtcggggt gggcctggc ggcggccaag      360 gcgctggcgg agacc                                                     375
```

<210> SEQ ID NO 452
<211> LENGTH: 326
<212> TYPE: DNA
<213> ORGANISM: Zea mays

<400> SEQUENCE: 452

```
aacaaaagcg catcgatctc gctgtcgtca ctcctcgtca cccagccacg aacagaggca    60
ccacccagca tggccctgca ggcggcgctc ctcccatcca ccctctcatc cgtccccaag   120
aagtgcagcc tcgccgtcgc ggcgaaggat caggcattcc ttagcgtatc ccagaagaag   180
gtgcaggcgg cgtcgctgtc ggtgagaacg cgggttgcga cgacggcgcc tgttgccacg   240
ccggggtcca gcacggcggc caaggatggg aagaagaccg tgcggcaagg cgtggtggtg   300
atcacgggcg cgtcgtcggg gttggg                                        326

<210> SEQ ID NO 453
<211> LENGTH: 338
<212> TYPE: DNA
<213> ORGANISM: Zea mays

<400> SEQUENCE: 453
gagtcacttc gccacgaaca aaagcgcatc gatctcgctg tcgtcactcc tcgtcaccca    60
gccacgaaca gaggcaccac ccagcatggc cctgcaggcg gcgctcctcc catccaccct   120
ctcatccgtc cccaagaagt gcagcctcgc cgtcgcggcg aaggacacgg cattccttag   180
cgtatcccag aagaaggtgc aggcggcgtc gctgtcggtg agaacgcggg tggcgacgac   240
ggcgcctgtg gccacgccgg ggtccagcac ggcggccaag gatgggaaga agaccgtgcg   300
gcagggcgtg gtggtgatca ctggcgcgtc gtcggggt                           338

<210> SEQ ID NO 454
<211> LENGTH: 273
<212> TYPE: DNA
<213> ORGANISM: Zea mays

<400> SEQUENCE: 454
cttcgccacg aacaaaagcg catcgatctc gctgtcgtca ctcctcgtca cccagccacg    60
aacagaggca ccacccagca tggccctgca ggcggcgctc ctcccatcca ccctctcatc   120
cgtccccaag aagtgcagcc tcgccgtcgc ggcgaaggac acggcattcc ttagcgtatc   180
ccagaagaag gtgcaggcgg cgtcgctgtc ggtgagaacg cgggtggcga cgacggcgcc   240
tgtggccacg ccggggtcca gcacggcggc caa                                273

<210> SEQ ID NO 455
<211> LENGTH: 296
<212> TYPE: DNA
<213> ORGANISM: Zea mays

<400> SEQUENCE: 455
gccacgaaca aaagcgcatc gatctcgctg tcgtcactcc tcgtcaccca gccacgaaca    60
gaggcaccac ccagcatggc cctgcaggcg gcgctcctcc catccaccct ctcatccgtc   120
cccaagaagt gcagcctcgc cgtcgcggcg aaggacacgg cattccttag cgtatcccag   180
aagaaggtgc aggcggcgtc gctgtcggtg agaacgcggg tggcgacgac ggcgcctgtg   240
gccacgccgg ggtccagcac ggcggccaag gatgggaaga agaccgtgcg gcaggg       296

<210> SEQ ID NO 456
<211> LENGTH: 314
<212> TYPE: DNA
<213> ORGANISM: Zea mays

<400> SEQUENCE: 456
cagagtcagt tcgccacgaa caaaagcgcg tcgatgtcgc tgtcgtcact cgtcgtcacc    60
```

|  |  |
| --- | --- |
| cagccacgaa cagaggcacc acccagcatg gccctgcagg cggcgggtcg tcggatccac | 120 |
| gctgtcatcc gtccccgaga agtgcagcct cgccgtcgcg gcgaaggtca cggcattcct | 180 |
| tagcgtatcc cagaagaagg tgcaggcggc gtcggtgtcg gtgagaacgc gggtggcgac | 240 |
| gacggcgcct gtggccacgc cggggtccag cacagcggcc aaggatggga agaagaccgt | 300 |
| gcggcagggc gtgg | 314 |

<210> SEQ ID NO 457
<211> LENGTH: 287
<212> TYPE: DNA
<213> ORGANISM: Zea mays

<400> SEQUENCE: 457

|  |  |
| --- | --- |
| gagtcacttc gccacgaaca aaagcgcatc gatctcgctg tcgtcactcc tcgtcaccca | 60 |
| gccacgaaca gaggcaccac ccagcatggc cctgcaggcg cgctcctcc catccaccct | 120 |
| ctcatccgtc cccaagaagt gcagcctcgc cgtcgcggcg aaggacacgg cattccttag | 180 |
| cgtatcccag aagaaggtgc aggcggcgtc gctgtcggtg agaacgcggg tggcgacgac | 240 |
| ggcgcctgtg gccacgccgg ggtccagcac ggcggccaag gatggga | 287 |

<210> SEQ ID NO 458
<211> LENGTH: 312
<212> TYPE: DNA
<213> ORGANISM: Zea mays

<400> SEQUENCE: 458

|  |  |
| --- | --- |
| cagagtcact tcgccacgaa caaaagcgca tcgatctcgc tgtcgtcact cctcgtcacc | 60 |
| cagccacgaa cagaggcacc acccagcatg gccctgcagg cggcgctcct cccatccacc | 120 |
| ctctcatccg tccccaagaa gtgcagcctc gccgtcgcgg cgaaggacac ggcattcctt | 180 |
| agcgtatccc agaagaaggt gcaggcggcg tcgctgtcgg tgagaacgcg ggtggcgacg | 240 |
| acggcgcctg tggccacgcc ggggtccagc acggcggcca aggatgggaa gaagaccgtg | 300 |
| cggcagggcg tg | 312 |

<210> SEQ ID NO 459
<211> LENGTH: 321
<212> TYPE: DNA
<213> ORGANISM: Zea mays

<400> SEQUENCE: 459

|  |  |
| --- | --- |
| gtcacttcgc cacgaacaaa agcgcatcga tctcgctgtc gtcactcctc gtcacccagc | 60 |
| cacgaacaga ggcaccaccc agcatggccc tgcaggcggc gctcctccca tccaccctct | 120 |
| catccgtccc caagaagtgc agcctcgccg tcgcggcgaa ggacacggca ttccttagcg | 180 |
| tatcccagaa gaaggtgcag gcggcgtcgc tgtcggtgag aacgcgggtg gcgacgacgg | 240 |
| cgcctgtggc cacgccgggg tccagcacgg cggccaagga tgggaagaag accgtgcggc | 300 |
| agggcgtggt ggtgatcacg g | 321 |

<210> SEQ ID NO 460
<211> LENGTH: 281
<212> TYPE: DNA
<213> ORGANISM: Zea mays

<400> SEQUENCE: 460

|  |  |
| --- | --- |
| cttcgccacg aacaaaagcg cgtcgatctc gctgtcgtca ctcctcgtca cccagccacg | 60 |
| aacagaggca ccacccagca tggccctgca ggcggcgctc ctcccatcca ccctctcatc | 120 |

```
cgtccccaag aagtgcagcc tcgccgtcgc ggcgaaggac acggcattcc ttagcgtatc      180
ccagaagaag gtgcaggcgg cgtcgctgtc ggtgagaacg cgggtggcga cgacggcgcc      240
tgtggccacg ccggggtcca gcaggcggcc aaggatggga a                          281
```

<210> SEQ ID NO 461
<211> LENGTH: 314
<212> TYPE: DNA
<213> ORGANISM: Zea mays

<400> SEQUENCE: 461

```
cagagtcact tcgccacgaa caaaagcgca tcgatctcgc tgtcgtcact cctcgtcacc      60
cagccacgaa cagaggcacc acccagcatg gccctgcagg cggcgctcct cccatccacc     120
ctctcatccg tccccaagaa gtgcagcctc gccgtcgcgg cgaaggacac ggcattcctt     180
agcgtatccc agaagaaggt gcaggcgcg tcgctgtcgg tgagaacgcg ggtggcgacg     240
acggcgcctg tggccacgcc ggggtccagc acggcggcca aggatgggaa gaagaccgtg     300
cggcatggcg tggt                                                        314
```

<210> SEQ ID NO 462
<211> LENGTH: 351
<212> TYPE: DNA
<213> ORGANISM: Zea mays

<400> SEQUENCE: 462

```
gtccggcaag atgctggcgc aggtggtcag cgaccccagc ctcaccaagt cgggggtgta      60
ctggagctgg aacaaggact cggcgtcgtt cgagaaccag ctgtcgcagg aggccagcga     120
tccggagaag gccaagaagc tctgggagat cagcgagaag ctcgtggggc ttgcctgagc     180
tcgccggcac ggcacagcga catgatggat ctgtcgagca gggagctttt cgcttcgttg     240
tattatgtgt accattagca tccatttgt ttgtttctag aagttggtaa tgaccgtcgg      300
agaagagcct gtaattgttc gatcatgtat tgcttacaat tttttttaa a               351
```

<210> SEQ ID NO 463
<211> LENGTH: 327
<212> TYPE: DNA
<213> ORGANISM: Zea mays

<400> SEQUENCE: 463

```
gtccggcaag atgctggcgc aggtggtcag cgaccccagc ctcaccaagt cgggggtgta      60
ctggagctgg aacaaggact cggcgtcgtt cgagaaccag ctgtcgcagg aggccagcga     120
tccggagaag gccaagaagc tctgggagat cagcgagaag ctcgtggggc ttgcctgagc     180
tcgccggcac gcgacagcga catgatggat ctgtcgagca gggagctttt cgcttcgttg     240
tattatgtgt accattagca tccatttgt ttgtttctag aagttggtaa tgaccgtcgg      300
agaagagcct gtaattgttc gatcatg                                          327
```

<210> SEQ ID NO 464
<211> LENGTH: 304
<212> TYPE: DNA
<213> ORGANISM: Zea mays

<400> SEQUENCE: 464

```
ggcctgccgc gacttcctca aggcggccaa ggcggccaag ggcgccggca tggcggacgg      60
cagctacacc atcatgcacc tggacctggc ctccttcgac agcgtgcggc agttcgtgga     120
```

```
cagcttccgg cgcgccggca tgccgctcga ctcgctcgtc tgcaacgccg ccatctaccg     180
gcccacggcg cggacgccga cgttcacggc ggacgggtac gagatgagcg tcggcgtcaa     240
ccacctgggc cacttcctcc tggcgcgcct gctcctggac gacatgcaga agtccgacta     300
cccg                                                                 304
```

<210> SEQ ID NO 465
<211> LENGTH: 285
<212> TYPE: DNA
<213> ORGANISM: Zea mays

<400> SEQUENCE: 465

```
cggcatggcg gacggcagct acaccatcat gcacctggac ctggcctccc tcgacagcgt     60
gcggcagttc gtggacagct ccggcgcgcg cggcatgccg ctcgactcgc tcgtctgcaa    120
cgccgccatc taccggccca cggcgcggac gccgacgttc acggcggacg ggtacgagat    180
gagcgtcggc gtcaaccacc tgggccactt cgtcctggcg cgcctgctcc tggacgacat    240
gcagaagtcc gactactcgt cccgccgcct cgtcatcctc ggctc                    285
```

<210> SEQ ID NO 466
<211> LENGTH: 147
<212> TYPE: DNA
<213> ORGANISM: Zea mays

<400> SEQUENCE: 466

```
cccacgcgtc cgcacacgcg tccggtggac agcttccggc gcgccggcat gccgctcgac     60
tcgctcgtct gcaacgccgc catctaccgg cccacgcgcg gacgccgac gttcacggcg    120 gacgggtacg agatgagcgt ccgcgtc                                        147
```

<210> SEQ ID NO 467
<211> LENGTH: 280
<212> TYPE: DNA
<213> ORGANISM: Zea mays

<400> SEQUENCE: 467

```
actaaatgcc gaggtgatgg aacttgacct gctctccctc gactcggtcg taaaatttgc     60
tgatgcttgg acagtcgta tggcaccgct gcacgtgttg atcaacaatg ctgagctctt    120
cgctatagga gaccccaac attttccaa ggatggacat gaagaacaca tgcaagtgaa    180
ccatcttgca cctgcattac tggcgatgct gcttatacct tcccttctcc gaggttctcc    240
cagcagaatt gtaaacgtta attcaatcat gcacagtgta                          280
```

<210> SEQ ID NO 468
<211> LENGTH: 277
<212> TYPE: DNA
<213> ORGANISM: Zea mays

<400> SEQUENCE: 468

```
ctcaaatagc aagctggcac aggtaaaatt cagtagcatg cttcacaaga aaattcctgc     60
agaggctggc atcggtgtag tttgcgcttc tcctggaatt gtcgcacga acgttgcaag    120 agctcttcct aagattgtcg tagccgcgta ccatttgatt ccctacttca tatttgacgc    180
tcaagaaggt tctaggagtg cactgtttgc agcatccgat ccccaagtcc cggaatactg    240
cgagacgctc aagtcggagg actggccagt ttgtgcc                             277
```

<210> SEQ ID NO 469
<211> LENGTH: 436

```
<212> TYPE: DNA
<213> ORGANISM: Zea mays

<400> SEQUENCE: 469
ggttctccca gcagaattgt taacgttaat tcaatcatgc acagtgtagg ttttgttgat      60
gctgaagatt tgaacttgag aaaacataaa tatagaagtt ggttggcgta ttcaaatagc     120
aagttggcac aggtaaaatt tagtagcatg cttcataaga gaattcctgc agaagctggc     180
atcagcataa tttgtgcttc tcctggaatt gtcgacacga atgttacaag agaccttcct     240
aagattgttg tagctgcata ccattttctt ccctacttca tattcgatgg tcaagaaggt     300
tctaggagtg cactgtttgc agcatgtgac ccccaagttc cagagtactg tgagatgctc     360
aagtcggaag actggccagt ctgtgcttgc attaactacg actgtaatcc gatgaacgcg     420
tctgaagaag cgcaca                                                    436

<210> SEQ ID NO 470
<211> LENGTH: 335
<212> TYPE: DNA
<213> ORGANISM: Zea mays

<400> SEQUENCE: 470
gtagaattta gtagcatgct tcataagata attcctgcag aagctggcat cagcataatt      60
tgtgcttctc ctggaattgt cgacacgaat gttacaagag accttcctaa gattgttgta     120
gctgcatacc gttttcttcc ctacttcata ttcgatggtc aagaaggttc taggagtgca     180
ctgtttgcag catgtgaccc ccaagttcca gagtactgtt gagatgctca gtcggaaga     240
ctggccagtc tgtgcttgca ttaactacga ctgtaatccg atgaacgcgt ctgaagaagc     300
gcacagcttg ataccttcgc agctggtctg ggaga                                335

<210> SEQ ID NO 471
<211> LENGTH: 343
<212> TYPE: DNA
<213> ORGANISM: Zea mays

<400> SEQUENCE: 471
gtaaaatgta gtagcatgct tcataagaga attcctgcag aagctggcat cagcataatt      60
tgtgcttctc ctggaattgt cgacacgaat gttacaagag accttcctaa gattgttgta     120
gctgcatacc gttttcttcc ctacttcata ttcgatggtc aagaaggttc taggagtgca     180
ctgtttgcag catgtgaccc ccaagttcca gagtactgtg atgctcaa gtcggtagac     240
tggccagtct gtgcttgcat taactacgac tgtaatccga tgaacgcgtc tgaagaagcg     300
cacagccttg aaacctcgca gctggtctgg gagaagcgct cga                      343

<210> SEQ ID NO 472
<211> LENGTH: 262
<212> TYPE: DNA
<213> ORGANISM: Zea mays

<400> SEQUENCE: 472
gtaaaattta gtagcatgct tcataagata attcctgcag aagctggcat cagcataatt      60
tgtgcttctc ctggaattgt cgacacgaat gttacaagag accttcctaa gattgttgta     120
gctgcatacc gttttcttcc ctacttcata ttcgatggtc aagaaggttc taggagtgca     180
ctgtttgcag catgtgaccc ccaagttcca gagtactgtg atgctcaa gtcggaagac     240
tggccagtct gtgcttgcat ta                                            262
```

<210> SEQ ID NO 473
<211> LENGTH: 256
<212> TYPE: DNA
<213> ORGANISM: Zea mays

<400> SEQUENCE: 473

```
gcttcataag agaattcctg cagaagctgg catcagcata atttgtgctt ctcctggaat      60
tgtcgacacg aatgttacaa gagaccttcc taagattgtt gtagctgcat accgttttct     120
tccctacttc atattcgatg gtcaagaagg ttctaggagt gcactgtttg cggcatgtga     180
ccccaagtt ccagagtact gtgagatgct caagtcggaa gactggccag tctgtgcttg     240
cattaactac gactgt                                                     256
```

<210> SEQ ID NO 474
<211> LENGTH: 208
<212> TYPE: DNA
<213> ORGANISM: Zea mays

<400> SEQUENCE: 474

```
gcttcataag agaattcctg cagaagctgg catcagcata atttgtgctt ctcctggaat      60
tgtcgacacg aatgttacaa gagaccttcc taagattgtt gtagctgcat accgttttct     120
tccctacttc atattcgatg gtcaagaagg ttctaggagt gcactgtttg cggcatgtga     180
ccccaagtt ccagagtact gtgagatg                                         208
```

<210> SEQ ID NO 475
<211> LENGTH: 338
<212> TYPE: DNA
<213> ORGANISM: Zea mays

<400> SEQUENCE: 475

```
gtatgattta gtagcatgct gcataagaga gttcctgcag aagctggcat cagcataatt      60
tgtgcttctc ctggaattct cgacacgaat gttacgagaa tccttcctaa gattgttgta     120
gctgcatacc gttgtcttcc ctacttcata ttcgatggtc aacaaggttc taggagtgca     180
ctgtctgcag catgtgaccc ccaagttcca gagtactgtg agatgctcaa gtcggaagac     240
tggccagtct gtgcttgcat taactacgac tgtaatccga tgaacgcgtc tgaagaagcg     300
cacagccttg aaacctcgca gctggtctgg agaagac                              338
```

<210> SEQ ID NO 476
<211> LENGTH: 248
<212> TYPE: DNA
<213> ORGANISM: Zea mays

<400> SEQUENCE: 476

```
gattgatgct gaagatttca acttgagaaa acataaatat agaagttggt tggcgtattc      60
aaatagcaag ttggcacagg taaaatttag tagcatgctt cataagagaa ttcctgcaga     120
agctggcatc agcataattt gtgcttctcc tggaattgtc gacacgaatg ttacaagaga     180
ccttcctaag attgttgtag ctgcatacgg tttcccccaa atcaaaatcg atggtcaaga     240
aggttcta                                                              248
```

<210> SEQ ID NO 477
<211> LENGTH: 341
<212> TYPE: DNA
<213> ORGANISM: Zea mays

<400> SEQUENCE: 477

```
gagatcttcc taagattgtc gtagccgcgt accatttgat tccctacttc atatttgacg      60
ctcaagaagg ttctaggagt gcactgtttg cagcatccga tccccaagtc ccggagtact     120
gcgagacgct caagtcggag gactggccag tttgtgcctg cattaactat gactgtagtc     180
cgatgaatgc gtctgaagaa gcgcacaatc tggagacctc gcagctggtc tgggagaaga     240
cactggagat ggtcggcctt ccgccggatg ccctggagaa gctcatcgcc ggagaatcag     300
ttcagtgccg ttacggacaa caggatacaa cttaactttt t                         341

<210> SEQ ID NO 478
<211> LENGTH: 383
<212> TYPE: DNA
<213> ORGANISM: Zea mays

<400> SEQUENCE: 478
gtgcactgtt tgcagcatcc gatccccaag tcccggaata ctgcgagacg ctcaagtcgg      60
aggactggcc agggggtgcc tgcattaact atgactgtag tccgatgaat gcgtctgaag     120
aagcgcacaa tcttgagacc tcgcagctgg tctgggagaa gacactggag atggtcggcc     180
ttccgccgga tgccctggag aagctcatcg ccggagaatc agttcagtgc cgttacggac     240
aacaggatac aacttttag ttagcagttt agaggtggtt tgttcggttg ttatgtcatt      300
ttgatcctaa atttgcaggg aggaaaacac agggaaagga gaaaagaat tgttgacag       360 ctacccaatc ttggctcttt tct                                            383

<210> SEQ ID NO 479
<211> LENGTH: 166
<212> TYPE: DNA
<213> ORGANISM: Zea mays

<400> SEQUENCE: 479
ggaggactgg ccattttgtg cctgcatgaa ctatgactgt agtccgatga atgcgtctta      60
caggagcgca caatcttgag acctcgcagc tggtctggga agacactg gagatggtcg      120 gcgttccgcc ggatgccctg gagaagctca tcgccggaga atcagt                    166

<210> SEQ ID NO 480
<211> LENGTH: 382
<212> TYPE: DNA
<213> ORGANISM: Zea mays
<220> FEATURE:
<223> OTHER INFORMATION: unsure at all n locations

<400> SEQUENCE: 480
agtgaggagt ngcttccaaa actgatgcat gnantcatgc aatacgcatt ccggtcgacc      60
actcgtaccc tggtaaaccc gaaggattgg atctgattat ccgctattct tgtgtccctt     120
acgcttggag cacgatggca gtatgatcat aaaccggatg aaggaaccgc cgaacgaaa     180 cttctataag cctgcataaa cccgatagat tggatctgat tatcccttat tcttgagatc     240
tttagttaga gttttccctt ctgtagggct aaaaccacgt gcagcttcat gatatatcct     300
gcctctgtac aatcgtgaac aaatattacg tattaatgct ctatctgcct gtattatata    360
tgctgctttt tgcccatgtg aa                                             382

<210> SEQ ID NO 481
<211> LENGTH: 358
<212> TYPE: DNA
<213> ORGANISM: Zea mays
```

<400> SEQUENCE: 481

| | |
|---|---|
| cctgcataaa cccgaaggat tggatctgat tagccgttat tcttgtgtcc cttccgcttg | 60 |
| cagcacgatg gcagtatgat cataaaccgg aagaaggaac cgaggaatgg aaacttctgg | 120 |
| aagcctgcat aaacccgaag gattggatct gattagccgt tattcttgag atcttttgtt | 180 |
| agagttttcc cttctgtagg gctaagacca cgtgcagttt cattatatat tttgcatctg | 240 |
| tagaatcgtg aataaatatg atgtagtaat gctgtagctg tctgtatcta tctgctgttt | 300 |
| tttccccatg tgaatgagag aaccattggc ttctgtatta cgaaggattc aggtttct | 358 |

<210> SEQ ID NO 482
<211> LENGTH: 275
<212> TYPE: DNA
<213> ORGANISM: Zea mays

<400> SEQUENCE: 482

| | |
|---|---|
| accggaagaa ggaaccgagg aatggaaact tctggaagcc tgcataaacc cgaaggattg | 60 |
| gatctgatta gccgtcattc ttgagatctt tgttagagt tttcccttct gtagggctaa | 120 |
| gaccacgtgc agtttcatta tttcttttg catctgtaga atcgtgaata aatatgatgt | 180 |
| agtaatgctg tagctgtttg tatctatctg ctgttttttc cccatgtgaa tgagtgaacc | 240 |
| attggcttct gtatttacga aggattcagg tttct | 275 |

<210> SEQ ID NO 483
<211> LENGTH: 335
<212> TYPE: DNA
<213> ORGANISM: Zea mays

<400> SEQUENCE: 483

| | |
|---|---|
| cttgaagagg acgtgaagca tttccattct gttcaaaagc aagcatgtga taaatttgat | 60 |
| ccaagttttc acccaagatt caaaaaatgg tgtgatgatt atttctatat taagcaccgt | 120 |
| aatgagcggc gtgggctagg tggaatattt tttgatgacc ttaatgatta cgatcaagaa | 180 |
| atgcttctca actttgctac agaatgtgcg gactctgtac ttcctgcgta cataccgatc | 240 |
| atagaacggc ggaagaacac tccgttcaat gaggagcaca gggcatggca gcaattgcgg | 300 |
| agaggtcgtt atgtggagtt caaccttgtc tacga | 335 |

<210> SEQ ID NO 484
<211> LENGTH: 475
<212> TYPE: DNA
<213> ORGANISM: Zea mays

<400> SEQUENCE: 484

| | |
|---|---|
| caagaaatgc ttctcaactt tgctacagaa tgtgcggact ctgtacttcc tgcgtacata | 60 |
| ccgatcatag aacggaggaa gaacactccg ttcaacgagg agcacagggc atggcagcaa | 120 |
| ttgcggagag gtcgttatgt ggagttcaac cttgtctacg accgtggtac aacatttggc | 180 |
| ctaaagactg gaggaaggat tgagagcata cttgtgtccc ttccacttac agcacgatgg | 240 |
| cagtatgatc ataaaccgga agaaggaacc gaggaatgga aacttctgga agcctgcata | 300 |
| aacccgaagg attggatctg attagccgtt attcttgaga tcttttgtta agtttccc | 360 |
| ttctgtaggg ctaagaccac gtgcagtttc attatatatt ttgcatctgt agaatcgtga | 420 |
| ataaatatga tgtagtgatg ttgtagctgt ttggatctat ctgctggttt ttccc | 475 |

<210> SEQ ID NO 485
<211> LENGTH: 329

<212> TYPE: DNA
<213> ORGANISM: Zea mays
<220> FEATURE:
<223> OTHER INFORMATION: unsure at all n locations

<400> SEQUENCE: 485

```
atcaagaaat gcttctcaac tttgctacag aatgtgcgga ctctgtactt cctgcgtaca    60
taccgatcat agaacggagg aagaacactc cgttcaacga ggagcacagg gcatggcagc   120
aattgcggag aggtcgttat gtggagttca accttgtcta cgaccgtggt acaacatttg   180
gcctaaagac tggaggaagg attgagagca tacttgtgtc ncttccactt acagcacgat   240
ggcagtatga tcatanaccg aagaaggaa ccgacgaatg ganacttctg gaagcctgca    300
tagacccgaa ggattggatc tgattagcg                                     329
```

<210> SEQ ID NO 486
<211> LENGTH: 270
<212> TYPE: DNA
<213> ORGANISM: Zea mays

<400> SEQUENCE: 486

```
caagattcaa aatatggtgt gatgattatt tctatattaa gcaccgtaat gagcggcgtg    60
ggctaggtgg aatatttttt gatgaccta atgattacga tcaagaaatg cttctcaact   120
ttgctacaga atgtgcggac tctgtacttc ctgcgtacat accgatcata gaacggagga   180
agaacactcc gttcaacgag gagcacaggg catggcagca attgcggaga ggtcgttatg   240
tggagttcaa ccttgtctac gaccgtggta                                    270
```

<210> SEQ ID NO 487
<211> LENGTH: 256
<212> TYPE: DNA
<213> ORGANISM: Zea mays

<400> SEQUENCE: 487

```
cgcggcgtgg gctaggtgga atatttttg atgaccttaa tgattacgat caagaaatgc    60
ttctcaactt tgctacagaa tgtgcggact ctgtacttcc tgcgtacata ccgatcatag   120
aacggaggaa gaacactccg ttcaacgagg agcacagggc atggcagcaa ttgcggagag   180
gtcgttatgt ggagttcaac cttgtctacg accgtggtac aacatttggc ctaaagactg   240
gaggacggat tgacag                                                   256
```

<210> SEQ ID NO 488
<211> LENGTH: 247
<212> TYPE: DNA
<213> ORGANISM: Zea mays

<400> SEQUENCE: 488

```
cttaatgatt acgatcaaga aatgcttctc aactttgcta cagaatgtgc ggactctgta    60
cttcctgcgt acataccgat catagaacgg cggaagaaca ctccgttcaa tgaggagcac   120
agggcatggc agcaattgcg gagaggtcgt tatgtggagt tcaaccttgt ctacgaccgt   180
ggtaccacat ttggcctaaa gactggagga aggattgaga gcatacttgt gtcccttccg   240
cttacag                                                             247
```

<210> SEQ ID NO 489
<211> LENGTH: 236
<212> TYPE: DNA
<213> ORGANISM: Zea mays

```
<400> SEQUENCE: 489
cccacgcgtc cgctccgttc aatgaggagc acagggcatg gcagcaattg cggagaggtc    60
gttatgtgga gttcaacctt gtctacgacc gtggtaccac atttggccta aagactggag   120
gaaggattga gagcatactt gtgtcccttc cgcttacagc acgatggcag tatgatcata   180
aaccggaaga aggaaccgag gaatggaaac ttctggaagc ctgcataaac ccgaag       236

<210> SEQ ID NO 490
<211> LENGTH: 430
<212> TYPE: DNA
<213> ORGANISM: Zea mays

<400> SEQUENCE: 490
gggggaggcc gccaagaacg gggccgccgc cgcggatggc cacaagcctg ggccggtggc    60
attcttcgcc gcggggatta gttcggtgct tcaccccaag aacccatttg ctccaacatt   120
gcattttaac taccgttact ttgagacgga tgcaccaaaa gatgcacctg gtgcaccaag   180
acaatggtgg ttcggcggtg gtactgactt gactccttca tatatcattg aagaggatgt   240
gaagcatttc cattctgttc aaaagcaagc atgtgataaa tttgatccaa gttttcaccc   300
aagattcaaa aaatggtgtg atgattattt ctatattaag caccgtaatg agcggcgtgg   360
gctaggtgga atattttttg atgaccttaa tgattacgat caagaaatgc ttctcaactt   420
tgctacagaa                                                         430

<210> SEQ ID NO 491
<211> LENGTH: 304
<212> TYPE: DNA
<213> ORGANISM: Zea mays

<400> SEQUENCE: 491
gggccgccgc cgcggatggc cacaagcctg gccccgtgcc attcttcgcc gcggggatta    60
gttcggtgct tcaccccaag aacccatttg ctccaacatt gcattttaac taccgttact   120
ttgagacgga tgcaccaaaa gatgcacctg gtgcaccaag acaatggtgg ttcggcggtg   180
gtactgactt gactccttca tacatcattg aagaggacgt gaagcatttc cattctgttc   240
aaaagcaagc atgtgataaa tttgatccaa gttttcaccc aagattcaaa aaatggtgtg   300
atga                                                               304

<210> SEQ ID NO 492
<211> LENGTH: 307
<212> TYPE: DNA
<213> ORGANISM: Zea mays

<400> SEQUENCE: 492
ggaggccgcc aagaacgggg ccgccgccgc ggatggccac aagcctggcc ccgtgccatt    60
cttcgccgcg gggattagtt cggtgcttca ccccaagaac ccatttgctc caacattgca   120
ttttaactac cgttactttg agacggatgc accaaaagat gcacctggtg caccaagaca   180
atggtggttc ggcggtggta ctgacttgac tccttcatac atcattgaag aggacgtgaa   240
gcatttccat tctgttcaaa agcaagcatg tgataaattt gatccaagtt ttcacccaag   300
attcaaa                                                            307

<210> SEQ ID NO 493
<211> LENGTH: 173
<212> TYPE: DNA
<213> ORGANISM: Zea mays
```

<400> SEQUENCE: 493

| | | |
|---|---|---|
| gcacgagaaa agatgcacct ggtgcaccaa gacaatggtg gttcggcggt ggtactgact | 60 |
| tgactccttc atacatcatt gaagaggacg tgaagcattt ccattctgtt caaaagcaag | 120 |
| catgtgataa atttgatcca agttttcacc caagattcaa aaaatggtgt gat | 173 |

<210> SEQ ID NO 494
<211> LENGTH: 118
<212> TYPE: DNA
<213> ORGANISM: Zea mays

<400> SEQUENCE: 494

| | | |
|---|---|---|
| gttactttga gacggatgca ccaaaagatg cacctggtgc accaagacaa tggtggttcg | 60 |
| gcggaggtac tgacttgact ccttcataca tcattgaaga ggacgtgaag catatcca | 118 |

<210> SEQ ID NO 495
<211> LENGTH: 304
<212> TYPE: DNA
<213> ORGANISM: Zea mays

<400> SEQUENCE: 495

| | | |
|---|---|---|
| agaagccgca aaaactgccc tggaccgagg tggctacgat gggctgttcc taggagggaa | 60 |
| ctatgttgca ggagttgacc tgggcagatg cgttgagggc gcgtatgaaa gtgcctcgca | 120 |
| aatatctgac ttcttgacca agtatgccta caagtgatga agaagtgga gcgctacttg | 180 |
| ttaattgttt atgttgcata gatgaggtgc ctacggggaa aaaaagcttt aatagtattt | 240 |
| tttattctta ttttgtaaat tgcatttctg ttctttttc tgtcattaat tacttatatt | 300 |
| ttag | 304 |

<210> SEQ ID NO 496
<211> LENGTH: 295
<212> TYPE: DNA
<213> ORGANISM: Zea mays

<400> SEQUENCE: 496

| | | |
|---|---|---|
| gagggaacta tgttgcagga gttgccctgg gcagatgcgt tgagggcgcg tatgaaagtg | 60 |
| cctcgcaaat atctgacttc ttgaccaagt atgcctacaa gtgatgaaag aagtggagcg | 120 |
| ctacttgtta atcgtttatg ttgcatagat gaggtgcctc cggggaaaaa aagcttgaat | 180 |
| agtatttttt attcttattt tgtaaattgc atttctgttc tttttctat cagtaattag | 240 |
| ttatatttta gttctgtagg agattgttct gttcactgcc cttcaaaaga atttt | 295 |

<210> SEQ ID NO 497
<211> LENGTH: 305
<212> TYPE: DNA
<213> ORGANISM: Zea mays

<400> SEQUENCE: 497

| | | |
|---|---|---|
| cgttcttcga tctcatgagc atcccaggga agctcagggc cggtctaggc gcgcttggca | 60 |
| tccgcccgcc tcctccaggc cgcgaagagt cagtggagga gttcgtgcgc cgaacttcgt | 120 |
| gctgaggtct tcgagcgcct cattgagcct ttctgctcag gtgtctatgc tggtgatcct | 180 |
| tctaagctca gcatgaaggc tgcatttggg aaggtttggc ggttggaaga aactggaggt | 240 |
| agtattattg gtggaaccat caagacaatt caggagagga gcaagaatcc aaaaccactg | 300 |
| aggga | 305 |

<210> SEQ ID NO 498
<211> LENGTH: 270
<212> TYPE: DNA
<213> ORGANISM: Zea mays

<400> SEQUENCE: 498

```
ggacctggcc gcccgcctcc tccaggccgc gaagagtcag tggaggagtt cgtgcgccgc    60
aatcttggtg ctgaggtctt cgagcgcctc attgagcctt tctgctcagg tgtctatgct   120
ggtgatcctt ctaagctcag catgaaggct gcatttggga aggtttggcg gttggaagaa   180
actggaggta gtattattgg tggaacatca agacaattca ggagaggagc aagaatccaa   240
aaccactgag ggatgcccgc cttccgaagc                                    270
```

<210> SEQ ID NO 499
<211> LENGTH: 423
<212> TYPE: DNA
<213> ORGANISM: Zea mays

<400> SEQUENCE: 499

```
atccaaagga agcaattaga aaagaatgct taattgatgg ggagctccag ggcgttgggc    60
agttgcatcc acgtagtcaa ggagttgaga cattaggaac aatatacagt tcctcactct   120
ttccaaatcg tgctcctgac ggtagggtgt tacttctaaa ctacatagga ggtgctacaa   180
acacaggaat tgtttccaag actgaaagtg agctggtcga agcagttgac cgtgacctcc   240
gaaaaatgct tataaattct acagcagtgg acccttagt ccttggtgtt cgagtttggc    300
cacaagccat acctcagttc ctggtaggac atcttgatct tctggaagcc gcaaaagctg   360
ccctggaccg aggtggctac gatgggctgt tcctaggagg gaactatgtt gcaggagttg   420
ccc                                                                423
```

<210> SEQ ID NO 500
<211> LENGTH: 314
<212> TYPE: DNA
<213> ORGANISM: Zea mays

<400> SEQUENCE: 500

```
cacgcccctg ccggccatcg gggtgccgtt cgatatctcg gactccaagg ggcccgtgat    60
ccaatcgcca gtacggtcca aagagcaggt gagggagctc gtccccatcg accttgatat   120
gctccagttc gtcggggagt cactaaagat tctgcgaaat gagattgatg gaaaagctgc   180
tttgctagga tttgtggggg ccccatggac aattgcaact tacattgttg aaggggggat   240
gaccaatacg tacacaaata taagagcat gtgccataca gctccagatg tcttgaaggg    300
tcttctctct cact                                                    314
```

<210> SEQ ID NO 501
<211> LENGTH: 287
<212> TYPE: DNA
<213> ORGANISM: Zea mays

<400> SEQUENCE: 501

```
gaaggaggtt catcaaagaa ctttacattg attaagaaaa tggccttctc agaaccagcg    60
attctacaca atttgctaca gaagttcaca acatcaatgg ctaactatat taaataccaa   120
gcggacaatg gggcgcaggc tgtccaaatt ttcgattcat gggctactga actcagcccg   180
actgattttg aggagtttag cctgccttat ctaaagcaga tagtggatag tgttagggaa   240
acacatccta acttgcctct gatactctac gcaagtggat ctgggggg               287
```

<210> SEQ ID NO 502
<211> LENGTH: 272
<212> TYPE: DNA
<213> ORGANISM: Zea mays

<400> SEQUENCE: 502

```
gtccagtgta tacagatatt tgattcatgg ggtggacagc ttccacctca tgtatgggag      60
cagtggtcaa aaccatatat caaacaggag ttgatgttat tgggcttgac tggacagtgg     120
acactactga tggaaggtgg cgccttggta atggcattag tgtacaaggg aatgtggatc     180
cagcattttt gttctcacca ttaccagtac tgactgatga aattcataga gttgtgaaag     240
cagctggtcc aaaaggtcat accttaatct gg                                   272
```

<210> SEQ ID NO 503
<211> LENGTH: 407
<212> TYPE: DNA
<213> ORGANISM: Zea mays

<400> SEQUENCE: 503

```
agggcagagg gcaggaaaag attgggatct aacacagcag tccaagggaa cgtggatcct      60
ggtgttcttt ttggatccaa agagtttata agcaggcgga tttacgacac tgtgcagaag     120
gctggcaatg ttgacatgt actgaacctt ggccatggca tcaaggttgg aactccggag      180
gaaaatgttg ctcacttctt cgaggtcgca aagggatca gatactaaag aaccttgcat      240
ggttctttcc tttctccaaa tcggcagaag ttgtagagtc ggcggtcgag gatagatgca     300
gaaagccatg tgcagtatag agtccctgaa acattttttg tgactgattc tgtctgtcgc     360
aattcaagtt ccggtttcaa tgtgatattg taagcagatt tgagacg                   407
```

<210> SEQ ID NO 504
<211> LENGTH: 418
<212> TYPE: DNA
<213> ORGANISM: Zea mays

<400> SEQUENCE: 504

```
agcaagtgaa ggccaggttg cgggaggcag gcctggcacc agtgcccatg atcatctttg      60
ctaaggatgg gcattttgcc ctggaggagc tggcccaagc tggctatgag gtggttgggc     120
ttgactggac agtggcccca agaaagccc gggagtgtgt ggggaagacg gtgacattgc      180
agggcaacct ggacccctgt gccttgtatg catctgagga ggagatcggg cagttggtga     240
agcagatgct ggatgacttt ggaccacatc gctacattgc caacctgggc catgggcttt     300
atcctgacat ggacccagaa catgtgggcg cctttgtgga tgctgtgcat aaacactcac     360
gtctgcttcg acagaactga gtgtataacct ttaccctcaa gtaccactaa cacagatg     418
```

<210> SEQ ID NO 505
<211> LENGTH: 508
<212> TYPE: DNA
<213> ORGANISM: Zea mays
<220> FEATURE:
<223> OTHER INFORMATION: unsure at all n locations

<400> SEQUENCE: 505

```
cgagctggct gccattagag ccttcgcaac agaaataant agctaccgtc agccaccggt      60
tccggtaatt cgccggggga ggacccaccg cgtgccgcga gcggctgcaa ccacctactc     120
attgcgtttt caatggcaac aacgtgtacg tcggtctcgg tgccgtgcac cttcctcttg     180
```

-continued

```
cgcggcaggt ccgcccgcac catgcccaga cgcaagcagc tcacggccgt ccgctgcagc    240
gccgtcagac aggccgtagt ggaagaggcc tcgcccggga ccgcggacga tccgctgctg    300
gtgagcgcaa tcagagggac gaaggtcgag aagccacccg tatggctcat gaggcacgcc    360
gggaggtaca tgaagagcta ccaattgctc tgcgagcggc atccttcgtt ccgtgaaaga    420
tcagaaaatg tcgacctagt tgttgagatc tctttgcaac catggaaggt tttcaagcct    480
gaaggaatca tcttggtctc ggacattc                                       508

<210> SEQ ID NO 506
<211> LENGTH: 387
<212> TYPE: DNA
<213> ORGANISM: Zea mays

<400> SEQUENCE: 506
cccacgcgtc cgcccactcg tccgaaattt tcgattcatg ggctactgag ctcagcccgg     60
ctgattttga ggagtttagc ctgccttatc taaagcagat agtggatagt gttagggaaa    120
cacatcctaa cttgcctctg atactctacg caagtggatc tgggggcttg ctggagaggc    180 ttccttttgac aggtgttgat gttgtcagct tggactggac ggtcgatatg cagagggca    240 ggaaaagatt gggatctaac acagcagtcc aagggaacgt ggatcctggt gttctttttg    300
gatccaaaga gtttataagc aggcggattt acgacactgt gcagaaggct ggcaatgttg    360
gacatgtact gaaccttggc catggca                                        387

<210> SEQ ID NO 507
<211> LENGTH: 288
<212> TYPE: DNA
<213> ORGANISM: Zea mays

<400> SEQUENCE: 507
gccgctgctg gtgagcgcaa tcagaaggag gaaggtcgag aagccacccg tctggctcat     60
gaggcaggcc gggaggtaca tgaagagcta ccaattgctc tgcgagcggt atccttgttc    120
cgtgaaagat cagaaaatgt cgacctagtt gttgagatct ctttgcaacc atggaaggtt    180
ttcaagcctg atggagtcat cttgttctcg gacatcctta ctccacttcc tgggatgaac    240
ataccttttg acattgtgaa gggaaaaggt ccagtgatct atgatcca                 288

<210> SEQ ID NO 508
<211> LENGTH: 409
<212> TYPE: DNA
<213> ORGANISM: Zea mays

<400> SEQUENCE: 508
gtccgcgagc gctgcagcac ctcggatccc gccccaatgg caacagcgtg tccgccgctc     60
tcgctgccgt ccacctccct cttccgcggc aggtccgccc gcgccgggcc cagacgcagg    120
cagctcacgg ccgtccgctg cagcgccgtc ggagaggcg tagtggagga ggcctcgccc    180
gggacggcgg aagagccgct gctggtgagc gcaatcagag ggaggaaggt cgagaggcca    240
cccgtctggc tcatgaggca ggccgggagg tacatgaaga gctaccaatt gctctgcgag    300
cggtatcctt cgttccgtga aagatcagaa aatgtcgacc tagttgttga gatctctttg    360
caaccatgga aggttttcaa gcctgatgga gtcatcttgt tctcggaca                409

<210> SEQ ID NO 509
<211> LENGTH: 407
<212> TYPE: DNA
<213> ORGANISM: Zea mays
```

```
<400> SEQUENCE: 509
agccaagtcg tcgcctcccc gacccaacgt tttgaccccc ttgcccgtcc gcgagcgctg      60
cagcacctgg gatcccgccc caatggcaac agcgtgtccg ccgctctcgc tgccgtccac    120
ctccctcttc cgcggcaggt ccgcccgcgc cgggcccaga cgcaggcagc tcacggccgt    180
ccgctgcagc gccgtcggag aggcggtagt ggaggaggcc tcgcccggga cggcggaaga    240
gccgctgctg gtgagcgcaa tcagagggag gaaggtcgag aggccacccg tctggctcat    300
gaggcaagcc gggaggtaca tgaagagcta ccaattgctc tgcgagcggt atccttcgtt    360
ccgtgaaaga tcagaaaatg tcgacctagt tgttgagatc tctttgc                  407

<210> SEQ ID NO 510
<211> LENGTH: 275
<212> TYPE: DNA
<213> ORGANISM: Zea mays

<400> SEQUENCE: 510
taaagattct gcgaaatgag attgatggaa aagctgcttt gctaggattt gtgggggccc      60
catggacaat tgcaacttac attgttaaag gggggatgac caacacatac acaaatataa    120
agaacatgtg ccatacagct cccgatgtct taggtgtctt ctatctcatc ttgcagtagc    180
gatatctgac tatatcattt accaagttaa ctccggggcc cagtgtatac agatatttga    240
ttcatggggc ggacaacttc cacctcatgt gtggg                                275

<210> SEQ ID NO 511
<211> LENGTH: 266
<212> TYPE: DNA
<213> ORGANISM: Zea mays
<220> FEATURE:
<223> OTHER INFORMATION: unsure at all n locations

<400> SEQUENCE: 511
tgccaagagc cgggccaagg ctgcgctcca cggccgtccg ggtcagcagc gagcaggagg      60
cggcggcggc cgtcnaggcg ccgtccggga ggaccatcga ggagtgcgag gccgacgccg    120
tcgctgggaa gttccctgct cccccgccgc tggttaggcc gaagcgcctg aaggaacgcc    180
ggagatcagg cccccttgaca tggcaaagcg ccccccgtcgc aaccgcaaat cacctgctct    240
tagggctgca ttccaggaga cgagca                                          266

<210> SEQ ID NO 512
<211> LENGTH: 293
<212> TYPE: DNA
<213> ORGANISM: Zea mays

<400> SEQUENCE: 512
gccgtacttg gacattatcc gactgcttcg ggatcattca gccctaccga ttgctgctta      60
ccaggtctcg ggcgagtact cgatgatcaa agccggcggg gccctgggca tggtggacga    120
gcagaaggtg atgatggagt cgctcatgtg cctgcgcgag ccggcgccga cgtcatcctg    180
acctacttcg cccgtcacgc cgccgcggtg ctgtgcggca tggggcccaa gtaggaggcg    240
aggcccgccc gccattcctg ccctgcactg tcattgtgga gttgagcgat gag           293

<210> SEQ ID NO 513
<211> LENGTH: 279
<212> TYPE: DNA
<213> ORGANISM: Zea mays
```

```
<400> SEQUENCE: 513
actagattca catccaagat ttggagataa gaagacgtac cagatgaacc cagctaacta      60
cagagaagcc ctcatagaaa ccgcatcgga cgaggcagaa ggagccgaca ttctgctagt     120
gaaaccggga ttgccgtact tggacattat ccgactgctt cgggatcatt cagccctacc     180
gagtgctgct taccaggtct cgggcgagta ctcgatgatc agagccggag gggccctggg     240
catggtggac gagcataagg tgatgatgga gtcgctcat                            279

<210> SEQ ID NO 514
<211> LENGTH: 287
<212> TYPE: DNA
<213> ORGANISM: Zea mays

<400> SEQUENCE: 514
cggacgcgtg gggttcattt tatggcccct ccgagaagct ttagattcaa atccaagatt      60
tggagataag acgacgtacc agatgaaccc agccaactac agagaagccc tcatagaaac     120
cgcagcggac gaggcagaag gagccgacat tctgctagtg aaaccgggat tgccgtactt     180
ggacatcatc cgactgcttc gggatcattc agccctaccg attgctgctt accaggtctc     240
gggcgagtac tcgatgatca aagccggcgg ggccctgggc atggtgg                   287

<210> SEQ ID NO 515
<211> LENGTH: 427
<212> TYPE: DNA
<213> ORGANISM: Zea mays

<400> SEQUENCE: 515
ctttgtgctc ccattgttta tccatgaagg agaagaagat gctcctatcg gagctatggc      60
agggtgctat aggcttgggt ggaggcacgg gctgcttgac gaggtttaca aggcccgcga     120
tgttggtgtt aatagtttcg ttctctttcc taaagttccc gatgcattga agtctccaac     180
aggagatgaa gcgtacaacg ataatggtct ggttccacgt acaatccgct tgctcaagga     240
caagttccct gatattgtta ctacacaga cgtcgcgtta gacccttatt catctgatgg      300
tcatgatggt attgtgaggg aagatggtgt aattatgaat gatgaaacag tttatcagtt     360
gtgcaaacag gctgtttcac aggctcgtgc cggtgctgat gttgtcagcc ctagtgacat     420
gatggat                                                              427

<210> SEQ ID NO 516
<211> LENGTH: 303
<212> TYPE: DNA
<213> ORGANISM: Zea mays

<400> SEQUENCE: 516
cccacgcgtc cgcaaggccc gcgatgttgg tgttaatagt ttcgttctct ttcctaaagt      60
tcccgatgca ttgaagtctc caacaggaga tgaagcgtac aacgataatg gtctggttcc     120
acgtacaatc cgcttgctca aggacaagtt ccctgatatt gttatctaca cagacgtcgc     180
gttagaccct tattcatctg atggtcatga tggtattgtc agggaagatg gtgtaattat     240
gaatgatgaa acagtttatc agttgtgcaa acaggctgtt tcacaggctc gtgccggtgc     300
tga                                                                  303

<210> SEQ ID NO 517
<211> LENGTH: 277
<212> TYPE: DNA
<213> ORGANISM: Zea mays
```

<400> SEQUENCE: 517

```
cttattcatc tgatggtcat gatggtattg tgagggaaga tggtgtaatt atgaatgatg     60
aaacagttta tcagttgtgc aaacaggctg tttcacaggc tcgtgccggt gctgatgttg    120
tcagccctag tgacatgatg gatggccgga ttggagcact tcgctctgct ctggacgccg    180
agggcttcca tgtgtctcc attatgtcct acaccgcaaa gtatgccagt tcattttatg     240
gccctttccg agaagcttta gattcaaatc caagatt                             277
```

<210> SEQ ID NO 518
<211> LENGTH: 300
<212> TYPE: DNA
<213> ORGANISM: Zea mays

<400> SEQUENCE: 518

```
cccacgcgtc cgcaaggccc gcgatgtagg tgttaatagt ttcgttctct ttcctaaagt     60
tcccgatgca ttgaagtctc caacaggaga tgaagcgtac aacgataatg gtctggttcc    120
acgtacaatc cgcttgctca aggacaagtt ccctgatatt gttatctaca cagacgtcgc    180
gttagaccct tattcatctg atggtcatga tggtattgtt agggaagatg gtgtaattat    240
gaatgatgaa acagtttatc agttgtgcaa acaggctgtt tcacaggctc gtgccggtgc    300
```

<210> SEQ ID NO 519
<211> LENGTH: 306
<212> TYPE: DNA
<213> ORGANISM: Zea mays

<400> SEQUENCE: 519

```
cccacgcgtc cgcccacgcg tccgcccacg cgtccgccca cgcgtccggg acaagttccc     60
tgatattgtt atctacacag acgtcgcgtt agacccttat tcatctgatg gtcatgatgg    120
tattgtgagg gaagatggtg taattatgaa tgatgaaaca gtttatcagt tgtgcaaaca    180
ggctgtttca caggctcgtg ccggtgctga tgttgtcagc cctagtgaca tgatggatgg    240
ccggattgga gcacttcgct ctgctctgga cgccagggc ttccatgatg tctccattat    300
gtccta                                                              306
```

<210> SEQ ID NO 520
<211> LENGTH: 391
<212> TYPE: DNA
<213> ORGANISM: Zea mays

<400> SEQUENCE: 520

```
acgaacgcgt gggcggacgc gtgggcggac gcgtgggaga acgcgtgggc ggacgcgtgg     60
gtgaaggaga agaagatgct cctatcggag ctatgccagg gtgctatagg cttgggtgga    120
ggcacgggct gcttgacgag gtttacaggg gcgcgcgatg ttggtgttaa tagttttgtt    180
ctctttccta aagttcccga tgcattgaag tctccaacag gagatgaagc gtacaacgat    240
aatggtctgg ttccacgtac aatccgcttg ctcaaggaca agttccctga tattgttatc    300
tacacagacg tctcttttt ttcttagtca tctgatggtc actatggtat tgttacggaa    360
gatggggtaa ttatgaatga tgaaacactt t                                  391
```

<210> SEQ ID NO 521
<211> LENGTH: 191
<212> TYPE: DNA
<213> ORGANISM: Zea mays

```
<400> SEQUENCE: 521
agatgctcct atcggagcta tgccagggtg ctataggctt gggtggaggc acgggctgct    60
tgacgaggtt tacaaggccc gcgatgttgg tgttaatagt ttcgttctct ttcctaaagt   120
tcccgatgca ttgaagtctc caacaggaga tgaagcgtac aacgataatg gtctggttcc   180
acgtacaatt c                                                        191

<210> SEQ ID NO 522
<211> LENGTH: 128
<212> TYPE: DNA
<213> ORGANISM: Zea mays

<400> SEQUENCE: 522
gttagaccct tattcatctg atggtcatga tggtattgtg agggaagatg gtgtaattat    60
gaatgatgaa acagtttatc agttgtgcaa acaggctgtt tcacaggctc gtgccggtgc   120
tgatgttg                                                            128

<210> SEQ ID NO 523
<211> LENGTH: 301
<212> TYPE: DNA
<213> ORGANISM: Zea mays

<400> SEQUENCE: 523
gcagcttctc cgtgctgctg cgtctcctcc tcatcgtcct ctccagtgtc cagctcggcc    60
atggcgttca ccgtctccct tctccccgcc aacgttcaga tgctccaggc taggagtggc   120
cacggccacg ccacctttgg aagctgttcc gccgtgccaa gagccgggcc aaggctgcgc   180
tccacggccg tccgggtcag cagcgagcag gaggcggcgg cggccgtcag ggcgccgtcc   240
gggaggacca tcgaggagtg cgaggccgac gccgtcgctg gaagttccc tgctcccccg    300 c                                                                   301

<210> SEQ ID NO 524
<211> LENGTH: 323
<212> TYPE: DNA
<213> ORGANISM: Zea mays

<400> SEQUENCE: 524
caggattagc agcttctccg tgctgctgcg tctcctcctc atcgtcctct ccagtgtcca    60
gctcggccat ggcgttcacc gtctccttct ccccgccaa cgttcagatg ctccaggcta   120
ggagtggcca cggccacgcc acctttggaa gctgttccgc cgtgccaaga gccgggccaa   180
ggctgcgctc cacggccgtc cgggtcagca gcgagcagga ggcggcgcg gccgtcaggg   240 cgccgtccgg gaggaccatc gaggagtgcg aggccgacgc cgtcgctggg aagttccctg   300
ctcccccgcc gctggttagg ccg                                           323

<210> SEQ ID NO 525
<211> LENGTH: 252
<212> TYPE: DNA
<213> ORGANISM: Zea mays

<400> SEQUENCE: 525
cagattagca gcttctccgt gctgctgcgt ctcctcctca tcgtcctctc cagtgtccag    60
ctcggccatg gcgttcaccg tctccttctc cccgccaac gttcagatgc tccaggctag   120
gagtggccac ggccacgcca cctttggaag ctgttccgcc gtgccaagag ccgggccaag   180
gctgcgctcc acggccgtcc gggtcagcag cgagcaggag gcggcggcgg ccgatcaggc   240
```

```
gccgtccggg ag                                                          252

<210> SEQ ID NO 526
<211> LENGTH: 304
<212> TYPE: DNA
<213> ORGANISM: Zea mays
<220> FEATURE:
<223> OTHER INFORMATION: unsure at all n locations

<400> SEQUENCE: 526
cacaggatta gcagcttctc cgtgctgctg cgtctcctcc tcatcgtcct ctccagtgtc       60
cagctcggcc atggcgttca ccgtctcctt ctcccccgcc aacgttcaga tgctccaggc      120
taggagntgg cacggccacg ccacctttgg aagctgttcc gccgtgccaa gagccgggcc      180
aaggctgcgc tccacggccg tccgggtcag cagcgagcag gaggcggcgg cggccgtcag      240
ggcgccgtcc gggaggacca tcgaggagtg cgaggccgac ccgtcgctg ggaagttccc       300 tgct                                                                  304

<210> SEQ ID NO 527
<211> LENGTH: 295
<212> TYPE: DNA
<213> ORGANISM: Zea mays
<220> FEATURE:
<223> OTHER INFORMATION: unsure at all n locations

<400> SEQUENCE: 527
cacaggatta gcagcttctc cgtgctgctg cgtctcctcc tcatcgtcct ctccagtgtc       60
aagctcggcc atggcgttca ccgtctcctt ctcccccgcc aacgttcaga tgctccaggc      120
taggagtggc cacggccacg ccacctttgg aagctgttcc gccgtgccaa gagccgggcc      180
aaggctgcgc tccacggccg tccgggtcag cagcgagcag gaggcggcgg cggccgtcag      240
gcgccgtccg ggaggaccat cgaggantcg aagccgacgc cgtgctggga nnttc          295

<210> SEQ ID NO 528
<211> LENGTH: 239
<212> TYPE: DNA
<213> ORGANISM: Zea mays

<400> SEQUENCE: 528
ccacgcgtcc gcagattagc agcttctccg tgctgctgcg tctcctcctc atcgtcctct       60
ccagtgtcca gctcggccat ggcgttcacc gtctccttct cccccgccaa cgttcagatg      120
ctccaggcta ggagtggcca cggccacgcc acctttggaa gctgttccgc cgtgccaaga      180
gccgggccaa ggctgcgctc cacggccgtc cgggtcagca gcgagcagga ggcggcggc      239

<210> SEQ ID NO 529
<211> LENGTH: 302
<212> TYPE: DNA
<213> ORGANISM: Zea mays

<400> SEQUENCE: 529
acaggattag cagcttctcc gtgctgctgc gtctcctcct catcgtcctc tccagtgtcc       60
agctcggcca tggcgttcac cgtctccttc tcccccgcca acgttcagat gctccaggct      120
aggagtggcc acgccacgc cacctttgga agctgttccg ccgtgccaag agccgggcca      180
aggctgcgct ccacggccgt ccgggtcagc agcgagcagg aggcggcggc ggccgtcaag      240
gcgccgtccg ggaggaccat cgaggagtgc gaggccgacg ccgtcgctgg gaagttccct      300
```

```
gc                                                                      302

<210> SEQ ID NO 530
<211> LENGTH: 242
<212> TYPE: DNA
<213> ORGANISM: Zea mays

<400> SEQUENCE: 530
gccacgggtc cgcagtatta gcagcttctc cgtgctgctg cgtctcctcc tcatcgtcct        60
ctccagtgtc cagctcggcc atggcgttca ccgtctcctt ctccccagcc aacgttcaga       120
tgctccaggc taggagtggc cacggccacg ccacctttgg aagctgttcc gccgtgccaa       180
gagccgggcc aaggctgcgc tcaacggccg tccgggtcag cagcgagcag gaggcggcgg       240
cg                                                                     242

<210> SEQ ID NO 531
<211> LENGTH: 255
<212> TYPE: DNA
<213> ORGANISM: Zea mays

<400> SEQUENCE: 531
cccacgcgtc cgaccacgcg tccgcggacg ctggccccgg cgatgatgga cctctccagt        60
gtccagctcg gccatggcgt tcaccgtctc cttctccccc gccaacgttc agatgctcca       120
ggctaggagt ggccacggcc acgccacctt tggaagctgt tccgccgtgc caagagccgg       180
gccaaggctg cgctccacgg ccgtccgggt cagcagcaag caaaaggcgg cgacggacgt       240
caggcggcgt cccgg                                                       255

<210> SEQ ID NO 532
<211> LENGTH: 280
<212> TYPE: DNA
<213> ORGANISM: Zea mays

<400> SEQUENCE: 532
ctcttttgac gacatggttg agatgggcaa agatgctggc catgagctga aggcaaaggc        60
tgggcctggc ttctttgata gcttgcaatg aaaagaatga gcgaccatga gcaatttcaa       120
ttgtcactct tttggttaga aacagagggc ccaagtagag tgtggagagg tttgttttg       180 tttcttcttt ctcctgctaa ttctgctaga gaagggtgta cctggtgtag tggtgagccg       240
agtcatcagg tcgcgggttc gaagcatcca gtctccgtat                            280

<210> SEQ ID NO 533
<211> LENGTH: 325
<212> TYPE: DNA
<213> ORGANISM: Zea mays

<400> SEQUENCE: 533
aaacacgcgt ccgcggacgc tggggacacg gttaaggaaa ctcaaggaag gagatgtgtc        60
tgctacattg taggcgcagg ctgagattaa ggcggctaaa tatggcagaa aatgcaacag       120
ctgtactatc agtggaagaa atgcttccgg cagttgccca aggtgctatt ggaatcgctt       180
gccgaagcaa cgatgacaaa atgatggagt atctgtcctc gttgaaccac gaggatacca       240
gactagctgt cacatgcgaa agagaattct tggcagttct tgatggcaac tgccgaactc       300
caattgcggc ctatgcttac cgtga                                            325

<210> SEQ ID NO 534
<211> LENGTH: 282
```

```
<212> TYPE: DNA
<213> ORGANISM: Zea mays

<400> SEQUENCE: 534
tgcattcata tgcttgactg caaattctct cgcggagctt cctgctggca gtgttggtgg      60
aagtgcttcc ttgcctagac aatctcacat tctctacaga tatccatcac tgaaagtagt     120
taacttcaga ggaaatgttc agacacggtt aaggaaactc actgaaggag atgtgtctgc     180
tacattgttg gcgctggctg gattaaggca gctaaatatt gcagaaaatg caacagctgt     240
actatcagtg gaagaaatgc ttccggcagt tgcccaagtg ct                        282

<210> SEQ ID NO 535
<211> LENGTH: 282
<212> TYPE: DNA
<213> ORGANISM: Zea mays

<400> SEQUENCE: 535
caggactgct cattccgggg cctactggct tcaccagacg gatctaaagt atttgagacg      60
gcaagaagtg gaccgtactc tttcgacgac atggtcgaga tgggcaaaga cgctggccac     120
gaactgaagg cgaaggctgg gcctggcttc ttcgatagcc ttcaatgaac agaatgtgcg     180
gccatgcgcg atttcagttg cacccctttc ggttgaaaac gagggccata gtaggttgtt     240
gaggggtttg ttttttgtttc ttcttttttt ctcctactac ta                       282

<210> SEQ ID NO 536
<211> LENGTH: 174
<212> TYPE: DNA
<213> ORGANISM: Zea mays

<400> SEQUENCE: 536
cgggaactgc tcattccggg gcctactgtc ttcaccagac ggatctaaag tatttgagac      60
ggcaagaagt ggaccgtact ctttcgacga catggtcgag atgggcaaag acgctggcca     120
cgagctgaag gcgaaggctg ggcctggctt cttcgatagc cttcaatgaa caga           174

<210> SEQ ID NO 537
<211> LENGTH: 315
<212> TYPE: DNA
<213> ORGANISM: Zea mays

<400> SEQUENCE: 537
cgggaactgc tcattccggg gcctactgtc ttcaccagac ggatctaaag tatttgagac      60
ggcaagaagt ggaccgtact ctttcgacga catggtcgag atgggcaaag acgctggcca     120
cgagctgaag gcgaaggctg ggcctggctt cttcgatagc cttcaatgaa cagaatgtgc     180
ggccatgcgc gatttcagtt ggcacccttt cggttgaaaa cgagggccaa gtaggttgt      240 tcagggctt gtttgtgata cttctgagtt tctcctacta ctaggtcctg ctagagcctt      300
gtactaccac tcatg                                                      315

<210> SEQ ID NO 538
<211> LENGTH: 338
<212> TYPE: DNA
<213> ORGANISM: Zea mays

<400> SEQUENCE: 538
ctctatgaaa gatgttccaa catatctacc tgaaggcaca atattgccct gtgagctccg      60
acgagaagat gtaagagatg cattcatatg cttgactgca aattcgctcg cggagcttcc     120
```

```
tgctggcagt gttgttggaa gtgcttcctt gcggagacaa tctcagattc tctacagata    180
tccatcactg aaagtagtta acttcagagg aaatgttcag acacggttaa agaaactcaa    240
ggaaagagat gtgtctgcta cattgttggc gctggctgga ttaaagcggc taaaaatggc    300
agaaaatgca acagctgtac tatcagtgga agaaatgc                            338

<210> SEQ ID NO 539
<211> LENGTH: 422
<212> TYPE: DNA
<213> ORGANISM: Zea mays

<400> SEQUENCE: 539
ccaaggtctc actcatccgg attgggacgc gtgggagtcc tctggctctt gcacaagccg     60
atgaaactcg ggaaaaactg aaagccgcac actctgagtt agctgaggag ggggctattg    120
agatcgtcat cataaagacc acaggagaca tgatcttgga caaacccctt gcagatattg    180
gaggcaaggg tttattcacc aaggagatag atgatgcact cttgcaggga aggattgata    240
tagctgtgca ctctatgaaa gatgttccaa catatctacc tgaaggcaca atattgccct    300
gtaacctccc acgagaagat gtaagagatg cattcatatg cttgactgca aattcgctcg    360
cggagcttcc tgctggcagt gttgttggaa gtgcttcctt gcggagacaa tctcagattc    420
tc                                                                   422

<210> SEQ ID NO 540
<211> LENGTH: 280
<212> TYPE: DNA
<213> ORGANISM: Zea mays

<400> SEQUENCE: 540
ctctggctct tgcacaagcc catgaaactc gggaaaaact gaaagccgca cactctgagt     60
tagctgagga gggggctatt gagatcgtca tcataaagac cacaggagac atgatcttgg    120
acaaacccct tgcagatatt ggaggcaagg gtttattcac caaggagata gatgatgcac    180
tcttgcaggg aaggattgat atagctgtgc actctatgaa agatgttcca acatatctac    240
ctgaaggcac aatattgccc tgtaacctcc cacgagaaga                          280

<210> SEQ ID NO 541
<211> LENGTH: 255
<212> TYPE: DNA
<213> ORGANISM: Zea mays
<220> FEATURE:
<223> OTHER INFORMATION: unsure at all n locations

<400> SEQUENCE: 541
gggtttattc accaaggaga tagatgatgc actcttgcag ggaaggattg atatagctgt     60
gcactctatg aaagatgttc caacatatct acctgaaggc acaatattgc cctgtaacct    120
cccacgagaa gatgtaagag atgcattcat atgcttgact gcaaattcgc tcgcggantt    180
cctgctggca gtgttgttgg aagtgcttcc ttgcggagac aatctcagat tctctacaga    240
tatccatcac tgaaa                                                     255

<210> SEQ ID NO 542
<211> LENGTH: 269
<212> TYPE: DNA
<213> ORGANISM: Zea mays

<400> SEQUENCE: 542
gcactcttgc agggaaggaa tgatatagct gagcactcta tgaaagatgt tccaacataa     60
```

```
ctacctgaag gcacaatatt gccctgtaac ctcccacgag aagatgtaag agatgcattc    120
atatgcttga ctgcaaattc gctcgcggag cttcctgctg gcagtgttgt tggaagtgct    180
tccttgcgga gacaatctca gattctctac agatatccat cactgaaagt agttaacttc    240
agaggaaatg ttcagacacg gttaaggaa                                      269

<210> SEQ ID NO 543
<211> LENGTH: 334
<212> TYPE: DNA
<213> ORGANISM: Zea mays

<400> SEQUENCE: 543
agagccacgc gtccgcccac gcgtccgcct tgtcaaagcc ggcaatggtg ttgccaccct     60
tggcctccct gactcccctg gcttccccaa cggggccacg taccacactt tgacggcacc    120
ctacaatgat gtgcaccgca gtgatcaaac tgttcgaaga caaacccgtg agattgcgg    180 gcgtcctcct cgaaccagtt gttggcaacg ctcgtttcat ccctccagag acatggtttc    240
cttaacgctc tccgcgactt gaccaggcag gatggtgcgc tccagggcgt cgatgaactg    300
atgaccggct tccgtctgtc ttacggtgga cctc                                334

<210> SEQ ID NO 544
<211> LENGTH: 429
<212> TYPE: DNA
<213> ORGANISM: Zea mays
<220> FEATURE:
<223> OTHER INFORMATION: unsure at all n locations

<400> SEQUENCE: 544
cccacgcgtt cggcgggaac cctctagcca tgaccgctgg gatccacacg ctcaagcggc     60
tgacagagcc cggcacctac gagtacttgg acaagatcac cggcgaactc gtccgtggga    120
tactggacgt cggtgcgaaa gcagggcatg atatgtgcgg aggacatatc agaggaatgt    180
ttggcttctt cttcaccggc gggcccgtcc acaacttcgg ggacgccaag aagagcgaca    240
ccgagaagtt cgggaggttc taccgtggca tgctggagga gggcgtgtac ttcgctccat    300
cgcagttcga ggcggngttc accagcttgg cgcacacctt ccaggacatc gagaagaccg    360
tcgaggccgc tgagaaggtt ctgaagcgga tatagggggt ccgcttcaag caagcatgca    420
gagagcatt                                                            429

<210> SEQ ID NO 545
<211> LENGTH: 403
<212> TYPE: DNA
<213> ORGANISM: Zea mays
<220> FEATURE:
<223> OTHER INFORMATION: unsure at all n locations

<400> SEQUENCE: 545
aatgggatcc acacgctcaa gcggctgaca gagcccggca cctacgagta cttggacaag     60
atcaccggcg aactcgtccg tgggatactg gacgtcggtg cgaaagcagg gcatgagatg    120
tgcggaggac atatcagagg aatgtttggc ttcttcttca ccggcgggcc cgtccacaac    180
ttcggggacg ccaagaagag cgacaccgag aagttcggga ggttctaccg tggcatgctg    240
gaggagggcg tgtacttcgc tccctcgcag ttcgaggcgg ggttcaccag cttggcgcac    300
acctcccagg acatcgagaa gaccgtcgag gccgctgaga aggttctgaa gcggatatan    360
ggggtccgct tcaagcaagc atgcagagag catttcctcg tat                      403
```

<210> SEQ ID NO 546
<211> LENGTH: 312
<212> TYPE: DNA
<213> ORGANISM: Zea mays

<400> SEQUENCE: 546

| | | | | | |
|---|---|---|---|---|---|
| agaaactgtt | cgaggacaac | gcggggggaga | ttgctgccgt | cttcctcgag | ccagttgttg | 60 |
| gcaacgctgg | tttcatcccc | ccacagcctg | gtttccttaa | cgctctccgc | gacttgacca | 120 |
| aacaggatgg | tgcgctcctg | gtcttcgatg | aagtgatgac | cggcttccgt | ctgtcttacg | 180 |
| gtggagctca | ggagtacttc | gggatcaccc | ctgacgtgac | gaccttgggc | aagatcatcg | 240 |
| ggggtggcct | ccccgttggt | gcctacggtg | ggagaaggga | catcatggag | atggttgccc | 300 |
| ccgaaggccg | at | | | | | 312 |

<210> SEQ ID NO 547
<211> LENGTH: 286
<212> TYPE: DNA
<213> ORGANISM: Zea mays

<400> SEQUENCE: 547

| | | | | | |
|---|---|---|---|---|---|
| ggttgccccc | gcaggccgat | gtaccaggca | ggaactctca | gcgggaaccc | tctagccatg | 60 |
| accgctggga | tccacacgct | caagcggctg | acagagcccg | gcacctacga | gtacttggac | 120 |
| aagatcaccg | gcgaactcgt | ccgtgggata | ctggacgtcg | gtgcgaaagc | agggcatgag | 180 |
| atgtgcggag | gacatatcag | aggaatgttt | ggcttcttct | tcaccggcgg | gcccgtccac | 240 |
| aacttcgggg | acgccaagaa | gagcgacacc | gagaagttcg | ggaggt | | 286 |

<210> SEQ ID NO 548
<211> LENGTH: 285
<212> TYPE: DNA
<213> ORGANISM: Zea mays

<400> SEQUENCE: 548

| | | | | | |
|---|---|---|---|---|---|
| cctgacgtga | cgaccttggg | caagatcatc | gggggtggcc | tccccgttgg | tgcctacggt | 60 |
| gggagaaggg | acatcatgga | gatggttgcc | cccgcaggcc | gatgtaccag | gcaggaactc | 120 |
| tcagcgggaa | ccctctagcc | atgaccgctg | ggatccacac | gctcaagcgg | ctgacagagc | 180 |
| ccggcaccta | cgagtacttg | gacaagatca | ccggcgaact | cgtccgtggg | atactggacg | 240 |
| tcggtgcgaa | agcagggcat | gagatgtgcg | gaggacatat | cagag | | 285 |

<210> SEQ ID NO 549
<211> LENGTH: 243
<212> TYPE: DNA
<213> ORGANISM: Zea mays

<400> SEQUENCE: 549

| | | | | | |
|---|---|---|---|---|---|
| gaccggcttc | cgtctgtctt | acggtggagc | tcaggagtac | ttcgggatca | cccctgacgt | 60 |
| gacgaccttg | ggcaagatca | tcggggggtgg | cctccccgtt | ggtgcctacg | gtgggagaag | 120 |
| ggacatcatg | gagatggttg | ccccgcagc | cgatgtacca | ggcaggaact | ctcagcggga | 180 |
| accctctagc | catgaccgct | gggatccaca | cgctcaagcg | gctgacagag | cccggcacct | 240 |
| acg | | | | | | 243 |

<210> SEQ ID NO 550
<211> LENGTH: 247
<212> TYPE: DNA
<213> ORGANISM: Zea mays

<400> SEQUENCE: 550

```
gtttccttaa cgctctccgc gacttgacca aacaggatgg tgcgctcctg gtcttcgatg    60
aagtgatgac cggcttccgt ctgtcttacg gtggagctca ggagtacttc gggatcaccc   120
ctgacgtgac gaccttgggc aagatcatcg ggggtggcct ccccgttggt gcctacggtg   180
ggagaaggga catcatggag atggttgccc ccgcaggccg atgtaccagg caggaactct   240
cagcggg                                                            247
```

<210> SEQ ID NO 551
<211> LENGTH: 223
<212> TYPE: DNA
<213> ORGANISM: Zea mays

<400> SEQUENCE: 551

```
gcacgaggca gggccgatgt accaggcagg aactctcagc gggaaccctc tagccatgac    60
cgctgggatc cacacgctca gcggctgaca gagcccggc acctacgagt acttggacaa   120
gatcaccggc gaactcgtcc gtgggatact ggacgtcggt gcgaaacagg gcatgagatg   180
tgcggaggac atatcagagg aatgtttggc ttcttcttca ccg                    223
```

<210> SEQ ID NO 552
<211> LENGTH: 218
<212> TYPE: DNA
<213> ORGANISM: Zea mays

<400> SEQUENCE: 552

```
gcacgaggca gggccgatgt accaggcagg aactctcagc gggaaccctc tagccatgac    60
cgctgggatc cacacgctca gcggctgaca gagcccggc acctacgagt acttggacaa   120
gatcaccggc gaactcgtcc gtgggatact ggacgtcggt gcgaaagcag gcatgagat   180 gtgcggagga catatcagag gaatgtttgg cttcttct                          218
```

<210> SEQ ID NO 553
<211> LENGTH: 275
<212> TYPE: DNA
<213> ORGANISM: Zea mays

<400> SEQUENCE: 553

```
gcgaaacagg gcatgagatg tgcggaggac atatcagagg aatgtttggc ttctacttca    60
ccggcgggcc cgtccacaac ttcggggacg ccaagaagag cgacaccgag aagttacaga   120
ggttctaccg tggcatgctg gaagaggcgt gtacttcgct ccctcgcagt tcgaggcggg   180
gttcaccagc ttggcgcaca cctcccagga catcgagaag accgtcgagg ccgtaatgaa   240
ggttctgaag cggatatagg gggtacgctt caagc                             275
```

<210> SEQ ID NO 554
<211> LENGTH: 252
<212> TYPE: DNA
<213> ORGANISM: Zea mays

<400> SEQUENCE: 554

```
cttcggggac gccaagaaga gcgacaccga gaagttcggg aggttctacc gtggcatgct    60
ggaggagggc gtgtacttcg ctccctcgca gttcgaggcg gggttcacca gcttggcgca   120
cacctcccag gacatcgaga gaccgtcga ggccgctgag aaggttctga agcggatata   180
gggggtccgc ttcaagcaag catgcagaga gcatttcctc gtatctacgt tcttgtactc   240
```
ttagttctat at                                                     252

<210> SEQ ID NO 555
<211> LENGTH: 295
<212> TYPE: DNA
<213> ORGANISM: Zea mays

<400> SEQUENCE: 555
ctctagccat gaccgctggg atccacacgc tcaagcggct gacagagccc ggcacctacg    60
agtacttgga caagatcacc ggcgaactcg tccgtgggat actggacgtc ggtgcgaaag   120
cagggcatga gatgtgcgga ggacatatca gaggaatgtt tggcttcttc ttcaccggcg   180
ggcccgtcca caacttcggg gacgccaaga agagcgacac cgagaagttc gggaggttct   240
acgtggcatg cctggagagg gcgtgtactt cggctccctc gcagttcgag gcggg        295

<210> SEQ ID NO 556
<211> LENGTH: 331
<212> TYPE: DNA
<213> ORGANISM: Zea mays

<400> SEQUENCE: 556
ccacgcgtcc gagggcgtgt acttcgctcc ctcgcagttc gaggcggggt tcaccagctt    60
ggcgcacacc tcccaggaca tcgagaagac cgtcgaggca gctgagaagg ttctgaagcg   120
gatatagggg gtccgcttca agcaagcatg cagagagcat ttcctcgtat ctacgttctt   180
gtactcttag ttctatatgc caccgaggtt ttgtattgtg cagcagcagg acagcttctg   240
taagttcctc tttctgaatt agtgggtctt gttttttgtca gtgccaataa atctctggtc   300
cacgattacg gtttcgttgt tgtactgatg t                                 331

<210> SEQ ID NO 557
<211> LENGTH: 423
<212> TYPE: DNA
<213> ORGANISM: Zea mays

<400> SEQUENCE: 557
gacccaatcg ccgcaaaccc ctccggaatt tcttatcccc cctcatctgc tccacctccg    60
acctcgcgcg agacgagcaa gcccaagtat ggccggagca gcagcagccg ccgtggcgtc   120
cggggtctcg gccggccgg ccgcgccgag gagggcttct gcgggacgcc gcgctcggct   180
gtcggtggtg cgggccgcga tatccctcga gaagggcgag aaggcgtaca cggtgcagaa   240
gtccgaggag atcttcaacg ccgccaagga gctgatgcct ggaggtgtta actcgccagt   300
ccgagccttc aaatctgttg gtgggcagcc agtagttttc gactctgtaa agggttctcg   360
tatgtgggat gttgatggga atgagtacat tgattacgtt ggttcctggg gtcctgcaat   420
cat                                                                423

<210> SEQ ID NO 558
<211> LENGTH: 302
<212> TYPE: DNA
<213> ORGANISM: Zea mays

<400> SEQUENCE: 558
cggacgcgtg gcggacgcg tgggcgccga ggagggcttc tgcgggacgc cgcgctcggc    60
tgtcggtggt gcgggccgcg atatccctcg agaagggcga gatagcgtac acggtgcagc   120
agtccgagga gatcttcaac gccgccaatg agctgatgcc tggaggtgtt aactcgccag   180
tccgagcctt caaatctgtt ggtgggcagc cagtagtttt cgactctgta aagggttctc   240

-continued

```
gtatgtggga tgttgatggg aatgagtaca ttgattacgt tggttcctgg ggtcctgcaa    300
tc                                                                   302

<210> SEQ ID NO 559
<211> LENGTH: 305
<212> TYPE: DNA
<213> ORGANISM: Zea mays
<220> FEATURE:
<223> OTHER INFORMATION: unsure at all n locations

<400> SEQUENCE: 559
ctgctccacc tccgacctcg cgcgagacga gcaagcccaa gtatggccgg agcagcagca    60
gccgccgtgg cgtccggagt ctcggcccgg ccggccgcgc cgaggagggc ttctgcggga   120
cgccgcgctc ggctgtcggt ggtgcgggcc gcgatatccc tcgagaangg cgagaaggcg   180
tacacggtgc agaagtccga ggagatcttc aaggccgcca aggagctgat gcctggaggt   240
gttaactcgc cagtccgagg cttcaaatct gttggtgggc agccagtagt ttcgactctg   300
taaag                                                                305

<210> SEQ ID NO 560
<211> LENGTH: 276
<212> TYPE: DNA
<213> ORGANISM: Zea mays

<400> SEQUENCE: 560
gctccacctc cgacctcgcg cgagacgagc aagcccaagt atggccggag cagcagcagc    60
cgccgtggcg tccggggtct cggcccggcc ggccgcgccg aggagggctt ctgcgggacg   120
ccgcgctcgg ctgtcggtgg tgcgggccgc gatatccctc gagaagggcg agaaggcgta   180
cacggtgcag aagtccgagg agatcttcaa cgccgccaag gagctgatgc ctggaggtgt   240
taactcgcca gtccgagcct tcaaatctgt tggtgg                             276

<210> SEQ ID NO 561
<211> LENGTH: 225
<212> TYPE: DNA
<213> ORGANISM: Zea mays

<400> SEQUENCE: 561
cccacgcgtc cgcccacgcg tccgcccacg cgtccgctgc gggacccgcg ctcggctgtc    60
ggtggtgcgg gccgcgatat ccctcgagaa gggcgagaag gcgtacacgg tgcagaagtc   120
cgaggagatc ttcaacgccg ccaaggagct gatgcctgga ggtgttaact cgccagtccg   180
agccttcaaa tctgtatgtg ggcagccagt agttttcgac tctgt                   225

<210> SEQ ID NO 562
<211> LENGTH: 276
<212> TYPE: DNA
<213> ORGANISM: Zea mays

<400> SEQUENCE: 562
cagacgcgtg ggcgagacgc gtgggctgct ccacctccga cctcgcgcga gacgagcaag    60
cccaagtatg gccggagcag cagcagccgc cgtggcgtcc ggggtctaca cccgccgga   120 cgcgccgagg agggcttctg cgggacgccg cgctcggctg tcggtggtgc gggccgcgat   180
atccctcgag aagggcgaga aggcgtacac ggtgcagaag tccgaggaga tcttcaacgc   240
cgccaaggag ctgatgcctg gaggtgttaa ctcgcc                             276
```

<210> SEQ ID NO 563
<211> LENGTH: 251
<212> TYPE: DNA
<213> ORGANISM: Zea mays

<400> SEQUENCE: 563

| | | | | | |
|---|---|---|---|---|---|
| ccacgcgtcc | gtccacctcc | gacctcgcgc | gagacgagca | agcccaagta | tggccggagc | 60 |
| agcagcagcc | gccgtggcgt | ccggggtctc | ggcccggccg | gccgcgccga | ggagggcttc | 120 |
| tgcgggacgc | cgcgctcggc | tgtcggtggt | gcgggccgcg | atatccctcg | agaagggcga | 180 |
| gaaggcgtac | acggtgcaga | agtccgagga | gatcttcaac | gccgccaagg | agctgatgcc | 240 |
| tggaggtgtt | a | | | | | 251 |

<210> SEQ ID NO 564
<211> LENGTH: 337
<212> TYPE: DNA
<213> ORGANISM: Zea mays

<400> SEQUENCE: 564

| | | | | | |
|---|---|---|---|---|---|
| caagtatcga | aatggtccgc | tttgtcaact | cagggacaga | agcctgcatg | ggagcgctcc | 60 |
| gcctcgtgcg | cgcattcacc | gggcgggaga | agatcatcaa | gttcgaaggc | tgctaccatg | 120 |
| gccatgccga | ttccttcctt | gtcaaagccg | gcagtggtgt | tgccacccct | ggcatcactg | 180 |
| actcccctgg | cgtccccaag | ggggccacct | acgagacttt | gacggcaccc | tacaatgatg | 240 |
| tcgcggcagt | gaagaaactg | ttcgacgaca | acgcggggga | gattgctgcc | gtcttcctcg | 300 |
| agtcagttgt | tggcaacgct | ggtttcaatc | ccccaca | | | 337 |

<210> SEQ ID NO 565
<211> LENGTH: 263
<212> TYPE: DNA
<213> ORGANISM: Zea mays

<400> SEQUENCE: 565

| | | | | | |
|---|---|---|---|---|---|
| gaaactctga | agaaaggaac | tagctttggt | gctccatgtt | tgctggagaa | cgtattggct | 60 |
| gagatggtca | tctctgccgt | gccaagtatc | gaaatggtcc | gctttgtcaa | ctcagggaca | 120 |
| gaagcctgca | tgggagcgct | ccgcctcgtg | cgcgcattca | ccgggcggga | gaagatcatc | 180 |
| aagttcgaag | gctgctacca | tggccatgcc | gattccttcc | ttgtcaaagc | cggcagtggt | 240 |
| gttgccaccc | ttggcctccc | tga | | | | 263 |

<210> SEQ ID NO 566
<211> LENGTH: 310
<212> TYPE: DNA
<213> ORGANISM: Zea mays

<400> SEQUENCE: 566

| | | | | | |
|---|---|---|---|---|---|
| gaacaccacg | aatcgtctgc | attcggctcg | aggacactct | gaagaaagga | actagctttg | 60 |
| gtgctccatg | tttgctggag | aacgtattgg | ctgagatggt | catctctgcc | gtgccaagta | 120 |
| tcgaaatggt | ccgctttgtc | aactcaggga | cagaagcctg | catgggagcg | ctccgcctcg | 180 |
| tgcgcgcatt | caccgggcgg | gagaagatca | tcaagttcga | aggctgctac | catggccatg | 240 |
| ccgattcctt | ccttgtcaaa | gccggcagtg | gtgttgccac | ccttggcctc | cctgactccc | 300 |
| ctggcgtccc | | | | | | 310 |

<210> SEQ ID NO 567
<211> LENGTH: 124

```
<212> TYPE: DNA
<213> ORGANISM: Zea mays

<400> SEQUENCE: 567
gctttgtcaa ctcagggaca gaagcctgca tgggagcgct ccgcctcgtg cgcgcattca      60
ccgggcggga gaagatcatc aagttcgaag gctgctacca tggccatggc gaatccttcc     120
ttgt                                                                  124

<210> SEQ ID NO 568
<211> LENGTH: 295
<212> TYPE: DNA
<213> ORGANISM: Zea mays
<220> FEATURE:
<223> OTHER INFORMATION: unsure at all n locations

<400> SEQUENCE: 568
cggacgcgtg gcgagacgcg tgggcggacg cgtgggcctt gtcaaagccg gcagtggtgt      60
tgccacccct ggcctccctg actcccctgg cgtcccacac ggggccacca cctgagactt     120
tgacangaac cctacaatga tgtcgcggca gtgaagaaac tgttcgagga caacgcgggg     180
gagattgctg ccgtcttcct cgagccagtt gttggcaacg ctggtttcat cccccccacag   240 cctggttttcc ttaacgctct ccgcgacttg accaaacagg atggtgcgct cctgg         295

<210> SEQ ID NO 569
<211> LENGTH: 253
<212> TYPE: DNA
<213> ORGANISM: Zea mays

<400> SEQUENCE: 569
cccacgcgtc cgcccacgcg tccgctcccc tggcgtcccc aaggggggcca cctacgagac     60 tttgacggca ccctacaatg atgtcgcggc agtgaagaaa ctgttcgagg acaacgcggg    120
ggagattgct gccgtcttcc tcgagccagt tgttggcaac gctggtttca tcccccccaca   180 gcctggtttc cttaacgctc tccgcgactt gaccaaacag gatggtgcgc tcctggtctt    240
cgatgaagtg atg                                                       253

<210> SEQ ID NO 570
<211> LENGTH: 363
<212> TYPE: DNA
<213> ORGANISM: Zea mays

<400> SEQUENCE: 570
ggtgcacggt agtgagtcgg aatcggctcg agtggcgatg gaaatctggg agctactgaa      60
agaattcttt gatgcagaaa ttagaaagct gaagctacaa ccatattatt tcgctattgt    120
tgttactgag aatgttctac agaaggaaaa ggaccacatt gagggctttg cacctgaggt    180
agcttgggtt actaaatctg gaaatctga cctggaagca ccgattgcaa gtgcgcccac     240
aggtgagctt gtaatgaacc cggctttctc catatggata agacgccacc gagacttacc    300
cttgaggtgt aatcaatggt gtcatgttgt tagatgggag tttagcgatc cgactccttt    360
cat                                                                  363

<210> SEQ ID NO 571
<211> LENGTH: 312
<212> TYPE: DNA
<213> ORGANISM: Zea mays

<400> SEQUENCE: 571
```

```
accacgcgtc cgcccacgcg tccgagaagc aggaattaga gttaaagtgg acgactcaga    60
gctgcgaact cctggatgga aattcaatca ctatgagatg aaaggggttc ctgtaagaat   120
atagataggt ccacgtgatg tcacaaataa gagtgttgtg gtttctaggc gtgatgtccc   180
tggaaagcaa ggaaaggagt ttggagtgtc tatggagcct tcgatattgg tgaaccatat   240
aaatggtcgt ctagatgaca tacaagcatg cctttacag aaggccttaa aatccgtgat    300
agtaacattg tc                                                       312
```

```
<210> SEQ ID NO 572
<211> LENGTH: 270
<212> TYPE: DNA
<213> ORGANISM: Zea mays
<220> FEATURE:
<223> OTHER INFORMATION: unsure at all n locations

<400> SEQUENCE: 572
ttaacttgca nngccaggtc aaggtctaga attcccaggc cgacctacga ctacacgtcg    60
gcccacccgt ccggccaaga tggctcctga gggctaagaa aagctgtaca ccaaggtcaa   120
gagcattcac gacagcctga tcgaggctgg tgtccgcgtc gagtccgact accgtgaggg   180
ctactccccc ggatggaagt tcaacgactg ggagctcaag ggtaatcctc ttcctaacca   240
attccgtccc aaggattccc aaaaaggttt                                    270
```

```
<210> SEQ ID NO 573
<211> LENGTH: 427
<212> TYPE: DNA
<213> ORGANISM: Zea mays

<400> SEQUENCE: 573
cccacgcgtc cgcccacgcg tccgcccacg cgtccgccca cgcgtccgtg ggaaaatgtg    60
gccagatgct tctgatactg atgcttcctc tcactataag cttccgttct caagaactgt   120
ctacattgag aaaactgatt ttcgccttaa ggactcaaaa gactactatg ggctggcccc   180
tggtaaatct gtcatgctaa ggtatgcgtt ccccataaaa tgcacagacg ttatctatgg   240
tgatactcct gatgatattg ttgaaattcg agcagaatat gatcctttga agacttctaa   300
acttaagggt gttctgcact gggttgctga gccagcacct ggtgtcgaac cattgaaggt   360
ggaagtaaga ctattcgaga aattgttcat gtcagagaat cctgctgaat ggaggattg   420 gcttggt                                                             427
```

```
<210> SEQ ID NO 574
<211> LENGTH: 273
<212> TYPE: DNA
<213> ORGANISM: Zea mays

<400> SEQUENCE: 574
gttgaggaga gtggaaattt atgaattcag ccgattgaat atggtttaca ctcttctaag    60
caagcgaaag cttctttggt ttgtacaaaa caagaaggtc gaagattgga cagacccacg   120
ttttcccact gtccaaggca tagtacgtcg gggcttgaag gttgatgcat tgatacagtt   180
tatactccaa cagggtgctt caaaaaatct gaatctcatg gaatgggata aactctggac   240
aatcaacaag aagataattg atccagtgtg cgc                                273
```

```
<210> SEQ ID NO 575
<211> LENGTH: 267
<212> TYPE: DNA
<213> ORGANISM: Zea mays
```

<400> SEQUENCE: 575

```
cccacgcgtc cggacggtat tgagtcaagg tgcagaaata ataccgtgga ggaaaatctc    60
tcattatgga aagagatggt taatggaact gaaaggggca tgcagtgctg tgtacggggt   120
aaacttgaca tgcaggatcc taacaagtca ctcaggatcc ctgtttacta ccgctgtaat   180
actgatccac accatcgtgt tggttcgaag tacaaggtct atccaacata tgactttgcg   240
tgcccatttg tcgatgcatt ggagggg                                      267
```

<210> SEQ ID NO 576
<211> LENGTH: 380
<212> TYPE: DNA
<213> ORGANISM: Zea mays

<400> SEQUENCE: 576

```
cggacgcgtg ggctgctgaa ttggaagatt ggcttggcga tcttaaccca cactcgaaag    60
aggtgataaa ggatgcttat gctgtaccat cacttgccac tgcggttctg ggtgacaagt   120
tccagtttga gcggcttggt tacttcgccg tggatactga ctccacacct gagaaactcg   180
tgttcaacag aactgttacc ctccgtgatt cgttcgggaa agctggaccc aagtgactgt   240
tcagtgtaat ttagggaggg cgctggtttt gatcggttgc agaagcgcac ctgaactata   300
caagttgtga agaaaatggt cgtctaatac agaacagttt aaagggcctt actctttata   360
aaatttaggg ttttttaaaa                                              380
```

<210> SEQ ID NO 577
<211> LENGTH: 373
<212> TYPE: DNA
<213> ORGANISM: Zea mays

<400> SEQUENCE: 577

```
actgttttaca cactcaatca atctgggatt tgagcggatc aggacacccg tgaaaattag    60
ctctccaggt tggaagtatt ctcactggga aatgaaaggt gttccattga gaattgagat   120
tggtccaaaa gatctggcaa acaaacaggt acgcattgtc cgccgggaca acggtgcaaa   180
ggttgacatt ccggtgacca atttggttga agatgttaaa gtgttattgg atgagattca   240
aaaaaatctg ttcaaaacag ctcaagaaag gagagatgca tgtgttcagg tcgtcaactc   300
ttgggatgaa ttcacaactg ctctgaataa caaaaggttg atcttggctc cttggtgcga   360
tgaggaggaa gtt                                                    373
```

<210> SEQ ID NO 578
<211> LENGTH: 299
<212> TYPE: DNA
<213> ORGANISM: Zea mays

<400> SEQUENCE: 578

```
cgtgattcca gtgccttata aggacgctga cacaactgcc ataaagggag cctgcgaatc    60
aactgtttac acactcaatc aatctgggat tcgagcggat caggacaccc gtgaaaatta   120
ctctccaggt tggaagtatt ctcactggga aatgaaaggt gttccattga gaattgagat   180
tggtccaaaa gatctggcaa acaaacaggt acgcattgtc cgccgggaca acggtgcaaa   240
ggttgacatt ccggtgacca atttggttga agatgttaaa gtgttattgg atgagattc    299
```

<210> SEQ ID NO 579
<211> LENGTH: 286
<212> TYPE: DNA

<213> ORGANISM: Zea mays

<400> SEQUENCE: 579

```
gccaatccag gtaattgtga ttccagtgcc ttataaggat gctgacacaa ctgccataaa      60
gggagcctgc gaatcaactg tttacacact cgatcaatct ggaattagag cggatcagga     120
cacccgtgaa aattactctc caggttggaa gtattcccac tgggaaatga aggtgttcc     180
attgagaatt gagattggtc caaaagatct ggcaaacaaa caggtgcgtg ttgtccgccg     240
ggacaacggt gcaaaggttg acatccctgt gaccaatttg gttgaa                    286
```

<210> SEQ ID NO 580
<211> LENGTH: 313
<212> TYPE: DNA
<213> ORGANISM: Zea mays

<400> SEQUENCE: 580

```
gatgacaaag gcttagtatt accaccaaag gtagcgccaa tccaggtaat tgtgattcca      60
gtgccttata aggatgctga cacaactgcc ataagggag cctgcgaatc aactgtttac     120
acactcgatc aatctggaat tagagcggat caggacaccc gtgaaaatta ctctccaggt     180
tggaagtatt cccactggga aatgaaaggt gttccattga gaattgagat tggtccaaaa     240
gatctggcaa acaaacaggt gcgtgttgtc cgccgggaca acggtgcaaa ggttgacatc     300
cctgtgacca att                                                        313
```

<210> SEQ ID NO 581
<211> LENGTH: 307
<212> TYPE: DNA
<213> ORGANISM: Zea mays

<400> SEQUENCE: 581

```
cccacgcgtc cgcacatggt gatgacaaag gcttagtatt accaccaaag gtagcgccaa      60
tccaggtaat tgtgattcca gtgccttata aggatgctga cacaactgcc ataagggag     120
cctgcgaatc aactgtttac acactcgatc aatctggaat tagagcggat caggacaccc     180
gtgaaaatta ctctccaggt tggaagtatt cccactggga aatgaaaggt gttccattga     240
gaattgagat tggtccaaaa gatctggcaa acaaacaggt gcgtgttgtc cgccgggaca     300
acggtgc                                                               307
```

<210> SEQ ID NO 582
<211> LENGTH: 227
<212> TYPE: DNA
<213> ORGANISM: Zea mays

<400> SEQUENCE: 582

```
cccacgcgtc cggaaaggtg ttccattgag aattgagatt ggtccaaaag atctggcaaa      60
caaacaggtg cgtgttgtcc gccgggacaa cggtgcaaag gttgacatcc ctgtgaccaa     120
tttggttgaa gaggttaaag tgttactgga tgagattcaa aaaatctgt tcaaaacagc     180
ccaagaaaag agagatgcct gtgttcatgt cgtgaacact gggatg                    227
```

<210> SEQ ID NO 583
<211> LENGTH: 427
<212> TYPE: DNA
<213> ORGANISM: Zea mays

<400> SEQUENCE: 583

```
ggttgacaat attacatgtg caccgaccac aaaccaaata atcagcaaaa tggatttcga      60
```

```
gtggcatctc aacatgcaca accttaggta aaagcttgag atggagaaac taaaagtttc    120
caacagcgaa cacaaagagt ggctggggct ggcctaggag gggaggaaga agagtgccat    180
cacacgaaaa ccatgacctc acagcattgg tgcagtaaca tttcactatt tagagcctat    240
gatcaggctt taaagagtgg ctggggctgg cctaggaggg gaggaagaag agtgccatca    300
ctaacaaaac agcccctcga accatggttg ttttgcgacc tctaaaggtg gtaataacta    360
acttggaaga aggaaaagta ctagaccttg atggcaaaat gtggcctgat gcttctgata    420
ctgatgc                                                              427

<210> SEQ ID NO 584
<211> LENGTH: 499
<212> TYPE: DNA
<213> ORGANISM: Zea mays

<400> SEQUENCE: 584
tgggtagtgt aacatcacaa tgctactgcc aactcatata ctaggactcg ttggtcgtta     60
caacactcta gattcactcg tattaaccga atctgtgagc catgtcgacc aacaagggca    120
gcgcggccaa gggcggcgga gggaagaaga aggaggtgaa gaaggagacg aagctcggga    180
tggcctataa gaaggacgac aacttcgggg agtggtactc cgaggttgtt gttaacagtg    240
aaatgattga gtactatgac atttctggtt gttatatatt gaggccatgg gcgatggaaa    300
tctgggagct actgaaagaa ttctttgatg cagaaattaa aaagctgaag ctcaaaccat    360
attatttccc tttgtttgtt actgagaatg ttctacagaa ggaaaaggac acattgagg     420 gctttgcacc tgaggtagct tgggttacta atctgggaa atctgacctg aagcaccga     480 ttgcaatccg ccccacaag                                                 499

<210> SEQ ID NO 585
<211> LENGTH: 284
<212> TYPE: DNA
<213> ORGANISM: Zea mays

<400> SEQUENCE: 585
gacatttctg gttgttatat attgaggcca tgggcgatgg aaatctggga gctactgaaa     60
gaattctttg atgcagaaat taaaaagctg aagctcaaac catattattt ccctttgttt    120
gttactgaga atgttctaca gaaggaaaag gaccacattg agggctttgc acctgaggta    180
gcttgggtta ctaaatctgg gaaatctgac ctggaagcac cgattgcaat ccgccccaca    240
agtgagactg tcatgtatcc gtacttctcc aaatggataa gaag                     284

<210> SEQ ID NO 586
<211> LENGTH: 271
<212> TYPE: DNA
<213> ORGANISM: Zea mays

<400> SEQUENCE: 586
ggaccgtggc ggtacgcgtg ggtttgtcga catatctgtc ccaaggaatg tcagcgcgtg     60
cgtctctgaa attggctccg agcgagtata caatgtcgac gacctgaaag aggtggtgga    120
agccaacaag gaagaccgtc tcaggaaagc gatggaggca cagacaatca tcgccgaaga    180
gctgaaacgg tttgaggcgt ggcggactc gctggagacc gttccaacca tcaagaagct    240
gaggtcttac gccgacagga tccgggcctc g                                   271

<210> SEQ ID NO 587
```

```
<211> LENGTH: 230
<212> TYPE: DNA
<213> ORGANISM: Zea mays

<400> SEQUENCE: 587
accatattga agaggctgct gtgcttagac ctgtaacaga atggaaattt atgtggtggc    60
cctatcatgg aaccgaggta tcagggaagt cgtggactgg atgtcgaaga aaagtggtat   120
tcctgcttct gagcttaggg aacacctatt catgctgcgt gacagtgatg ctacacgcca   180
tctgtttgag gtatcggctg ggttggactc tctggttctc ggtgaaggac              230

<210> SEQ ID NO 588
<211> LENGTH: 229
<212> TYPE: DNA
<213> ORGANISM: Zea mays

<400> SEQUENCE: 588
gtggccccgt gctattcaag aactcactag cctgaaccat attgaagagg ctgctgttct    60
tagtacctgt aatagaatgg aaatttatgt ggtggcgcta tcatggaacc gtggtatcag   120
agaagtagtg gactggatgt cgaagaaaag tggtattccc gcttccgagc ttagggagca   180
cctgttcatc ttgcgaacag tgatgccaca cgccatctgt ttgaggtgt                229

<210> SEQ ID NO 589
<211> LENGTH: 492
<212> TYPE: DNA
<213> ORGANISM: Zea mays
<220> FEATURE:
<223> OTHER INFORMATION: unsure at all n locations

<400> SEQUENCE: 589
aggttaaagt ntgtaataga tgggatgtac tgtacacttc tccggnttnn nnnnnnggng    60
gggagccacg cgtccggaaa tgttaacgca ttaaaaggta tacggtatca gtaaaccttg   120
caagtgtgat gccaagggaa aacggcatca gctgacacat tgctatattc ctgtttattt   180
cgtccgaata agtatataa cttaagaaag gggctcttgc cccacagcag ctcaagcaaa   240
aatgtacaaa gaaaagcagc tcgagtagag agaatttgcc actctctcga cagattgagc   300
tgctgccatg gcgctaattc acgacacatt tgatgtctcg gcaagacggg gaggagctca   360
gtaagtgaga tgataaaaaa atagaatcag gttggagggt aagtatacac gggtagaaaa   420
attgcctcct tggccttaat tntgggtctt ctccaccttg gccttgatct tctgctcgat   480
gattgccttc tc                                                       492

<210> SEQ ID NO 590
<211> LENGTH: 313
<212> TYPE: DNA
<213> ORGANISM: Zea mays

<400> SEQUENCE: 590
cgtggaaaac tttccggttc caaaggacct ttggcccctt ccttttaaga acctacctgg    60 gtaaacccctt tttgaaaagg ctcctgtcct aatacttgta taaaatgaaa attatgtggt   120
agccctatca tggaaccgaa gtatcagaga agtagttgac tggatgtcaa agaaaagtgg   180
tattcctgct tctgagctta aggagcacct attcatgctg cgtgacagtg atgctacacg   240
ccatctgttc taagtatcag caaggttgga ctctttggtt ctcggtgaac gacaaatcct   300
tgctcaagtc aaa                                                      313
```

```
<210> SEQ ID NO 591
<211> LENGTH: 457
<212> TYPE: DNA
<213> ORGANISM: Zea mays

<400> SEQUENCE: 591
agcccacgcg tccgcccacg cgtccggtga atcccgcac  ctacctcctt cctctctcac      60
cgaggaccct cgcaccaaga actgagcggg aagagaggta gagaggcaag cgcacgagag     120
tttctgctcc tagtctcgtc tcgccccgcc tccgtctcct ttccctctct ggttctctct     180
ctgcgattct cgtcgcattg gttccgttcc ctcacgaaag gcggtagctt tctgtcttcc     240
ctgatctatc tagataatgg cgaccacgac gtcagcgacc accgccgcag cagcagccgc     300
caccatcgcc aagccgcggg ggtcgtcgtc ggacctctgc cagagggtgg ccggcggcgg     360
caggcggtgc tccggggtgg tgccgtgcga cgccgccggc gtggaggccc aggcgcatgc     420
cgtggcaaat gcggccagcg tcgccgcccct cgagcag                            457

<210> SEQ ID NO 592
<211> LENGTH: 267
<212> TYPE: DNA
<213> ORGANISM: Zea mays

<400> SEQUENCE: 592
gaaggttgtt gtggtgaacc gctccgtgga aagggtggat gctattcgtg aggagatgaa      60
agatatagag atcgtgtaca ggcctctctc agacatgtat caagctgctg ctgaagctga     120
tgtcgtgttc accagcaccg catctgaaac ttcattgttc gcaaaagaac acgcagaggc     180
actcccccct gtctctgata ctatgggagg tgttcgcctg tttgtcgaca tatctgtccc     240
caggaatgtc agcgcatgtg tgtctga                                        267

<210> SEQ ID NO 593
<211> LENGTH: 264
<212> TYPE: DNA
<213> ORGANISM: Zea mays

<400> SEQUENCE: 593
cccacgcgtc cgcccacgcg tccgggatgc aagaaggttg ttgtggtgaa ccgctccgtg      60
gaaagggtgg atgctattcg tgaggagatg aaagatatag atcgtgtaca caggcctctc     120
tcagacatgt atcaagctgc tgctgaagct gatgtcgtgt tcaccagcac cgcatctgaa     180
acttcattgt tcgcaaaaga acacgcagag gcactccccc ctgtctctga tactatggga     240
ggtgttcgcc tgtttgtcga cata                                           264

<210> SEQ ID NO 594
<211> LENGTH: 310
<212> TYPE: DNA
<213> ORGANISM: Zea mays

<400> SEQUENCE: 594
atcttattgc caaaggatgc aagaaggtgg ttgtggtcaa ccgttcagtg gaaagggtgg      60
atgccatccg cgaggagatg aaaggtatcg agattgtgta caggcctctt tcagagatgt     120
acgaagctgc tgctgaagct gatgtcctat tcacgagcac tgcatctgaa acccccattgt     180
tcacaaaaga gcacgcagag gcacttccca caatttccga tgccatggat ggtgcccggc     240
tttttgtcga catatctgtc ccaaggaatg tcagcgcgtg cgtctctgaa attggctccg     300
cgcgagtata                                                           310
```

<210> SEQ ID NO 595
<211> LENGTH: 290
<212> TYPE: DNA
<213> ORGANISM: Zea mays

<400> SEQUENCE: 595

```
gtggtcaacc gttcagcaca aagggtggat gccatccgcg aggagattaa agctatcgag    60
attgtgtaca ggcctctctc ggagatgtat gaagctgctg ctgaagctga cgtcgtgttc   120
acgagcaccg catctgaaac cccattgttc acaaaagagc acgcagatgc acttcccact   180
gtttctgatg ccatgggcgg tgtccggctc tttgtcgaca tatctgtccc aaggaatgtc   240
agcgcgtgtg tctctgaaat tggctccgcg cgagtgtaca atgttgatga              290
```

<210> SEQ ID NO 596
<211> LENGTH: 168
<212> TYPE: DNA
<213> ORGANISM: Zea mays

<400> SEQUENCE: 596

```
ggtggttgtg gtcaaccgtt cagtggaaag ggtggatgcc atccgcgagg agatgaaagg    60
tatcgagatt gtgtacaggc ctctttcaga gatgtacgaa gctgctgctg aagctgatgt   120
cctattcacg agcactgcat ctgaaacccc attgttcaca aaagagca                168
```

<210> SEQ ID NO 597
<211> LENGTH: 254
<212> TYPE: DNA
<213> ORGANISM: Zea mays

<400> SEQUENCE: 597

```
acctgaaaga ggtggtggaa gccaacaagg aagaccgtct caggaaagcg atggaggcac    60
agacaatcat cgccgaagag ctgaaacggt tgaggcgtg gcgggactcg ctggagaccg   120
ttccaaccat caagaagctg aggtcttacg ccgacaggat ccgggcctcg agctcgaga   180
agtgcctgca gaagatcggg gacgacgctc tcaccaagaa gacgaggaga gccatcgagg   240
agctaagcac cggc                                                    254
```

<210> SEQ ID NO 598
<211> LENGTH: 270
<212> TYPE: DNA
<213> ORGANISM: Zea mays

<400> SEQUENCE: 598

```
cggctcgagg aaagaggtgg tggaagccaa caaggaagac cgtctcagga aggcaatgga    60
ggcgcagaca atcatcaccg aagagctgaa acggtttgag gcatggcggg actcgctgga   120
gaccgttcca accatcaaga agctgaggtc atatgccgac aggatccgag cctcagagct   180
cgatgagtgc ctacagaaga tcggggatga cgttctcacc aagaagatga ggagagccat   240
cgaggagcta agcaccggca tcgtgaacaa                                   270
```

<210> SEQ ID NO 599
<211> LENGTH: 422
<212> TYPE: DNA
<213> ORGANISM: Zea mays

<400> SEQUENCE: 599

```
cgaccatcaa gaagctgagg tcgtacgcgg acaggatcag ggcctcggag ctcgagaagt    60
gcctgcagaa agtaggtgag gacgccctca ccaagaagat gaggagagcc atcgaggagc   120
```

```
tgagcaccgg catcgttaac aagctcctcc atggcccgct gcagcacctg aggtgcgacg    180
gcagcgacag ccgcacccct tgacgagacgc tcgagaacat gcacgccctc aaccggatgt   240
tcagcctcga catggagaag gcgatcatcg agcagaagat caaggccaag gtggagaaga    300
cacaaaactg aggccaggaa gcaattttc taccaccatt atctatatat atagcgtctc     360
caatctcatt ccattttttt atcctttcac tcagtgagcc cttcccctgc tcactgtgat    420
cg                                                                   422
```

<210> SEQ ID NO 600
<211> LENGTH: 282
<212> TYPE: DNA
<213> ORGANISM: Zea mays

<400> SEQUENCE: 600

```
gacaggatca gggcctcgga gctcgagaag tgcctgcaga aagtaggtga ggacgccctc    60
accaagaaga tgaggagagc catcgaggag ctgagcaccg gcatcgttaa caagctcctc    120
catggcccgc tgcagcacct gaggtgcgac ggcagcgaca ccgcacccct tgacgagacg    180
ctcgagaaca tgcacgctct caaccggatg ttcagcctcg acatggagaa ggcgatcatc    240
gagcagaaga tcaaggccaa ggtggagaag acacaaaact ga                       282
```

<210> SEQ ID NO 601
<211> LENGTH: 262
<212> TYPE: DNA
<213> ORGANISM: Zea mays

<400> SEQUENCE: 601

```
tgacgttctc accaagaaga tgaggagagc catcgaggag ctaagcaccg gcatcgtgaa    60
caagctcctc cacggcccgc tgcagcacct gaggtgcgac ggtagtaaca gccgcaccct    120
tgatgagacg ctcgagaaca tgcatgctct caaccggatg ttcagcctcg acacggagaa    180
ggcgatcatc gagcagaaga tcaaggccaa ggtggagaag acccagaatt gaggcctgga    240
gtcaattttt ctacccgtgt at                                             262
```

<210> SEQ ID NO 602
<211> LENGTH: 288
<212> TYPE: DNA
<213> ORGANISM: Zea mays

<400> SEQUENCE: 602

```
gacgccctca ccaagaagat gaggagagcc atcgaggagc tgagcaccgg catcgttaac    60
aagctcctcc atggcccgct gcagcacctg atgctggacg gcagcgacag ccgcacccct    120
gacgagacgc tcgagaacat gcacgccctc aaccggatgt tcagcctcga catggagaag    180
gcgatcatcg agcagaagat caaggccaag gtggagaaga cacaaaactg aggccaggaa    240 gcaattttc taccaccatt atctatatat atagcgtctc caatctca                  288
```

<210> SEQ ID NO 603
<211> LENGTH: 139
<212> TYPE: DNA
<213> ORGANISM: Zea mays

<400> SEQUENCE: 603

```
cgatcatcga gcagaagatc aaggccaagg tggagaagac acaaaactga ggccaggaag    60 caattttct accaccatta tctatatata tagcgtctcc aatctcattc catttttta     120
```
tcctttcact cagtgagcc                                             139

<210> SEQ ID NO 604
<211> LENGTH: 460
<212> TYPE: DNA
<213> ORGANISM: Zea mays

<400> SEQUENCE: 604
cccacgcgtg cgcccactcg tccggtggta ttcccgcttg cgagcttagg gagcacctgg    60
tcatcttgcg aagcagtgat gccacacgcc atctgtttga ggtgtcagct ggccttgact   120
ctttggttct cggtgaagga caaatccttg ctcaggttaa acaagttgtg aggagtggac   180
agaacagtgg aggcttggga agaacattg ataggatgtt caaggatgca atcactgctg    240
gaaagcgtgt ccgctgcgag accaacatat catctggtgc tgtttctgtc agttcagcgg   300
cggttgaact ggccctgatg aagcttccga agtctgaagc actgtcagct aggatgcttc   360
tgattggtgc tggtaaaatg ggaaagctag tgatcaaaca tctggttgcc aaaggatgca   420
tgaaggttgt tgtggtgaac cgctccgtgg aaagggtgga                        460

<210> SEQ ID NO 605
<211> LENGTH: 322
<212> TYPE: DNA
<213> ORGANISM: Zea mays

<400> SEQUENCE: 605
aacaagttgt gaggagtgga cagaacagtg gaggcttggg aaagaacatc gataggatgt    60
tcaaggatgc aatcactgct ggaaagcgtg tccgcagcga gaccaacata tcatctggtg   120
ctgtttctgt cagttcagcg gcggttgaac tggccctgat gaagcttccg aagtctgaag   180
cactgtcagc taggatgctt ctgattggtg ctggtaaaat gggaaagcta gtgatcaaac   240
atctggttgc caaaggatgc aagaaggttg ttgtggtgaa ccgctccgtg aaagggtgg    300 atgctattcg tgaggagatg aa                                           322

<210> SEQ ID NO 606
<211> LENGTH: 310
<212> TYPE: DNA
<213> ORGANISM: Zea mays

<400> SEQUENCE: 606
tcccgcttcc gagcttaggg agcacctgtt catcttgcga agcagtgatg ccacacgcca    60
tctgtttgag gtgtcagctg gccttgactc tttggttctc ggtgaaggac aaatccttgc   120
tcaggttaaa caagttgtga ggagtggaca gaacagtgga ggcttgggaa agaacattga   180
taggatgttc aaggatgcaa tcactgctgg aaagcgtgtc cgctgcgaga ccaacatatc   240
atctggtgct gtttctgtca gttcagcggc ggttgaactg gccctgatga agcttccgaa   300
gtctgaagca                                                         310

<210> SEQ ID NO 607
<211> LENGTH: 298
<212> TYPE: DNA
<213> ORGANISM: Zea mays

<400> SEQUENCE: 607
gtgaaggaca aatccttgct caggttaaac aagttgtgag gagtggacag aacagtggag    60
gcttgggaaa gaacatcgat aggatgttca aggatgcaat cactgctgga aagcgtgtcc   120
gcagcgagac caacatatca tctggtgctg tttctgtcag ttcagcggcg gttgaactgg   180

-continued

```
ccctgatgaa gcttccgaag tctgaagcac tgtcagctag gatgcttctg attggtgctg    240
gtaaaatggg aaagctagtg atcaaacatc tggttgccaa aggatgcaag aaggttgt     298
```

<210> SEQ ID NO 608
<211> LENGTH: 300
<212> TYPE: DNA
<213> ORGANISM: Zea mays

<400> SEQUENCE: 608

```
agcgtgtccg cagcgagacc aacatatcat ctggtgctgt ttctgtcagt tcagcggcgg    60
ttgaactggc cctgatgaag cttccgaagt ctgaagcact gtcagctagg atgcttctga   120
ttggtgctgg taaaatggga aagctagtga tcaaacatct ggttgcgaaa ggatgcaaga   180
aggttgttgt ggtgaaccgc tccgtggaaa gggtggatgc tattcgtgag gagatgaaag   240
atatagagat cgtgtacagg cctctctcag acatgtatca agctgctgct gaagctgatg   300
```

<210> SEQ ID NO 609
<211> LENGTH: 234
<212> TYPE: DNA
<213> ORGANISM: Zea mays

<400> SEQUENCE: 609

```
gttgaactgg ccctgatgaa gcttccgaag tctgaagcac tgtcagctag gatgcttctg    60
attggtgctg gtaaaatggg aaagctagtg atcaaacatc tggttgccaa aggatgcaag   120
aaggttgttg tggtgaaccg ctccgtggaa agggtggatg ctattcgtga ggagatgaaa   180
gatatagaga tcgtgtacag gcctctctca gacatgtatc aagctgctgc tgaa         234
```

<210> SEQ ID NO 610
<211> LENGTH: 278
<212> TYPE: DNA
<213> ORGANISM: Zea mays

<400> SEQUENCE: 610

```
cgtgagactg gcggtggata acgcgtcatg gaccgacgat aagcagctcc aggacatgta    60
cctgatctgc aagtccgtcg cgatgcgaca tcgacgcacc tgggagcggg catgagagga   120
gaagctcaag gcgttcgagc tcgcactggc gacggcagag gccacgttct agaacctcga   180
ctcgtcggag atctcactga cggacgtgag ccactacttc gactcggacc cgatcaagct   240
cgtgcattgg ctgctcaaag acgggcgagc ggcgtcct                           278
```

<210> SEQ ID NO 611
<211> LENGTH: 251
<212> TYPE: DNA
<213> ORGANISM: Zea mays

<400> SEQUENCE: 611

```
gaagatgtgt acaggggaag tgacaagggc atactggctg acgtcgagct tctgaggcag    60
atcactgagg cttcgcgcgg cgccatcacc gccttcgttg agaagaccac aaacagcaaa   120
gggcaagtcg tcaatgttac caacaacctc agcaagatac ttggtttcgg tctgtcggaa   180
ccatgggtgc agtacctgtc cacgaccaag ttcgtcagag cggacagaga gaagatgagg   240
gttctgtttg g                                                        251
```

<210> SEQ ID NO 612
<211> LENGTH: 126
<212> TYPE: DNA

<213> ORGANISM: Zea mays

<400> SEQUENCE: 612

```
gttctagatc gccagtctct tctcctcctt agttttcctc ttcagttctg cccatctgat      60
ggctctagtg cagagctgct ccactctctt gtgcaatgca tgtgacttcc ctgtcctggg     120
gtcccg                                                                126
```

<210> SEQ ID NO 613
<211> LENGTH: 296
<212> TYPE: DNA
<213> ORGANISM: Zea mays

<400> SEQUENCE: 613

```
acgggatttg ccaaggatac aaacttgttc tcagtgtcga tgacaagaag ggacattcct      60
gccttgtcat cgaactgaga caagtgtatc cacgggattt gccaaggaaa ttgcaagggt     120
tgcccagggg aaatattatt acctccctaa tgcttcagat gctgtaattt ctgctgactc     180
caagaccgcc ctgacagact tgaagagctc atgattttgc agcagcggca cccgttttct     240
gtacctttg ataggggatgg tgaaccttca ttcatgcagt aattttttgcg taggcc         296
```

<210> SEQ ID NO 614
<211> LENGTH: 286
<212> TYPE: DNA
<213> ORGANISM: Zea mays

<400> SEQUENCE: 614

```
gtgaacactt gcttgatcgt attgcaatta atttaagtgc tgatcttcca atgagttttg      60
atgaccgcgt tgaagcagtg gatattgcaa cacggtttca ggagtctagc aaagaagttt     120
tcaaattggt ggaagaaaaa actgaaactg caaaaactca gataattttt gcaagagagt     180
atctgaagga tgttactatt agcacagagc agctcaaata tcttgtcatg gaagctatac     240
gaggtggctg tcagggcat cgtgctgagt tgtatgctgc ccgagt                      286
```

<210> SEQ ID NO 615
<211> LENGTH: 239
<212> TYPE: DNA
<213> ORGANISM: Zea mays

<400> SEQUENCE: 615

```
cggacgcgtg gcaaccacgg ctgccttgaa gagcgccaag atcgtcgtgg accgtctcct      60
ggagaggcag acggctgaca atggcggcaa gtaccctgag acggtcgcac ttgtcctgtg     120
gggcaccgac aacatcaaga cctatggtga gtcactagcc caggtgctgt ggatgattgg     180
agttcggcca gttgccgaca ccttcggccg tgtcaaccgt gtggagcctg tcagccttg      239
```

<210> SEQ ID NO 616
<211> LENGTH: 233
<212> TYPE: DNA
<213> ORGANISM: Zea mays

<400> SEQUENCE: 616

```
gggagtgctt gaagctcgtg gtacaggaca atgagctggg cagcggcaga ggctactggg      60
agacatcgga ggagaacctg gacaggctca gggagctcta ctcggaggtt gaagacaaga     120
ttgaggggat tgaccggtaa accgatttgc cagattcaaa ggaatgagaa gcttggaact     180
cttgtgtctc attgaggctc ttgtacaatg tgtgtgtagc ttatatatat ata             233
```

<210> SEQ ID NO 617
<211> LENGTH: 302
<212> TYPE: DNA
<213> ORGANISM: Zea mays
<220> FEATURE:
<223> OTHER INFORMATION: unsure at all n locations

<400> SEQUENCE: 617

```
cggacgctgc gggtacgaga gggctcgttt cgacagggat ccgaagacgt tccgtgagtc      60
gtatcatgac gatcangaga atctccagca gcagatatca tctgcacgga gtaaccttgg     120
cgctgtgcag attgaccatg acctccgtgt caagatatcc aaggtgtgct ctgagttgaa     180
cgttgatgga ctcagaggtg acattgtgac taacatggct gccaaggcgc tggctgcgtt     240
gaaaagaatg acagcgtca ccgtggagga cattgctact gtcattccca actgcttgag      300
gc                                                                    302
```

<210> SEQ ID NO 618
<211> LENGTH: 261
<212> TYPE: DNA
<213> ORGANISM: Zea mays
<220> FEATURE:
<223> OTHER INFORMATION: unsure at all n locations

<400> SEQUENCE: 618

```
gtttggggttc ttgggggagt gcctgangct cgtcgtgcaa gacaacgagc tgggaagctt     60
gaagcttgcc ctcgagggaa gctacgtcga gcctngccct ngcggcganc cgatncgtan    120
cncnaagngc tcccgacagg gnagancatc canntctcga tncgcaggtt atccnaaaca    180
aagctnccctt tnaagaancc aaaatngnnn gtggncnggt tncttggagn ngtgaaggnt   240
ggaanatgng gaaantaccc g                                              261
```

<210> SEQ ID NO 619
<211> LENGTH: 262
<212> TYPE: DNA
<213> ORGANISM: Zea mays

<400> SEQUENCE: 619

```
ggggcatcgt gctgagttgt atgctgcccg agttgcaaaa tgtctagctg ctatggaagg      60
acgtgaaaaa gtatttgtgg atgacctcaa gaaagctgta gagctggtca ttctacctcg    120
ctccatccta tctgataatc cacaggatca gcagcaagag catccacccc cacccccgcc    180
gccaccacct ccagaaaatc aagattcttc agaagaccaa gatgaggaag acgaagacca    240
agaggatgat gaagaagaaa at                                             262
```

<210> SEQ ID NO 620
<211> LENGTH: 125
<212> TYPE: DNA
<213> ORGANISM: Zea mays
<220> FEATURE:
<223> OTHER INFORMATION: unsure at all n locations

<400> SEQUENCE: 620

```
ccagttctgg ctcggcggct cgtcggacaa tctccagaac ttccttaaga tgatcggcgg      60
ctggtacntg cctgccctca aaggcgccgg catcaagtac gacgaccccc gtgctctacc    120
tcgac                                                                125
```

<210> SEQ ID NO 621
<211> LENGTH: 280
<212> TYPE: DNA

<213> ORGANISM: Zea mays

<400> SEQUENCE: 621

```
gcaagggttg cccagggaa atattattac ctccctaatg cttcagatgc tgtaatttct      60
gctgccacca agaccgccct gacagacttg aagagctcat gattttgcag cagcggcacc    120
cgttttctgt accttttgat agggatggtg aaccttcatt catgcagtaa tttttgcgta    180
ggcctctaca atgacagggg gaaacaaacc cgagcatggc atcgtgtaaa gtgttaaggt    240
ccaatggcct cctgtccacg tttggcgatg taaatcctcc                          280
```

<210> SEQ ID NO 622
<211> LENGTH: 274
<212> TYPE: DNA
<213> ORGANISM: Zea mays

<400> SEQUENCE: 622

```
cagtaaggag gttagctgtt gatgccacgc ttagagcagc tgcaccatac caaaaactgc     60
gcagagagaa agaacgtgac aaaacaagaa aggttttcgt tgaaaagact gacatgagag    120
ccaaaagaat ggctcgaaaa gcaggtgctc tagtcatatt tgttgtggac gctagtggta    180
gcatggctct gaatcgtatg cagaatgcta aggtgcggc gttgaagttg cttgcagaaa     240
gctacaccag cagagatcag gtttcaatta ttcc                                274
```

<210> SEQ ID NO 623
<211> LENGTH: 252
<212> TYPE: DNA
<213> ORGANISM: Zea mays

<400> SEQUENCE: 623

```
aaagcctatg cttcctaagg gtccagtaag gaggttagct gttgatgcca cgcttagagc     60
agctgcacca taccaaaaac tgcgcagaga gaaagaacgt gacaaaacaa gaaaggtttt   120
tgttgaaaag actgacatga gagccaaaag aatggctcga aaagcaggtg ctctagtcat   180
atttgttgtg gacgctagtg gtagcatggc tctgaatcgt atgcagaatg ctaaaggtgc   240
ggcgttgaag tt                                                        252
```

<210> SEQ ID NO 624
<211> LENGTH: 252
<212> TYPE: DNA
<213> ORGANISM: Zea mays

<400> SEQUENCE: 624

```
aaagcctatg cttcctaagg gtccagtaag gaggttagct gttgatccca cgcttagagc     60
agctccacca taccaaaaac tgcgcagaga gaaagaacgt gacaaaacaa gaaaggtttt   120
tgttgaaaag actgacatga gagccaaaag aatggctcga aaagcaggtg ctctagtcat   180
atttgttgtg gacgctagtg gtagcatggc tctgaatcgt atgcagaatg ctaaaggtgc   240
ggcgttgaag tt                                                        252
```

<210> SEQ ID NO 625
<211> LENGTH: 260
<212> TYPE: DNA
<213> ORGANISM: Zea mays

<400> SEQUENCE: 625

```
caaaaacagc gcagagagaa agaacgtgac aaaacaagaa aggttttgt tgaaaagact      60
gacatgagac ccaaaagaat ggctcgaaaa gcaggtgctc tagtcatatt tgttgtagac   120
```

-continued

```
gctagtagta gcatggctct gaatcgtatg cagaatgcta aggtgcggc gttgaagttg      180 cttgcagaaa gctacaccag cagagatcag gtttcaatat tccttttcgt ggagattatc    240
tgaggtttgc tccaccatca                                                260

<210> SEQ ID NO 626
<211> LENGTH: 260
<212> TYPE: DNA
<213> ORGANISM: Zea mays

<400> SEQUENCE: 626
caacccatca gaggccacgg tgccaagcg ccggagctac gcgaacacca tcagctacct     60
gaccccaccg gccgagaacg ccggcctcta caagggctc aagcagctgt cagagctcat   120
ctcttcctac cagtctctca aggacaccgg gcgtggtcct cagattgtga gctccatcgt   180
cagcactgca aagcagtgca acctcgacaa ggatgtcccg ctgcccgagg aagggggagga 240 gtcccaccaa aggagcgtga                                              260

<210> SEQ ID NO 627
<211> LENGTH: 122
<212> TYPE: DNA
<213> ORGANISM: Zea mays

<400> SEQUENCE: 627
caaggacacc gggcgtggtc ctcagattgt gagctccatc gtcagcactg caaagcatgc    60
aacctcgaca aggatgtccc cctgcctgag gaaggggagg agctcccacc aaaggagcgt  120
ga                                                                  122

<210> SEQ ID NO 628
<211> LENGTH: 306
<212> TYPE: DNA
<213> ORGANISM: Zea mays

<400> SEQUENCE: 628
gtcgacgtgc tgctggattc cgctgcgtcg gggtggaaca cggtggagag ggacggtatc    60
tccatatccc accctgctcg cttcatcctc atcggctctg gtaacccgga ggaaggggag  120
ctcaggcccc agctgctgga ccggttcggg atgcacgcgc aggttggtac cgtcaggac   180 gccgagctca gggtgaagat cgtggaggag agggctcgtt tcgacaggga tccgaagacg  240
ttccgtgagt cgtatcatga cgagcaggag aagctccagc agatatc atctgcacgg     300 agtaac                                                              306

<210> SEQ ID NO 629
<211> LENGTH: 269
<212> TYPE: DNA
<213> ORGANISM: Zea mays

<400> SEQUENCE: 629
acctcgttga cgtgctgctg gattccgctg cgtcggggtg gaacacggtg gagagggagg    60
gtatctccat atcccacccct gctcgcttca tcctcatcgg ctctggtaac ccggggaagg  120
ggagctcagg ccccagctgc tggaccggtt cgggatgcac gcgcaggttg gtaccgtcag  180
ggacgccgag ctcagggtga agatcgtgga ggagagggct cgtttcgaca gggatccgaa  240
gacgttccgt gagtcgacca tgacgagca                                    269

<210> SEQ ID NO 630
```

<211> LENGTH: 269
<212> TYPE: DNA
<213> ORGANISM: Zea mays

<400> SEQUENCE: 630

```
caccctgctc gcttcatcct catcggctct ggtaacccgg aggaagggga gctcaggccc      60
cagctgctgg accggttcgg gatgcacgcg caggttggta ccgtcaggga cgccgagctc     120
agggtgaaga tcgtggagga gagggctcgt ttcgacaggg atccgaagac gttccgtgag     180
tcgtaccatg acgagcagga gaagtccagc agcagatatc atctgcacgg ataacttggc     240
gctgtgcaga ttgaccatga ctccgtgtc                                       269
```

<210> SEQ ID NO 631
<211> LENGTH: 433
<212> TYPE: DNA
<213> ORGANISM: Zea mays

<400> SEQUENCE: 631

```
cgtcgacctg ctcccggaca tccgcgtcgt cgtcggcgac cccttcaact ccgacccgga      60
cgaccccgag gtcatgggcc ccgaggtccg ccagcgggtc ctgcaggggg acaccggcct     120
ccccgtcacc accgccaaga tcaccatggt cgacctgccc ctcggcgcca ccgaggaccg     180
cgtctgcggc accattgaca tcgagaaggc gctcaccgag ggcgtcaagg cgttcgagcc     240
cggcctgctc gccaaggcca acaggggcat actgtacgtc gacgaggtca acctgctgga     300
cgaccacctc gtcgacgtgc tgctggattc cgctgcgtcg gggtggaaca cggtggagag     360
ggagggtatc tccatatccc accctgctcg cttcatcctc atcggctctg gtaacccgga     420
ggaagggagg ctc                                                        433
```

<210> SEQ ID NO 632
<211> LENGTH: 281
<212> TYPE: DNA
<213> ORGANISM: Zea mays

<400> SEQUENCE: 632

```
ggggcacggg gaagtccacc accgtccgct ccctcgtcga cctgctcccg gacatccgtc      60
gtcgtcgtcg gcgaccccct caactccgac ccggacgacc ccgaggtcat gggcccgag     120
gtccgccagc gggtcctgca gggggacacc ggcctccccg tcaccaccgc caagatcacc     180
atggtcgacc tgccccctcg gcgccaccga gaccgcgtct gcggcaccat tgacatcgag     240
aaggcgctca ccgagggcgt caaggcgttc gagcccggcc t                         281
```

<210> SEQ ID NO 633
<211> LENGTH: 273
<212> TYPE: DNA
<213> ORGANISM: Zea mays

<400> SEQUENCE: 633

```
tgcccctcgg cgccaccgag gaccgcgtct gcggcaccat tgacatcgag aaggcgctca      60
ccgagggcgt caaggcgttc gagcccggcc tgctcgccaa ggccaacagg gcatactgt     120
acgtcgacga ggtcaacctg ctggacgacc acctcgtcga cgtgctgctg gattccgctg     180
cgtcggggtg gaacacggtg gagagggagg gtatctccat atcccaccct gctcgcttca     240
tcctcatcgg ctctggtaac cggaggaag ggg                                   273
```

<210> SEQ ID NO 634
<211> LENGTH: 227

<212> TYPE: DNA
<213> ORGANISM: Zea mays

<400> SEQUENCE: 634

```
agatcggcgg cgtcatgatc atgggcgaca ggggcacggg gaagtccacc accgtccgct    60
ccctcgtcga cctgctcccg gacatccgcg tcgtcgtcgg cgaccccttc aactccgacc   120
cggacgaccc cgaggtcatg gccccgagg tccgccagcg ggtcctgcag ggggacaccg    180
gcctccccgt caccaccgcc aagatcacca tggtcgacct gcccctc                 227
```

<210> SEQ ID NO 635
<211> LENGTH: 372
<212> TYPE: DNA
<213> ORGANISM: Zea mays

<400> SEQUENCE: 635

```
cccacgcgtc cgggcaagtc gtcaatgttg ccaacaacct cagcaagata cttggtttcg    60
gcctgtcgga accatgggtg cagtacctgt ccacgaccaa gttcgtcaga gcggacagag   120
agaagatgag ggttctgttt gggttcttgg gggagtgcct gaggctcgtc gtgcaagaca   180
acgagctggg aagcttgaag cttgccctcg agggaagcta cgtcgagcct ggccctggcg   240
gcgacccgat ccgtaacccg aaggtgctcc gacagggaa gaacatccac gctctcgatc    300
cgcaggccat cccaaccacg gctgccttga gagcgccaa gatcgtcgtg taccgtctcc    360
tggagaggca ga                                                       372
```

<210> SEQ ID NO 636
<211> LENGTH: 263
<212> TYPE: DNA
<213> ORGANISM: Zea mays

<400> SEQUENCE: 636

```
gttcgtcaga gcggacagag agaagatgag ggttctgttt gggttcttgg gggagtgcct    60
gacggtcgtc gtgcaagaca acgagctggg aagcttgaag cttgccctcg agggaagcta   120
cgtcgagcct ggccctggcg gcgacccgat ccgtaacccg aaggtgctcc gacagggaa    180
gaacatccac gctctcgatc cgcaggccat cccaaccacg gctgccttga gagcgccaa    240
gatcgtcgtg gaccgtctcc tgg                                           263
```

<210> SEQ ID NO 637
<211> LENGTH: 272
<212> TYPE: DNA
<213> ORGANISM: Zea mays

<400> SEQUENCE: 637

```
cccacgcgtc cggttgccaa caacctcagc aagatacttg gtttcggcct gtcggaacca    60
tgggtgcagt acctgtccac gaccaagttc gtcagagcgg acagagagaa gatgagggtt   120
ctgtttgggt tcttggggga gtgcctgatg ctcgtcgtgc aagacaacga gctgggaagc   180
ttgaagcttg ccctcgaggg aagctacgtc gagcctggcc ctggcggcga cccgatccgt   240
aacccgaagg tgctcccgac agggaagaac at                                 272
```

<210> SEQ ID NO 638
<211> LENGTH: 273
<212> TYPE: DNA
<213> ORGANISM: Zea mays
<220> FEATURE:
<223> OTHER INFORMATION: unsure at all n locations

```
<400> SEQUENCE: 638
gtttgggttc ttgggggagt gcctgangnt cgtcgtgcan acaangagc ttggaatctt      60 gaatcttgcc ctcgagggaa gctacgtcga gcctggccct gcggcgacc cgattncgta    120 acccgaaggt gctcccgaca ggaagaacat ctangctctt nnatccgcan gccatcccaa    180
ccacggctgc cttgaagagc gncaagatcg tcgtggaccg tctcctggag aggcagaagg    240
ctgacaatgg nggcaagtac cctgagacgg tcg                                 273

<210> SEQ ID NO 639
<211> LENGTH: 301
<212> TYPE: DNA
<213> ORGANISM: Zea mays

<400> SEQUENCE: 639
acttgctgaa gcacatagag gtgttcttta tgttgatgaa ataaatctat tggatgatgg     60
cataagcaat ctacttctga atgtcttgac ggagggagtt aacattgtgg aaagagaggg    120 cattagctt  cgccatcct gcaaaccact tctaattgct acttacaatc cagaggaagg    180
gtctgtacgt gaacacttgc ttgatcgtat tgcaattaat ttaagtgctg atcttccaat    240
gagttttgat gaccgcgttg aagcagtgga tattgcaaca cggtttcagg agtctagcaa    300
a                                                                    301

<210> SEQ ID NO 640
<211> LENGTH: 307
<212> TYPE: DNA
<213> ORGANISM: Zea mays

<400> SEQUENCE: 640
ggtgttcttt atgttgatga aataaatcta ttggatgatg gcataagcaa tctacttctg     60
aatgtcttga cggagggagt taacattgtg gaaagagagg gcattagctt tcgccatccc    120
tgcaaaccac ttctaattgc tacttacaat ccagaggaag gatctgtacg tgaacacttg    180
cttgatcgta tttgcagttaa tttaagtgct gatcttccaa tgagttttga tgaccgcgtt    240
gaagcagtgg atattgcaac acggtttcag gagtctaggc aagaagtttt caaattggtg    300
gaagaaa                                                              307

<210> SEQ ID NO 641
<211> LENGTH: 278
<212> TYPE: DNA
<213> ORGANISM: Zea mays
<220> FEATURE:
<223> OTHER INFORMATION: unsure at all n locations

<400> SEQUENCE: 641
tgttgatgaa ataaatctat tggatgatgg cataagcaat ctacttctgn atgtcgtgac     60
ggagggagtt aacattgtgg aaagagaggg gattagcttt cgccatccct gcaaaccact    120
tctaattgct acttacaatc cagaggaagg atctgtacgt gaacactctg ctgatcgtat    180
tgcattaatt aagtgctgat cagcaatgag tttgatgacg cgttgaacat ggatatcaca    240
ccggttcaga gctacaagaa tttcaatcgt ggagaaaa                            278

<210> SEQ ID NO 642
<211> LENGTH: 426
<212> TYPE: DNA
<213> ORGANISM: Zea mays

<400> SEQUENCE: 642
```

```
cccacgcgtt cgcccacgcg ttcgcggtga caagggtgtt ctcgaacgca tcaggctggt      60
actcgtccaa cgtgaacctg ccgtggagaa cgcgtcatg gaccgacgag aagcagctcc     120
aggacatgta cctgagccgc aagtccttcg cgttcgacag cgacgcccca ggggcaggca    180
tgaaggagaa gcgcaaggcg ttcgagctcg ccctggcgac ggcggacgcc acgttccaga    240
acctcgactc gtcggagatc tcgctgacgg acgtgagcca ctacttcgac tcggaccccga   300 ccaagctcgt gcaggggctg cgcaaggacg ggcgggcgcc gtcctcgtac atagccgaca    360
ccaccacggc gaacgcccag gtgaggacgc tgtcggagac ggtgcgcctc gacgcgagga    420
ccaagc                                                               426

<210> SEQ ID NO 643
<211> LENGTH: 312
<212> TYPE: DNA
<213> ORGANISM: Zea mays

<400> SEQUENCE: 643
ccgcgtgtcg ctaagggagg cggcgacaag ggtgttctcg aacgcatcac gctcctactc     60
gtccaacgtg aacctggccg tggagaacgc gtcatggacc gacgagaagc agctccagga   120
catgtacctg acccgcaagt ccttcgcgtt cgacagcgac gccccagggg caggcatgaa   180
ggagaagcgc aaggcgttcg acctcgccct ggcgacggcg gacgccacgt tccagaacct   240
cgactcgtcg gagatctcgc tgacggacgt gagccactac ttcgactcgg acccgaccaa   300
gctcgtgcag gg                                                       312

<210> SEQ ID NO 644
<211> LENGTH: 287
<212> TYPE: DNA
<213> ORGANISM: Zea mays

<400> SEQUENCE: 644
acgtgagcca ctacttcgac tcggacccga ccaagctcgt gcaggggctg cgcaaggacg     60
ggcgggcgcc gtcctcgtac atagccgaca ccaccacggc gaacgccagg tgaggacgct   120
gtcggagacg gtgcgcctcg acgcgaggac caagctgctg aaccccaagt ggtacgaggg   180
gatgatgaag agcgggtacg agggggtcag ggagatcgag aagcggctca ccaacaccgt   240
cgggtggagc gccacgtctg ggcaggtcga caactgggtc tacgagg                 287

<210> SEQ ID NO 645
<211> LENGTH: 279
<212> TYPE: DNA
<213> ORGANISM: Zea mays

<400> SEQUENCE: 645
gtacctgagc cgcaagtcct tcgcgttcga cagcgacgcc caggggcag gcatgaagga     60 gaagcgcaag gcgttcgagc tcgccctggc gacggcggac gccacgttcc agaacctcga   120
ctcgtcggag atctcgctga cggacgtgag ccactacttc gactcggacc cgaccaagct   180
cgtgcagggg ctgcgcaagg acgggcgggc gccgtcctcg tacatagccg acaccaccac   240
ggcgaacgcc aggtgaggac gctgtcggag acggtgcgc                          279

<210> SEQ ID NO 646
<211> LENGTH: 280
<212> TYPE: DNA
<213> ORGANISM: Zea mays
```

```
<400> SEQUENCE: 646
aagatggtgg ccgaactgga cgagccagca gagatgaact acgtgcgaat accccaggag      60
taggcggagg agctcggcgt gtcgctaagg gaagcggcga caagggtgtt ctcgaacgca     120
tcaggctcct actcgtccaa cgtgaacctg gcggtggaga acgcgtcatg gaccgacgat     180
aagcagctcc aggacatgta cctgagccgc aagtccttcg cgttcgacag cgacgcccct     240
ggggcaggca tgaaggagaa cgcaaggcg ttcgagctcg                            280

<210> SEQ ID NO 647
<211> LENGTH: 213
<212> TYPE: DNA
<213> ORGANISM: Zea mays

<400> SEQUENCE: 647
ggcgacggcg gacgccacgt tccagaacct cgactcgtcg gagatctcga tgacggacgt      60
gagccactac ttcgactcgg acccgaccaa gctcgtgcag gggctgcgca aggacgggcg     120
ggcgccgtcc tcgtacatag ccgacaccac cacggcgaac gcccaggtga ggacgctgtc     180
ggagacggtg cgcctcgacg cgaggaccaa gct                                  213

<210> SEQ ID NO 648
<211> LENGTH: 166
<212> TYPE: DNA
<213> ORGANISM: Zea mays

<400> SEQUENCE: 648
aagcacgccc aggagcaggc ggaggagctc ggcgtgtcgc taagggaggc ggcgacaagg      60
gtgttctcga acgcatcagg ctcctactcg tccaacgtga acctgacggt ggagaacgcg     120
tcatggaccg acgagaagca gctccaggac atgtacctga gccgca                    166

<210> SEQ ID NO 649
<211> LENGTH: 449
<212> TYPE: DNA
<213> ORGANISM: Zea mays

<400> SEQUENCE: 649
gggatgatga agagcgggta cgaggggggtc agggagatcg agaagcggct caccaacacg      60
cgtcgggtgg agcgccacgt ctgggcaggt cgacaactgg gtctacgagg aggccaactc     120
cacgttcatc gaggacgagg cgatgaggaa gaggctcatg gacaccaacc ccaattcgtt     180
caggaagttg gtgcagacct tcctggaagc cagtggcaga ggctactggg agacaacgga     240
ggagaacctg gacaggctca gggagctcta ttcggaggtt gaagacaaga ttgaggggat     300
tgacaggtaa attgatttgc cagatcggtc ggccgatcgg ttccagcatt caacccataa     360
cgagcttgga actcttctgc ctcattggga ctcttgtaca atgtctgggt gtgtgattta     420
tatatatata aaagtgtaac atgtaatac                                       449

<210> SEQ ID NO 650
<211> LENGTH: 305
<212> TYPE: DNA
<213> ORGANISM: Zea mays

<400> SEQUENCE: 650
cgagaagcgg ctcaccaaca ccgtcgggtg gagcgccacg tctgggcagg tcgacaactg      60
ggtctacgag gaggccaact ccacgttcat cgaggacgag gcgatgagga agaggctcat     120
ggacaccaac cccaattcgt tcaggaagtt ggtgcagacc ttcctggaag ccagtggcag     180
```

```
aggctactgg gagacaacgg aggagaacct ggacaggctc agggagctct attcggaggt    240
tgaagacaag attgagggga ttgacaggta aattgatttg ccagatcggt cggccgatcg    300
gttcc                                                               305

<210> SEQ ID NO 651
<211> LENGTH: 270
<212> TYPE: DNA
<213> ORGANISM: Zea mays

<400> SEQUENCE: 651
gacgcgagga ccaagctgct gaaccccaag tggtacgagg ggatgatgaa gagcgggtac     60
gagggggtca gggagatcga gaagcggctc accaacaccg tcgggtggag cgccacgtct    120
gggcaggtcg acaactgggt ctacgaggag gccaactcca cgttcatcga ggacgaggcg    180
atgaggaaga ggctcatgga caccaacccc aattcgttca ggaagttggt gcagaccttc    240
ctggaagcca gtggcagagg ctactgggag                                    270

<210> SEQ ID NO 652
<211> LENGTH: 440
<212> TYPE: DNA
<213> ORGANISM: Zea mays
<220> FEATURE:
<223> OTHER INFORMATION: unsure at all n locations

<400> SEQUENCE: 652
cattgttcag ctgccggctc agtatctgag actcgtgggt cgtcacaagc ctctacactg     60
acgtcctact aggacgaggc gatgaggaag aggctcatgg acaccaaccc caattcgttc    120
aggaagttgg tgcagacctt cctggaagcc agtggcagag gctactggga gacaacggag    180
gagaacctgg acaggctcag ggagctctat tcggaggttg aagacaagat tgagggatt     240 gacaggtaaa ttgatttgcc agatcggtcg gccgatcggt ccagcattc aacccataac     300 gagcttggaa ctcttctgcc tcattgggac tcttgtacaa tgtctgggtg tgtgatttat    360
atatatataa aaagttgtaa catgtaatac tggaggatac aatatttaac anagagggtg    420
gcggttgttc catccaaaac                                               440

<210> SEQ ID NO 653
<211> LENGTH: 213
<212> TYPE: DNA
<213> ORGANISM: Zea mays

<400> SEQUENCE: 653
tgcagatccg gacattatcc gtcttcctag gctctttcgc tttctgcaga agccacttgc     60
aaaattcata tcagaagtga gagcaccaaa aagtaaggaa ggttatgcat ccataggtgg    120
cggttctcct ctacgacaaa ttactgatgc acaggctgaa gcactgaggg aggcattaca    180
tgggaaagat gccctgccaa cgtgtatgtt gga                                 213

<210> SEQ ID NO 654
<211> LENGTH: 261
<212> TYPE: DNA
<213> ORGANISM: Zea mays

<400> SEQUENCE: 654
cccacgcgtc cgggtaccct ttcacagaag aggccattga tcaaattaaa aaggataaga     60
ttaccaagct cgttgttctt cccctttacc ctcagtactc catatcaaca agtgggtcaa    120
```

```
gcattcgtgt tctccaagac attgtcaagg aagattcata tttttctggt ttgccaattt    180
ccattattga atcatggtac caacgagatg gctatgtgaa atcaatgtct gacctaattg    240
aaaaggagct ctcggccttc t                                              261
```

```
<210> SEQ ID NO 655
<211> LENGTH: 291
<212> TYPE: DNA
<213> ORGANISM: Zea mays

<400> SEQUENCE: 655
tgagatccag aggaatctta aatggtcaca ctttggcgta tcagagtcgg gtgggaccag    60
ttcaatggct gaagccatat actgatgaag ttttagtaga aattggtcag aacggtgtga    120
agagcctcct ggctgttcca gtaagcttcg tgagcgagca cattgagaca ctggaagaaa    180
tagacatgga gtacaaggag ttggctctgg aatcaggcat tgagaactgg gccgggtcc    240 ctgctcttgg atgcacttcg acgttcatct ccgacttgca gatgcggttg t            291
```

```
<210> SEQ ID NO 656
<211> LENGTH: 275
<212> TYPE: DNA
<213> ORGANISM: Zea mays

<400> SEQUENCE: 656
actgctagca gcatacgact cgaagcgcga tgagctccct ccaccggtaa tcgtgtggga    60
gtggggctgg acaaagagcg cggagacctg aatagccgt gcggcgatgc tggccgtgct    120
ggctctcctg gtgctggaag tgaccaacgg cgaagggttc ctgcatcaat ggggaatcct    180
gcctctgttc cgctgagccg acaattctgt tcatgatggg gtcataattt tgctgcagcc    240
gaaggaagtt ttgaacttct gatgctgtat atgaa                              275
```

```
<210> SEQ ID NO 657
<211> LENGTH: 261
<212> TYPE: DNA
<213> ORGANISM: Zea mays
<220> FEATURE:
<223> OTHER INFORMATION: unsure at all n locations

<400> SEQUENCE: 657
atcaagagga atcttagata gtcatacttt ggcgtaccag aatcgggtgg agctagttca    60
atggctgaag ctatatactg atgaagtatt agtagaactt ggtgaaaagg gtgtgaagag    120
cctactggct gttacagtaa gccttgagag taaagacatc gagacattgg aagaaattga    180
catggagtac aaggagttgg ctctggaatc aggcatcaag aactggggtc gggttcctgc    240
tctgatnnac acttcaacat t                                              261
```

```
<210> SEQ ID NO 658
<211> LENGTH: 398
<212> TYPE: DNA
<213> ORGANISM: Zea mays

<400> SEQUENCE: 658
acggacgcgt gggtttagca taacacgggg tgcatgcaca tgtatccgat tccctgcatc    60
actcacacct cacttttttct gctaaattgt ggcagtggtg ataattgata tgcatagact    120
gtacttattt aatgactatg aaataccatt aacatagct attgtgcctg acagggtaaa    180
tctaccaagg acacacatag ttaagccttg ctcagctgac gactgctaag gaatttctgt    240
taagtgcagt ttgggggggtc ttctcaaccca ttgcttgact taaggcaaca cattagagga   300
```

```
tattcatcag catcagaggc aattcttccc aatctgattt gagaaaaaaa tttgttggca    360
acgaaaaatt agtgttttct tgctgaatct tgggggc                            398

<210> SEQ ID NO 659
<211> LENGTH: 356
<212> TYPE: DNA
<213> ORGANISM: Zea mays

<400> SEQUENCE: 659
gctttgatca tgggggagtt aagatcaaga ggaatcttaa atagtcacac tttggcgtac     60
caggtaaatg ctattaaaat ttggtaggta attgtttcac taacaacgga gttgtgccct    120
tatgttttaa tgatcacctt gtaagaacac taggaatgga aactgccaag ttatataggc    180
ttcaggagtt accagttcct taattttcca ggtcaccatt aactagtgtt aacatttatt    240
gtacacgcag agtcgggtgg ggccagttca atggctgaag ccatatactg atgaagtttt    300
agtagaactt ggtcaaaagg gtgttaagag cctcctggct gttccagtaa gctttg        356

<210> SEQ ID NO 660
<211> LENGTH: 266
<212> TYPE: DNA
<213> ORGANISM: Zea mays

<400> SEQUENCE: 660
cccacgcgtc cgaaagatgt tcctgccaac gtgtatgttg aatgcggta ttggcatccc      60 ttcactgaag aagccataga acaaataaaa cgggatggaa tcacgaaact tgttgtgttg    120
cctctatacc ctcagttctc catatcaact agtggttcaa gtctccgttt attggagagc    180
atattcagag aggatgagta tctcgtgaat atgcaacata cagttatacc ttcctggtac    240
caacgtgaag gatatatcaa ggctat                                         266

<210> SEQ ID NO 661
<211> LENGTH: 260
<212> TYPE: DNA
<213> ORGANISM: Zea mays

<400> SEQUENCE: 661
cggacgcgtg gcgcgacgcg tgggcggacg cgtgggcgga cggtggggaa agatgttcct     60
gccaacgtgt atgttggaat gcggtattgg catccctatc actgaagaag ccatagaaca    120
aacaaaacgg gatgcaatca cgaaacttgt tgtgttgcct ctatacctc agttctccat    180 atcaactagt ggttcaagtc tccgtttatt ggagagcata ttcagagagg atgagtatct    240
cgtgaatatg caacatacag                                                260

<210> SEQ ID NO 662
<211> LENGTH: 195
<212> TYPE: DNA
<213> ORGANISM: Zea mays

<400> SEQUENCE: 662
cccacgcgtc cgcccacgcg tccgcccacg cgtccgccca cgcgtccgat ggaatcacga     60
aacttgttgt gttgcctcta taccctcagt tctccatatc aactagtggt tcaagtctcc    120
gtttattgga gagcatattc agagaggatg agtatctcgt gaatatgcaa catacagtta    180
taccttcctg gtacc                                                     195

<210> SEQ ID NO 663
```

```
<211> LENGTH: 430
<212> TYPE: DNA
<213> ORGANISM: Zea mays
<220> FEATURE:
<223> OTHER INFORMATION: unsure at all n locations

<400> SEQUENCE: 663
gccgccgttg ggccttttgc cggcgacggg aacccatcac accaggtcat ggggcaaaac      60
aacctccaca agttttactg gttctaccac caaacatgag cagagcttgc atggaaatgt     120
taagccgttg caattggcgg caaatgaatc ctctcgtttg cttacagaa gtccagcact      180 taaaaaccag tggaatcttc ctgctagttc ttcctccact aatgtggtta ccacctttga     240
tgataacgaa cacgtgtctt ccagtgttat tgaagaaaaa gttggagtac tgttattaaa     300
ccttggtggt ccagagacac ttgacgatgt tcaaccattt ttattcaacc tatttgctga     360
tccagatatc attcgactcc ctangctctt caagtttcct cnaagacact gggcaaacnt     420 ntatttaatt                                                             430

<210> SEQ ID NO 664
<211> LENGTH: 199
<212> TYPE: DNA
<213> ORGANISM: Zea mays

<400> SEQUENCE: 664
aaacaacctc cacaagtttt actggttcta ccaccaaaca tgagcagagc ttgcatggaa      60
atgttaagcc gttgcaattg gcggcaaatg aatcctctcg tttggcttac agaagtccag     120
cacttaaaaa ccagtggaat cttcctgcta gttcttcctc cactaatgtg gttaccacct     180
ttgatgataa cgaacacgt                                                   199

<210> SEQ ID NO 665
<211> LENGTH: 443
<212> TYPE: DNA
<213> ORGANISM: Zea mays

<400> SEQUENCE: 665
gccacgtttg gtagttgcta cttgctacac cggaggaaga agaacaagta gtgcttttct      60
tctcttgtca cgttcacggg gcggccgatc gaccgttcac ctcgcccgac ggcccaagca     120
gcccatgtct tcgtcgggcc cctccccggc gacgggaatc cacgcgtcgc cgccgttggg     180
ccttttgccg gcgacgggaa cccatcacac caggtcatgg ggcaaaacaa cctccacaag     240
ttttactggt tctaccacca aacatgagca gagcttgcat ggaaatgtta agccgttgca     300
attggcggca aatgaatcct ctcgtttggc ttacagaagt ccagcactta aaaaccagtg     360
gaatcttcct gctagttctt cctccactaa tgtggttacc acctttgatg ataacgaaca     420
cgtgtcctcc agtgttattg aag                                              443

<210> SEQ ID NO 666
<211> LENGTH: 304
<212> TYPE: DNA
<213> ORGANISM: Zea mays

<400> SEQUENCE: 666
gagactccat atcaacaagt agcatatttt ttactaagaa gaagagaagg gaagattcat      60
atttttctgg cttgccaatc tccattatcg aatcatggta ccaacgtgat ggctatgtga     120
aatcaatggc tgacctaatt gaaaagagc tatctgcctt ttccaatcct gaagaggtaa     180
tgatatgctt cagtgcacat ggtgtgccac ttacctatgt tcaggatgct ggagatcctt     240
```

```
acagagatca gatggaggat tgtatttctg tgatcatggg ggagctgaga tccagaggaa    300
tctt                                                                 304
```

<210> SEQ ID NO 667
<211> LENGTH: 256
<212> TYPE: DNA
<213> ORGANISM: Zea mays

<400> SEQUENCE: 667

```
ttcgtgttct ccgaaatgtt gtcaagggag attcatattt ttctggcttg gcaatctcca    60
gtatcgaatc atggtagcaa cgtgatggct atgtgaaatc agtggctgac ctgattgaga   120
aagaggtatc tgccttttcc agtcctgaag aggtagtgat attcttcagt gcacatagtg   180
tgccacttag ctatgtgcag gatgctggag atccttacag agatcagatg gatgattgta   240
tttctttgat cgtggg                                                    256
```

<210> SEQ ID NO 668
<211> LENGTH: 263
<212> TYPE: DNA
<213> ORGANISM: Zea mays

<400> SEQUENCE: 668

```
agaggttatg atattcttca gtgcacatgg tgtgccactt acctatgttg aggatgctgg    60
agatccttac agagatcaga tggaggattg tattgctttg atcatggggg agttaagatc   120
aagaggaatc ttaaatagtc acactttggc gtaccagagt cgggtggggc cagttcaatg   180
gctgaagcca tatactgatg aagttttagt agaacttggt caaaagggtg tgaagagcct   240
catggctgtt ccagtaagct ttg                                            263
```

<210> SEQ ID NO 669
<211> LENGTH: 266
<212> TYPE: DNA
<213> ORGANISM: Zea mays

<400> SEQUENCE: 669

```
agaggttatg atattcttca gtgcacatgg tgtgccactt acctatgttg aggatgctgg    60
agatccttac agagatcaga tggaggattg tattgctttg atcatggggg agttaagatc   120
aagaggaatc ttaaatagtc acactttggc gtaccagagt cgggtggggc cagttcaatg   180
gctgaagcca tatactgatg aagttttagt agaacttggt caaaagggtg tgaagagcct   240
cctggctgtt ccagtaagct ttgtga                                         266
```

<210> SEQ ID NO 670
<211> LENGTH: 276
<212> TYPE: DNA
<213> ORGANISM: Zea mays

<400> SEQUENCE: 670

```
atctgccttt tccaatcctg aagaggtaat gatattcttc agtgcacatg gtgtgccact    60
tacctatgtt caggatgctg gagatcctta cagagatcag atggaggatt gtatttcttt   120
gctcatgggg gagctgagat ccagaggaat cttaaatggt cacactttgg cgtatcagag   180
tcgggtggga ccagttcaat ggctgaagcc atatactgat gaagttttag tagaacttgg   240
tcagaacggt gtgaagagcc tcctggctgt tccagt                              276
```

<210> SEQ ID NO 671

<211> LENGTH: 307
<212> TYPE: DNA
<213> ORGANISM: Zea mays

<400> SEQUENCE: 671

```
ctgttattaa accttggtgg tccagagaca cttgacgatg ttcaaccatt tttattcaac      60
ctatttgctg atccagatat cattcgactc cctaggctct tcaggtttct tcaaagacca     120
ctggccaaac ttatttctac ttttagagct cctaagagta aagaagggta tgcttcaatg     180
gtggtgggtc gccgttaagg aaaattactg atgaacaggc gaatgctttg aagattgccc     240
tggaaaagaa aaaattgaac gcaaacatat atgttgggat gcggtattgg tacccttttca    300
cagaaga                                                              307
```

<210> SEQ ID NO 672
<211> LENGTH: 310
<212> TYPE: DNA
<213> ORGANISM: Zea mays

<400> SEQUENCE: 672

```
ctgttattaa accttggtgg tccagagaca cttgacgatg ttcaaccatt tttattcaac      60
ctatttgctg atccagatat cattcgactc cctaggctct tcaggtttct tcaaagacca     120
ctggccaaac ttatttctac ttttagagct cctaagagta aagaagggta tgcttcaatt     180
ggtggtgggt cgccgttaag gaaaattact gatgaacagg cgaatgcttt gaagattgcc     240
ctggaaaaga aaaaattgaa cgcaaacata tatgttggga tgcggtattg gtaccctttc     300
acagaagagg                                                            310
```

<210> SEQ ID NO 673
<211> LENGTH: 122
<212> TYPE: DNA
<213> ORGANISM: Zea mays

<400> SEQUENCE: 673

```
cccacgcgtc cggcttcaat cggtggtggg tcaccattga ggaaaattac tgatgagcag      60
gcaaatgctt tgaagattgc tctggaaaag aaaaaattga acgcaaatat atatgttggg    120
at                                                                   122
```

<210> SEQ ID NO 674
<211> LENGTH: 431
<212> TYPE: DNA
<213> ORGANISM: Zea mays
<220> FEATURE:
<223> OTHER INFORMATION: unsure at all n locations

<400> SEQUENCE: 674

```
cggacgcgtg ggttggacca gtggaatggc tgaaaccgta cactgatgag acagtgatgg      60
agcttgggca gaaaggggta aagagcctgc ttgctgttcc cattagtttt gttagcgaac     120
acattgaaac tttggaagaa atcgatgtgg agtacaaaga gttggctttg aatctggca     180
tcaagcactg gggacgggtt ccagcactag gttgcgaacc cacattcatt tcggatcttg     240
ctgatgctgt tattgaaagc ctaccttatg ttggcgcaat ggcagtttcc aatcttgagg     300
ctcggcagtc tctcgtaccc ctcggagcg tggaggagct gctagcagca tacgactcga     360
agcgcgatga gctccctcca ccggtaatcg tgtgggagtg gngctggaca aagagcgcgg     420
agacctggaa t                                                         431
```

```
<210> SEQ ID NO 675
<211> LENGTH: 298
<212> TYPE: DNA
<213> ORGANISM: Zea mays

<400> SEQUENCE: 675
agactggaaa aaagaggaat aacaaatccg tgcatacttg cttatcagag ccgagttgga        60
ccagtggaat ggctgaaacc gtacactgat gagacaatta ttgagcttgg gcagaaaggg       120
gtaaagagcc tgcttgctgt tcccattagt tttgttagcg aacacattga aactttggaa      180
gaaatcgatg tggagtacaa agagttggct ttggaatctg gcatcaagca ctggggacgg      240
gttccagcac taggttgcga acccacattc atttcggatc ttgctgatgc tgttattg        298

<210> SEQ ID NO 676
<211> LENGTH: 308
<212> TYPE: DNA
<213> ORGANISM: Zea mays

<400> SEQUENCE: 676
gagacgcgtg gcggacgcgt gggcggacgc gtgggccga gttggaccag tggaatggct        60
gaaaccgacc actgatgaga ctattattga gattgggcag aaagggtaa agagcctgct       120 tgctgttccc attagttttg ttagcgaaca cattgaaact ttggaagaaa tcgatgtgga      180
gtacaaagag ttggctttgg aatctggcat caagcactgg gacgggttc cagcactagg      240 ttgcgaaccc acattcattt cgtatcttgc tgatgctgtt attgaaacct accttatgtt      300
ggcgcatg                                                               308

<210> SEQ ID NO 677
<211> LENGTH: 174
<212> TYPE: DNA
<213> ORGANISM: Zea mays

<400> SEQUENCE: 677
cccacgcgtc cggcttgggc agaaaggggt aaagagcctg cttgctgttc ccattagttt        60
tgttagcgaa cacattgaaa ctttggaaga aatcgatgtg gagtacaaag agttggcttt      120
ggaatctggc atcaagcact ggggacgggt tccagcacta ggttgcgaac ccac            174
```

NUCLEIC ACID MOLECULES ENCODING A FERROCHELATASE ENZYME OR FRAGMENT THEREOF

CROSS-REFERENCE TO RELATED APPLICATIONS

This application is a continuation of U.S. application Ser. No. 09/233,218 filed Jan. 20, 1999 now abandoned, which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998 and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998 application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998 application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998, and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22 , 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998 application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998, and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No.

60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. All of the above-listed applications are herein incorporated by reference in their entirety.

INCORPORATION OF SEQUENCE LISTING

This application contains a sequence listing, which is contained on three identical CD-ROMs: two copies of a sequence listing (Copy 1 and Copy 2) and a sequence listing Computer Readable Form (CRF), all of which are herein incorporated by reference. All three CD-ROMs each contain one file called "15090C seq list.txt" which is 329,728 bytes in size (measured in Windows XP) and which was created on Jan. 11, 2006.

FIELD OF THE INVENTION

The present invention is in the field of plant biochemistry. More specifically the invention relates to nucleic acid sequences from plant cells, in particular, nucleic acid sequences from maize and soybean plants associated with the tetrapyrrole pathway in plants. The invention encompasses nucleic acid molecules that encode proteins and fragments of proteins. In addition, the invention also encompasses proteins and fragments of proteins so encoded and antibodies capable of binding these proteins or fragments. The invention also relates to methods of using the nucleic acid molecules, proteins and fragments of proteins and antibodies, for example for genome mapping, gene identification and analysis, plant breeding, preparation of constructs for use in plant gene expression and transgenic plants.

BACKGROUND OF THE INVENTION

I. Biosynthesis of Tetrapyrroles

The biosynthesis of tetrapyrroles such as heme and chlorophyll as well as a number of other tetrapyrroles such as siroheme, the cofactor for sulfite and nitrite reductases, cobalamin (vitamin B12), and the chromophore of phytochrome, can be subdivided into three major phases; ALA synthesis, porphyrin ring synthesis and synthesis of final products. The pathway is conserved among species except for the synthesis of 5-aminolevulinate, also known as 5-aminolevulinic acid ("ALA") (Porra, *Photochemistry and Photobiology* 65:492-516 (1997); von Wettstein et al., *Plant Cell* 7:1039-1057 (1995), both of which are herein incorporated by reference).

The first phase of the biosynthesis of tetrapyrroles, such as heme and chlorophyll, is the synthesis of ALA. Yeast, fungi, mammals and some bacteria (the α-group of proteobacteria or purple bacteria, e.g. *Bradyrhizobium japonicum* and *Rhodobacter capsulatus*) biosynthesize tetrapyrroles via the single step four-carbon (C4), or Shemin pathway. In this pathway ALA synthase (E.C. 2.3.1.37) catalyzes the condensation of glycine with succinyl-CoA to generate ALA.

Plants, green algae, cyanobacteria, most eubacteria (e.g. *E. coli* and *Bacillus subtilis*), and archaebacteria biosynthesize ALA via the three-step five-carbon ("C5") pathway, which includes glutamyl-tRNA synthetase ("GluRS"), glutamyl-tRNA reductase ("GluTR") and glutamate-1-semialdehyde aminotransferase ("GSA-AT"). In plants and algae, the C5 pathway is localized in the chloroplast. The formation of ALA via the C5 pathway is reported to be the rate-limiting step in the biosynthesis of heme and chlorophyll (Kumar et al., *Trends in Plant Science* 1:371-376 (1996); Tanaka et al., *Plant Physiol.* 110:1223-30 (1996); Masuda et al., *Plant Physiol. Biochem.* 34:11-16 (1996); Hungerer et al., *J. Bacteriol.* 177:1435-43 (1995); Ilag et al., *Plant Cell* 6:265-75 (1994), all of which are herein incorporated by reference in their entirety).

Chloroplastic GluRS (E.C. 6.1.1.17), also known as glutamate-tRNA ligase, converts glutamate to glutamyl-tRNA ("Glu-tRNA") activating the C-1 of glutamate in an ATP dependent reaction (Porra, *Photochemistry and Photobiology* 65:492-516 (1997); von Wettstein et al., *Plant Cell* 7:1039-1057 (1995)). Glu-tRNA is reported to be the first intermediate in the C5 pathway and it also reported to serve as a source of glutamate in protein biosynthesis. GluRS is a soluble plastid enzyme which has been isolated from higher plants (barley, wheat) and other organisms. Reported GluRS enzymes are homodimers encoded by a nuclear gene and synthesized in the cytoplasm and have a molecular weight of 54 kD (barley) and 56 kD (wheat).

GluTR, the first committed enzyme reported in heme and chlorophyll biosynthesis, catalyzes the NADPH dependent reduction of Glu-tRNA to glutamate 1-semialdehyde "GSA") with the release of intact tRNA (Porra, *Photochemistry and Photobiology* 65:492-516 (1997); von Wettstein et al., *Plant Cell* 7:1039-1057 (1995)). GluTR is reported as the rate limiting step in ALA formation and is present only at low levels in all organisms examined (Masuda et al., *Plant Physiol. Biochem.* 34:11-16 (1996); Schroeder et al., *Biochem. J.* 281: 843-50 (1992), the entirety of which is herein incorporated by reference; Masuda et al., *Plant Cell Physiol.* 36:1237-43 (1995), the entirety of which is herein incorporated by reference). Plant GluTR is a soluble enzyme localized in plastids and encoded in the nucleus. GluTR has been reported to exist as a multimer of a single subunit. The purified barley enzyme has a molecular weight of 270 kD with a monomeric subunit size of 54 kD (Pontoppidan and Kannangara, *Eur. J. Biochem.* 225:529-37 (1994), the entirety of which is herein incorporated by reference). *Arabidopsis* and cucumber enzymes have similar subunit molecular weights (Tanaka et al., *Plant Physiol.* 110:1223-30 (1996); Ilag et al., *Plant Cell* 6:265-75 (1994); Kumar et al., *Plant Mol. Biol.* 30:419-26 (1996), the entirety of which is herein incorporated by reference).

GluTR genes (also known as HEMA genes) have been cloned and the amino acid sequences determined for a number of sources including three higher plants; *Arabidopsis*, barley, and cucumber. The deduced amino acid sequence of GluTR from all sources exhibit about 60% overall similarity with stretches of amino acid identity. Barley, *Arabidopsis*, and cucumber show over 70% identity at the deduced amino acid level (Vothknecht et al., *Proc. Natl. Acad. Sci. (U.S.A.)*

93:9287-9291 (1996), the entirety of which is herein incorporated by reference). Two different GluTR genes have been isolated from three higher plants; *Arabidopsis* (Ilag et al., *Plant Cell* 6:265-75 (1994)), barley (Bougri and Grimm, *Plant J.* 9:867-878 (1996), the entirety of which is herein incorporated by reference), and cucumber (Masuda et al., *Plant Cell Physiol.* 36:1237-43 (1995), the entirety of which is herein incorporated by reference). In *Arabidopsis* and cucumber, one GluTR gene is expressed in all tissues and a second is expressed in a tissue specific manner. These genes are also reported to be differentially regulated by light (Tanaka et al., *Plant Physiol.* 110:1223-30 (1996); Masuda et al., *Plant Physiol. Biochem.* 34:11-16 (1996); Ilag et al., *Plant Cell* 6:265-75 (1994); Masuda et al., *Plant Cell Physiol.* 36:1237-43 (1995); Kumar et al., *Plant Mol. Biol.* 30:419-26 (1996); Hori et al., *Plant Physiol. Biochem.* 34:3-9 (1996), the entirety of which is herein incorporated by reference).

GSA-AT (glutamate-1-semialdehyde aminotransferase (E.C. 5.4.3.8)), catalyzes the conversion of GSA to ALA. GSA-AT is a soluble protein localized in the chloroplast and encoded in the nucleus (Porra, *Photochemistry and Photobiology* 65:492-516 (1997); von Wettstein et al., *Plant Cell* 7:1039-1057 (1995)). It has a subunit molecular weight of about 45 kD. The holoenzyme consists of two identical subunits and utilizes pyridoxal phosphate ("PLP") as a cofactor (Kumar et al., *Trends in Plant Science* 1:371-376 (1996); Gough et al., *Glutamate 1-semialdehyde aminotransferase as a target for herbicides*, Boeger, Ed., Lewis, Boca Raton, Fl., (1993), the entirety of which is herein incorporated by reference). GSA-AT is reported to be inhibited by gabaculine, which has also been shown to inhibit chlorophyll biosynthesis in barley leaves (Rogers and Smith, *BCPC Monogr.* 42:183-93 (1989), the entirety of which is herein incorporated by reference). QSA-AT has been crystallized from *Synechococcus* (Hennig et al., *J. Mol. Biol.* 242:591-594 (1994); Hennig et al., *Proc. Natl. Acad. Sci. (U.S.A.)* 94:4866-4871 (1997), both of which are herein incorporated by reference in their entirety).

GSA-AT genes have been cloned from a number of plants including *Arabidopsis*. The deduced amino acid sequences from plants are highly conserved. As with GluTR, two GSA-AT genes have been found in *Arabidopsis* and they may be differentially regulated by light. It has been reported that the presence of two genes for both enzymes of the C5 pathway indicate that there are two routes for ALA formation in chloroplasts (Kumar et al., *Trends in Plant Science* 1:371-376 (1996)). Transgenic tobacco plants that express antisense RNA to GSA-AT have been reported to show varying degrees of chlorophyll deficiency. Antisense plants with chlorophyll contents less than about 25% of that in the wild type plants which were maintained in the greenhouse under high light conditions, did not survive (Hennig et al., *Proc. Natl. Acad Sci. (U.S.A.)* 94:4866-4871 (1997); Hoefgen, et al., *Proc. Natl. Acad. Sci. (U.S.A.)* 91:1726-1730 (1994), both of which are herein incorporated by reference in their entirety).

The second phase of the biosynthesis of tetrapyrroles involves the formation of the porphyrin ring. The intermediates involved in this portion of the chlorophyll/heme biosynthetic pathway, from ALA to protoporphyrin IX, appear to be essentially the same in all organisms including plants and mammals.

Porphobilinogen synthase (E.C. 4.2.1.24), also known as ALA dehydratase, catalyzes the asymmetric condensation of two molecules of ALA to yield porphobilinogen (Porra, *Photochemistry and Photobiology* 65:492-516 (1997); von Wettstein et al., *Plant Cell* 7:1039-1057 (1995)). Porphobilinogen synthase is a metalloenzyme and there are different types of the enzyme categorized according to metal ion usage. Porphobilinogen synthase has been identified in several plants including spinach, pea, tomato, radish, and soybean. In higher plants the enzyme is located in the plastid, is a hexamer (40-50 kD subunits) and binds $Mg^{+2}$. The mammalian enzyme is an octamer and binds $Zn^{2+}$ (Cheung et al., *Biochemistry* 36:1148-1156 (1997); Senior et al., *Biochem. J.* 320:401-412 (1996), both of which are herein incorporated by reference in their entirety). Several studies have shown that porphobilinogen synthase is both developmentally and light regulated in plants (Kyriacou et al., *J. Am. Soc. Hortic. Sci.* 121:91-95 (1996), the entirety of which is herein incorporated by reference in its entirety).

Hydroxymethylbilane synthase (E.C. 4.3.1.8), also known as porphobilinogen deaminase, catalyzes the formation of the linear tetrapyrrole hydroxymethylbilane (Porra, *Photochemistry and Photobiology* 65:492-516 (1997); von Wettstein et al., *Plant Cell* 7:1039-1057 (1995)). The reaction involves the deamination and polymerization of four molecules of the monopyrrole porphobilinogen. Hydroxymethylbilane synthase is unusual in that it contains a novel dipyrromethane cofactor at the active site, which is self-assembled by the apoenzyme and is covalently attached to an invariant cysteine. The enzyme has been identified in mammals, yeast, bacteria, and plants (e.g., pea, spinach, *Arabidopsis*). Hydroxymethylbilane synthase exists as a monomer with a molecular weight of 33-44 kD. Hydroxymethylbilane synthase from *Arabidopsis* has been cloned and found to be localized in the plastid in both roots and leaves (Witty et al., *Planta* 199:557-564 (1996), the entirety of which is herein incorporated by reference). The 3-dimensional structure of porphobilinogen deaminase from *E. coli* has been determined (Louie et al., *Proteins: Struct., Funct., Genet.* 25:48-78 (1996), the entirety of which is herein incorporated by reference).

Uroporphyrinogen III (co)synthase (E.C. 4.2.1.75) catalyzes the ring closure of the unstable linear tetrapyrrole hydroxymethylbilane and the simultaneous isomerization of the acetyl and propionyl groups at pyrrole ring D forming uroporphyrinogen III (Porra, *Photochemistry and Photobiology* 65:492-516 (1997); von Wettstein et al., *Plant Cell* 7:1039-1057 (1995)). Uroporphyrinogen III (co)synthase has been isolated from a number of sources including mammals, bacteria, and plants (spinach). Uroporphyrinogen III (co)synthase has a molecular weight of about 30 kD and is highly diverse in primary structure depending on the source.

Uroporphyrinogen III decarboxylase (E.C. 4.1.1.37) catalyzes the stepwise decarboxylation of all four acetate side chains of uroporphyrinogen III starting with ring D followed by rings A, B, and C, respectively, to form coproporphyrinogen III (Porra, *Photochemistry and Photobiology* 65:492-516 (1997); von Wettstein et al., *Plant Cell* 7:1039-1057 (1995)). At high substrate concentrations, decarboxylation can occur randomly. Uroporphyrinogen III decarboxylase has been isolated from mammals, yeast, bacteria and plants (e.g., tobacco, barley). It is a monomeric enzyme with a molecular weight of about 40 kD. The barley and tobacco enzymes are reported to be light regulated (Mock et al., *Plant Mol. Biol.* 28:245-256 (1995), the entirety of which is herein incorporated by reference). Antisense tobacco plants have been generated and decreased levels of the enzyme were accompanied by a light-dependent necrotic phenotype and accumulation of uroporphyrinogen. It has been reported that the lesions may be caused by reactive oxygen species generated by photooxidized uroporphyrinogen (Mock et al., *Plant Mol. Biol.* 28:245-256 (1995), the entirety of which is herein incorporated by reference).

In aerobic organisms including plants, coproporphyrinogen III oxidase (E.C. 1.3.3.3), catalyzes the oxygen dependent sequential oxidative decarboxylation of the A and B propionyl side chains of coproporphyrinogen III to yield two vinyl groups and protoporphyrinogen IX (Porra, *Photochemistry and Photobiology* 65:492-516 (1997); von Wettstein et al., *Plant Cell* 7:1039-1057 (1995)). A separate enzyme is reported to catalyze the anaerobic reaction.

Coproporphyrinogen III oxidase has been studied in a number of organisms including plants (tobacco, pea). The enzyme is a homodimer and has a subunit molecular weight of about 35-40 kD and is located in plastids. It has been reported that coproporphyrinogen III oxidase is peripherally associated with the membrane. It has been isolated from soybean, barley and tobacco and these sequences show 70% identity at the amino acid level. Transcript levels are reportedly similar in etiolated and green leaves (barley) but higher in developing cells than in mature cells (Kruse et al., *Planta* 196:796-803 (1995), the entirety of which is herein incorporated by reference). Antisense tobacco plants have been reported with decreased levels of the enzyme. The decreased level was accompanied by accumulation of coproporphyrinogen, slightly reduced chlorophyll content and a necrotic phenotype. The prominent phenotype indicates photodynamic damage (Kruse et al., *EMBO J.* 14:3712-3720 (1995), the entirety of which is herein incorporated by reference).

Protoporphyrinogen IX oxidase (E.C. 1.3.3.4) catalyzes the formation of the aromatic protoporphyrin IX by the six electron oxidation of protoporphyrinogen IX (Porra, *Photochemistry and Photobiology* 65:492-516 (1997); von Wettstein et al., *Plant Cell* 7:1039-1057 (1995)). This is the last reported common step in tetrapyrrole biosynthesis. In aerobic organisms, the reaction is catalyzed by a flavoprotein that utilizes oxygen as an oxidant and, under anaerobic conditions, the oxidation is achieved by passing electrons to the electron transport chain. The enzyme has been purified from a number of sources including mammals and plants (barley) and is an integral membrane protein. The barley enzyme has a molecular weight of 36 kD and activity has been found in both plastidal and mitochondrial extracts.

The plastidal and mitochondrial forms of protoporphyrinogen IX oxidase have been cloned from tobacco and were found to exhibit low homology. The mitochondrial form is associated with heme biosynthesis. The plastidic enzyme functions primarily in the formation of chlorophyll and to a lesser extent in the formation of heme required for plastid proteins (Lermontova et al., *Proc. Natl. Acad. Sci.* (*U.S.A.*) 94:8895-8900 (1997), the entirety of which is herein incorporated by reference). Protoporphyrinogen IX oxidase is susceptible to inhibition by a number of herbicides including diphenyl ethers. Phytotoxicity has been explained as due to the accumulation of excess protoporphyrinogen which is rapidly oxidized to protoporphyrin in the cytoplasm. Protoporphyrin has been reported as a potent photosensitizer which generates singlet oxygen and causes rapid lipid peroxidation and cell death.

In the third and final phase of tetrapyrrole biosynthesis, magnesium or iron is inserted into protoporphyrin IX and subsequent modifications lead to the synthesis of the final tetrapyrrole products, such as chlorophyll and heme.

Mg-chelatase catalyzes the conversion of protoporphyrin IX to magnesium protoporphyrin IX by the insertion of $Mg^{+2}$ (Porra, *Photochemistry and Photobiology* 65:492-516 (1997); von Wettstein et al., *Plant Cell* 7:1039-1057 (1995)). Mg-chelatase, which requires ATP, is reportedly a three component enzyme. The three protein components have molecular weights of about 140, 40, and 70 kD. The reaction takes place in two steps, an ATP-dependent activation followed by an ATP-dependent chelation step. Mg-chelatase activity has been demonstrated in peas, cucumber, and barley and reportedly is localized in the chloroplast. Barley, *Arabidopsis*, and soybean genes encoding the 140 and 40 kD subunits have been cloned. Studies with the two identified plant genes show that Mg-chelatase expression is light regulated (Walker and Willows, *Biochem. J.* 327:321-333 (1997), the entirety of which is herein incorporated by reference).

Mg-protoporphyrin IX O-methyltransferase (E.C. 2.1.1.11) esterifies the propionic side chain of ring III of Mg-protoporphyrin IX to form Mg-protoporphyrin IX monomethylester (Porra, *Photochemistry and Photobiology* 65:492-516 (1997); von Wettstein et al., *Plant Cell* 7:1039-1057 (1995)). The methyl group is donated by the cofactor S-adenosyl-L-methionine. The enzyme has been isolated from bacteria and plants (wheat). The gene for Mg-protoporphyrin. IX O-methyltransferase has been cloned from bacteria including *Synechocystis* (Smith et al., *Plant Mol. Biol.* 30:1307-1314 (1996), the entirety of which is herein incorporated by reference).

Mg-protoporphyrin IX monomethyl ester cyclase catalyzes the cyclization of Mg-protoporphyrin IX monomethylester to form the isocyclic ring E of divinyl protochlorophyllide (Porra, *Photochemistry and Photobiology* 65:492-516 (1997)). In aerobic organisms the enzymatic reaction is dependent on $O_2$ and NADPH. Evidence suggests that Mg-protoporphyrin IX monomethyl ester cyclase is a membrane-bound monooxygenase of the iron-sulfur protein or copper protein type. Mg-protoporphyrin IX monomethyl ester cyclase has been extracted from chloroplasts of higher plants including cucumber and wheat. A cucumber enzyme has been shown to consist of two components, a soluble and a membrane-bound component. The soluble component has a molecular weight of 30 kD (Bollivar and Beale, *Plant Physiol.* 112:105-114 (1996), the entirety of which is herein incorporated by reference).

The reduction of divinyl protochlorophyllide to monovinyl protochlorophyllide has been reported based on product characterization, this reaction is catalyzed by 8-vinyl reductase (Porra, *Photochemistry and Photobiology* 65:492-516 (1997)). It has been reported that Mg-protoporphyrin IX monomethylester may also act as a substrate. NADPH is the most likely reductant. 8-vinyl reductase has been detected in higher plants including wheat and cucumber.

Protochlorophyllide reductase ("POR") (E.C. 1.3.1.33) catalyzes the reduction of the double bond between carbons 7 and 8 of the D ring of protochlorophyllide producing chlorophyllide (Porra, *Photochemistry and Photobiology* 65:492-516 (1997); von Wettstein et al., Plant Cell 7:1039-1057 (1995)). In angiosperms this is a light-dependent reaction. Non-flowering land plants, algae, and cyanobacteria contain both a light-dependent and a light-independent enzyme. Some other organisms contain only the light-independent enzyme. Three chloroplast genes have been identified that are essential for the light-independent enzyme (chlL, chlN and chlB).

The light-dependent POR ("L-POR") has been purified from barley, oat, and *Arabidopsis*. L-POR has a molecular weight of 35-38 kD and forms different multimers and aggregates with other proteins. L-POR is localized in the plastid and encoded in the nucleus. The genes encoding L-POR have been cloned from, for example, barley, *Arabidopsis*, pea, and oat. Two distinct and differentially light-regulated L-POR genes, POR A and POR B, have been identified in *Arabidopsis* and barley. POR A and POR B have biochemically equivalent light-dependent activities, with different expression patterns. POR B is reported to be present throughout the plant life cycle, while POR A is reported to function only in the very early stages of greening of etiolated tissue (Runge et al., *Plant J.* 9:513-523 (1996); Holtorf and Apel, *Plant Mol. Biol.* 31:387-392 (1996); Martin et al., *Biochem. J.* 325:139-145 (1997), all of which are herein incorporated by reference in their entirety).

Chlorophyll synthetase catalyzes the last reported step in chlorophyll a biosynthesis (Porra, *Photochemistry and Photobiology* 65:492-516 (1997); von Wettstein et al., *Plant Cell* 7:1039-1057 (1995)). Chlorophyll synthetase esterifies the propionic acid side chain of ring D of chlorophyllide with either phytyl pyrophosphate in green plants or geranylgeranyl pyrophosphate in greening etiolated seedlings. The enzyme is located in the plastid. A gene that encodes the enzyme in *Synechocystis* (chlG) and a gene that encodes the enzyme in *Arabidopsis* (G4) have been cloned and expressed in *E. coli*. The *Synechocystis* enzyme has the preferred substrate specificity reported for green plants. The cloned and expressed enzyme from *Arabidopsis* has the preferred substrate specificity reported for etiolated plants (Oster et al., *J. Biol. Chem.* 272:9671-9676 (1997); Oster and Rudiger, *Bot. Acta* 110: 420-423 (1997), both of which are herein incorporated by reference).

Ferrochelatase (E.C. 4.99.1.1) catalyzes the conversion of protoporphyrin IX to heme. In plants the enzyme is located in both mitochondria and plastids. Ferrochelatase is reported to be a single soluble protein. Two ferrochelatase genes have been identified in *Arabidopsis* Ferrochelatase-II encodes a protein targeted to the chloroplast and ferrochelatase-I encodes a protein targeted to both chloroplasts and mitochondria (Roper and Smith, *Eur. J. Biochem.* 246:32-37 (1997); Chow et al., *J. Biol. Chem.* 272:27565-27571 (1997), both of which are herein incorporated by reference).

II. Expressed Sequence Tag Nucleic Acid Molecules

Expressed sequence tags, or ESTs are randomly sequenced members of a cDNA library (or complementary DNA)(McCombie et al., *Nature Genetics* 1:124-130 (1992); Kurata et al., *Nature Genetics* 8.365-372 (1994); Okubo et al., *Nature Genetics* 2:173-179 (1992), all of which references are incorporated herein in their entirety). The randomly selected clones comprise insets that can represent a copy of up to the full length of a mRNA transcript.

Using conventional methodologies, cDNA libraries can be constructed from the mRNA (messenger RNA) of a given tissue or organism using poly dT primers and reverse transcriptase (Efstratiadis et al., *Cell* 7:279-3680 (1976), the entirety of which is herein incorporated by reference; Higuchi et al., *Proc. Natl. Acad. Sci.* (*U.S.A.*) 73:3146-3150 (1976), the entirety of which is herein incorporated by reference; Maniatis et al., *Cell* 8:163-182 (1976) the entirety of which is herein incorporated by reference; Land et al., *Nucleic Acids Res.* 9:2251-2266 (1981), the entirety of which is herein incorporated by reference; Okayama et al., *Mol. Cell. Biol.* 2:161-170 (1982), the entirety of which is herein incorporated by reference; Gubler et al., *Gene* 25:263-269 (1983), the entirety of which is herein incorporated by reference).

Several methods may be employed to obtain full-length cDNA constructs. For example, terminal transferase can be used to add homopolymeric tails of dC residues to the free 3' hydroxyl groups (Land et al., *Nucleic Acids Res.* 9:2251-2266 (1981), the entirety of which is herein incorporated by reference). This tail can then be hybridized by a poly dG oligo which can act as a primer for the synthesis of full length second strand cDNA. Okayama and Berg, *Mol. Cell. Biol.* 2:161-170 (1982), the entirety of which is herein incorporated by reference, report a method for obtaining full length cDNA constructs. This method has been simplified by using synthetic primer-adapters that have both homopolymeric tails for priming the synthesis of the first and second strands and restriction sites for cloning into plasmids (Coleclough et al., *Gene* 34:305-314 (1985), the entirety of which is herein incorporated by reference) and bacteriophage vectors (Krawinkel et al., *Nucleic Acids Res.* 14:1913 (1986), the entirety of which is herein incorporated by reference; Han et al., *Nucleic Acids Res.* 15:6304 (1987), the entirety of which is herein incorporated by reference).

These strategies have been coupled with additional strategies for isolating rare mRNA populations. For example, a typical mammalian cell contains between 10,000 and 30,000 different mRNA sequences (Davidson, *Gene Activity in Early Development*, 2nd ed., Academic Press, New York (1976), the entirety of which is herein incorporated by reference). The number of clones required to achieve a given probability that a low-abundance mRNA will be present in a cDNA library is $N=(\ln(1-P))/(\ln(1-1/n))$ where N is the number of clones required, P is the probability desired and 1/n is the fractional proportion of the total mRNA that is represented by a single rare mRNA (Sambrook et al., Molecular Cloning: A Laboratory Manual, 2nd ed., Cold Spring Harbor Laboratory Press (1989), the entirety of which is herein incorporated by reference).

A method to enrich preparations of mRNA for sequences of interest is to fractionate by size. One such method is to fractionate by electrophoresis through an agarose gel (Pennica et al., *Nature* 301:214-221 (1983), the entirety of which is herein incorporated by reference). Another such method employs sucrose gradient centrifugation in the presence of an agent, such as methylmercuric hydroxide that denatures secondary structure in RNA (Schweinfest et al., *Proc. Natl. Acad. Sci.* (*U.S.A.*) 79:4997-5000 (1982), the entirety of which is herein incorporated by reference).

A frequently adopted method is to construct equalized or normalized cDNA libraries (Ko, *Nucleic Acids Res.* 18:5705-5711 (1990), the entirety of which is herein incorporated by reference; Patanjali et al., *Proc. Natl. Acad. Sci.* (*U.S.A.*) 88:1943-1947 (1991), the entirety of which is herein incorporated by reference). Typically, the cDNA population is normalized by subtractive hybridization (Schmid et al., *J. Neurochem.* 48:307-312 (1987), the entirety of which is herein incorporated by reference; Fargnoli et al., *Anal. Biochem.* 187:364-373 (1990), the entirety of which is herein incorporated by reference; Travis et al., *Proc. Natl. Acad. Sci.* (*U.S.A.*) 85:1696-1700 (1988), the entirety of which is herein incorporated by reference; Kato, *Eur. J. Neurosci.* 2:704-711 (1990); and Schweinfest et al., *Genet. Anal. Tech. Appl.* 7:64-70 (1990), the entirety of which is herein incorporated by reference). Subtraction represents another method for reducing the population of certain sequences in the cDNA library (Swaroop et al., *Nucleic Acids Res.* 19:1954 (1991), the entirety of which is herein incorporated by reference).

ESTs can be sequenced by a number of methods. Two basic methods may be used for DNA sequencing, the chain termination method of Sanger et al., *Proc. Natl. Acad. Sci.* (*U.S.A*) 74:5463-5467 (1977), the entirety of which is herein incorporated by reference and the chemical degradation method of Maxam and Gilbert, *Proc. Nat. Acad. Sci.* (*U.S.A.*). 74:560-564 (1:977), the entirety of which is herein incorporated by reference. Automation and advances in technology such as the replacement of radioisotopes with fluorescence-based sequencing have reduced the effort required to sequence DNA (Craxton, *Methods* 2:20-26 (1991), the entirety of which is herein incorporated by reference; Ju et al., *Proc. Natl. Acad. Sci.* (*U.S.A.*) 92:4347-4351 (1995), the entirety of which is herein incorporated by reference; Tabor and Richardson, *Proc. Natl. Acad. Sci.* (*U.S.A.*) 92:6339-6343 (1995), the entirety of which is herein incorporated by reference). Automated sequencers are available from, for example, Pharmacia Biotech, Inc., Piscataway, N.J. (Pharmacia ALF), LI-COR, Inc., Lincoln, Nebr. (LI-COR 4,000) and Millipore, Bedford, Mass. (Millipore BaseStation).

In addition, advances in capillary gel electrophoresis have also reduced the effort required to sequence DNA and such advances provide a rapid high resolution approach for sequencing DNA samples (Swerdlow and Gesteland, *Nucleic Acids Res.* 18:1415-1419 (1990); Smith, *Nature* 349:812-813 (1991); Luckey et al., *Methods Enzymol.* 218:154-172 (1993); Lu et al., *J. Chromatog.* 680:497-501 (1994); Carson et al., *Anal. Chem.* 65:3219-3226 (1993); Huang et al., *Anal. Chem.* 64:2149-2154 (1992); Kheterpal et al., *Electrophoresis* 17:1852-18:59 (1996); Quesada and Zhang, *Electrophoresis* 17:1841-1851 (1996); Baba, *Yakugaku Zasshi* 11.7: 265-281 (1997), all of which are herein incorporated by reference in their entirety).

ESTs longer than 150 nucleotides have been found to be useful for similarity searches and mapping (Adams et al., *Science* 252: 1651-1656 (1991), herein incorporated by reference). ESTs, which can represent copies of up to the full length transcript, may be partially or completely sequenced. Between 150-450 nucleotides of sequence information is usually generated as this is the length of sequence information that is routinely and reliably produced using single run sequence data. Typically, only single run sequence data is obtained from the cDNA library (Adams et al., *Science* 252: 1651-1656 (1991). Automated single run sequencing typically results in an approximately 2-3% error or base ambiguity rate (Boguski et al., *Nature Genetics* 4:332-333 (1993), the entirety of which is herein incorporated by reference).

EST databases have been constructed or partially constructed from, for example, *C. elegans* (McCombrie et al., *Nature Genetics* 1:124-131 (1992)), human liver cell line HepG2 (Okubo et al., *Nature Genetics* 2:173-179 (1992)), human brain RNA (Adams et al., *Science* 252:1651-1656 (1991); Adams et al., *Nature* 355:632-635 (1992)), *Arabidopsis*, (Newman et al., *Plant Physiol.* 106:1241-1255 (1994)); and rice (Kurata et al., *Nature Genetics* 8:365-372 (1994)).

III. Sequence Comparisons

A characteristic feature of a DNA sequence is that it can be compared with other DNA sequences. Sequence comparisons can be undertaken by determining the similarity of the test or query sequence with sequences in publicly available or proprietary databases ("similarity analysis") or by searching for certain motifs ("intrinsic sequence analysis")(e.g. cis elements)(Coulson, *Trends in Biotechnology* 12:76-80 (1994), the entirety of which is herein incorporated by reference); Birren et al., Genome Analysis 1: Cold Spring Harbor Laboratory Press, Cold Spring Harbor, N.Y. 543-559 (1997), the entirety of which is herein incorporated by reference).

Similarity analysis includes database search and alignment. Examples of public databases include the DNA Database of Japan (DDBJ)(on the Worldwide web at ddbj.nig.acjp/); Genebank (on the Worldwide web at ncbi.nlm.nih.gov/Web/Search/Index.htlm); and the European Molecular Biology Laboratory Nucleic Acid Sequence Database (EMBL) (on the Worldwide web at ebi.ac.uk/ebi_ docs/em-bl_db/embl-db.html). Other appropriate databases include dbEST (on the Worldwide web at ncbi.nlm.nih.gov/dbEST/index.html), Swissprot (on the Worldwide web at ebi.ac.uk/ebi_docs/swisprot db/swisshome.html), PIR (on the Worldwide web at nbrt.georgetown.edu/pir/) and The Institute for Genome Research (on the Worldwide web at tigr.org/tdb/tdb.html).

A number of different search algorithms have been developed, one example of which are the suite of programs referred to as BLAST programs. There are five implementations of BLAST, three designed for nucleotide sequences queries (BLASTN, BLASTX and TBLASTX) and two designed for protein sequence queries (BLASTP and TBLASTN) (Coulson, *Trends in Biotechnology* 12:76-80 (1994); Birren et al., Genome Analysis 1, Cold Spring Harbor Laboratory Press, Cold Spring Harbor, N.Y. 543-559 (1997)).

BLASTN takes a nucleotide sequence (the query sequence) and its reverse complement and searches them against a nucleotide sequence database. BLASTN was designed for speed, not maximum sensitivity and may not find distantly related coding sequences. BLASTX takes a nucleotide sequence, translates it in three forward reading frames and three reverse complement reading frames and then compares the six translations against a protein sequence database. BLASTX is useful for sensitive analysis of preliminary (single-pass) sequence data and is tolerant of sequencing errors (Gish and States, *Nature Genetics* 3:266-272 (1993), the entirety of which is herein incorporated by reference). BLASTN and BLASTX may be used in concert for analyzing EST data (Coulson, *Trends in Biotechnology* 12:76-80 (1994); Birren et al., *Genome Analysis* 1:543-559 (1997)).

Given a coding nucleotide sequence and the protein it encodes, it is often preferable to use the protein as the query sequence to search a database because of the greatly increased sensitivity to detect more subtle relationships. This is due to the larger alphabet of proteins (20 amino acids) compared with the alphabet of nucleic acid sequences (4 bases), where it is far easier to obtain a match by chance. In addition, with nucleotide alignments, only a match (positive score) or a mismatch (negative score) is obtained, but with proteins, the presence of conservative amino acid substitutions can be taken into account. Here, a mismatch may yield a positive score if the non-identical residue has physical/chemical properties similar to the one it replaced. Various scoring matrices are used to supply the substitution scores of all possible amino acid pairs. A general purpose scoring system is the BLOSUM62 matrix (Henikoff and Henikoff, *Proteins* 17:49-61 (1993), the entirety of which is herein incorporated by reference), which is currently the default choice for BLAST programs. BLOSUM62 is tailored for alignments of moderately diverged sequences and thus may not yield the best results under all conditions. Altschul, *J. Mol. Biol.* 36:290-300 (1993), the entirety of which is herein incorporated by reference, describes a combination of three matrices to cover all contingencies. This may improve sensitivity, but at the expense of slower searches. In practice, a single BLOSUM62 matrix is often used but others (PAM40 and PAM250) may be attempted when additional analysis is necessary. Low PAM matrices are directed at detecting very strong but localized sequence similarities, whereas high PAM matrices are directed at detecting long but weak alignments between very distantly related sequences.

Homologues in other organisms are available that can be used for comparative sequence analysis. Multiple alignments are performed to study similarities and differences in a group of related sequences. CLUSTAL W is a multiple sequence alignment package that performs progressive multiple sequence alignments based on the method of Feng and Doolittle, *J. Mol. Evol.* 25:351-360 (1987), the entirety of which is herein incorporated by reference. Each pair of sequences is aligned and the distance between each pair is calculated; from this distance matrix, a guide tree is calculated and all of the sequences are progressively aligned based on this tree. A feature of the program is its sensitivity to the effect of gaps on the alignment; gap penalties are varied to encourage the insertion of gaps in probable loop regions instead of in the middle of structured regions. Users can specify gap penalties, choose between a number of scoring matrices, or supply their own scoring matrix for both pairwise alignments and multiple alignments. CLUSTAL W for UNIX and VMS systems is available at: ftb.ebi.ac.uk. Another program is MACAW (Schuler et al., *Proteins Struct. Func. Genet.* 9:180-190 (1991), the entirety of which is herein incorporated by reference, for which both Macintosh and Microsoft Windows versions are available. MACAW uses a graphical interface, provides a choice of several alignment algorithms and is available by anonymous ftp at: ncbi.nlm.nih.gov (directory/pub/macaw).

Sequence motifs are derived from multiple alignments and can be used to examine individual sequences or an entire database for subtle patterns. With motifs, it is sometimes possible to detect distant relationships that may not be demonstrable based on comparisons of primary sequences alone. Currently, the largest collection of sequence motifs in the world is PROSITE (Bairoch and Bucher, *Nucleic Acid Resedrch* 22:3583-3589 (1994), the entirety of which is herein incorporated by reference). PROSITE may be accessed via either the ExPASy server on the World Wide Web or anonymous ftp site. Many commercial sequence analysis packages also provide search programs that use PROSITE data.

A resource for searching protein motifs is the BLOCKS E-mail server developed by Henikoff, *Trends Biochem Sci.* 18:267-268 (1993), the entirety of which is herein incorporated by reference; Henikoff and Henikoff, *Nucleic Acid Research* 19:6565-6572 (1991), the entirety of which is herein incorporated by reference; Henikoff and Henikoff, *Proteins* 17:49-61 (1993). BLOCKS searches a protein or nucleotide sequence against a database of protein motifs or "blocks." Blocks are defined as short, ungapped multiple alignments that represent highly conserved protein patterns. The blocks themselves are derived from entries in PROSITE as well as other sources. Either a protein query or a nucleotide query can be submitted to the BLOCKS server; if a nucleotide sequence is submitted, the sequence is translated in all six reading frames and motifs are sought for these conceptual translations. Once the search is completed, the server will return a ranked list of significant matches, along with an alignment of the query sequence to the matched BLOCKS entries.

Conserved protein domains can be represented by two-dimensional matrices, which measure either the frequency or probability of the occurrences of each amino acid residue and deletions or insertions in each position of the domain. This type of model, when used to search against protein databases, is sensitive and usually yields more accurate results than simple motif searches. Two popular implementations of this approach are profile searches such as GCG program ProfileSearch and Hidden Markov Models (HMMs)(Krough et al., *J. Mol Biol.* 235:1501-1531, (1994); Eddy, *Current Opinion in Structural Biology* 6:361-365, (11996), both of which are herein incorporated by reference in their entirety). In both cases, a large number of common protein domains have been converted into profiles, as present in the PROSITE library, or HHM models, as in the Pfam protein domain library (Sonnhammer et al., *Proteins* 28:405-420 (1997), the entirety of which is herein incorporated by reference). Pfam contains more than 500 HMM models for enzymes, transcription factors, signal transduction molecules and structural proteins. Protein databases can be queried with these profiles or HMM models, which will identify proteins containing the domain of interest. For example, HMMSW or HMMFS, two programs in a public domain package called HMMER (Sonnhammer et al., *Proteins* 28:405-420 (1997)) can be used.

PROSITE and BLOCKS represent collected families of protein motifs. Thus, searching these databases entails submitting a single sequence to determine whether or not that sequence is similar to the members of an established family. Programs working in the opposite direction compare a collection of sequences with individual entries in the protein databases. An example of such a program is the Motif Search Tool, or MoST (Tatusov et al., *Proc. Natl. Acad. Sci.* (*U.S.A.*) 91: 12091-12095 (1994), the entirety of which is herein incorporated by reference). On the basis of an aligned set of input sequences, a weight matrix is calculated by using one of four methods (selected by the user). A weight matrix is simply a representation, position by position of how likely a particular amino acid will appear. The calculated weight matrix is then used to search the databases. To increase sensitivity, newly found sequences are added to the original data set, the weight matrix is recalculated and the search is performed again. This procedure continues until no new sequences are found.

SUMMARY OF THE INVENTION

The present invention provides a substantially purified nucleic acid molecule that encodes a maize or soybean tetrapyrrole pathway protein or fragment thereof, wherein the maize or soybean tetrapyrrole pathway protein is selected from the group consisting of: (a) putative chlorophyll synthetase enzyme; (b) protochlorophyllide reductase enzyme; (c) putative protochlorophyllide reductase enzyme; (d) coproporphyrinogen oxidase enzyme; (e) protoporphyrinogen oxidase enzyme; (f) uroporphyrinogen decarboxylase enzyme; (g) putative uroporphyrinogen decarboxylase enzyme (h) porphobilinogen synthase enzyme; (i) hydroxymethylbilane synthase enzyme; (j)) glutamate-1-semialdehyde 2,1-aminomutase enzyme; (k) glutamate tRNA ligase enzyme; (l) glutamyl-tRNA reductase enzyme; (m) Mg-chelatase enzyme, and (n) ferrochelatase enzyme.

The present invention also provides a substantially purified nucleic acid molecule that encodes a plant tetrapyrrole pathway protein or fragment thereof, wherein the nucleic acid molecule is selected from the group consisting of a nucleic acid molecule that encodes a putative maize or soybean chlorophyll synthetase enzyme or fragment thereof, a nucleic acid molecule that encodes a maize or soybean protochlorophyllide reductase enzyme or fragment thereof, a nucleic acid molecule that encodes a putative maize or soybean protochlorophyllide reductase enzyme or fragment thereof, a nucleic acid molecule that encodes a maize or soybean coproporphyrinogen oxidase enzyme or fragment thereof, a nucleic acid molecule that encodes a maize or soybean protoporphyrinogen oxidase enzyme or fragment thereof, a nucleic acid molecule that encodes a maize or soybean uroporphyrinogen decarboxylase enzyme or fragment thereof, a nucleic acid molecule that encodes a putative maize or soybean uroporphyrinogen decarboxylase enzyme or fragment thereof, a nucleic acid molecule that encodes a maize or soybean porphobilinogen synthase enzyme or fragment thereof, a nucleic acid molecule that encodes a maize or soybean hydroxymethylbilane synthase enzyme or fragment thereof, a nucleic acid molecule that encodes a maize or soybean glutamate-1-semialdehyde 2,1-aminomutase enzyme or fragment thereof, a nucleic acid molecule that encodes a maize or soybean glutamate tRNA ligase enzyme or fragment thereof, a nucleic acid molecule that encodes a maize or soybean glutamyl-tRNA reductase enzyme or fragment thereof, a nucleic acid molecule that encodes a maize or soybean Mg-chelatase enzyme or fragment thereof and a nucleic acid molecule that encodes a maize or soybean ferrochelatase enzyme or fragment thereof.

The present invention also provides a substantially purified maize or soybean tetrapyrrole pathway protein or fragment thereof, wherein the maize or soybean tetrapyrrole pathway protein is selected from the group consisting of (a) putative chlorophyll synthetase enzyme or fragment thereof; (b) putative protochlorophyllide reductase enzyme or fragment thereof; (c) protochlorophyllide reductase enzyme or fragment thereof; (d) coproporphyrinogen oxidase enzyme or fragment thereof; (e) protoporphyrinogen oxidase enzyme or fragment thereof; (f) uroporphyrinogen decarboxylase enzyme or fragment thereof; (g) putative uroporphyrinogen decarboxylase enzyme or fragment thereof; (h) porphobilinogen synthase enzyme or fragment thereof; (i) hydroxymethylbilane synthase enzyme or fragment thereof; (j) glutamate-1-semialdehyde 2,1-aminomutase enzyme or fragment thereof; (k) glutamate tRNA ligase enzyme or fragment thereof; (l) glutamyl-tRNA reductase enzyme or fragment thereof; (m) Mg-chelatase enzyme or fragment thereof; and (n) ferrochelatase enzyme or fragment thereof.

The present invention also provides a substantially purified maize or soybean tetrapyrrole pathway protein or fragment thereof encoded by a first nucleic acid molecule which specifically hybridizes to a second nucleic acid molecule, the second nucleic acid molecule having a nucleic acid sequence selected from the group consisting of a complement of SEQ ID NO: 1 through SEQ ID NO: 677.

The present invention also provides a substantially purified maize or soybean putative chlorophyll synthetase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 1 through SEQ ID NO: 8 and SEQ ID NO: 384 through SEQ ID NO: 397.

The present invention also provides a substantially purified maize or soybean putative chlorophyll synthetase enzyme or fragment thereof encoded by a nucleic acid sequence selected from the group consisting of SEQ ID NO: 1 through SEQ ID NO: 8 and SEQ ID NO: 384 through SEQ ID NO: 397.

The present invention also provides a substantially purified maize or soybean protochlorophyllide reductase enzyme or fragment thereof encoded by a first nucleic acid molecule which specifically hybridizes to a second nucleic acid molecule, the second nucleic acid molecule having a nucleic acid sequence selected from the group consisting of a complement SEQ ID NO: 9 through SEQ ID NO: 94 and SEQ ID NO: 398 through SEQ ID NO: 466.

The present invention also provides a substantially purified maize or soybean protochlorophyllide reductase enzyme or fragment thereof encoded by a nucleic acid sequence selected from the group consisting of SEQ ID NO: 9 through SEQ ID NO: 94 and SEQ ID NO: 398 through SEQ ID NO: 466.

The present invention also provides a substantially purified maize or soybean putative protochlorophyllide reductase enzyme or fragment thereof encoded by a first nucleic acid molecule which specifically hybridizes to a second nucleic acid molecule, the second nucleic acid molecule having a nucleic acid sequence selected from the group consisting of a complement SEQ ID NO: 95 through SEQ ID NO: 96 and SEQ ID NO: 467 through SEQ ID NO: 479.

The present invention also provides a substantially purified maize or soybean putative protochlorophyllide reductase enzyme or fragment thereof encoded by a nucleic acid sequence selected from the group consisting of SEQ ID NO: 95 through SEQ ID NO: 96 and SEQ ID NO: 467 through SEQ ID NO: 479.

The present invention also provides a substantially purified maize or soybean coproporphyrinogen oxidase enzyme or fragment thereof encoded by a first nucleic acid molecule which specifically hybridizes to a second nucleic acid molecule, the second nucleic acid molecule having a nucleic acid sequence consisting of a complement of SEQ ID NO: 97 through SEQ ID NO: 128 and SEQ ID NO: 480 through SEQ ID NO: 494.

The present invention also provides a substantially purified maize or soybean coproporphyrinogen oxidase enzyme or fragment thereof encoded by a nucleic acid sequence consisting of SEQ ID NO: 97 through SEQ ID NO: 128 and SEQ ID NO: 480 through SEQ ID NO: 494.

The present invention also provides a substantially purified maize or soybean protoporphyrinogen oxidase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 129 through SEQ ID NO: 131 and SEQ ID NO: 495 through SEQ ID NO: 499.

The present invention also provides a substantially purified maize or soybean protoporphyrinogen oxidase enzyme or fragment thereof encoded by a nucleic acid sequence selected from the group consisting of SEQ ID NO: 129 through SEQ ID NO: 131 and SEQ ID NO: 495 through SEQ ID NO: 499.

The present invention also provides a substantially purified maize or soybean uroporphyrinogen decarboxylase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 132 through SEQ ID NO: 144 and SEQ ID NO: 500 through SEQ ID NO: 509.

The present invention also provides a substantially purified maize or soybean uroporphyrinogen decarboxylase enzyme or fragment thereof encoded by a nucleic acid sequence selected from the group consisting of SEQ ID NO: 132 through SEQ ID NO: 144 and SEQ ID NO: 500 through SEQ ID NO: 509.

The present invention also provides a substantially purified a maize putative uroporphyrinogen decarboxylase enzyme or fragment thereof encoded by a first nucleic acid molecule which specifically hybridizes to a second nucleic acid molecule, the second nucleic acid molecule having a nucleic acid sequence consisting of a complement of SEQ ID NO: 510.

The present invention also provides a substantially purified maize putative uroporphyrinogen decarboxylase enzyme or fragment thereof encoded by a nucleic acid sequence consisting of SEQ ID NO: 510.

The present invention also provides a substantially purified soybean porphobilinogen synthetase enzyme or fragment thereof encoded by a first nucleic acid molecule which specifically hybridizes to a second nucleic acid molecule, the second nucleic acid molecule having a nucleic acid sequence selected from the group consisting of SEQ ID NO: 145 through SEQ ID NO: 191 and SEQ ID NO: 511 through SEQ ID NO: 531.

The present invention also provides a substantially purified maize or soybean porphobilinogen synthetase enzyme or fragment thereof encoded by a nucleic acid sequence selected from the group consisting of SEQ ID NO: 145 through SEQ ID NO: 191 and SEQ ID NO: 511 through SEQ ID NO: 531.

The present invention also provides a substantially purified maize or soybean hydroxymethylbilane synthase enzyme or fragment thereof encoded by a first nucleic acid molecule which specifically hybridizes to a second nucleic acid molecule, the second nucleic acid molecule having a nucleic acid sequence selected from the group consisting of a complement SEQ ID NO: 154, SEQ ID NO: 192 through SEQ ID NO: 217 and SEQ ID NO: 532 through SEQ ID NO: 542.

The present invention also provides a substantially purified maize or soybean hydroxymethylbilane enzyme or fragment thereof encoded by a nucleic acid sequence selected from the group consisting of SEQ ID NO: 154, SEQ ID NO: 192 through SEQ ID NO: 217 and SEQ ID NO: 532 through SEQ ID NO: 542.

The present invention also provides a substantially purified maize or soybean glutamate-1-semialdehyde 2,1-aminomutase enzyme or fragment thereof encoded by a first nucleic acid molecule which specifically hybridizes to a second nucleic acid molecule, the second nucleic acid molecule having a nucleic acid sequence consisting of a complement of SEQ ID NO: 218 through SEQ ID NO: 265 and SEQ ID NO: 543 through SEQ ID NO: 569.

The present invention also provides a substantially purified maize or soybean glutamate-1-semialdehyde 2,1-aminomutase enzyme or fragment thereof encoded by a nucleic acid sequence consisting of SEQ ID NO: 218 through SEQ ID NO: 265 and SEQ ID NO: 543 through SEQ ID NO: 569.

The present invention also provides a substantially purified maize or soybean glutamate tRNA ligase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 266 through SEQ ID NO: 289 and SEQ ID NO: 570 through SEQ ID NO: 585.

The present invention also provides a substantially purified maize or soybean glutamate tRNA ligase enzyme or fragment thereof encoded by a nucleic acid sequence selected from the group consisting of SEQ ID NO: 266 through SEQ ID NO: 289 and SEQ ID NO: 570 through SEQ ID NO: 585.

The present invention also provides a substantially purified maize or soybean glutamyl-tRNA reductase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 266 through SEQ ID NO: 289 and SEQ ID NO: 570 through SEQ ID NO: 585.

The present invention also provides a substantially purified maize or soybean glutamyl-tRNA reductase enzyme fragment thereof encoded by a nucleic acid sequence selected from the group consisting of SEQ ID NO: 266 through SEQ ID NO: 289 and SEQ ID NO: 570 through SEQ ID NO: 585.

The present invention also provides a substantially purified maize or soybean Mg-chelatase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 290 through SEQ ID NO: 306 and SEQ ID NO: 586 through SEQ ID NO: 609.

The present invention also provides a substantially purified maize or soybean Mg-chelatase enzyme or fragment thereof encoded by a nucleic acid sequence selected from the group consisting of SEQ ID NO: 290 through SEQ ID NO: 306 and SEQ ID NO: 586 through SEQ ID NO: 609.

The present invention also provides a substantially purified maize or soybean ferrochelatase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 372 through SEQ ID NO: 383 and SEQ ID NO: 653 through SEQ ID NO:677.

The present invention also provides a substantially purified maize or soybean ferrochelatase enzyme or fragment thereof encoded by a nucleic acid sequence selected from the group consisting of SEQ ID NO: 372 through SEQ ID NO: 383 and SEQ ID NO: 653 through SEQ ID NO:677.

The present invention also provides a purified antibody or fragment thereof which is capable of specifically binding to a maize or soybean tetrapyrrole pathway protein or fragment thereof, wherein the maize or soybean tetrapyrrole pathway protein or fragment thereof is encoded by a nucleic acid molecule comprising a nucleic acid sequence selected from the group consisting of consisting of SEQ ID NO: 1 through SEQ ID NO: 677.

The present invention also provides a substantially purified antibody or fragment thereof, the antibody or fragment thereof capable of specifically binding to a putative maize or soybean chlorophyll synthetase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 1 through SEQ ID NO: 8 and SEQ ID NO: 384 through SEQ ID NO: 397 or a nucleic acid sequence selected from the group consisting SEQ ID NO: 1 through SEQ ID NO: 8 and SEQ ID NO: 384 through SEQ ID NO: 397.

The present invention also provides a substantially purified antibody or fragment thereof, the antibody or fragment thereof capable of specifically binding to a maize or soybean protochlorophyllide reductase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 9 through SEQ ID NO: 94 and SEQ ID NO: 398 through SEQ ID NO: 466 or a nucleic acid sequence selected from the group consisting of SEQ ID NO: 95 through SEQ ID NO: 96 and SEQ ID NO: 398 through SEQ ID NO: 466.

The present invention also provides a substantially purified antibody or fragment thereof, the antibody or fragment thereof capable of specifically binding to a maize or soybean putative protochlorophyllide reductase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 95 through SEQ ID NO: 96 and SEQ ID NO: 467 through SEQ ID NO: 479 or a nucleic acid sequence selected from the group consisting of SEQ ID NO: 95 through SEQ ID NO: 96 and SEQ ID NO: 467 through SEQ ID NO: 479.

The present invention also provides a substantially purified antibody or fragment thereof, the antibody or fragment thereof capable of specifically binding to a maize or soybean coproporphyrinogen oxidase or fragment thereof encoded by a first nucleic acid molecule which specifically hybridizes to a second nucleic acid molecule, the second nucleic acid molecule consisting of a compliment of a nucleic acid sequence having a nucleic acid sequence selected from the group consisting of SEQ ID NO: 97 through SEQ ID NO: 128 and SEQ ID NO: 480 through SEQ ID NO: 494 or a nucleic acid sequence selected from the group consisting of SEQ ID NO: 97 through SEQ ID NO: 128 and SEQ ID NO: 480 through SEQ ID NO: 494.

The present invention also provides a substantially purified antibody or fragment thereof, the antibody or fragment thereof capable of specifically binding to a maize or soybean protoporphyrinogen oxidase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 129 through SEQ ID NO: 131 and SEQ ID NO: 495 through SEQ ID NO: 499 or a nucleic acid sequence selected from the group consisting SEQ ID NO: 129 through SEQ ID NO: 131 and SEQ ID NO: 495 through SEQ ID NO: 499.

The present invention also provides a substantially purified antibody or fragment thereof, the antibody or fragment thereof capable of specifically binding to a maize or soybean uroporphyrinogen decarboxylase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 132 through SEQ ID NO: 144 and SEQ ID NO: 500 through SEQ ID NO: 509 or a nucleic acid sequence selected from the group consisting SEQ ID NO: 132 through SEQ ID NO: 144 and SEQ ID NO: 500 through SEQ ID NO: 509.

The present invention also provides a substantially purified antibody or fragment thereof, the antibody or fragment thereof capable of specifically binding to a putative maize uroporphyrinogen decarboxylase enzyme or fragment thereof encoded by a first nucleic acid molecule which specifically hybridizes to a second nucleic acid molecule, the second nucleic acid molecule having a nucleic acid sequence consisting of a complement of SEQ ID NO: 510 or a nucleic acid sequence consisting SEQ ID NO: 510.

The present invention also provides a substantially purified antibody or fragment thereof, the antibody or fragment thereof capable of specifically binding to a maize or soybean porphobilinogen enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 145 through SEQ ID NO: 191 and SEQ ID NO: 511 through SEQ ID NO: 531 or a nucleic acid sequence selected from the group consisting SEQ ID NO: 145 through SEQ ID NO: 191 and SEQ ID NO: 511 through SEQ ID NO: 531.

The present invention also provides a substantially purified antibody or fragment thereof, the antibody or fragment thereof capable of specifically binding to a maize or soybean hydroxymethylbilane synthase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 154, SEQ ID NO: 192 through SEQ ID NO: 217 and SEQ ID NO: 532 through SEQ ID NO: 542 or a nucleic acid sequence selected from the group consisting of SEQ ID NO: 154, SEQ ID NO: 192 through SEQ ID NO: 217 and SEQ ID NO: 532 through SEQ ID NO: 542.

The present invention also provides a substantially purified antibody or fragment thereof, the antibody or fragment thereof capable of specifically binding to a maize or soybean glutamate-1-semialdehyde 2,1-aminomutase enzyme or fragment thereof encoded by a first nucleic acid molecule which specifically hybridizes to a second nucleic acid molecule, the second nucleic acid molecule consisting of a compliment of a nucleic acid sequence having a nucleic acid sequence selected from the group consisting of SEQ ID NO: 218 through SEQ ID NO.: 265 and SEQ ID NO: 543 through SEQ ID NO: 569 or a nucleic acid sequence selected from the group consisting of SEQ ID NO: 218 through SEQ ID NO: 265 and SEQ ID NO: 543 through SEQ ID NO: 569.

The present invention also provides a substantially purified antibody or fragment thereof, the antibody or fragment thereof capable of specifically binding to a maize or soybean glutamate tRNA ligase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 266 through SEQ ID NO: 289 and SEQ ID NO: 570 through SEQ ID NO: 585 or a nucleic acid sequence selected from the group consisting SEQ ID NO: 266 through SEQ ID NO: 289 and SEQ ID NO: 570 through SEQ ID NO: 585.

The present invention also provides a substantially purified antibody or fragment thereof, the antibody or fragment thereof capable of specifically binding to a maize or soybean glutamyl-tRNA reductase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 290 through SEQ ID NO: 306 and SEQ ID NO: 586 through SEQ ID NO: 609 or a nucleic acid sequence selected from the group consisting SEQ ID NO: 290 through SEQ ID NO: 306 and SEQ ID NO: 586 through SEQ ID NO: 609.

The present invention also provides a substantially purified antibody or fragment thereof, the antibody or fragment thereof capable of specifically binding to a maize or soybean Mg-chelatase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 307 through SEQ ID NO: 371 and SEQ ID NO: 610 through SEQ ID NO: 652 or a nucleic acid sequence selected from the group consisting SEQ ID NO: 307 through SEQ ID NO: 371 and SEQ ID NO: 610 through SEQ ID NO: 652.

The present invention also provides a substantially purified antibody or fragment thereof, the antibody or fragment thereof capable of specifically binding to a maize or soybean ferrochelatase enzyme or fragment thereof encoded by a first nucleic acid molecule which specifically hybridizes to a second nucleic acid molecule, the second nucleic acid molecule having a nucleic acid sequence selected from the group consisting of a complement of SEQ. ID NO: 372 through SEQ ID NO: 383 and SEQ ID NO: 653 through SEQ ID NO: 677 or a nucleic acid sequence selected from the group consisting SEQ ID NO: 372 through SEQ ID NO: 383 and SEQ ID NO: 653 through SEQ ID NO: 677.

The present invention also provides a transformed plant having a nucleic acid molecule which comprises: (A) an exogenous promoter region which functions in a plant cell to cause the production of a mRNA molecule; (B) a structural nucleic acid molecule comprising a nucleic acid sequence selected from the group consisting of (a) a nucleic acid sequence which encodes for a putative chlorophyll synthetase enzyme or fragment thereof; (b) a nucleic acid sequence which encodes for a protochlorophyllide reductase or fragment thereof; (c) a nucleic acid sequence which encodes for a putative protochlorophyllide reductase or fragment thereof; (d) a nucleic acid sequence which encodes for a coproporphyrinogen oxidase or fragment thereof; (e) a nucleic acid sequence which encodes for a protoporphyrinogen oxidase enzyme or fragment thereof; (f) a nucleic acid sequence which encodes for a uroporphyrinogen decarboxylase enzyme or fragment thereof; (g) a nucleic acid sequence which encodes for a putative uroporphyrinogen decarboxylase enzyme or fragment thereof; (h) a nucleic acid sequence which encodes for a porphobilinogen synthase enzyme or fragment thereof; (i) a nucleic acid sequence which encodes for a hydroxymethylbilane synthase enzyme or fragment thereof; (j) a nucleic acid sequence which encodes for a glutamate-1-semialdehyde 2,1-aminomutase enzyme or fragment thereof; (k) a nucleic acid sequence which encodes for a glutamate tRNA ligase enzyme or fragment thereof; (l) a nucleic acid sequence which encodes for a glutamyl-tRNA reductase enzyme or fragment thereof; (m) a nucleic acid sequence which encodes for a Mg-chelatase enzyme or fragment thereof; and (n) a nucleic acid sequence which encodes for a ferrochelatase enzyme or fragment thereof (m) a nucleic acid sequence which is complementary to any of the nucleic acid sequences of (a) through (n); and (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a structural nucleic acid molecule, wherein the structural nucleic acid molecule encodes a plant tetrapyrrole pathway protein or fragment thereof, the structural nucleic acid molecule comprising a nucleic acid sequence selected from the group consisting of SEQ ID NO: 1 through SEQ ID NO: 677 or fragment thereof; which is linked to (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a structural nucleic acid molecule, wherein the structural nucleic acid molecule is selected from the group consisting of a nucleic acid molecule that encodes a putative maize or soybean chlorophyll synthetase enzyme or fragment thereof, a nucleic acid molecule that encodes a maize or soybean protochlorophyllide reductase enzyme or fragment thereof, a nucleic acid molecule that encodes a putative maize or soybean protochlorophyllide reductase enzyme or fragment thereof, a nucleic acid sequence which encodes a maize or soybean coproporphyrinogen oxidase or fragment thereof, a nucleic acid sequence which encodes a maize or soybean protoporphyrinogen oxidase enzyme or fragment thereof, a nucleic acid sequence which encodes a maize or soybean uroporphyrinogen decarboxylase enzyme or fragment thereof, a nucleic acid sequence which encodes a putative maize uroporphyrinogen decarboxylase enzyme or fragment thereof, a nucleic acid sequence which encodes a maize or soybean porphobilinogen synthase enzyme or fragment thereof, a nucleic acid sequence which encodes a maize or soybean hydroxymethylbilane synthase enzyme or fragment thereof, a nucleic acid sequence which encodes a maize or soybean glutamate-1-semialdehyde 2,1-aminomutase enzyme or fragment thereof, a nucleic acid sequence which encodes a maize or soybean glutamate tRNA ligase enzyme or fragment thereof, a nucleic acid sequence which encodes a maize or soybean glutamyl-tRNA reductase enzyme or fragment thereof, a nucleic acid sequence which encodes a maize or soybean Mg-chelatase enzyme or fragment thereof, and a nucleic acid sequence which encodes a maize or soybean ferrochelatase enzyme or fragment thereof; which is linked to (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a transcribed nucleic acid molecule with a transcribed strand and a non-transcribed strand, wherein the transcribed strand is complementary to a nucleic acid molecule comprising a nucleic acid sequence selected from the group consisting of SEQ ID NO: 1 through SEQ ID NO: 677 or fragment thereof; which is linked to (C) a 3' non-translated sequence that functions in plant cells to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to: (B) a transcribed nucleic acid molecule with a transcribed strand and a non-transcribed strand, wherein a transcribed mRNA of the transcribed strand is complementary to an endogenous mRNA molecule having a nucleic acid sequence selected from the group consisting of an endogenous mRNA molecule that encodes a putative maize or soybean putative chlorophyll synthetase enzyme or fragment thereof, an endogenous mRNA molecule that encodes a maize or soybean protochlorophyllide reductase enzyme or fragment thereof, an endogenous mRNA molecule that encodes a putative maize or soybean protochlorophyllide reductase enzyme or fragment thereof, an endogenous mRNA molecule that encodes a maize or soybean coproporphyrinogen oxidase enzyme or fragment thereof, an endogenous mRNA molecule that encodes a maize or soybean protoporphyrinogen oxidase enzyme or fragment thereof, an endogenous mRNA molecule that encodes a maize or soybean uroporphyrinogen decarboxylase enzyme or fragment thereof, an endogenous mRNA molecule that encodes a putative maize uroporphyrinogen decarboxylase enzyme or fragment thereof, an endogenous mRNA molecule that encodes a maize or soybean porphobilinogen synthase enzyme or fragment thereof, an endogenous mRNA molecule that encodes a maize or soybean hydromethylbilane synthase enzyme or fragment thereof, an endogenous mRNA molecule that encodes a maize or soybean glutamate-1-semialdehyde 2,1-aminomutase enzyme or fragment thereof, an endogenous mRNA molecule that encodes a maize or soybean glutamate tRNA ligase enzyme or fragment thereof an endogenous mRNA molecule that encodes a maize or soybean glutamyl-tRNA reductase enzyme or fragment thereof, an endogenous mRNA molecule that encodes a maize or soybean Mg-chelatase enzyme or fragment thereof and an endogenous mRNA molecule that encodes a maize or soybean ferrochelatase enzyme or fragment thereof; which is linked to (C) a 3' non-translated sequence that functions in the plant cell to cause termination of transcription and addition of polyadenylated ribonucleotides to a 3' end of the mRNA molecule.

The present invention also provides a method for determining a level or pattern of a plant tetrapyrrole pathway protein in a plant cell or plant tissue comprising: (A) incubating, under conditions permitting nucleic acid hybridization, a marker nucleic acid molecule, the marker nucleic acid molecule having a nucleic acid sequence selected from the group consisting of SEQ. ID NO: 1 through SEQ ID NO: 677 or complements thereof or fragment of either, with a complementary nucleic acid molecule obtained from the plant cell or plant tissue, wherein nucleic acid hybridization between the marker nucleic acid molecule and the complementary nucleic acid molecule obtained from the plant cell or plant tissue permits the detection of the plant tetrapyrrole pathway protein; (B) permitting hybridization between the marker nucleic acid molecule and the complementary nucleic acid molecule obtained from the plant cell or plant tissue; and (C) detecting the level or pattern of the complementary nucleic acid, wherein the detection of the complementary nucleic acid is predictive of the level or pattern of the plant tetrapyrrole pathway protein.

The present invention also provides a method for determining a level or pattern of a plant tetrapyrrole pathway protein in a plant cell or plant tissue comprising: (A) incubating, under conditions permitting nucleic acid hybridization, a marker nucleic acid molecule, the marker nucleic acid molecule comprising a nucleic acid molecule that encodes a putative maize or soybean chlorophyll synthetase enzyme or complement thereof or fragment of either, a nucleic acid molecule that encodes a maize or soybean protochlorophyllide reductase enzyme or complement thereof or fragment of either, a nucleic acid molecule that encodes a putative maize or soybean protochlorophyllide reductase enzyme or complement thereof or fragment of either, a nucleic acid molecule that encodes a maize or soybean coproporphyrinogen oxidase enzyme or complement thereof or fragment of either, a nucleic acid molecule that encodes a maize or soybean protoporphyrinogen oxidase enzyme or complement thereof or fragment of either, a nucleic acid molecule that encodes a maize or soybean uroporphyrinogen decarboxylase enzyme or complement thereof or fragment of either, a nucleic acid molecule that encodes a putative maize uroporphyrinogen decarboxylase enzyme or complement thereof or fragment of either, a nucleic acid molecule that encodes a maize or soybean porphobilinogen synthase enzyme or complement thereof or fragment of either, a nucleic acid molecule that encodes a maize or soybean hydroxymethylbilane synthase enzyme or complement thereof or fragment of either, a nucleic acid molecule that encodes a maize or soybean glutamate-1-semialdehyde 2,1-aminomutase enzyme or complement thereof or fragment of either, a nucleic acid molecule that encodes a maize or soybean glutamate tRNA ligase enzyme or complement thereof or fragment of either, a nucleic acid molecule that encodes a maize or soybean glutamyl-tRNA reductase enzyme or complement thereof or fragment of either, a nucleic acid molecule that encodes a maize or soybean Mg-chelatase enzyme or complement thereof or fragment of either and a nucleic acid molecule that encodes a maize or soybean ferrochelatase enzyme or complement thereof or fragment of either, with a complementary nucleic acid molecule obtained from the plant cell or plant tissue, wherein nucleic acid hybridization between the marker nucleic acid molecule and the complementary nucleic acid molecule obtained from the plant cell or plant tissue permits the detection of the plant tetrapyrrole pathway protein; (B) permitting hybridization between the marker nucleic acid molecule and the complementary nucleic acid molecule obtained from the plant cell or plant tissue; and (C) detecting the level or pattern of the complementary nucleic acid, wherein the detection of the complementary nucleic acid is predictive of the level or pattern of the plant tetrapyrrole pathway protein.

The present invention also provides a method for determining a level or pattern of a plant tetrapyrrole pathway protein in a plant cell or plant tissue under evaluation which comprises assaying the concentration of a molecule, whose concentration is dependent upon the expression of a gene, the gene specifically hybridizes to a nucleic acid molecule having a nucleic acid sequence selected from the group consisting of SEQ ID NO: 1 through SEQ ID NO: 677 or complements thereof, in comparison to the concentration of that molecule present in a reference plant cell or a reference plant tissue with a known level or pattern of the plant tetrapyrrole pathway protein, wherein the assayed concentration of the molecule is compared to the assayed concentration of the molecule in the reference plant cell or reference plant tissue with the known level or pattern of the plant tetrapyrrole pathway protein.

The present invention also provides a method for determining a level or pattern of a plant tetrapyrrole pathway protein in a plant cell or plant tissue under evaluation which comprises assaying the concentration of a molecule, whose concentration is dependent upon the expression of a gene, the gene specifically hybridizes to a nucleic acid molecule selected from the group consisting of a nucleic acid molecule that encodes a putative maize or soybean chlorophyll synthetase enzyme or complement thereof, a nucleic acid molecule that encodes a maize or soybean protochlorophyllide reductase enzyme or complement thereof, a nucleic acid molecule that encodes a putative maize or soybean protochlorophyllide reductase enzyme or complement thereof, a nucleic acid molecule that encodes a maize or soybean coproporphyrinogen oxidase enzyme or complement thereof, a nucleic acid molecule that encodes a maize or soybean protoporphyrinogen oxidase enzyme or complement thereof, a nucleic acid molecule that encodes a maize or soybean uroporphyrinogen decarboxylase enzyme or complement thereof, a nucleic acid molecule that encodes a putative maize uroporphyrinogen decarboxylase enzyme or complement thereof, a nucleic acid molecule that encodes a maize or soybean porphobilinogen synthase enzyme or complement thereof, a nucleic acid molecule that encodes a maize or soybean hydroxymethylbilane synthase enzyme or complement thereof, a nucleic acid molecule that encodes a maize or soybean glutamate-1-semialdehyde 2,1-aminomutase enzyme or complement thereof, a nucleic acid molecule that encodes a maize or soybean glutamate tRNA ligase enzyme or complement thereof, a nucleic acid molecule that encodes a maize or soybean glutamyl-tRNA reductase enzyme or complement thereof, a nucleic acid molecule that encodes a maize or soybean Mg-chelatase enzyme or complement thereof and a nucleic acid molecule that encodes a maize or soybean ferrochelatase enzyme or complement thereof, in comparison to the concentration of that molecule present in a reference plant cell or a reference plant tissue with a known level or pattern of the plant tetrapyrrole pathway protein, wherein the assayed concentration of the molecule is compared to the assayed concentration of the molecule in the reference plant cell or the reference plant tissue with the known level or pattern of the plant tetrapyrrole pathway protein.

The present invention provides a method of determining a mutation in a plant whose presence is predictive of a mutation affecting a level or pattern of a protein comprising the steps: (A) incubating, under conditions permitting nucleic acid hybridization, a marker nucleic acid, the marker nucleic acid selected from the group of marker nucleic acid molecules which specifically hybridize to a nucleic acid molecule having a nucleic acid sequence selected from the group of SEQ ID NO: 1 through SEQ ID NO: 677 or complements thereof or fragment of either and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the protein in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method for determining a mutation in a plant whose presence is predictive of a mutation affecting the level or pattern of a plant tetrapyrrole pathway protein comprising the steps: (A) incubating, under conditions permitting nucleic acid hybridization, a marker nucleic acid molecule, the marker nucleic acid molecule comprising a nucleic acid molecule that is linked to a gene, the gene specifically hybridizes to a nucleic acid molecule having a nucleic acid sequence selected from the group consisting of SEQ ID NO: 1 through. SEQ ID NO: 677 or complements thereof and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the plant tetrapyrrole pathway protein in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method for determining a mutation in a plant whose presence is predictive of a mutation affecting the level or pattern of a plant tetrapyrrole pathway protein comprising the steps: (A) incubating, under conditions permitting nucleic acid hybridization, a marker nucleic acid molecule, the marker nucleic acid molecule comprising a nucleic acid molecule that is linked to a gene, the gene specifically hybridizes to a nucleic acid molecule selected from the group consisting of a nucleic acid molecule that encodes a putative maize or soybean chlorophyll synthetase enzyme or complement thereof, a nucleic acid molecule that encodes a maize or soybean protochlorophyllide reductase enzyme or complement thereof, a nucleic acid molecule that encodes a putative maize or soybean protochlorophyllide reductase enzyme or complement thereof, a nucleic acid molecule that encodes a maize or soybean coproporphyrinogen oxidase enzyme or complement thereof, a nucleic acid molecule that encodes a maize or soybean protoporphyrinogen oxidase enzyme or complement thereof, a nucleic acid molecule that encodes a maize or soybean uroporphyrinogen decarboxylase enzyme or complement thereof, a nucleic acid molecule that encodes a putative maize uroporphyrinogen decarboxylase enzyme or complement thereof, a nucleic acid molecule that encodes a maize or soybean porphobilinogen synthase enzyme or complement thereof, a nucleic acid molecule that encodes a maize or soybean hydroxymethylbilane synthase enzyme or complement thereof, a nucleic acid molecule that encodes a maize or soybean glutamate-1-semialdehyde 2,1-aminomutase enzyme or complement thereof, a nucleic acid molecule that encodes a maize or soybean glutamate tRNA ligase enzyme or complement thereof, a nucleic acid molecule that encodes a maize or soybean glutamyl-tRNA reductase enzyme or complement thereof, a nucleic acid molecule that encodes a maize or soybean Mg-chelatase enzyme or complement thereof and a nucleic acid molecule that encodes a maize or soybean ferrochelatase enzyme or complement thereof and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the plant tetrapyrrole pathway protein in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method of producing a plant containing an overexpressed protein comprising: (A) transforming the plant with a functional nucleic acid molecule, wherein the functional nucleic acid molecule comprises a promoter region, wherein the promoter region is linked to a structural region, wherein the structural region has a nucleic acid sequence selected from group consisting of SEQ ID NO: 1 through SEQ ID NO: 677 wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the protein; and (B) growing the transformed plant.

The present invention also provides a method of producing a plant containing an overexpressed plant tetrapyrrole pathway protein comprising: (A) transforming the plant with a functional nucleic acid molecule, wherein the functional nucleic acid molecule comprises a promoter region, wherein the promoter region is linked to a structural region, wherein the structural region comprises a nucleic acid molecule having a nucleic acid sequence selected from the group consisting of SEQ ID NO: 1 through SEQ ID NO: 677 or fragment thereof; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the plant tetrapyrrole pathway protein; and (B) growing the transformed plant.

The present invention also provides a method of producing a plant containing an overexpressed plant tetrapyrrole pathway protein comprising: (A) transforming the plant with a functional nucleic acid molecule, wherein the functional nucleic acid molecule comprises a promoter region, wherein the promoter region is linked to a structural region, wherein the structural region comprises a nucleic acid molecule selected from the group consisting of a nucleic acid molecule that encodes a putative maize or soybean chlorophyll synthetase enzyme or complement thereof or fragment, a nucleic acid molecule that encodes a maize or soybean protochlorophyllide reductase enzyme or complement thereof or fragment, a nucleic acid molecule that encodes a putative maize or soybean protochlorophyllide reductase enzyme or complement thereof or fragment, a nucleic acid molecule that encodes a maize or soybean coproporphyrinogen oxidase enzyme or complement thereof or fragment, a nucleic acid molecule that encodes a maize or soybean protoporphyrinogen oxidase enzyme or complement thereof or fragment, a nucleic acid molecule that encodes a maize or soybean uroporphyrinogen decarboxylase enzyme or complement thereof or fragment, a nucleic acid molecule that encodes a putative maize uroporphyrinogen decarboxylase enzyme or complement thereof or fragment, a nucleic acid molecule that encodes a maize or soybean porphobilinogen synthase enzyme or complement thereof or fragment, a nucleic acid molecule that encodes a maize or soybean hydroxymethylbilane synthase enzyme or complement thereof or fragment, a nucleic acid molecule that encodes a maize or soybean glutamate-1-semialdehyde 2,1-aminomutase enzyme or complement thereof or fragment, a nucleic acid molecule that encodes a maize or soybean glutamate tRNA ligase enzyme or complement thereof or fragment, a nucleic acid molecule that encodes a maize or soybean glutamyl-tRNA reductase enzyme or complement thereof or fragment, a nucleic acid molecule that encodes a maize or soybean Mg-chelatase enzyme or complement thereof or fragment and a nucleic acid molecule that encodes a maize or soybean ferrochelatase enzyme or complement thereof or fragment of either, wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the plant tetrapyrrole pathway protein; and (B) growing the transformed plant.

The present invention also provides a method of producing a plant containing reduced levels of a plant tetrapyrrole pathway protein comprising: (A) transforming the plant with a functional nucleic acid molecule, wherein the functional nucleic acid molecule comprises a promoter region, wherein the promoter region is linked to a structural region, wherein the structural region comprises a nucleic acid molecule having a nucleic acid sequence selected from the group consisting of SEQ ID NO: 1 through SEQ ID NO: 677; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in co-suppression of the plant tetrapyrrole pathway protein; and (B) growing the transformed plant.

The present invention also provides a method of producing a plant containing reduced levels of a plant tetrapyrrole pathway protein comprising: (A) transforming the plant with a functional nucleic acid molecule, wherein the functional nucleic acid molecule comprises a promoter region, wherein the promoter region is linked to a structural region, wherein the structural region comprises a nucleic acid molecule having a nucleic acid sequence selected from the group consisting of a nucleic acid molecule that encodes a putative maize or soybean chlorophyll synthetase enzyme or complement thereof or fragment, a nucleic acid molecule that encodes a maize or soybean protochlorophyllide reductase enzyme or complement thereof or fragment, a nucleic acid molecule that encodes a putative maize or soybean protochlorophyllide reductase enzyme or complement thereof or fragment, a nucleic acid molecule that encodes a maize or soybean coproporphyrinogen oxidase enzyme or complement thereof or fragment, a nucleic acid molecule that encodes a maize or soybean protoporphyrinogen oxidase enzyme or complement thereof or fragment, a nucleic acid molecule that encodes a maize or soybean uroporphyrinogen decarboxylase enzyme or complement thereof or fragment, a nucleic acid molecule that encodes a putative maize uroporphyrinogen decarboxylase enzyme or complement thereof or fragment, a nucleic acid molecule that encodes a maize or soybean porphobilinogen synthase enzyme or complement thereof or fragment, a nucleic acid molecule that encodes a maize or soybean hydroxymethylbilane synthase enzyme or complement thereof or fragment, a nucleic acid molecule that encodes a maize or soybean glutamate-1-semialdehyde 2,1-aminomutase enzyme or complement thereof or fragment, a nucleic acid molecule that encodes a maize or soybean glutamate tRNA ligase enzyme or complement thereof or fragment, a nucleic acid molecule that encodes a maize or soybean glutamyl-tRNA reductase enzyme or complement thereof or fragment, a nucleic acid molecule that encodes a maize or soybean Mg-chelatase enzyme or complement thereof or fragment and a nucleic acid molecule that encodes a maize or soybean ferrochelatase enzyme or complement thereof or fragment of either, wherein the structural region is linked to a 3' non-translated sequence that functions in the plant to cause termination of transcription and addition of polyadenylated ribonucleotides to a 3' end of a mRNA molecule; and wherein the functional nucleic acid molecule results in co-suppression of the plant tetrapyrrole pathway protein; and (B) growing the transformed plant.

The present invention also provides a method for reducing expression of a plant tetrapyrrole pathway protein in a plant comprising: (A) transforming the plant with a nucleic acid molecule, the nucleic acid molecule having an exogenous promoter region which functions in a plant cell to cause the production of a mRNA molecule, wherein the exogenous promoter region is linked to a transcribed nucleic acid molecule having a transcribed strand and a non-transcribed strand, wherein the transcribed strand is complementary to a nucleic acid molecule having a nucleic acid sequence selected from the group consisting of SEQ ID NO: 1 through SEQ ID NO: 677 or complements thereof or fragments of either and the transcribed strand is complementary to an endogenous mRNA molecule; and wherein the transcribed nucleic acid molecule is linked to a 3' non-translated sequence that functions in the plant cell to cause termination of transcription and addition of polyadenylated ribonucleotides to a 3' end of a mRNA molecule; and (B) growing the transformed plant.

The present invention also provides a method for reducing expression of a plant tetrapyrrole pathway protein in a plant comprising: (A) transforming the plant with a nucleic acid molecule, the nucleic acid molecule having an exogenous promoter region which functions in a plant cell to cause the production of a mRNA molecule, wherein the exogenous promoter region is linked to a transcribed nucleic acid molecule having a transcribed strand and a non-transcribed strand, wherein a transcribed mRNA of the transcribed strand is complementary to a nucleic acid molecule selected from the group consisting of an endogenous mRNA molecule that encodes a putative maize or soybean chlorophyll synthetase enzyme or fragment thereof, an endogenous mRNA molecule that encodes a maize or soybean protochlorophyllide reductase enzyme or fragment thereof, an endogenous mRNA molecule that encodes a putative maize or soybean protochlorophyllide reductase enzyme or fragment thereof, an endogenous mRNA molecule that encodes a maize or soybean coproporphyrinogen oxidase enzyme or fragment thereof an endogenous mRNA molecule that encodes a maize or soybean protoporphyrinogen oxidase enzyme or fragment thereof, an endogenous mRNA molecule that encodes a maize or soybean uroporphyrinogen decarboxylase enzyme or fragment thereof, an endogenous mRNA molecule that encodes a putative maize uroporphyrinogen decarboxylase enzyme or fragment thereof, an endogenous mRNA molecule that encodes a maize or soybean porphobilinogen synthase enzyme or fragment thereof, an endogenous mRNA molecule that encodes a maize or soybean hydromethylbilane synthase enzyme or fragment thereof, an endogenous mRNA molecule that encodes a maize or soybean glutamate-1-semialdehyde 2,1-aminomutase enzyme or fragment thereof, an endogenous mRNA molecule that encodes a maize or soybean glutamate tRNA ligase enzyme or fragment thereof, an endogenous mRNA molecule that encodes a maize or soybean glutamyl-tRNA reductase enzyme or fragment thereof, an endogenous mRNA molecule that encodes a maize or soybean Mg-chelatase enzyme or fragment thereof and an endogenous mRNA molecule that encodes a maize or soybean ferrochelatase enzyme or fragment thereof, and wherein the transcribed nucleic acid molecule is linked to a 3' non-translated sequence that functions in the plant cell to cause termination of transcription and addition of polyadenylated ribonucleotides to a 3' end of a mRNA molecule; and (B) growing the transformed plant.

The present invention also provides a method of determining an association between a polymorphism and a plant trait comprising: (A) hybridizing a nucleic acid molecule specific for the polymorphism to genetic material of a plant, wherein the nucleic acid molecule has a nucleic acid sequence selected from the group consisting of SEQ ID NO: 1 through SEQ ID NO: 677 or complements thereof or fragment of either; and (B) calculating the degree of association between the polymorphism and the plant trait.

The present invention also provides a method of determining an association between a polymorphism and a plant trait comprising: (A) hybridizing a nucleic acid molecule specific for the polymorphism to genetic material of a plant, wherein the nucleic acid molecule is selected from the group consisting of a nucleic acid molecule that encodes a putative maize or soybean chlorophyll synthetase enzyme or complement thereof or fragment of either, a nucleic acid molecule that encodes a maize or soybean protochlorophyllide reductase enzyme or complement thereof or fragment of either, a nucleic acid molecule that encodes a putative maize or soybean protochlorophyllide reductase enzyme or complement thereof or fragment of either, a nucleic acid molecule that encodes a maize or soybean coproporphyrinogen oxidase enzyme or complement thereof or fragment of either, a nucleic acid molecule that encodes a maize or soybean protoporphyrinogen oxidase enzyme or complement thereof or fragment of either, a nucleic acid molecule that encodes a maize or soybean uroporphyrinogen decarboxylase enzyme or complement thereof or fragment of either, nucleic acid molecule that encodes a putative maize uroporphyrinogen decarboxylase enzyme or complement thereof or fragment of either, a nucleic acid molecule that encodes a maize or soybean porphobilinogen synthase enzyme or complement thereof or fragment of either, a nucleic acid molecule that encodes a maize or soybean hydroxymethylbilane synthase enzyme or complement thereof or fragment of either, a nucleic acid molecule that encodes a maize or soybean glutamate-1-semialdehyde 2,1-aminomutase enzyme or complement thereof or fragment of either, a nucleic acid molecule that encodes a maize or soybean glutamate tRNA ligase enzyme or complement thereof or fragment of either, a nucleic acid molecule that encodes a maize or soybean glutamyl-tRNA reductase enzyme or complement thereof or fragment of either, a nucleic acid molecule that encodes a maize or soybean Mg-chelatase enzyme or complement thereof or fragment of either and a nucleic acid molecule that encodes a maize or soybean ferrochelatase enzyme or complement thereof or fragment of either and (B) calculating the degree of association between the polymorphism and the plant trait.

The present invention also provides a method of isolating a nucleic acid that encodes a plant tetrapyrrole pathway protein or fragment thereof comprising: (A) incubating under conditions permitting nucleic acid hybridization, a first nucleic acid molecule comprising a nucleic acid sequence selected from the group consisting of SEQ ID NO: 1 through SEQ ID NO: 677 or complements thereof or fragment of either with a complementary second nucleic acid molecule obtained from a plant cell or plant tissue; (B) permitting hybridization between the first nucleic acid molecule and the second nucleic acid molecule obtained from the plant cell or plant tissue; and (C) isolating the second nucleic acid molecule.

The present invention also provides a method of isolating a nucleic acid molecule that encodes a plant tetrapyrrole pathway protein or fragment thereof comprising: (A) incubating under conditions permitting nucleic acid hybridization, a first nucleic acid molecule selected from the group consisting of a nucleic acid molecule that encodes a putative maize or soybean chlorophyll synthetase enzyme or complement thereof or fragment of either, a nucleic acid molecule that encodes a maize or soybean protochlorophyllide reductase enzyme or complement thereof or fragment of either, a nucleic acid molecule that encodes a putative maize or soybean protochlorophyllide reductase enzyme or complement thereof or fragment of either, a nucleic acid molecule that encodes a maize or soybean coproporphyrinogen oxidase enzyme or complement thereof or fragment of either, a nucleic acid molecule that encodes a maize or soybean protoporphyrinogen oxidase enzyme or complement thereof or fragment of either, a nucleic acid molecule that encodes a maize or soybean uroporphyrinogen decarboxylase enzyme or complement thereof or fragment of either, a nucleic acid molecule that encodes a putative maize uroporphyrinogen decarboxylase enzyme or complement thereof or fragment of either, a nucleic acid molecule that encodes a maize or soybean porphobilinogen synthase enzyme or complement thereof or fragment of either, a nucleic acid molecule that encodes a maize or soybean hydroxymethylbilane synthase enzyme or complement thereof or fragment of either, a nucleic acid molecule that encodes a maize or soybean glutamate-1-semialdehyde 2,1-aminomutase enzyme or complement thereof or fragment of either, a nucleic acid molecule that encodes a maize or soybean glutamate tRNA ligase enzyme or complement thereof or fragment of either, a nucleic acid molecule that encodes a maize or soybean glutamyl-tRNA reductase enzyme or complement thereof or fragment of either, a nucleic acid molecule that encodes a maize or soybean Mg-chelatase enzyme or complement thereof or fragment of either and a nucleic acid molecule that encodes a maize or soybean ferrochelatase enzyme or complement thereof or fragment of either, with a complementary second nucleic acid molecule obtained from a plant cell or plant tissue; (B) permitting hybridization between the plant tetrapyrrole pathway protein nucleic acid molecule and the complementary nucleic acid molecule obtained from the plant cell or plant tissue; and (C) isolating the second nucleic acid molecule .

DETAILED DESCRIPTION OF THE INVENTION

Definitions and Agents of the Present Invention

Definitions

As used herein, a tetrapyrrole pathway enzyme is any molecule that is associated with the biosynthesis or degradation of tetrapyrroles.

As used herein, ALA refers to 5-aminolevunic acid and 4-aminolevulinate.

As used herein, ALA synthase (E.C. 2.3.1.37) refers to any enzyme that catalyzes the condensation of glycine with succinyl-CoA to generate ALA.

As used herein, glutamyl-tRNA synthetase (GluRS) (E.C. 6.1.1.17) refers to any enzyme that converts glutamate to glutamyl-tRNA (Glu-tRNA).

As used herein, glutamyl-tRNA reductase (GluTR) refers to any enzyme that catalyzes the NADPH dependent reduction of Glu-tRNA to glutamate 1-semialdehyde (GSA) with the release of intact tRNA.

As used herein, glutamate-1-semialdehyde aminotransferase (GSA-AT) (E.C. 5.4.3.8) refers to any enzyme that catalyzes the conversion of GSA to ALA As used herein, porphobilinogen synthase (ALA dehydratase) (E.C. 4.2.1.24) refers to any enzyme that catalyzes the asymmetric condensation of two molecules of ALA to yield porphobilinogen.

As used herein, porphobilinogen deaminase (hydroxymethylbilane synthase) (E.C. 4.3.1.8) refers to any enzyme that catalyzes the formation of the linear tetrapyrrole hydroxymethylbilane.

As used herein, uroporphyrinogen III (co)synthase (E.C. 4.2.1.75) refers to any enzyme that catalyzes the ring closure of the unstable linear tetrapyrrole hydroxymethylbilane and the simultaneous isomerization of the acetyl and propionyl groups at pyrrole ring D forming uroporphyrinogen III.

As used herein, uroporphyrinogen III decarboxylase (E.C. 4.1.1.37) refers to any enzyme that catalyzes the stepwise decarboxylation of all four acetate side chains of uroporphyrinogen III starting with ring D followed by rings A, B, and C respectively to form coproporphyrinogen III.

As used herein, coproporphyrinogen III oxidase (E.C. 1.3.3.3) refers to any enzyme that catalyzes the oxygen dependent sequential oxidative decarboxylation of the A and B propionyl side chains of coproporphyrinogen III to yield two vinyl groups and protoporphyrinogen IX.

As used herein, protoporphyrinogen IX oxidase (E.C. 1.3.3.4) refers to any enzyme that catalyzes the formation of the aromatic protoporphyrin IX by the six electron oxidation of protoporphyrinogen IX.

As used herein, Mg-chelatase refers to any enzyme that catalyzes the conversion of protoporphyrin IX to magnesium protoporphyrin IX by the insertion $Mg^{+2}$.

As used herein, Mg-protoporphyrin IX O-methyltransferase (E.C. 2.1.1.11) refers to any enzyme that esterifies the propionic side chain of ring III of Mg-protoporphyrin IX to form Mg-protoporphyrin IX monomethylester.

As used herein, Mg-protoporphyrin IX monomethyl ester cyclase refers to any enzyme that catalyzes the cyclization of Mg-protoporphyrin IX monomethylester to form the isocyclic ring E of divinyl protochlorophyllide.

As used herein, 8-vinyl reductase refers to any enzyme that can reduce divinyl-protochlorophyllide or Mg-protoporphyrin IX monomethylester to monovinyl protochlorophyllide.

As used herein, protochlorophyllide reductase ("POR") (E.C. 1.3.1.33) refers to any enzyme that catalyzes the reduction of the double bond between carbons 7 and 8 of the D ring of protochlorophyllide producing chlorophyllide As used herein, chlorophyll synthetase refers to any enzyme that esterifies the propionic acid side chain of ring D of chlorophyllide with either phytyl pyrophosphate or geranylgeranyl pyrophosphate.

As used herein, ferrochelatase (E.C. 4.99.1.1) refers to any enzyme that catalyzes the conversion of protoporphyrin IX to heme.

Agents (a) Nucleic Acid Molecules

Agents of the present invention include plant nucleic acid molecules and more preferably include maize, soybean and *Arabidopsis thaliana* nucleic acid molecules and more preferably include nucleic acid molecules of the maize genotypes B73 (Illinois Foundation Seeds, Champaign, Ill. U.S.A.), B73×Mo17 (Illinois Foundation Seeds, Champaign, Ill. U.S.A.), DK604 (Dekalb Genetics, Dekalb, Ill. U.S.A.), H99 (Illinois Foundation Seeds, Champaign, Ill. U.S.A.), RX601 (Asgrow Seed Company, Des Moines, Iowa), Mo17 (Illinois Foundation Seeds, Champaign, Ill. U.S.A.), and soybean types Asgrow 3244 (Asgrow Seed Company, Des Moines, Iowa), C1944 (United States Department of Agriculture (USDA) Soybean Germplasm Collection, Urbana, Ill. U.S.A.), Cristalina (USDA Soybean Gemmplasm Collection, Urbana, Ill. U.S.A.), FT108 (Monsoy, Brazil), Hartwig (USDA Soybean Germplasm Collection, Urbana, Ill. U.S.A.), BW211S Null (Tohoku University, Morioka, Japan), P1507354 (USDA Soybean Germplasm Collection, Urbana, Ill. U.S.A.), Asgrow A4922 (Asgrow Seed Company, Des Moines, Iowa U.S.A.), PI227687 (USDA Soybean Germplasm Collection, Urbana, Ill. U.S.A.), P1229358 (USDA Soybean Germplasm Collection, Urbana, Ill. U.S.A.) and Asgrow A3237 (Asgrow Seed Company, Des Moines, Iowa U.S.A.).

A subset of the nucleic acid molecules of the present invention includes nucleic acid molecules that are marker molecules. Another subset of the nucleic acid molecules of the present invention include nucleic acid molecules that encode a protein or fragment thereof. Another subset of the nucleic acid molecules of the present invention are EST molecules.

Fragment nucleic acid molecules may encode significant portion(s) of, or indeed most of, these nucleic acid molecules. Alternatively, the fragments may comprise smaller oligonucleotides (having from about 15 to about 250 nucleotide residues and more preferably, about 15 to about 30 nucleotide residues).

As used herein, an agent, be it a naturally occurring molecule or otherwise may be "substantially purified," if desired, such that one or more molecules that is or may be present in a naturally occurring preparation containing that molecule will have been removed or will be present at a lower concentration than that at which it would normally be found.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

It is understood that the agents of the present invention may be labeled with reagents that facilitate detection of the agent (e.g. fluorescent labels, Prober et al., *Science* 238:336-340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448, all of which are hereby incorporated by reference in their entirety).

It is further understood, that the present invention provides recombinant bacterial mammalian, microbial, insect, fungal and plant cells and viral constructs comprising the agents of the present invention. (See, for example, Uses of the Agents of the Invention, Section (a) Plant Constructs and Plant Transformants; Section (b) Fungal Constructs and Fungal Transformants; Section (c) Mammalian Constructs and Transformed Mammalian Cells; Section (d) Insect Constructs and Transformed Insect Cells; and Section (e) Bacterial Constructs and Transformed Bacterial Cells)

Nucleic acid molecules or fragments thereof of the present invention are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one anther with sufficient stability to permit them to remain annealed to one another under conventional "high-stringency" conditions. Conventional stringency conditions are described by Sambrook et al., *Molecular Cloning*, A Laboratory Manual, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985), the entirety of which is herein incorporated by reference. Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2× SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NO: 1 through SEQ ID NO: 677 or complements thereof under moderately stringent conditions, for example at about 2.0×SSC and about 65° C.

In a particularly preferred embodiment, a nucleic acid of the present invention will include those nucleic acid molecules that specifically hybridize to one or more of the nucleic acid molecules set forth in SEQ ID NO: 1 through SEQ ID NO: 677 or complements thereof under high stringency conditions such as 0.2×SSC and about 65° C.

In one aspect of the present invention, the nucleic acid molecules of the present invention have one or more of the nucleic acid sequences set forth in SEQ ID NO: 1 through SEQ ID NO: 677 or complements thereof. In another aspect of the present invention, one or more of the nucleic acid molecules of the present invention share between 100% and 90% sequence identity with one or more of the nucleic acid sequences set forth in SEQ ID NO: 1 through SEQ ID NO: 677 or complements thereof. In a further aspect of the present invention, one or more of the nucleic acid molecules of the present invention share between 100% and 95% sequence identity with one or more of the nucleic acid sequences set forth in SEQ ID NO: 1 through SEQ ID NO: 677 or complements thereof. In a more preferred aspect of the present invention, one or more of the nucleic acid molecules of the present invention share between 100% and 98% sequence identity with one or more of the nucleic acid sequences set forth in SEQ ID NO: 1 through SEQ ID NO: 677 or complements thereof. In an even more preferred aspect of the present invention, one or more of the nucleic acid molecules of the present invention share between 100% and 99% sequence identity with one or more of the sequences set forth in SEQ ID NO: 1 through SEQ ID NO: 677 or complements thereof.

In a further more preferred aspect of the present invention, one or more of the nucleic acid molecules of the present invention exhibit 100% sequence identity with a nucleic acid molecule present within MONN01, SATMON001, SATMON003 through SATMON014, SATMON016 through SATMON031, SATMON033, SATMON034, SATMON6001, SATMONN01, SATMONN04 through SATMONN006, CMz029 through CMz031, CMz033 through CMz037, CMz039 through CMz042, CMz044 through CMz045, CMz047 through CMz050, SOYMON001 through SOYMON038, Soy51 through Soy56, Soy58 through Soy62, Soy65 through Soy73 and Soy76 through Soy77, Lib9, Lib22 through Lib25, Lib35, and Lib146 (Monsanto Company, St. Louis, Mo. U.S.A.).

(i) Nucleic Acid Molecules Encoding Proteins or Fragments Thereof

Nucleic acid molecules of the present invention can comprise sequences that encode a tetrapyrrole pathway enzyme or fragment thereof. Such transcription factors or fragments thereof include homologues of known transcription factors in other organisms.

In a preferred embodiment of the present invention, a maize or soybean tetrapyrrole pathway enzyme or fragment thereof of the present invention is a homologue of another plant tetrapyrrole pathway protein. In another preferred embodiment of the present invention, a maize or soybean tetrapyrrole pathway enzyme or fragment thereof of the present invention is a homologue of a fungal tetrapyrrole pathway enzyme. In another preferred embodiment of the present invention, a maize or soybean tetrapyrrole pathway enzyme of the present invention is a homologue of mammalian transcription factor. In another preferred embodiment of the present invention, a maize or soybean tetrapyrrole pathway enzyme or fragment thereof of the present invention is a homologue of a bacterial transcription factor. In another preferred embodiment of the present invention, a maize or soybean tetrapyrrole pathway enzyme or fragment thereof of the present invention is a homologue of a maize tetrapyrrole pathway enzyme. In another preferred embodiment of the present invention, a maize or soybean tetrapyrrole pathway enzyme homologue or fragment thereof of the present invention is a homologue of a soybean transcription factor.

In a preferred embodiment of the present invention, the nucleic acid molecule of the present invention encodes a maize or soybean tetrapyrrole pathway enzyme or fragment thereof where a maize or soybean tetrapyrrole pathway enzyme exhibits a BLAST probability score of greater than 1E-12, preferably a BLAST probability score of between about 1E-30 and about 1E-12, even more preferably a BLAST probability score of greater than 1E-30 with its homologue.

In another preferred embodiment of the present invention, the nucleic acid molecule encoding a maize or soybean tetrapyrrole pathway enzyme or fragment thereof exhibits a % identity with its homologue of between about 25% and about 40%, more preferably of between about 40 and about 70%, even more preferably of between about 70% and about 90% and even more preferably between about 90% and 99%. In another preferred embodiment, of the present invention, a maize or soybean tetrapyrrole enzyme or fragment thereof exhibits a % identity with its homologue of 100%.

In a preferred embodiment of the present invention, the nucleic molecule of the present invention encodes a maize or soybean tetrapyrrole pathway enzyme or fragment thereof where a maize or soybean tetrapyrrole pathway enzyme exhibits a BLAST score of greater than 120, preferably a BLAST score of between about 1450 and about 120, even more preferably a BLAST score of greater than 1450 with its homologue.

Nucleic acid molecules of the present invention also include non-maize, non-soybean homologues. Preferred non-homologues are selected from the group consisting of alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm and *Phaseolus*.

In a preferred embodiment, nucleic acid molecules having SEQ ID NO: 1 through SEQ. ID NO: 677 or complements and fragments of either can be utilized to obtain such homologues.

The degeneracy of the genetic code, which allows different nucleic acid sequences to code for the same protein or peptide, is known in the literature. (U.S. Pat. No. 4,757,006, the entirety of which is herein incorporated by reference).

In an aspect of the present invention, one or more of the nucleic acid molecules of the present invention differ in nucleic acid sequence from those encoding a maize or soybean tetrapyrrole pathway enzyme or fragment thereof in SEQ ID NO: 1 through SEQ ID NO: 677 due to the degeneracy in the genetic code in that they encode the same transcription factor but differ in nucleic acid sequence.

In another further aspect of the present invention, one or more of the nucleic acid molecules of the present invention differ in nucleic acid sequence from those encoding a maize or soybean tetrapyrrole pathway enzyme or fragment thereof in SEQ ID NO: 1 through SEQ ID NO: 677 due to fact that the different nucleic acid sequence encodes a transcription factor having one or more conservative amino acid residue. Examples of conservative substitutions are set forth in Table 1. It is understood that codons capable of coding for such conservative substitutions are known in the art.

TABLE 1

| Original Residue | Conservative Substitutions |
| --- | --- |
| Ala | Ser |
| Arg | Lys |
| Asn | Gln; His |
| Asp | Glu |
| Cys | Ser; Ala |
| Gln | Asn |
| Glu | Asp |
| Gly | Pro |

TABLE 1-continued

| Original Residue | Conservative Substitutions |
| --- | --- |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

In a further aspect of the present invention, one or more of the nucleic acid molecules of the present invention differ in nucleic acid sequence from those encoding a maize or soybean tetrapyrrole or fragment thereof set forth in SEQ ID NO: 1 through SEQ ID NO: 677 or fragment thereof due to the fact that one or more codons encoding an amino acid has been substituted for a codon that encodes a nonessential substitution of the amino acid originally encoded.

Agents of the present invention include nucleic acid molecules that encode a maize, or soybean tetrapyrrole pathway enzyme or fragment thereof and particularly substantially purified nucleic acid molecules selected from the group consisting of a nucleic acid molecule that encodes a putative maize or soybean chlorophyll synthetase enzyme or fragment, a nucleic acid molecule that encodes a maize or soybean protochlorophyllide reductase enzyme or fragment, a nucleic acid molecule that encodes a putative maize or soybean protochlorophyllide reductase enzyme or fragment, a nucleic acid molecule that encodes a maize or soybean coproporphyrinogen oxidase enzyme or fragment, a nucleic acid molecule that encodes a maize or soybean protoporphyrinogen oxidase enzyme or fragment, a nucleic acid molecule that encodes a maize or soybean uroporphyrinogen decarboxylase enzyme or fragment, a nucleic acid molecule that encodes a putative maize uroporphyrinogen decarboxylase enzyme or fragment, a nucleic acid molecule that encodes a maize or soybean porphobilinogen synthase enzyme or fragment, a nucleic acid molecule that encodes a maize or soybean hydroxylmethylbilane synthase enzyme or fragment, a nucleic acid molecule that encodes a maize or soybean glutamate-semialdehyde 2,1-aminomutase enzyme or fragment, a nucleic acid molecule that encodes a maize or soybean glutamate tRNA ligase enzyme fragment, a nucleic acid molecule that encodes a maize or soybean glutamyl-tRNA reductase enzyme or fragment, a nucleic acid molecule that encodes a maize or soybean Mg-chelatase enzyme or fragment and a nucleic acid molecule that encodes a maize or soybean ferrochelatase enzyme or fragment.

Non-limiting examples of such nucleic acid molecules of the present invention are nucleic acid molecules comprising: SEQ ID NO: 1 through SEQ ID NO: 677 or fragment thereof that encode for a plant tetrapyrrole pathway protein or fragment thereof, SEQ ID NO: 1 through SEQ ID NO: 8 and SEQ ID NO: 384 through SEQ ID NO: 397 or fragment thereof that encode for a putative chlorophyll synthetase enzyme or fragment thereof, SEQ ID NO: 9 through SEQ ID NO: 94 and SEQ ID NO: 398 through SEQ ID NO: 466 or fragment thereof that encode for a protochlorophyllide reductase enzyme or fragment thereof, SEQ ID NO: 95 through SEQ ID NO: 96 and SEQ ID NO: 467 through SEQ ID NO: 479 or fragment thereof that encode for a putative protochlorophyllide reductase enzyme or fragment thereof, SEQ ID NO: 97 through SEQ ID NO: 128 and SEQ ID NO: 480 through SEQ ID NO: 494 or fragment thereof that encodes for a coproporphyrinogen oxidase enzyme or fragment thereof, SEQ ID NO: 129 through SEQ ID NO: 131 and SEQ ID NO: 495 through SEQ ID NO: 499 or fragment thereof that encode for a protoporphyrinogen oxidase enzyme or fragment thereof, SEQ ID NO: 132 through SEQ ID NO: 144 and SEQ ID NO: 500 through SEQ ID NO: 509 or fragment thereof that encode for an uroporphyrinogen decarboxylase enzyme or fragment thereof, SEQ ID NO: 510 or fragment thereof that encode for a putative uroporphyrinogen decarboxylase enzyme or fragment thereof, SEQ ID NO: 145 through SEQ ID NO: 191 and SEQ ID NO: 511 through SEQ ID NO: 531 or fragment thereof that encode for a porphobilinogen synthase enzyme or fragment thereof, SEQ ID NO: 154, SEQ ID NO: 192 through SEQ ID NO: 217 and SEQ ID NO: 532 through SEQ. ID NO: 542 or fragment thereof that encode for a hydroxymethylbilane synthase enzyme or fragment thereof, SEQ ID NO: 218 through SEQ ID NO: 265 and SEQ ID NO: 543 through SEQ ID NO: 569 or fragment thereof that encodes for a glutamate-1-semialdehyde 2,1-aminomutase enzyme or fragment thereof, SEQ ID NO: 266 through SEQ ID NO: 289 and SEQ ID NO: 570 through SEQ ID NO: 585 or fragment thereof that encode for a glutamate tRNA ligase enzyme or fragment thereof, SEQ ID NO: 290 through SEQ ID NO: 306 and SEQ ID NO: 586 through SEQ ID NO: 609 or fragment thereof that encode for an glutamyl-tRNA reductase enzyme or fragment thereof, SEQ ID NO: 307 through SEQ ID NO: 371 and SEQ ID NO: 610 through SEQ ID NO: 652 or fragment thereof that encode for a Mg-chelatase enzyme or fragment thereof, and SEQ ID NO: 372 through SEQ ID NO: 383 and SEQ ID NO: 653 through SEQ ID NO: 677 or fragment thereof that encode for an ferrochelatase enzyme or fragment thereof.

A nucleic acid molecule of the present invention can also encode an homologue of a putative maize or soybean chlorophyll synthetase enzyme or fragment thereof, a maize or soybean protochlorophyllide reductase enzyme or fragment or fragment thereof, a putative maize or soybean protochlorophyllide reductase enzyme or fragment or fragment thereof, a maize or soybean coproporphyrinogen oxidase enzyme or fragment thereof, a maize or soybean protoporphyrinogen oxidase enzyme or fragment thereof, a maize or soybean uroporphyrinogen decarboxylase enzyme or fragment thereof, a putative maize uroporphyrinogen decarboxylase enzyme or fragment thereof, a maize or soybean porphobilinogen synthase enzyme or fragment thereof, a maize or soybean hydroxymethylbilane synthase enzyme or fragment thereof, a maize or soybean glutamate-1-semialdehyde 2,1-aminomutase enzyme or fragment thereof, a maize or soybean glutamate tRNA ligase enzyme fragment thereof, a maize or soybean glutamyl-tRNA reductase enzyme or fragment thereof, a maize or soybean Mg-chelatase enzyme or fragment thereof and a nucleic acid molecule that encodes a maize or soybean ferrochelatase enzyme or fragment thereof. As used herein a homologue protein molecule or fragment thereof is a counterpart protein molecule or fragment thereof in a second species (e.g., maize chlorophyll synthetase is a homologue of *Arabidopsis*' chlorophyll synthetase).

(ii) Nucleic Acid Molecule Markers and Probes

One aspect of the present invention concerns markers that include nucleic acid molecules SEQ ID NO: 1 through SEQ ID NO: 677 or complements thereof or fragments of either that can act as markers or other nucleic acid molecules of the present invention that can act as markers. Genetic markers of the present invention include "dominant" or "codominant" markers "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is present in either the homozygous or heterozygous condition. The absence of the dominant marker phenotype (e.g. absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

SNPs are single base changes in genomic DNA sequence. They occur at greater frequency and are spaced with a greater uniformly throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a results of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.* 32:314-331 (1980), the entirety of which is herein incorporated reference; Konieczny and Ausubel, *Plant J.* 4:403-410 (1993), the entirety of which is herein incorporated by reference), enzymatic and chemical mismatch assays (Myers et al., *Nature* 313:495-498 (1985), the entirety of which is herein incorporated by reference), allele-specific PCR (Newton et al., *Nucl. Acids Res.* 17:2503-2516 (1989), the entirety of which is herein incorporated by reference; Wu et al., *Proc. Natl. Acad. Sci. (U.S.A.)* 86:2757-2760 (1989), the entirety of which is herein incorporated by reference), ligase chain reaction (Barany, *Proc. Natl. Acad. Sci. (U.S.A.)* 88:189-193 (1991), the entirety of which is herein incorporated by reference), single-strand conformation polymorphism analysis (Labrune et al., *Am. J. Hum. Genet.* 48: 1115-1120 (1991), the entirety of which is herein incorporated by reference), primer-directed nucleotide incorporation assays (Kuppuswami et al., *Proc. Natl. Acad. Sci. USA* 88:1143-1147 (1991), the entirety of which is herein incorporated by reference), dideoxy fingerprinting (Sarkar et al., *Genomics* 13:441-443 (1992), the entirety of which is herein incorporated by reference), solid-phase ELISA-based oligonucleotide ligation assays (Nikiforov et al., *Nucl. Acids Res.* 22:4167-4175 (1994), the entirety of which is herein incorporated by reference), oligonucleotide fluorescence-quenching assays (Livak et al., *PCR Methods Appl.* 4:357-362 (1995), the entirety of which is herein incorporated by reference), 5'-nuclease allele-specific hybridization TaqMan assay (Livak et al., *Nature Genet.* 9:341-342 (1995); the entirety of which is herein incorporated by reference), template-directed dye-terminator incorporation (TDI) assay (Chen and Kwok, *Nucl. Acids Res.* 25:347-353 (1997), the entirety of which is herein incorporated by reference), allele-specific molecular beacon assay (Tyagi et al., *Nature Biotech.* 16: 49-53 (1998), the entirety of which is herein incorporated by reference), PinPoint assay (Haff and Smirnov, *Genome Res.* 7: 378-388 (1997), the entirety of which is herein incorporated by reference) and dCAPS analysis (Neff et al., *Plant J.* 14:387-392 (1998), the entirety of which is herein incorporated by reference).

Additional markers, such as AFLP markers, RFLP markers and RAPD markers, can be utilized (Walton, *Seed World* 22-29 (July, 1993), the entirety of which is herein incorporated by reference; Burow and Blake, *Molecular Dissection of Complex Traits,* 13-29, Paterson (ed.), CRC Press, New York (1988), the entirety of which is herein incorporated by reference): DNA markers can be developed from nucleic acid molecules using restriction endonucleases, the PCR and/or DNA sequence information. RFLP markers result from single base changes or insertions/deletions. These codominant markers are highly abundant in plant genomes, have a medium level of polymorphism and are developed by a combination of restriction endonuclease digestion and Southern blotting hybridization. CAPS are similarly developed from restriction nuclease digestion but only of specific PCR products. These markers are also codominant, have a medium level of polymorphism and are highly abundant in the genome. The CAPS result from single base changes and insertions/deletions.

Another marker type, RAPDs, are developed from DNA amplification with random primers and result from single base changes and insertions/deletions in plant genomes. They are dominant markers with a medium level of polymorphisms and are highly abundant. AFLP markers require using the PCR on a subset of restriction fragments from extended adapter primers. These markers are both dominant and codominant are highly abundant in genomes and exhibit a medium level of polymorphism.

SSRs require DNA sequence information. These codominant markers result from repeat length changes, are highly polymorphic and do not exhibit as high a degree of abundance in the genome as CAPS, AFLPs and RAPDs SNPs also require DNA sequence information. These codominant markers result from single base substitutions. They are highly abundant and exhibit a medium of polymorphism (Rafalski et al., In: *Nonmammalian Genomic Analysis*, Birren and Lai (ed.), Academic Press, San Diego, Calif., pp. 75-134 (1996), the entirety of which is herein incorporated by reference). It is understood that a nucleic acid molecule of the present invention may be used as a marker.

A PCR probe is a nucleic acid molecule capable of initiating a polymerase activity while in a double-stranded structure to with another nucleic acid. Various methods for determining the structure of PCR probes and PCR techniques exist in the art. Computer generated searches using programs such as Primer3 (on the Worldwide web at genome.wi.mit.edu/cgi-bin/primer/primer3.cgi), STSPipeline (on the Worldwide web at genome.wi.mit.edu/cgi-bin/www-STS_Pipeline), or GeneUp (Pesole et al., *BioTechniques* 25:112-123 (1998) the entirety of which is herein incorporated by reference), for example, can be used to identify potential PCR primers.

It is understood that a fragment of one or more of the nucleic acid molecules of the present invention may be a probe and specifically a PCR probe.

(b) Protein and Peptide Molecules

A class of agents comprises one or more of the protein or fragments thereof or peptide molecules encoded by SEQ ID NO: 1 through SEQ ID NO: 677 or one or more of the protein or fragment thereof and peptide molecules encoded by other nucleic acid agents of the present invention. As used herein, the term "protein molecule" or "peptide molecule" includes any molecule that comprises five or more amino acids. It is well known in the art that proteins may undergo modification, including post-translational modifications, such as, but not limited to, disulfide bond formation, glycosylation, phosphorylation, or oligomerization. Thus, as used herein, the term "protein molecule" or "peptide molecule" includes any protein molecule that is modified by any biological or non-biological process. The terms "amino acid" and "amino acids" refer to all naturally occurring L-amino acids. This definition is meant to include norleucine, ornithine, homocysteine and homoserine.

Non-limiting examples of the protein or fragment thereof of the present invention include a maize or soybean tetrapyrrole pathway enzyme or fragment thereof, a putative maize or soybean chlorophyll synthetase enzyme or fragment thereof, a maize or soybean protochlorophyllide reductase enzyme or fragment or fragment thereof, a putative maize or soybean protochlorophyllide reductase enzyme or fragment or fragment thereof, a maize or soybean coproporphyrinogen oxidase enzyme or fragment thereof, a maize or soybean protoporphyrinogen oxidase enzyme or fragment thereof, a maize or soybean uroporphyrinogen decarboxylase enzyme or fragment thereof, a putative maize uroporphyrinogen decarboxylase enzyme or fragment thereof, a maize or soybean porphobilinogen synthase enzyme or fragment thereof, a maize or soybean hydroxymethylbilane synthase enzyme or fragment thereof, a maize or soybean glutamate-1-semialdehyde 2,1-aminomutase enzyme or fragment thereof, a maize or soybean glutamate tRNA ligase enzyme fragment thereof, a maize or soybean glutamyl-tRNA reductase enzyme or fragment thereof, a maize or soybean Mg-chelatase enzyme or fragment thereof and a nucleic acid molecule that encodes a maize or soybean ferrochelatase enzyme or fragment thereof.

Non-limiting examples of the protein or fragment molecules of the present invention are a transcription factor or fragment thereof encoded by: SEQ ID NO: 1 through SEQ ID NO: 677 or fragment thereof that encode for a tetrapyrrole pathway enzyme or fragment thereof, SEQ ID NO: 1 through SEQ ID NO: 8 and SEQ ID NO: 384 through SEQ ID NO: 397 or fragment thereof that encode for a putative chlorophyll synthetase enzyme or fragment thereof, SEQ ID NO: 9 through SEQ ID NO: 94 and SEQ ID NO: 398 through SEQ ID NO: 466 or fragment thereof that encode for a protochlorophyllide reductase enzyme or fragment thereof, SEQ ID NO: 95 through SEQ ID NO: 96 and SEQ ID NO: 467 through SEQ ID NO: 479 or fragment thereof that encode for a putative protochlorophyllide reductase enzyme or fragment thereof, SEQ ID NO: 97 through SEQ ID NO: 128 and SEQ ID NO: 480 through SEQ ID NO: 494 fragment thereof that encodes for a coproporphyrinogen oxidase enzyme or fragment thereof, SEQ ID NO: 129 through SEQ ID NO: 131 and SEQ ID NO: 495 through SEQ ID NO: 499 or fragment thereof that encode for a protoporphyrinogen oxidase enzyme or fragment thereof, SEQ ID NO: 132 through SEQ ID NO: 144 and SEQ ID NO: 500 through SEQ ID NO: 509 or fragment thereof that encode for an uroporphyrinogen decarboxylase enzyme or fragment thereof, SEQ ID NO: 510 or fragment thereof that encode for a putative uroporphyrinogen decarboxylase enzyme or fragment thereof, SEQ ID NO: 145 through SEQ ID NO: 191 and SEQ ID NO: 511 through SEQ ID NO: 531 or fragment thereof that encode for a porphobilinogen synthase enzyme or fragment thereof, SEQ ID NO: 154, SEQ ID NO: 192 through SEQ ID NO: 217 and SEQ ID NO: 532 through SEQ ID NO: 542 or fragment thereof that encode for a hydroxymethylbilane synthase enzyme or fragment thereof, SEQ ID NO: 218 through SEQ ID NO: 265 and SEQ ID NO: 543 through SEQ ID NO: 569 or fragment thereof that encodes for a glutamate-1-semialdehyde 2,1-aminomutase enzyme or fragment thereof, SEQ ID NO: 266 through SEQ ID NO: 289 and SEQ ID NO: 570 through SEQ ID NO: 585 or fragment thereof that encode for a glutamate tRNA ligase enzyme or fragment thereof, SEQ ID NO: 290 through SEQ ID NO: 306 and SEQ ID NO: 586 through SEQ ID NO: 609 or fragment thereof that encode for an glutamyl-tRNA reductase enzyme or fragment thereof, SEQ ID NO: 307 through SEQ ID NO: 371 and SEQ ID NO: 610 through SEQ ID NO: 652 or fragment thereof that encode for a Mg-chelatase enzyme or fragment thereof, and SEQ ID NO: 372 through SEQ ID NO: 383 and SEQ ID NO: 653 through SEQ ID NO: 677 or fragment thereof that encode for an ferrochelatase enzyme or fragment thereof.

One or more of the protein or fragment of peptide molecules may be produced via chemical synthesis, or more preferably, by expressing in a suitable bacterial or eucaryotic host. Suitable methods for expression are described by Sambrook et al., (In: *Molecular Cloning, A Laboratory Manual, 2nd Edition*, Cold Spring Harbor Press, Cold Spring Harbor, N.Y. (1989)), or similar texts. For example, the protein may be expressed in, for example, Uses of the Agents of the Invention, Section (a) Plant Constructs and Plant Transformants; Section (b) Fungal Constructs and Fungal Transformants; Section (c) Mammalian Constructs and Transformed Mammalian Cells; Section (d) Insect Constructs and Transformed Insect. Cells; and Section (e) Bacterial Constructs and Transformed Bacterial Cells.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin, etc.). Fusion protein or peptide molecules of the present invention are preferably produced via recombinant means.

Another class of agents comprise protein or peptide molecules or fragments or fusions thereof encoded by SEQ ID NO: 1 through SEQ ID NO: 677 or complements thereof in which conservative, non-essential or non-relevant amino acid residues have been added, replaced or deleted. Computerized means for designing modifications in protein structure are known in the art (Dahiyat and Mayo, *Science* 278:82-87 (1997), the entirety of which is herein incorporated by reference).

The protein molecules of the present invention include plant homologue proteins. An example of such a homologue is a homologue protein of a non-maize or non soybean plant species, that include but not limited to alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm, *Phaseolus* etc. Particularly preferred non-maize or non-soybean for use for the isolation of homologs would include, *Arabidopsis*, barley, cotton, oat, oilseed rape, rice, canola, ornamentals, sugarcane, sugarbeet, tomato, potato, wheat and turf grasses. Such a homologue can be obtained by any of a variety of methods. Most preferably, as indicated above, one or more of the disclosed sequences (SEQ ID NO: 1 through SEQ ID NO: 677 or complements thereof) will be used to define a pair of primers that may be used to isolate the homologue-encoding nucleic acid molecules from any desired species. Such molecules can be expressed to yield homologues by recombinant means.

(c) Antibodies

One aspect of the present invention concerns antibodies, single-chain antigen binding molecules, or other proteins that specifically bind to one or more of the protein or peptide molecules of the present invention and their homologues, fusions or fragments. Such antibodies may be used to quantitatively or qualitatively detect the protein or peptide molecules of the present invention. As used herein, an antibody or peptide is said to "specifically bind" to a protein or peptide molecule of the present invention if such binding is not competitively inhibited by the presence of non-related molecules.

Nucleic acid molecules that encode all or part of the protein of the present invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the present invention may be expressed, via recombinant means, to yield proteins or peptides encoded by these nucleic acid molecules.

The antibodies that specifically bind proteins and protein fragments of the present invention may be polyclonal or monoclonal and may comprise intact immuno globulins, or antigen binding portions of immunoglobulins fragments (such as (F(ab'), F(ab')$_2$), or single-chain immunoglobulins producible, for example, via recombinant means. It is understood that practitioners are familiar with the standard resource materials which describe specific conditions and procedures for the construction, manipulation and isolation of antibodies (see, for example, Harlow and Lane, In: *Antibodies: A Laboratory Manual*, Cold Spring Harbor Press, Cold Spring Harbor, N.Y. (1988), the entirety of which is herein incorporated by reference).

Murine monoclonal antibodies are particularly preferred. BALB/c mice are preferred for this purpose, however, equivalent strains may also be used. The animals are preferably immunized with approximately 25 µg of purified protein (or fragment thereof) that has been emulsified in a suitable adjuvant (such as TiterMax adjuvant (Vaxcel, Norcross, Ga.)). Immunization is preferably conducted at two intramuscular sites, one intraperitoneal site and one subcutaneous site at the base of the tail. An additional i.v. injection of approximately 25 µg of antigen is preferably given in normal saline three weeks later. After approximately 11 days following the second injection, the mice may be bled and the blood screened for the presence of anti-protein or peptide antibodies. Preferably, a direct binding Enzyme-Linked Immunoassay (ELISA) is employed for this purpose.

More preferably, the mouse having the highest antibody titer is given a third i.v. injection of approximately 25 µg of the same protein or fragment. The splenic leukocytes from this animal may be recovered 3 days later and then permitted to fuse, most preferably, using polyethylene glycol, with cells of a suitable myeloma cell line (such as, for example, the P3X63Ag8.653 myeloma cell line). Hybridoma cells are selected by culturing the cells under "HAT" (hypoxanthine-aminopterin-thymine) selection for about one week. The resulting clones may then be screened for their capacity to produce monoclonal antibodies ("mAbs"), preferably by direct ELISA.

In one embodiment, anti-protein or peptide monoclonal antibodies are isolated using a fusion of a protein or peptide of the present invention, or conjugate of a protein or peptide of the present invention, as immunogens. Thus, for example, a group of mice can be immunized using a fusion protein emulsified in Freund's complete adjuvant (e.g. approximately 50 μg of antigen per immunization). At three week intervals, an identical amount of antigen is emulsified in Freund's incomplete adjuvant and used to immunize the animals. Ten days following the third immunization, serum samples are taken and evaluated for the presence of antibody. If antibody titers are too low, a fourth booster can be employed. Polysera capable of binding the protein or peptide can also be obtained using this method.

In a preferred procedure for obtaining monoclonal antibodies, the spleens of the above-described immunized mice are removed, disrupted and immune splenocytes are isolated over a ficoll gradient. The isolated splenocytes are fused, using polyethylene glycol with BALB/c-derived HGPRT (hypoxanthine guanine phosphoribosyl transferase) deficient P3×63×Ag8.653 plasmacytoma cells. The fused cells are plated into 96 well microtiter plates and screened for hybridoma fusion cells by their capacity to grow in culture medium supplemented with hypothanthine, aminopterin and thymidine for approximately 2-3 weeks.

Hybridoma cells that arise from such incubation are preferably screened for their capacity to produce an immunoglobulin that binds to a protein of interest. An indirect ELISA may be used for this purpose. In brief, the supernatants of hybridomas are incubated in microtiter wells that contain immobilized protein. After washing, the titer of bound immunoglobulin can be determined using, for example, a goat anti-mouse antibody conjugated to horseradish peroxidase. After additional washing, the amount of immobilized enzyme is determined (for example through the use of a chromogenic substrate). Such screening is performed as quickly as possible after the identification of the hybridoma in order to ensure that a desired clone is not overgrown by non-secreting neighbor cells. Desirably, the fusion plates are screened several times since the rates of hybridoma growth vary. In a preferred sub-embodiment, a different antigenic form may be used to screen the hybridoma. Thus, for example, the splenocytes may be immunized with one immunogen, but the resulting hybridomas can be screened using a different immunogen. It is understood that any of the protein or peptide molecules of the present invention may be used to raise antibodies.

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the present invention permits the identification of mimetic compounds of those molecules. A "mimetic compound" is a compound that is not that compound, or a fragment of that compound, but which nonetheless exhibits an ability to specifically bind to antibodies directed against that compound.

It is understood that any of the agents of the present invention can be substantially purified and/or be biologically active and/or recombinant.

Uses of the Agents of the Invention

Nucleic acid molecules and fragments thereof of the present invention may be employed to obtain other nucleic acid molecules from the same species (e.g., ESTs or fragment thereof from maize may be utilized to obtain other nucleic acid molecules from maize). Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries obtained from maize or soybean. Methods for forming such libraries are well known in the art.

Nucleic acid molecules and fragments thereof of the present invention may also be employed to obtain nucleic acid homologues. Such homologues include the nucleic acid molecule of other plants or other organisms (e.g., alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm, *Phaseolus*, etc.) including the nucleic acid molecules that encode, in whole or in part, protein homologues of other plant species or other organisms, sequences of genetic elements such as promoters and transcriptional regulatory elements. Such molecules can be readily obtained by using the above-described nucleic acid molecules or fragments thereof to screen cDNA or genomic libraries obtained from such plant species. Methods for forming such libraries are well known in the art. Such homologue molecules may differ in their nucleotide sequences from those found in one or more of SEQ ID NO: 1 through SEQ ID NO: 677 or complements thereof because complete complementarity is not needed for stable hybridization. The nucleic acid molecules of the present invention therefore also include molecules that, although capable of specifically hybridizing with the nucleic acid molecules may lack "complete complementarity."

Any of a variety of methods may be used to obtain one or more of the above-described nucleic acid molecules (Zamechik et al., *Proc. Natl. Acad. Sci.* (*U.S.A.*) 83:4143-4146 (1986), the entirety of which is herein incorporated by reference; Goodchild et al., *Proc. Natl. Acad. Sci.* (*U.S.A.*) 85:5507-5511 (1988), the entirety of which is herein incorporated by reference; Wickstrom et al., *Proc. Natl. Acad. Sci.* (*U.S.A.*) 85:1028-1032 (1988), the entirety of which is herein incorporated by reference; Holt et al., *Molec. Cell. Biol.* 8:963-973 (1988), the entirety of which is herein incorporated by reference; Gerwirtz et al., *Science* 242:1303-1306 (1988), the entirety of which is herein incorporated by reference; Anfossi et al., *Proc. Natl. Acad. Sci.* (*U.S.A.*) 86:3379-3383 (1989), the entirety of which is herein incorporated by reference; Becker et al., *EMBO J.* 8:3685-3691 (1989); the entirety of which is herein incorporated by reference). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263-273 (1986); Erlich et al., European Patent 50,424; European Patent 84,796; European Patent 258,017; European Patent 237,362; Mullis, European Patent 201,184; Mullis et al., U.S. Pat. No. 4,683,202; Erlich, U.S. Pat. No. 4,582,788; and Saiki et al., U.S. Pat. No. 4,683,194, all of which are herein incorporated by reference in their entirety) to amplify and obtain any desired nucleic acid molecule or fragment.

Promoter sequence(s) and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating EST nucleic acid molecules or preferably fragments thereof with members of genomic libraries (e.g. maize and soybean) and recovering clones that hybridize to the EST nucleic acid molecule or fragment thereof. In a second embodiment, methods of "chromosome walking," or inverse PCR may be used to obtain such sequences (Frohman et al., *Proc. Natl. Acad. Sci. (U.S.A.)* 85:8998-9002 (1988); Ohara et al., *Proc. Natl. Acad. Sci. (U.S.A.)* 86:5673-5677 (1989); Panrg et al., *Biotechniques* 22:1046-1048 (1977); Huang et al., *Methods Mol. Biol.* 69:89-96 (1997); Huang et al., *Method Mol. Biol.* 67:287-294 (1997); Benkel et al., *Genet. Anal.* 13:123-127 (1996); Hartl et al., *Methods Mol. Biol.* 58:293-301 (1996), all of which are herein incorporated by reference in their entirety).

The nucleic acid molecules of the present invention may be used to isolate promoters of cell enhanced, cell specific, tissue enhanced, tissue specific, developmentally or environmentally regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (See, for example, Birren et al., *Genome Analysis: Analyzing DNA,* 1, (1997) Cold Spring Harbor Laboratory Press, Cold Spring Harbor, N.Y., the entirety of which is herein incorporated by reference). Promoters obtained utilizing the nucleic acid molecules of the present invention could also be modified to affect their control characteristics. Examples of such modifications would include but are not limited to enhanced sequences as reported in Uses of the Agents of the Invention, Section (a) Plant Constructs and Plant Transformants. Such genetic elements could be used to enhance gene expression of new and existing traits for crop improvements.

In one sub-aspect, such an analysis is conducted by determining the presence and/or identity of polymorphism(s) by one or more of the nucleic acid molecules of the present invention and more preferably one or more of the EST nucleic acid molecule or fragment thereof which are associated with a phenotype, or a predisposition to that phenotype.

Any of a variety of molecules can be used to identify such polymorphism(s). In one embodiment, one or more of the EST nucleic acid molecules (or a sub-fragment thereof) may be employed as a marker nucleic acid molecule to identify such polymorphism(s). Alternatively, such polymorphisms can be detected through the use of a marker nucleic acid molecule or a marker protein that is genetically linked to (i.e., a polynucleotide that co-segregates with) such polymorphism(s).

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s) and more preferably within 100 kb of the polymorphism(s) and most preferably within 10 kb of the polymorphism(s) can be employed.

The genomes of animals and plants naturally undergo spontaneous mutation in the course of their continuing evolution (Gusella, *Ann. Rev. Biochem.* 55:831-854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e., the original "allele") whereas other members may have the variant sequence (i.e., the variant "allele"). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity analysis (Weber, U.S. Pat. No. 5,075,217; Armour et al., *FEBS Lett.* 307:113-115 (1992); Jones et al., *Eur. J. Haematol.* 39: 144-147(1987); Horn et al., PCT Patent Application WO91/14003; Jeffreys, European Patent Application 370,719; Jeffreys, U.S. Pat. No. 5,175,082; Jeffreys et al., *Amer. J. Hum. Genet.* 39:11-24 (1986); Jeffreys et al., *Nature* 316:76-79 (1985); Gray et al., *Proc. R. Acad Soc. Lond.* 243:241-253 (1991); Moore et al., *Genomics* 10:654-660 (1991); Jeffreys et al., *Anim. Genet.* 18:1-15 (1987); Hillel et al., *Anim. Genet.* 20:145-155 (1989); Hillel et al., *Genet.* 1247.83-789 (1990), all of which are herein incorporated by reference in their entirety).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

The most preferred method of achieving such amplification employs the polymerase chain reaction ("PCR") (Mullis et al., *Cold Spring Harbor Symp. Quant. Biol.* 51:263-273 (1986); Erlich et al., European Patent Appln. 50,424; European Patent Appln. 84,796; European Patent Application 258,017; European Patent Appln. 237,362; Mullis, European Patent Appln. 201,184; Mullis et al., U.S. Pat. No. 4,683,202; Erlich, U.S. Pat. No. 4,582,788; and Saiki et al., U.S. Pat. No. 4,683,194), using primer pairs that are capable of hybridizing to the proximal sequences that define a polymorphism in its double-stranded form.

In lieu of PCR, alternative methods, such as the "Ligase Chain Reaction" ("LCR") may be used (Barany, *Proc. Natl. Acad. Sci. (U.S.A.)* 88:189-193 (1991), the entirety of which is herein incorporated by reference). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069, the entirety of which is herein incorporated by reference).

The "Oligonucleotide Ligation Assay" ("OLA") may alternatively be employed (Landegren et al., Science 241:1077-1080 (1988), the entirety of which is herein incorporated by reference). The OLA protocol uses two oligonucleotides which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson et al., have described a nucleic acid detection assay that combines attributes of PCR and OLA (Nickerson et al., Proc. Natl. Acad. Sci. (U.S.A.) 87:8923-8927 (1990); the entirety of which is herein incorporated by reference). In this method, PCR is used to achieve the exponential amplification of target DNA, which is then detected using OLA. In addition to requiring multiple and separate, processing steps, one problem associated with such combinations is that they inherit all of the problems associated with PCR and OLA.

Schemes based on ligation of two (or more) oligonucleotides in the presence of nucleic acid having the sequence of the resulting "di-oligonucleotide", thereby amplifying the di oligonucleotide, are also known (Wu et al., Genomics 4:560-569 (1989), the entirety of which is herein incorporated by reference) and may be readily adapted to the purposes of the present invention.

Other known nucleic acid amplification procedures, such as allele-specific oligomers, branched DNA technology, transcription-based amplification systems, or isothermal amplification methods may also be used to amplify and analyze such polymorphisms (Malek et. al., U.S. Pat. No. 5,130,238; Davey et al., European Patent Application 329,822; Schuster et al., U.S. Pat. No. 5,169,766; Miller et al., PCT Patent Application WO 89/06700; Kwoh et al., Proc. Natl. Acad. Sci. (U.S.A.) 86:1173-1177 (1989); Gingeras et al., PCT Patent Application WO 88/10315; Walker et al., Proc. Natl. Acad. Sci. (U.S.A.) 89:392-396 (19-92), all of which are herein incorporated by reference in their entirety).

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms" ("RFLPs"). RFLPs have been widely used in human and plant genetic analyses (Glassberg, UK Patent Application 2135774; Skolnick et al., Cytogen. Cell Genet. 32:58-67 (1982); Botstein et al., Ann. J. Hum. Genet. 32:314-331 (1980); Fischer et al., (PCT Application WO90/13668); Uhlen, PCT Application WO90/11369).

Polymorphisms can also be identified by Single Strand Conformation Polymorphism (SSCP) analysis. SSCP is a method capable of identifying most sequence variations in a single strand of DNA, typically between 150 and 250 nucleotides in length (Elles, Methods in Molecular Medicine Molecular Diagnosis of Genetic Diseases, Humana Press (1996), the entirety of which is herein incorporated by reference); Orita et al., Genomics 5:874-879 (1989), the entirety of which is herein incorporated by reference). Under denaturing conditions a single strand of DNA will adopt a conformation that is uniquely dependent on its sequence conformation. This conformation usually will be different, even if only a single base is changed. Most conformations have been reported to alter the physical configuration or size sufficiently to be detectable by electrophoresis. A number of protocols have been described for SSCP including, but not limited to, Lee et al., Anal. Biochem. 205:289-293 (1992), the entirety of which is herein incorporated by reference; Suzuki et al., Anal. Biochem. 192:82-84(1991), the entirety of which is herein incorporated by reference; Lo et al., Nucleic Acids Research 20:1005-1009 (1992), the entirety of which is herein incorporated by reference; Sarkar et al., Genomics 13:441-443 (1992), the entirety of which is herein incorporated by reference. It is understood that one or more of the nucleic acids of the present invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA (Vos et al., Nucleic Acids Res. 23:4407-4414 (1995), the entirety of which is herein incorporated by reference). This method allows for the specific co-amplification of high numbers of restriction fragments, which can be visualized by PCR without knowledge of the nucleic acid sequence.

AFLP employs basically three steps. Initially, a sample of genomic DNA is cut with restriction enzymes and oligonucleotide adapters are ligated to the restriction fragments of the DNA. The restriction fragments are then amplified using PCR by using the adapter and restriction sequence as target sites for primer annealing. The selective amplification is achieved by the use of primers that extend into the restriction fragments, amplifying only those fragments in which the primer extensions match the nucleotide flanking the restriction sites. These amplified fragments are then visualized on a denaturing polyacrylamide gel.

AFLP analysis has been performed on Salix (Beismann et al., Mol. Ecol. 6:989-993 (1997), the entirety of which is herein incorporated by reference), Acinetobacter (janssen et al., Int. J. Syst. Bacteriol. 47:1179-1187 (1997), the entirety of which is herein incorporated by reference), Aeromonas popoffi (Huys et al., Int. J. Syst. Bacteriol. 47:1165-1171 (1997), the entirety of which is herein incorporated by reference), rice (McCouch et al., Plant Mol. Biol. 35:89-99 (1997), the entirety of which is herein incorporated by reference; Nandi et al., Mol. Gen. Genet. 255:1-8 (1997), the entirety of which is herein incorporated by reference; Cho et al., Genome 39:373-378 (1996), the entirety of which is herein incorporated by reference), barley (Hordeum vulgare)(Simons et al., Genomics 44:61-70 (1997), the entirety of which is herein incorporated by reference; Waugh et al., Mol. Gen. Genet. 255:311-321 (1997), the entirety of which is herein incorporated by reference; Qi et al., Mol. Gen. Genet. 254:330-336 (1997), the entirety of which is herein incorporated by reference; Becker et al., Mol. Gen. Genet. 249:65-73 (1995), the entirety of which is herein incorporated by reference), potato (Van der Voort et al., Mol. Gen. Genet. 255:438-447 (1997), the entirety of which is herein incorporated by reference;

Meksem et al., *Mol. Gen. Genet.* 249:74-81 (1995), the entirety of which is herein incorporated by reference), *Phytophthora infestans* (Van der Lee et al., *Fungal Genet. Biol.* 21:278-291 (1997), the entirety of which is herein incorporated by reference), *Bacillus anthracis* (Keim et al., *J. Bacteriol.* 179:818-824 (1997), the entirety of which is herein incorporated by reference), *Astragalus cremnophylax* (Travis et al., *Mol. Ecol.* 5:735-745 (1996), the entirety of which is herein incorporated by reference), *Arabidopsis* (Cnops et al., *Mol. Gen. Genet.* 253:32-41 (1996), the entirety of which is herein incorporated by reference), *Escherichia coli* (Lin et al., *Nucleic Acids Res.* 24:3649-3650 (1996), the entirety of which is herein incorporated by reference), *Aeromonas* (Huys et al., *Int. J. Syst. Bacteriol.* 46:572-580 (1996), the entirety of which is herein incorporated by reference), nematode (Folkertsma et al., *Mol. Plant. Microbe Interact.* 9:47-54 (1996), the entirety of which is herein incorporated by reference), tomato (Thomas et al., *Plant J.* 8:785-794 (1995), the entirety of which is herein incorporated by reference) and human (Latorra et al., *PCR Methods Appl.* 3:351-358 (1994), the entirety of which is herein incorporated by reference). AFLP analysis has also been used for fingerprinting mRNA (Money et al., *Nucleic Acids Res.* 24:2616-2617 (1996), the entirety of which is herein incorporated by reference; Bachem et al., *Plant J.* 9:745-753 (1996), the entirety of which is herein incorporated by reference). It is understood that one or more of the nucleic acids of the present invention, may be utilized as markers or probes to detect polymorphisms by AFLP analysis or for fingerprinting RNA.

Polymorphisms may also be found using random amplified polymorphic DNA (RAPD) (Williams et al., *Nucl. Acids Res.* 18:6531-6535 (1990), the entirety of which is herein incorporated by reference) and cleavable amplified polymorphic sequences (CAPS) (Lyamichev et al., *Science* 260:778-783 (1993), the entirety of which is herein incorporated by reference). It is understood that one or more of the nucleic acid molecules of the present invention, may be utilized as markers or probes to detect polymorphisms by RAPD or CAPS analysis.

Through genetic mapping, a fine scale linkage map can be developed using DNA markers and, then, a genomic DNA library of large-sized fragments can be screened with molecular markers linked to the desired trait. Molecular markers are advantageous for agronomic traits that are otherwise difficult to tag, such as resistance to pathogens, insects and nematodes, tolerance to abiotic stress, quality parameters and quantitative traits such as high yield potential.

The essential requirements for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botsteiri, *Genetics* 121:185-199 (1989) and the interval mapping, based on maximum likelihood methods described by Lander and Botstein, *Genetics* 121:185-199 (1989) and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$(MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics* 121:185-199 (1989) the entirety of which is herein incorporated by reference and further described by Arus and Moreno-González, *Plant Breeding*, Hayward et al., (eds.) Chapman & Hall, London, pp. 314-331 (1993), the entirety of which is herein incorporated by reference.

Additional models can be used. Many modifications and alternative approaches to interval mapping have been reported, including the use non-parametric methods (Kruglyak and Lander, *Genetics* 139:1421-1428 (1995), the entirety of which is herein incorporated by reference). Multiple regression methods or models can be also be used, in which the trait is regressed on a large number of markers (Jansen, *Biometrics in Plant Breeding*, van Oijen and Jansen (eds.), Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994), both of which is herein incorporated by reference in their entirety). Procedures combining interval mapping with regression analysis, whereby the phenotype is regressed onto a single putative QTL at a given marker interval and at the same time onto a number of markers that serve as 'cofactors,' have been reported by Jansen and Stam, *Genetics* 136:1447-1455 (1994), the entirety of which is herein incorporated by reference and Zeng, *Genetics* 136:1457-1468 (1994) the entirety of which is herein incorporated by reference. Generally, the use of cofactors reduces the bias and sampling error of the estimated QTL positions (Utz and Melchinger, *Biometrics in Plant Breeding*, van Oijen and Jansen (eds.) Proceedings of the Ninth Meeting of the Eucarpia Section Biometrics in Plant Breeding, The Netherlands, pp. 195-204 (1994), the entirety of which is herein incorporated by reference, thereby improving the precision and efficiency of QTL mapping (Zeng, *Genetics* 136:1457-1468 (1994)). These models can be extended to multi-environment experiments to analyze genotype-environment interactions (Jansen et al., *Theo. Appl. Genet.* 91:33-37 (1995), the entirety of which is herein incorporated by reference).

Selection of an appropriate mapping populations is important to map construction. The choice of appropriate mapping population depends on the type of marker systems employed (Tanksley et al., *Molecular Mapping Plant Chromosomes. Chromosome Structure and Function: Impact of New Concepts*, Gustafson and Appels (eds.), Plenum Press, New York, pp 157-173 (1988), the entirety of which is herein incorporated by reference). Consideration must be given to the source of parents (adapted vs. exotic) used in the mapping population. Chromosome pairing and recombination rates can be severely disturbed (suppressed) in wide crosses (adapted× exotic) and generally yield greatly reduced linkage distances. Wide crosses will usually provide segregating populations with a relatively large array of polymorphisms when compared to progeny in a narrow cross (adapted×adapted).

An $F_2$ population is the first generation of selfing after the hybrid seed is produced. Usually a single $F_1$ plant is selfed to generate a population segregating for all the genes in Mendelian (1:2:1) fashion. Maximum genetic information is obtained from a completely classified $F_2$ population using a codominant marker system (Mather, *Measurement of Linkage in Heredity*, Methuen and Co., (1938), the entirety of which is herein incorporated by reference). In the case of dominant markers, progeny tests (e.g. $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually $>F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al., *Proc. Natl. Acad. Sci.* (*U.S.A.*) 89:1477-1481 (1992), the entirety of which is herein incorporated by reference). However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci.* (*U.S.A.*) 89:1477-1481 (1992)). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al., *Proc. Natl. Acad. Sci.* (*U.S.A.*) 88:9828-9832 (1991), the entirety of which is herein incorporated by reference). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

It is understood that one or more of the nucleic acid molecules of the present invention may be used as molecular markers. It is also understood that one or more of the protein molecules of the present invention may be used as molecular markers.

In accordance with this aspect of the present invention, a sample nucleic acid is obtained from plants cells or tissues. Any source of nucleic acid may be used. Preferably, the nucleic acid is genomic DNA. The nucleic acid is subjected to restriction endonuclease digestion. For example, one or more nucleic acid molecule or fragment thereof of the present invention can be used as a probe in accordance with the above-described polymorphic methods. The polymorphism obtained in this approach can then be cloned to identify the mutation at the coding, region which alters the protein's structure or regulatory region of the gene which affects its expression level.

In an aspect of the present invention, one or more of the nucleic molecules of the present invention are used to determine the level (i.e., the concentration of mRNA in a sample, etc.) in a plant (preferably maize or soybean) or pattern (i.e., the kinetics of expression, rate of decomposition, stability profile, etc.) of the expression of a protein encoded in part or whole by one or more of the nucleic acid molecule of the present invention (collectively, the "Expression Response" of a cell or tissue). As used herein, the Expression Response manifested by a cell or tissue is said to be "altered" if it differs from the Expression Response of cells or tissues of plants not exhibiting the phenotype. To determine whether an Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g. disease resistance, pest tolerance, environmental tolerance such as tolerance to abiotic stress, male sterility, quality improvement or yield etc.). A change in genotype or phenotype may be transient or permanent. Also as used herein, a tissue sample is any sample that comprises more than one cell. In a preferred aspect, a tissue sample comprises cells that share a common characteristic e.g. derived from root, seed, flower, leaf, stem or pollen etc.).

In one aspect of the present invention, an evaluation can be conducted to determine whether a particular mRNA molecule is present. One or more of the nucleic acid molecules of the present invention, preferably one or more of the EST nucleic acid molecules or fragments thereof of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A principle of in situ hybridization is that a labeled, single-stranded nucleic acid probe will hybridize to a complementary strand of cellular DNA or RNA and, under the appropriate conditions, these molecules will form a stable hybrid. When nucleic acid hybridization is combined with histological techniques, specific DNA or RNA sequences can be identified within a single cell. An advantage of in situ hybridization over more conventional techniques for the detection of nucleic acids is that it allows an investigator to determine the precise spatial population (Angerer et al., *Dev. Biol.* 101:477-484 (1984), the entirety of which is herein incorporated by reference; Angerer et al., *Dev. Biol.* 112:157-166 (1985), the entirety of which is herein incorporated by reference; Dixon et al., *EMBO J.* 10:1317-1324 (1991), the entirety of which is herein incorporated by reference). In situ hybridization may be used to measure the steady-state level of RNA accumulation. It is a sensitive technique and RNA sequences present in as few as 5-10 copies per cell can be detected (Hardin et al., *J. Mol. Biol.* 202:417-431 (1989), the entirety of which is herein incorporated by reference). A number of protocols have been devised for in situ hybridization, each with tissue preparation, hybridization and washing conditions (Meyerowitz, *Plant Mol. Biol. Rep.* 5:242-250 (1987), the entirety of which is herein incorporated by reference; Cox and Goldberg, In: *Plant Molecular Biology: A Practical Approach*, Shaw (ed.), pp 1-35, IRL Press, Oxford (1988), the entirety of which is herein incorporated by reference; Raikhel et al., In situ RNA hybridization in plant tissues, in: *Plant Molecular Biology Manual*, vol. B9:1-32, Kluwer Academic Publisher, Dordrecht, Belgium (1989), the entirety of which is herein incorporated by reference).

In situ hybridization also allows for the localization of proteins within a tissue or cell (Wilkinson, *In Situ Hybridization*, Oxford University Press, Oxford (1992), the entirety of which is herein incorporated by reference; Langdale, In Situ Hybridization In: *The Maize Handbook*, Freeling and Walbot (eds.), pp 165-179, Springer-Verlag, New York (1994), the entirety of which is herein incorporated by reference). It is understood that one or more of the molecules of the present invention, preferably one or more of the EST nucleic acid molecules or fragments thereof of the present invention or one or more of the antibodies of the present invention may be utilized to detect the level or pattern of a transcription factor or mRNA thereof by in situ hybridization.

Fluorescent in situ hybridization allows the localization of a particular DNA sequence along a chromosome which is useful, among other uses, for gene mapping, following chromosomes in hybrid lines or detecting chromosomes with translocations, transversions or deletions. In situ hybridization has been used to identify chromosomes in several plant species (Griffor et al., *Plant Mol. Biol.* 17:101-109 (1991), the entirety of which is herein incorporated by reference; Gustafson et al., *Proc. Natl. Acad. Sci. (U.S.A.)* 87:1899-1902 (1990), herein incorporated by reference; Mukai and Gill, *Genome* 34:448-452 (1991), the entirety of which is herein incorporated by reference; Schwarzacher and Heslop-Harrison, *Genome* 34:317-323 (1991); Wang et al., *Jpn. J. Genet.* 66:313-316 (1991), the entirety of which is herein incorporated by reference; Parra and Windle, *Nature Genetics* 5:17-21 (1993), the entirety of which is herein incorporated by reference). It is understood that the nucleic acid molecules of the present invention may be used as probes or markers to localize sequences along a chromosome.

Another method to localize the expression of a molecule is tissue printing. Tissue printing provides a way to screen, at the same time on the same membrane many tissue sections from different plants or different developmental stages. Tissue-printing procedures utilize films designed to immobilize proteins and nucleic acids. In essence, a freshly cut section of a tissue is pressed gently onto nitrocellulose paper, nylon membrane or polyvinylidene difluoride membrane. Such membranes are commercially available (e.g. Millipore, Bedford, Mass. U.S.A.). The contents of the cut cell transfer onto the membrane and the contents and are immobilized to the membrane. The immobilized contents form a latent print that can be visualized with appropriate probes. When a plant tissue print is made on nitrocellulose paper, the cell walls leave a physical print that makes the anatomy visible without further treatment (Varner and Taylor, *Plant Physiol.* 91:31-33 (1989), the entirety of which is herein incorporated by reference).

Tissue printing on substrate films is described by Daoust, *Exp. Cell Res.* 12:203-211 (1957), the entirety of which is herein incorporated by reference, who detected amylase, protease, ribonuclease and deoxyribonuclease in animal tissues using starch, gelatin and agar films. These techniques can be applied to plant tissues (Yomo and Taylor, *Planta* 112:35-43 (1973); the entirety of which is herein incorporated by reference; Harris and Chrispeels, *Plant Physiol.* 56:292-299 (1975), the entirety of which is herein incorporated by reference). Advances in membrane technology have increased the range of applications of Daoust's tissue-printing techniques allowing (Cassab and Varner, *J. Cell. Biol.* 105:2581-2588 (1987), the entirety of which is herein incorporated by reference) the histochemical localization of various plant enzymes and deoxyribonuclease on nitrocellulose paper and nylon (Spruce et al., *Phytochemistry* 26:2901-2903 (1987), the entirety of which is herein incorporated by reference; Barres et al., *Neuron* 5:527-544 (1990), the entirety of which is herein incorporated by reference; Reid and Pont-Lezica, *Tissue Printing: Tools for the Study of Anatomy, Histochemistry and Gene Expression*, Academic Press, New York, N.Y. (1992), the entirety of which is herein incorporated by reference; Reid et al., *Plant Physiol.* 93:160-165 (1990), the entirety of which is herein incorporated by reference; Ye et al., *Plant J.* 1:175-183 (1991), the entirety of which is herein incorporated by reference).

It is understood that one or more of the molecules of the present invention, preferably one or more of the EST nucleic acid molecules or fragments thereof of the present invention or one or more of the antibodies of the present invention may be utilized to detect the presence or quantity of a transcription factor by tissue printing.

Further it is also understood that any of the nucleic acid molecules of the present invention may be used as marker nucleic acids and or probes in connection with methods that require probes or marker nucleic acids. As used herein, a probe is an agent that is utilized to determine an attribute or feature (e.g. presence or absence, location, correlation, etc.) of a molecule, cell, tissue or plant. As used herein, a marker nucleic acid is a nucleic acid molecule that is utilized to determine an attribute or feature (e.g., presence or absence, location, correlation, etc.) or a molecule, cell, tissue or plant.

A microarray-based method for high-throughput monitoring of plant gene expression may be utilized to measure gene-specific hybridization targets. This 'chip'-based approach involves using microarrays of nucleic acid molecules as gene-specific hybridization targets to quantitatively measure expression of the corresponding plant genes (Schena et al., *Science* 270:467-470 (1995), the entirety of which is herein incorporated by reference; Shalon, Ph.D. Thesis, Stanford University (1996), the entirety of which is herein incorporated by reference). Every nucleotide in a large sequence can be queried at the same time. Hybridization can be used to efficiently analyze nucleotide sequences.

Several microarray methods have been described. One method compares the sequences to be analyzed by hybridization to a set of oligonucleotides representing all possible subsequences (Bains and Smith, *J. Theor. Biol.* 135:303-307 (1989), the entirety of which is herein incorporated by reference). A second method hybridizes the sample to an array of oligonucleotide or cDNA molecules. An array consisting of oligonucleotides complementary to subsequences of a target sequence can be used to determine the identity of a target sequence, measure its amount and detect differences between the target and a reference sequence. Nucleic acid molecules microarrays may also be screened with protein molecules or fragments thereof to determine nucleic acid molecules that specifically bind protein molecules or fragments thereof.

The microarray approach may be used with polypeptide targets (U.S. Pat. No. 5,445,934; U.S. Pat. No. 5,143,854; U.S. Pat. No. 5,079,600; U.S. Pat. No. 4,923,901, all of which are herein incorporated by reference in their entirety). Essentially, polypeptides are synthesized on a substrate (microarray) and these polypeptides can be screened with either protein molecules or fragments thereof or nucleic acid molecules in order to screen for either protein molecules or fragments thereof or nucleic acid molecules that specifically bind the target polypeptides. (Fodor et al., *Science* 251:767-773 (1991), the entirety of which is herein incorporated by reference). It is understood that one or more of the nucleic acid molecules or protein or fragments thereof of the present invention may be utilized in a microarray based method.

In a preferred embodiment of the present invention microarrays may be prepared that comprise nucleic acid molecules where such nucleic acid molecules encode at least one, preferably at least two, more preferably at least three tetrapyrrole pathway enzymes. In a preferred embodiment the nucleic acid molecules are selected from the group consisting of a putative maize or soybean chlorophyll synthetase enzyme or fragment thereof, a nucleic acid molecule that encodes a maize or soybean protochlorophyllide reductase enzyme or fragment thereof, a nucleic acid molecule that encodes a putative maize or soybean protochlorophyllide reductase enzyme or fragment thereof, a nucleic acid molecule that encodes a maize or soybean coproporphyrinogen oxidase enzyme or fragment thereof, a nucleic acid molecule that encodes a maize or soybean protoporphyrinogen oxidase enzyme or fragment thereof, a nucleic acid molecule that encodes a maize or soybean uroporphyrinogen decarboxylase enzyme or fragment thereof, a nucleic acid molecule that encodes a putative maize uroporphyrinogen decarboxylase enzyme or fragment thereof, a nucleic acid molecule that encodes a maize or soybean porphobilinogen synthase enzyme or fragment thereof, a nucleic acid molecule that encodes a maize or soybean hydroxymethylbilane synthase enzyme or fragment thereof, a nucleic acid molecule that encodes a maize or soybean glutamate-1-semialdehyde 2,1-aminomutase enzyme or fragment thereof, a nucleic acid molecule that encodes a maize or soybean glutamate tRNA ligase enzyme or fragment thereof, a nucleic acid molecule that encodes a maize or soybean glutamyl-tRNA reductase enzyme or fragment thereof, a nucleic acid molecule that encodes a maize or soybean Mg-chelatase enzyme or fragment thereof and a nucleic acid molecule that encodes a maize or soybean ferrochelatase enzyme or fragment thereof.

Site directed mutagenesis may be utilized to modify nucleic acid sequences, particularly as it is a technique that allows one or more of the amino acids encoded by a nucleic acid molecule to be altered (e.g. a threonine to be replaced by a methionine). Three basic methods for site directed mutagenesis are often employed. These are cassette mutagenesis (Wells et al., *Gene* 34:315-323 (1985), the entirety of which is herein incorporated by reference), primer extension (Gilliam et al., *Gene* 12:129-137 (1980), the entirety of which is herein incorporated by reference; Zoller and Smith, *Methods Enzymol.* 100:468-500 (1983), the entirety of which is herein incorporated by reference; Dalbadie-McFarland et al., *Proc. Natl. Acad. Sci. (U.S.A)* 79:6409-6413 (1982), the entirety of which is herein incorporated by reference) and methods based upon PCR (Scharf et al., *Science* 233:1076-1078 (1986), the entirety of which is herein incorporated by reference; Higuchi et al., *Nucleic Acids Res.* 16:7351-7367 (1988), the entirety of which is herein incorporated by reference). Site directed mutagenesis approaches are also described in European Patent 0 385 962, the entirety of which is herein incorporated by reference; European Patent 0 359 472, the entirety of which is herein incorporated by reference and PCT Patent Application WO 93/07278, the entirety of which is herein incorporated by reference.

Site directed mutagenesis strategies have been applied to plants for both in vitro as well as in vivo site directed mutagenesis (Lanz et al., *J. Biol. Chem.* 266:9971-9976 (1991), the entirety of which is herein incorporated by reference; Kovgan and Zhdanov, *Biotekhnologiya* 5:148-154; No. 207160n, Chemical Abstracts 110:225 (1989), the entirety of which is herein incorporated by reference; Ge et al., *Proc. Natl. Acad. Sci. (U.S.A.)* 86:4037-4041 (1989), the entirety of which is herein incorporated by reference; Zhu et al., *J. Biol. Chem.* 271-18494-18498 (1996), the entirety of which is herein incorporated by reference; Chu et al., *Biochemistry* 33:6150-6157 (1994), the entirety of which is herein incorporated by reference; Small et al., *EMBO J.* 11:1291-1296 (1992), the entirety of which is herein incorporated by reference; Cho et al., *Mol. Biotechnol.* 8:13-16 (1997), the entirety of which is herein incorporated by reference; Kita et al., *J. Biol. Chem.* 271:26529-26535 (1996), the entirety of which is herein incorporated by reference, Jin et al., *Mol. Microbiol.* 7:555-562 (1993), the entirety of which is herein incorporated by reference; Hatfield and Vierstra, *J. Biol. Chem.* 267:14799-14803 (1992), the entirety of which is herein incorporated by reference; Zhao et al., *Biochemistry* 31:5093-5099 (1992), the entirety of which is herein incorporated by reference).

Any of the nucleic acid molecules of the present invention may either be modified by site directed mutagenesis or used as, for example, nucleic acid molecules that are used to target other nucleic acid molecules for modification. It is understood that mutants with more than one altered nucleotide can be constructed using techniques that practitioners are familiar with such as isolating restriction fragments and ligating such fragments into an expression vector (see, for example, Sambrook et al., *Molecular Cloning: A Laboratory Manual*, Cold Spring Harbor Press (1989)).

Sequence-specific DNA-binding proteins play a role in the regulation of transcription. The isolation of recombinant cDNAs encoding these proteins facilitates the biochemical analysis of their structural and functional properties. Genes encoding such DNA-binding proteins have been isolated using classical genetics (Vollbrecht et al., *Nature* 350: 241-243 (1991), the entirety of which is herein incorporated by reference) and molecular biochemical approaches, including the screening of recombinant cDNA libraries with antibodies (Landschulz et al., *Genes Dev.* 2:786-800 (1988), the entirety of which is herein incorporated by reference) or DNA probes (Bodner et al., *Cell* 55:505-518 (1988), the entirety of which is herein incorporated by reference). In addition, an in situ screening procedure has been used and has facilitated the isolation of sequence-specific DNA-binding proteins from various plant species (Gilmartin et al., *Plant Cell* 4:839-849 (1992), the entirety of which is herein incorporated by reference; Schindler et al., *EMBO J.* 11:1261-1273 (1992), the entirety of which is herein incorporated by reference). An in situ screening protocol does not require the purification of the protein of interest (Vinson et al., *Genes Dev.* 2:801-806 (1988), the entirety of which is herein incorporated by reference; Singh et al., *Cell* 52:415-423 (1988), the entirety of which is herein incorporated by reference).

Two steps may be employed to characterize DNA-protein interactions. The first is to identify promoter fragments that interact with DNA-binding proteins, to titrate binding activity, to determine the specificity of binding and to determine whether a given DNA-binding activity can interact with related DNA sequences (Sambrook et al., *Molecular Cloning: A Laboratory Manual*, $2^{nd}$ edition, Cold Spring Harbor Laboratory Press, Cold Spring Harbor, N.Y. (1989)). Electrophoretic mobility-shift assay is a widely used assay. The assay provides a rapid and sensitive method for detecting DNA-binding proteins based on the observation that the mobility of a DNA fragment through a nondenaturing, low-ionic strength polyacrylamide gel is retarded upon association with a DNA-binding protein (Fried and Crother, *Nucleic Acids Res.* 9:6505-6525 (1981), the entirety of which is herein incorporated by reference). When one or more specific binding activities have been identified, the exact sequence of the DNA bound by the protein may be determined. Several procedures for characterizing protein/DNA-binding sites are used, including methylation and ethylation interference assays (Maxam and Gilbert, *Methods Enzymol.* 65:499-560 (1980), the entirety of which is herein incorporated by reference; Wissman and Hillen, *Methods Enzymol.* 208:365-379 (1991), the entirety of which is herein incorporated by reference), footprinting techniques employing DNase I (Galas and Schmitz, *Nucleic Acids Res.* 5:3157-3170 (1978), the entirety of which is herein incorporated by reference), 1,10-phenanthroline-copper ion methods (Sigman et al., *Methods Enzymol.* 208:414-433 (1991'), the entirety of which is herein incorporated by reference) and hydroxyl radicals methods (Dixon et al., *Methods Enzymol.* 208:414-433 (1991), the entirety of which is herein incorporated by reference). It is understood that one or more of the nucleic acid molecules of the present invention may be utilized to identify a protein or fragment thereof that specifically binds to a nucleic acid molecule of the present invention. It is also understood that one or more of the protein molecules or fragments thereof of the present invention may be utilized to identify a nucleic acid molecule that specifically binds to it.

A two-hybrid system is based on the fact that many cellular functions are carried out by proteins, such as transcription factors, that interact (physically) with one another. Two-hybrid systems have been used to probe the function of new proteins (Chien et al., *Proc. Natl. Acad. Sci.* (*U.S.A.*) 88:9578-9582 (1991) the entirety of which is herein incorporated by reference; Durfee et al., *Genes Dev.* 7:555-569 (1993) the entirety of which is herein incorporated by reference; Choi et al., *Cell* 78:499-512 (1994), the entirety of which is herein incorporated by reference; Kranz et al., *Genes Dev:* 8:313-327 (1994), the entirety of which is herein incorporated by reference).

Interaction mating techniques have facilitated a number of two-hybrid studies of protein-protein interaction. Interaction mating has been used to examine interactions between small sets of tens of proteins (Finley and Brent, *Proc. Natl. Acad. Sci.* (*U.S.A.*) 91:12098-12984 (199.4), the entirety of which is herein incorporated by reference), larger sets of hundreds of proteins (Bendixen et al., *Nucl. Acids Res.* 22:1778-1779 (1994), the entirety of which is herein incorporated by reference) and to comprehensively map proteins encoded by a small genome (Bartel et al., *Nature Genetics* 12:72-77 (1996), the entirety of which is herein incorporated by reference). This technique utilizes proteins fused to the DNA-binding domain and proteins fused to the activation domain. They are expressed in two different haploid yeast strains of opposite mating type and the strains are mated to determine if the two proteins interact. Mating occurs when haploid yeast strains come into contact and result in the fusion of the two haploids into a diploid yeast strain. An interaction can be determined by the activation of a two-hybrid reporter gene in the diploid strain. An advantage of this technique is that it reduces the number of yeast transformations needed to test individual interactions. It is understood that the protein-protein interactions of protein or fragments thereof of the present invention may be investigated using the two-hybrid system and that any of the nucleic acid molecules of the present invention that encode such proteins or fragments thereof may be used to transform yeast in the two-hybrid system.

(a) Plant Constructs and Plant Transformants

One or more of the nucleic acid molecules of the present invention may be used in plant transformation or transfection. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism. Such genetic material may be transferred into either monocotyledons and dicotyledons including, but not limited to maize (pp 63-69), soybean (pp 50-60), *Arabidopsis* (p 45), *phaseolus* (pp 47-49), peanut (pp 49-50), alfalfa (p 60), wheat (pp 69-71), rice (pp 72-79), oat (pp 80-81), sorghum (p 83), rye (p 84), tritordeum (p 84), millet (185), fescue (p 85), perennial ryegrass (p 86), sugarcane (p 87), cranberry (p 101), papaya (pp 101-102), banana (p 103), banana (p 103), muskmelon (p 104), apple (p 104), cucumber (p 105), dendrobium (p 109), gladiolus (p 110), chrysanthemum (p 110), liliacea (p 111), cotton (pp 113-114), eucalyptus (p 115), sunflower (p 118), canola (p 118), turfgrass (p 121), sugarbeet (p 122), coffee (p 122) and dioscorea (p 122), (Christou, In: *Particle Bombardment for Genetic Engineering of Plants*, Biotechnology Intelligence Unit. Academic Press, San Diego, Calif. (1996), the entirety of which is herein incorporated by reference).

Transfer of a nucleic acid that encodes for a protein can result in overexpression of that protein in a transformed cell or transgenic plant. One or more of the proteins or fragments thereof encoded by nucleic acid molecules of the present invention may be overexpressed in a transformed cell or transformed plant. Particularly, any of the transcription factors or fragments thereof may be overexpressed in a transformed cell or transgenic plant. Such overexpression may be the result of transient or stable transfer of the exogenous genetic material.

Exogenous genetic material may be transferred into a plant cell and the plant cell by the use of a DNA vector or construct designed for such a purpose. Design of such a vector is generally within the skill of the art (See, *Plant Molecular Biology: A Laboratory Manual*, Clark (ed.), Springier, N.Y. (1997), the entirety of which is herein incorporated by reference).

A construct or vector may include a plant promoter to express the protein or protein fragment of choice. A number of promoters which are active in plant cells have been described in the literature. These include the nopaline synthase (NOS) promoter (Ebert et al., *Proc. Natl. Acad. Sci. (U.S.A.)* 84:5745-5749 (1987), the entirety of which is herein incorporated by reference), the octopine synthase (OCS) promoter (which are carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324 (1987), the entirety of which is herein incorporated by reference) and the CAMV 35S promoter (Odell et al., *Nature* 313:810-812 (1985), the entirety of which is herein incorporated by reference), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci.* (USA.) 84:6624-6628 (1987), the entirety of which is herein incorporated by reference), the sucrose synthase promoter (Yang et al., *Proc. Natl. Acad. Sci. (U.S.A.)* 87:4144-4148 (1990), the entirety of which is herein incorporated by reference), the R gene complex promoter (Chandler et. al., *The Plant Cell* 1:1175-1183 (1989), the entirety of which is herein incorporated by reference) and the chlorophyll a/b binding protein gene promoter, etc. These promoters have been used to create DNA constructs which have been expressed in plants; see, e.g., PCT publication WO 84/02913, herein incorporated by reference in its entirety.

Promoters which are known or are found to cause transcription of DNA in plat cells can be used in the present invention. Such promoters may be obtained from a variety of sources such as plants and plant viruses. It is preferred that the particular promoter selected should be capable of causing sufficient expression to result in the production of an effective amount of the transcription factor to cause the desired phenotype. In addition to promoters that are known to cause transcription of DNA in plant cells, other promoters may be identified for use in the current invention by screening a plant cDNA library for genes which are selectively or preferably expressed in the target tissues or cells.

For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea (Edwards et al., *Proc. Natl. Acad. Sci. (U.S.A.)* 87:3459-3463 (1990), herein incorporated by reference in its entirety), the chloroplast fructose-1,6-biphosphatase. (FBPase) promoter from wheat (Lloyd et al., *Mol. Gen. Genet.* 225:209-216 (1991), herein incorporated by reference in its entirety), the nuclear photosynthetic ST-LS1 promoter from potato (Stockhaus et al., *EMBO J.* 8:2445-2451 (1989), herein incorporated by reference in its entirety), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773-778 (1994) herein incorporated by reference in its entirety), the promoter for the Cab-1 gene from wheat (Fejes et al., *Plant Mol. Biol.* 15:921-932 (1990), herein incorporated by reference in its entirety), the promoter for the CAB-1 gene from spinach (Lubberstedt et al., *Plant Physiol.* 104:997-1006 (1994), herein incorporated by reference in its entirety), the promoter for the cabiR gene from rice (Luan et al., *Plant Cell.* 4:971-981 (1992), the entirety of which is herein incorporated by reference), the pyruvate, orthophosphate dikinase (PPDK) promoter from maize (Matsuoka et al., *Proc. Natl. Acad. Sci. (U.S.A.)* 90: 9586-9590 (1993), herein incorporated by reference in its entirety), the promoter for the tobacco Lhcb1*2 gene (Cerdan et al., *Plant Mol. Biol.* 33:245-255 (1997), herein incorporated by reference in its entirety), the *Arabidopsis thaliana* SUC2 sucrose-H+ symporter promoter (Truernit et al., *Planta.* 196:564-570 (1995), herein incorporated by reference in its entirety) and the promoter for the thylakoid membrane proteins from spinach (psaD, psaF, psae, PC, FNR, atpC, atpD, cab, rbcS). Other promoters for the chlorophyll a/b-binding proteins may also be utilized in the present invention, such as the promoters for LhcB gene and PsbP gene from white mustard (Sinapis alba; Kretsch et al., *Plant Mol. Biol.* 28:219-229 (1995), the entirety of which is herein incorporated by reference).

For the purpose of expression in sink tissues of the plant, such as the tuber of the potato plant, the fruit of tomato, or the seed of maize, wheat, rice and barley, it is preferred that the promoters utilized in the present invention have relatively high expression in these specific tissues. A number of promoters for genes with tuber-specific or -enhanced expression are known, including the class I patatin promoter (Bevan et al., EMBO J. 8:1899-1906(1986), Jefferson et al., *Plant Mol. Biol.* 14:995-1006 (1990), both of which are herein incorporated by reference in its entirety), the promoter for the potato tuber ADPGPP genes, both the large and small subunits, the sucrose synthase promoter (Salanoubat and Belliard, *Gene.* 60:47-56 (1987), Salanoubat and Belliard, *Gene.* 84:181-185 (1989), both of which are incorporated by reference in their entirety), the promoter for the major tuber proteins including the 22 kd protein complexes and proteinase inhibitors (Hannapel, *Plant Physiol.* 101:703-704 (1993), herein incorporated by reference in its entirety), the promoter for the granule bound starch synthase gene (GBSS) (Visser et al., *Plant Mol. Biol.* 17:691-699 (1991), herein incorporated by reference in its entirety) and other class I and II patatins promoters (Koster-Topfer et al., *Mol Gen Genet.* 219:390-396 (1989); Mignery et al., *Gene.* 62:27-44 (1988), both of which are herein incorporated by reference in their entirety) .

Other promoters can also be used to express a transcription factor or fragment thereof in specific tissues, such as seeds or fruits. The promoter for β-conglycinin (Chen et al., *Dev. Genet.* 10: 112-122 (1989), herein incorporated by reference in its entirety) or other seed-specific: promoters such as the napin and phaseolin promoters, can be used. The zeins are a group of storage proteins found in maize endosperm. Genomic clones for zein genes have been isolated (Pedersen et al., *Cell* 29:1015-1026 (1982), herein incorporated by reference in its entirety) and the promoters from these clones, including the 15 kD, 16 kD, 19 kD, 22 kD, 27 kD and γ genes, could also be used. Other promoters known to function, for example, in maize include the promoters for the following genes: waxy, Brittle, Shrunken 2, Branching enzymes I and II, starch synthases, debranching enzymes, oleosins, glutelins and sucrose synthases. A particularly preferred promoter for maize endosperm expression is the promoter for the glutelin gene from rice, more particularly the Osgt-1 promoter (Zheng et al., *Mol. Cell. Biol.* 13:5829-5842 (1993), herein incorporated by reference in its entirety). Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins.

Root specific promoters may also be used. An example of such a promoter is the promoter for the acid chitinase gene (Samac et al., *Plant Mol. Biol.* 25:587-596 (1994), the entirety of which is herein incorporated by reference). Expression in root tissue could also be accomplished by utilizing the root specific subdomains of the CaMV35S promoter that have been identified (Lam et al., *Proc. Natl. Acad. Sci.* (*U.S.A.*) 86:7890-7894 (1989), herein incorporated by reference in its entirety). Other root cell specific promoters include those reported by Conkling et al. (Conkling et al., *Plant Physiol.* 93:1203-1211 (1990), the entirety of which is herein incorporated by reference).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436, all of which are herein incorporated in their entirety. In addition, a tissue specific enhancer may be used (Fromm et al., *The Plant Cell* 1:977-984 (1989), the entirety of which is herein incorporated by reference).

Constructs or vectors may also include with the coding region of interest a nucleic acid sequence that acts, in whole or in part, to terminate transcription of that region. For example, such sequences have been isolated including the Tr7 3' sequence and the NOS 3' sequence (Ingelbrecht et al., *The Plant Cell* 1:671-680 (1989), the entirety of which is herein incorporated by reference; Bevan et al., *Nucleic Acids Res.* 11:369-385 (1983), the entirety of which is herein incorporated by reference), or the like.

A vector or construct may also include regulatory elements. Examples of such include the Adh intron 1 (Callis et al., *Genes and Develop.* 1:1183-1200 (1987), the entirety of which is herein incorporated by reference), the sucrose synthase intron (Vasil et al., *Plant Physiol.* 91:1575-1579 (1989), the entirety of which is herein incorporated by reference) and the TMV omega element (Gallie et al., *The Plant Cell* 1:301-311 (1989), the entirety of which is herein incorporated by reference). These and other regulatory elements may be included when appropriate.

A vector or construct may also include a selectable marker. Selectable markers may also be used to select for plants or plant cells that contain the exogenous genetic material. Examples of such include, but are not limited to, a neo gene (Potrykus et al., *Mol. Gen. Genet.* 199:183-188 (1985), the entirety of which is herein incorporated by reference) which codes for kanamycin resistance and can be selected for using kanamycin, G418, etc.; a bar gene which codes for bialaphos resistance; a mutant EPSP synthase gene (Hinchee et al., *Bio/Technology* 6:915-922 (1988), the entirety of which is herein incorporated by reference) which encodes glyphosate resistance; a nitrilase gene which confers resistance to bromoxynil (Stalker et al., *J. Biol. Chem.* 263:6310-6314 (1988), the entirety of which is herein incorporated by reference); a mutant acetolactate synthase gene (ALS) which confers imidazolinone or sulphonylurea resistance (European Patent Application 154,204 (Sep. 11, 1985), the entirety of which is herein incorporated by reference); and a methotrexate resistant DHFR gene (Thillet et al., *J. Biol. Chem.* 263:12500-12508 (1988), the entirety of which is herein incorporated by reference).

A vector or construct may also include a transit peptide. Incorporation of a suitable chloroplast transit peptide may also be employed (European Patent Application Publication Number 0218571, the entirety of which is herein incorporated by reference). Translational enhancers may also be incorporated as part of the vector DNA. DNA constructs could contain one or more 5' non-translated leader sequences which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393-405 (1996), the entirety of which is herein incorporated by reference.

A vector or construct may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387-405 (1987), the entirety of which is herein incorporated by reference; Jefferson et al., *EMBO J.* 6:3901-3907 (1987), the entirety of which is herein incorporated by reference); an R-locus gene, which encodes a product that regulates the production of anthocyanin pigments (red color) in plant tissues (Dellaporta et al., Stadler Symposium 11:263-282 (1988), the entirety of which is herein incorporated by reference); a β-lactamase gene (Sutcliffe et al., *Proc. Natl. Acad. Sci.* (*U.S.A.*) 75:3737-3741 (1978), the entirety of which is herein incorporated by reference), a gene which encodes an enzyme for which various chromogenic substrates are known (e.g., PADAC, a chromogenic cephalosporin); a luciferase gene (Ow et al., *Science* 234:856-859 (1986), the entirety of which is herein incorporated by reference); a xylE gene (Zukowsky et al., *Proc. Natl. Acad. Sci.* (*U.S.A.*) 80:110-1105 (1983), the entirety of which is herein incorporated by reference) which encodes a catechol dioxygenase that can convert chromogenic catechols; an α-amylase gene (Ikatu et al., *Bio/Technol.* 8:241-242 (1990), the entirety of which is herein incorporated by reference); a tyrosinase gene (Katz et al., *J. Gen. Microbiol.* 129:2703-2714 (1983), the entirety of which is herein incorporated by reference) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, etc (Potrykus, *Ann. Rev. Plant Physiol. Plant Mol. Biol.* 42:205-225 (1991), the entirety of which is herein incorporated by reference; Vasil, *Plant Mol. Biol.* 25:925-937 (1994), the entirety of which is herein incorporated by reference). For example, electroporation has been used to transform maize protoplasts (Fromm et al., *Nature* 312:791-793 (1986), the entirety of which is herein incorporated by reference).

Other vector systems suitable for introducing transforming DNA into a host plant cell include but are not limited to binary artificial chromosome (BIBAC) vectors (Hamilton et al. *Gene* 200:107-1116 (1997), the entirety of which is herein incorporated by reference); and transfection with RNA viral vectors (Della-Cioppa et al., *Ann. N.Y. Acad. Sci.* (1996), 792 (Engineering Plants for Commercial Products and Applications), 57-61, the entirety of which is herein incorporated by reference). Additional vector systems also include plant selectable YAC vectors such as those described in Mullen et al., *Molecular Breeding* 4:449-457 (1988), the entirety of which is herein incorporated by reference).

Technology for introduction of DNA into cells is well known to those of skill in the art. Four general methods for delivering a gene into cells have been described: (1) chemical methods (Graham and van der Eb, *Virology* 54:536-539 (1973), the entirety of which is herein incorporated by reference); (2) physical methods such as microinjection (Capecchi, *Cell* 22:479-488 (1980), the entirety of which is herein incorporated by reference), electroporation (Wong and Neumann, *Biochem. Biophys. Res. Commun.* 107:584-587 (1982); Fromm et al., *Proc. Natl. Acad. Sci. (U.S.A.)* 82:5824-5828 (1985); U.S. Pat. No. 5,384,253, all of which are herein incorporated in their entirety); and the gene gun (Johnston and Tang, *Methods Cell Biol.* 43:353-365 (1994), the entirety of which is herein incorporated by reference); (3) viral vectors (Clapp, *Clin. Perinatol.* 20:155-168 (1993); Lu et al., *J. Exp. Med.* 178:2089-2096 (1993); Eglitis and Anderson, *Biotechniques* 6:608-614 (1988), all of which are herein incorporated in their entirety); and (4) receptor-mediated mechanisms (Curiel et al., *Hum. Gen. Ther.* 3:147-154 (1992), Wagner et al., *Proc. Natl. Acad. Sci. (USA)* 89:6099-6103 (1992), both of which are incorporated by reference in their entirety).

Acceleration methods that may be used include, for example, microprojectile bombardment and the like. One example of a method for delivering transforming nucleic acid molecules to plant cells is microprojectile bombardment. This method has been reviewed by Yang and Christou (eds.), *Particle Bombardment Technology for Gene Transfer*, Oxford Press, Oxford, England (1994), the entirety of which is herein incorporated by reference). Non-biological particles (microprojectiles) that may be coated with nucleic acids and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol.* 87:671-674 (1988), the entirety of which is herein incorporated by reference) nor the susceptibility of *Agrobacterium* infection are required. An illustrative embodiment of a method for delivering DNA into maize cells by acceleration is a biolistics α-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell* 2:603-618 (1990), the entirety of which is herein incorporated by reference). The screen disperses the tungsten nucleic acid particles so that they are not delivered to the recipient cells in large aggregates. A particle delivery system suitable for use with the present invention is the helium acceleration PDS-1000/He gun is available from Bio-Rad Laboratories (Bio-Rad, Hercules, Calif.)(Sanford et al., *Technique* 3:3-16 (1991), the entirety of which is herein incorporated by reference).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles Biological factors include all steps involved in manipulation of cells before and immediately after bombardment, the osmotic adjustment of target cells to help alleviate the trauma associated with bombardment and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci. (U.S.A.)* 87:8526-8530(1990); Svab and Maliga, *Proc. Natl. Acad. Sci. (U.S.A.)* 90:913-917 (1993); Staub and Maliga, *EMBO J.* 12:601-606 (1993); U.S. Pat. Nos. 5,451,513 and 5,545,818, all of which are herein incorporated by reference in their entirety).

Accordingly, it is contemplated that one may wish to adjust various aspects of the bombardment parameters in small scale studies to fully optimize the conditions. One may particularly wish to adjust physical parameters such as gap distance, flight distance, tissue distance and helium pressure. One may also minimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See for example the methods described by Fraley et al., *Bio/Technology* 3:629-635 (1985) and Rogers et al., *Methods Enzymol.* 153:253-277 (1987), both of which are herein incorporated by reference in their entirety. Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.* 205:34 (1986), the entirety of which is herein incorporated by reference).

Modern *Agrobacterium* transformation vectors are capable of replication in *E. coli* as well as *Agrobacterium*, allowing for convenient manipulations as described (Klee et al., In: *Plant DNA Infectious Agents*, Hohn and Schell (eds.), Springer-Verlag, New York, pp. 179-203 (1985), the entirety of which is herein incorporated by reference. Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker-regions flanked by a promoter and a polyadenylation site for direct expression of inserted polypeptide coding genes and are suitable for present purposes (Rogers et al., *Methods Enzymol.* 153:253-277 (1987)). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for the gene of interest.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (See, for example, Potrykus et al., *Mol. Gen. Genet.* 205:193-200 (1986); Lorz et al., *Mol. Gen. Genet.* 199:178 (1985); Fromm et al., *Nature* 319:791 (1986); Uchimiya et al., *Mol. Gen. Genet.* 204:204 (1986); Marcotte et al., *Nature* 335:454-457 (1988), all of which are herein incorporated by reference in their entirety).

Application of these systems to different plant strains depends upon the ability to regenerate that particular plant strain from protoplasts. Illustrative methods for the regeneration of cereals from protoplasts are described (Fujimura et al., *Plant Tissue Culture Letters* 2:74 (1985); Toriyama et al., *Theor Appl. Genet.* 205:34 (1986); Yamada et al. *Plant Cell Rep.* 4:85 (1986); Abdullah et al., *Biotechnology* 4:1087 (1986), all of which are herein incorporated by reference in their entirety).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology* 6:397 (1988), the entirety of which is herein incorporated by reference). In addition, "particle gun" or high-velocity microprojectile technology can be utilized (Vasil et al., *Bio/Technology* 10:667 (1992), the entirety of which is herein incorporated by reference).

Using the latter technology, DNA is carried through the cell wall and into the cytoplasm on the surface of small metal particles as described (Klein et al., *Nature* 328:70 (1987); Klein et al., *Proc. Natl. Acad. Sci. (U.S.A.)* 85:8502-8505 (1988); McCabe et al., *Bio/Technology* 6:923 (1988), all of which are herein incorporated by reference in their entirety). The metal particles penetrate through several layers of cells and thus allow the transformation of cells within tissue explants.

Other methods of cell transformation can also be used and include but are not limited to introduction of DNA into plants by direct DNA transfer into pollen (Zhou et al., *Methods Enzymol.* 101:433 (1983); Hess et al., *Intern Rev. Cytol.* 107: 367 (1987); Luo et al., *Plant Mol. Biol. Reporter* 6:165 (1988), all of which are herein incorporated by reference in their entirety), by direct injection of DNA into reproductive organs of a plant (Pena et al., *Nature* 325.274 (1987), the entirety of which is herein incorporated by reference), or by direct injection of DNA into the cells of immature embryos followed by the rehydration of desiccated embryos (Neuhaus et al., *Theor. Appl. Genet.* 75:30 (1987), the entirety of which is herein incorporated by reference).

The regeneration, development and cultivation of plants from single plant protoplast transformants or from various transformed explants is well known in the art (Weissbach and Weissbach, In: *Methods for Plant Molecular Biology*, Academic Press, San Diego, Calif., (1988), the entirety of which is herein incorporated by reference). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants.

Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. No. 5,004,863, U.S. Pat. No. 5,159,135; U.S. Pat. No. 5,518,908, all of which are herein incorporated by reference in their entirety); soybean (U.S. Pat. No. 5,569,834; U.S. Pat. No. 5,416,011; McCabe et. al., *Biotechnology* 6:923 (1988); Christou et al., *Plant Physiol.* 87:671-674 (1988); all of which are herein incorporated by reference in their entirety); *Brassica* (U.S. Pat. No. 5,463,174, the entirety of which is herein incorporated by reference); peanut (Cheng et al., *Plant Cell Rep.* 15:653-657 (1996), McKently et al., *Plant Cell Rep.* 14:699-703 (1995), all of which are herein incorporated by reference in their entirety); papaya; and pea (Grant et al., *Plant Cell Rep.* 15:254-258 (1995), the entirety of which is herein incorporated by reference).

Transformation of monocotyledons using electroporation, particle bombardment and *Agrobacterium* have also been reported. Transformation and plant regeneration have been achieved in asparagus (Bytebier et al., *Proc. Natl. Acad. Sci.* (*USA*) 84:5354 (1987), the entirety of which is herein incorporated by reference); barley (Wan and Lemaux, *Plant Physiol* 104:37 (1994), the entirety of which is herein incorporated by reference); maize (Rhodes et al., *Science* 240:204 (1988); Gordon-Kamm et al., *Plant Cell* 2:603-618 (1990); Fromm et al., *Bio/Technology* 8:833 (1990); Koziel et al., *Bio/Technology* 11:194(1993); Armstrong et al., *Crop Science* 35:550-557 (1995); all of which are herein incorporated by reference in their entirety); oat (Somers et al., *Bio/Technology* 10:1589 (1992), the entirety of which is herein incorporated by reference); orchard grass (Horn et al., *Plant Cell Rep.* 7:469 (1988), he entirety of which is herein incorporated by reference); rice (Toriyama et al., *Theor Appl. Genet.* 205: 34 (1986); Part et al., *Plant Mol. Biol.* 32:1135-1148 (1996); Abedinia et al., *Aust. J. Plant Physiol* 24:133-141 (1997); Zhang and Wu, *Theor. Appl. Genet.* 76:835 (1988); Zhang et al., *Plant Cell Rep.* 7:379(1988); Battraw and Hall, *Plant Sci.* 86:191-202 (1992); Christou et al., *Bio/Technology* 9:957 (1991), all of which are herein incorporated by reference in their entirety) rye (De la Pena et al., *Nature* 325:274 (1987), the entirety of which is herein incorporated by reference); sugarcane (Bower and Birch, *Plant J.* 2:409 (1992), the entirety of which is herein incorporated by reference); tall fescue (Wang et al., *Bio/Technology* 10:691 (1992), the entirety of which is herein incorporated by reference) and wheat (Vasil et al., *Bio/Technology* 10:667 (1992), the entirety of which is herein incorporated by reference; U.S. Pat. No. 5,631,152, the entirety of which is herein incorporated by reference.)

Assays for gene expression based on the transient expression of cloned nucleic acid constructs have been developed by introducing the nucleic acid molecules into plant cells by polyethylene glycol treatment, electroporation, or particle bombardment (Marcotte et al; *Nature* 335:454-457 (1988), the entirety of which is herein incorporated by reference; Marcotte et al., *Plant Cell* 1:523-532 (1989), the entirety of which is herein incorporated by reference, McCarty et al., *Cell* 66:895-905 (1991), the entirety of which is herein incorporated by reference; Hattori et al., *Genes Dev.* 6:609-618 (1992), the entirety of which is herein incorporated by reference; Goff et al., *EMBO J.* 9:2517-2522 (1990), the entirety of which is herein incorporated by reference). Transient expression systems may be used to functionally dissect gene constructs (see generally, Mailga et al., *Methods in Plant Molecular Biology*, Cold Spring Harbor Press (1995)).

Any of the nucleic acid molecules of the present invention may be introduced into a plant cell in a permanent or transient manner in combination with other genetic elements such as vectors, promoters, enhancers etc. Further, any of the nucleic acid molecules of the present invention may be introduced into a plant cell in a manner that allows for overexpression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279-289 (1990), the entirety of which is herein incorporated by reference; van der Krol et al., *Plant Cell* 2:291-299 (1990), the entirety of which is herein incorporated by reference). Cosuppression may result from stable transformation with a single copy nucleic acid molecule that is homologous to a nucleic acid sequence found with the cell (Prolls and Meyer, *Plant J.* 2:465-475 (1992), the entirety of which is herein incorporated by reference) or with multiple copies of a nucleic acid molecule that is homologous to a nucleic acid sequence found with the cell (Mittlesten et al., *Mol. Gen. Genet.* 244:325-330 (1994), the entirety of which is herein incorporated by reference). Genes, even though different, linked to homologous promoters may result in the cosuppression of the linked genes (Vaucheret, *C. R. Acad. Sci. III* 316:1471-1483 (1993), the entirety of which is herein incorporated by reference).

This technique has, for example, been applied to generate white flowers from red petunia and tomatoes that do not ripen on the vine. Up to 50% of petunia transformants that contained a sense copy of the glucoamylase (CHS) gene produced white flowers or floral sectors; this was as a result of the post-transcriptional loss of mRNA encoding CHS (Flavell, *Proc. Natl. Acad. Sci.* (*U.S.A.*) 91:3490-3496 (1994), the entirety of which is herein incorporated by reference), van Blokland et al., *Plant J.* 6:861-877 (1994), the entirety of which is herein incorporated by reference). Cosuppression may require the coordinate transcription of the transgene and the endogenous gene and can be reset by a developmental control mechanism (Jorgensen, *Trends Biotechnol.* 8:340-344 (1990), the entirety of which is herein incorporated by reference; Meins and Kunz, In: *Gene Inactivation and Homologous Recombination in Plants*, Paszkowski (ed.), pp. 335-348, Kluwer Academic, Netherlands (1994), the entirety of which is herein incorporated by reference).

It is understood that one or more of the nucleic acids of the present invention may be introduced into a plant cell and transcribed using an appropriate promoter with such transcription resulting in the cosuppression of an endogenous transcription factor.

Antisense approaches are a way of preventing or reducing gene function by targeting the genetic material (Mol et al., *FEBS Lett.* 268:427-430 (1990), the entirety of which is herein incorporated by reference). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.) Vol. 11, New York: Plenum 49-63 (1989), the entirety of which is herein incorporated by reference).

The principle of regulation by antisense RNA is that RNA that is complementary to the target mRNA is introduced into cells, resulting in specific RNA:RNA duplexes being formed by base pairing between the antisense substrate and the target mRNA (Green et al., *Annu. Rev. Biochem.* 55:569-597 (1986), the entirety of which is herein incorporated by reference). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155-184 (1990), the entirety of which is herein incorporated by reference). An antisense vector is constructed by standard procedures and introduced into cells by transformation, transfection, electroporation microinjection, infection, etc. The type of transformation and choice of vector will determine whether expression is transient or stable. The promoter used for the antisense gene may influence the level, timing, tissue, specificity, or inducibility of the antisense inhibition.

It is understood that the activity of a transcription factor in a plant cell may be reduced or depressed by growing a transformed plant cell containing a nucleic acid molecule whose non-transcribed strand encodes a transcription factor or fragment thereof.

Antibodies have been expressed in plants (Hiatt et al., *Nature* 342:76-78 (1989), the entirety of which is herein incorporated by reference; Conrad and Fielder, *Plant Mol. Biol.* 26: 1023-1030 (1994), the entirety of which is herein incorporated by reference). Cytoplasmic expression of a scFv (single-chain Fv antibodies) has been reported to delay infection by artichoke mottled crinkle virus. Transgenic plants that express antibodies directed against endogenous proteins may exhibit a physiological effect (Philips et al., *EMBO J.* 16:4489-4496 (1997), the entirety of which is herein incorporated by reference; Marion-Poll, *Trends in Plant Science* 2:447-448 (1997), the entirety of which is herein incorporated by reference). For example, expressed anti-abscisic antibodies have been reported to result in a general perturbation of seed development (Philips et al., *EMBO J.* 16: 4489-4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15:1313-1315 (1997), the entirety of which is herein incorporated by reference; Baca et al., *Ann. Rev. Biophys. Biomol. Struct.* 26:461-493 (1997), the entirety of which is herein incorporated by reference). The catalytic abilities of abzymes may be enhanced by site directed mutagenesis. Examples of abzymes are, for example, set forth in U.S. Pat. No. 5,658,753; U.S. Pat. No. 5,632,990; U.S. Pat. No. 5,631,137; U.S. Pat. No. 5,602,015; U.S. Pat. No. 5,559,538; U.S. Pat. No. 5,576,174; U.S. Pat. No. 5,500,358; U.S. Pat. No. 5,318,897; U.S. Pat. No. 5,298,409; U.S. Pat. No. 5,258,289 and U.S. Pat. No. 5,194,585, all of which are herein incorporated in their entirety.

It is understood that any of the antibodies of the present invention may be expressed in plants and that such expression can result in a physiological effect. It is also understood that any of the expressed antibodies may be catalytic.

(b) Fungal Constructs and Fungal Transformants

The present invention also relates to a fungal recombinant vector comprising exogenous genetic material. The present invention also relates to a fungal cell comprising a fungal recombinant vector. The present invention also relates to methods for obtaining a recombinant fungal host cell comprising introducing into a fungal host cell exogenous genetic material.

Exogenous genetic material may be transferred into a fungal cell. In a preferred embodiment the exogenous genetic material includes a nucleic acid molecule of the present invention having a sequence selected from the group consisting of SEQ ID NO: 1 through SEQ ID NO: 677 or complements thereof or fragments of either or other nucleic acid molecule of the present invention. The fungal recombinant vector may be any vector which can be conveniently subjected to recombinant DNA procedures. The choice of a vector will typically depend on the compatibility of the vector with the fungal host cell into which the vector is to be introduced. The vector may be a linear or a closed circular plasmid. The vector system may be a single vector or plasmid or two or more vectors or plasmids which together contain the total DNA to be introduced into the genome of the fungal host.

The fungal vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the fungal cell, is integrated into the genome and replicated together with the chromosome(s) into which it has been integrated. For integration, the vector may rely on the nucleic acid sequence of the vector for stable integration of the vector into the genome by homologous or nonhomologous recombination. Alternatively, the vector may contain additional nucleic acid sequences for directing integration by homologous recombination into the genome of the fungal host. The additional nucleic acid sequences enable the vector to be integrated into the host cell genome at a precise location(s) in the chromosome(s). To increase the likelihood of integration at a precise location, there should be preferably two nucleic acid sequences which individually contain a sufficient number of nucleic acids, preferably 400 bp to 1500 bp, more preferably 800 bp to 1000 bp, which are highly homologous with the corresponding target sequence to enhance the probability of homologous recombination. These nucleic acid sequences may be any sequence that is homologous with a target sequence in the genome of the fungal host cell and, furthermore, may be non-encoding or encoding sequences.

For autonomous replication, the vector may further comprise an origin of replication enabling the vector to replicate autonomously in the host cell in question. Examples of origin of replications for use in a yeast host cell are the 2 micron origin of replication and the combination of CEN3 and ARS 1. Any origin of replication may be used which is compatible with the fungal host cell of choice.

The fungal vectors of the present invention preferably contain one or more selectable markers which permit easy selection of transformed cells. A selectable marker is a gene the product of which provides, for example biocide or viral resistance, resistance to heavy metals, prototrophy to auxotrophs and the like. The selectable marker may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase) and sC (sulfate adenyltransferase) and trpC (anthranilate synthase). Preferred for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, the entirety of which is herein incorporated by reference. A nucleic acid sequence of the present invention may be operably linked to a suitable promoter sequence. The promoter sequence is a nucleic acid sequence which is recognized by the fungal host cell for expression of the nucleic acid sequence. The promoter sequence contains transcription and translation control sequences which mediate the expression of the protein or fragment thereof.

A promoter may be any nucleic acid sequence which shows transcriptional activity in the fungal host cell of choice and may be obtained from genes encoding polypeptides either homologous or heterologous to the host cell. Examples of suitable promoters for directing the transcription of a nucleic acid construct of the invention in a filamentous fungal host are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase and hybrids thereof. In a yeast host, a useful promoter is the *Saccharomyces cerevisiae* enolase (eno-1) promoter. Particularly preferred promoters are the TAKA amylase, NA2-tpi (a hybrid of the promoters from the genes encoding *Aspergillus niger* neutral alpha-amylase and *Aspergillus oryzae* triose phosphate isomerase) and glaA promoters.

A protein or fragment thereof encoding nucleic acid molecule of the present invention may also be operably linked to a terminator sequence at its 3' terminus. The terminator sequence may be native to the nucleic acid sequence encoding the protein or fragment thereof or may be obtained from foreign sources. Any terminator which is functional in the fungal host cell of choice may be used in the present invention, but particularly preferred terminators are obtained from the genes encoding *Aspergillus oryzae* TAKA amylase, *Aspergillus niger* glucoamylase, *Aspergillus nidulans* anthranilate synthase, *Aspergillus niger* alpha-glucosidase and *Saccharomyces cerevisiae* enolase.

A protein or fragment thereof encoding nucleic acid molecule of the present invention may also be operably linked to a suitable leader sequence. A leader sequence is a nontranslated region of a mRNA which is important for translation by the fungal host. The leader sequence is operably linked to the 5' terminus of the nucleic acid sequence encoding the protein or fragment thereof. The leader sequence may be native to the nucleic acid sequence encoding the protein or fragment thereof or may be obtained from foreign sources. Any leader sequence which is functional in the fungal host cell of choice may be used in the present invention, but particularly preferred leaders are obtained from the genes encoding *Aspergillus oryzae* TAKA amylase and *Aspergillus oryzae* triose phosphate isomerase.

A polyadenylation sequence may also be operably linked to the 3' terminus of the nucleic acid sequence of the present invention. The polyadenylation sequence is a sequence which when transcribed is recognized by the fungal host to add polyadenosine residues to transcribed mRNA. The polyadenylation sequence may be native to the nucleic acid sequence encoding the protein or fragment thereof or may be obtained from foreign sources. Any polyadenylation sequence which is functional in the fungal host of choice may be used in the present invention, but particularly preferred polyadenylation sequences are obtained from the genes encoding *Aspergillus oryzae* TAKA amylase, *Aspergillus niger* glucoamylase, *Aspergillus nidulans* anthranilate synthase and *Aspergillus niger* alpha-glucosidase.

To avoid the necessity of disrupting the cell to obtain the protein or fragment thereof and to minimize the amount of possible degradation of the expressed protein or fragment thereof within the cell, it is preferred that expression of the protein or fragment thereof gives rise to a product secreted outside the cell. To this end, a protein or fragment thereof of the present invention may be linked to a signal peptide linked to the amino terminus of the protein or fragment thereof. A signal peptide is an amino acid sequence which permits the secretion of the protein or fragment thereof from the fungal host into the culture medium. The signal peptide may be native to the protein or fragment thereof of the invention or may be obtained from foreign sources. The 5' end of the coding sequence of the nucleic acid sequence of the present invention may inherently contain a signal peptide coding region naturally linked in translation reading frame with the segment of the coding region which encodes the secreted protein or fragment thereof. Alternatively, the 5' end of the coding sequence may contain a signal peptide coding region which is foreign to that portion of the coding sequence which encodes the secreted protein or fragment thereof. The foreign signal peptide may be required where the coding sequence does not normally contain a signal peptide coding region. Alternatively, the foreign signal peptide may simply replace the natural signal peptide to obtain enhanced secretion of the desired protein or fragment thereof. The foreign signal peptide coding region may be obtained from a glucoamylase or an amylase gene from an *Aspergillus* species, a lipase or proteinase gene from *Rhizomucor miehei*, the gene for the alpha-factor from *Saccharomyces cerevisiae*, or the calf preprochymosin gene. An effective signal peptide for fungal host cells is the *Aspergillus oryzae* TAKA amylase signal, *Aspergillus niger* neutral amylase signal, the *Rhizomucor miehei* aspartic proteinase signal, the *Humicola lanuginosus* cellulase signal, or the *Rhizomucor miehei* lipase signal. However, any signal peptide capable of permitting secretion of the protein or fragment thereof in a fungal host of choice may be used in the present invention.

A protein or fragment thereof encoding nucleic acid molecule of the present invention may also be linked to a propeptide coding region. A propeptide is an amino acid sequence found at the amino terminus of a proprotein or proenzyme. Cleavage of the propeptide from the proprotein yields a mature biochemically active protein. The resulting polypeptide is known as a propolypeptide or proenzyme (or a zymogen in some cases). Propolypeptides are generally inactive and can be converted to mature active polypeptides by catalytic or autocatalytic cleavage of the propeptide from the propolypeptide or proenzyme. The propeptide coding region may be native to the protein or fragment thereof or may be obtained from foreign sources. The foreign propeptide coding region may be obtained from the *Saccharomyces cerevisiae* alpha-factor gene or *Myceliophthora thermophila* laccase gene (WO 95/33836, the entirety of which is herein incorporated by reference).

The procedures used to ligate the elements described above to construct the recombinant expression vector of the present invention are well known to one skilled in the art (see, for example, Sambrook et al., *Molecular Cloning, A Laboratory Manual,* 2nd ed., Cold Spring Harbor, N.Y., (1989)).

The present invention also relates to recombinant fungal host cells produced by the methods of the present invention which are advantageously used with the recombinant vector of the present invention. The cell is preferably transformed with a vector comprising a nucleic acid sequence of the invention followed by integration of the vector into the host chromosome. The choice of fungal host cells will to a large extent depend upon the gene encoding the protein or fragment thereof and its source. The fungal host cell may, for example, be a yeast cell or a filamentous fungal cell.

"Yeast" as used herein includes *Ascosporogenous* yeast (Endomycetales), *Basidiosporogenous* yeast and yeast belonging to the *Fungi Imperfecti* (Blastomycetes). The *Ascosporogenous* yeasts are divided into the families Spermophthbraceae and Saccharomycetaceae. The latter is comprised of four subfamilies, Schizosaccharomycoideae (for example, genus *Schizosaccharomyces*), Nadsonioideae, Lipomycoideae and Saccharomycoideae (for example, genera *Pichia, Kluyveromyces* and *Saccharomyces*). The Basidiosporogenous yeasts include the genera *Leucosporidim, Rhodosporidium, Sporidiobolus, Filobasidium* and *Filobasidiella*. Yeast belonging to the Fungi Imperfecti are divided into two families, Sporobolomycetaceae (for example, genera *Sorobolomyces* and *Bullera*) and Cryptococca ceae (for example, genus *Candida*). Since the classification of yeast may change in the future, for the purposes of this invention, yeast shall be defined as described in Biology and Activities of Yeast (Skinner et al., *Soc. App. Bacteriol. Symposium Series* No. 9, (1980), the entirety of which is herein incorporated by reference). The biology of yeast and manipulation of yeast genetics are well known in the art (see, for example, *Biochemistry and Genetics of Yeast,* Bacil et al. (ed.), 2nd edition, 1987; *The Yeasts,* Rose and Harrison (eds.), 2nd ed., (1987); and *The Molecular Biology of the Yeast Saccharomyces,* Strathem et al. (eds.), (1981), all of which are herein incorporated by reference in their entirety).

"Fungi" as used herein includes the phyla Ascomycota, Basidiomycota, Chytridiomycota and Zykomycota (as defined by Hawksworth et al., In: Ainsworth and Bisby's *Dictionary of The Fungi,* 8th edition, 1995, CAB International, University Press, Cambridge, UK; the entirety of which is herein incorporated by reference) as well as the Oomycota (as cited iri Hawksworth et al., In: Ainsworth and Bisby's *Dictionary of The Fungi,* 8th edition, 1995, CAB International, University Press, Cambridge, UK) and all mitosporic fungi (Hawksworth et al., In: Ainsworth and Bisby's Dictionary of The Fungi, 8th edition, 1995, CAB International, University Press, Cambridge, UK). Representative groups of Ascomycota include, for example, *Neurospora, Eupenicillium* (=*Penicillium*), *Emericella* (=*Aspergillus*), *Eurotiun* (=*Aspergillus*) and the true yeasts listed above. Examples of Basidiomycota include mushrooms, rusts and smuts. Representative groups of Chytridiomycota include, for example, *Allomyces, Blast ocladiella, Coelomomyces* and aquatic fungi. Representative groups of Oomycota include, for example, Saprolegniomycetous aquatic fungi (water molds) such as *Achlya*. Examples of mitosporic fungi include *Aspergillus, Penicillium, Candida* and *Alternaria*. Representative groups of Zygomycota include, for example, *Rhizopus* and *Mucor*.

"Filamentous fungi" include all filamentous forms of the subdivision Eumycota and Oomycota (as defined by Hawksworth et al., In: Ainsworth and Bisby's *Dictionary of The Fungi,* 8th edition, 1995, CAB International, University Press, Cambridge, UK). The filamentous fungi are characterized by a vegetative mycelium composed of chitin, cellulose, glucan, chitosan, mannan and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In one embodiment, the fungal host cell is a yeast cell. In a preferred embodiment, the yeast host cell is a cell of the species of *Candida, Kluyveromyces, Saccharomyces, Schizosaccharomyces, Pichia* and *Yarrowia*. In a preferred embodiment, the yeast host cell is a *Saccharomyces cerevisiae* cell, a *Saccharomyces carlsbergensis, Saccharomyces diastaticus* cell, a *Saccharomyces douglasii* cell, a *Saccharomyces kluyveri* cell, a *Saccharomyces norbensis* cell, or a *Saccharomyces oviformis* cell. In another preferred embodiment, the yeast host cell is a *Kluyverbmyces lactis* cell. In another preferred embodiment, the yeast host cell is a *Yarrowia lipolytica* cell.

In another embodiment, the fungal host cell is a filamentous fungal cell. In a preferred embodiment, the filamentous fungal host cell is a cell of the species of, but not limited to, *Acremonium, Aspergillus, Fusarium, Humicola, Myceliophthora, Mucor, Neurospora, Penicillium, Thielavia, Tolypocladium* and *Trichoderma*. In a preferred embodiment, the filamentous fungal host cell is an *Aspergillus* cell. In another preferred embodiment, the filamentous fungal host cell is an *Acremonium* cell. In another preferred embodiment, the filamentous fungal host cell is a *Fusarium* cell. In another preferred embodiment, the filamentous fungal host cell is a *Humicola* cell. In another preferred embodiment, the filamentous fungal host cell is a *Myceiophthora* cell. In another even preferred embodiment, the filamentous fungal host cell is a *Mucor* cell. In another preferred embodiment, the filamentous fungal host cell is a *Neurospora* cell. In another preferred embodiment, the filamentous fungal host cell is a *Penicillium* cell. In another preferred embodiment, the filamentous fungal host cell is a *Thielavia* cell. In another preferred embodiment, the filamentous fungal host cell is a *Tolypocladiun* cell. In another preferred embodiment, the filamentous fungal host cell is a *Trichoderma* cell. In a preferred embodiment, the filamentous fungal host cell is an *Aspergillus oryzae* cell, an *Aspergillus niger* cell, an *Aspergillus foetidus* cell, or an *Aspergillus japonicus* cell. In another preferred embodiment, the filamentous fungal host cell is a *Fusarium oxysporum* cell or a *Fusarium graminearum* cell. In another preferred embodiment, the filamentous fungal host cell is a *Humicola insolens* cell or a *Humicola lanuginosus* cell. In another preferred embodiment, the filamentous fungal host cell is a *Myceliophthora thermophila* cell. In a most preferred embodiment, the filamentous fungal host cell is a *Mucor miehei* cell. In a most preferred embodiment, the filamentous fungal host cell is a *Neurospora crassa* cell. In a most preferred embodiment, the filamentous fungal host cell is a *Penicillium purpurogenum* cell. In another most preferred embodiment, the filamentous fungal host cell is a *Thielavia terrestris* cell. In another most preferred embodiment, the *Trichoderma* cell is a *Trichoderma reesei* cell, a *Trichoderma viride* cell, a *Trichoderma longibrachiatum* cell, a *Tricho-* derma harzianum cell, or a *Trichoderma koningii* cell. In a preferred embodiment, the fungal host cell is selected from an *A. nidulans* cell, an *A. niger* cell, an *A. oryzae* cell and an *A. sojae* cell. In a further preferred embodiment, the fungal host cell is an *A. nidulans* cell.

The recombinant fungal host cells of the present invention may further comprise one or more sequences which encode one or more factors that are advantageous in the expression of the protein or fragment thereof, for example, an activator (e.g., a trans-acting factor), a chaperone and a processing protease. The nucleic acids encoding one or more of these factors are preferably not operably linked to the nucleic acid encoding the protein or fragment thereof. An activator is a protein which activates transcription of a nucleic acid sequence encoding a polypeptide (Kudla et al., *EMBO* 9:1355-1364 (1990); Jarai and Buxton, *Current Genetics* 26:2238-244 (1994); Verdier, *Yeast* 6:271-297 (1990), all of which are herein incorporated by reference in their entirety). The nucleic acid sequence encoding an activator may be obtained from the genes encoding *Saccharomyces cerevisiae* heme activator protein 1 (hap1), *Saccharomyces cerevisiae* galactose metabolizing protein 4 (gal4) and *Aspergillus nidulans* ammonia regulation protein (areA). For further examples, see Verdier, *Yeast* 6:271-297 (1990); MacKenzie et al., *Journal of Gen. Microbiol.* 139:2295-2307 (1993), both of which are herein incorporated by reference in their entirety). A chaperone is a protein which assists another protein in folding properly (Hartl et al., *TIBS* 19:20-25 (1994); Bergeron et al., *TIBS* 19:124-128 (1994); Demolder et al., *J. Biotechnology* 32:179-189 (1994); Craig, *Science* 260:1902-1903 (1993); Gething and Sambrook, *Nature* 355:33-45 (1992); Puig and Gilbert, *J. Biol. Chem.* 269:7764-7771 (1994); Wang and Tsou, *FASEB Journal* 7:1515-11157 (1993); Robisono et al., *Bio/Technology* 1:381-384 (1994), all of which are herein incorporated by reference in their entirety). The nucleic acid sequence encoding a chaperone may be obtained from the genes encoding *Aspergillus oryzae* protein disulphide isomerase, *Saccharomyces cerevisiae* calnexin *Saccharomyces cerevisiae* BiP/GRP78 and *Saccharomyces cerevisiae* Hsp70. For further examples, see Gething and Sambrook, *Nature* 355:33-45 (1992); Hartl et al., *TIBS* 19:20-25 (1994). A processing protease is a protease that cleaves a propeptide to generate a mature biochemically active polypeptide (Enderlin and Ogrydziak, *Yeast* 10:67-79 (1994); Fuller et al., *Proc. Natl. Acad. Sci.* (*U.S.A.*) 86:1434-1438 (1989); Julius et al., *Cell* 37:1075-1089 (1984); Julius et al., *Cell* 32:839-852 (1983), all of which are incorporated by reference in their entirety). The nucleic acid sequence encoding a processing protease may be obtained from the genes encoding *Aspergillus niger* Kex2, *Saccharomyces cerevisiae* dipeptidylaminopeptidase, *Saccharomyces cerevisiae* Kex2 and *Yarrowia lipolytica* dibasic processing endoprotease (xpr6). Any factor that is functional in the fungal host cell of choice may be used in the present invention.

Fungal cells may be transformed by a process involving protoplast formation, transformation of the protoplasts and regeneration of the cell wall in a manner known per se. Suitable procedures for transformation of *Aspergillus* host cells are described in EP 238 023 and Yelton et al., *Proc. Natl. Acad. Sci.* (*U.S.A.*) 81:1470-1474 (1984), both of which are herein incorporated by reference in their entirety. A suitable method of transforming *Fusarium* species is described by Malardier et al., *Gene* 78:147-156 (1989), the entirety of which is herein incorporated by reference. Yeast may be transformed using the procedures described by Becker and Guarente, In: Abelson and Simon, (eds.), *Guide to Yeast Genetics and Molecular Biology, Methods Enzymol. Volume* 194, pp 182-187, Academic Press, Inc., New York; Ito et al., *J. Bacteriology* 153:163 (1983); Hinnen et al., *Proc. Natl. Acad. Sci.* (*U.S.A.*) 75:1920 (1978), all of which are herein incorporated by reference in their entirety.

The present invention also relates to methods of producing the protein or fragment thereof comprising culturing the recombinant fungal host cells under conditions conducive for expression of the protein or fragment thereof. The fungal cells of the present invention are cultivated in a nutrient medium suitable for production of the protein or fragment thereof using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the protein or fragment thereof to be expressed and/or isolated. The cultivation takes place in a suitable nutrient medium comprising carbon and nitrogen sources and inorganic salts, using procedures known in the art (see, e.g., Bennett and LaSure (eds.), *More Gene Manipulations in Fungi*, Academic Press, Calif., (1991), the entirety of which is herein incorporated by reference). Suitable media are available from commercial suppliers or may be prepared according to published compositions (e.g., in catalogues of the American Type Culture Collection, Manassas, Va.). If the protein or fragment thereof is secreted into the nutrient medium, a protein or fragment thereof can be recovered directly from the medium. If the protein or fragment thereof is not secreted, it is recovered from cell lysates.

The expressed protein or fragment thereof may be detected using methods known in the art that are specific for the particular protein or fragment. These detection methods may include the use of specific antibodies, formation of an enzyme product, or disappearance of an enzyme substrate. For example, if the protein or fragment thereof has enzymatic activity, an enzyme assay may be used. Alternatively, if polyclonal or monoclonal antibodies specific to the protein or fragment thereof are available, immunoassays may be employed using the antibodies to the protein or fragment thereof. The techniques of enzyme assay and immunoassay are well known to those skilled in the art.

The resulting protein or fragment thereof may be recovered by methods known in the arts. For example, the protein or fragment thereof may be recovered from the nutrient medium by conventional procedures including, but not limited to, centrifugation, filtration, extraction, spray-drying, evaporation, or precipitation. The recovered protein or fragment thereof may then be further purified by a variety of chromatographic procedures, e.g., ion exchange chromatography, gel filtration chromatography, affinity chromatography, or the like.

(c) Mammalian Constructs and Transformed Mammalian Cells

The present invention also relates to methods for obtaining a recombinant mammalian host cell, comprising introducing into a mammalian host cell exogenous genetic material. The present invention also relates to a mammalian cell comprising a mammalian recombinant vector. The present invention also relates to methods for obtaining a recombinant mammalian host cell, comprising introducing into a mammalian cell exogenous genetic material. In a preferred embodiment the exogenous genetic material includes a nucleic acid molecule of the present invention having a sequence selected from the group consisting of SEQ ID NO: 1 through SEQ ID NO: 677 or complements thereof or fragments of either or other nucleic acid molecule of the present invention.

Mammalian cell lines available as hosts for expression are known in the art and include many immortalized cell lines available from the American Type Culture Collection (ATCC, Manassas, Va.), such as HeLa cells, Chinese hamster ovary (CHO) cells, baby hamster kidney (BHK) cells and a number of other cell lines. Suitable promoters for mammalian cells are also known in the art and include viral promoters such as that from Simian Virus 40 (SV40) (Fiers et al., *Nature* 273: 113 (1978), the entirety of which is herein incorporated by reference), Rous sarcoma virus (RSV), adenovirus (ADV) and bovine papilloma virus (BPV). Mammalian cells may also require terminator sequences and poly-A addition sequences. Enhancer sequences which increase expression may also be included and sequences which promote amplification of the gene may also be desirable (for example methotrexate resistance genes).

Vectors suitable for replication in mammalian cells may include viral replicons, or sequences which insure integration of the appropriate sequences encoding HCV epitopes into the host genome. For example, another vector used to express foreign DNA is vaccinia virus. In this case, for example, a nucleic acid molecule encoding a protein or fragment thereof is inserted into the vaccinia genome. Techniques for the insertion of foreign DNA into the vaccinia virus genome are known in the art and may utilize, for example, homologous recombination. Such heterologous DNA is generally inserted into a gene which is non-essential to the virus, for example, the thymidine kinase gene (tk), which also provides a selectable marker. Plasmid vectors that greatly facilitate the construction of recombinant viruses have been described (see, for example, Mackett et al., *J Virol*. 49:857 (1984); Chakrabarti et al., *Mol. Cell. Biol.* 5:3403 (1985); Moss, In: *Gene Transfer Vectors For Mammalian Cells* (Miller and Calos, eds., Cold Spring Harbor Laboratory, N.Y., p. 10, (1987); all of which are herein incorporated by reference in their entirety). Expression of the HCV polypeptide then occurs in cells or animals which are infected with the live recombinant vaccinia virus.

The sequence to be integrated into the mammalian sequence may be introduced into the primary host by any convenient means, which includes calcium precipitated DNA, spheroplast fusion, transformation, electroporation, biolistics, lipofection, microinjection, or other convenient means. Where an amplifiable gene is being employed, the amplifiable gene may serve as the selection marker for selecting hosts into which the amplifiable gene has been introduced. Alternatively, one may include with the amplifiable gene another marker, such as a drug resistance marker, e.g. neomycin resistance (G418 in mammalian cells), hygromycin in resistance etc., or an auxotrophy marker (HIS3, TRP1, LEU2, URA3, ADE2, LYS2, etc.) for use in yeast cells.

Depending upon the nature of the modification and associated targeting construct, various techniques may be employed for identifying targeted integration. Conveniently, the DNA may be digested with one or more restriction enzymes and the fragments probed with an appropriate DNA fragment which will identify the properly sized restriction fragment associated with integration.

One may use different promoter sequences, enhancer sequences, or other sequence which will allow for enhanced levels of expression in the expression host. Thus, one may combine an enhancer from one source, a promoter region from another source, a 5'-noncoding region upstream from the initiation methionine from the same or different source as the other sequences and the like. One may provide for an intron in the non-coding region with appropriate splice sites or for an alternative 3'-untranslated sequence or polyadenylation site. Depending upon the particular purpose of the modification, any of these sequences may be introduced, as desired.

Where selection is intended, the sequence to be integrated will have with it a marker gene, which allows for selection. The marker gene may conveniently be downstream from the target gene and may include resistance to a cytotoxic agent, e.g. antibiotics, heavy metals, or the like, resistance or susceptibility to HAT, gancyclovir, etc., complementation to an auxotrophic host, particularly by using an auxotrophic yeast as the host for the subject manipulations, or the like. The marker gene may also be on a separate DNA molecule, particularly with primary mammalian cells. Alternatively, one may screen the various transformants, due to the high efficiency of recombination in yeast, by using hybridization analysis, PCR, sequencing, or the like.

For homologous recombination, constructs can be prepared where the amplifiable gene will be flanked, normally on both sides with DNA homologous with the DNA of the target region. Depending upon the nature of the integrating DNA and the purpose of the integration, the homologous DNA will generally be within 100 kb, usually 50 kb, preferably about 25 kb, of the transcribed region of the target gene, more preferably within 2 kb of the target gene. Where modeling of the gene is intended, homology will usually be present proximal to the site of the mutation. The homologous DNA may include the 5'-upstream region outside of the transcriptional regulatory region or comprising any enhancer sequences, transcriptional initiation sequences, adjacent sequences, or the like. The homologous region may include a portion of the coding region, where the coding region may be comprised only of an open reading frame or combination of exons and introns. The homologous region may comprise all or a portion of an intron, where all or a portion of one or more exons may also be present. Alternatively, the homologous region may comprise the 3'-region, so as to comprise all or a portion of the transcriptional termination region, or the region 3' of this region. The homologous regions may extend over all or a portion of the target gene or be outside the target gene comprising all or a portion of the transcriptional regulatory regions and/or the structural gene.

The integrating constructs may be prepared in accordance with conventional ways, where sequences may be synthesized, isolated from natural sources, manipulated, cloned, ligated, subjected to in vitro mutagenesis, primer repair, or the like. At various stages, the joined sequences may be cloned and analyzed by restriction analysis, sequencing, or the like. Usually during the preparation of a construct where various fragments are joined, the fragments, intermediate constructs and constructs will be carried on a cloning vector comprising a replication system functional in a prokaryotic host, e.g., *E. coli* and a marker for selection, e.g., biocide resistance, complementation to an auxotrophic host, etc. Other functional sequences may also be present, such as polylinkers, for ease of introduction and excision of the construct or portions thereof, or the like. A large number of cloning vectors are available such as pBR322, the pUC series, etc. These constructs may then be used for integration into the primary mammalian host.

In the case of the primary mammalian host, a replicating vector may be used. Usually, such vector will have a viral replication system, such as SV40, bovine papilloma virus, adenovirus, or the like. The linear DNA sequence vector may also have a selectable marker for identifying transfected cells. Selectable markers include the neo gene, allowing for selection with G418, the herpes tk gene for selection with HAT medium, the gpt gene with mycophenolic acid, complementation of an auxotrophic host, etc.

The vector may or may not be capable of stable maintenance in the host. Where the vector is capable of stable maintenance, the cells will be screened for homologous integration of the vector into the genome of the host, where various techniques for curing the cells may be employed. Where the vector is not capable of stable maintenance, for example, where a temperature sensitive replication system is employed, one may change the temperature from the permissive temperature to the non-permissive temperature, so that the cells may be cured of the vector. In this case, only those cells having integration of the construct comprising the amplifiable gene and, when present, the selectable marker, will be able to survive selection.

Where a selectable marker is present, one may select for the presence of the targeting construct by means of the selectable marker. Where the selectable marker is not present, one may select for the presence of the construct by the amplifiable gene. For the neo gene or the herpes tk gene, one could employ a medium for growth of the transformants of about 0.1-1 mg/ml of G418 or may use HAT medium, respectively. Where DHFR is the amplifiable gene, the selective medium may include from about 0.01-0.5 µM of methotrexate or be deficient in glycine-hypoxanthine-thymidine and have dialysed serum (GHT media).

The DNA can be introduced into the expression host by a variety of techniques that include calcium phosphate/DNA co-precipitates, microinjection of DNA into the nucleus, electroporation, yeast protoplast fusion with intact cells, transfection, polycations, e.g., polybrene, polyornithine, etc., or the like. The DNA may be single or double stranded DNA, linear or circular. The various techniques for transforming mammalian cells are well known (see Keown et al., *Methods Enzymol.* (1989); Keown et al., *Methods Enzymol.* 185:527-537 (1990); Mansour et al., *Nature* 336:348-352, (1988); all of which are herein incorporated by reference in their entirety).

(d) Insect Constructs and Transformed Insect Cells

The present invention also relates to an insect recombinant vectors comprising exogenous genetic material. The present invention also relates to an insect cell comprising an insect recombinant vector. The present invention also relates to methods for obtaining a recombinant insect host cell, comprising introducing into an insect cell exogenous genetic material. In a preferred embodiment the exogenous genetic material includes a nucleic acid molecule of the present invention having a sequence selected from the group consisting of SEQ ID NO: 1 through SEQ ID NO: 677 or complements thereof or fragments of either or other nucleic acid molecule of the present invention.

The insect recombinant vector may be any vector which can be conveniently subjected to recombinant DNA procedures and can bring about the expression of the nucleic acid sequence. The choice of a vector will typically depend on the compatibility of the vector with the insect host cell into which the vector is to be introduced. The vector may be a linear or a closed circular plasmid. The vector system may be a single vector or plasmid or two or more vectors or plasmids which together contain the total DNA to be introduced into the genome of the insect host. In addition, the insect vector may be an expression vector. Nucleic acid molecules can be suitably inserted into a replication vector for expression in the insect cell under a suitable promoter for insect cells. Many vectors are available for this purpose and selection of the appropriate vector will depend mainly on the size of the nucleic acid molecule to be inserted into the vector and the particular host cell to be transformed with the vector. Each vector contains various components depending on its function (amplification of DNA or expression of DNA) and the particular host cell with which it is compatible. The vector components for insect cell transformation generally include, but are not limited to, one or more of the following: a signal sequence, origin of replication, one or more marker genes and an inducible promoter.

The insect vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the insect cell, is integrated into the genome and replicated together with the chromosome(s) into which it has been integrated. For integration, the vector may rely on the nucleic acid sequence of the vector for stable integration of the vector into the genome by homologous or nonhomologous recombination. Alternatively, the vector may contain additional nucleic acid sequences for directing integration by homologous recombination into the genome of the insect host. The additional nucleic acid sequences enable the vector to be integrated into the host cell genome at a precise location(s) in the chromosome(s). To increase the likelihood of integration at a precise location, there should be preferably two nucleic acid sequences which individually contain a sufficient number of nucleic acids, preferably 400 bp to 1500 bp, more preferably 800 bp to 1000 bp, which are highly homologous with the corresponding target sequence to enhance the probability of homologous recombination. These nucleic acid sequences may be any sequence that is homologous with a target sequence in the genome of the insect host cell and, furthermore, may be non-encoding or encoding sequences.

Baculovirus expression vectors (BEVs) have become important tools for the expression of foreign genes, both for basic research and for the production of proteins with direct clinical applications in human and veterinary medicine (Doerfler, *Curr. Top. Microbiol. Immunol.* 131:51-68 (1968); Luckow and Summers, *Bio/Technology* 6:47-55 (1988a); Miller, *Annual Review of Microbiol.* 42:177-199 (1988); Summers, *Curr. Comm. Molecular Biology*, Cold Spring Harbor Press, Cold Spring Harbor, N.Y. (1988); all of which are herein incorporated by reference in their entirety). BEVs are recombinant insect viruses in which the coding sequence for a chosen foreign gene has been inserted behind a baculovirus promoter in place of the viral gene e.g., polyhedrin (Smith and Summers, U.S. Pat. No. 4,745,051, the entirety of which is incorporated herein by reference).

The use of baculovirus vectors relies upon the host cells being derived from *Lepidopteran* insects such as *Spodoptera frugiperda* or *Trichoplusia ni*. The preferred *Spodoptera frugiperda* cell line is the cell line Sf9. The *Spodoptera frugiperda* Sf9 cell line was obtained from American Type Culture Collection (Manassas, Va.) and is assigned accession number ATCC CRL 1711 (Summers and Smith, *A Manual of Methods for Baculovirus Vectors and Insect Cell Culture Procedures*, Texas Ag. Exper. Station Bulletin No. 1555 (1988), the entirety of which is herein incorporated by reference). Other insect cell systems, such as the silkworm *B. mori* may also be used.

The proteins expressed by the BEVs are, therefore, synthesized, modified and transported in host cells derived from Lepidopteran insects. Most of the genes that have been inserted and produced in the baculovirus expression vector system have been derived from vertebrate species. Other baculovirus genes in addition to the polyhedrin promoter may be employed to advantage in a baculovirus expression system. These include immediate-early (alpha), delayed-early (β), late (γ), or very late (delta), according to the phase of the viral infection during which they are expressed. The expression of these genes occurs sequentially, probably as the result of a "cascade" mechanism of transcriptional regulation. (Guarino and Summers, *J. Virol.* 57:563-571 (1986); Guarino and Summers, *J. Virol.* 61:2091-2099 (1987); Guarino and Summers, *Virol.* 162:444-451 (1988); all of which are herein incorporated by reference in their entirety).

Insect recombinant vectors are useful as intermediates for the infection or transformation of insect cell systems. For example, an insect recombinant vector containing a nucleic acid molecule encoding a baculovirus transcriptional promoter followed downstream by an insect signal DNA sequence is capable of directing the secretion of the desired biologically active protein from the insect cell. The vector may utilize a baculovirus transcriptional promoter region derived from any of the over 500 baculoviruses generally infecting insects, such as for example the Orders Lepidoptera, Diptera, Orthoptera, Coleoptera and Hymenoptera, including for example but not limited to the viral DNAs of *Autographa californica MNPV, Bombyx mori NPV, Trichoplusia ni MNPV, Rachiplusia ou MNPV* or *Galleria mellonella MNPV*, wherein said baculovirus transcriptional promoter is a baculovirus immediate-early gene IE1 or IEN promoter; an immediate-early gene in combination with a baculovirus delayed-early gene promoter region selected from the group consisting of 39K and a HindIII-k fragment delayed-early gene or a baculovirus late gene promoter. The immediate-early or delayed-early promoters can be enhanced with transcriptional enhancer elements. The insect signal DNA sequence may code for a signal peptide of a Lepidopteran adipokinetic hormone precursor or a signal peptide of the *Manduca sexta* adipokinetic hormone precursor (Summers, U.S. Pat. No. 5,155,037; the entirety of which is herein incorporated by reference). Other insect signal DNA sequences include a signal peptide of the Orthoptera Schistocerca gregaria locust adipokinetic hormone precursor and the *Drosophila melanogaster* cuticle genes CP1, CP2, CP3 or CP4 or for an insect signal peptide having substantially a similar chemical composition and function (Summers, U.S. Pat. No. 5,155,037).

Insect cells are distinctly different from animal cells. Insects have a unique life cycle and have distinct cellular properties such as the lack of intracellular plasminogen activators in which are present in vertebrate cells. Another difference is the high expression levels of protein products ranging from 1 to greater than 500 mg/liter and the ease at which cDNA can be cloned into cells (Frasier, *In Vitro Cell. Dev. Biol.* 25:225 (1989); Summers and Smith, In: *A Manual of Methods for Baculovirus Vectors and Insect Cell Culture Procedures*, Texas Ag. Exper. Station Bulletin No. 1555 (1988), both of which are incorporated by reference in their entirety).

Recombinant protein expression in insect cells is achieved by viral infection or stable transformation. For viral infection, the desired gene is cloned into baculovirus at the site of the wild-type polyhedron gene (Webb and Summers, *Technique* 2:173 (1990); Bishop and Posse, *Adv. Gene Technol.* 1:55 (1990); both of which are incorporated by reference in their entirety). The polyhedron gene is a component of a protein coat in occlusions which encapsulate virus particles. Deletion or insertion in the polyhedron gene results the failure to form occlusion bodies. Occlusion negative viruses are morphologically different from occlusion positive viruses and enable one skilled in the art to identify and purify recombinant viruses.

The vectors of present invention preferably contain one or more selectable markers which permit easy selection of transformed cells. A selectable marker is a gene the product of which provides, for example biocide or viral resistance, resistance to heavy metals, prototrophy to auxotrophs and the like. Selection may be accomplished by co-transformation, e.g., as described in WO 91/17243, a nucleic acid sequence of the present invention may be operably linked to a suitable promoter sequence. The promoter sequence is a nucleic acid sequence which is recognized by the insect host cell for expression of the nucleic acid sequence. The promoter sequence contains transcription and translation control sequences which mediate the expression of the protein or fragment thereof. The promoter may be any nucleic acid sequence which shows transcriptional activity in the insect host cell of choice and may be obtained from genes encoding polypeptides either homologous or heterologous to the host cell.

For example, a nucleic acid molecule encoding a protein or fragment thereof may also be operably linked to a suitable leader sequence. A leader sequence is a nontranslated region of a mRNA which is important for translation by the fungal host. The leader sequencer is operably linked to the 5' terminus of the nucleic acid sequence encoding the protein or fragment thereof The leader sequence may be native to the nucleic acid sequence encoding the protein or fragment thereof or may be obtained from foreign sources. Any leader sequence which is functional in the insect host cell of choice may be used in the present invention.

A polyadenylation sequence may also be operably linked to the 3' terminus of the nucleic acid sequence of the present invention. The polyadenylation sequence is a sequence which when transcribed is recognized by the insect host to add polyadenosine residues to transcribed in RNA. The polyadenylation sequence may be native to the nucleic acid sequence encoding the protein or fragment thereof or may be obtained from foreign sources. Any polyadenylation sequence which is functional in the fungal host of choice may be used in the present invention.

To avoid the necessity of disrupting the cell to obtain the protein or fragment thereof and to minimize the amount of possible degradation of the expressed polypeptide within the cell, it is preferred that expression of the polypeptide gene gives rise to a product secreted outside the cell. To this end, the protein or fragment thereof of the present invention may be linked to a signal peptide linked to the amino terminus of the protein or fragment thereof. A signal peptide is an amino acid sequence which permits the secretion of the protein or fragment thereof from the insect host into the culture medium. The signal peptide may be native to the protein or fragment thereof of the invention or may be obtained from foreign sources. The 5' end of the coding sequence of the nucleic acid sequence of the present invention may inherently contain a signal peptide coding region naturally linked in translation reading frame with the segment of the coding region which encodes the secreted protein or fragment thereof.

At present, a mode of achieving secretion of a foreign gene product in insect cells is by way of the foreign gene's native signal peptide. Because the foreign genes are usually from non-insect organisms, their signal sequences may be poorly recognized by insect cells and hence, levels of expression may be suboptimal. However, the efficiency of expression of foreign gene products seems to depend primarily on the characteristics of the foreign protein. On average, nuclear localized or non-structural proteins are most highly expressed, secreted proteins are intermediate and integral membrane proteins are the least expressed. One factor generally affecting the efficiency of the production of foreign gene products in a heterologous host system is the presence of native signal sequences (also termed presequences, targeting signals, or leader sequences) associated with the foreign gene. The signal sequence is generally coded by a DNA sequence immediately following (5' to 3') the translation start site of the desired foreign gene.

The expression dependence on the type of signal sequence associated with a gene product can be represented by the following example: If a foreign gene is inserted at a site downstream from the translational start site of the baculovirus polyhedrin gene so as to produce a fusion protein (containing the N-terminus of the polyhedrin structural gene), the fused gene is highly expressed. But less expression is achieved when a foreign gene is inserted in a baculovirus expression vector immediately following the transcriptional start site and totally replacing the polyhedrin structural gene.

Insertions into the region −50 to −1 significantly alter (reduce) steady state transcription which, in turn, reduces translation of the foreign gene product. Use of the pVL941 vector optimizes transcription of foreign genes to the level of the polyhedrin gene transcription. Even though the transcription of a foreign gene may be optimal, optimal translation may vary because of several factors involving processing: signal peptide recognition, mRNA and ribosome binding, glycosylation, disulfide bond formation, sugar processing, oligomerization, for example.

The properties of the insect signal peptide are expected to be more optimal for the efficiency of the translation process in insect cells than those from, vertebrate proteins. This phenomenon can generally be explained by the fact that proteins secreted from cells are synthesized as precursor molecules containing hydrophobic N-terminal signal peptides. The signal peptides direct transport of the select protein to its target membrane and are then cleaved by a peptidase on the membrane, such as the endoplasmic reticulum, when the protein passes through it.

Another exemplary insect signal sequence is the sequence encoding for Drosophila cuticle proteins such as CP1, CP2, CP3 or CP4 (Summers, U.S. Pat. No. 5,278,050; the entirety of which is herein incorporated by reference). Most of a 9 kb region of the Drosophila genome containing genes for the cuticle proteins has been sequenced. Four of the five cuticle genes contains a signal peptide coding sequence interrupted by a short intervening sequence (about 60 base pairs) at a conserved site. Conserved sequences occur in the 5' mRNA untranslated region, in the adjacent 35 base pairs of upstream flanking sequence and at −200 base pairs from the mRNA start position in each of the cuticle genes.

Standard methods of insect cell culture, cotransfection and preparation of plasmids are set forth in Summers and Smith (Summers and Smith, *A Manual of Methods for Baculovirus Vectors and Insect Cell Culture Procedures*, Texas Agricultural Experiment Station Bulletin No. 1555, Texas A&M University (1987)). Procedures for the cultivation of viruses and cells are described in Volkman and Summers, *J. Virol.* 19:820-832 (1975) and Volkman et al., *J. Virol.* 19:820-832 (1976); both of which are herein incorporated by reference in their entirety.

(e) Bacterial Constructs and Transformed Bacterial Cells

The present invention also relates to a bacterial recombinant vector comprising exogenous genetic material. The present invention also relates to a bacteria cell comprising a bacterial recombinant vector. The present invention also relates to methods for obtaining a recombinant bacteria host cell, comprising introducing into a bacterial host cell exogenous genetic material. In a preferred embodiment the exogenous genetic material includes a nucleic acid molecule of the present invention having a sequence selected from the group: consisting of SEQ ID NO: 1 through SEQ ID NO: 677 or complements thereof or fragments of either or other nucleic acid molecule of the present invention.

The bacterial recombinant vector may be any vector which can be conveniently subjected to recombinant DNA procedures. The choice of a vector will typically depend on the compatibility of the vector with the bacterial host cell into which the vector is to be introduced. The vector may be a linear or a closed circular plasmid. The vector system may be a single vector or plasmid or two or more vectors or plasmids which together contain the total DNA to be introduced into the genome of the bacterial host. In addition, the bacterial vector may be an expression vector. Nucleic acid molecules encoding protein homologues or fragments thereof can, for example, be suitably inserted into a replicable vector for expression in the bacterium under the control of a suitable promoter for bacteria. Many vectors are available forth is purpose and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more marker genes and an inducible promoter.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, E. coli is typically transformed using pBR322, a plasmid derived from an *E. coli* species (see, e.g., Bolivar et al., *Gene* 2:95 (1977); the entirety of which is herein incorporated by reference). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

Nucleic acid molecules encoding protein or fragments thereof may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequences elected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, penicillinase, lpp, or heat-stable enterotoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA and includes origins of replication or autonomously replicating sequences. Such sequences are well known for a variety of bacteria. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*. One example of a selection scheme utilizes a drug to arrest growth of a host cell. Those cells that are successfully transformed with a heterologous protein homologue or fragment thereof produce a protein conferring drug resistance and thus survive the selection regimen.

The expression vector for producing a protein or fragment thereof can also contains an inducible promoter that is recognized by the host bacterial organism and is operably linked to the nucleic acid encoding, for example, the nucleic acid molecule encoding the protein homologue or fragment thereof of interest. Inducible promoters suitable for use with bacterial hosts include the β-lactamase and lactose promoter systems (Chang et al., *Nature* 275:615 (1978); Goeddel et al., *Nature* 281:544 (1979); both of which are herein incorporated by reference in their entirety), the arabinose promoter system (Guzman et al., *J. Bacteriol.* 174:7716-7728 (1992); the entirety of which is herein incorporated by reference), alkaline phosphatase, a tryptophan (trp) promoter system (Goeddel, *Nucleic Acids Res.* 8:4057 (1980); EP 36,776; both of which are herein incorporated by reference in their entirety) and hybrid promoters such as the tac promoter (deBoer et al., *Proc. Natl. Acad. Sci.* (*USA*) 80:21-25 (1983); the entirety of which is herein incorporated by reference). However, other known bacterial inducible promoters are suitable (Siebenlist et al., *Cell* 20:269 (1980); the entirety of which is herein incorporated by reference).

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

Construction of suitable vectors containing one or more of the above-listed components employs standard ligation techniques. Isolated plasmids or DNA fragments are cleaved, tailored and re-ligated in the form desired to generate the plasmids required. Examples of available bacterial expression vectors include, but are not limited to, the multifunctional *E. coli* cloning and expression vectors such as Bluescript™ (Stratagene, La Jolla, Calif.), in which, for example, encoding an *A. nidulans* protein homologue or fragment thereof homologue, may be ligated into the vector in frame with sequences for the amino-terminal Met and the subsequent 7 residues of β-galactosidase so that a hybrid protein is produced; pIN vectors (Van Heeke and Schuster, *J. Biol. Chem.* 264:5503-5509 (1989), the entirety of which is herein incorporated by reference); and the like. pGEX vectors (Promega, Madison Wis. U.S.A.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

Suitable host bacteria for a bacterial vector include archaebacteria and eubacteria, especially eubacteria and most preferably Enterobacteriaceae. Examples of useful bacteria include *Escherichia, Enterobacter, Azotobacter, Erwinia, Bacillus, Pseudomonas, Klebsiella, Proteus, Salmonella, Serratia, Shigella, Rhizobia, Vitreoscilla* and *Paracoccus*. Suitable *E. coli* hosts include *E. coli* W3110 (American Type Culture Collection (ATCC) 27,325, Manassas, Va. U.S.A.), *E. coli* 294 (ATCC 31,446), *E. coli* B and *E. coli* X1776 (ATCC 31,537). These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. *E. coli* strain W3110 is a preferred host or parent host because it is a common host strain for recombinant DNA product fermentations. Preferably, the host cell should secrete minimal amounts of proteolytic enzymes.

Host cells are transfected and preferably transformed with the above-described vectors and cultured in conventional nutrient media modified as appropriate for inducing promoters, selecting transformants, or amplifying the genes encoding the desired sequences.

Numerous methods of transfection are known to the ordinarily skilled artisan, for example, calcium phosphate and electroporation. Depending on the host cell used, transformation is done using standard techniques appropriate to such cells. The calcium treatment employing calcium chloride, as described in section 1.82 of Sambrook et al. *Molecular Cloning: A Laboratory Manual*, New York: Cold Spring Harbor Laboratory Press, (1989), is generally used for bacterial cells that contain substantial cell-wall barriers. Another method for transformation employs polyethylene glycol/DMSO, as described in Chung and Miller (Chung and Miller, *Nucleic Acids Res.* 16:3580 (1988); the entirety of which is herein incorporated by reference). Yet another method is the use of the technique termed electroporation.

Bacterial cells used to produce the polypeptide of interest for purposes of this invention are cultured in suitable media in which the promoters for the nucleic acid encoding the heterologous polypeptide can be artificially induced as described generally, e.g., in Sambrook et al., *Molecular Cloning: A Laboratory Manual*, New York: Cold Spring Harbor Laboratory Press, (1989). Examples of suitable media are given in U.S. Pat. Nos. 5,304,472 and 5,342,763; both of which are incorporated by reference in their entirety.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Mailga et al., *Methods in Plant Molecular Biology*, Cold Spring Harbor Press (1995), the entirety of which is herein incorporated by reference; Birren et al., *Genome Analysis: Analyzing DNA*, 1, Cold Spring Harbor, N.Y., the entirety of which is herein incorporated by reference).

(f) Computer Readable Media

The nucleotide sequence provided in SEQ ID NO: 1 through SEQ ID NO: 677 or fragment thereof, or complement thereof, or a nucleotide sequence at least 90% identical preferably 95%, identical even more preferably 99% or 100% identical to the sequence provided in SEQ ID NO: 1 through SEQ ID NO: 677 or fragment thereof, or complement thereof, can be "provided" in a variety of mediums to facilitate use. Such a medium can also provide a subset thereof in a form that allows a skilled artisan to examine the sequences.

A preferred subset of nucleotide sequences are those nucleic acid sequences that encode a nucleic acid molecule that encodes a putative maize or soybean chlorophyll synthetase enzyme or complement thereof or fragment of either, a nucleic acid molecule that encodes a maize or soybean protochlorophyllide reductase enzyme or complement thereof or fragment of either, a nucleic acid molecule that encodes a putative maize or soybean protochlorophyllide reductase enzyme or complement thereof or fragment of either, a nucleic acid molecule that encodes a maize or soybean coproporphyrinogen oxidase enzyme or complement thereof or fragment of either, a nucleic acid molecule that encodes a maize or soybean protoporphyrinogen oxidase enzyme or complement thereof or fragment of either, a nucleic acid molecule that encodes a maize or soybean uroporphyrinogen decarboxylase enzyme or complement thereof or fragment of either, a nucleic acid molecule that encodes a putative maize uroporphyrinogen decarboxylase enzyme or complement thereof or fragment of either, a nucleic acid molecule that encodes a maize or soybean porphobilinogen synthase enzyme or complement thereof or fragment of either, a nucleic acid molecule that encodes a maize or soybean hydroxymethylbilane synthase enzyme or complement thereof or fragment of either, a nucleic acid molecule that encodes a maize or soybean glutamate-1-semialdehyde 2,1-aminomutase enzyme or complement thereof or fragment of either, a nucleic acid molecule that encodes a maize or soybean glutamate tRNA ligase enzyme or complement thereof or fragment of either, a nucleic acid molecule that encodes maize or soybean glutamyl-tRNA reductase enzyme or complement thereof or fragment of either, a nucleic acid molecule that encodes a maize or soybean Mg-chelatase enzyme or complement thereof or fragment of either and a nucleic acid molecule that encodes a maize or soybean ferrochelatase enzyme or complement thereof or fragment of either.

A further preferred subset of nucleic acid sequences is where the subset of sequences is two proteins or fragments thereof, more preferably three proteins or fragments thereof and even more preferable four transcription factors or fragments thereof, these nucleic acid sequences are selected from the group that comprises a nucleic acid molecule that encodes a putative maize or soybean chlorophyll synthetase enzyme or complement thereof or fragment of either, a nucleic acid molecule that encodes a maize or soybean protochlorophyllide reductase enzyme or complement thereof or fragment of either, a nucleic acid molecule that encodes a putative maize or soybean protochlorophyllide reductase enzyme or complement thereof or fragment of either, a nucleic acid molecule that encodes a maize or soybean coproporphyrinogen oxidase enzyme or complement thereof or fragment of either, a nucleic acid molecule that encodes a maize or soybean protoporphyrinogen oxidase enzyme or complement thereof or fragment of either, a nucleic acid molecule that encodes a maize or soybean uroporphyrinogen decarboxylase enzyme or complement thereof or fragment of either, a nucleic acid molecule that encodes a putative maize uroporphyrinogen decarboxylase enzyme or complement thereof or fragment of either, a nucleic acid molecule that encodes a maize or soybean porphobilinogen synthase enzyme or complement thereof or fragment of either, a nucleic acid molecule that encodes a maize or soybean hydroxymethylbilane synthase enzyme or complement thereof or fragment of either, a nucleic acid molecule that encodes a maize or soybean glutamate-1-semialdehyde-2,1-aminomutase enzyme or complement thereof or fragment of either, a nucleic acid molecule that encodes a maize or soybean glutamate tRNA ligase enzyme or complement thereof or fragment of either, a nucleic acid molecule that encodes a maize or soybean glutamyl-tRNA reductase enzyme or complement thereof or fragment of either, a nucleic acid molecule that encodes a maize or soybean Mg-chelatase enzyme or complement thereof or fragment of either and a nucleic acid molecule that encodes a maize or soybean ferrochelatase enzyme or complement thereof or fragment of either.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium and magnetic tape: optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing one or more of nucleotide sequences of the present invention, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403-410 (1990), the entirety of which is herein incorporated by reference) and BLAZE (Brutlag et al., *Comp. Chem.* 17:203-207 (1993), the entirety of which is herein incorporated by reference) search algorithms on a Sybase system can be used to identify open reading frames (ORFs)

within the genome that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification and DNA replication, restriction, modification, recombination and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware means, software means and data storage means used to analyze the nucleotide sequence information of the present invention. The minimum hardware means of the computer-based systems of the present invention comprises a central processing unit (CPU), input means, output means and data storage means. A skilled artisan can readily appreciate that any one of the currently available computer-based system are suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the sequence of the present invention that match a particular target sequence or target motif. A variety of known algorithms are disclosed publicly and a variety of commercially available software for conducting search means are available can be used in the computer-based systems of the present invention. Examples of such software include, but are not limited to, MacPattern (EMBL), BLASTIN and BLASTIX (NCBIA). One of the available algorithms or implementing software packages for conducting homology searches can be adapted for use in the present computer-based systems.

The most preferred sequence length of a target sequence is from about 10 to 100 amino acids or from about 30 to 300 nucleotide residues. However, it is well recognized that during searches for commercially important fragments of the nucleic acid molecules of the present invention, such as sequence fragments involved in gene expression and protein processing, may be of shorter length.

As used herein, "a target structural motif," or "target motif," refers to any rationally selected sequence or combination of sequences in which the sequences the sequence(s) are chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures and inducible expression elements (protein binding sequences).

Thus, the present invention further provides an input means for receiving a target sequence, a data storage means for storing the target sequences of the present invention sequence identified using a search means as described above and an output means for outputting the identified homologous sequences. A variety of structural formats for the input and output means can be used to input and output information in the computer-based systems of the present invention. A preferred format for an output means ranks fragments of the sequence of the present invention by varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments sequence of the present invention. For example, implementing software which implement the BLAST and BLAZE algorithms (Altschul et al., *J. Mol. Biol.* 215:403-410 (1990)) can be used to identify open frames within the nucleic acid molecules of the present invention. A skilled artisan can readily recognize that any one of the publicly available homology search programs can be used as the search means for the computer-based systems of the present invention.

Having now generally described the invention, the same will be more readily understood through reference to the following examples which are provided by way of illustration and are not intended to be limiting of the present invention, unless specified.

EXAMPLE 1

The MONN01 cDNA library is a normalized library generated from maize (DK604, Dekalb Genetics, Dekalb, Ill. U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by: 1000 W sodium vapor lamps. Tissue is collected when the maize plant is at the 6-leaf development stage. The older, more juvenile leaves, which are in a basal position, as well as the younger, more adult leaves, which are more apical are cut at the base of the leaves. The leaves are then pooled and immediately transferred to liquid nitrogen containers in which the pooled leaves are crushed. The harvested tissue is then stored at −80° C. until RNA preparation.

The SATMON001 cDNA library is generated from maize (B73, Illinois Foundation Seeds, Champaign, Ill. U.S.A.) immature tassels at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue from the maize plant is collected at the V6 stage. At that stage the tassel is an immature tassel of about 2-3 cm in length. The tassels are removed and frozen in liquid nitrogen. The harvested tissue is then stored at −80° C. until RNA preparation.

The SATMON003 library is generated from maize (B73×Mo17, Illinois Foundation Seeds, Champaign, Ill. U.S.A.) roots at the V6 developmental stage. Seeds are planted at a depth of approximately 3 cm in coil into 2-3 inch peat pots containing Metro 200 growing medium. After 2-3 weeks growth, the seedlings are transplanted into 10 inch pots containing the Metro 200 growing medium. Plants are watered daily before transplantation and approximately 3 times a week after transplantation. Peters 15-16-17 fertilizer is applied approximately three times per week after transplanting at a concentration of 150 ppm N. Two to three times during the life time of the plant from transplanting to flowering a total of approximately 900 mg Fe is added to each pot. Maize plants are grown in the green house in approximately 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6 leaf development stage. The root system is cut from maize plant and washed with water to free it from the soil. The tissue is then immediately frozen in liquid nitrogen. The harvested tissue is then stored at −80° C. until RNA preparation.

The SATMON004 cDNA library is generated from maize (B73×Mo17, Illinois. Foundation Seeds, Champaign, Ill. U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older, more juvenile leaves, which are in a basal position, as well as the younger, more adult leaves, which are more apical are cut at the base of the leaves. The leaves are then pooled and immediately transferred to liquid nitrogen containers in which the pooled leaves are crushed. The harvested tissue is then stored at −80° C. until RNA preparation.

The SATMON005 cDNA library is generated from maize (B73×Mo17, Ill. Foundation Seeds, Champaign Ill., U.S.A.) root tissue at the V6 development stage Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The root system is cut from the mature maize plant and washed with water to free it from the soil. The tissue is immediately frozen in liquid nitrogen and the harvested tissue is then stored at −80° C. until RNA preparation.

The SATMON006 cDNA library is generated from maize (B73×Mo117, Illinois Foundation Seeds, Champaign Ill., U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older more juvenile leaves, which are in a basal position, as well as the younger more adult leaves, which are more apical are cut at the base of the leaves. The leaves are then pooled and immediately transferred to liquid nitrogen containers in which the pooled leaves are crushed. The harvested tissue is then stored at −80° C. until RNA preparation.

The SATMON007 cDNA library is generated from the primary root tissue of 5 day old maize (DK604, Dekalb Genetics, Dekalb, Ill. U.S.A.) seedlings. Seeds are planted on a moist filter paper on a covered tray that is kept in the dark until germination (one day). After germination, the trays, along with the moist paper, are moved to a greenhouse where the maize plants are grown in the greenhouse in 15 hr day/9 hr night cycles for approximately 5 days. The daytime temperature is approximately 80° F. and the nighttime temperature is approximately 70° F. Supplemental lighting is provided by 1000 W sodium vapor lamps. The primary root tissue is collected when the seedlings are 5 days old. At this stage, the primary root (radicle) is pushed through the coleorhiza which itself is pushed through the seed coat. The primary root, which is about 2-3 cm long, is cut and immediately frozen in liquid nitrogen and then stored at −80° C. until RNA preparation.

The SATMON008 cDNA library is generated from the primary shoot (coleoptile 2-3 cm) of maize (DK604, Dekalb Genetics, Dekalb, Ill. U.S.A.) seedlings which are approximately 5 days old. Seeds are planted on a moist filter paper on a covered tray that is kept in the dark until germination (one day). Then the trays containing the seeds are moved to a greenhouse at 15 hr daytime/9 hr nighttime cycles and grown until they are 5 days post germination. The daytime temperature is approximately 80° F. and the nighttime temperature is approximately 70° F. Tissue is collected when the seedlings are 5 days old. At this stage, the primary shoot (coleoptile) is pushed through the seed coat and is about 2-3 cm long. The coleoptile is dissected away from the rest of the seedling, immediately frozen in liquid nitrogen and then stored at −80° C. until RNA preparation.

The SATMON009 cDNA library is generated from maize (DK604, Dekalb Genetics, Dekalb, Ill. U.S.A.) leaves at the 8 leaf stage (V8 plant development stage). Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is 80° F. and the nighttime temperature is 70° F. Supplemental lighting is provided by 1000 W sodium vapor lamps. Tissue is collected when the maize plant is at the 8-leaf development stage. The older more juvenile leaves, which are in a basal position, as well as the younger more adult leaves, which are more apical, are cut at the base of the leaves. The leaves are then pooled and then immediately transferred to liquid nitrogen containers in which the pooled leaves are crushed. The harvested tissue is then stored at −80° C. until RNA preparation.

The SATMON010 cDNA library is generated from maize (DK604, Dekalb Genetics, Dekalb, Ill. U.S.A.) root tissue at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is 80° F. and the nighttime temperature is 70° F. Supplemental lighting is provided by 1000 W sodium vapor lamps. Tissue is collected when the maize plant is at the V8 development stage. The root system is cut from this mature maize plant and washed with water to free it from the soil. The tissue is immediately frozen in liquid nitrogen. The harvested tissue is then stored at −80° C. until RNA preparation.

The SATMON011 cDNA library is generated from undeveloped maize (DK604, Dekalb Genetics, Dekalb, Ill. U.S.A.) leaf at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The second youngest leaf which is at the base of the apical leaf of V6 stage maize plant is cut at the base and immediately transferred to liquid nitrogen containers in which the leaf is crushed. The harvested tissue is then stored at −80° C. until RNA preparation.

The SATMON012 cDNA library is generated from 2 day post germination maize (DK604, Dekalb Genetics, Dekalb, Ill. U.S.A.) seedlings. Seeds are planted on a moist filter paper on a covered tray that is kept in the dark until germination (one day). Then the trays containing the seeds are moved to the greenhouse and grown at 15 hr daytime/9 hr nighttime cycles until 2 days post germination. The daytime temperature is approximately 80° F. and the nighttime temperature is approximately 70° F. Tissue is collected when the seedlings are 2 days old. At the two day stage, the coleorhiza is pushed through the seed coat and the primary root (the radicle) is pierced the coleorhiza but is barely visible. Also, at this two day stage, the coleoptile is just emerging from the seed coat. The 2 days post germination seedlings are then immersed in liquid nitrogen and crushed. The harvested tissue is stored at −80° C. until preparation of total RNA.

The SATMON013 cDNA library is generated from apical maize (DK604, Dekalb Genetics, Dekalb, Ill. U.S.A.) meristem founder at the V4 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Prior to tissue collection, the plant is at the 4 leaf stage. The lead at the apex of the V4 stage maize plant is referred to as the meristem founder. This apical meristem founder is cut, immediately frozen in liquid nitrogen and crushed. The harvested tissue is then stored at −80° C. until RNA preparation.

The SATMON014 cDNA library is generated from maize (DK604, Dekalb Genetics, Dekalb, Ill. U.S.A.) endosperm fourteen days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps; After the V10 stage, the maize plant ear shoots are ready for fertilization. At this stage, the ear shoots are enclosed in a paper bag before silk emergence to withhold the pollen. The ear shoots are pollinated and 14 days after pollination, the ears are pulled out and then the kernels are plucked out of the ears. Each kernel is then dissected into the embryo and the endosperm and the aleurone layer is removed. After dissection, the endosperms are immediately frozen in liquid nitrogen and then stored at −80° C. until RNA preparation.

The SATMON016 library is a maize (DK604, Dekalb Genetics, Dekalb, Ill. U.S.A.) sheath library collected at the V8 developmental stage. Seeds are planted in a depth of approximately 3 cm in solid into 2-3 inch pots containing Metro growing medium. After 2-3 weeks growth, they are transplanted into 10" pots containing the same. Plants are watered daily before transplantation and approximately the times a week after transplantation. Peters 15-16-17 fertilizer is applied approximately three times per week after transplanting, at a strength of 150 ppm N. Two to three times during the life time of the plant from transplanting to flowering, a total of approximately 900 mg Fe is added to each pot. Maize plants are grown in the green, house in 15 hr day/9 hr night cycles. The daytime temperature is approximately 80° F. and the nighttime temperature is approximately 70° F. Supplemental lighting is provided by 1000 W sodium vapor lamps. When the maize plants are at the V8 stage the $5^{th}$ and $6^{th}$ leaves: from the bottom exhibit fully developed leaf blades. At the base of these leaves, the ligule is differentiated and the leaf blade is joined to the sheath. The sheath is dissected away from the base of the leaf then the sheath is frozen in liquid nitrogen and crushed. The tissue is then stored at −80° C. until RNA preparation.

The SATMON017 cDNA library is generated from maize (DK604, Dekalb Genetics Dekalb, Ill. U.S.A.) embryo seventeen days after pollination. Seeds are planted at a depth of approximately 3 cm into 2-3 inch peat pots containing Metro 200 growing medium. After 2-3 weeks growth the seeds are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. After the V10 stage, the ear shoots of maize plant, which are ready for fertilization, are enclosed in a paper bag before silk emergence to withhold the pollen. The ear shoots are fertilized and 21 days after pollination, the ears are pulled out and the kernels are plucked out of the ears. Each kernel is then dissected into the embryo and the endosperm and the aleurone layer is removed. After dissection, the embryos are immediately frozen in liquid nitrogen and then stored at −80° C. until RNA preparation.

The SATMON019 (Lib3054) cDNA library is generated from maize (DK604, Dekalb Genetics, Dekalb, Ill. U.S.A.) culm (stem) at the V8 developmental stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. When the maize plant is at the V8 stage, the 5th and 6th leaves from the bottom have fully developed leaf blades. The region between the nodes of the 5th and the sixth leaves from the bottom is the region of the stem that is collected. The leaves are pulled out and the sheath is also torn away from the stem. This stem tissue is completely free of any leaf and sheath tissue. The stem tissue is then frozen in liquid nitrogen and stored at −80° C. until RNA preparation.

The SATMON020 cDNA library is from a maize (DK604, Dekalb Genetics, Dekalb, Ill. U.S.A.) Hill Type II-Initiated Callus. Petri plates containing approximately 25 ml of Type II initiation media are prepared. This medium contains N6 salts and vitamins, 3% sucrose, 2.3 g/liter proline 0.1 g/liter enzymatic casein hydrolysate, 2 mg/liter 2,4-dichloro phenoxyacetic acid (2,4, D), 15.3 mg/liter $AgNO_3$ and 0.8% bacto agar and is adjusted to pH 6.0 before autoclaving. At 9-11 days after pollination, an ear with immature embryos measuring approximately 1-2 mm in length is chosen. The husks and silks are removed and then the ear is broken into halves and placed in an autoclaved solution of Clorox/TWEEN 20 sterilizing solution. Then the ear is rinsed with deionized water. Then each embryo is extracted from the kernel. Intact embryos are placed in contact with the medium, scutellar side up). Multiple embryos are plated on each plate and the plates are incubated in the dark at 25° C. Type II calluses are friable, can be subcultured with a spatula, frequently regenerate via somatic embryogenesis and are relatively undifferentiated. As seen in the microscope, the Tape II calluses show color ranging from translucent to light yellow and heterogeneity on with respect to embryoid structure as well as stage of embryoid development. Once Type II callus are formed, the calluses is transferred to type II callus maintenance medium without $AgNO_3$. Every 7-10 days, the callus is subcultured. About 4 weeks after embryo isolation the callus is removed from the plates and then frozen in liquid nitrogen. The harvested tissue is stored at −80° C. until RNA preparation.

The SATMON021 cDNA library is generated from the immature maize (DK604, Dekalb Genetics, Dekalb Ill., U.S.A.) tassel at the V8 plant development stage. Seeds are planted at a depth of approximately 3 cm into 2-3 inch peat pots containing Metro 200 growing medium After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. As the maize plant enters the V8 stage, tassels which are 15-20 cm in length are collected and frozen in liquid nitrogen. The harvested tissue is stored at −80° C. until RNA preparation.

The SATMON022 cDNA library is generated from maize (DK604, Dekalb Genetics, Dekalb, Ill. U.S.A.) ear (growing silks) at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. *Zea mays* plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the plant is in the V8 stage. At this stage, some immature ear shoots are visible. The immature ear shoots (approximately 1 cm in length) are pulled out, frozen in liquid nitrogen and then stored at −80° C. until RNA preparation.

The SATMON23 cDNA library is generated from maize (DK604, Dekalb Genetics, Dekalb, Ill. U.S.A.) ear (growing silk) at the V8 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. When the tissue is harvested at the V8 stage, the length of the ear that is harvested is about 10-15 cm and the silks are just exposed (approximately 1 inch). The ear along with the silks is frozen in liquid nitrogen and then the tissue is stored at −80° C. until RNA preparation.

The SATMON024 cDNA library is generated from the immature maize (DK604, Dekalb. Genetics, Dekalb, Ill. U.S.A.) tassel at the V9 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. As a maize plant enters the V9 stage, the tassel is rapidly developing and a 37 cm tassel along with the glume, anthers and pollen is collected and frozen in liquid nitrogen. The harvested tissue is stored at −80° C. until RNA preparation.

The SATMON025 cDNA library is from maize (DK604, Dekalb Genetics, Dekalb, Ill. U.S.A.) Hill Type II-Regenerated Callus. Type II callus is grown in initiation media as described for SATMON020 and then the embryoids on the surface of the Type II callus are allowed to mature and germinate. The 1-2 gm fresh weight of the soft friable type callus containing numerous embryoids are transferred to 100×15 mm petri plates containing 25 ml of regeneration media. Regeneration media consists of Murashige and Skoog (MS) basal salts, modified White's vitamins (0.2 g/liter glycine and 0.5 g/liter myo-inositol and 0.8% bacto agar (6SMS0D)). The plates are then placed in the dark after covering with parafilm. After 1 week, the plates are moved to a lighted growth chamber with 16 hr light and 8 hr dark photoperiod. Three weeks after plating the Type II callus to 6SMS0D, the callus exhibit shoot formation. The callus and the shoots are transferred to fresh 6SMS0D plates for another 2 weeks. The callus and the shoots are then transferred to petri plates with reduced sucrose (3SMS0D). Upon distinct formation of a root and shoot, the newly developed green plants are then removed out with a spatula and frozen in liquid nitrogen containers. The harvested tissue is then stored at −80° C. until RNA preparation.

The SATMON026 cDNA library is generated from maize (DK604, Dekalb Genetics, Dekalb, Ill. U.S.A.) juvenile/adult shift leaves at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plants are at the 8-leaf development stage. Leaves are founded sequentially around the meristem over weeks of time and the older, more juvenile leaves arise earlier and in a more basal position than the younger, more adult leaves, which are in a more apical position. In a V8 plant, some leaves which are in the middle portion of the plant exhibit characteristics of both juvenile as well as adult leaves. They exhibit a yellowing color but also exhibit, in part, a green color. These leaves are termed juvenile/adult shift leaves. The juvenile/adult shift leaves (the 4th, 5th leaves from the bottom) are cut at the base, pooled and transferred to liquid nitrogen in which they are then crushed. The harvested tissue is then stored at −80° C. until RNA preparation.

The SATMON027 cDNA library is generated from 6 day maize (DK604, Dekalb Genetics, Dekalb, Ill. U.S.A.) leaves. Seeds are planted at a depth of approximately 3 cm into 2-3 inch peat pots containing Metro 200 growing medium. After 2-3 weeks growth they are transplanted into 10 inch pots containing the Metro 200 growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. *Zea mays* plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Prior to tissue collection, when the plant is at the 8-leaf stage, water is held back for six days. The older, more juvenile leaves, which are in a basal position, as well as the younger, more adult leaves, which are more apical, are all cut at the base of the leaves. All the leaves exhibit significant wilting. The leaves are then pooled and immediately transferred to liquid nitrogen containers in which the pooled leaves are then crushed. The harvested tissue is then stored at −80° C. until RNA preparation.

The SATMON028 cDNA library is generated from maize (DK604, Dekalb Genetics Dekalb, Ill. U.S.A.) roots at the V8 developmental stage that are subject to six days water stress. Seeds are planted at a depth of approximately 3 cm into 2-3 inch peat pots containing Metro 200 growing medium. After 2-3 weeks growth they are transplanted into 10 inch pots containing the Metro 200 growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Prior to tissue collection, when the plant is at the 8-leaf stage, water is held back for six days. The root system is cut, shaken and washed to remove soil. Root tissue is then pooled and immediately transferred to liquid nitrogen containers in which the pooled leaves are then crushed. The harvested tissue is then stored at −80° C. until RNA preparation.

The SATMON029 cDNA library is generated from maize (DK604, Dekalb Genetics, Dekalb, Ill. U.S.A.) seedlings at the etiolated stage. Seeds are planted on a moist filter paper on a covered tray that is kept in the dark for 4 days at approximately 70° F. Tissue is collected when the seedlings are 4 days old. By 4 days, the primary root has penetrated the coleorhiza and is about 4-5 cm and the secondary lateral roots have also made their appearance. The coleoptile has also pushed through the seed coat and is about 4-5 cm long. The seedlings are frozen in liquid nitrogen and crushed. The harvested tissue is then stored at −80° C. until RNA preparation.

The SATMON030 cDNA library is generated from maize (DK604, Dekalb Genetics, Dekalb, Ill. U.S.A.) root tissue at the V4 plant development stage. Seeds are planted at a depth of approximately 3 cm into 2-3 inch peat pots containing Metro 200 growing medium. After 2-3 weeks growth, they are transplanted into 10 inch pots containing the same. Plants are watered daily before transplantation and approximately 3 times a week after transplantation. Peters 15-16-17 fertilizer is applied approximately three times per week after transplanting, at a strength of 150 ppm N. Two to three times during the life time of the plant, from transplanting to flowering, a total of approximately 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 sodium vapor lamps. Tissue is collected when the maize plant is at the 4 leaf development stage. The root system is cut from the mature maize plant and washed with water to free it from the soil. The tissue is then immediately frozen in liquid nitrogen. The harvested tissue is then stored at −80° C. until RNA preparation.

The SATMON031 cDNA library is generated from the maize (DK604, Dekalb Genetics, Dekalb, Ill. U.S.A.) leaf tissue at the V4 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is 80° F. and the nighttime temperature is 70° F. Supplemental lighting is provided by 1000 W sodium vapor lamps. Tissue is collected when the maize plant is at the 4-leaf development stage. The third leaf from the bottom is cut at the base and immediately frozen in liquid nitrogen and crushed. The tissue is immediately frozen in liquid nitrogen. The harvested tissue is then stored at −80° C. until RNA preparation.

The SATMON033 cDNA library is generated from maize (DK604, Dekalb Genetics, Dekalb, Ill. U.S.A.) embryo tissue 13 days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 1-50 ppm N. Two to three times during the lifetime of the plant, from transplanting to flowering, a total of 900 mg Fe is added to each pot. Maize plants are grown in the green-house in 15 hr day/9 hr night cycles. The daytime temperature is approximately 80° F. and the nighttime temperature is approximately 70° F. Supplemental lighting is provided by 1000 W sodium vapor lamps. After the V10 stage, the ear shoots of the maize plant, which are ready for fertilization, are enclosed in a paper bag before silk emergent to withhold the pollen. The ear shoots are pollinated and 13 days after pollination, the ears are pulled out and then the kernels are plucked out of the ears. Each kernel is then dissected into the embryo and the endosperm and the aleurone layer is removed. After dissection, the embryos are immediately frozen in liquid nitrogen and then stored at −80° C. until RNA preparation.

The SATMON034 cDNA library is generated from cold stressed maize (DK604, Dekalb Genetics, Dekalb, Ill. U.S.A.) seedlings. Seeds are planted on a moist filter paper on a covered tray that is kept on at 110° C. for 7 days. After 7 days, the temperature is shifted to 15° C. for one day until germination of the seed. Tissue is collected once the seedlings are 1 day old. At this point, the coleorhiza has just pushed out of the seed coat and the primary root is just making its appearance. The coleoptile has not yet pushed completely through the seed coat and is also just making its appearance. These 1 day old cold stressed seedlings are frozen in liquid nitrogen and crushed. The harvested tissue is then stored at −80° C. until RNA preparation.

The SATMON~001 (Lib36, Lib83, Lib84) cDNA library is generated from maize leaves at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue from the maize plant is collected at the V8 stage. The older more juvenile leaves in a basal position was well as the younger more adult leaves which are more apical are all cut at the base, pooled and frozen in liquid nitrogen. The harvested tissue is then stored at −80° C. until RNA preparation.

The SATMONN01 cDNA library is generated from maize (B73, Illinois Foundation Seeds, Champaign, Ill. U.S.A.) normalized immature tassels at the V6 plant development stage normalized tissue. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue from the maize plant is collected at the V6 stage. At that stage the tassel is an immature tassel of about 2-3 cm in length. The tassels are removed and frozen in liquid nitrogen. The harvested tissue is then stored at −80° C. until RNA preparation. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The SATMONN04 cDNA library is generated from maize (B73×Mo17, Illinois Foundation Seeds, Champaign, Ill. U.S.A.) normalized total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older, more juvenile leaves, which are in a basal position, as well as the younger, more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The SATMONN05 cDNA library is generated from maize (B73×Mo17, Illinois Foundation Seeds, Champaign Ill., U.S.A.) normalized root tissue at the V6 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The root system is cut from the mature maize plant and washed with water to free it from the soil. The tissue is immediately frozen in liquid nitrogen and the harvested tissue is then stored at −80° C. until RNA preparation. The single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The SATMONN06 cDNA library is generated from maize (B73×Mo17, Illinois Foundation Seeds, Champaign Ill., U.S.A.) normalized total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older more juvenile leaves, which are in a basal position, as well a the younger more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The CMZ029 (SATMON036) cDNA library is generated from maize (DK604, Dekalb Genetics, Dekalb, Ill. U.S.A.) endosperm 22 days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. After the V10 stage, the ear shoots of the maize plant, which are ready for fertilization, are enclosed in a paper bag before silk emergent to withhold the pollen. The ear shoots are pollinated and 22 days after pollination, the ears are pulled out and then the kernels are plucked out of the ears. Each kernel is then dissected into the embryo and the endosperm and the alurone layer is removed. After dissection, the endosperms are immediately frozen in liquid nitrogen and then stored at –80° C. until RNA preparation.

The CMz030 (Lib143) cDNA library is generated from maize seedling tissue two days post germination. Seeds are planted on a moist filter paper on a covered try that is keep in the dark until germination. The trays are then moved to the bench top at 15 hr daytime/9 hr nighttime cycles for 2 days post-germination. The day time temperature is 80° F. and the nighttime temperature is 70° F. Tissue is collected when the seedlings are 2 days old. At this stage, the colehrhiza has pushed through the seed coat and the primary root (the radicle) is just piercing the colehrhiza and is barely visible. The seedlings are placed at 42° C. for 1 hour. Following the heat shock treatment, the seedlings are immersed in liquid nitrogen and crushed. The harvested tissue is stored at –80° C. until RNA preparation.

The CMz031 (Lib148) cDNA library is generated from maize pollen tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants. The ear shoots, which are ready for fertilization, are enclosed in a paper bag to withhold pollen. Twenty-one days after pollination, prior to removing the ears, the paper bag is shaken to collect the mature pollen. The mature pollen is immediately frozen in liquid nitrogen containers and the pollen is crushed. The harvested tissue is then stored at –80° C. until RNA preparation.

The CMz033 (Lib189) cDNA library is generated from maize pooled leaf tissue. Samples are harvested from open pollinated plants. Tissue is collected from maize leaves at the anthesis stage. The leaves are collect from 10-12 plants and frozen in liquid nitrogen. The harvested tissue is then stored at –80° C. until RNA preparation.

The CMz034 (Lib3060) cDNA library is generated from maize mature tissue at 40 days post pollination plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from leaves located two leaves below the ear leaf. This sample represents those genes expressed during onset and early stages of leaf senescence. The leaves are pooled and immediately transferred to liquid nitrogen. The harvested tissue is then stored at –80° C. until RNA preparation.

The CMz035 (Lib3061) cDNA library is generated from maize endosperm tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants. The ear shoots, which are ready for fertilization, are enclosed in a paper bag prior to silk emergence to withhold pollen. Thirty-two days after pollination, the ears are pulled out and the kernels are removed from the cob. Each kernel is dissected into the embryo and the endosperm and the aleurone layer is removed. After dissection, the endosperms are immediately transferred to liquid nitrogen. The harvested tissue is then stored at –80° C. until RNA preparation.

The CMz036 (Lib3062) cDNA library is generated from maize husk tissue at the 8 week old plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from 8 week old plants. The husk is separated from the ear and immediately transferred to liquid nitrogen containers. The harvested tissue is then stored at –80° C. until RNA preparation.

The CMz037 (Lib3059) cDNA library is generated from maize pooled kernel at 12-15 days after pollination plant development stage. Sample were collected from field grown material. Whole kernels from hand pollinated (control pollination) are harvested as whole ears and immediately frozen on dry ice. Kernels from 10-12 ears were pooled and ground together in liquid nitrogen. The harvested tissue is then stored at –80° C. until RNA preparation.

The CMz039 (Lib3066) cDNA library is generated from maize immature anther tissue at the 7 week old immature tassel stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 7 week old immature tassel stage. At this stage, prior to anthesis, the immature anthers are green and enclosed in the staminate spikelet. The developing anthers are dissected away from the 7 week old immature tassel and immediately frozen in liquid nitrogen. The harvested tissue is then stored at −80° C. until RNA preparation.

The CMz040 (Lib3067) cDNA library is generated from maize kernel tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants. The ear shoots, which are ready for fertilization, are enclosed in a paper bag before silk emergence to withhold pollen. Five to eight days after controlled pollination. The ears are pulled and the kernels removed. The kernels are immediately frozen in liquid nitrogen. The harvested kernels tissue is then stored at −80° C. until RNA preparation. This sample represents gene expressed in early kernel development, during periods of cell division, amyloplast biogenesis and early carbon flow across the material to filial tissue.

The CMz041 (Lib3068) cDNA library is generated from maize pollen germinating silk tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants when the ear shoots are ready for fertilization at the silk emergence stage. The emerging silks are pollinated with an excess of pollen under controlled pollination conditions in the green house. Eighteen hours after pollination the silks are removed from the ears and immediately frozen in liquid nitrogen containers. This sample represents genes expressed in both pollen and silk tissue early in pollination. The harvested tissue is then stored at −80° C. until RNA preparation.

The CMz042 (Lib3069) cDNA library is generated from maize ear tissue excessively pollinated at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants and the ear shoots which are ready for fertilization are at the silk emergence stage. The immature ears are pollinated with an excess of pollen under controlled pollination conditions. Eighteen hours post-pollination, the ears are removed and immediately transferred to liquid nitrogen containers. The harvested tissue is then stored at −80° C. until RNA preparation.

The CMz044 (Lib3075) cDNA library is generated from maize microspore tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from immature anthers from 7 week old tassels. The immature anthers are first dissected from the 7 week old tassel with a scalpel on a glass slide covered with water. The microspores (immature pollen) are released into the water and are recovered by centrifugation. The microspore suspension is immediately frozen in liquid nitrogen. The harvested tissue is then stored at −80° C. until RNA preparation.

The CMz045 (Lib3076) cDNA library is generated from maize immature ear megaspore tissue. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from immature ear (megaspore) obtained from 7 week old plants. The immature ears are harvested from the 7 week old plants and are approximately 2.5 to 3 cm in length. The kernels are removed from the cob immediately frozen in liquid nitrogen. The harvested tissue is then stored at −80° C. until RNA preparation.

The CMz047 (Lib3078) cDNA library is generated from maize $CO_2$ treated high exposure shoot tissue at the V10+ plant development stage. RX601 maize seeds are sterilized for minute with a 10% clorox solution. The seeds are rolled in germination paper, and germinated in 0.5 mM calcium sulfate solution for two days ate 30° C. The seedlings are planted at a depth of approximately 3 cm into 2-3 inch peat pots containing Metro 200 growing medium at a rate of 2-3 seedlings per pot. Twenty pots are placed into a high $CO_2$ environment (approximately 1000 ppm $CO_2$). Twenty plants were grown under ambient greenhouse $CO_2$ (approximately 450 ppm $CO_2$). Plants are watered daily before transplantation and three times a week after transplantation. Peters 20-20-20 fertilizer is also lightly applied. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. At ten days post planting, the shoots from both atmosphere are frozen in liquid nitrogen and lightly ground. The roots are washed in deionized water to remove the support media and the tissue is immediately transferred to liquid nitrogen containers. The harvested tissue is then stored at −80° C. until RNA preparation.

The CMz048 (Lib3079) cDNA library is generated from maize basal endosperm transfer layer tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ maize plants. The ear shoots, which are ready for fertilization, are enclosed in a paper bag prior to silk emergence, to withhold the pollen. Kernels are harvested at 12 days post-pollination and placed on wet ice for dissection. The kernels are cross sectioned laterally, dissecting just above the pedicel region, including 1-2 mm of the lower endosperm and the basal endosperm transfer region. The pedicel and lower endosperm region containing the basal endosperm transfer layer is pooled and immediately frozen in liquid nitrogen. The harvested tissue is then stored at −80° C. until RNA preparation.

The CMz049(Lib3088) cDNA library is generated from maize immature anther tissue at the 7 week old immature tassel stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 7 week old immature tassel stage. At this stage, prior to anthesis, the immature anthers are green and enclosed in the staminate spikelet. The developing anthers are dissected away from the 7 week old immature tassel and immediately transferred to liquid nitrogen container. The harvested tissue is then stored at −80° C. until RNA preparation.

The CMz050 (Lib3114) cDNA library is generated from maize silk tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is beyond the 10-leaf development stage and the ear shoots are approximately 15-20 cm in length. The ears are pulled and silks are separated from the ears and immediately transferred to liquid nitrogen containers. The harvested tissue is then stored at −80° C. until RNA preparation.

The SOYMON001 cDNA library is generated from soybean cultivar Asgrow 3244 (Asgrow Seed Company, Des Moines, Iowa U.S.A.) total leaf tissue at the V4 plant development stage. Leaf tissue from 38, field grown V4 stage plants is harvested from the $4^{th}$ node. Leaf tissue is removed from the plants and immediately frozen in dry-ice. The harvested tissues then stored at −80° C. until RNA preparation.

The SOYMON002 cDNA library is generated from soybean cultivar Asgrow 3244 (Asgrow Seed Company, Des Moines, Iowa U.S.A.) root tissue at the V4 plant development stage. Root tissue from 76, field grown V4 stage plants is harvested. The root systems is cut from the soybean plant and washed with water to free it from the soil and immediately frozen in dry-ice. The harvested tissue is then stored at −80° C. until RNA preparation.

The SOYMON003 cDNA library is generated from soybean cultivar Asgrow 3244 (Asgrow Seed Company, Des Moines, Iowa U.S.A.) seedling hypocotyl axis tissue harvested 2 day post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 2 days after the start of imbibition. The 2 days after imbibition samples are separated into 3 collections after removal of any adhering seed coat. At the 2 day stage, the hypocotyl axis is emerging from the soil. A few seedlings have cracked the soil surface and exhibited slight greening of the exposed cotyledons. The seedlings are washed in water to remove soil, hypocotyl axis harvested and immediately frozen in liquid nitrogen. The harvested tissue is then stored at −80° C. until RNA preparation.

The SOYMON004 cDNA library is generated from soybean cultivar Asgrow 3244 (Asgrow Seed Company, Des Moines, Iowa U.S.A.) seedling cotyledon tissue harvested 2 day post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 2 days after the start of imbibition. The 2 days after imbibition samples are separated into 3 collections after removal of any adhering seed-coat. At the 2 day stage, the hypocotyl axis is emerging from the soil. A few seedlings have cracked the sol surface and exhibited slight greening of the exposed cotyledons. The seedlings are washed in water to remove soil, hypocotyl axis harvested and immediately frozen in liquid nitrogen. The harvested tissue is then stored at −80° C. until RNA preparation.

The SOYMON005 cDNA library is generated from soybean cultivar Asgrow 3244 (Asgrow Seed Company, Des Moines, Iowa U.S.A.) seedling hypocotyl axis tissue harvested 6 hour post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 6 hours after the start of imbibition. The 6 hours after imbibition samples are separated into 3 collections after removal of any adhering seed coat. The 6 hours after imbibition sample is collected over the course of approximately 2 hours starting at 6 hours post imbibition. At the 6 hours after imbibition stage, not all cotyledons have become fully hydrated and germination, or radicle protrusion, has not occurred. The seedlings are washed in water to remove soil, hypocotyl axis harvested and immediately frozen in liquid nitrogen. The harvested tissue is then stored at −80° C. until RNA preparation.

The SOYMON006 cDNA library is generated from soybean cultivar Asgrow 3244 (Asgrow Seed Company, Des Moines, Iowa U.S.A.) seedling cotyledons tissue harvest 6 hour post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 6 hours after imbibition. The 6 hours after imbibition samples are separated into 3 collections after removal of any adhering seed coat. The 6 hours after imbibition sample is collected over the course of approximately 2 hours starting at 6 hours post-imbibition. At the 6 hours after imbibition, not all cotyledons have become fully hydrated and germination or radicle protrusion, have not occurred. The seedlings are washed in water to remove soil, cotyledon harvested and immediately frozen in liquid nitrogen. The harvested tissue is then stored at −80° C. until RNA preparation.

The SOYMON007 cDNA library is generated from soybean cultivar Asgrow 3244 (Asgrow Seed Company, Des Moines, Iowa U.S.A.) seed tissue harvested 25 and 35 days post-flowering. Seed pods from field grown plants are harvested 25 and 35 days after flowering and the seeds extracted from the pods. Approximately 4.4 g and 19.3 g of seeds are harvested from the respective seed pods and immediately frozen in dry ice. The harvested tissue is then stored at −80° C. until RNA preparation.

The SOYMON008 cDNA library is generated from soybean cultivar Asgrow 3244 (Asgrow Seed Company, Des Moines, Iowa U.S.A.) leaf tissue harvested from 25 and 35 days post-flowering plants. Total leaf tissue is harvested from field grown plants. Approximately 19 g and 29 g of leaves are harvested from the fourth node of the plant 25 and 35 days post-flowering and immediately frozen in dry ice. The harvested tissue is then stored at −80° C. until RNA preparation.

The SOYMON009 cDNA library is generated from soybean cultivar C1944 (USDA Soybean Germplasm Collection, Urbana, Ill. U.S.A.) pod and seed tissue harvested 15 days post-flowering. Pods from field grown plants are harvested 15 days post-flowering. Approximately 3 g of pod tissue is harvested and immediately frozen in dry-ice. The harvested tissue is then stored at −80° C. until RNA preparation.

The SOYMON010 cDNA library is generated from soybean cultivar C1944 (USDA Soybean Germplasm Collection, Urbana, Ill. U.S.A.) seed tissue harvested 40 days post-flowering. Pods from field grown plants are harvested 40 days post-flowering. Pods and seeds are separated, approximately 19 g of seed tissue is harvested and immediately frozen in dry-ice. The harvested tissue is then stored at −80° C. until RNA preparation.

The SOYMON011 cDNA library is generated from soybean cultivars Cristalina (USDA Soybean Germplasm Collection, Urbana, Ill. U.S.A.) and FT108 (Monsoy, Brazil) (tropical germ plasma) leaf tissue. Leaves are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 30 g of leaves are harvested from the $4^{th}$ node of each of the Cristalina and FT108 cultivars and immediately frozen in dry ice. The harvested tissue is then stored at −80° C. until RNA preparation.

The SOYMON012 cDNA library is generated from soybean cultivar Asgrow 3244 (Asgrow Seed Company, Des Moines, Iowa U.S.A.) leaf tissue. Leaves from field grown plants are harvested from the fourth node 15 days post-flowering. Approximately 12 g of leaves are harvested and immediately frozen in dry ice. The harvested tissue is then stored at −80° C. until RNA preparation.

The SOYMON013 cDNA library is generated from soybean cultivar Asgrow 3244 (Asgrow Seed Company, Des Moines, Iowa U.S.A.) root and nodule tissue. Approximately, 28 g of root tissue from field grown plants is harvested 15 days post-flowering. The root system is cut from the soybean plant, washed with water to free it from the soil and immediately frozen in dry-ice. The harvested tissue is then stored at −80° C. until RNA preparation.

The SOYMON014 cDNA library is generated from soybean cultivar Asgrow 3244 (Asgrow Seed Company, Des Moines, Iowa U.S.A.) seed tissue harvested 25 and 35 days after flowering. Seed pods from field grown plants are harvested 15 days after flowering and the seeds extracted from the pods. Approximately 5 g of seeds are harvested from the respective seed pods and immediately frozen in dry ice. The harvested tissue is then stored at −80° C. until RNA preparation.

The SOYMON015 cDNA is generated from soybean cultivar Asgrow 3244 (Asgrow Seed Company, Des Moines, Iowa U.S.A.) seed tissue harvested 45 and 55 days post-flowering. Seed pods from field grown plants are harvested 45 and 55 days after flowering and the seeds extracted from the pods. Approximately 19 g and 31 g of seeds are harvested from the respective seed pods and immediately frozen in dry ice. The harvested tissue is then stored at −80° C. until RNA preparation.

The SOYMON016 cDNA library is generated from soybean cultivar Asgrow 3244 (Asgrow Seed Company, Des Moines, Iowa U.S.A.) root tissue. Approximately, 61 g and 38 g of root tissue from field grown plants is harvested 25 and 35 days post-flowering is harvested. The root system is cut from the soybean plant and washed with water to free it from the soil. The tissue is placed in 14 ml polystyrene tubes and immediately frozen in dry-ice. The harvested tissue is then stored at −80° C. until RNA preparation.

The SOYMON017 cDNA library is generated from soybean cultivar Asgrow 3244 (Asgrow Seed Company, Des Moines, Iowa U.S.A.) root tissue. Approximately 28 g of root tissue from field grown plants is harvested 45 and 55 days post-flowering. The root system is cut from the soybean plant, washed with water to free it from the soil and immediately frozen in dry-ice. The harvested tissue is then stored at −80° C. until RNA preparation.

The SOYMON018 cDNA is generated from soybean cultivar Asgrow 3244 (Asgrow Seed Company, Des Moines, Iowa U.S.A.) leaf tissue harvested 45 and 55 days post-flowering. Leaves from field grown plants are harvested 45 and 55 days after flowering from the fourth node. Approximately 27 g and 33 g of seeds are harvested from the respective seed pods and immediately frozen in dry ice. The harvested tissue is then stored at −80° C. until RNA preparation.

The SOYMON019 cDNA library is generated from soybean cultivars Cristalina (USDA Soybean Germplasm Collection, Urbana, Ill. U.S.A.) and FT108 (Monsoy, Brazil) (tropical germ plasma) root tissue. Roots are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 50 g and 56 g of roots are harvested from each of the Cristalina and FT108 cultivars and immediately frozen in dry ice. The harvested tissue is then stored at −80° C. until RNA preparation.

The SOYMON020 cDNA is generated from soybean cultivar Asgrow 3244 (Asgrow Seed Company, Des Moines, Iowa U.S.A.) seed tissue harvested 65 and 75 days post-flowering. Seed pods from field grown plants are harvested 45 and 55 days after flowering and the seeds extracted from the pods. Approximately 14 g and 31 g of seeds are harvested from the respective seed pods and immediately frozen in dry ice. The harvested tissue is then stored at −80° C. until. RNA preparation.

The SOYMON021 cDNA library is generated from Soybean Cyst Nematode-resistant soybean cultivar Hartwig (USDA Soybean Germplasm Collection, Urbana, Ill. U. SA.) root tissue. Plants are grown in tissue culture at room temperature. At approximately 6 weeks post-germination, the plants are exposed to sterilized Soybean Cyst Nematode eggs. Infection is then allowed to progress for 10 days. After the 10 day infection process, the tissue is harvested. Agar from the culture medium and nematodes are removed and the root tissue is immediately frozen in dry ice. The harvested tissue is then stored at −80° C. until RNA preparation.

The SOYMON022 (Lib3030) cDNA library is generated from soybean cultivar Asgrow 3244 (Asgrow Seed Company, Des Moines, Iowa U.S.A.) partially opened flower tissue. Partially to fully opened flower tissue is harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. A total of 3 g of flower tissue is harvested and immediately frozen in dry ice. The harvested tissue is then stored at −80° C. until RNA preparation.

The SOYMON023 cDNA library is generated from soybean genotype BW211S Null (Tohoku University, Morioka, Japan) seed tissue harvested 15 and 40 days post-flowering. Seed pods from field grown plants are harvested 15 and 40 days post-flowering and the seeds extracted from the pods. Approximately 0.7 g and 14.2 g of seeds are harvested from the respective seed pods and immediately frozen in dry ice. The harvested tissue is then stored at −80° C. until RNA preparation.

The SOYMON024 cDNA library is generated from soybean cultivar Asgrow 3244 (Asgrow Seed Company, Des Moines, Iowa U.S.A.) internode-2 tissue harvested 18 days post-imbibition. Seeds are planted at a depth of approximately 2 cm into 2-3 inch peat pots containing Metromix 350 medium. The plants are grown in a greenhouse for 18 days after the start of imbibition at ambient temperature. Soil is checked and watered daily to maintain even moisture conditions. Stem tissue is harvested 18 days after the start of imbibition. The samples are divided into hypocotyl and internodes 1 through 5. The fifth internode contains some leaf bud material. Approximately 3 g of each sample is harvested and immediately frozen in dry ice. The harvested tissue is then stored at −80° C. until RNA preparation.

The SOYMON025 cDNA library is generated from soybean cultivar Asgrow 3244 (Asgrow Seed Company, Des Moines, Iowa U.S.A.) leaf tissue harvested 65 days post-flowering. Leaves are harvested from the fourth node of field grown plants 65 days post-flowering. Approximately 18.4 g of leaf tissue is harvested and immediately frozen in dry ice. The harvested tissue is then stored at −80° C. until RNA preparation.

SOYMON026 cDNA library is generated from soybean cultivar Asgrow 3244 (Asgrow Seed Company, Des Moines, Iowa U.S.A.) root tissue harvested 65 and 75 days post-flowering. Approximately 27 g and 40 g of root tissue from field grown plants is harvested 65 and 75 days post-flowering. The root system is cut from the soybean plant, washed with water to free it from the soil and immediately frozen in dry-ice. The harvested tissue is then stored at −80° C. until RNA preparation.

The SOYMON027 cDNA library is generated from soybean cultivar Asgrow 3244 (Asgrow Seed Company, Des Moines, Iowa U.S.A.) seed tissue harvested 25 days post-flowering. Seed pods from field grown plants are harvested 25 days post-flowering and the seeds extracted from the pods. Approximately 17 g of seeds are harvested from the seed pods and immediately frozen in dry ice. The harvested tissue is then stored at −80° C. until RNA preparation.

The SOYMON028 cDNA library is generated from soybean cultivar Asgrow 3244 (Asgrow Seed Company, Des Moines, Iowa U.S.A.) drought-stressed root tissue. The plants are grown in an environmental chamber under 12 hr daytime/12 hr nighttime cycles. The daytime temperature is approximately 29° C. and the nighttime temperature 24° C. Soil is checked and watered daily to maintain even moisture conditions. At the R3 stage of development, water is withheld from half of the plant collection (drought stressed population). After 3 days, half of the plants from the drought stressed condition and half of the plants from the control population are harvested. After another 3 days (6 days post drought induction) the remaining plants are harvested. A total of 27 g and 40 g of root tissue is harvested and immediately frozen in dry ice. The harvested tissue is then stored at −80° C. until RNA preparation.

The SOYMON029 cDNA library is generated from Soybean Cyst Nematode-resistant soybean cultivar P107354 (USDA Soybean Germplasm Collection, Urbana, Ill. U.S.A.) root tissue. Late fall to early winter greenhouse grown plants are exposed to Soybean Cyst Nematode eggs. At 10 days post-infection, the plants are uprooted, rinsed briefly and the roots frozen in liquid nitrogen. Approximately 20 grams of root tissue is harvested from the infected plants. The harvested tissue is then stored at −80° C. until RNA preparation.

The SOYMON030 cDNA library is generated from soybean cultivar Asgrow 3244 (Asgrow Seed Company, Des Moines, Iowa U.S.A.) flower bud tissue. Seeds are planted at a depth of approximately 2 cm into 2-3 inch peat pots containing Metromix 350 medium and the plants are grown in an environmental chamber under 12 hr daytime/112 hr nighttime cycles. The daytime temperature is approximately 29° C. and the nighttime temperature approximately 24° C. Soil is checked and watered daily to maintain even moisture conditions. Flower buds are removed from the plant at the pedicel. A total of 100 mg of flower buds are harvested and immediately frozen in liquid nitrogen. The harvested tissue is then stored at −80° C. until RNA preparation.

The SOYMON031 cDNA library is generated from soybean cultivar Asgrow 3244 (Asgrow Seed Company, Des Moines, Iowa U.S.A.) carpel and stamen tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature approximately 24° C. Soil is checked and watered daily to maintain even moisture conditions. Flower buds are removed from the plant at the pedicel. Flowers are dissected to separate petals, sepals and reproductive structures (carpels and stamens). A total of 300 mg of carpel and stamen tissue are harvested and immediately frozen in liquid nitrogen. The harvested tissue is then stored at −80° C. until RNA preparation.

The SOYMON032 cDNA library is prepared from the Asgrow cultivar A4922 (Asgrow. Seed Company, Des Moines, Iowa U.S.A.) rehydrated dry soybean seed meristem tissue. Surface sterilized seeds are germinated in liquid media for 24 hours. The seed axis is then excised from the barely germinating seed, placed on tissue culture media and incubated overnight at 20° C. in the dark. The supportive tissue is removed from the explant prior to harvest. Approximately 570 mg of tissue is harvested and frozen in liquid nitrogen. The harvested tissue is then stored at −80° C. until RNA preparation.

The SOYMON033 cDNA library is generated from soybean cultivar Asgrow 3244 (Asgrow Seed Company, Des Moines, Iowa U.S.A.) heat-shocked seedling tissue without cotyledons. Seeds are imbibed and germinated in vermiculite for 2 days under constant illumination. After 48 hours, the seedlings are transferred to an incubator set at 4° C. under constant illumination. After 30, 60 and 180 minutes seedlings are harvested and dissected. A portion of the seedling consisting of the root, hypocotyl and apical hook is frozen in liquid nitrogen and stored at −80° C. The seedlings after 2 days of imbibition are beginning to emerge from the vermiculite surface. The apical hooks are dark green in appearance. Total. RNA and poly A$^+$ RNA is prepared from equal amounts of pooled tissue.

The SOYMON034 cDNA library is generated from soybean cultivar Asgrow 3244 (Asgrow Seed Company, Des Moines, Iowa U.S.A.) cold-shocked seedling tissue without cotyledons. Seeds are imbibed and germinated in vermiculite for 2 days under constant illumination. After 48 hours, the seedlings are transferred to a cold room set at 5° C. under constant illumination. After 30, 60 and 180 minutes seedlings are harvested and dissected. A portion of the seedling consisting of the root, hypocotyl and apical hook is frozen in liquid nitrogen and stored at −80° C. The seedlings after 2 days of imbibition are beginning to emerge from the vermiculite surface. The apical hooks are dark green in appearance.

The SOYMON035 cDNA library is generated from soybean cultivar Asgrow 3244 (Asgrow Seed Company, Des Moines, Iowa U.S.A.) seed coat tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Seeds are harvested from mid to nearly full maturation (seed coats are not yellowing). The entire embryo proper is removed from the seed coat sample and the seed coat tissue are harvested and immediately frozen in liquid nitrogen. The harvested tissue is then stored at −80° C. until RNA preparation.

The SOYMON036 cDNA library is generated from soybean cultivars PI171451, P1227687 and PI229358 (USDA Soybean Germplasm Collection, Urbana, Ill. U.S.A.) insect challenged leaves. Plants from each of the three cultivars are grown in screenhouse conditions. The screenhouse is divided in half and one half of the screenhouse is infested with soybean looper and the other half infested with velvetbean caterpillar. A single leaf is taken from each of the representative plants at 3 different time points, 11 days after infestation, 2 weeks after infestation and 5 weeks after infestation and immediately frozen in liquid nitrogen. The harvested tissue is then stored at −80° C. until RNA preparation. Total RNA and poly A+ RNA is isolated from pooled tissue consisting of equal quantities of all 18 samples (3 genotypes×3 sample times×2 insect genotypes).

The SOYMON037 cDNA library is generated from soybean cultivar A3244 (Asgrow Seed Company, Des Moines, Iowa U.S.A.) etiolated axis and radical tissue. Seeds are planted in moist vermiculite, wrapped and kept at room temperature in complete darkness until harvest. Etiolated axis and hypocotyl tissue is harvested at 2, 3 and 4 days postplanting. A total of 1 gram of each tissue type is harvested at 2, 3 and 4 days after planting and immediately frozen in liquid nitrogen. The harvested tissue is then stored at −80° C. until RNA preparation.

The SOYMON038 cDNA library is generated from soybean variety Asgrow A3237 (Asgrow Seed Company, Des Moines, Iowa U.S.A.) rehydrated dry seeds. Explants are prepared for transformation after germination of surface-sterilized seeds on solid tissue media. After 6 days, at 28° C. and 18 hours of light per day, the germinated seeds are cold shocked at 4° C. for 24 hours. Meristemic tissue and part of the hypocotyl is remove and cotyledon excised. The prepared explant is then wounded for *Agrobacterium* infection. The 2 grams of harvested tissue is frozen in liquid nitrogen and stored at −80° C. until RNA preparation.

The Soy51 (LIB3027) cDNA library is prepared from equal amounts tissue harvested from SOYMON007, SOYMON015 and SOYMON020 prepared tissue. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The Soy52 (LIB3028) cDNA library is generated from normalized flower DNA. Single stranded DNA representing approximately 1×10⁶ colony forming units of SOYMON022 harvested tissue is used as the starting material for normalization. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The Soy53 (LIB3039) cDNA library is generated from soybean cultivar Asgrow 3.244 (Asgrow Seed Company, Des Moines, Iowa U.S.A.) seedling shoot apical meristem tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Apical tissue is harvested from seedling shoot meristem tissue, 7-8 days after the start of imbibition. The apex of each seedling is dissected to include the fifth node to the apical meristem. The fifth node corresponds to the third trifoliate leaf in the very early stages of development. Stipules completely envelop the leaf primordia at this time. A total of 200 mg of apical tissue is harvested and immediately frozen in liquid nitrogen. The harvested tissue is then stored at −80° C. until RNA preparation.

The Soy54 (LIB3040) cDNA library is generated from soybean cultivar Asgrow 3244 (Asgrow Seed Company, Des Moines, Iowa U.S.A.) heart to torpedo stage embryo tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Seeds are collected and embryos removed from surrounding endosperm and maternal tissues. Embryos from globular to young torpedo stages (by corresponding analogy to *Arabidopsis*) are collected with a bias towards the middle of this spectrum. Embryos which are beginning to show asymmetric development of cotyledons are considered the upper developmental boundary for the collection and are excluded. A total of 12 mg embryo tissue is frozen in liquid nitrogen. The harvested tissue is stored at −80° C. until RNA preparation.

Soy55 (LIB3049) cDNA library is generated from soybean cultivar Asgrow 3244 (Asgrow Seed Company, Des Moines, Iowa U.S.A.) young seed tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Seeds are collected from very young pods (5 to 15 days after flowering). A total of 100 mg of seeds are harvested and frozen in liquid nitrogen. The harvested tissue is stored at −80° C. until RNA preparation.

Soy56 (LIB3029) cDNA library is prepared from equal amounts tissue harvested from SOYMON007, SOYMON015 and SOYMON020 prepared tissue. Single stranded and double stranded DNA representing approximately 1×10⁶ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are not converted to double stranded form and represent a non-normalized seed pool for comparison to Soy51 cDNA libraries.

The Soy58 (LIB3050) cDNA library is generated from soybean cultivar Asgrow 3244 (Asgrow Seed Company, Des Moines, Iowa U.S.A.) drought stressed root tissue subtracted from control root tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. At the R3 stage of the plant drought is induced by withholding water. After 3 and 6 days root tissue from both drought stressed and control (watered regularly) plants are collected and frozen in dry-ice. The harvested tissue is stored at −80° C. until RNA preparation. For subtraction, target cDNA is made from the drought stressed tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 μl 2×SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.).

The Soy59 (LIB3051) cDNA library is generated from soybean cultivar Asgrow 3244 (Asgrow Seed Company, Des Moines, Iowa U.S.A.) endosperm tissue. Seeds are germinated on paper towels under laboratory ambient light conditions. At 8, 10 and 14 hours after imbibition, the seed coats are harvested. The endosperm consists of a very thin layer of tissue affixed to the inside of the seed coat. The seed coat and endosperm are frozen immediately after harvest in liquid nitrogen. The harvested tissue is stored at −80° C. until RNA preparation.

The Soy60 (LIB3072) cDNA library is generated from soybean cultivar Asgrow 3244 (Asgrow Seed Company, Des Moines, Iowa U.S.A.) drought stressed seed plus pod subtracted from control seed plus pod tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 26° C. and the nighttime temperature 21° C. and 70% relative humidity. Soil is checked and watered daily to maintain even moisture conditions. At the R3 stage of the plant drought is induced by withholding water. After 3 and 6 days seeds and pods from both drought stressed and control (watered regularly) plants are collected from the fifth and sixth node and frozen in dry-ice. The harvested tissue is stored at −80° C. until RNA preparation. For subtraction, target cDNA is made from the drought stressed tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 µl 2×SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.).

The Soy61 (LIB3073) cDNA library is generated from soybean cultivar Asgrow 3244 (Asgrow Seed Company, Des Moines, Iowa U.S.A.) jasmonic acid treated seedling subtracted from control tissue. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. For subtraction, target cDNA is made from the jasmonic acid treated tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 µl 2×SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.). For this library's construction, the eighth fraction of the cDNA size fractionation step was used for ligation.

The Soy62 (LIB3074) cDNA library is generated from soybean cultivar Asgrow 3244 (Asgrow Seed Company, Des Moines, Iowa U.S.A.) jasmonic acid treated seedling subtracted from control tissue. Seeds are planted at a depth of approximately 2 cm into 2-3 inch peat pots containing Metromix 350 medium and the plants are grown in a greenhouse . The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. For subtraction, target cDNA is made from the jasmonic acid treated tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using. Dynabeads oligo-dT. The target second strand cDNA is then hybridized to the driver cDNA in 400 µl 2×SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.). For this library's construction, the ninth fraction of the cDNA size fractionation step was used for ligation.

The Soy65 (LIB3107) 07cDNA library is generated from soybean cultivar Asgrow 3244 (Asgrow Seed Company, Des Moines, Iowa U.S.A.) drought-stressed abscission zone tissue. Seeds are planted at a depth of approximately 2 cm into 2-3 inch peat pots containing Metromix 350 medium and the plants are grown in an environmental chamber under 12 hr daytime/2 hr nighttime cycles. The daytime temperature is approximately 29° C. and the nighttime temperature 24° C. Soil is checked and watered daily to maintain even moisture conditions. Plants are irrigated with 15-16-17 Peter's Mix. At the R3 stage of development, drought is imposed by withholding water. At 3, 4, 5 and 6 days, tissue is harvested and wilting is not obvious until the fourth day. Abscission layers from reproductive organs are harvested by cutting less than one millimeter proximal and distal to the layer and immediately frozen in liquid nitrogen. The harvested tissue is stored at −80° C. until RNA preparation.

The Soy66 (LIB3109) cDNA library is generated from soybean cultivar Asgrow 3244 (Asgrow Seed Company, Des Moines, Iowa U.S.A.) non-drought stressed abscission zone tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature approximately 24° C. Soil is checked and watered daily to maintain even moisture conditions. Plants are irrigated with 15-16-17 Peter's Mix. At 3, 4, 5 and 6 days, control abscission layer tissue is harvested. Abscission layers from reproductive organs are harvested by cutting less than one millimeter proximal and distal to the layer and immediately frozen in liquid nitrogen. The harvested tissue is stored at −80° C. until RNA preparation.

Soy67 (LIB3065) cDNA library is prepared from equal amounts tissue harvested from SOYMON007, SOYMON015 and SOYMON020 prepared tissue. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. Captured hybrids are eluted with water.

Soy68 (LIB3052) cDNA library is prepared from equal amounts tissue harvested from SOYMON007, SOYMON015 and SOYMON020 prepared tissue. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. Captured hybrids are eluted with water.

Soy69 (LIB3053) cDNA library is generated from soybean cultivars Cristalina (USDA Soybean Germplasm Collection, Urbana, Ill. U.S.A.) and FT108 (Monsoy, Brazil) (tropical germ plasma) normalized leaf tissue. Leaves are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 30 g of leaves are harvested from the $4^{th}$ node of each of the Cristalina and FT108 cultivars and immediately frozen in dry ice. The harvested tissue is then stored at −80° C. until RNA preparation. Single stranded and double stranded DNA representing approximately $1 \times 10^6$ colony forming units are isolated using standard protocols. RNA, complementary to the single stranded DNA, is synthesized: using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

Soy70 (LIB3055) cDNA library is generated from soybean cultivars Cristalina (USDA Soybean Germplasm Collection, Urbana, Ill. U.S.A.) and FT108 (Monsoy, Brazil) (tropical germ plasma) leaf tissue. Leaves are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 30 g of leaves are harvested from the $4^{th}$ node of each of the Cristalina and FT108 cultivars and immediately frozen in dry ice. The harvested tissue is then stored at −80° C. until RNA preparation.

Soy71 (LIB3056) cDNA library is generated from soybean cultivars Cristalina and FT108 (tropical germ plasma) root tissue. Roots are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 50 g and 56 g of roots are harvested from each of the Cristalina and FT108 cultivars and immediately frozen in dry ice. The harvested tissue is then stored at −80° C. until RNA preparation.

Soy72 (LIB3093) cDNA library is generated from soybean cultivar Asgrow 3244. (Asgrow Seed Company, Des Moines, Iowa U.S.A.) drought stressed leaf control tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 26° C. and the nighttime temperature 21° C. and 70% relative humidity. Soil is checked and watered daily to maintain even moisture conditions. At the R3 stage of the plant drought is induced by withholding water. After 3 and 6 days seeds and pods from both drought stressed and control (watered regularly) plants are collected from the fifth and sixth node and frozen in dry-ice. The harvested tissue is stored at −80° C. until RNA preparation. For subtraction, target cDNA is made from the drought stressed tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 µl 2×SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.).

Soy73 (LIB3093) cDNA library is generated from soybean cultivar Asgrow 3244 (Asgrow Seed Company, Des Moines, Iowa U.S.A.) drought stressed leaf subtracted from control tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 26° C. and the nighttime temperature 21° C. and 70% relative humidity. Soil is checked and watered daily to maintain even moisture conditions. At the R3 stage of the plant drought is induced by withholding water. After 3 and 6 days seeds and pods from both drought stressed and control (watered regularly) plants are collected from the fifth and sixth node and frozen in dry-ice. The harvested tissue is stored at −80° C. until RNA preparation. For subtraction, target cDNA is made from the drought stressed tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y.

U.S.A.). The target cDNA is then heat denatured and the second strand trapped using Dynabeads oligo-dT. The target second strand cDNA is then hybridized to the driver cDNA in 400 µl 2×SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.).

The Soy76 (Lib3106) cDNA library is generated from soybean cultivar Asgrow 3244 (Asgrow Seed Company, Des Moines, Iowa U.S.A.) jasmonic acid and arachidonic treated seedling subtracted from control tissue. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. Arachidonic treated seedlings are sprayed with 1 m/ml arachidonic acid in 0.1% Tween-20. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. The RNA from the arachidonic treated seedlings is isolated separately. For subtraction, target cDNA is made from the jasmonic acid treated tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400-112×SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.). Fraction 10 of the size fractionated cDNA is ligated into the pSPORT vector (Invitrogen, Carlsbad Calif. U.S.A.) in order to capture some of the smaller transcripts characteristic of antifungal proteins.

Soy77 (LIB3108) cDNA library is generated from soybean cultivar Asgrow 3244 (Asgrow Seed Company, Des Moines, Iowa U.S.A.) jasmonic acid control tissue. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. Arachidonic treated seedlings are sprayed with 1 m/ml arachidonic acid in 0.1% Tween-20. After 18 hours, 24 hours and 48 hours post treatment, the cotyledons are removed and the remaining leaf and stem tissue above the soil is harvested and frozen in liquid nitrogen . The harvested tissue is stored at −80° C. until RNA preparation. To make RNA, the three sample timepoints were combined and ground. The RNA from the arachidonic treated seedlings is isolated separately. For subtraction, target cDNA is made from the jasmonic acid treated tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 µl 2×SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.). Fraction 10 of the size fractionated cDNA is ligated into the pSPORT vector in order to capture some of the smaller transcripts characteristic of antifungal proteins.

The Lib9 cDNA library is prepared from *Arabidopsis thaliana*, Columbia ecotype, leaf tissue. Wild type *Arabidopsis thaliana* seeds are planted in commonly used planting pots and grown in an environmental chamber. Leaf blades were cut with sharp scissors at seven weeks after planting. The tissue was immediately frozen in liquid nitrogen. The harvested tissue is stored at −80° C. until RNA extraction. PolyA mRNA is purified from the total RNA preparation using Dynabeads® Oligo(dT)$_{25}$ (Dynal Inc., Lake Success, N.Y.), or equivalent methods. This library was normalized using a PCR-based protocol.

The Lib22 cDNA library is prepared from *Arabidopsis thaliana* Columbia ecotype, root tissue. Wild type *Arabidopsis thaliana* seeds are planted in commonly used planting pots and grown in an environmental chamber. After 5-6 weeks the plants are in the reproductive growth phase. Stems are bolting from the base of the plants. After 7 weeks, more stems, floral buds appear, and a few flowers are starting to open. The 7-week old plants are rinsed intensively by tope water remove dirt from the roots, and blotted by paper towel. The tissues are immediately frozen in liquid nitrogen. The harvested tissue is stored at −80° C. until RNA preparation.

The Lib23 cDNA library is prepared from *Arabidopsis thaliana*, Columbia ecotype, stem tissue. Wild type *Arabidopsis thaliana* seeds are planted in commonly used planting pots and grown in an environmental chamber. Stems were collected seven to eight weeks after planting by cutting the stems from the base and cutting the top of the plant to remove the floral tissue. The tissue was immediately frozen in liquid nitrogen and stored at −80° C. until total RNA extraction. PolyA mRNA is purified from the total RNA preparation using Dynabeads® Oligo(dT)$_{25}$ (Dynal Inc., Lake Success, N.Y.), or equivalent methods. This library was normalized using a PCR-based protocol.

The Lib24 cDNA library is prepared from *Arabidopsis thaliana*, Columbia ecotype, flower bud tissue. Wild type

*Arabidopsis thaliana* seeds are planted in commonly used planting pots and grown in an environmental chamber. Flower buds are green and unopened and harvested about seven weeks after planting. The tissue is immediately frozen in liquid nitrogen. The harvested tissue is stored at −80° C. until total RNA extraction. PolyA mRNA is purified from the total RNA preparation using Dynabeads® Oligo(dT)$_{25}$ (Dynal Inc., Lake Success, N.Y.), or equivalent methods. This library was normalized: using a PCR-based protocol; The Lib25 cDNA library is prepared from *Arabidopsis thaliana*, Columbia ecotype, open flower tissue. Wild type *Arabidopsis thaliana* seeds are planted in commonly used planting pots and grown in an environmental chamber. Flowers are completely opened with all parts of floral structure observable, but no siliques are appearing. The tissue was immediately frozen in liquid nitrogen and stored at −80° C. until total RNA extraction. PolyA mRNA is purified from the total RNA preparation using Dynabeads® Oligo(dT)$_{25}$ (Dynal Inc., Lake Success, N.Y.), or equivalent methods. This library was normalized using a PCR-based protocol.

The Lib35 cDNA library of the present invention, was prepared from *Arabidopsis thaliana* Columbia ecotype leaf tissue. Wild type *Arabidopsis thaliana* seeds are planted in commonly used planting pots and grown in an environmental chamber. After 5-6 weeks the plants are in the reproductive growth phase. Stems are bolting from the base of the plants. After 7 weeks, more stems and floral buds appeared and a few flowers were starting to open. Leaf blades were collected by cutting with sharp scissors. The tissues were immediately frozen in liquid nitrogen and stored at −80° C. until use. PolyA mRNA is purified from the total RNA preparation using Dynabeads® Oligo(dT)$_{25}$ (Dynal Inc., Lake Success, N.Y.), or equivalent methods. This library was normalized using a PCR-based protocol.

The Lib146 cDNA library is prepared from *Arabidopsis thaliana*, Columbia ecotype, immature seed tissue. Wild type *Arabidopsis thaliana* seeds are, planted in commonly used planting pots and grown in an environmental chamber. At approximately 7-8 weeks of age, the seeds are harvested. The seeds ranged in maturity from the smallest seeds that could be dissected from silques to just before starting to turn yellow in color. The tissue is immediately frozen in liquid nitrogen. The harvested tissue is stored at −80° C. until RNA extraction. PolyA mRNA is purified from the total RNA preparation using Dynabeads® Oligo(dT)$_{25}$ (Dynal Inc., Lake. Success, N.Y.), or equivalent methods. This library is normalized using a PCR-based protocol.

The Lib3032 (Lib80) cDNA libraries are generated from *Brassica napus* seeds harvested 30 days after pollination. The cDNA libraries are constructed using the SuperScript Plasmid system for cDNA synthesis and plasmid cloning (Life Technologies, Gaithersburg, Md. U.S.A.) according to the manufacturers protocol with the following modification: 40 micrograms of total RNA is used as the starting material for cDNA synthesis, and first strand cDNA synthesis is carried out at 45° C.

The Lib3034 (Lib82) cDNA libraries are generated from *Brassica napus* seeds harvested 15 and 18 days after pollination. The cDNA libraries are constructed using the SuperScript Plasmid system for cDNA synthesis and plasmid cloning (Life Technologies, Gaithersburg Md. U.S.A.) according to the manufacturers protocol with the following modification: 40 micrograms of total RNA is used as the starting material for cDNA synthesis, and first strand cDNA synthesis was carried out at 45° C.

The Lib3099 cDNA library is generated by a subtraction procedure. The library contains cDNAs whose abundance is enriched in the *Brassica napus* 15 and 18 day after pollination seed tissues when compared to *Brassica* leaf tissues. The cDNA synthesis is performed on *Brassica* leaf RNA and *Brassica* RNA isolated from seeds harvested 15 and 18 days after pollination using a Smart PCR cDNA synthesis kit according to the manufacturers protocol (Clonetech, Palo Alto, Calif. U.S.A.). The subtracted cDNA is generated using the Clontech PCR-Select subtraction kit according to the manufacturers protocol (Clontech, Palo Alto, Calif. U.S.A.). The subtracted cDNA was cloned into plasmid vector pCR2.1 according to the manufacturers protocol (Invitrogen, Carlsbad, Calif. U.S.A.).

The Lib3033 (Lib81) cDNA libraries are generated from the *Schizochytrium* species cells. The *Schizochytrium* species cells are grown in liquid media until saturation: The culture is centrifuged to pellet the cells, the medium is decanted off, and pellet immediately frozen in liquid nitrogen. Wax esters are produced under such dark, anaerobic, rich-medium conditions. High wax production by the cultures is verified by microscopy (fluorescein staining of wax bodies) and by lipid extraction/TLC/GC. The harvested cells are stored at −80° C. until RNA preparation. RNA is prepared from the frozen Euglena cell pellet as follows. The pellet is pulverized to a powder in liquid nitrogen using a mortar and pestle. The powder is transferred to tubes containing 6 ml each of lysis buffer (100 mM Tris, pH 8, 0.6 M NaCl, 10 mM EDTA, and 4% (w/v) SDS) and buffered phenol, vortexed, and disrupted with a Polytron. The mixture is centrifuged 20 min at 10,000×g in Corex glass tubes to separate the phases. 5 ml of the upper phase is removed, vortexed with 5 ml fresh phenol, and centrifuged. The upper phase is removed and the RNA is precipitated overnight at 4° C. by adding 1.5 volumes of 4 M LiCl. The RNA is further purified on Rneasy columns according to the manufacturers protocol (Qiagen, Valencia, Calif. U.S.A.). The cDNA library is constructed using the SuperScript Plasmid system for cDNA synthesis and plasmid cloning (Life Technologies, Gaithersburg, Md. U.S.A.) according to the manufacturers protocol with the following modification: 40 micrograms of total RNA was used as the starting material for cDNA synthesis, and first strand cDNA synthesis was carried out at 45° C.

The Lib47 cDNA library is generated from *Euglena gracilus* strain 753 (ATTC No. 30285, ATCC Manassas, Va. U.S.A.) grown in liquid culture. A liquid culture is inoculated with ⅒ volume of a previously-grown saturated culture, and the new culture for 4 days under near-anaerobic conditions (near-anaerobic cultures are not agitated, just gently swirled once a day) in the dark in 2× Beef (10 g/l bacto peptone, 4 g/l yeast extract, 2 g/l beef extract, 6 g/l glucose). The culture is then centrifuged to pellet the cells, the medium is decanted off, and pellet immediately frozen in liquid nitrogen. Wax esters are produced under such dark, anaerobic, rich-medium conditions. High wax production by the cultures is verified by microscopy (fluorescein staining of wax bodies) and by lipid extraction/TLC/GC. The harvested cells are stored at −80° C. until RNA preparation. RNA is prepared from the frozen Euglena cell pellet as follows. The pellet is pulverized to a powder in liquid nitrogen using a mortar and pestle. The powder is transferred to tubes containing 6 ml each of lysis buffer (100 mM Tris, pH 8, 0.6 M NaCl, 10 mM EDTA, and 4% (w/v) SDS) and buffered phenol, vortexed, and disrupted with a Polytron. The mixture is centrifuged 20 min at 10,000×g in Corex glass tubes to separate the phases. 5 ml of the upper phase is removed, vortexed with 5 ml fresh phenol, and centrifuged. The upper phase is removed and the RNA is precipitated overnight at 4° C. by adding 1.5 volumes of 4 M LiCl. The RNA is further purified on Rneasy columns according to the manufacturers protocol (Qiagen, Valencia, Calif. U.S.A.). The cDNA library is constructed using the Super- Script Plasmid system for cDNA synthesis and plasmid cloning (Life. Technologies, Gaithersburg, Md. U.S.A.) according to the manufacturers protocol with the following modification: 40 micrograms of total RNA was used as the starting material for cDNA synthesis, and first strand cDNA synthesis was carried out at 45° C.

The Lib44 cDNA library is generated from *Phaeodactylum tricornatum* grown in modified Jones medium for 3 days. The cells were harvested by centrifugation and the resulting pellet frozen immediately in liquid nitrogen. The harvested cells are stored at −80° C. until RNA preparation. RNA is prepared from the frozen *Phaeodactylum* cell pellet as follows. The pellet is pulverized to a powder in liquid nitrogen using a mortar and pestle. The powder is transferred to tubes containing 6 ml each of lysis buffer (100 mM Tris, pH 8, 0.6 µM NaCl, 10 mM EDTA, and 4% (w/v) SDS) and buffered phenol, vortexed, and disrupted with a Polytron. The mixture is centrifuged 20 min at 10,000×g in Corex glass tubes to separate the phases. 5 ml of the upper phase is removed, vortexed with 5 ml fresh phenol, and centrifuged. The upper phase is removed and the RNA is precipitated overnight at 4° C. by adding 1.5 volumes of 4M LiCl. The RNA is further purified on Rneasy columns according to the manufacturers protocol (Qiagen, Valencia, Calif. U.S.A.). The cDNA library is constructed using the SuperScript Plasmid system for cDNA synthesis and plasmid cloning (Life Technologies, Gaithersburg, Md. U.S.A.) according to the manufacturers protocol with the following modification: 40 micrograms of total RNA was used as the starting material for cDNA synthesis, and first strand cDNA synthesis was carried out at 45 degrees centigrade.

The LIB3036 genomic library is generated from *Mycobacterium neoaurum* US52 (ATCC No. 23072, ATCC, Manassas, Va. U.S.A.) cells. *Mycobacterium neoaurum* US52 is a gram-positive Actinomycete bacterium. *Mycobacterium neoaurum* US52 is genetically related to *Mycobacterium tuberculosis*, but there is no reason to believe that it is a primary pathogen. It normally is saprophytic, i.e. it lives in soil and gets nutrients from decaying matter. Genomic DNA obtained from *Mycobacterium neoaurum* US52 is digested for various times with the restriction enzyme Sau3A. The DNA fractions are size-separated on an agarose gel, and the first fraction wherein most of the partially-digested fragments are about 10 kB is used to isolated fragments in the range of 2-3 kB. For LIB3036, the 2-3 kB DNA is cloned into vector pRY401 (Invitrogen, Carlsbad, Calif. U.S.A.). The vector pZERO-2 (Invitrogen, Carlsbad, Calif. U.S.A.). is used for the construction of LIB3104.

The stored RNA is purified using Trizol reagent from Life Technologies (Gibco BRL, Life Technologies, Gaithersburg, Md. U.S.A.), essentially as recommended by the manufacturer. Poly A+ RNA (mRNA) is purified using magnetic oligo dT beads essentially as recommended by the manufacturer (Dynabeads, Dynal Corporation, Lake Success, N.Y. U.S.A.).

Construction of plant cDNA libraries is well-known in the art and a number of cloning strategies exist. A number of cDNA library construction kits are commercially available. The Superscript™ Plasmid System for cDNA synthesis and Plasmid Cloning (Gibco-BRL, Life Technologies, Gaithersburg, Md. U.S.A.) is used, following the conditions suggested by the manufacturer.

Normalized libraries are made using essentially the Soares procedure (Soares et al., *Proc. Natl. Acad. Sci. (U.S.A.)* 91:9228-9232 (1994), the entirety of which is herein incorporated by reference). This approach is designed to reduce the initial 10,000-fold variation in individual cDNA frequencies to achieve abundances within one order of magnitude while maintaining the overall sequence complexity of the library. In the normalization process, the prevalence of high-abundance cDNA clones decreases dramatically, clones with mid-level abundance are relatively unaffected and clones for rare transcripts are effectively increased in abundance.

EXAMPLE 2

The cDNA libraries are plated on LB agar containing the appropriate antibiotics for selection and incubated at 37° for a sufficient time to allow the growth of individual colonies. Single colonies are individually placed in each well of a 96-well microtiter plates containing LB liquid including the selective antibiotics. The plates are incubated overnight at approximately 37° C. with gentle shaking to promote growth of the cultures. The plasmid DNA is isolated from each clone using Qiaprep plasmid isolation kits, using the conditions recommended by the manufacturer (Qiagen Inc., Santa Clara, Calif. U.S.A.).

Template plasmid DNA clones are used for subsequent sequencing. For sequencing, the ABI PRISM dRhodamine Terminator Cycle Sequencing Ready Reaction Kit with AmpliTaq® DNA Polymerase, FS, is used (PE Applied Biosystems, Foster City, Calif. U.S.A.).

EXAMPLE 3

Nucleic acid sequences that encode for the following tetrapyrrole pathway enzymes: putative chlorophyll synthetase, protochlorophyllide reductase, putative protochlorophyllide reductase, coproporphyrinogen oxidase, protoporphyrinogen oxidase, uroporphyrinogen decarboxylase, putative uroporphyrinogen decarboxylase, porphobilinogen synthase enzyme, hydroxymethylbilane synthase enzyme, glutamate-1-semialdehyde 2,1-aminomutase enzyme, glutamate tRNA ligase enzyme, glutamyl-tRNA reductase enzyme, Mg-chelatase enzyme, and ferrochelatase enzyme are identified from the Monsanto EST PhytoSeq database using TBLASTN (default values)(TBLASTN compares a protein query against the six reading frames of a nucleic acid sequence). Matches found with BLAST P values equal or less than 0.001 (probability) or BLAST Score of equal or greater than 90 are classified as hits. If the program used to determine the hit is HMMSW then the score refers to HMMSW score.

In addition, the GenBank database is searched with BLASTN and BLASTX (default values) using ESTs as queries. EST that pass the hit probability threshold of $10e^{-8}$ for the following enzymes are combined with the hits generated by using TBLASTN (described above) and classified by enzyme (see Table A below).

A cluster refers to a set of overlapping clones in the PhytoSeq database. Such an overlapping relationship among clones is designated as a "cluster" when BLAST scores from pairwise sequence comparisons of the member clones meets a predetermined minimum value or product score of 50 or more (Product Score=(BLAST SCORE×Percentage Identity)/(5×minimum [length (Seq1), length (Seq2)]))

Since clusters are formed on the basis of single-linkage relationships, it is possible for two non-overlapping clones to be members of the same cluster if, for instance, they both overlap a third clone with at least the predetermined minimum BLAST score (stringency). A cluster ID is arbitrarily assigned to all of those clones which belong to the same cluster at a given stringency and a particular clone will belong to only one cluster at a given stringency. If a cluster contains only a single clone (a "singleton"), then the cluster U) number will be negative, with an absolute value equal to the clone ID number of its single member. Clones grouped in a cluster in most cases represent a contiguous sequence.

TABLE A*

| Seq No. | Cluster ID | CloneID | Library | NCBI gi | Method | Score | P-value | % Ident |
|---|---|---|---|---|---|---|---|---|
| \multicolumn{9}{c}{SOYBEAN PUTATIVE CHLOROPHYLL SYNTHETASE} |
| 1 | −700941050 | 700941050H1 | SOYMON024 | g972938 | BLASTX | 349 | 1e-41 | 75 |
| 2 | −701212263 | 701212263H1 | SOYMON035 | g972938 | BLASTX | 75 | 1e-9 | 65 |
| 3 | −701213734 | 701213734H1 | SOYMON035 | g972937 | BLASTN | 191 | 1e-27 | 83 |
| 4 | 14458 | LIB3049-005-Q1-E1-F12 | LIB3049 | g3068709 | BLASTX | 101 | 1e-35 | 59 |
| 5 | 14458 | 700975706H1 | SOYMON009 | g972938 | BLASTX | 75 | 1e-9 | 50 |
| 6 | 14458 | 701047496H1 | SOYMON032 | g972938 | BLASTX | 75 | 1e-9 | 52 |
| 7 | 26375 | 701156709H1 | SOYMON031 | g972938 | BLASTX | 102 | 1e-15 | 92 |
| 8 | 26375 | 701156060H1 | SOYMON031 | g972937 | BLASTN | 275 | 1e-13 | 80 |
| \multicolumn{9}{c}{SOYBEAN PROTOCHLOROPHYLLIDE REDUCTASE} |
| 9 | −700654876 | 700654876H1 | SOYMON004 | g20829 | BLASTN | 269 | 1e-23 | 82 |
| 10 | −700657235 | 700657235H1 | SOYMON004 | g20829 | BLASTN | 728 | 1e-57 | 83 |
| 11 | −700657437 | 700657437H1 | SOYMON004 | g20829 | BLASTN | 668 | 1e-46 | 84 |
| 12 | −700757662 | 700757662H1 | SOYMON015 | g20829 | BLASTN | 1012 | 1e-83 | 89 |
| 13 | −700842232 | 700842232H1 | SOYMON020 | g20829 | BLASTN | 442 | 1e-32 | 81 |
| 14 | −700976426 | 700976426H1 | SOYMON009 | g2244613 | BLASTN | 1038 | 1e-77 | 85 |
| 15 | 11407 | 700652980H1 | SOYMON003 | g2244613 | BLASTN | 741 | 1e-52 | 71 |
| 16 | 11407 | 700735503H1 | SOYMON010 | g2244613 | BLASTN | 505 | 1e-33 | 70 |
| 17 | 11407 | 701142847H1 | SOYMON038 | g2244613 | BLASTN | 509 | 1e-33 | 67 |
| 18 | 11407 | 700652452H1 | SOYMON003 | g2244613 | BLASTN | 535 | 1e-33 | 69 |
| 19 | 11407 | 700735307H1 | SOYMON010 | g2244613 | BLASTN | 491 | 1e-32 | 70 |
| 20 | 11407 | 701107638H1 | SOYMON036 | g2244613 | BLASTN | 493 | 1e-32 | 70 |
| 21 | 11407 | 700952613H1 | SOYMON022 | g2244613 | BLASTN | 479 | 1e-31 | 70 |
| 22 | 11407 | 701118520H1 | SOYMON037 | g2244613 | BLASTN | 475 | 1e-29 | 70 |
| 23 | 11407 | 700731513H1 | SOYMON010 | g2244613 | BLASTN | 455 | 1e-28 | 72 |
| 24 | 11407 | 701037153H1 | SOYMON029 | g2244613 | BLASTN | 455 | 1e-27 | 72 |
| 25 | 11407 | 700838406H1 | SOYMON020 | g2244614 | BLASTX | 229 | 1e-24 | 57 |
| 26 | 11407 | 700736971H1 | SOYMON010 | g2244613 | BLASTN | 389 | 1e-22 | 75 |
| 27 | 11407 | 701208151H1 | SOYMON035 | g2244613 | BLASTN | 387 | 1e-21 | 76 |
| 28 | 11407 | 700658204H1 | SOYMON004 | g2244614 | BLASTX | 173 | 1e-16 | 61 |
| 29 | 11407 | 700657759H1 | SOYMON004 | g2244614 | BLASTX | 120 | 1e-14 | 54 |
| 30 | 11407 | 700854307H1 | SOYMON023 | g20829 | BLASTN | 190 | 1e-12 | 80 |
| 31 | 2160 | LIB3039-002-Q1-E1-G10 | LIB3039 | g2244613 | BLASTN | 690 | 1e-46 | 84 |
| 32 | 2160 | 701107175H1 | SOYMON036 | g20829 | BLASTN | 628 | 1e-43 | 88 |
| 33 | 21731 | 700660488H1 | SOYMON004 | g20829 | BLASTN | 796 | 1e-59 | 86 |
| 34 | 21731 | 701134573H1 | SOYMON038 | g20829 | BLASTN | 646 | 1e-44 | 84 |
| 35 | 21739 | 700655688H1 | SOYMON004 | g2244613 | BLASTN | 298 | 1e-35 | 84 |
| 36 | 21739 | 700655588H1 | SOYMON004 | g20830 | BLASTX | 125 | 1e-21 | 88 |
| 37 | 2977 | 700763883H1 | SOYMON018 | g20829 | BLASTN | 892 | 1e-80 | 83 |
| 38 | 2977 | 701139350H1 | SOYMON038 | g20829 | BLASTN | 614 | 1e-72 | 88 |
| 39 | 2977 | 700849172H1 | SOYMON021 | g20829 | BLASTN | 956 | 1e-70 | 87 |
| 40 | 2977 | 700993334H1 | SOYMON011 | g20829 | BLASTN | 793 | 1e-69 | 87 |
| 41 | 2977 | 700980689H1 | SOYMON009 | g20829 | BLASTN | 765 | 1e-66 | 83 |
| 42 | 2977 | 700754834H1 | SOYMON014 | g20829 | BLASTN | 910 | 1e-66 | 86 |
| 43 | 2977 | 701054679H1 | SOYMON032 | g20829 | BLASTN | 501 | 1e-60 | 81 |
| 44 | 2977 | 701142549H1 | SOYMON038 | g20829 | BLASTN | 595 | 1e-59 | 82 |
| 45 | 2977 | 700909828H1 | SOYMON022 | g20829 | BLASTN | 695 | 1e-59 | 84 |
| 46 | 2977 | 701153047H1 | SOYMON031 | g20829 | BLASTN | 715 | 1e-50 | 87 |
| 47 | 2977 | 700981305H1 | SOYMON009 | g2244613 | BLASTN | 645 | 1e-44 | 70 |
| 48 | 2977 | 700737910H1 | SOYMON012 | g2244613 | BLASTN | 598 | 1e-41 | 69 |
| 49 | 2977 | 701106762H1 | SOYMON036 | g2244613 | BLASTN | 602 | 1e-41 | 70 |
| 50 | 2977 | 700893019H1 | SOYMON024 | g2244613 | BLASTN | 595 | 1e-40 | 70 |
| 51 | 2977 | 700888819H1 | SOYMON024 | g2244613 | BLASTN | 555 | 1e-37 | 69 |
| 52 | 2977 | 700557617H1 | SOYMON001 | g2244613 | BLASTN | 557 | 1e-37 | 69 |
| 53 | 2977 | 700989268H1 | SOYMON001 | g20829 | BLASTN | 297 | 1e-35 | 80 |
| 54 | 2977 | 700978858H1 | SOYMON009 | g2244613 | BLASTN | 529 | 1e-35 | 69 |
| 55 | 2977 | 701063251H1 | SOYMON033 | g2244613 | BLASTN | 525 | 1e-34 | 63 |
| 56 | 2977 | 700737989H1 | SOYMON012 | g20829 | BLASTN | 190 | 1e-33 | 72 |
| 57 | 2977 | LIB3054-001-Q1-B1-A11 | LIB3054 | g2244613 | BLASTN | 487 | 1e-32 | 70 |
| 58 | 2977 | 701057704H1 | SOYMON033 | g2244613 | BLASTN | 470 | 1e-29 | 72 |
| 59 | 2977 | 701139740H1 | SOYMON038 | g2244613 | BLASTN | 477 | 1e-29 | 69 |
| 60 | 2977 | LIB3039-043-Q1-E1-F3 | LIB3039 | g2244614 | BLASTX | 99 | 1e-28 | 55 |
| 61 | 2977 | 701105971H1 | SOYMON036 | g2244613 | BLASTN | 454 | 1e-28 | 71 |
| 62 | 2977 | 700789775H1 | SOYMON011 | g2244613 | BLASTN | 429 | 1e-26 | 72 |
| 63 | 2977 | 700732675H1 | SOYMON010 | g2244613 | BLASTN | 437 | 1e-26 | 69 |
| 64 | 2977 | 701137164H1 | SOYMON038 | g2244613 | BLASTN | 429 | 1e-25 | 72 |
| 65 | 2977 | 700788180H1 | SOYMON011 | g2244613 | BLASTN | 431 | 1e-25 | 72 |
| 66 | 2977 | 700680942H1 | SOYMON008 | g20829 | BLASTN | 349 | 1e-24 | 72 |
| 67 | 2977 | 700953017H1 | SOYMON022 | g2244613 | BLASTN | 395 | 1e-22 | 71 |
| 68 | 2977 | 700962368H1 | SOYMON022 | g2244613 | BLASTN | 395 | 1e-22 | 71 |
| 69 | 2977 | 700737258H1 | SOYMON010 | g2244613 | BLASTN | 395 | 1e-22 | 71 |

TABLE A*-continued

| Seq No. | Cluster ID | CloneID | Library | NCBI gi | Method | Score | P-value | % Ident |
|---|---|---|---|---|---|---|---|---|
| 70 | 2977 | 701058308H1 | SOYMON033 | g2244613 | BLASTN | 244 | 1e-14 | 78 |
| 71 | 2977 | 701108820H1 | SOYMON036 | g968974 | BLASTN | 254 | 1e-14 | 76 |
| 72 | 2977 | 700658246H1 | SOYMON004 | g20830 | BLASTX | 123 | 1e-13 | 76 |
| 73 | 2977 | 700990646H1 | SOYMON011 | g20829 | BLASTX | 255 | 1e-12 | 92 |
| 74 | 2977 | 700548092H1 | SOYMON001 | g20830 | BLASTX | 92 | 1e-11 | 79 |
| 75 | 2977 | 701136902H1 | SOYMON038 | g2244613 | BLASTN | 265 | 1e-11 | 69 |
| 76 | 2977 | 701152877H1 | SOYMON031 | g20830 | BLASTX | 128 | 1e-10 | 76 |
| 77 | 2977 | 700994862H1 | SOYMON011 | g20830 | BLASTX | 128 | 1e-10 | 76 |
| 78 | 2977 | 701148824H1 | SOYMON031 | g20830 | BLASTX | 128 | 1e-10 | 76 |
| 79 | 2977 | 701047440H1 | SOYMON032 | g20830 | BLASTX | 128 | 1e-10 | 76 |
| 80 | 2977 | 700556683H1 | SOYMON001 | g968974 | BLASTN | 252 | 1e-10 | 76 |
| 81 | 2977 | 701146931H1 | SOYMON031 | g2244613 | BLASTN | 253 | 1e-10 | 72 |
| 82 | 2977 | 701142178H1 | SOYMON038 | g20830 | BLASTX | 122 | 1e-9 | 73 |
| 83 | 2977 | 701152593H1 | SOYMON031 | g20830 | BLASTX | 123 | 1e-9 | 75 |
| 84 | 2977 | 700737725H1 | SOYMON012 | g20829 | BLASTX | 218 | 1e-9 | 74 |
| 85 | 2977 | 700683007H1 | SOYMON008 | g2244613 | BLASTN | 241 | 1e-9 | 70 |
| 86 | 2977 | 700739072H1 | SOYMON012 | g2244613 | BLASTN | 244 | 1e-9 | 71 |
| 87 | 4903 | 700658027H1 | SOYMON004 | g20829 | BLASTN | 820 | 1e-59 | 79 |
| 88 | 4903 | 700852934H1 | SOYMON023 | g20829 | BLASTN | 453 | 1e-48 | 78 |
| 89 | 6970 | LIB3052-012-Q1-N1-A11 | LIB3052 | g968974 | BLASTN | 934 | 1e-69 | 78 |
| 90 | 6970 | 700660679H1 | SOYMON004 | g20829 | BLASTN | 862 | 1e-67 | 87 |
| 91 | 6970 | 700682420H2 | SOYMON008 | g968976 | BLASTN | 864 | 1e-63 | 80 |
| 92 | 6970 | 700979758H2 | SOYMON009 | g2244613 | BLASTN | 865 | 1e-63 | 82 |
| 93 | 6970 | 700790842H1 | SOYMON011 | g968974 | BLASTN | 642 | 1e-57 | 82 |
| 94 | 6970 | 700994812H1 | SOYMON011 | g968976 | BLASTN | 423 | 1e-43 | 78 |
| SOYBEAN PUTATIVE PROTOCHLOROPHYLLIDE REDUCTASE | | | | | | | | |
| 95 | −701065431 | 701065431H1 | SOYMON034 | g348719 | BLASTN | 767 | 1e-55 | 83 |
| 96 | 4640 | 700982771H1 | SOYMON009 | g348718 | BLASTX | 162 | 1e-15 | 93 |
| SOYBEAN COPROPORPHYRINOGEN OXIDASE | | | | | | | | |
| 97 | −700671956 | 700671956H1 | SOYMON006 | g414665 | BLASTN | 291 | 1e-16 | 96 |
| 98 | −701053612 | 701053612H1 | SOYMON032 | g414665 | BLASTN | 335 | 1e-27 | 94 |
| 99 | −701208513 | 701208513H1 | SOYMON035 | g414665 | BLASTN | 639 | 1e-92 | 94 |
| 100 | 11665 | 700656318H1 | SOYMON004 | g414665 | BLASTN | 656 | 1e-93 | 98 |
| 101 | 11665 | 700964466H1 | SOYMON022 | g414665 | BLASTN | 611 | 1e-88 | 98 |
| 102 | 11665 | 700899782H1 | SOYMON027 | g414665 | BLASTN | 648 | 1e-87 | 98 |
| 103 | 11665 | 700844365H1 | SOYMON021 | g414665 | BLASTN | 648 | 1e-83 | 98 |
| 104 | 11665 | 701146220H1 | SOYMON031 | g414665 | BLASTN | 630 | 1e-75 | 98 |
| 105 | 11665 | 700660179H1 | SOYMON004 | g414665 | BLASTN | 530 | 1e-55 | 94 |
| 106 | 11665 | 700662658H1 | SOYMON005 | g1213066 | BLASTN | 742 | 1e-53 | 78 |
| 107 | 11665 | 701152413H1 | SOYMON031 | g1213066 | BLASTN | 742 | 1e-53 | 78 |
| 108 | 6121 | LIB3065-002-Q1-N1-G8 | LIB3065 | g414665 | BLASTN | 1383 | 1e-128 | 96 |
| 109 | 6121 | 701108945H1 | SOYMON036 | g414665 | BLASTN | 1388 | 1e-106 | 98 |
| 110 | 6121 | 700789601H2 | SOYMON011 | g414665 | BLASTN | 1301 | 1e-99 | 99 |
| 111 | 6121 | 700994436H1 | SOYMON011 | g414665 | BLASTN | 858 | 1e-97 | 98 |
| 112 | 6121 | 700747416H1 | SOYMON013 | g414665 | BLASTN | 925 | 1e-94 | 100 |
| 113 | 6121 | 700978804H1 | SOYMON009 | g414665 | BLASTN | 941 | 1e-89 | 95 |
| 114 | 6121 | 701109318H1 | SOYMON036 | g414665 | BLASTN | 729 | 1e-85 | 96 |
| 115 | 6121 | 700873742H1 | SOYMON018 | g414665 | BLASTN | 484 | 1e-82 | 94 |
| 116 | 6121 | 701209226H1 | SOYMON035 | g414665 | BLASTN | 789 | 1e-81 | 97 |
| 117 | 6121 | 701060931H1 | SOYMON033 | g414665 | BLASTN | 768 | 1e-79 | 96 |
| 118 | 6121 | 701066887H1 | SOYMON034 | g414665 | BLASTN | 262 | 1e-68 | 90 |
| 119 | 6121 | 700899224H1 | SOYMON027 | g414665 | BLASTN | 434 | 1e-57 | 84 |
| 120 | 6121 | 700906273H1 | SOYMON022 | g414665 | BLASTN | 555 | 1e-37 | 97 |
| 121 | 6121 | 700992008H1 | SOYMON011 | g414665 | BLASTN | 560 | 1e-37 | 97 |
| 122 | 6121 | 700786848H2 | SOYMON011 | g414665 | BLASTN | 408 | 1e-25 | 98 |
| 123 | 6121 | 700734585H1 | SOYMON010 | g414665 | BLASTN | 250 | 1e-16 | 100 |
| 124 | 7272 | 700786276H2 | SOYMON011 | g414665 | BLASTN | 1170 | 1e-88 | 97 |
| 125 | 7272 | 700683451H1 | SOYMON008 | g414665 | BLASTN | 1019 | 1e-87 | 97 |
| 126 | 7272 | 700662424H1 | SOYMON005 | g414665 | BLASTN | 932 | 1e-84 | 98 |
| 127 | 7882 | 700680869H1 | SOYMON008 | g414665 | BLASTN | 763 | 1e-54 | 99 |
| 128 | 7882 | 700680628H1 | SOYMON008 | g414665 | BLASTN | 516 | 1e-34 | 94 |
| SOYBEAN PROTOPORPHYRINOGEN OXIDASE | | | | | | | | |
| 129 | −700657957 | 700657957H1 | SOYMON004 | g1183006 | BLASTN | 729 | 1e-51 | 76 |
| 130 | −700681258 | 700681258H1 | SOYMON008 | g1183006 | BLASTN | 651 | 1e-46 | 76 |
| 131 | −701063830 | 701063830H1 | SOYMON034 | g2370335 | BLASTX | 142 | 1e-15 | 79 |
| SOYBEAN UROPORPHYRINOGEN DECARBOXYLASE | | | | | | | | |
| 132 | −700730557 | 700730557H1 | SOYMON009 | g1009428 | BLASTN | 444 | 1e-38 | 69 |
| 133 | −700789740 | 700789740H1 | SOYMON011 | g1009428 | BLASTN | 760 | 1e-54 | 80 |
| 134 | −700974704 | 700974704H1 | SOYMON005 | g1016347 | BLASTX | 272 | 1e-30 | 55 |
| 135 | −701048641 | 701048641H1 | SOYMON032 | g1009427 | BLASTN | 580 | 1e-39 | 71 |

TABLE A*-continued

| Seq No. | Cluster ID | CloneID | Library | NCBI gi | Method | Score | P-value | % Ident |
|---|---|---|---|---|---|---|---|---|
| 136 | −GM17920 | LIB3055-003-Q1-N1-H10 | LIB3055 | g142136 | BLASTX | 97 | 1e-29 | 61 |
| 137 | 19517 | 701104233H1 | SOYMON036 | g1009429 | BLASTX | 228 | 1e-24 | 49 |
| 138 | 19517 | 701000103H1 | SOYMON018 | g1009429 | BLASTX | 167 | 1e-22 | 46 |
| 139 | 19517 | 701108875H1 | SOYMON036 | g1009429 | BLASTX | 137 | 1e-19 | 49 |
| 140 | 19517 | 700737952H1 | SOYMON012 | g1009429 | BLASTX | 188 | 1e-18 | 39 |
| 141 | 4729 | 700753974H1 | SOYMON014 | g1009427 | BLASTN | 816 | 1e-59 | 82 |
| 142 | 4729 | 701126044H1 | SOYMON037 | g1009427 | BLASTN | 799 | 1e-57 | 82 |
| 143 | 4729 | 700870535H1 | SOYMON018 | g1009427 | BLASTN | 405 | 1e-54 | 82 |
| 144 | 8117 | 700752125H1 | SOYMON014 | g1009428 | BLASTN | 444 | 1e-26 | 75 |
| | | SOYBEAN PORPHOBILINOGEN SYNTHASE | | | | | | |
| 145 | −700678901 | 700678901H1 | SOYMON007 | g493019 | BLASTN | 1259 | 1e-101 | 97 |
| 146 | −700680455 | 700680455H1 | SOYMON008 | g493019 | BLASTN | 915 | 1e-105 | 98 |
| 147 | −700897467 | 700897467H1 | SOYMON027 | g493019 | BLASTN | 1091 | 1e-98 | 97 |
| 148 | −700994415 | 700994415H1 | SOYMON011 | g493019 | BLASTN | 381 | 1e-21 | 97 |
| 149 | −701002563 | 701002563H1 | SOYMON018 | g493019 | BLASTN | 608 | 1e-41 | 96 |
| 150 | −701208590 | 701208590H1 | SOYMON035 | g493019 | BLASTN | 366 | 1e-21 | 92 |
| 151 | −GM8017 | LIB3039-038-Q1-E1-H8 | LIB3039 | g493019 | BLASTN | 224 | 1e-29 | 86 |
| 152 | −GM9259 | LIB3049-002-Q1-E1-G5 | LIB3049 | g493019 | BLASTN | 281 | 1e-16 | 84 |
| 153 | −GM9536 | LIB3049-003-Q1-E1-D4 | LIB3049 | g493019 | BLASTN | 426 | 1e-61 | 82 |
| 154 | 11129 | 700660017H1 | SOYMON004 | g313724 | BLASTX | 176 | 1e-17 | 51 |
| 155 | 22115 | 701208693H1 | SOYMON035 | g493019 | BLASTN | 1353 | 1e-103 | 97 |
| 156 | 22115 | 701151960H1 | SOYMON031 | g493019 | BLASTN | 1245 | 1e-94 | 100 |
| 157 | 22115 | 700846243H1 | SOYMON021 | g493019 | BLASTN | 571 | 1e-75 | 99 |
| 158 | 23112 | 701207084H1 | SOYMON035 | g493019 | BLASTN | 1408 | 1e-108 | 97 |
| 159 | 23112 | 700654971H1 | SOYMON004 | g493019 | BLASTN | 1236 | 1e-94 | 98 |
| 160 | 25460 | 700656593H1 | SOYMON004 | g493019 | BLASTN | 1296 | 1e-99 | 99 |
| 161 | 25460 | 701050212H1 | SOYMON032 | g493019 | BLASTN | 1235 | 1e-94 | 98 |
| 162 | 25460 | 701123120H1 | SOYMON037 | g493019 | BLASTN | 1245 | 1e-94 | 100 |
| 163 | 25460 | 701055012H1 | SOYMON032 | g493019 | BLASTN | 868 | 1e-93 | 99 |
| 164 | 3678 | LIB3039-036-Q1-E1-D2 | LIB3039 | g493019 | BLASTN | 1757 | 1e-137 | 99 |
| 165 | 3678 | LIB3039-031-Q1-E1-F9 | LIB3039 | g493019 | BLASTN | 1736 | 1e-135 | 99 |
| 166 | 3678 | 700553643H1 | SOYMON001 | g493019 | BLASTN | 1383 | 1e-106 | 98 |
| 167 | 3678 | 700558620H1 | SOYMON001 | g493019 | BLASTN | 1361 | 1e-104 | 98 |
| 168 | 3678 | 701046832H1 | SOYMON032 | g493019 | BLASTN | 1185 | 1e-100 | 96 |
| 169 | 3678 | 701109455H1 | SOYMON036 | g493019 | BLASTN | 1282 | 1e-98 | 97 |
| 170 | 3678 | LIB3056-002-Q1-B1-D5 | LIB3056 | g493019 | BLASTN | 1286 | 1e-98 | 98 |
| 171 | 3678 | 700844432H1 | SOYMON021 | g493019 | BLASTN | 1274 | 1e-97 | 99 |
| 172 | 3678 | 700847337H1 | SOYMON021 | g493019 | BLASTN | 1242 | 1e-94 | 98 |
| 173 | 3678 | 700994748H1 | SOYMON011 | g493019 | BLASTN | 1221 | 1e-92 | 98 |
| 174 | 3678 | 701213656H1 | SOYMON035 | g493019 | BLASTN | 1176 | 1e-89 | 99 |
| 175 | 3678 | 700969539H1 | SOYMON005 | g493019 | BLASTN | 1120 | 1e-88 | 95 |
| 176 | 3678 | 700862858H1 | SOYMON020 | g493019 | BLASTN | 775 | 1e-85 | 98 |
| 177 | 3678 | 701109689H1 | SOYMON036 | g493019 | BLASTN | 968 | 1e-85 | 97 |
| 178 | 3678 | 701105613H1 | SOYMON036 | g493019 | BLASTN | 1127 | 1e-85 | 98 |
| 179 | 3678 | 700762772H1 | SOYMON015 | g493019 | BLASTN | 1039 | 1e-84 | 97 |
| 180 | 3678 | LIB3039-047-Q1-E1-D4 | LIB3039 | g493019 | BLASTN | 619 | 1e-82 | 94 |
| 181 | 3678 | 700962419H1 | SOYMON022 | g493019 | BLASTN | 670 | 1e-82 | 99 |
| 182 | 3678 | 700975590H1 | SOYMON009 | g493019 | BLASTN | 965 | 1e-82 | 93 |
| 183 | 3678 | 701108204H1 | SOYMON036 | g493019 | BLASTN | 1069 | 1e-80 | 99 |
| 184 | 3678 | 700725416H1 | SOYMON009 | g493019 | BLASTN | 633 | 1e-66 | 89 |
| 185 | 3678 | 701055787H1 | SOYMON032 | g493019 | BLASTN | 790 | 1e-57 | 100 |
| 186 | 3678 | 700996808H1 | SOYMON018 | g493019 | BLASTN | 740 | 1e-52 | 100 |
| 187 | 3678 | 701210127H1 | SOYMON035 | g493019 | BLASTN | 545 | 1e-36 | 100 |
| 188 | 3678 | 700739360H1 | SOYMON012 | g493019 | BLASTN | 245 | 1e-21 | 99 |
| 189 | 3678 | 700742044H1 | SOYMON012 | g493019 | BLASTN | 313 | 1e-17 | 98 |
| 190 | 3678 | 701065288H1 | SOYMON034 | g493019 | BLASTN | 335 | 1e-17 | 100 |
| 191 | 3678 | 701110261H1 | SOYMON036 | g493019 | BLASTN | 211 | 1e-12 | 99 |
| | | SOY BEAN HYDROXYMETHYLBILANE SYNTHASE | | | | | | |
| 154 | 11129 | 700660017H1 | SOYMON004 | g313724 | BLASTX | 176 | 1e-17 | 51 |
| 192 | −700653648 | 700653648H1 | SOYMON003 | g313723 | BLASTN | 262 | 1e-60 | 90 |
| 193 | −700666293 | 700666293H1 | SOYMON005 | g313723 | BLASTN | 772 | 1e-65 | 82 |
| 194 | −700975534 | 700975534H1 | SOYMON009 | g313723 | BLASTN | 498 | 1e-76 | 89 |
| 195 | −701064190 | 701064190H1 | SOYMON034 | g313723 | BLASTN | 450 | 1e-62 | 85 |
| 196 | −701125566 | 701125566H1 | SOYMON037 | g313723 | BLASTN | 474 | 1e-55 | 83 |
| 197 | 11129 | 700656680H1 | SOYMON004 | g313723 | BLASTN | 834 | 1e-73 | 85 |
| 198 | 12006 | 700556506H1 | SOYMON001 | g313723 | BLASTN | 652 | 1e-69 | 83 |
| 199 | 12006 | 700557751H1 | SOYMON001 | g313723 | BLASTN | 652 | 1e-65 | 83 |

TABLE A*-continued

| Seq No. | Cluster ID | CloneID | Library | NCBI gi | Method | Score | P-value | % Ident |
|---|---|---|---|---|---|---|---|---|
| 200 | 12006 | 700556513H1 | SOYMON001 | g313723 | BLASTN | 572 | 1e-61 | 83 |
| 201 | 12006 | 700848102H1 | SOYMON021 | g313723 | BLASTN | 459 | 1e-54 | 81 |
| 202 | 20966 | 701108946H1 | SOYMON036 | g313150 | BLASTX | 148 | 1e-13 | 83 |
| 203 | 20966 | 701054125H1 | SOYMON032 | g313150 | BLASTX | 148 | 1e-13 | 83 |
| 204 | 20966 | 701108239H1 | SOYMON036 | g313150 | BLASTX | 122 | 1e-9 | 83 |
| 205 | 8428 | LIB3052-015-Q1-N1-G5 | LIB3052 | g313723 | BLASTN | 865 | 1e-79 | 79 |
| 206 | 8428 | LIB3055-013-Q1-N1-H6 | LIB3055 | g313723 | BLASTN | 1021 | 1e-76 | 80 |
| 207 | 8428 | 701140841H1 | SOYMON038 | g313723 | BLASTN | 942 | 1e-69 | 85 |
| 208 | 8428 | 700559220H1 | SOYMON001 | g313723 | BLASTN | 871 | 1e-63 | 82 |
| 209 | 8428 | 700998668H1 | SOYMON018 | g313723 | BLASTN | 872 | 1e-63 | 84 |
| 210 | 8428 | 701047766H1 | SOYMON032 | g313723 | BLASTN | 855 | 1e-62 | 85 |
| 211 | 8428 | 701055336H1 | SOYMON032 | g313723 | BLASTN | 848 | 1e-61 | 85 |
| 212 | 8428 | 700558405H1 | SOYMON001 | g313723 | BLASTN | 733 | 1e-57 | 85 |
| 213 | 8428 | 700758672H1 | SOYMON015 | g313723 | BLASTN | 406 | 1e-50 | 85 |
| 214 | 8428 | 700904365H1 | SOYMON022 | g313723 | BLASTN | 392 | 1e-48 | 85 |
| 215 | 8428 | 700987727H1 | SOYMON009 | g313723 | BLASTN | 563 | 1e-38 | 84 |
| 216 | 8428 | 701119125H1 | SOYMON037 | g313723 | BLASTN | 386 | 1e-21 | 84 |
| 217 | 8428 | 700833610H1 | SOYMON019 | g313723 | BLASTN | 314 | 1e-17 | 84 |
| | | SOYBEAN GLUTAMATE-1-SEMIALDEHYDE 2,1-AMINOMUTASE | | | | | | |
| 218 | –700659530 | 700659530H1 | SOYMON004 | g310566 | BLASTN | 1138 | 1e-86 | 94 |
| 219 | –700733492 | 700733492H1 | SOYMON010 | g310566 | BLASTN | 552 | 1e-47 | 87 |
| 220 | –700737926 | 700737926H1 | SOYMON012 | g310566 | BLASTN | 421 | 1e-34 | 84 |
| 221 | –700757107 | 700757107H1 | SOYMON015 | g310566 | BLASTN | 640 | 1e-91 | 96 |
| 222 | –700852479 | 700852479H1 | SOYMON023 | g310566 | BLASTN | 1162 | 1e-88 | 98 |
| 223 | –700971066 | 700971066H1 | SOYMON005 | g310566 | BLASTN | 1208 | 1e-91 | 96 |
| 224 | –700982010 | 700982010H1 | SOYMON009 | g310566 | BLASTN | 1016 | 1e-90 | 97 |
| 225 | –700986986 | 700986986H1 | SOYMON009 | g310566 | BLASTN | 1313 | 1e-100 | 95 |
| 226 | –701042351 | 701042351H1 | SOYMON029 | g310566 | BLASTN | 1238 | 1e-94 | 99 |
| 227 | 10046 | LIB3051-102-Q1-K1-E2 | LIB3051 | g747967 | BLASTN | 549 | 1e-106 | 90 |
| 228 | 10046 | 700554665H1 | SOYMON001 | g310566 | BLASTN | 981 | 1e-86 | 94 |
| 229 | 10046 | LIB3040-061-Q1-E11-A4 | LIB3040 | g310566 | BLASTN | 441 | 1e-80 | 83 |
| 230 | 10046 | 700560249H1 | SOYMON001 | g310566 | BLASTN | 773 | 1e-70 | 91 |
| 231 | 10046 | 700995521H1 | SOYMON011 | g310566 | BLASTN | 773 | 1e-70 | 91 |
| 232 | 10046 | 700741513H1 | SOYMON012 | g310566 | BLASTN | 608 | 1e-69 | 90 |
| 233 | 10046 | 701207555H1 | SOYMON035 | g310566 | BLASTN | 748 | 1e-68 | 91 |
| 234 | 10046 | 701109782H1 | SOYMON036 | g310566 | BLASTN | 615 | 1e-67 | 90 |
| 235 | 10046 | 701047870H1 | SOYMON032 | g310566 | BLASTN | 493 | 1e-57 | 89 |
| 236 | 10046 | 701108348H1 | SOYMON036 | g310566 | BLASTN | 441 | 1e-51 | 88 |
| 237 | 10046 | 701041675H1 | SOYMON029 | g310566 | BLASTN | 613 | 1e-51 | 89 |
| 238 | 10046 | 700659465H1 | SOYMON004 | g310566 | BLASTN | 407 | 1e-30 | 91 |
| 239 | 10046 | 701144580H1 | SOYMON031 | g310566 | BLASTN | 218 | 1e-9 | 89 |
| 240 | 11600 | 700788311H1 | SOYMON011 | g310566 | BLASTN | 1234 | 1e-94 | 95 |
| 241 | 11600 | 700902195H1 | SOYMON027 | g310566 | BLASTN | 1209 | 1e-91 | 96 |
| 242 | 11600 | 701135233H1 | SOYMON038 | g310566 | BLASTN | 1177 | 1e-89 | 96 |
| 243 | 12473 | 701104293H1 | SOYMON036 | g310566 | BLASTN | 884 | 1e-83 | 93 |
| 244 | 12473 | 701104392H1 | SOYMON036 | g310566 | BLASTN | 754 | 1e-76 | 93 |
| 245 | 13619 | 700877188H1 | SOYMON018 | g310566 | BLASTN | 1323 | 1e-101 | 99 |
| 246 | 13619 | 700845619H1 | SOYMON021 | g310566 | BLASTN | 948 | 1e-70 | 93 |
| 247 | 20047 | 700660491H1 | SOYMON004 | g310566 | BLASTN | 718 | 1e-67 | 93 |
| 248 | 20047 | 700989453H1 | SOYMON011 | g310566 | BLASTN | 369 | 1e-21 | 95 |
| 249 | 5811 | LIB3049-032-Q1-E1-A12 | LIB3049 | g747967 | BLASTN | 1188 | 1e-131 | 96 |
| 250 | 5811 | LIB3049-030-Q1-E1-C2 | LIB3049 | g747967 | BLASTN | 1245 | 1e-98 | 100 |
| 251 | 5811 | 701142371H1 | SOYMON038 | g747967 | BLASTN | 1209 | 1e-93 | 96 |
| 252 | 5811 | 701155760H1 | SOYMON031 | g747967 | BLASTN | 1215 | 1e-92 | 100 |
| 253 | 5811 | 700983730H1 | SOYMON009 | g310566 | BLASTN | 417 | 1e-85 | 96 |
| 254 | 5811 | 701064792H1 | SOYMON034 | g310566 | BLASTN | 952 | 1e-81 | 97 |
| 255 | 5811 | 700561468H1 | SOYMON002 | g747967 | BLASTN | 757 | 1e-75 | 90 |
| 256 | 5811 | 700945376H1 | SOYMON024 | g310566 | BLASTN | 884 | 1e-73 | 98 |
| 257 | 5811 | 700756262H1 | SOYMON014 | g747967 | BLASTN | 722 | 1e-72 | 88 |
| 258 | 5811 | 700981893H1 | SOYMON009 | g747967 | BLASTN | 610 | 1e-70 | 92 |
| 259 | 5811 | 700562668H1 | SOYMON002 | g747967 | BLASTN | 807 | 1e-58 | 98 |
| 260 | 5811 | 700979322H1 | SOYMON009 | g747967 | BLASTN | 465 | 1e-54 | 97 |
| 261 | 5811 | 700905434H1 | SOYMON022 | g747967 | BLASTN | 707 | 1e-50 | 97 |
| 262 | 5811 | 700733377H1 | SOYMON010 | g747967 | BLASTN | 640 | 1e-48 | 93 |
| 263 | 5811 | 700562340H1 | SOYMON002 | g747967 | BLASTN | 629 | 1e-43 | 97 |
| 264 | 5811 | 701211223H1 | SOYMON035 | g747967 | BLASTN | 506 | 1e-41 | 94 |
| 265 | 5811 | 700565140H1 | SOYMON002 | g310566 | BLASTN | 416 | 1e-34 | 91 |

TABLE A*-continued

| Seq No. | Cluster ID | CloneID | Library | NCBI gi | Method | Score | P-value | % Ident |
|---|---|---|---|---|---|---|---|---|
| | | | SOYBEAN GLUTAMATE tRNA LIGASE | | | | | |
| 266 | −700653562 | 700653562H1 | SOYMON003 | g1008482 | BLASTN | 280 | 1e-27 | 64 |
| 267 | −700740810 | 700740810H1 | SOYMON012 | g2370487 | BLASTX | 217 | 1e-22 | 43 |
| 268 | −700893754 | 700893754H1 | SOYMON024 | g1008483 | BLASTX | 121 | 1e-8 | 34 |
| 269 | −701009959 | 701009959H2 | SOYMON019 | g603849 | BLASTX | 175 | 1e-17 | 97 |
| 270 | −701011820 | 701011820H1 | SOYMON019 | g1322915 | BLASTX | 129 | 1e-20 | 58 |
| 271 | −701051674 | 701051674H1 | SOYMON032 | g2370487 | BLASTX | 221 | 1e-23 | 57 |
| 272 | −701052937 | 701052937H1 | SOYMON032 | g1322915 | BLASTX | 236 | 1e-30 | 69 |
| 273 | −701060112 | 701060112H1 | SOYMON033 | g1322915 | BLASTX | 121 | 1e-20 | 48 |
| 274 | −701109025 | 701109025H1 | SOYMON036 | g157564 | BLASTX | 179 | 1e-18 | 67 |
| 275 | −GM18124 | LIB3065-002-Q1-N1-C2 | LIB3065 | g2995454 | BLASTN | 758 | 1e-66 | 78 |
| 276 | −GM36590 | LIB3051-050-Q1-K1-D3 | LIB3051 | g603849 | BLASTX | 91 | 1e-37 | 67 |
| 277 | 20438 | 700976589H1 | SOYMON009 | g2370487 | BLASTX | 253 | 1e-31 | 59 |
| 278 | 24353 | 701054537H1 | SOYMON032 | g157564 | BLASTX | 232 | 1e-24 | 56 |
| 279 | 24353 | 701054523H1 | SOYMON032 | g157564 | BLASTX | 192 | 1e-19 | 70 |
| 280 | 24353 | 701054530H1 | SOYMON032 | g157564 | BLASTX | 195 | 1e-19 | 69 |
| 281 | 27156 | 701137188H1 | SOYMON038 | g1008483 | BLASTX | 246 | 1e-26 | 53 |
| 282 | 27156 | 701207661H1 | SOYMON035 | g1008483 | BLASTX | 211 | 1e-24 | 52 |
| 283 | 27156 | 700726789H1 | SOYMON009 | g1008483 | BLASTX | 182 | 1e-22 | 52 |
| 284 | 32173 | 701202848H1 | SOYMON035 | g416260 | BLASTX | 443 | 1e-54 | 78 |
| 285 | 32173 | LIB3049-020-Q1-E1-G4 | LIB3049 | g416260 | BLASTN | 733 | 1e-52 | 77 |
| 286 | 32173 | 700846868H1 | SOYMON021 | g157564 | BLASTX | 136 | 1e-20 | 67 |
| 287 | 7264 | LIB3051-061-Q1-K1-B9 | LIB3051 | g2995454 | BLASTN | 841 | 1e-100 | 81 |
| 288 | 7712 | 700669928H1 | SOYMON006 | g157564 | BLASTX | 276 | 1e-30 | 56 |
| 289 | 7712 | 700665965H1 | SOYMON009 | g157564 | BLASTX | 263 | 1e-29 | 55 |
| | | | SOYBEAN GLUTAMYL-tRNA REDUCTASE | | | | | |
| 290 | −700670004 | 700670004H1 | SOYMON006 | g1694925 | BLASTN | 397 | 1e-34 | 75 |
| 291 | −700728413 | 700728413H1 | SOYMON009 | g1049056 | BLASTN | 696 | 1e-49 | 80 |
| 292 | −700994105 | 700994105H1 | SOYMON011 | g1694925 | BLASTN | 771 | 1e-55 | 82 |
| 293 | −700995896 | 700995896H1 | SOYMON011 | g1049057 | BLASTX | 84 | 1e-13 | 86 |
| 294 | −701099031 | 701099031H1 | SOYMON028 | g1015318 | BLASTN | 459 | 1e-28 | 69 |
| 295 | −701128557 | 701128557H1 | SOYMON037 | g1694925 | BLASTN | 432 | 1e-27 | 79 |
| 296 | −GM35481 | LIB3051-036-Q1-K1-G6 | LIB3051 | g1694925 | BLASTN | 1070 | 1e-80 | 73 |
| 297 | 25545 | 701123925H1 | SOYMON037 | g1694925 | BLASTN | 719 | 1e-51 | 78 |
| 298 | 25545 | 700727539H1 | SOYMON009 | g1694925 | BLASTN | 639 | 1e-44 | 79 |
| 299 | 2655 | 700553888H1 | SOYMON001 | g1694925 | BLASTN | 242 | 1e-20 | 74 |
| 300 | 2655 | 700553887H1 | SOYMON001 | g1694926 | BLASTX | 74 | 1e-8 | 93 |
| 301 | 2885 | 700728635H1 | SOYMON009 | g1015318 | BLASTN | 816 | 1e-59 | 78 |
| 302 | 2885 | 701097007H1 | SOYMON028 | g1015318 | BLASTN | 706 | 1e-50 | 80 |
| 303 | 3203 | 700986371H1 | SOYMON009 | g1694925 | BLASTN | 501 | 1e-69 | 80 |
| 304 | 3203 | 700556832H1 | SOYMON001 | g1694925 | BLASTN | 446 | 1e-47 | 81 |
| 305 | 3203 | 700995693H1 | SOYMON011 | g1039331 | BLASTN | 390 | 1e-39 | 72 |
| 306 | 33811 | LIB3051-105-Q1-K1-B10 | LIB3051 | g1694925 | BLASTN | 573 | 1e-36 | 78 |
| | | | SOYBEAN Mg-CHELATASE | | | | | |
| 307 | −700554488 | 700554488H1 | SOYMON001 | g1732468 | BLASTN | 835 | 1e-66 | 85 |
| 308 | −700657604 | 700657604H1 | SOYMON004 | g2318116 | BLASTN | 975 | 1e-72 | 89 |
| 309 | −700658239 | 700658239H1 | SOYMON004 | g1732468 | BLASTN | 1095 | 1e-92 | 100 |
| 310 | −700737719 | 700737719H1 | SOYMON012 | g2318116 | BLASTN | 973 | 1e-72 | 87 |
| 311 | −700902101 | 700902101H1 | SOYMON027 | g1732468 | BLASTN | 181 | 1e-15 | 89 |
| 312 | −700943788 | 700943788H1 | SOYMON024 | g1732468 | BLASTN | 402 | 1e-23 | 91 |
| 313 | −700992328 | 700992328H1 | SOYMON011 | g1732468 | BLASTN | 856 | 1e-62 | 87 |
| 314 | −700996107 | 700996107H1 | SOYMON018 | g1732468 | BLASTN | 1208 | 1e-96 | 95 |
| 315 | −701050458 | 701050458H1 | SOYMON032 | g1732468 | BLASTN | 881 | 1e-67 | 97 |
| 316 | −701053810 | 701053810H1 | SOYMON032 | g1732468 | BLASTN | 1133 | 1e-99 | 99 |
| 317 | −701119309 | 701119309H1 | SOYMON037 | g2318116 | BLASTN | 944 | 1e-83 | 91 |
| 318 | −701128728 | 701128728H1 | SOYMON037 | g1732468 | BLASTN | 358 | 1e-28 | 90 |
| 319 | −701134728 | 701134728H2 | SOYMON038 | g1732468 | BLASTN | 994 | 1e-85 | 95 |
| 320 | −GM16990 | LIB3055-002-Q1-B1-F10 | LIB3055 | g3059094 | BLASTN | 1141 | 1e-86 | 83 |
| 321 | −GM18022 | LIB3055-011-Q1-N1-A4 | LIB3055 | g3059094 | BLASTN | 1079 | 1e-138 | 99 |
| 322 | −GM1974 | LIB3028-009-Q1-B1-G12 | LIB3028 | g3059094 | BLASTN | 561 | 1e-66 | 89 |
| 323 | −GM22404 | LIB3030-009-Q1-B1-A1 | LIB3030 | g3059094 | BLASTN | 1104 | 1e-93 | 83 |
| 324 | 20034 | 700944453H1 | SOYMON024 | g2318116 | BLASTN | 1089 | 1e-81 | 90 |
| 325 | 20034 | 700834945H1 | SOYMON019 | g2318116 | BLASTN | 944 | 1e-69 | 87 |
| 326 | 20915 | 700993045H1 | SOYMON011 | g1732468 | BLASTN | 412 | 1e-23 | 97 |

TABLE A*-continued

| Seq No. | Cluster ID | CloneID | Library | NCBI gi | Method | Score | P-value | % Ident |
|---|---|---|---|---|---|---|---|---|
| 327 | 20915 | 700978188H1 | SOYMON009 | g1732468 | BLASTN | 400 | 1e-22 | 95 |
| 328 | 22044 | LIB3028-007-Q1-B1-A8 | LIB3028 | g2318116 | BLASTN | 1719 | 1e-134 | 89 |
| 329 | 22044 | 701063842H1 | SOYMON034 | g2318116 | BLASTN | 1084 | 1e-81 | 92 |
| 330 | 22044 | 700725383H1 | SOYMON009 | g2318116 | BLASTN | 1028 | 1e-76 | 90 |
| 331 | 22044 | 701001558H1 | SOYMON018 | g2318116 | BLASTN | 668 | 1e-75 | 89 |
| 332 | 26346 | LIB3039-010-Q1-E1-G5 | LIB3039 | g1732468 | BLASTN | 441 | 1e-25 | 84 |
| 333 | 26346 | 700972265H1 | SOYMON005 | g1732468 | BLASTN | 287 | 1e-12 | 84 |
| 334 | 26346 | 701052502H1 | SOYMON032 | g1732468 | BLASTN | 241 | 1e-9 | 82 |
| 335 | 2822 | LIB3054-010-Q1-N1-G10 | LIB3054 | g1732468 | BLASTN | 850 | 1e-120 | 93 |
| 336 | 2822 | LIB3065-011-Q1-N1-D8 | LIB3065 | g1732468 | BLASTN | 841 | 1e-104 | 83 |
| 337 | 2822 | 700686645H1 | SOYMON008 | g1732468 | BLASTN | 868 | 1e-82 | 91 |
| 338 | 2822 | 700997745H1 | SOYMON018 | g1732468 | BLASTN | 878 | 1e-81 | 92 |
| 339 | 2822 | 700994426H1 | SOYMON011 | g1732468 | BLASTN | 1084 | 1e-81 | 89 |
| 340 | 2822 | 700739971H1 | SOYMON012 | g1732468 | BLASTN | 871 | 1e-80 | 95 |
| 341 | 2822 | 701138070H1 | SOYMON038 | g1732468 | BLASTN | 449 | 1e-65 | 87 |
| 342 | 2822 | 701203251H1 | SOYMON035 | g1732468 | BLASTN | 605 | 1e-65 | 87 |
| 343 | 2822 | 701206105H1 | SOYMON035 | g1732468 | BLASTN | 698 | 1e-65 | 88 |
| 344 | 2822 | 700895378H1 | SOYMON027 | g1732468 | BLASTN | 486 | 1e-62 | 83 |
| 345 | 2822 | 701105638H1 | SOYMON036 | g1732468 | BLASTN | 739 | 1e-61 | 90 |
| 346 | 2822 | 700898271H1 | SOYMON027 | g1732468 | BLASTN | 746 | 1e-61 | 89 |
| 347 | 2822 | LIB3040-024-Q1-E1-H2 | LIB3040 | g1732468 | BLASTN | 652 | 1e-49 | 84 |
| 348 | 2822 | 700898124H1 | SOYMON027 | g1732468 | BLASTN | 578 | 1e-39 | 80 |
| 349 | 2822 | 700901555H1 | SOYMON027 | g1732468 | BLASTN | 529 | 1e-35 | 97 |
| 350 | 2822 | 700743195H1 | SOYMON012 | g1732468 | BLASTN | 324 | 1e-33 | 90 |
| 351 | 2822 | 700740845H1 | SOYMON012 | g1732468 | BLASTN | 478 | 1e-29 | 97 |
| 352 | 2822 | 700995694H1 | SOYMON012 | g1732468 | BLASTN | 314 | 1e-27 | 90 |
| 353 | 2822 | 700760635H1 | SOYMON011 | g1732468 | BLASTN | 438 | 1e-27 | 88 |
| 354 | 2822 | 701208243H1 | SOYMON015 | g1732468 | BLASTN | 429 | 1e-26 | 90 |
| 355 | 2822 | 700992554H1 | SOYMON035 | g1732468 | BLASTN | 348 | 1e-20 | 89 |
| 356 | 33722 | LIB3030-005-Q1-B1-F12 | LIB3030 | g2318116 | BLASTN | 620 | 1e-48 | 81 |
| 357 | 33722 | 700653412H1 | SOYMON003 | g2318116 | BLASTN | 514 | 1e-32 | 88 |
| 358 | 4037 | 700982624H1 | SOYMON009 | g1732468 | BLASTN | 1353 | 1e-103 | 96 |
| 359 | 4037 | 701136660H1 | SOYMON038 | g1732468 | BLASTN | 1316 | 1e-100 | 96 |
| 360 | 4037 | 700979310H1 | SOYMON009 | g1732468 | BLASTN | 1010 | 1e-98 | 99 |
| 361 | 4037 | 700978952H1 | SOYMON009 | g1732468 | BLASTN | 1016 | 1e-91 | 92 |
| 362 | 4037 | 701104668H1 | SOYMON036 | g1732468 | BLASTN | 1152 | 1e-87 | 93 |
| 363 | 4037 | 700557049H1 | SOYMON001 | g1732468 | BLASTN | 1060 | 1e-79 | 92 |
| 364 | 4037 | 701107647H1 | SOYMON036 | g1732468 | BLASTN | 1030 | 1e-77 | 93 |
| 365 | 4037 | 701150771H1 | SOYMON031 | g1732468 | BLASTN | 1005 | 1e-74 | 92 |
| 366 | 4037 | 701154966H1 | SOYMON031 | g1732468 | BLASTN | 985 | 1e-73 | 100 |
| 367 | 4037 | 700989839H1 | SOYMON011 | g1732468 | BLASTN | 736 | 1e-52 | 93 |
| 368 | 4037 | 700756564H1 | SOYMON014 | g1732468 | BLASTN | 609 | 1e-41 | 93 |
| 369 | 4037 | 700753388H1 | SOYMON014 | g1732468 | BLASTN | 563 | 1e-38 | 93 |
| 370 | 4037 | 700850857H1 | SOYMON023 | g1732468 | BLASTN | 493 | 1e-32 | 92 |
| 371 | 4037 | 701150639H1 | SOYMON031 | g1732468 | BLASTN | 148 | 1e-17 | 82 |
| SOYBEAN FERROCHELATASE | | | | | | | | |
| 372 | −700839666 | 700839666H1 | SOYMON020 | g2623989 | BLASTN | 736 | 1e-52 | 82 |
| 373 | −700846363 | 700846363H1 | SOYMON021 | g439482 | BLASTN | 732 | 1e-52 | 77 |
| 374 | −700901570 | 700901570H1 | SOYMON027 | g2623989 | BLASTN | 848 | 1e-61 | 81 |
| 375 | −700907558 | 700907558H1 | SOYMON022 | g439482 | BLASTN | 700 | 1e-49 | 75 |
| 376 | −701048026 | 701048026H1 | SOYMON032 | g439482 | BLASTN | 654 | 1e-45 | 71 |
| 377 | −701064702 | 701064702H1 | SOYMON034 | g439482 | BLASTN | 439 | 1e-26 | 68 |
| 378 | −701105159 | 701105159H1 | SOYMON036 | g2429612 | BLASTN | 487 | 1e-50 | 77 |
| 379 | 26592 | 701208376H1 | SOYMON035 | g439482 | BLASTN | 722 | 1e-51 | 78 |
| 380 | 26592 | 701097475H1 | SOYMON028 | g439482 | BLASTN | 729 | 1e-51 | 75 |
| 381 | 26592 | 701119601H1 | SOYMON037 | g439482 | BLASTN | 518 | 1e-40 | 78 |
| 382 | 28079 | 701015447H1 | SOYMON019 | g439482 | BLASTN | 840 | 1e-61 | 81 |
| 383 | 28079 | 701102766H1 | SOYMON028 | g439482 | BLASTN | 789 | 1e-56 | 82 |
| MAIZE PUTATIVE CHLOROPHYLL SYNTHETASE | | | | | | | | |
| 384 | −700214815 | 700214815H1 | SATMON016 | g972938 | BLASTX | 244 | 1e-26 | 80 |
| 385 | −700222875 | 700222875H1 | SATMON011 | g972937 | BLASTX | 340 | 1e-27 | 77 |
| 386 | −L30662921 | LIB3066-008-Q1-K1-C6 | LIB3066 | g3068702 | BLASTN | 504 | 1e-31 | 69 |
| 387 | 11381 | LIB3078-007-Q1-K1-H2 | LIB3078 | g3068702 | BLASTN | 281 | 1e-57 | 75 |
| 388 | 11381 | 700084837H1 | SATMON011 | g972937 | BLASTN | 281 | 1e-48 | 74 |
| 389 | 11381 | 700088129H1 | SATMON011 | g972937 | BLASTN | 317 | 1e-44 | 78 |
| 390 | 11381 | 700045204H1 | SATMON004 | g972938 | BLASTX | 363 | 1e-43 | 73 |
| 391 | 11381 | 700084253H1 | SATMON011 | g972937 | BLASTN | 317 | 1e-35 | 79 |

TABLE A*-continued

| Seq No. | Cluster ID | CloneID | Library | NCBI gi | Method | Score | P-value | % Ident |
|---|---|---|---|---|---|---|---|---|
| 392 | 11381 | 700427169H1 | SATMONN01 | g972938 | BLASTX | 225 | 1e-33 | 73 |
| 393 | 11381 | 700104418H1 | SATMON010 | g972937 | BLASTN | 317 | 1e-26 | 77 |
| 394 | 17510 | 700218357H1 | SATMON016 | g972937 | BLASTN | 173 | 1e-12 | 72 |
| 395 | 17510 | 700217457H1 | SATMON016 | g972937 | BLASTN | 173 | 1e-11 | 72 |
| 396 | 1913 | 700243564H1 | SATMON010 | g972937 | BLASTN | 357 | 1e-38 | 78 |
| 397 | 1913 | 700577332H1 | SATMON031 | g972938 | BLASTX | 165 | 1e-15 | 68 |
| MAIZE PROTOCHLOROPHYLLIDE REDUCTASE | | | | | | | | |
| 398 | −700346250 | 700346250H1 | SATMON021 | g16117 | BLASTN | 338 | 1e-47 | 86 |
| 399 | −700430255 | 700430255H1 | SATMONN01 | g19060 | BLASTN | 619 | 1e-42 | 93 |
| 400 | −L30681828 | LIB3068-021-Q1-K1-A7 | LIB3068 | g19060 | BLASTN | 212 | 1e-14 | 69 |
| 401 | −L30782362 | LIB3078-006-Q1-K1-G6 | L1B3078 | g19060 | BLASTN | 472 | 1e-47 | 73 |
| 402 | 18503 | 700321674H1 | SATMON025 | g683475 | BLASTN | 260 | 1e-50 | 82 |
| 403 | 18503 | 700220580H1 | SATMON011 | g683475 | BLASTN | 179 | 1e-16 | 80 |
| 404 | 2096 | LIB36-005-Q1-E1-G5 | LIB36 | g683475 | BLASTN | 1633 | 1e-127 | 90 |
| 405 | 2096 | LIB3062-018-Q1-K1-E9 | LIB3062 | g510676 | BLASTN | 1436 | 1e-116 | 84 |
| 406 | 2096 | LIB3078-008-Q1-K1-H8 | LIB3078 | g19060 | BLASTN | 1017 | 1e-115 | 85 |
| 407 | 2096 | LIB3078-004-Q1-K1-D7 | LIB3078 | g19060 | BLASTN | 1325 | 1e-101 | 84 |
| 408 | 2096 | LIB3062-010-Q1-K1-G7 | LIB3062 | g19060 | BLASTN | 1159 | 1e-90 | 81 |
| 409 | 2096 | 700043426H1 | SATMON004 | g683475 | BLASTN | 1189 | 1e-90 | 93 |
| 410 | 2096 | 700093887H1 | SATMON008 | g19060 | BLASTN | 1194 | 1e-90 | 87 |
| 411 | 2096 | 700045326H1 | SATMON004 | g19060 | BLASTN | 1115 | 1e-84 | 92 |
| 412 | 2096 | 700439164H1 | SATMON026 | g683475 | BLASTN | 620 | 1e-81 | 89 |
| 413 | 2096 | 700093546H1 | SATMON008 | g19060 | BLASTN | 821 | 1e-81 | 88 |
| 414 | 2096 | 700081986H1 | SATMON011 | g510676 | BLASTN | 1076 | 1e-80 | 85 |
| 415 | 2096 | 700044764H1 | SATMON004 | g683475 | BLASTN | 1056 | 1e-79 | 89 |
| 416 | 2096 | 700098537H1 | SATMON009 | g510676 | BLASTN | 760 | 1e-73 | 87 |
| 417 | 2096 | 700340891H1 | SATMON020 | g683475 | BLASTN | 591 | 1e-70 | 88 |
| 418 | 2096 | 700100677H1 | SATMON009 | g683475 | BLASTN | 890 | 1e-65 | 89 |
| 419 | 2096 | 700265286H1 | SATMON017 | g683475 | BLASTN | 578 | 1e-53 | 88 |
| 420 | 2096 | 700212436H1 | SATMON016 | g16117 | BLASTN | 718 | 1e-51 | 83 |
| 421 | 2096 | 700046348H1 | SATMON004 | g683475 | BLASTN | 726 | 1e-51 | 87 |
| 422 | 2096 | 700968694H1 | SATMONN04 | g19060 | BLASTN | 306 | 1e-28 | 87 |
| 423 | 2096 | 700453783H1 | SATMON029 | g19060 | BLASTN | 197 | 1e-12 | 78 |
| 424 | 5587 | LIB3062-053-Q1-K1-C4 | LIB3062 | g683475 | BLASTN | 1366 | 1e-111 | 91 |
| 425 | 5587 | 700087630H1 | SATMON011 | g683475 | BLASTN | 1021 | 1e-91 | 92 |
| 426 | 5587 | 700088983H1 | SATMON011 | g683475 | BLASTN | 708 | 1e-88 | 86 |
| 427 | 5587 | 700100889H1 | SATMON009 | g683475 | BLASTN | 1149 | 1e-87 | 89 |
| 428 | 5587 | 700470729H1 | SATMON025 | g683475 | BLASTN | 1006 | 1e-85 | 90 |
| 429 | 5587 | 700100883H1 | SATMON009 | g683475 | BLASTN | 839 | 1e-80 | 90 |
| 430 | 5587 | 700214072H1 | SATMON016 | g683475 | BLASTN | 910 | 1e-73 | 91 |
| 431 | 5587 | 700044664H1 | SATMON004 | g683475 | BLASTN | 587 | 1e-56 | 84 |
| 432 | 5587 | LIB189-007-Q1-E1-A7 | LIB189 | g683475 | BLASTN | 403 | 1e-53 | 79 |
| 433 | 5587 | 700042060H1 | SATMON004 | g683475 | BLASTN | 734 | 1e-52 | 84 |
| 434 | 5587 | LIB83-011-Q1-E1-A8 | LIB83 | g683475 | BLASTN | 310 | 1e-32 | 74 |
| 435 | 5587 | 700083223H1 | SATMON011 | g683475 | BLASTN | 310 | 1e-31 | 79 |
| 436 | 5587 | 700442503H1 | SATMON026 | g683475 | BLASTN | 458 | 1e-29 | 89 |
| 437 | 5587 | 700101540H1 | SATMON009 | g683475 | BLASTN | 310 | 1e-28 | 78 |
| 438 | 5587 | 700207961H1 | SATMON016 | g683475 | BLASTN | 304 | 1e-26 | 82 |
| 439 | 5587 | 700092960H1 | SATMON008 | g683475 | BLASTN | 310 | 1e-26 | 72 |
| 440 | 5587 | 700041761H1 | SATMON004 | g683475 | BLASTN | 301 | 1e-24 | 86 |
| 441 | 5587 | 700087935H1 | SATMON011 | g2244614 | BLASTX | 141 | 1e-12 | 100 |
| 442 | 5632 | LIB3069-036-Q1-K1-A5 | LIB3069 | g510676 | BLASTN | 849 | 1e-76 | 81 |
| 443 | 5632 | 700243480H1 | SATMON010 | g16117 | BLASTN | 806 | 1e-73 | 89 |
| 444 | 5632 | 700198041H1 | SATMON016 | g16117 | BLASTN | 738 | 1e-52 | 90 |
| 445 | 5632 | 700097480H1 | SATMON009 | g19060 | BLASTN | 712 | 1e-50 | 80 |
| 446 | 5632 | 700088645H1 | SATMON011 | g19060 | BLASTN | 659 | 1e-46 | 79 |
| 447 | 5632 | LIB3068-012-Q1-K1-C6 | LIB3068 | g19061 | BLASTX | 129 | 1e-35 | 90 |
| 448 | 5632 | LIB3069-026-Q1-K1-G11 | LIB3069 | g19060 | BLASTN | 496 | 1e-34 | 75 |
| 449 | 5632 | 700081934H1 | SATMON011 | g16117 | BLASTN | 519 | 1e-34 | 89 |
| 450 | 5632 | LIB3062-050-Q1-K1-B3 | LIB3062 | g16117 | BLASTN | 348 | 1e-29 | 83 |
| 451 | 5632 | LIB3069-042-Q1-K1-D6 | LIB3069 | g19060 | BLASTN | 404 | 1e-25 | 72 |

TABLE A*-continued

| Seq No. | Cluster ID | CloneID | Library | NCBI gi | Method | Score | P-value | % Ident |
|---|---|---|---|---|---|---|---|---|
| 452 | 5632 | 700095961H1 | SATMON008 | g19060 | BLASTN | 277 | 1e-23 | 68 |
| 453 | 5632 | 700091061H1 | SATMON011 | g19061 | BLASTX | 86 | 1e-10 | 64 |
| 454 | 5632 | 700224365H1 | SATMON011 | g19060 | BLASTN | 213 | 1e-10 | 63 |
| 455 | 5632 | 700089289H1 | SATMON011 | g19060 | BLASTN | 213 | 1e-10 | 63 |
| 456 | 5632 | 700094923H1 | SATMON008 | g19060 | BLASTN | 183 | 1e-9 | 63 |
| 457 | 5632 | 700094625H1 | SATMON008 | g19060 | BLASTN | 206 | 1e-9 | 63 |
| 458 | 5632 | 700093380H1 | SATMON008 | g19060 | BLASTN | 206 | 1e-9 | 63 |
| 459 | 5632 | 700093964H1 | SATMON008 | g19060 | BLASTN | 213 | 1e-9 | 69 |
| 460 | 5632 | 700083043H1 | SATMON011 | g19060 | BLASTN | 193 | 1e-8 | 63 |
| 461 | 5632 | 700095165H1 | SATMON008 | g510676 | BLASTN | 195 | 1e-8 | 65 |
| 462 | 5633 | 700094759H1 | SATMON008 | g510676 | BLASTN | 629 | 1e-43 | 86 |
| 463 | 5633 | 700094711H1 | SATMON008 | g16117 | BLASTN | 468 | 1e-32 | 89 |
| 464 | 9949 | 700213043H1 | SATMON016 | g16117 | BLASTN | 1192 | 1e-90 | 87 |
| 465 | 9949 | 700084670H1 | SATMON011 | g16117 | BLASTN | 1125 | 1e-85 | 88 |
| 466 | 9949 | 700213929H1 | SATMON016 | g16117 | BLASTN | 439 | 1e-27 | 84 |
| MAIZE PUTATIVE PROTOCHLOROPHYLLIDE REDUCTASE | | | | | | | | |
| 467 | −700353742 | 700353742H1 | SATMON024 | g348717 | BLASTN | 512 | 1e-33 | 73 |
| 468 | −700423111 | 70042311H1 | SATMONN01 | g348717 | BLASTN | 684 | 1e-48 | 72 |
| 469 | 15163 | LIB3069-040-Q1-K1-F9 | LIB3069 | g348717 | BLASTN | 874 | 1e-64 | 70 |
| 470 | 15163 | 700623844H1 | SATMON034 | g348717 | BLASTN | 752 | 1e-53 | 69 |
| 471 | 15163 | 700623744H1 | SATMON034 | g348717 | BLASTN | 725 | 1e-51 | 70 |
| 472 | 15163 | 700623644H1 | SATMON034 | g348717 | BLASTN | 661 | 1e-46 | 72 |
| 473 | 15163 | 700612907H1 | SATMON033 | g348717 | BLASTN | 597 | 1e-40 | 73 |
| 474 | 15163 | 700612808H1 | SATMON033 | g348717 | BLASTN | 579 | 1e-39 | 74 |
| 475 | 15163 | 700623852H1 | SATMON034 | g348717 | BLASTN | 489 | 1e-30 | 67 |
| 476 | 15163 | 700475540H1 | SATMON025 | g348717 | BLASTN | 413 | 1e-26 | 65 |
| 477 | 22562 | 700571483H1 | SATMON030 | g348717 | BLASTN | 447 | 1e-26 | 72 |
| 478 | 30690 | LIB3062-046-Q1-K1-D4 | LIB3062 | g348719 | BLASTN | 514 | 1e-31 | 69 |
| 479 | 30690 | 700425786H2 | SATMONN01 | g348720 | BLASTX | 168 | 1e-17 | 54 |
| MAIZE COPROPORPHYRINOGEN OXIDASE | | | | | | | | |
| 480 | −L30623969 | LIB3062-019-Q1-K1-A9 | LIB3062 | g1213067 | BLASTX | 123 | 1e-25 | 76 |
| 481 | 26808 | LIB3062-022-Q1-K1-A9 | LIB3062 | g1213067 | BLASTX | 195 | 1e-35 | 89 |
| 482 | 26808 | LIB36-007-Q1-E1-H7 | LIB36 | g414665 | BLASTN | 235 | 1e-8 | 85 |
| 483 | 5948 | 700614009H1 | SATMON033 | g1212993 | BLASTN | 1318 | 1e-101 | 87 |
| 484 | 5948 | LIB3078-027-Q1-K1-C2 | LIB3078 | g1212993 | BLASTN | 1185 | 1e-89 | 83 |
| 485 | 5948 | 700207069H1 | SATMON003 | g1212993 | BLASTN | 1003 | 1e-82 | 81 |
| 486 | 5948 | 701183985H1 | SATMONN06 | g1212993 | BLASTN | 1064 | 1e-79 | 88 |
| 487 | 5948 | 700043235H1 | SATMON004 | g1212993 | BLASTN | 944 | 1e-69 | 85 |
| 488 | 5948 | 700237643H1 | SATMON010 | g1212993 | BLASTN | 920 | 1e-67 | 85 |
| 489 | 5948 | 700167142H1 | SATMON013 | g1212993 | BLASTN | 832 | 1e-60 | 85 |
| 490 | 98 | LIB3062-011-Q1-K1-B9 | LIB3062 | g1212993 | BLASTN | 1515 | 1e-120 | 85 |
| 491 | 98 | 700089965H1 | SATMON011 | g1212993 | BLASTN | 1129 | 1e-85 | 85 |
| 492 | 98 | 700473370H1 | SATMON025 | g1212993 | BLASTN | 812 | 1e-79 | 83 |
| 493 | 98 | 700018492H1 | SATMON001 | g1212993 | BLASTN | 650 | 1e-45 | 87 |
| 494 | 98 | 700336060H1 | SATMON019 | g1212993 | BLASTN | 423 | 1e-26 | 83 |
| MAIZE PROTOPORPHYRINOGEN OXIDASE | | | | | | | | |
| 495 | 13987 | 700397414H1 | SATMONN01 | g1877018 | BLASTX | 152 | 1e-13 | 72 |
| 496 | 13987 | 700377840H1 | SATMON019 | g2370333 | BLASTX | 115 | 1e-8 | 75 |
| 497 | 21128 | 700087081H1 | SATMON011 | g1183006 | BLASTN | 851 | 1e-62 | 75 |
| 498 | 21128 | 700222959H1 | SATMON011 | g1183006 | BLASTN | 551 | 1e-47 | 74 |
| 499 | 8675 | LIB3062-009-Q1-K1-F6 | LIB3062 | g3093409 | BLASTN | 1093 | 1e-82 | 72 |
| MAIZE UROPORPHYRINOGEN DECARBOXYLASE | | | | | | | | |
| 500 | −700210906 | 700210906H1 | SATMON016 | g1009429 | BLASTX | 172 | 1e-25 | 50 |
| 501 | −700334993 | 700334993H1 | SATMON019 | g1009427 | BLASTN | 515 | 1e-70 | 84 |
| 502 | −700432067 | 700432067H1 | SATMONN01 | g216564 | BLASTX | 123 | 1e-14 | 39 |
| 503 | −L1891364 | LIB189-002-Q1-E1-E8 | LIB189 | g1009427 | BLASTN | 914 | 1e-78 | 85 |
| 504 | −L30625966 | LIB3062-056-Q1-K1-D10 | LIB3062 | g1322019 | BLASTX | 660 | 1e-102 | 100 |
| 505 | −L30626254 | LIB3062-058-Q1-K1-D9 | LIB3062 | g1009427 | BLASTN | 516 | 1e-32 | 81 |
| 506 | −L30783694 | LIB3078-054-Q1-K1-D9 | LIB3078 | g1009427 | BLASTN | 1355 | 1e-104 | 84 |
| 507 | 30392 | 700090031H1 | SATMON011 | g1009427 | BLASTN | 794 | 1e-79 | 92 |

TABLE A*-continued

| Seq No. | Cluster ID | CloneID | Library | NCBI gi | Method | Score | P-value | % Ident |
|---|---|---|---|---|---|---|---|---|
| 508 | 30392 | LIB3062-053-Q1-K1-D9 | LIB3062 | g1009427 | BLASTN | 762 | 1e-54 | 89 |
| 509 | 30392 | LIB3069-027-Q1-K1-G9 | LIB3069 | g1009427 | BLASTN | 664 | 1e-44 | 83 |
| MAIZE PUTATIVE UROPORPHYRINOG EN DECARBOXYLASE | | | | | | | | |
| 510 | −700799143 | 700799143H1 | SATMON036 | g48040 | BLASTX | 128 | 1e-21 | 47 |
| MAIZE PORPHOBILINOGEN SYNTHASE | | | | | | | | |
| 511 | −700082696 | 700082696H1 | SATMON011 | g1041422 | BLASTN | 544 | 1e-64 | 86 |
| 512 | −700421637 | 700421637H1 | SATMONN01 | g1041422 | BLASTN | 591 | 1e-57 | 85 |
| 513 | 10331 | 700049523H1 | SATMON003 | g1041422 | BLASTN | 694 | 1e-73 | 84 |
| 514 | 10331 | 700214149H1 | SATMON016 | g1041422 | BLASTN | 986 | 1e-73 | 84 |
| 515 | 6252 | LIB3060-049-Q1-K1-D11 | LIB3060 | g1041422 | BLASTN | 1296 | 1e-119 | 85 |
| 516 | 6252 | 700104193H1 | SATMON010 | g1041422 | BLASTN | 1117 | 1e-84 | 87 |
| 517 | 6252 | 700043614H1 | SATMON004 | g1041422 | BLASTN | 1081 | 1e-81 | 87 |
| 518 | 6252 | 700104333H1 | SATMON010 | g1041422 | BLASTN | 757 | 1e-76 | 86 |
| 519 | 6252 | 700099573H1 | SATMON009 | g1041422 | BLASTN | 969 | 1e-71 | 85 |
| 520 | 6252 | LIB189-034-Q1-E1-G11 | LIB189 | g1041422 | BLASTN | 829 | 1e-64 | 82 |
| 521 | 6252 | 700150031H1 | SATMON007 | g1041422 | BLASTN | 715 | 1e-50 | 80 |
| 522 | 6252 | 700150305H1 | SATMON007 | g1041422 | BLASTN | 494 | 1e-32 | 88 |
| 523 | 6664 | 700098341H1 | SATMON009 | g1041422 | BLASTN | 861 | 1e-62 | 80 |
| 524 | 6664 | 700097010H1 | SATMON009 | g1041422 | BLASTN | 861 | 1e-62 | 80 |
| 525 | 6664 | 700150830H1 | SATMON007 | g1041422 | BLASTN | 655 | 1e-45 | 78 |
| 526 | 6664 | 700088427H1 | SATMON011 | g1041422 | BLASTN | 598 | 1e-41 | 85 |
| 527 | 6664 | 700216648H1 | SATMON016 | g1041422 | BLASTN | 586 | 1e-40 | 78 |
| 528 | 6664 | 700150750H1 | SATMON007 | g1041422 | BLASTN | 562 | 1e-38 | 77 |
| 529 | 6664 | 700089504H1 | SATMON011 | g1041422 | BLASTN | 349 | 1e-35 | 81 |
| 530 | 6664 | 700150781H1 | SATMON007 | g1041422 | BLASTN | 473 | 1e-30 | 71 |
| 531 | 6664 | 700071849H1 | SATMON007 | g1041423 | BLASTX | 158 | 1e-14 | 66 |
| MAIZE HYDROXYMETHYLBILANE SYNTHASE | | | | | | | | |
| 532 | −700042853 | 700042853H1 | SATMON004 | g2661765 | BLASTN | 1319 | 1e-101 | 96 |
| 533 | −700209530 | 700209530H1 | SATMON016 | g2661765 | BLASTN | 1046 | 1e-96 | 91 |
| 534 | −L30784536 | LIB3078-039-Q1-K1-D10 | LIB3078 | g2661765 | BLASTN | 980 | 1e-73 | 81 |
| 535 | 18 | 700434552H1 | SATMONN01 | g2661765 | BLASTN | 819 | 1e-59 | 77 |
| 536 | 18 | 700621233H1 | SATMON034 | g2661765 | BLASTN | 606 | 1e-44 | 85 |
| 537 | 18 | 700621333H1 | SATMON034 | g2661765 | BLASTN | 607 | 1e-41 | 88 |
| 538 | 22370 | LIB3078-049-Q1-K1-D11 | LIB3078 | g2661765 | BLASTN | 1197 | 1e-91 | 93 |
| 539 | 22370 | LIB3078-007-Q1-K1-F2 | LIB3078 | g313723 | BLASTN | 745 | 1e-72 | 71 |
| 540 | 22370 | 700223478H1 | SATMON011 | g313723 | BLASTN | 712 | 1e-50 | 72 |
| 541 | 22370 | 700216196H1 | SATMON016 | g313723 | BLASTN | 508 | 1e-45 | 74 |
| 542 | 22370 | 700551081H1 | SATMON022 | g2661765 | BLASTN | 328 | 1e-36 | 91 |
| MAIZE GLUTAMATE-1-SEMIALDEHYDE 2,1-AMINOMUTASE | | | | | | | | |
| 543 | −L841669 | LIB84-026-Q1-E1-D6 | LIB84 | g506383 | BLASTX | 164 | 1e-42 | 69 |
| 544 | 11095 | LIB3078-054-Q1-K1-E2 | LIB3078 | g556018 | BLASTN | 1229 | 1e-93 | 81 |
| 545 | 11095 | LIB83-005-Q1-E1-B11 | LIB83 | g556018 | BLASTN | 1169 | 1e-88 | 80 |
| 546 | 11095 | 700101450H1 | SATMON009 | g556018 | BLASTN | 1024 | 1e-76 | 81 |
| 547 | 11095 | 700342512H1 | SATMON021 | g556018 | BLASTN | 995 | 1e-74 | 82 |
| 548 | 11095 | 700265085H1 | SATMON017 | g556018 | BLASTN | 996 | 1e-74 | 82 |
| 549 | 11095 | 700154602H1 | SATMON007 | g556018 | BLASTN | 491 | 1e-58 | 82 |
| 550 | 11095 | 700154908H1 | SATMON007 | g556018 | BLASTN | 722 | 1e-58 | 81 |
| 551 | 11095 | 700017624H1 | SATMON001 | g556018 | BLASTN | 775 | 1e-55 | 83 |
| 552 | 11095 | 700018108H1 | SATMON001 | g556018 | BLASTN | 758 | 1e-54 | 84 |
| 553 | 11095 | 700443671H1 | SATMON027 | g556018 | BLASTN | 662 | 1e-46 | 73 |
| 554 | 11095 | 700442812H1 | SATMON026 | g556018 | BLASTN | 578 | 1e-39 | 80 |
| 555 | 11095 | 700343762H1 | SATMON021 | g556018 | BLASTN | 565 | 1e-38 | 80 |
| 556 | 11095 | 700094251H1 | SATMON008 | g19873 | BLASTX | 167 | 1e-16 | 89 |
| 557 | 11225 | LIB3060-054-Q1-K1-C12 | LIB3060 | g556018 | BLASTN | 817 | 1e-69 | 77 |
| 558 | 11225 | 700100123H1 | SATMON009 | g556018 | BLASTN | 787 | 1e-56 | 85 |
| 559 | 11225 | 700405062H1 | SATMON027 | g556018 | BLASTN | 453 | 1e-34 | 75 |
| 560 | 11225 | 700219159H1 | SATMON011 | g556018 | BLASTN | 328 | 1e-26 | 74 |
| 561 | 11225 | 700209352H1 | SATMON016 | g506383 | BLASTX | 174 | 1e-17 | 70 |
| 562 | 11225 | 700053276H1 | SATMON008 | g506383 | BLASTX | 131 | 1e-10 | 96 |
| 563 | 11225 | 700156122H2 | SATMON007 | g506383 | BLASTX | 120 | 1e-9 | 100 |
| 564 | 15553 | 700084357H1 | SATMON011 | g556018 | BLASTN | 1104 | 1e-83 | 80 |
| 565 | 15553 | 700441108H1 | SATMON026 | g556018 | BLASTN | 1071 | 1e-80 | 86 |

TABLE A*-continued

| Seq No. | Cluster ID | CloneID | Library | NCBI gi | Method | Score | P-value | % Ident |
|---|---|---|---|---|---|---|---|---|
| 566 | 15553 | 700441006H1 | SATMON026 | g556018 | BLASTN | 1062 | 1e-79 | 86 |
| 567 | 15553 | 700087059H1 | SATMON011 | g556018 | BLASTN | 421 | 1e-26 | 82 |
| 568 | 20096 | 700089246H1 | SATMON011 | g556018 | BLASTN | 474 | 1e-49 | 82 |
| 569 | 20096 | 700171369H1 | SATMON013 | g556018 | BLASTN | 560 | 1e-37 | 78 |
| | | MAIZE GLUTAMATE tRNA LIGASE | | | | | | |
| 570 | −700614160 | 700614160H1 | SATMON033 | g31958 | BLASTX | 113 | 1e-10 | 56 |
| 571 | −L1892744 | LIB189-012-Q1-E1-F8 | LIB189 | g31958 | BLASTX | 146 | 1e-28 | 50 |
| 572 | −L1894036 | LIB189-029-Q1-E1-B1 | LIB189 | g157564 | BLASTX | 143 | 1e-28 | 62 |
| 573 | 12385 | LIB3067-058-Q1-K1-H9 | LIB3067 | g2995455 | BLASTX | 416 | 1e-70 | 69 |
| 574 | 13776 | 700344387H1 | SATMON021 | g157564 | BLASTX | 108 | 1e-19 | 57 |
| 575 | 21786 | 700221143H1 | SATMON011 | g157564 | BLASTX | 287 | 1e-32 | 59 |
| 576 | 26250 | LIB3069-031-Q1-K1-E6 | LIB3069 | g2995455 | BLASTX | 166 | 1e-43 | 74 |
| 577 | 3350 | LIB3069-025-Q1-K1-F6 | LIB3069 | g157564 | BLASTX | 232 | 1e-44 | 46 |
| 578 | 3350 | 700072785H1 | SATMON007 | g157564 | BLASTX | 249 | 1e-26 | 45 |
| 579 | 3350 | 700049536H1 | SATMON003 | g157564 | BLASTX | 227 | 1e-24 | 50 |
| 580 | 3350 | 700077013H1 | SATMON007 | g157564 | BLASTX | 232 | 1e-24 | 49 |
| 581 | 3350 | 700209830H1 | SATMON016 | g157564 | BLASTX | 210 | 1e-22 | 52 |
| 582 | 3350 | 700168681H1 | SATMON013 | g157564 | BLASTX | 156 | 1e-14 | 40 |
| 583 | 5345 | LIB3059-036-Q1-K1-G10 | LIB3059 | g2995455 | BLASTX | 148 | 1e-28 | 67 |
| 584 | 9230 | LIB143-053-Q1-E1-G8 | LIB143 | g31958 | BLASTX | 341 | 1e-55 | 58 |
| 585 | 9230 | 700331892H1 | SATMON019 | g157564 | BLASTX | 162 | 1e-31 | 55 |
| | | MAIZE GLUTAMYL-tRNA REDUCTASE | | | | | | |
| 586 | −700094403 | 700094403H1 | SATMON008 | g1039331 | BLASTN | 740 | 1e-63 | 83 |
| 587 | −700151003 | 700151003H1 | SATMON007 | g1039331 | BLASTN | 885 | 1e-64 | 87 |
| 588 | −700167046 | 700167046H1 | SATMON013 | g1039331 | BLASTN | 772 | 1e-64 | 89 |
| 589 | −L30661635 | LIB3066-003-Q1-K1-A8 | LIB3066 | g1666078 | BLASTN | 298 | 1e-18 | 77 |
| 590 | −L30661878 | LIB3066-012-Q1-K1-F3 | LIB3066 | g2967440 | BLASTN | 485 | 1e-29 | 85 |
| 591 | −L362024 | LIB36-016-Q2-E2-H11 | LIB36 | g2920319 | BLASTN | 170 | 1e-9 | 70 |
| 592 | 22014 | 700045741H1 | SATMON004 | g1039331 | BLASTN | 921 | 1e-67 | 82 |
| 593 | 22014 | 700214783H1 | SATMON016 | g1039331 | BLASTN | 860 | 1e-62 | 83 |
| 594 | 22618 | 700086081H1 | SATMON011 | g1039331 | BLASTN | 1064 | 1e-79 | 82 |
| 595 | 22618 | 700104481H1 | SATMON010 | g1039331 | BLASTN | 955 | 1e-70 | 81 |
| 596 | 22618 | 700356789H1 | SATMON024 | g1039331 | BLASTN | 644 | 1e-44 | 86 |
| 597 | 30084 | LIB3062-026-Q1-K1-H5 | LIB3062 | g2920319 | BLASTN | 1043 | 1e-78 | 87 |
| 598 | 30084 | 701179026H1 | SATMONN05 | g1039331 | BLASTN | 753 | 1e-72 | 88 |
| 599 | 6787 | LIB36-021-Q1-E1-D9 | LIB36 | g1039331 | BLASTN | 1281 | 1e-97 | 87 |
| 600 | 6787 | 701163632H1 | SATMONN04 | g1039331 | BLASTN | 941 | 1e-79 | 86 |
| 601 | 6787 | 700162337H1 | SATMON012 | g1039331 | BLASTN | 901 | 1e-66 | 84 |
| 602 | 6787 | 700100879H1 | SATMON009 | g1039331 | BLASTN | 608 | 1e-65 | 86 |
| 603 | 6787 | 700425112H1 | SATMONN01 | g1039331 | BLASTN | 230 | 1e-9 | 81 |
| 604 | 9690 | LIB3078-023-Q1-K1-F12 | LIB3078 | g1039331 | BLASTN | 1755 | 1e-137 | 88 |
| 605 | 9690 | 700097404H1 | SATMON009 | g1039331 | BLASTN | 1311 | 1e-100 | 89 |
| 606 | 9690 | 700099954H1 | SATMON009 | g1039331 | BLASTN | 1132 | 1e-92 | 90 |
| 607 | 9690 | 700213724H1 | SATMON016 | g1039331 | BLASTN | 1211 | 1e-92 | 89 |
| 608 | 9690 | 700468009H1 | SATMON025 | g1039331 | BLASTN | 1187 | 1e-90 | 88 |
| 609 | 9690 | 700042554H1 | SATMON004 | g1039331 | BLASTN | 931 | 1e-68 | 88 |
| | | MAIZE Mg-CHELATASE | | | | | | |
| 610 | −700042626 | 700042626H1 | SATMON004 | g861198 | BLASTN | 489 | 1e-31 | 67 |
| 611 | −700045010 | 700045010H1 | SATMON004 | g861198 | BLASTN | 824 | 1e-59 | 80 |
| 612 | −700046489 | 700046489H1 | SATMON004 | g861198 | BLASTN | 246 | 1e-11 | 93 |
| 613 | −700090155 | 700090155H1 | SATMON011 | g2239151 | BLASTX | 226 | 1e-24 | 84 |
| 614 | −700100867 | 700100867H1 | SATMON009 | g2239150 | BLASTN | 944 | 1e-69 | 81 |
| 615 | −700152555 | 700152555H1 | SATMON007 | g861198 | BLASTN | 800 | 1e-57 | 83 |
| 616 | −700166615 | 700166615H1 | SATMON013 | g861198 | BLASTN | 438 | 1e-27 | 88 |
| 617 | −700214027 | 700214027H1 | SATMON016 | g847872 | BLASTN | 683 | 1e-67 | 80 |
| 618 | −700216016 | 700216016H1 | SATMON016 | g861198 | BLASTN | 408 | 1e-24 | 78 |
| 619 | −700219682 | 700219682H1 | SATMON011 | g2318116 | BLASTN | 616 | 1e-42 | 70 |
| 620 | −L30606220 | LIB3060-019-Q1-K1-D2 | LIB3060 | g861199 | BLASTX | 106 | 1e-32 | 67 |
| 621 | 15513 | 700379674H1 | SATMON021 | g2239151 | BLASTX | 138 | 1e-11 | 87 |
| 622 | 15984 | 700223402H1 | SATMON011 | g2318116 | BLASTN | 830 | 1e-60 | 78 |

TABLE A*-continued

| Seq No. | Cluster ID | CloneID | Library | NCBI gi | Method | Score | P-value | % Ident |
|---|---|---|---|---|---|---|---|---|
| 623 | 15984 | 701185568H1 | SATMONN06 | g2318116 | BLASTN | 787 | 1e-56 | 79 |
| 624 | 15984 | 701185572H1 | SATMONN06 | g2239150 | BLASTN | 528 | 1e-48 | 78 |
| 625 | 15984 | 700257978H1 | SATMON017 | g2239150 | BLASTN | 454 | 1e-33 | 72 |
| 626 | 19005 | 700025578H1 | SATMON004 | g861198 | BLASTN | 874 | 1e-63 | 84 |
| 627 | 19005 | 700442062H1 | SATMON026 | g861198 | BLASTN | 226 | 1e-23 | 81 |
| 628 | 19969 | 700100921H1 | SATMON009 | g847872 | BLASTN | 1183 | 1e-89 | 87 |
| 629 | 19969 | 700422986H1 | SATMONN01 | g847872 | BLASTN | 598 | 1e-75 | 88 |
| 630 | 19969 | 700215568H1 | SATMON016 | g847872 | BLASTN | 822 | 1e-59 | 89 |
| 631 | 21239 | LIB36-010-Q1-E1-H9 | LIB36 | g847872 | BLASTN | 1338 | 1e-139 | 88 |
| 632 | 21239 | 700053384H1 | SATMON009 | g847872 | BLASTN | 596 | 1e-85 | 88 |
| 633 | 21239 | 700043650H1 | SATMON004 | g847872 | BLASTN | 1122 | 1e-84 | 90 |
| 634 | 21239 | 700160759H1 | SATMON012 | g847872 | BLASTN | 760 | 1e-74 | 89 |
| 635 | 29840 | LIB84-024-Q1-E1-B8 | L1B84 | g861198 | BLASTN | 1195 | 1e-90 | 80 |
| 636 | 29840 | 700046445H1 | SATMON004 | g861198 | BLASTN | 898 | 1e-65 | 82 |
| 637 | 29840 | 700099676H1 | SATMON009 | g861198 | BLASTN | 755 | 1e-54 | 79 |
| 638 | 29840 | 700216064H1 | SATMON016 | g861198 | BLASTN | 433 | 1e-25 | 74 |
| 639 | 3221 | 700342738H1 | SATMON021 | g2239150 | BLASTN | 678 | 1e-74 | 82 |
| 640 | 3221 | 700090050H1 | SATMON011 | g2239150 | BLASTN | 556 | 1e-66 | 80 |
| 641 | 3221 | 700259555H1 | SATMON017 | g2239151 | BLASTX | 215 | 1e-27 | 72 |
| 642 | 5373 | LIB3078-054-Q1-K1-A2 | LIB3078 | g861198 | BLASTN | 1220 | 1e-92 | 82 |
| 643 | 5373 | 700097131H1 | SATMON009 | g861198 | BLASTN | 1071 | 1e-80 | 82 |
| 644 | 5373 | 700043508H1 | SATMON004 | g861198 | BLASTN | 1017 | 1e-75 | 83 |
| 645 | 5373 | 700046404H1 | SATMON004 | g861198 | BLASTN | 988 | 1e-73 | 83 |
| 646 | 5373 | 700431104H1 | SATMONN01 | g861198 | BLASTN | 769 | 1e-65 | 82 |
| 647 | 5373 | 700043839H1 | SATMON004 | g861198 | BLASTN | 747 | 1e-53 | 83 |
| 648 | 5373 | 700433984H2 | SATMONN01 | g861198 | BLASTN | 493 | 1e-32 | 76 |
| 649 | 5953 | LIB3078-052-Q1-K1-A9 | LIB3078 | g861198 | BLASTN | 1148 | 1e-92 | 81 |
| 650 | 5953 | 700045450H1 | SATMON004 | g861198 | BLASTN | 1005 | 1e-74 | 83 |
| 651 | 5953 | 700041735H1 | SATMON004 | g861198 | BLASTN | 969 | 1e-71 | 83 |
| 652 | 5953 | LIB83-001-Q1-E1-F5 | LIB83 | g861198 | BLASTN | 706 | 1e-58 | 83 |
| | | | MAIZE FERROCHELATASE | | | | | |
| 653 | −700214704 | 700214704H1 | SATMON016 | g2429617 | BLASTN | 822 | 1e-59 | 85 |
| 654 | −700239147 | 700239147H1 | SATMON010 | g439480 | BLASTN | 905 | 1e-66 | 87 |
| 655 | −700382669 | 700382669H1 | SATMON024 | g439480 | BLASTN | 1079 | 1e-81 | 87 |
| 656 | −700441938 | 700441938H1 | SATMON026 | g2429617 | BLASTN | 766 | 1e-55 | 84 |
| 657 | −700579576 | 700579576H1 | SATMON031 | g439480 | BLASTN | 739 | 1e-52 | 75 |
| 658 | −L1892866 | LIB189-014-Q1-E1-E6 | LIB189 | g2429617 | BLASTN | 248 | 1e-15 | 78 |
| 659 | −L832454 | LIB83-005-Q1-E1-F4 | LIB83 | g2460250 | BLASTN | 303 | 1e-35 | 88 |
| 660 | 11690 | 700151225H1 | SATMON007 | g2429617 | BLASTN | 1083 | 1e-81 | 91 |
| 661 | 11690 | 700106040H1 | SATMON010 | g2429617 | BLASTN | 627 | 1e-59 | 90 |
| 662 | 11690 | 700167395H1 | SATMON013 | g2429617 | BLASTN | 637 | 1e-44 | 91 |
| 663 | 14766 | LIB143-007-Q1-E1-D5 | LIB143 | g439480 | BLASTN | 580 | 1e-56 | 77 |
| 664 | 14766 | 700263637H1 | SATMON017 | g439480 | BLASTN | 259 | 1e-10 | 72 |
| 665 | 14766 | LIB36-007-Q1-E1-C9 | LIB36 | g2460250 | BLASTN | 243 | 1e-8 | 72 |
| 666 | 16136 | 700354263H1 | SATMON024 | g439480 | BLASTN | 987 | 1e-76 | 87 |
| 667 | 16136 | 700222207H1 | SATMON011 | g439480 | BLASTN | 903 | 1e-66 | 82 |
| 668 | 17054 | 700158001H1 | SATMON012 | g439480 | BLASTN | 1091 | 1e-82 | 90 |
| 669 | 17054 | 700157069H1 | SATMON012 | g439480 | BLASTN | 1096 | 1e-82 | 90 |
| 670 | 17054 | 700453159H1 | SATMON028 | g439480 | BLASTN | 816 | 1e-73 | 88 |
| 671 | 394 | 700622934H1 | SATMON034 | g439480 | BLASTN | 763 | 1e-84 | 86 |
| 672 | 394 | 700621391H1 | SATMON034 | g439480 | BLASTN | 775 | 1e-82 | 86 |
| 673 | 394 | 700098357H1 | SATMON009 | g2460251 | BLASTX | 155 | 1e-13 | 83 |
| 674 | 9731 | LIB3078-007-Q1-K1-B10 | LIB3078 | g2429617 | BLASTN | 1299 | 1e-123 | 85 |
| 675 | 9731 | 700355823H1 | SATMON024 | g2429617 | BLASTN | 826 | 1e-84 | 87 |
| 676 | 9731 | 700208201H1 | SATMON016 | g2429617 | BLASTN | 702 | 1e-64 | 82 |
| 677 | 9731 | 700167772H1 | SATMON013 | g2429617 | BLASTN | 648 | 1e-45 | 88 |

*Table Headings
Cluster ID
A cluster ID is arbitrarily assigned to all of those clones which belong to the same cluster at a given stringency and a particular clone will belong to only one cluster at a given stringency. If a cluster contains only a single clone (a "singleton"), then the cluster ID number will be negative, with an absolute value equal to the clone ID number of its single member. The cluster ID entries in the table refer to the cluster with which the particular clone in each row is associated.
Clone ID TABLE A*-continued

| Seq No. | Cluster ID | CloneID | Library | NCBI gi | Method | Score | P-value | % Ident |
|---------|------------|---------|---------|---------|--------|-------|---------|---------|

The clone ID number refers to the particular clone in the PhytoSeq database. Each clone ID entry in the table refers to the clone whose sequence is used for (1) the sequence comparison whose scores are presented and/or (2) assignment to the particular cluster which is presented. Note that a clone may be included in this table even if its sequence comparison scores fail to meet the minimum standards for similarity. In such a case, the clone is included due solely to its association with a particular cluster for which sequences of one or more other member clones possess the required level of similarity.
Library
The library ID refers to the particular cDNA library from which a given clone is obtained. Each cDNA library is associated with the particular tissue(s), line(s) and developmental stage(s) from which it is isolated.
NCBI gi
Each sequence in the GenBank public database is arbitrarily assigned a unique NCBI gi (National Center for Biotechnology Information GenBank Identifier) number. In this table, the NCBI gi number which is associated (in the same row) with a given clone refers to the particular GenBank sequence which is used in the sequence comparison. This entry is omitted when a clone is included solely due to its association with a particular cluster.
Method
The entry in the "Method" column of the table refers to the type of BLAST search that is used for the sequence comparison. "CLUSTER" is entered when the sequence comparison scores for a given clone fail to meet the minimum values required for significant similarity. In such cases, the clone is listed in the table solely as a result of its association with a given cluster for which sequences of one or more other member clones possess the required level of similarity.
Score
Each entry in the "Score" column of the table refers to the BLAST score that is generated by sequence comparison of the designated clone with the designated GenBank sequence using the designated BLAST method. This entry is omitted when a clone is included solely due to its association with a particular cluster. If the program used to determine the hit is HMMSW then the score refers to HMMSW score.
P-Value
The entries in the P-Value column refer to the probability that such matches occur by chance.
% Ident
The entries in the "% Ident" column of the table refer to the percentage of identically matched nucleotides (or residues) that exist along the length of that portion of the sequences which is aligned by the BLAST comparison to generate the statistical scores presented. This entry is omitted when a clone is included solely due to its association with a particular cluster.

We claim:

1. A substantially purified nucleic acid molecule comprising a nucleic acid sequence that shares between 100% and 90% sequence identity with the nucleic acid sequence of SEQ ID NO: 654.

2. The substantially purified nucleic acid molecule according to claim 1, wherein said nucleic acid sequence shares between 100% and 95% sequence identity with the nucleic acid sequence of SEQ ID NO: 654.

3. The substantially purified nucleic acid molecule according to claim 1, wherein said nucleic acid sequence shares between 100% and 98% sequence identity with the nucleic acid sequence of SEQ ID NO: 654.

4. The substantially purified nucleic acid molecule according to claim 1, wherein said nucleic acid sequence shares between 100% and 99% sequence identity with the nucleic acid sequence of SEQ ID NO: 654.

5. The substantially purified nucleic acid molecule according to claim 1, wherein said nucleic acid molecule shares 100% sequence identity with the nucleic acid sequence of SEQ ID NO: 654.

6. A transformed plant comprising a nucleic acid molecule which comprises a nucleic acid sequence, wherein said nucleic acid sequence shares between 100% and 90% sequence identity with SEQ ID NO: 654.

7. The transformed plant according to claim 6, wherein said nucleic acid sequence shares between 100% and 95% sequence identity with SEQ ID NO: 654.

8. The transformed plant according to claim 7, wherein said nucleic acid sequence shares between 100% and 98% sequence identity with SEQ ID NO: 654.

9. The transformed plant according to claim 8, wherein said nucleic acid sequence shares between 100% and 99% sequence identity with SEQ ID NO: 654.

10. The transformed plant according to claim 9, wherein said nucleic acid sequence shares 100% sequence identity with SEQ ID NO: 654.

11. A transformed seed comprising a transformed plant cell comprising a nucleic acid molecule which comprises a nucleic acid sequence, wherein said nucleic acid sequence shares between 100% and 90% sequence identity with SEQ ID NO: 654.

12. The transformed seed according to claim 11, wherein said nucleic acid sequence shares between 100% and 95% sequence identity with SEQ ID NO: 654.

13. The transformed seed according to claim 12, wherein said nucleic acid sequence shares between 100% and 98% sequence identity with SEQ ID NO: 654.

14. The transformed seed according to claim 13, wherein said nucleic acid sequence shares between 100% and 99% sequence identity with SEQ ID NO: 654.

15. The transformed seed according to claim 14, wherein said nucleic acid sequence shares 100% sequence identity with SEQ ID NO: 654.

* * * * *

UNITED STATES PATENT AND TRADEMARK OFFICE
CERTIFICATE OF CORRECTION

PATENT NO. : 7,625,738 B1  Page 1 of 1
APPLICATION NO. : 11/329175
DATED : December 1, 2009
INVENTOR(S) : CaJacob et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 96 days.

Signed and Sealed this

Second Day of November, 2010

David J. Kappos
*Director of the United States Patent and Trademark Office*